(12) United States Patent
Cha et al.

(10) Patent No.: US 11,532,792 B2
(45) Date of Patent: Dec. 20, 2022

(54) ORGANIC LIGHT EMITTING DIODE HAVING HIGH EFFICIENCY

(71) Applicant: SFC CO., LTD., Cheongju-si (KR)

(72) Inventors: Soon-Wook Cha, Cheongju-si (KR); Sang-Woo Park, Cheongju-si (KR); Jung-Ho Yoo, Cheongju-si (KR); Yoona Shin, Cheongju-si (KR); Yu-Rim Lee, Cheongju-si (KR); Sung Woo Kim, Cheongju-si (KR); Jiwon Lee, Cheongju-si (KR)

(73) Assignee: SFC CO., LTD., Cheongju-si (KR)

(*) Notice: Subject to any disclaimer, the term of this patent is extended or adjusted under 35 U.S.C. 154(b) by 403 days.

(21) Appl. No.: 16/625,752

(22) PCT Filed: Jul. 11, 2018

(86) PCT No.: PCT/KR2018/007876
§ 371 (c)(1),
(2) Date: Dec. 22, 2019

(87) PCT Pub. No.: WO2019/013556
PCT Pub. Date: Jan. 17, 2019

(65) Prior Publication Data
US 2020/0127209 A1 Apr. 23, 2020

(30) Foreign Application Priority Data
Jul. 11, 2017 (KR) .................. 10-2017-0087728

(51) Int. Cl.
*H01L 51/00* (2006.01)
*C07D 307/94* (2006.01)
(Continued)

(52) U.S. Cl.
CPC ........ *H01L 51/0061* (2013.01); *C07D 307/94* (2013.01); *C07D 407/14* (2013.01);
(Continued)

(58) Field of Classification Search
None
See application file for complete search history.

(56) References Cited

U.S. PATENT DOCUMENTS

| 2017/0012214 A1* | 1/2017 | Pyo ...................... C07D 493/04 |
| 2017/0062729 A1* | 3/2017 | Cha ...................... C07D 307/77 |

(Continued)

FOREIGN PATENT DOCUMENTS

| CN | 105778891 A | * | 7/2016 | ............. C09K 11/06 |
| KR | 101074193 B1 | | 10/2011 | |

(Continued)

OTHER PUBLICATIONS

Machine translation of CN-105778891, translation generated Jan. 2022, 42 pages. (Year: 2022).*

(Continued)

*Primary Examiner* — Robert S Loewe
(74) *Attorney, Agent, or Firm* — STIP Law Group, LLC

(57) ABSTRACT

The present invention relates to an organic light emitting diode comprising: a first electrode; a second electrode facing the first electrode; a hole injecting layer or a hole transport layer, which is interposed between the first electrode and the second electrode; and a light emitting layer, wherein the hole injecting layer or the hole transport layer comprises at least one type of amine compound represented by chemical formula A or chemical formula B, and the chemical formula A and the chemical formula B are the same as those included in the description of the invention.

16 Claims, 1 Drawing Sheet

(51) Int. Cl.
 *C07D 407/14* (2006.01)
 *C07D 493/10* (2006.01)
 *H01L 51/50* (2006.01)

(52) U.S. Cl.
 CPC ........ *C07D 493/10* (2013.01); *H01L 51/0073* (2013.01); *H01L 51/5012* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | |
|---|---|---|---|
| 2017/0133600 A1 | 5/2017 | Pyo et al. | |
| 2017/0141321 A1* | 5/2017 | Pyo | C09K 11/025 |
| 2018/0166638 A1* | 6/2018 | Park | H01L 51/0074 |
| 2019/0326517 A1* | 10/2019 | Koo | C07D 491/22 |

FOREIGN PATENT DOCUMENTS

| | | | |
|---|---|---|---|
| KR | 101455156 B1 | 10/2014 | |
| KR | 1020160141359 A | 12/2016 | |
| KR | 1020160141360 A | 12/2016 | |
| KR | 1020160141361 A | 12/2016 | |
| KR | 1020170018276 A | 2/2017 | |
| KR | 1020170056717 A | 5/2017 | |
| WO | WO-2014171779 A1 * | 10/2014 | ........... C07D 495/10 |
| WO | WO2015022051 A1 | 2/2015 | |

OTHER PUBLICATIONS

International Search Report of PCT/KR2018/007876, dated Oct. 16, 2018, English translation.
The extended European search report of EP18 83 1305, dated Mar. 9, 2021.

* cited by examiner

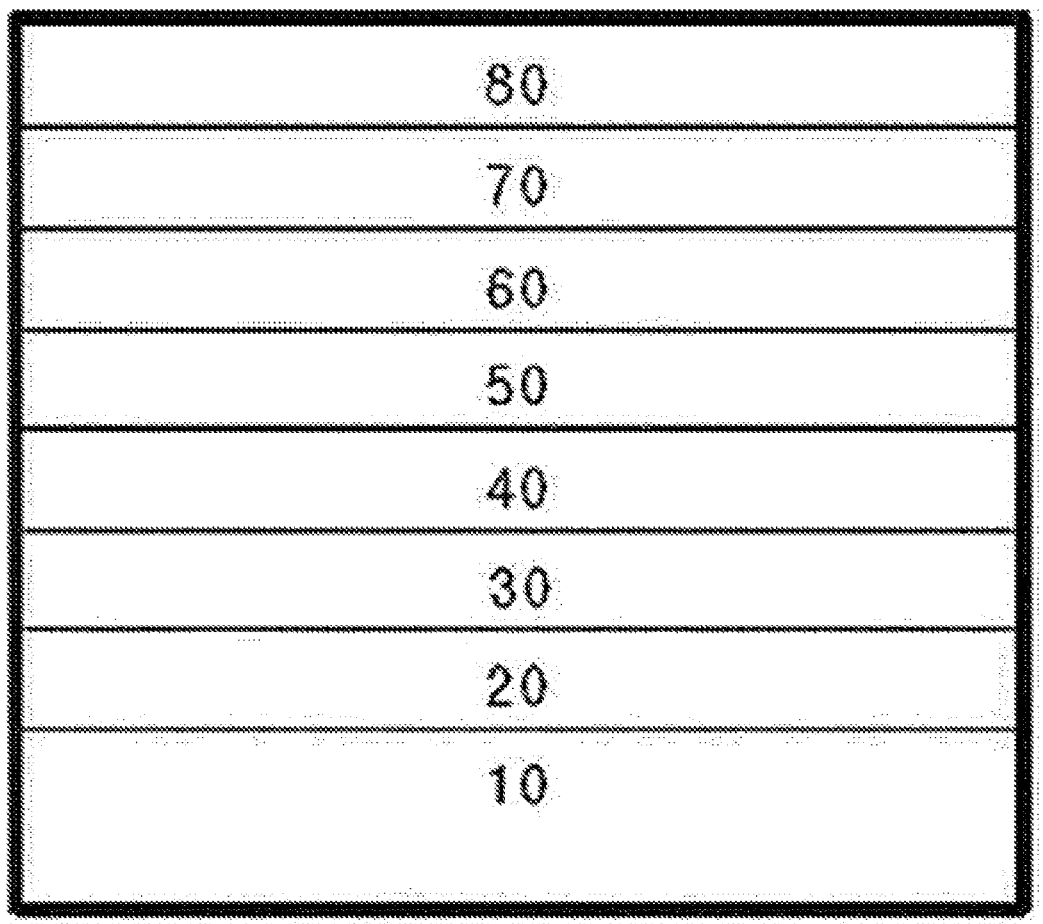

ORGANIC LIGHT EMITTING DIODE HAVING HIGH EFFICIENCY

CROSS-REFERENCE TO RELATED APPLICATIONS

This application is the U.S. National Phase under 35 U.S.C. § 371 of International Application No. PCT/KR2018/007876 filed on Jul. 11, 2018, which in turn claims the benefit of Korean Application No. 10-2017-0087728, filed on Jul. 11, 2017, the disclosures of which are incorporated by reference into the present application.

TECHNICAL FIELD

The present disclosure pertains to an organic light-emitting diode having high efficiency and, more particularly, to an organic light-emitting diode exhibiting high efficiency, in which a material having a specific structure is used for a hole injecting layer or a hole transport layer in a light-emitting layer.

BACKGROUND ART

Organic light-emitting diodes (OLEDs), based on self-luminescence, are used to create digital displays with the advantage of having a wide viewing angle and being able to be made thinner and lighter than liquid crystal displays. In addition, an OLED display exhibits a very fast response time. Accordingly, OLEDs find applications in the full color display field or the illumination field.

In general, the term "organic light-emitting phenomenon" refers to a phenomenon in which electrical energy is converted to light energy by means of an organic material. An organic light-emitting diode using the organic light-emitting phenomenon has a structure usually including an anode, a cathode, and an organic layer interposed therebetween.

In this regard, the organic layer may have, for the most part, a multilayer structure consisting of different materials, for example, a hole injecting layer, a hole transport layer, a light-emitting layer, an electron transport layer, and an electron injecting layer in order to enhance the efficiency and stability of the organic light-emitting diode. In the organic light-emitting diode having such a structure, application of a voltage between the two electrodes injects a hole from the anode and an electron from the cathode to the organic layer. In the luminescent zone, the hole and the electron recombine to produce an exciton. When the exciton returns to the ground state from the excited state, the molecule of the organic layer emits light. Such an organic light-emitting diode is known to have characteristics such as self-luminescence, high luminance, high efficiency, low driving voltage, a wide viewing angle, high contrast, and high-speed response.

Materials used as organic layers in OLEDs may be divided into luminescent materials and charge transport materials, for example, a hole injecting material, a hole transport material, an electron injection material, and an electron transport material according to the functions thereof and, as needed, further into an electron-blocking material or a hole-blocking material.

With regard to related arts pertaining to hole transport layers, reference may be made to Korean Patent No. 10-1074193 (issued Oct. 14, 2011), which describes an organic light-emitting diode using as a hole transport layer a compound having a core structure in which a carbazole structure is fused with at least one benzene ring, and Korean Patent No. 10-1455156 (issued Oct. 27, 2014), which describes an organic light-emitting diode in which the HOMO energy level of an auxiliary light-emitting layer is set between those of a hole transport layer and a light-emitting layer.

In spite of enormous effort for fabricating organic light-emitting diodes as in conventional technologies including the cited documents, however, there is still continued need to develop novel organic light-emitting diodes having more improved emission efficacy.

DETAILED DESCRIPTION OF THE INVENTION

Technical Problem

Therefore, the purpose of the present disclosure is to provide a novel organic light-emitting diode (OLED) with high efficiency, wherein a hole injecting layer or hole transport layer material having a specific structure is employed.

Technical Solution

The present disclosure provides an organic light-emitting diode, comprising: a first electrode; a second electrode facing the first electrode; a hole injecting layer or a hole transport layer interposed between the first electrode and the second electrode; and a light-emitting layer, wherein the hole injecting layer or the hole transport layer comprises at least one of the amine compounds represented by the following Chemical Formula A or B:

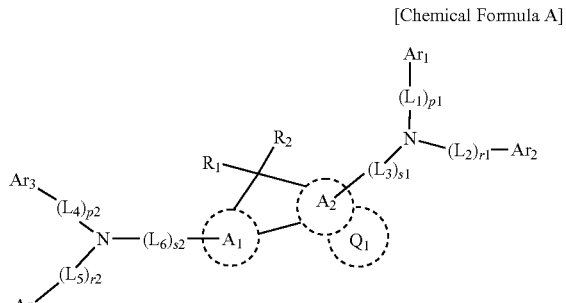

[Chemical Formula A]

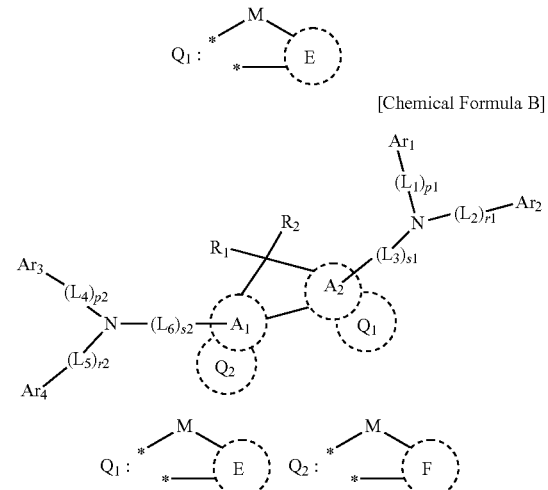

[Chemical Formula B]

wherein, $A_1$, $A_2$, E, and F, which may be the same or different, are each independently a substituted or unsubstituted aromatic hydrocarbon ring of 6 to 50 carbon atoms, or a substituted or unsubstituted heteroaromatic ring of 2 to 40 carbon atoms;

wherein two adjacent carbon atoms within the aromatic ring of $A_1$ and two adjacent carbon atoms within the aromatic ring of $A_2$ form a 5-membered ring with a carbon atom connected to both substituents $R_1$ and $R_2$, thus establishing a fused ring structure;

linkers $L_1$ to $L_6$, which may be the same or different, are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is selected from among N—$R_3$, $CR_4R_5$, $SiR_6R_7$, $GeR_8R_9$, O, S, and Se;

$R_1$ to $R_9$ and $Ar_1$ to $Ar_4$, which may be the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 1 to 30 carbon atoms, a cyano, a nitro, and a halogen, wherein $R_1$ and $R_2$ may be connected to each other to form a mono- or polycyclic aliphatic or aromatic ring which may bear at least one heteroatom selected from among N, O, P, Si, S, Ge, Se, and Te as a ring member;

p1 and p2, r1 and r2, and s1 and s2 are each independently an integer of 1 to 3, under which when any of them is 2 or greater, the corresponding linkers $L_1$ to $L_6$ may be the same or different, $Ar_1$ and $Ar_2$ may be connected to each other to form a ring and $Ar_3$ and $Ar_4$ may be connected to each other to form a ring;

two adjacent carbon atoms within the $A_2$ ring in Chemical Formula A are linked to respective * of structure formula $Q_1$ to form a fused ring; and two adjacent carbon atoms within the $A_1$ ring in Chemical Formula B are linked to respective * of structure formula $Q_2$ to form a fused ring and two adjacent carbon atoms within the $A_2$ ring in Chemical Formula B are linked to respective * of structure formula $Q_1$ to form a fused ring.

Advantageous Effect

The organic light-emitting diode according to the present disclosure can exhibit more improved emission efficacy than conventional organic light-emitting diodes.

BRIEF DESCRIPTION OF THE DRAWINGS

FIG. 1 is a schematic view of an organic light-emitting diode according to an embodiment of the present disclosure.

BEST MODE FOR INVENTION

Hereinafter, a detailed description will be given of the present disclosure.

The present disclosure provides an organic light-emitting diode, comprising: a first electrode; a second electrode facing the first electrode; a hole injecting layer or a hole transport layer interposed between the first electrode and the second electrode; and a light-emitting layer, wherein the hole injecting layer or the hole transport layer comprises at least one of the amine compounds represented by the following Chemical Formula A or B:

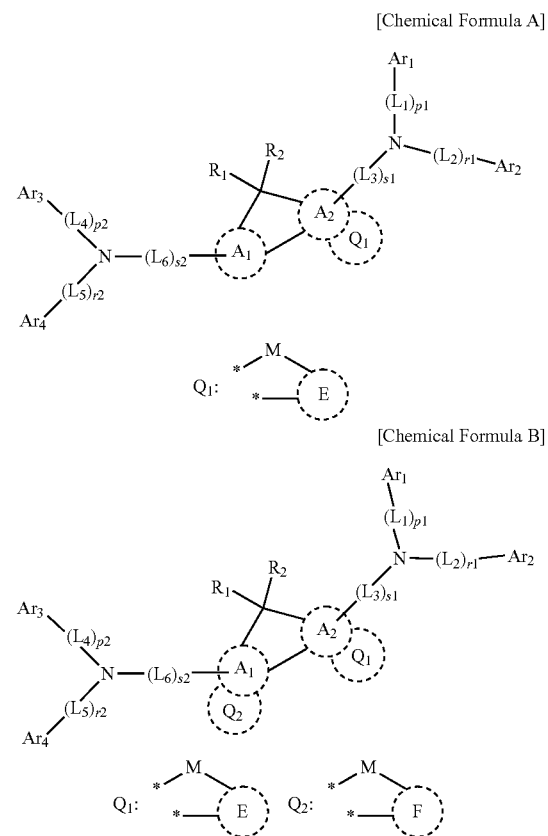

wherein, $A_1$, $A_2$, E, and F, which may be the same or different, are each independently a substituted or unsubstituted aromatic hydrocarbon ring of 6 to 50 carbon atoms, or a substituted or unsubstituted heteroaromatic ring of 2 to 40 carbon atoms;

wherein two adjacent carbon atoms within the aromatic ring of $A_1$ and two adjacent carbon atoms within the aromatic ring of $A_2$ form a 5-membered ring with a carbon atom connected to both substituents $R_1$ and $R_2$, thus establishing a fused ring structure;

linkers $L_1$ to $L_6$, which may be the same or different, are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is selected from among N—$R_3$, $CR_4R_5$, $SiR_5R_7$, $GeR_8R_9$, O, S, and Se;

$R_1$ to $R_9$ and $Ar_1$ to $Ar_4$, which may be the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 1 to 30 carbon atoms, a cyano, a nitro, and a halogen, wherein $R_1$ and $R_2$ may be connected to each other to form a mono- or polycyclic aliphatic or aromatic ring which may bear at least one heteroatom selected from among N, O, P, Si, S, Ge, Se, and Te as a ring member;

p1 and p2, r1 and r2, and s1 and s2 are each independently an integer of 1 to 3, under which when any of them is 2 or greater, the corresponding linkers $L_1$ to $L_6$ may be the same or different, $Ar_1$ and $Ar_2$ may be connected to each other to form a ring and $Ar_3$ and $Ar_4$ may be connected to each other to form a ring;

two adjacent carbon atoms within the $A_2$ ring in Chemical Formula A are linked to respective * of structure formula $Q_1$ to form a fused ring; and two adjacent carbon atoms within the $A_1$ ring in Chemical Formula B are linked to respective * of structure formula $Q_2$ to form a fused ring and two adjacent carbon atoms within the $A_2$ ring in Chemical Formula B are linked to respective * of structure formula $Q_1$ to form a fused ring, wherein the term "substituted" in the expression "substituted or unsubstituted" used for [Chemical Formula A] and [Chemical Formula B] means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms, such as "a substituted or unsubstituted alkyl of 1 to 24 carbon atoms", "a substituted or unsubstituted aryl of 6 to 24 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical, derived from an aromatic hydrocarbon by removing one hydrogen atom. Further, the aromatic system may include a fused ring that is formed by adjacent substituents on the aryl radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl at least one hydrogen atom of which may be substituted by a deuterium atom, a halogen atom, a hydroxy, a nitro, a cyano, a silyl, an amino (—NH2, —NH(R), —N(R')(R") wherein R' and R" are each independently an alkyl of 1 to 10 alkyl, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a heteroaromatic radical bearing one to four heteroatoms selected from among N, O, P, Se, Te, Si, Ge, and S in each ring of the aryl, wherein the two or more rings may be fused. One or more hydrogen atoms on the heteroaryl may be substituted by the same substituents as on the aryl.

As used herein, the term "heteroaromatic ring" refers to an individual ring in an aromatic hydrocarbon system, which bears as a ring member at least one and preferably one to four heteroatoms selected from among N, O, P, Se, Te, Si, Ge, and S, wherein the rings of the aromatic hydrocarbon system may be fused to each other. One or more hydrogen atoms on the heteroaromatic ring may be substituted by the same substituents as on the heteroaryl.

Examples of the substituent alkyl useful in the present disclosure include methyl, ethyl, propyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the compound of the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the compound of the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

Meanwhile, the amine compound represented by Chemical Formula A or B, used in the organic light-emitting diode according to the present disclosure, is characterized in that two adjacent carbon atoms within the $A_2$ ring in Chemical Formula A are linked to respective * of structure formula $Q_1$ to form a fused ring, and two adjacent carbon atoms within the $A_1$ ring in Chemical Formula B are linked to respective * of structure formula $Q_2$ to form a fused ring and two adjacent carbon atoms within the $A_2$ ring in Chemical Formula B are linked to respective * of structure formula $Q_2$ to form a fused ring, wherein the $A_1$ ring and the $A_2$ ring within Chemical Formulas A and B both bear an amine group. The use of the amine compound of Chemical Formula A or B having such structural features in the hole injecting layer or hole transport layer guarantees high emission efficacy in the organic light-emitting diode.

According to a particular embodiment of the present disclosure, the amine compound represented by Chemical Formula A or B may be used in a hole transport layer.

According to one embodiment of the present disclosure, $A_1$, $A_2$, E, and F in [Chemical Formula A] or [Chemical Formula B], which may be the same or different, are each independently a substituted or unsubstituted aromatic hydrocarbon ring of 6 to 50 carbon atoms. When $A_1$, $A_2$, E, and F in [Chemical Formula A] or [Chemical Formula B] each correspond to a substituted or unsubstituted aromatic hydrocarbon ring of 6 to 50 carbon atoms as mentioned above, the substituted or unsubstituted aromatic hydrocarbon rings of 6 to 50 carbon atoms may be the same or different and are each independently one selected from among [Structural Formula 10] to [Structural Formula 21]:

[Structural Formula 10]

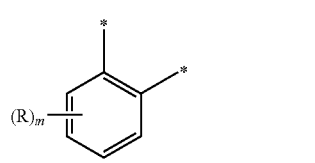

[Structural Formula 11]

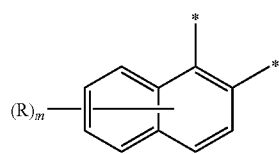

[Structural Formula 12]

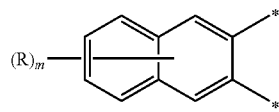

[Structural Formula 13]

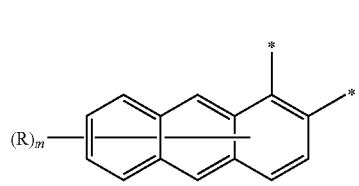

[Structural Formula 14]

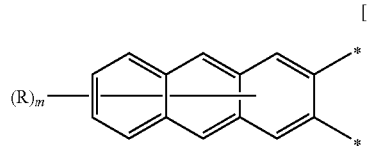

[Structural Formula 15]

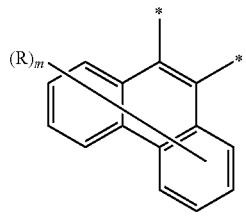

[Structural Formula 16]

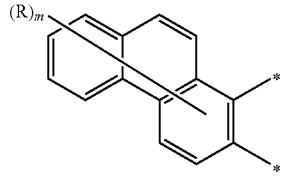

[Structural Formula 17]

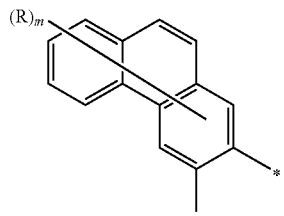

[Structural Formula 18]

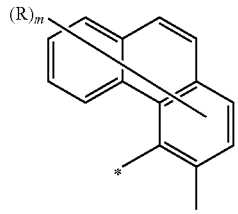

[Structural Formula 19]

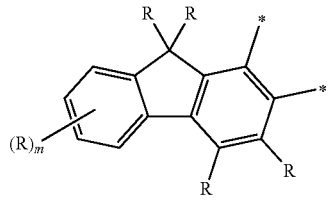

[Structural Formula 20]

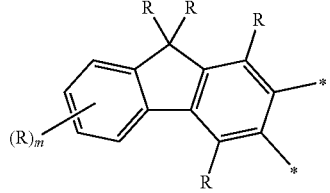

[Structural Formula 21]

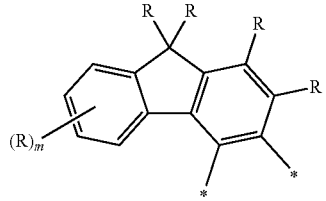

wherein

"-*" denotes a bonding site for forming a 5-membered ring bearing the carbon atom connected to the substituents $R_1$ and $R_2$ or a bonding site for forming a 5-membered ring bearing M of Structural Formula $Q_1$ and $Q_2$;

when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R is as defined for $R_1$ and $R_2$ above; and m is an integer of 1 to 8 wherein when m is 2 or greater or when R exists as multiple radicals, the resulting R's may be the same or different.

In addition, the linkers $L_1$ to $L_{12}$ in Chemical Formulas A and B may each be independently a single bond or any one selected from among the following Structural Formulas 22 to 30. In this case, p1 and p2, r1 and r2, and s1 and s2 may each be 1 or 2:

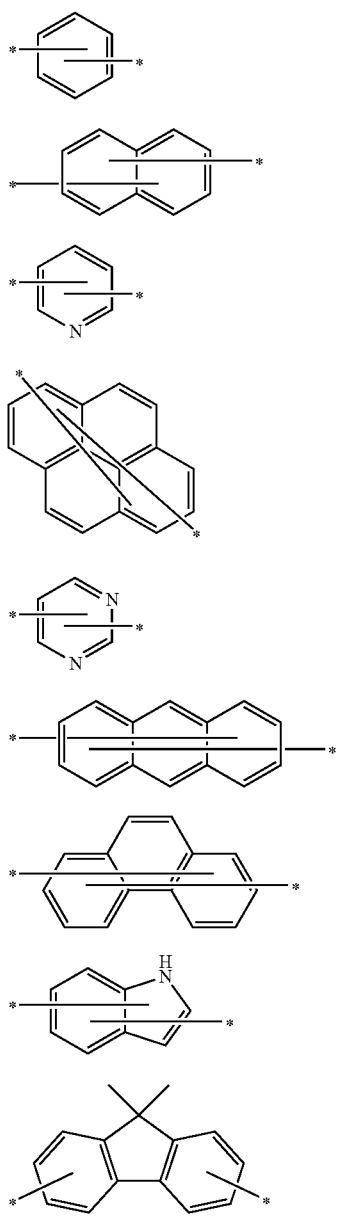

[Structural Formula 22]

[Structural Formula 23]

[Structural Formula 24]

[Structural Formula 25]

[Structural Formula 26]

[Structural Formula 27]

[Structural Formula 28]

[Structural Formula 29]

[Structural Formula 30]

In the linkers, each of the unsubstituted carbon atoms of the aromatic ring moiety is bound with a hydrogen atom or a deuterium atom.

In addition, the moieties $R_1$ and $R_2$ in Chemical Formulas A and B may be the same or different and may be connected to each other to form a ring or may each be a substituted or unsubstituted aryl of 6 to 50 carbon atoms remaining unconnected.

Meanwhile, the amine compound represented by Chemical Formula A or B may be any one of the compounds represented by the following Chemical Formulas 1 to 144, but is not limited to:

<Chemical Formula 1>

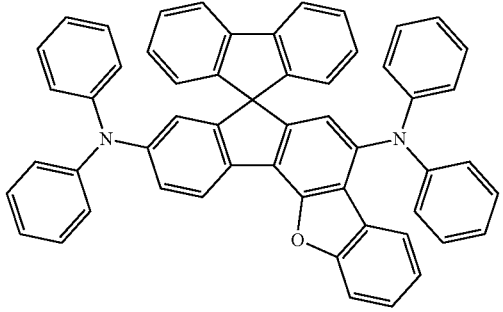

<Chemical Formula 2>

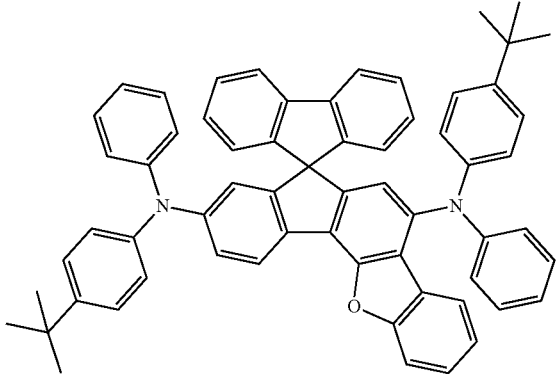

<Chemical Formula 3>

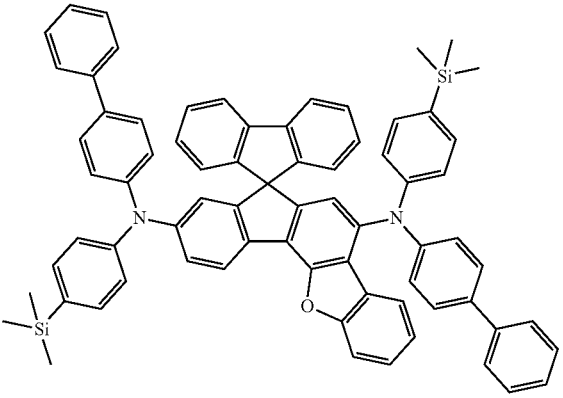

<Chemical Formula 4>
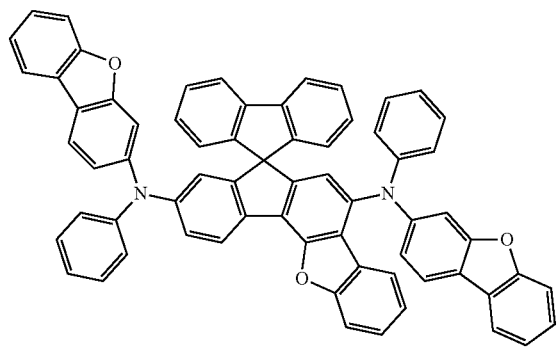
<Chemical Formula 5>
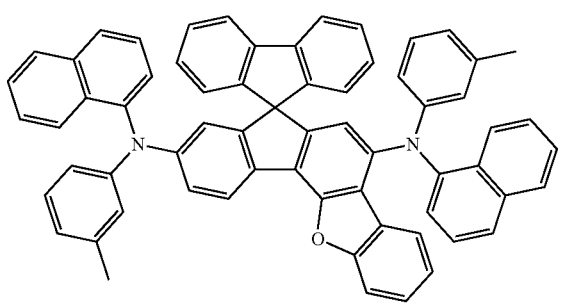
<Chemical Formula 6>
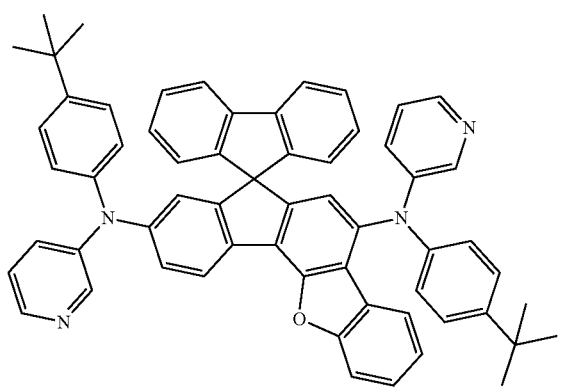
<Chemical Formula 7>
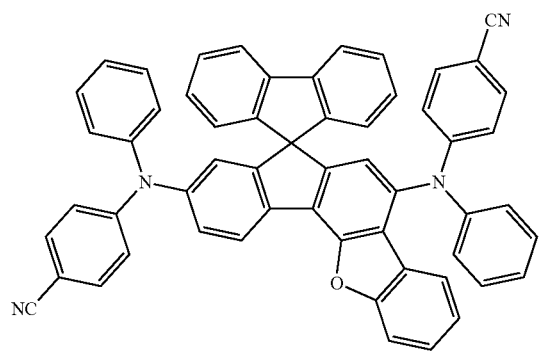
<Chemical Formula 8>
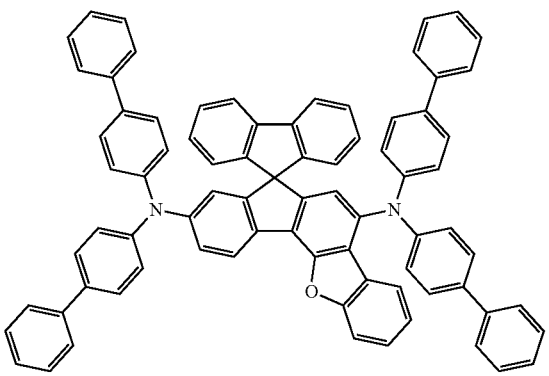
<Chemical Formula 9>
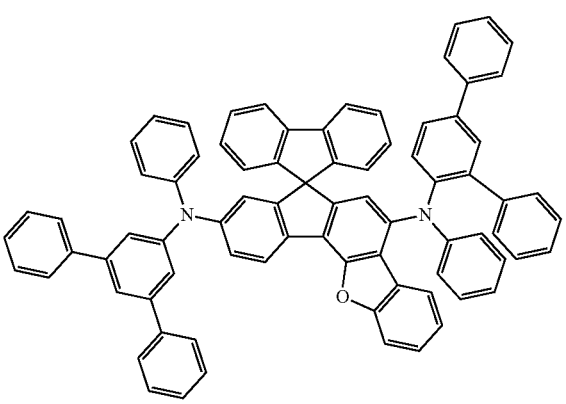
<Chemcial Formula 10>
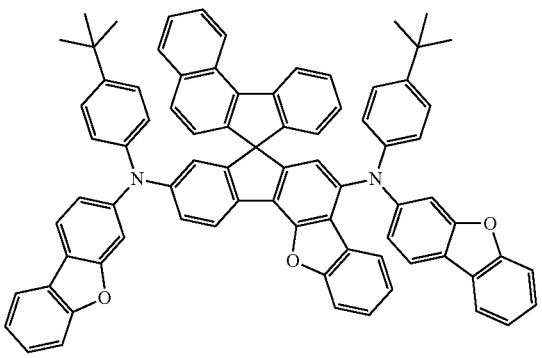
<Chemical Formula 11>
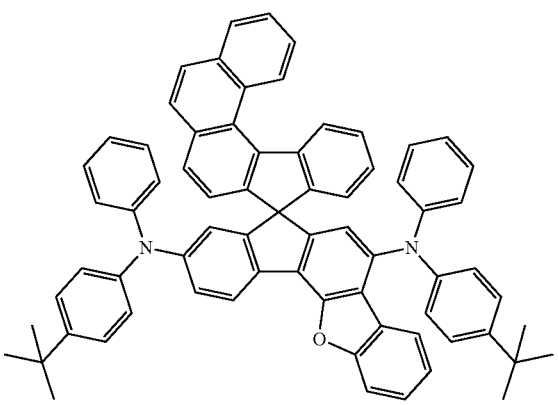

-continued
<Chemical Formula 12>
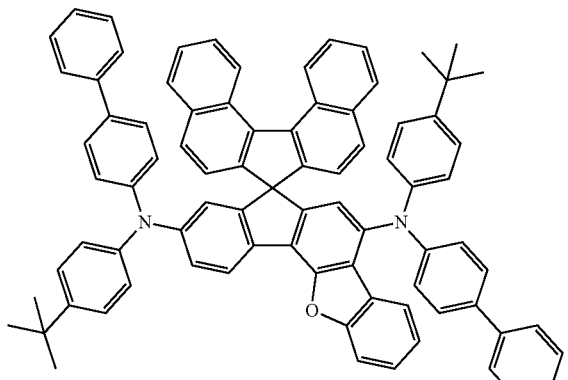
<Chemical Formula 13>
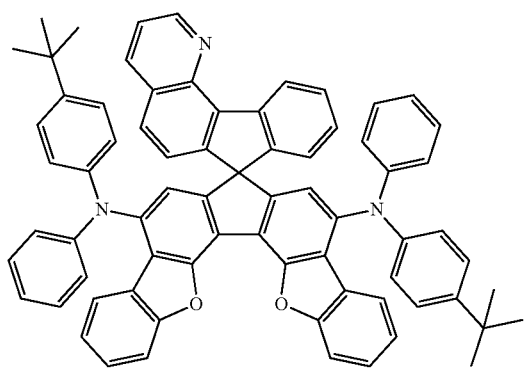
<Chemical Formula 14>
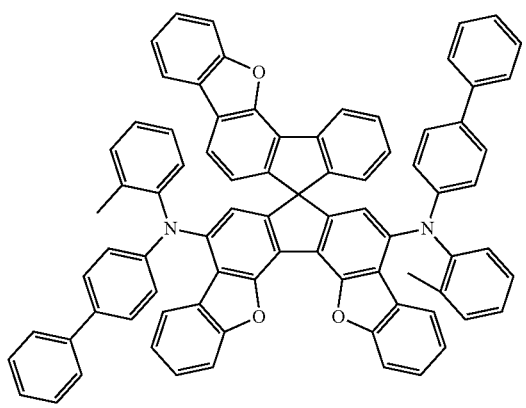
<Chemical Formula 15>
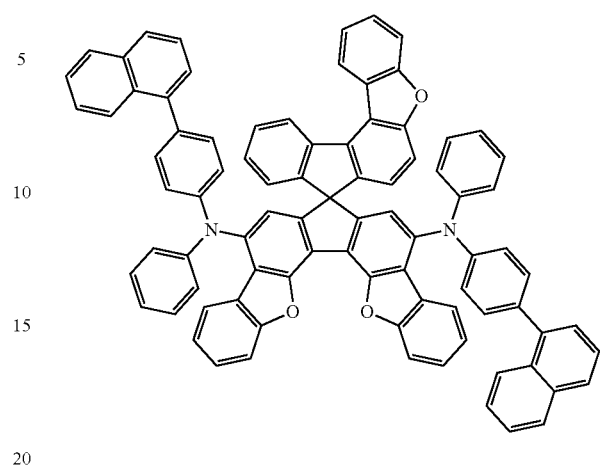
<Chemical Formula 16>
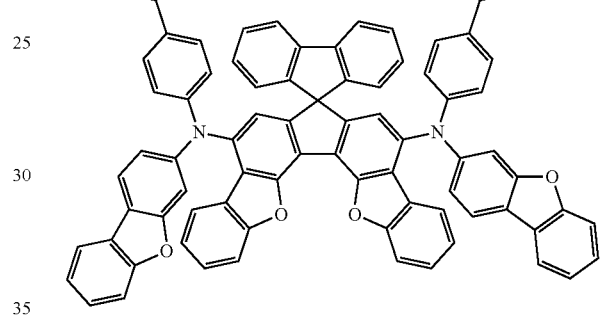
<Chemical Formula 17>
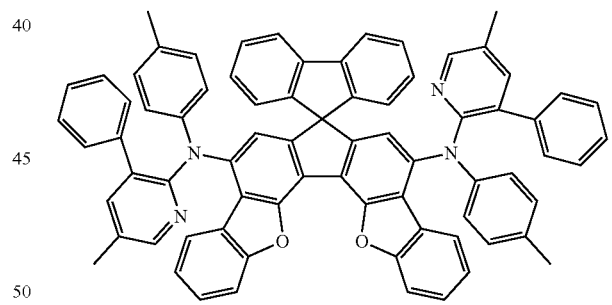
<Chemical Formula 18>
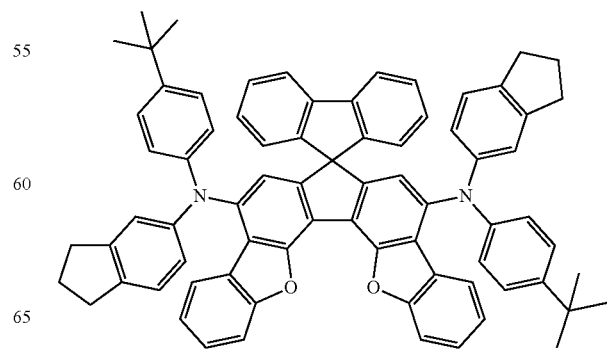

<Chemical Formula 19>
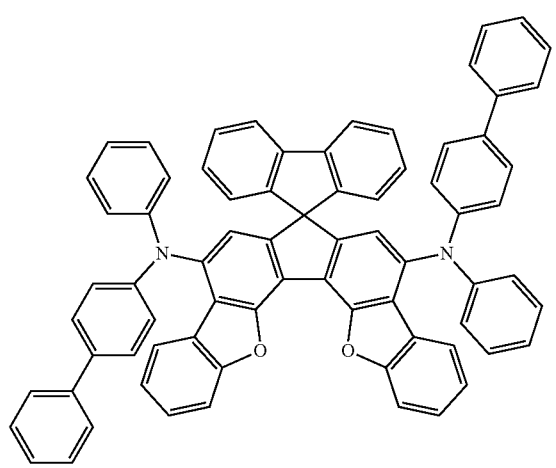
<Chemical Formula 20>
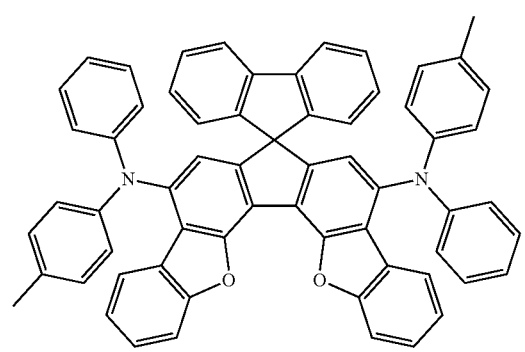
<Chemical Formula 21>
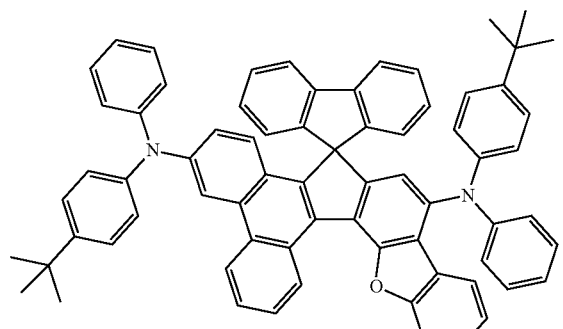
<Chemical Formula 22>
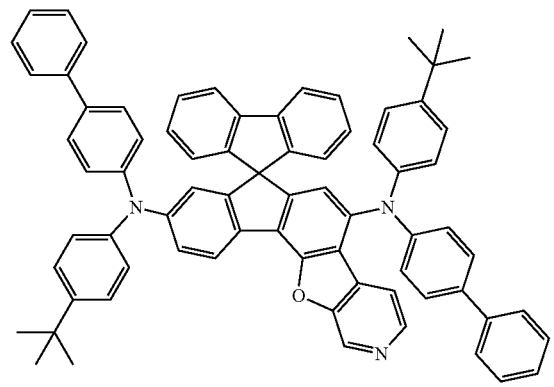
<Chemical Formula 23>
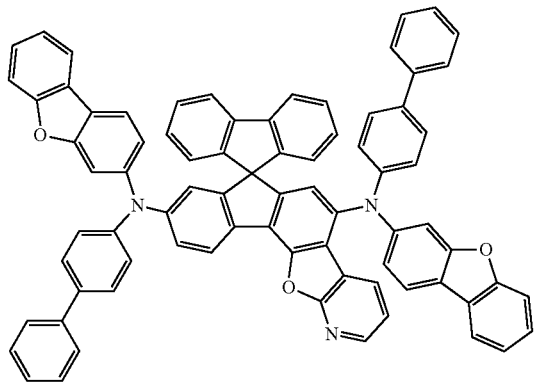
<Chemical Formula 24>
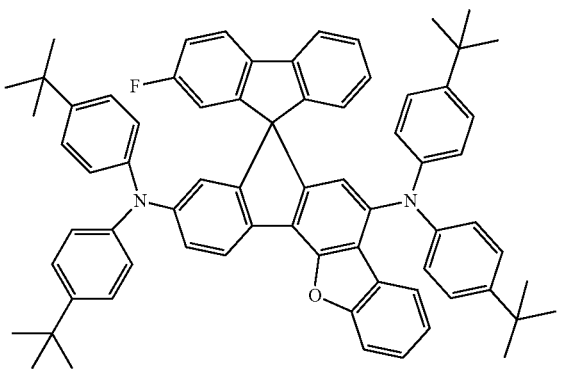
<Chemical Formula 25>
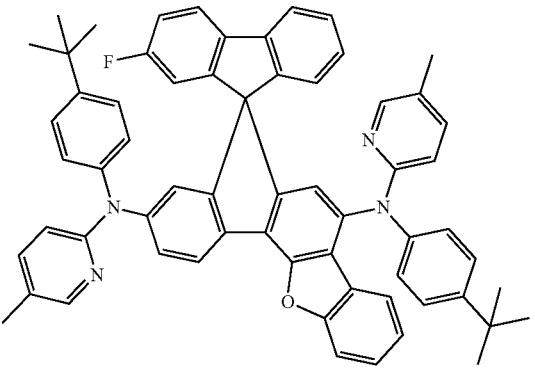
<Chemical Formula 26>
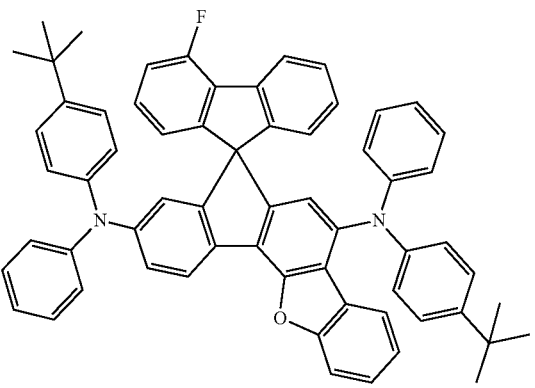

<Chemical Formula 27>
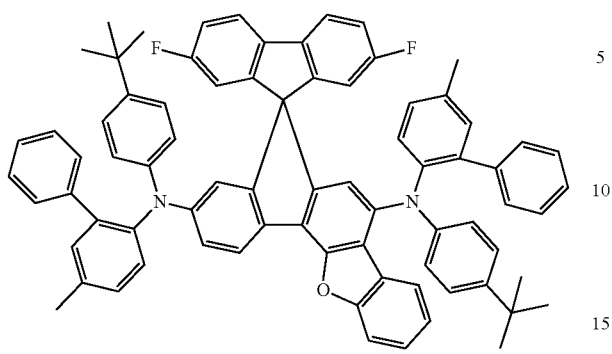
<Chemical Formula 28>
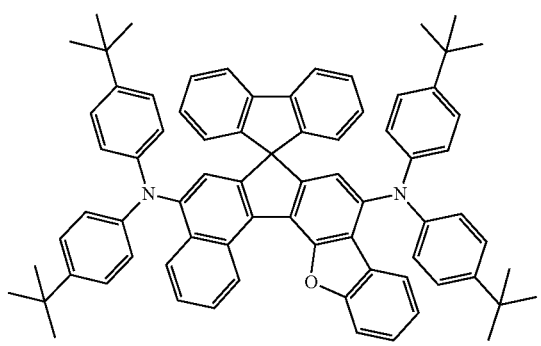
<Chemical Formula 29>
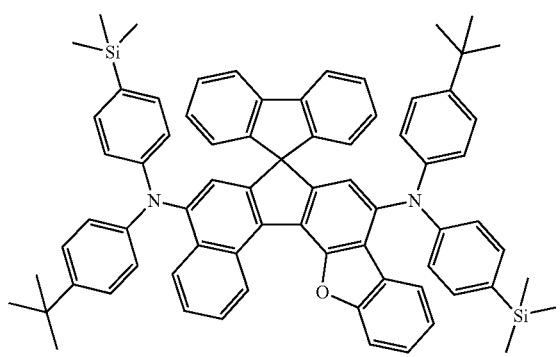
<Chemical Formula 30>
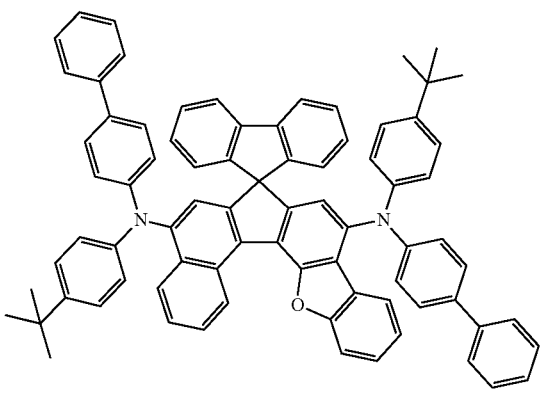
<Chemical Formula 31>
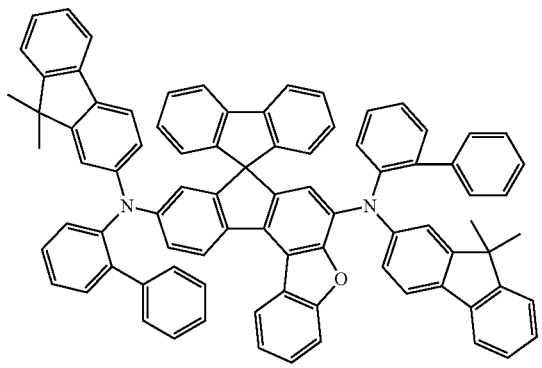
<Chemical Formula 32>
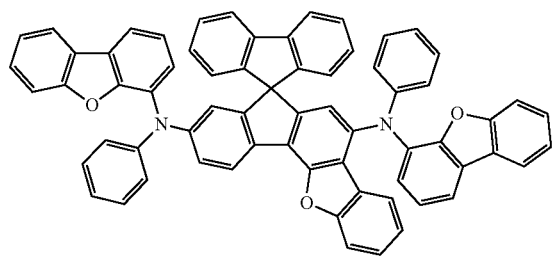
<Chemical Formula 33>
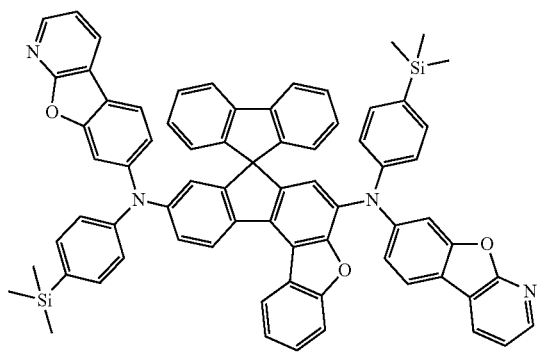
<Chemical Formula 34>
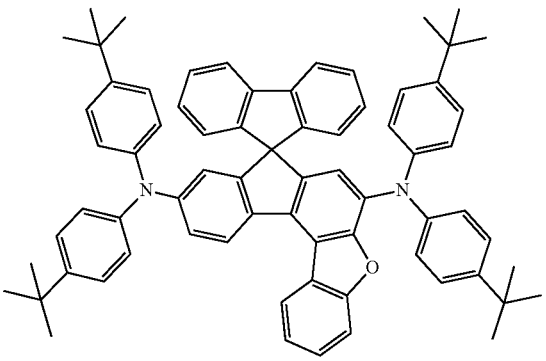

<Chemical Formula 35>
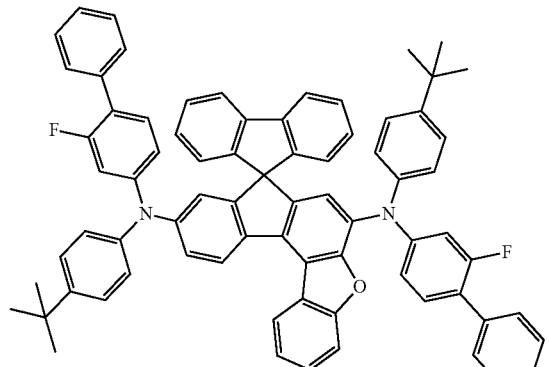
<Chemical Formula 36>
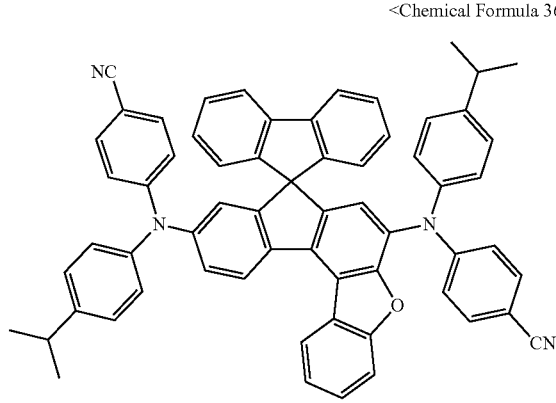
<Chemical Formula 37>
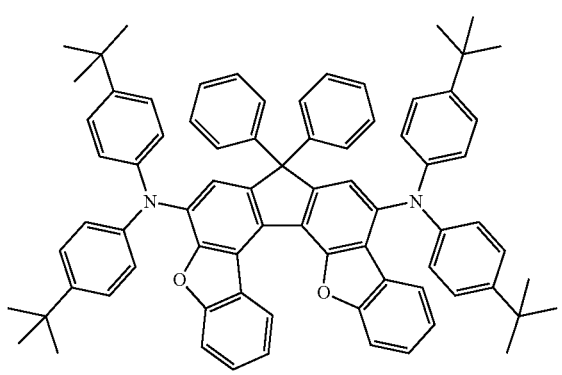
<Chemical Formula 38>
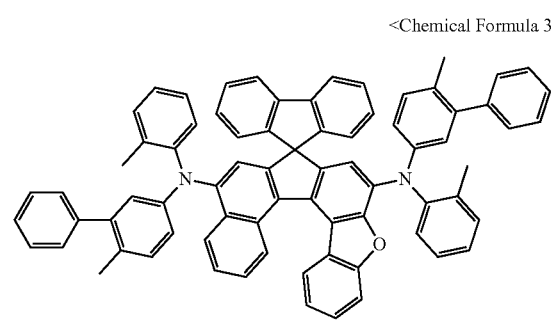
<Chemical Formula 39>
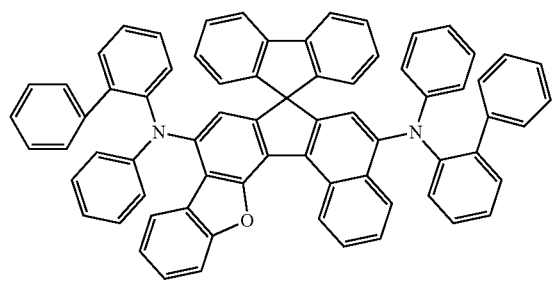
<Chemical Formula 40>
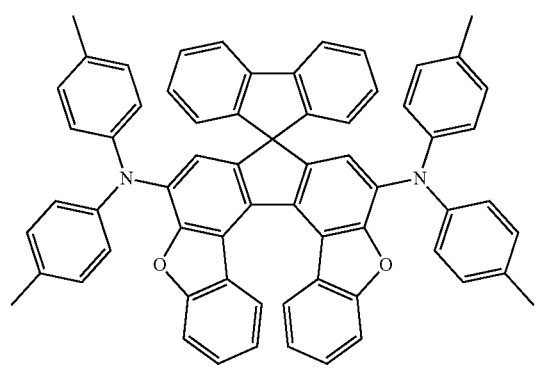
<Chemical Formula 41>
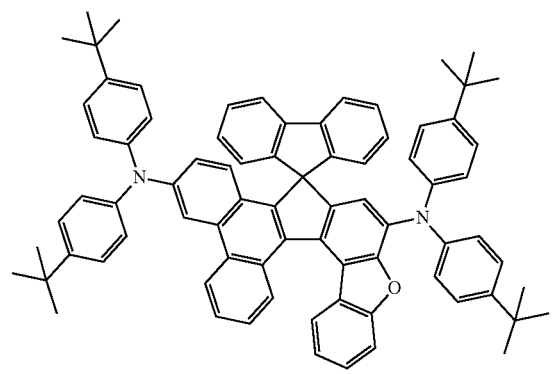
<Chemicval Formula 42>
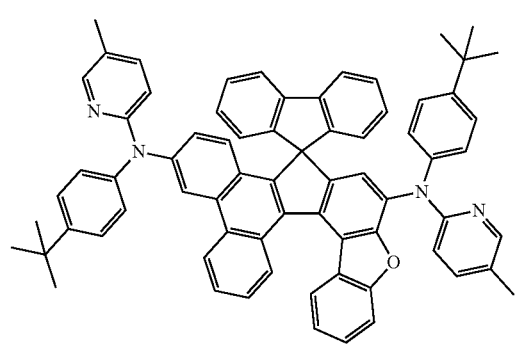

<Chemical Formula 43>
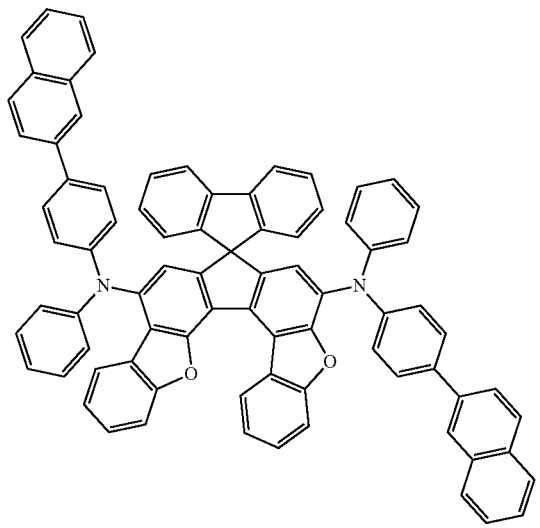
<Chemical Formula 44>
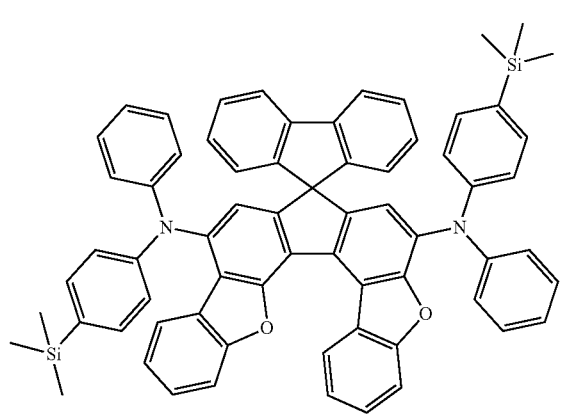
<Chemical Formula 45>
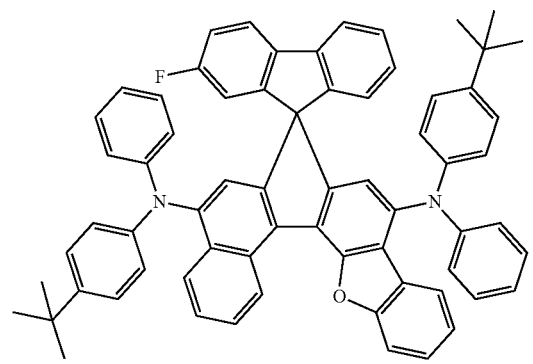
<Chemical Formula 46>
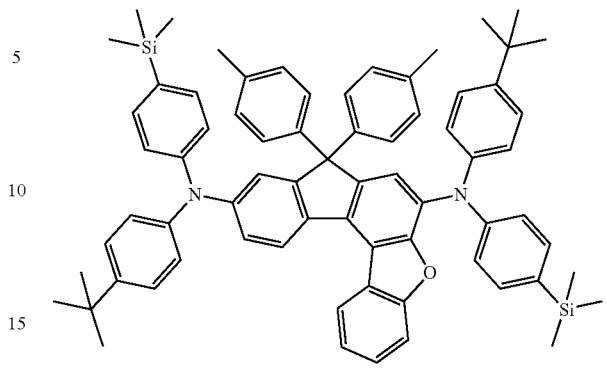
<Chemical Formula 47>
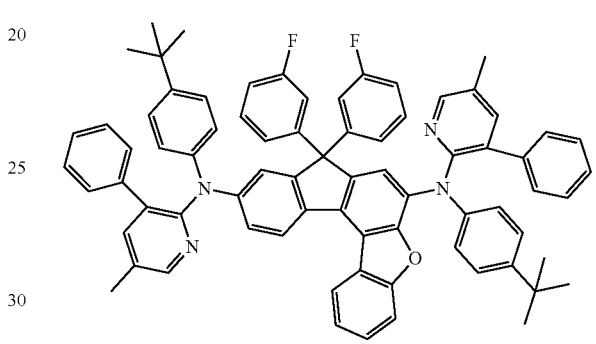
<Chemical Formula 48>
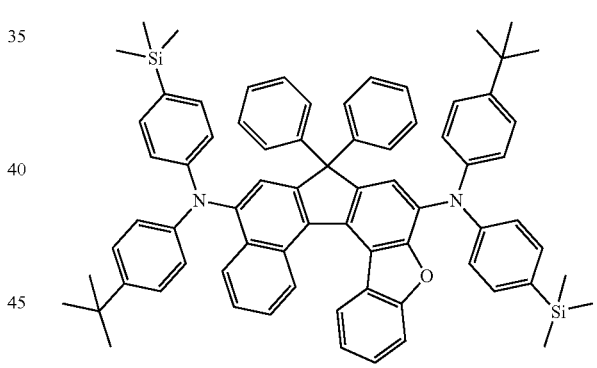
Chemical Formula 49>
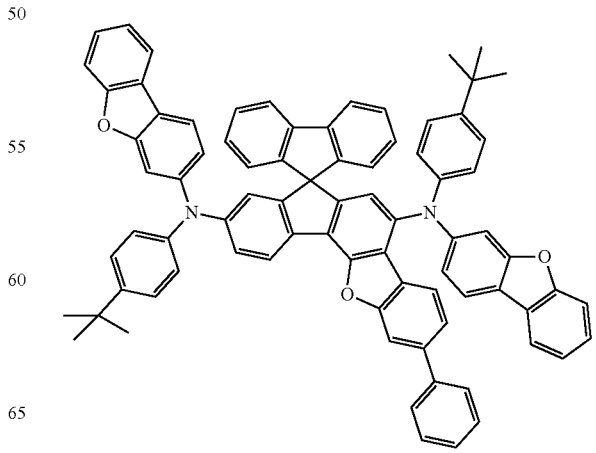

<Chemical Formula 50>
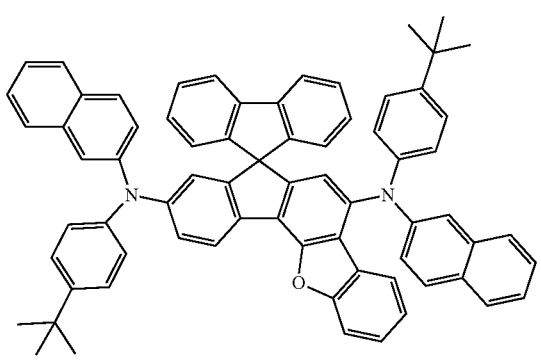
<Chemical Formula 51>
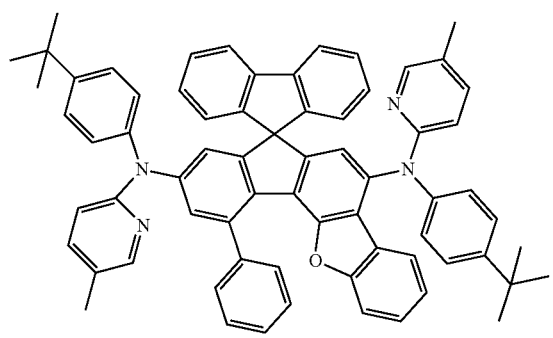
<Chemical Formula 52>
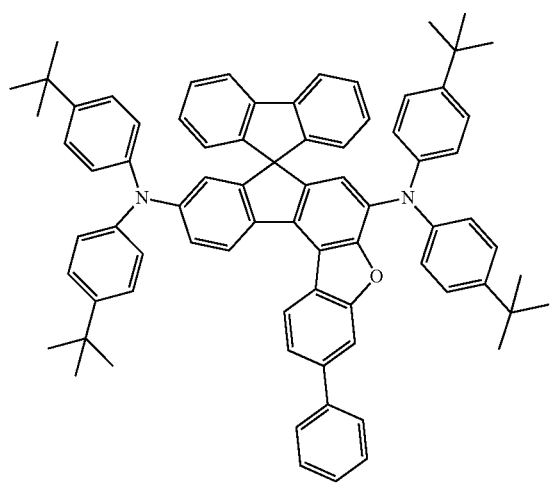
<Chemical Formula 53>
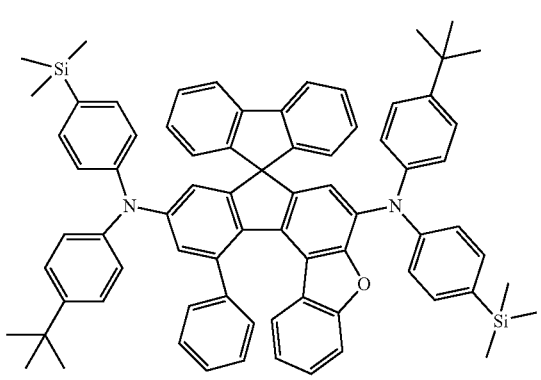
<Chemical Formula 54>
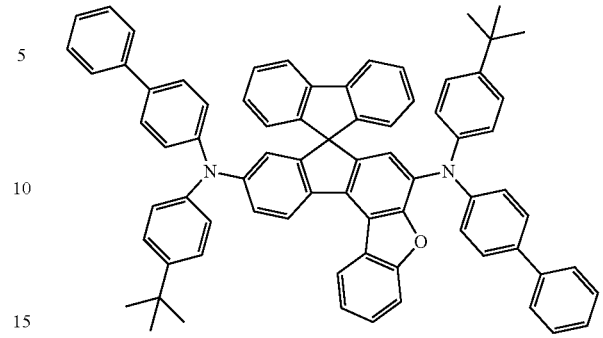
<Chemical Formula 55>
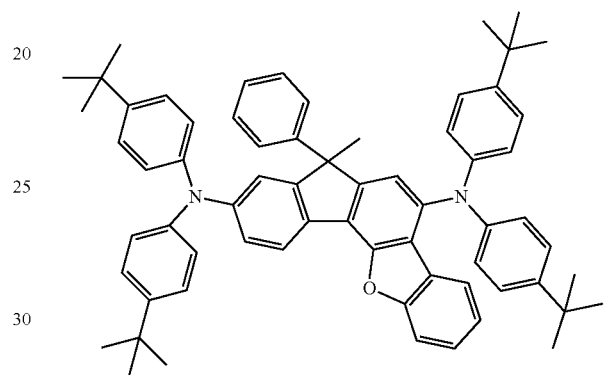
<Chemical Formula 56>
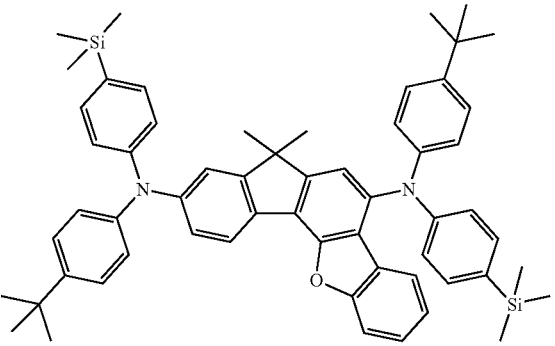
<Chemical Formula 57>
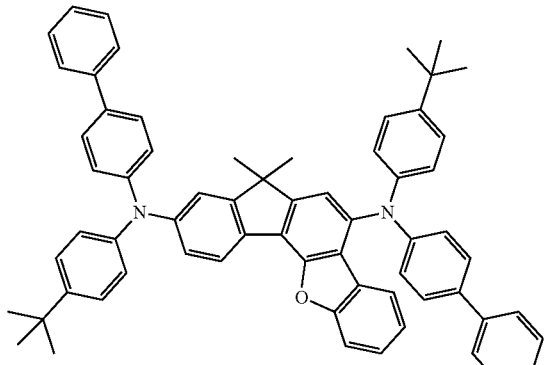

<Chemical Formula 58>
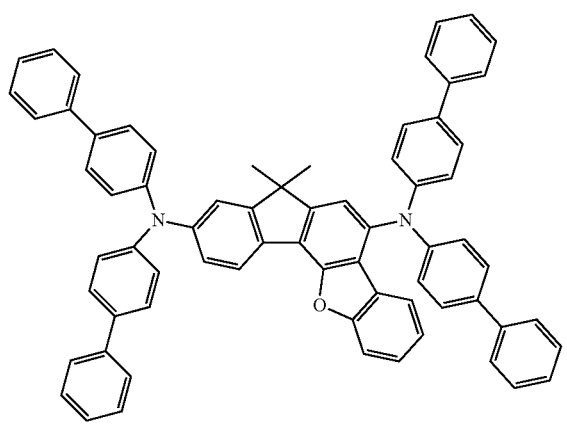
<Chemiical Formula 59>
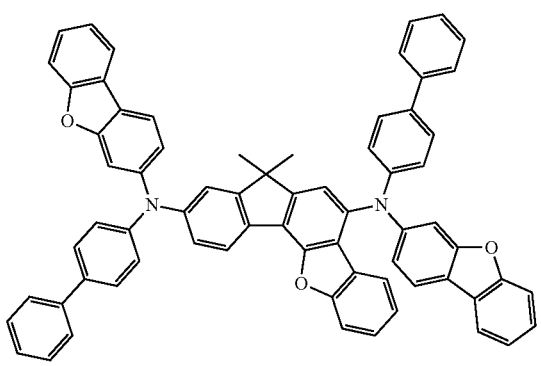
<Chemical Formula 60>
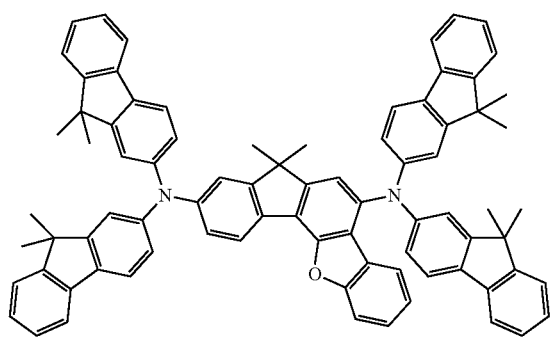
<Chemical Formula 61>
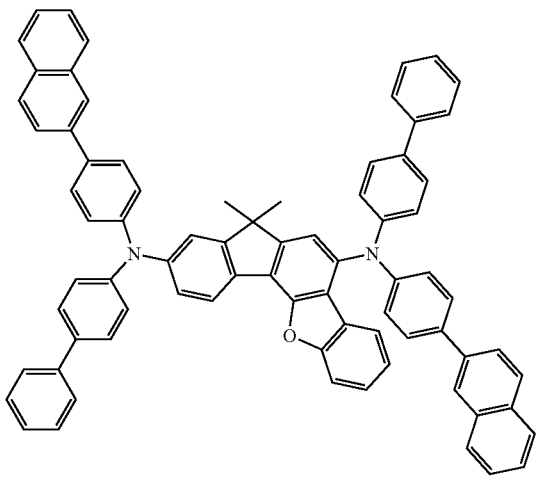
<Chemical Formula 62>
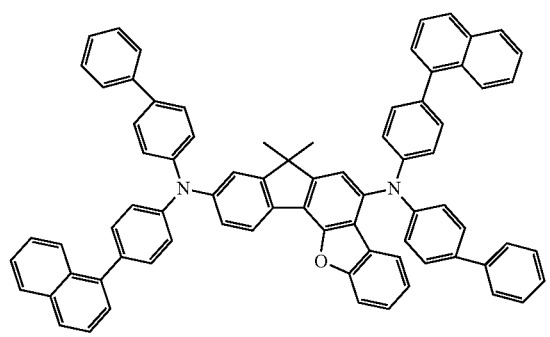
<Chemical Formula 63>
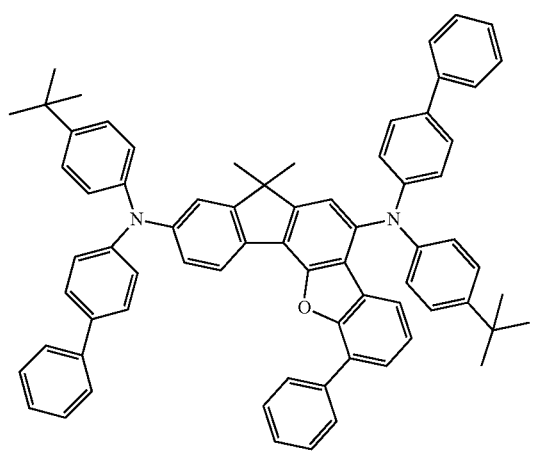

-continued
<Chemical Formula 64>
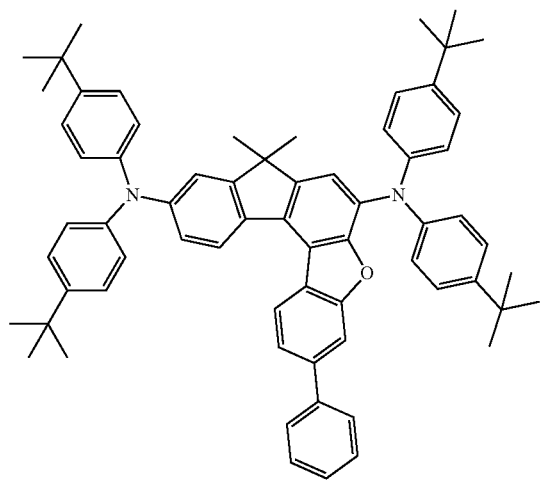
<Chemical Formula 65>
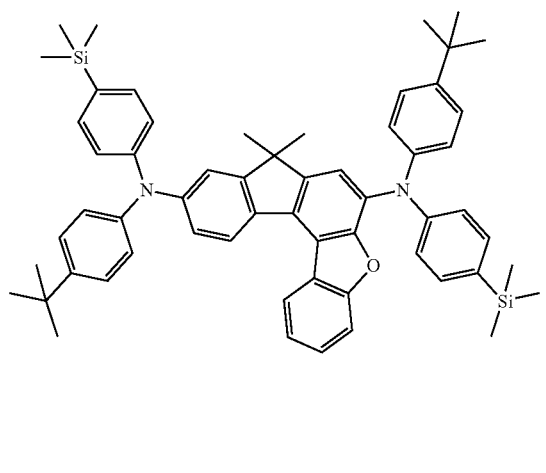
<Chemical Formula 66>
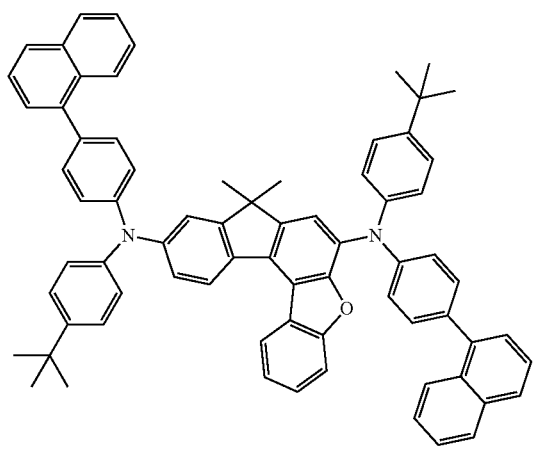
-continued
<Chemical Formula 67>
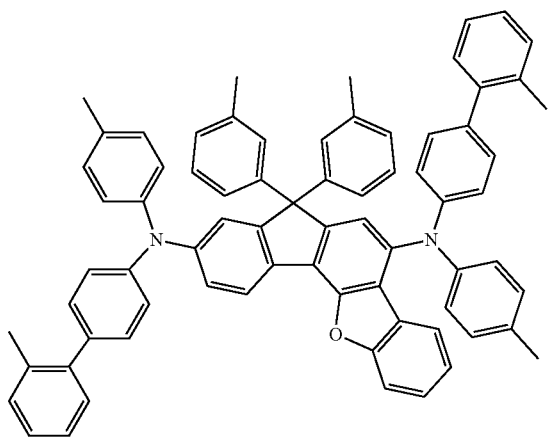
<Chemical Formula 68>
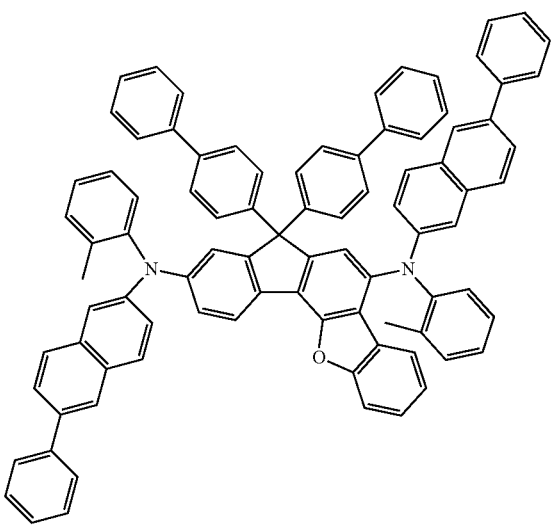
<Chemical Formula 69>
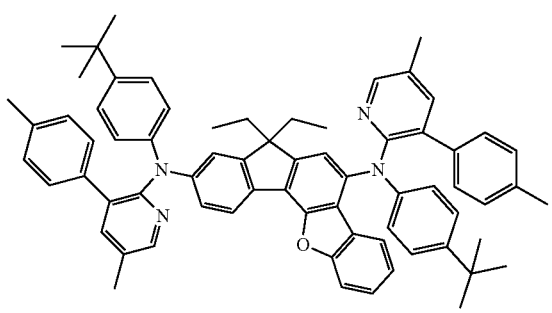

<Chemical Formula 70>
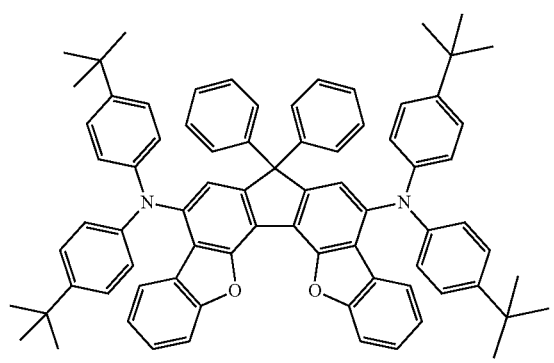
<Chemical Formula 71>
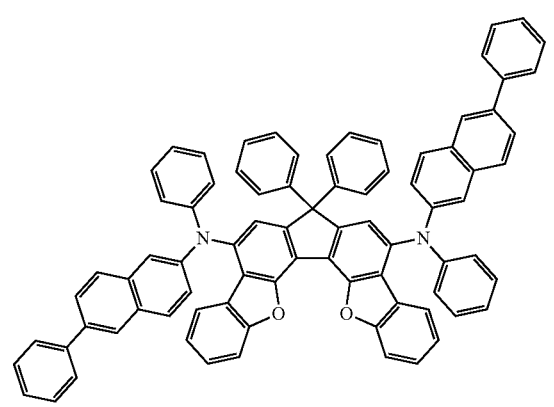
<Chemical Formula 72>

<Chemical Formula 73>
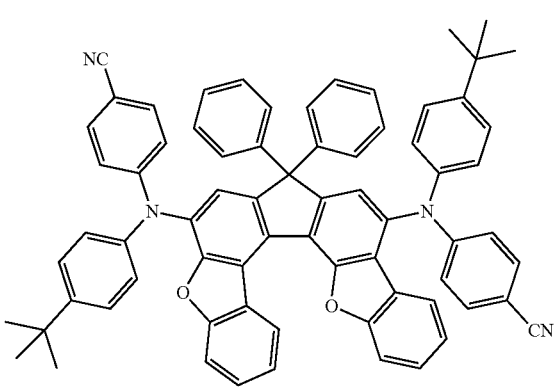
<Chemical Formula 74>
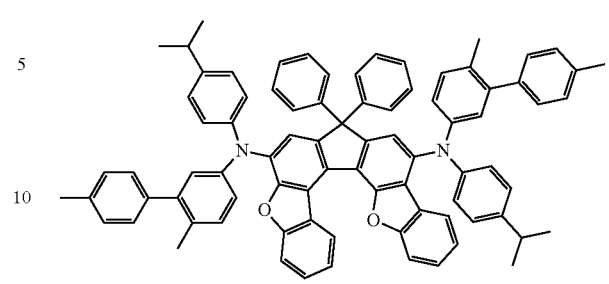
<Chemical Formula 75>
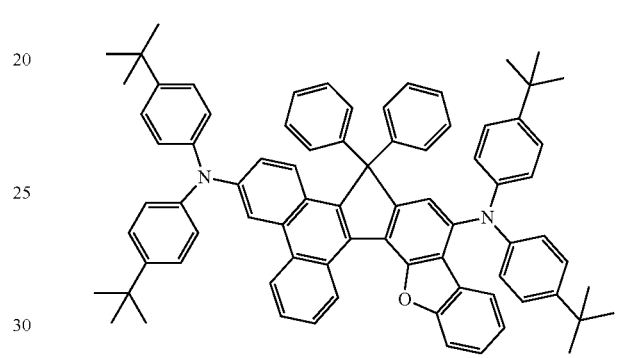
<Chemical Formula 76>
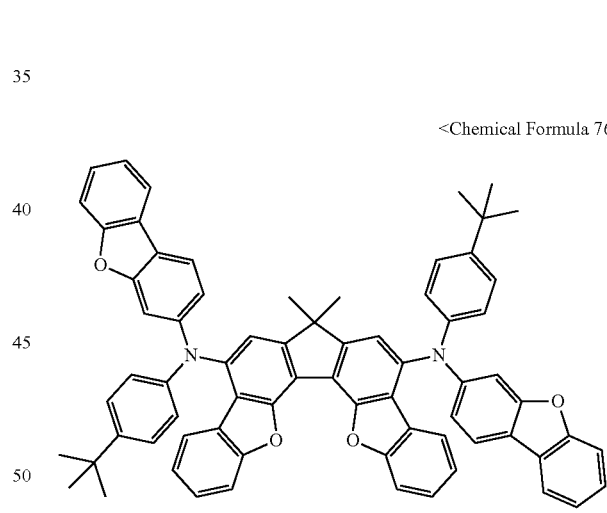
<Chemical Formula 77>
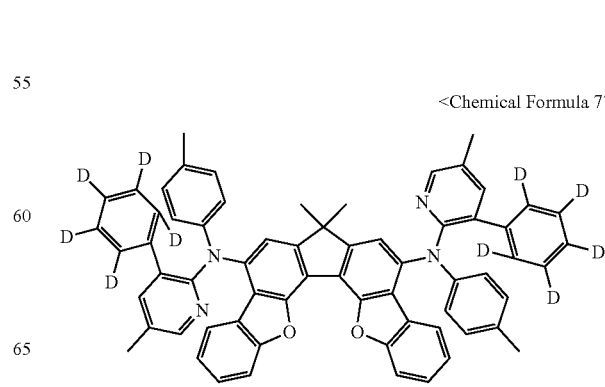

<Chemical Formula 78>
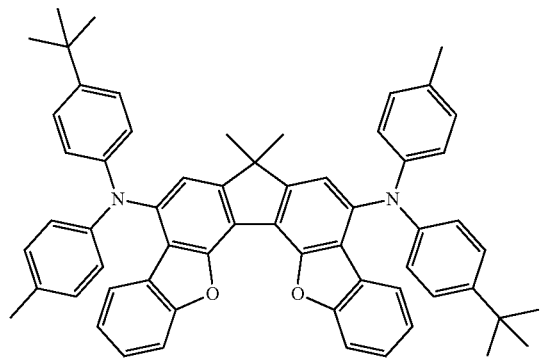
<Chemical Formula 79>
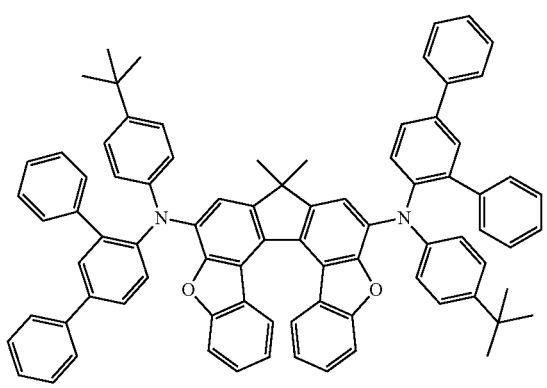
<Chemical Formula 80>
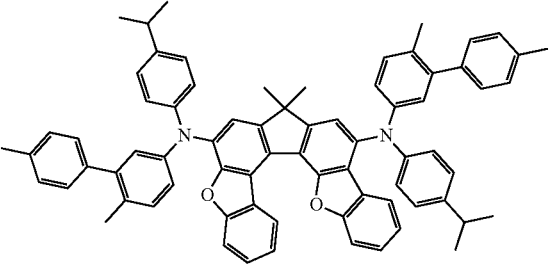
<Chemical Formula 81>
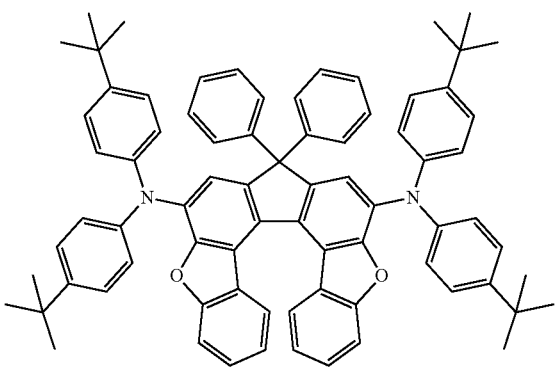
<Chemical Formula 82>
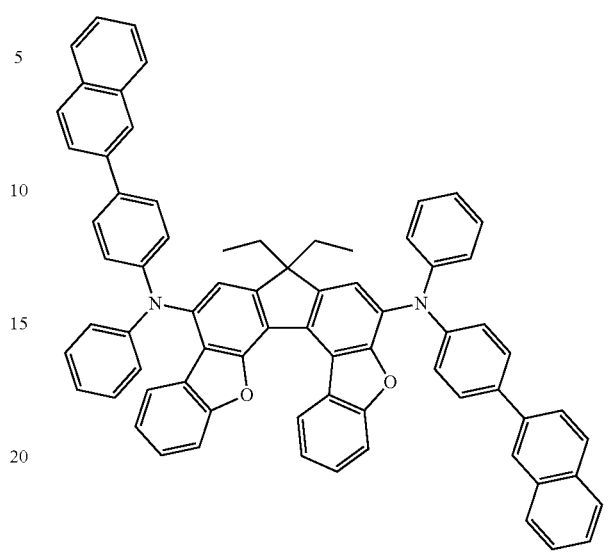
<Chemical Formula 83>
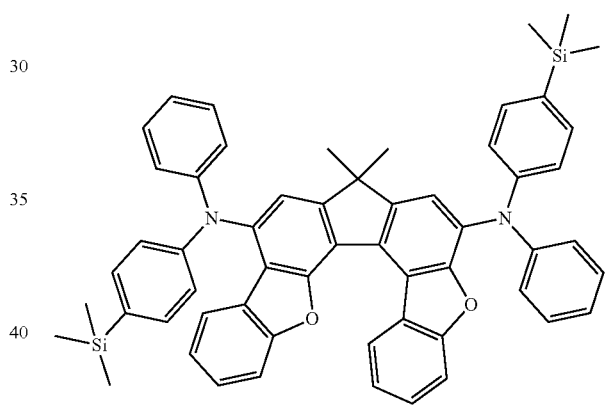
<Chemical Formula 84>
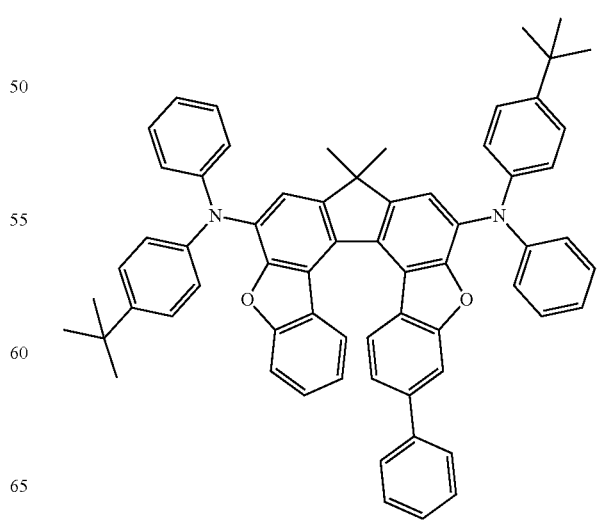

<Chemical Formula 85>
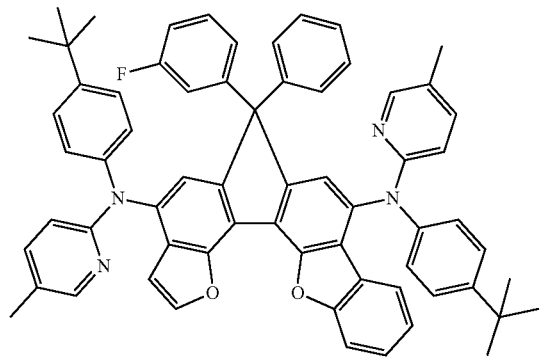
<Chemical Formula 86>
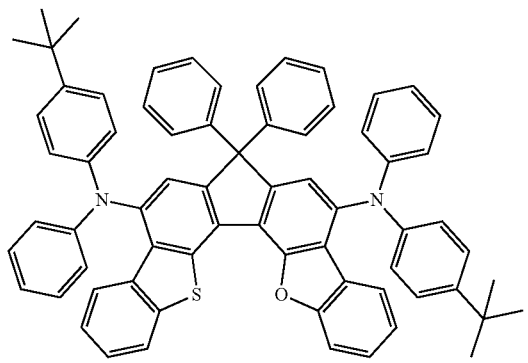
<Chemical Formula 87>
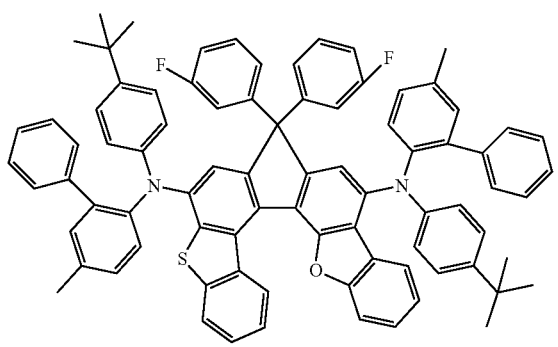
<Chemical Formula 88>
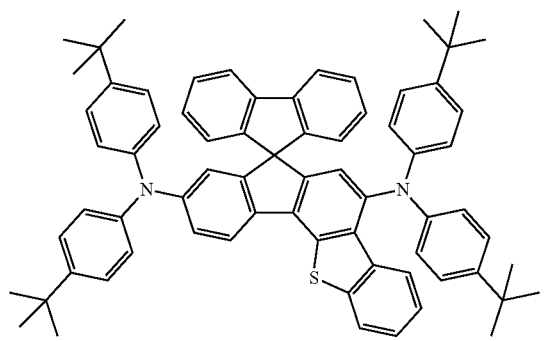
<Chemical Formula 89>
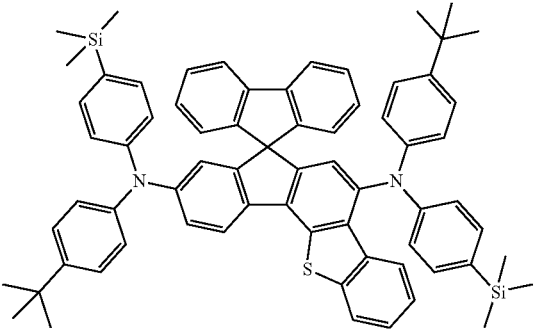
<Chemical Formula 90>
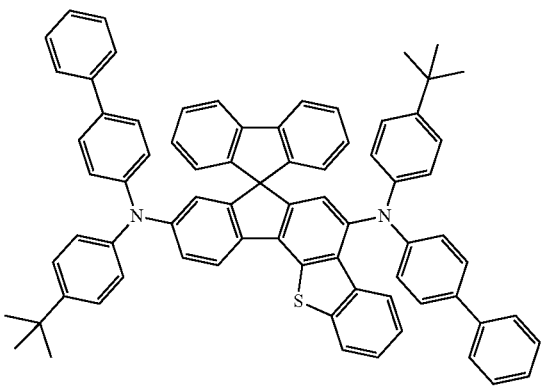
<Chemical Formula 91>
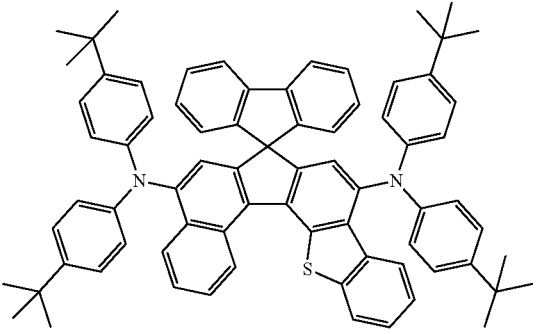
<Chemical Formula 92>
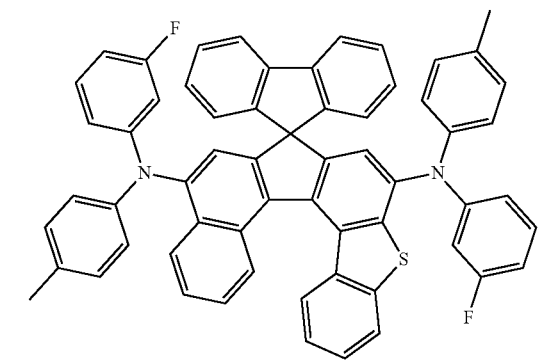

<Chemical Formula 93>
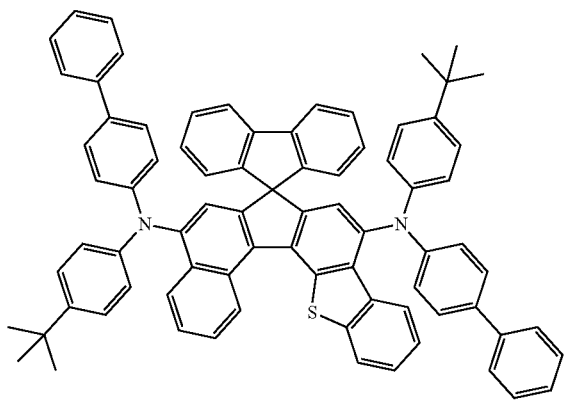
<Chemical Formula 94>
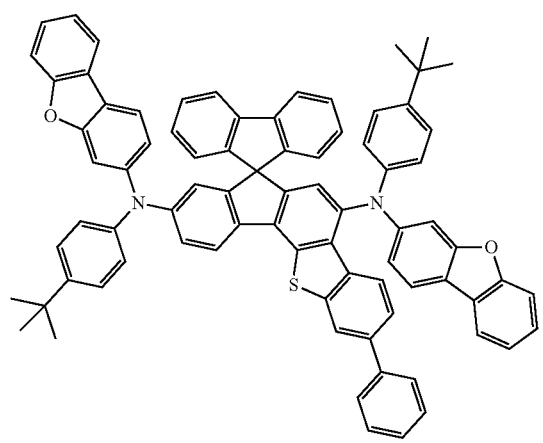
<Chemical Formula 95>
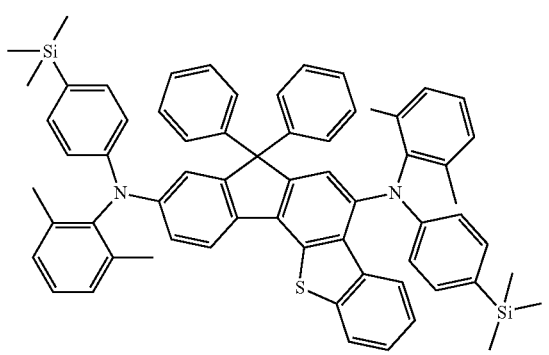
<Chemical Formula 96>
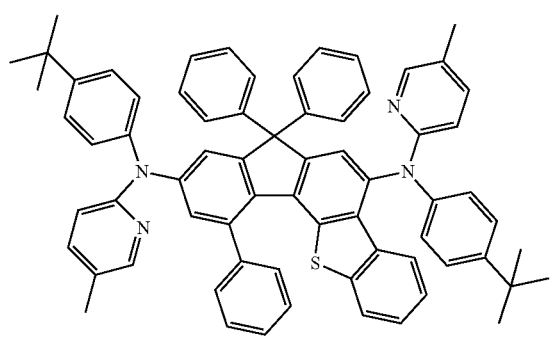
<Chemical Formula 97>
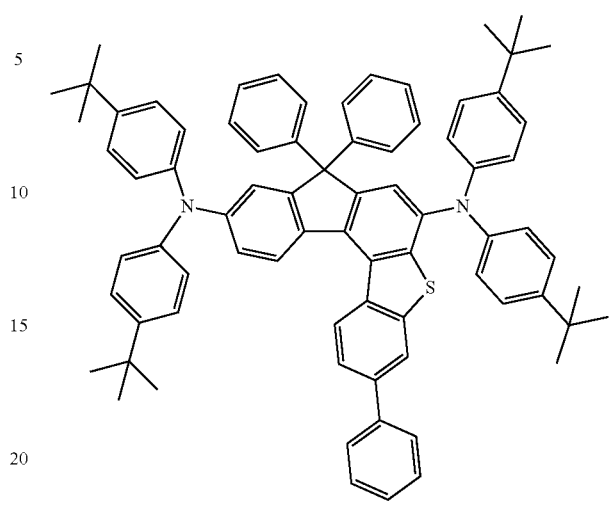
<Chemical Formula 98>
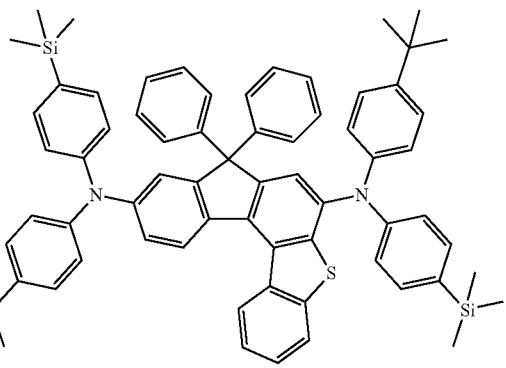
<Chemical Formula 99>
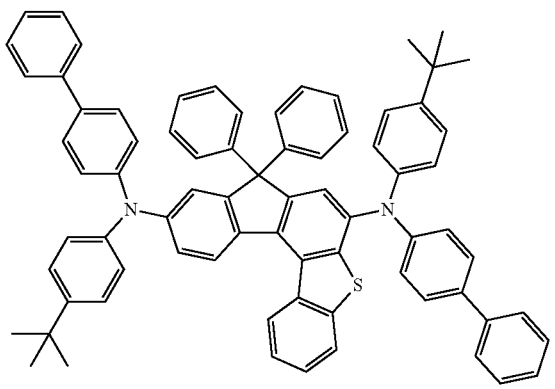

<Chemical Formula 100>
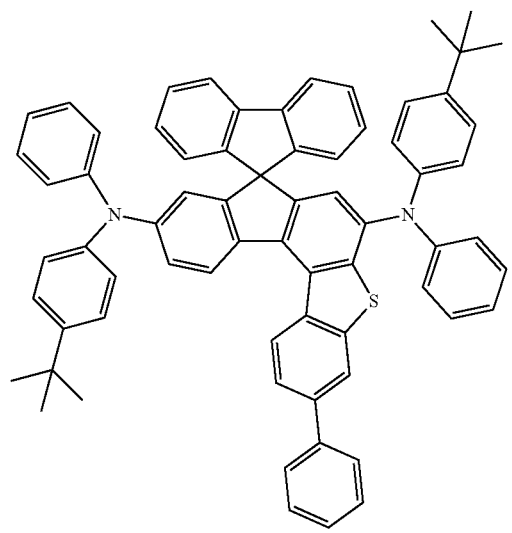
<Chemical Formula 101>
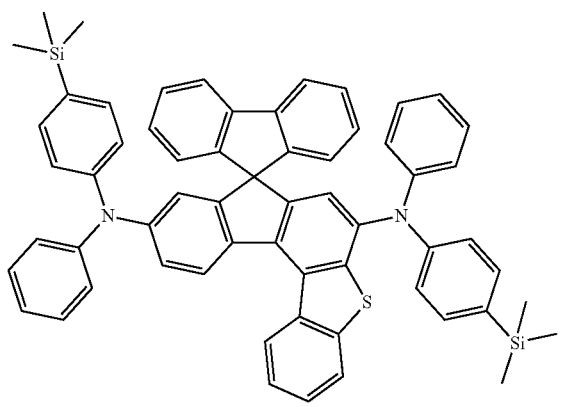
<Chemical Formula 102>
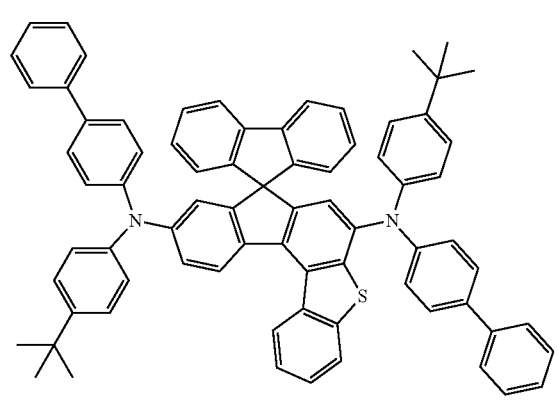
<Chemical Formula 103>
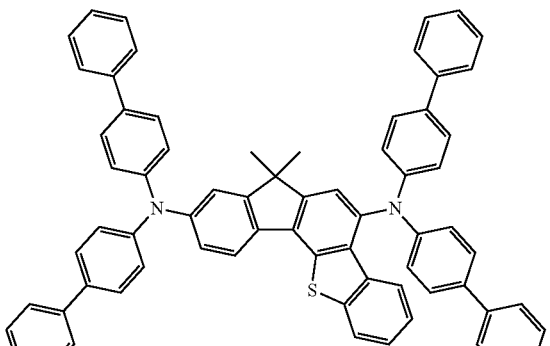
<Chemical Formula 104>
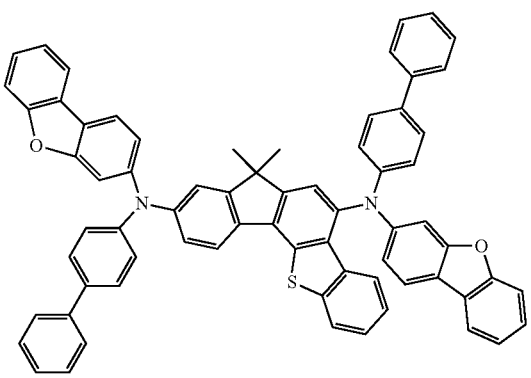
<Chemical Formula 105>
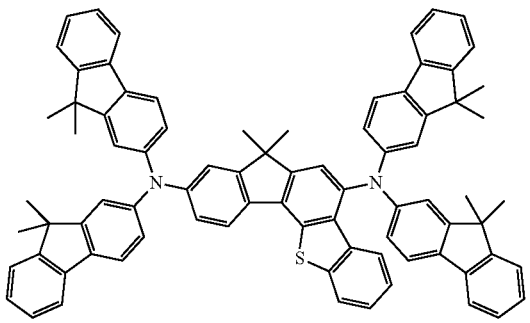
<Chemical Formula 106>
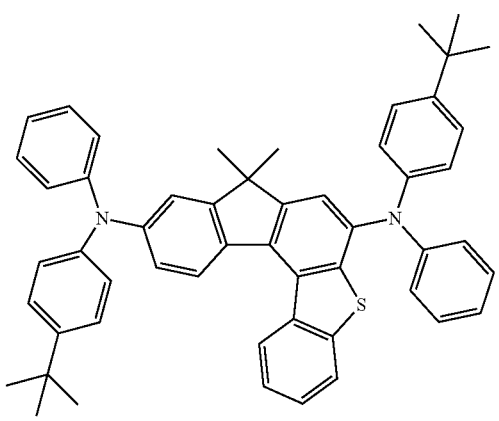

<Chemical Formula 107>
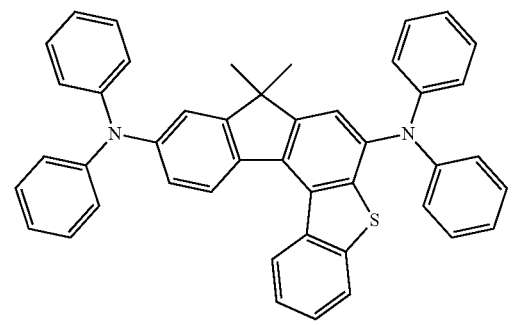
<Chemical Formula 108>
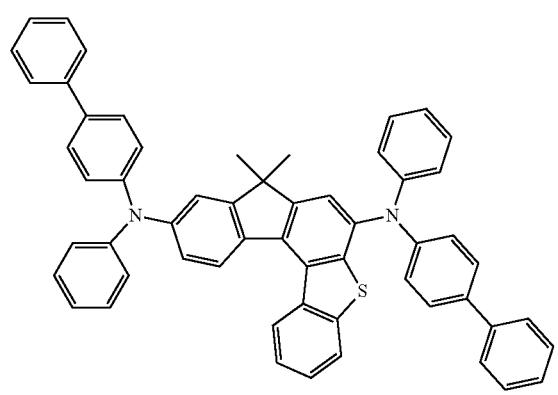
<Chemical Formula 109>
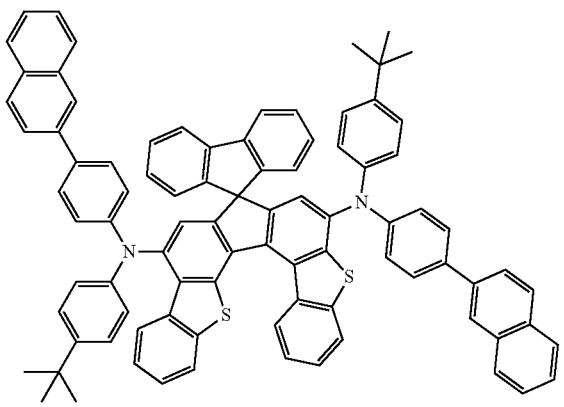
<Chemical Formula 110>
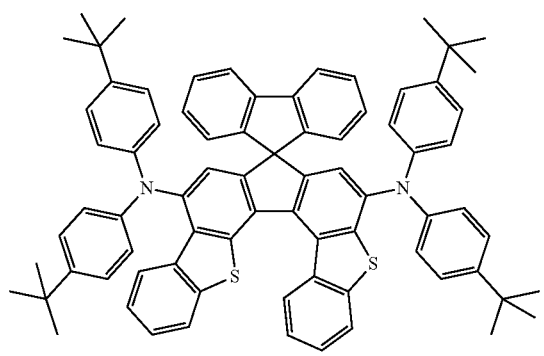
<Chemical Formula 111>
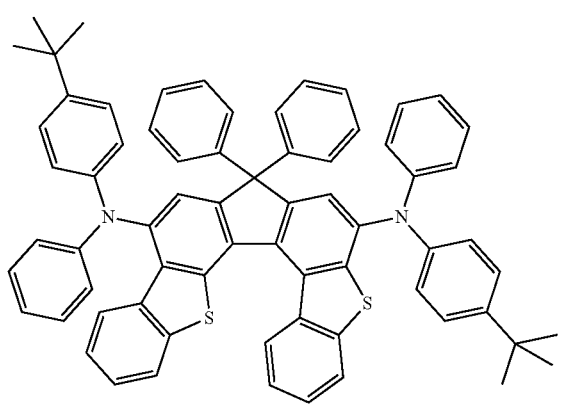
<Chemical Formula 112>
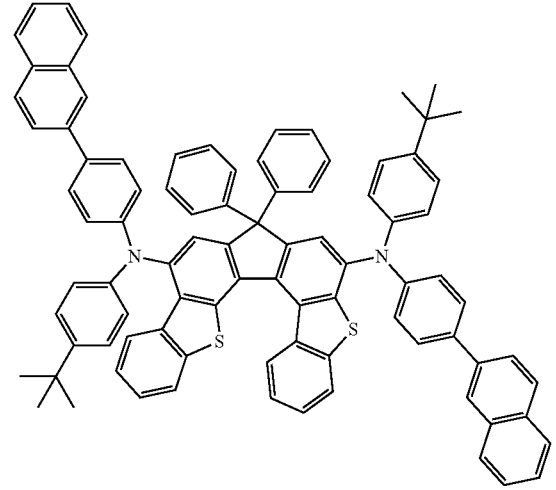
<Chemical Formula 113>
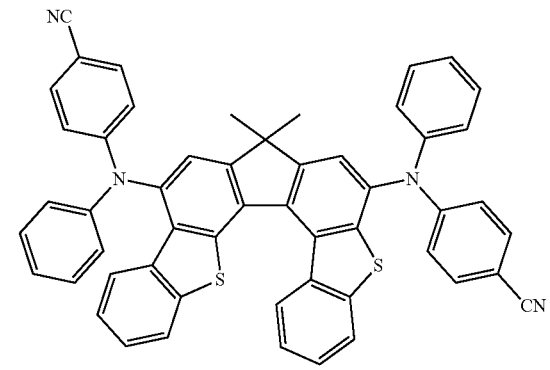

<Chemical Formula 114>
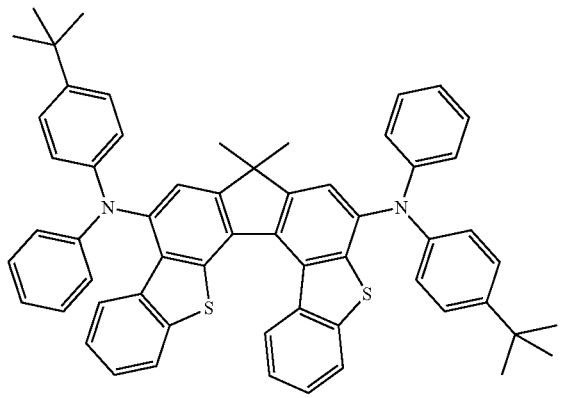
<Chemical Formula 115>
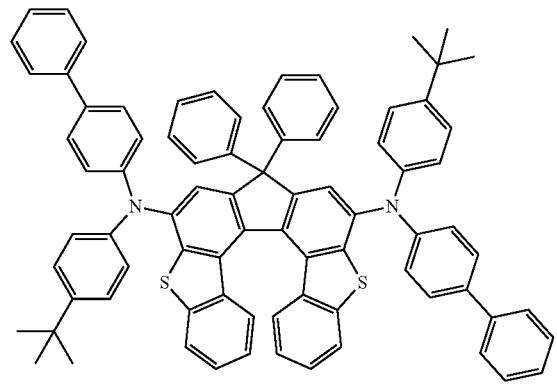
<Chemical Formula 116>
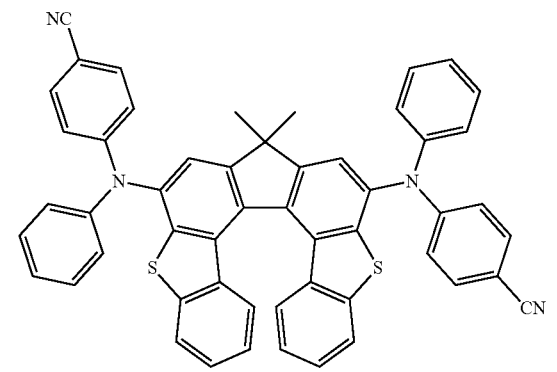
<Chemical Formula 117>
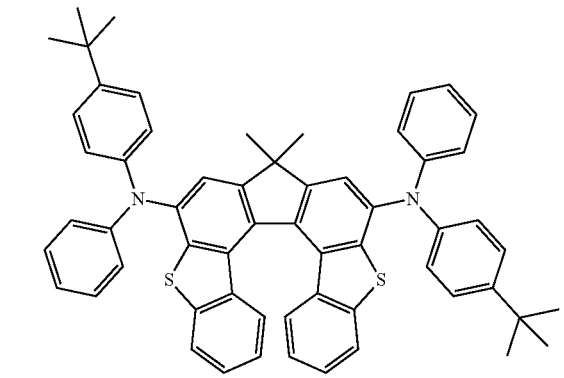
<Chemical Formula 118>
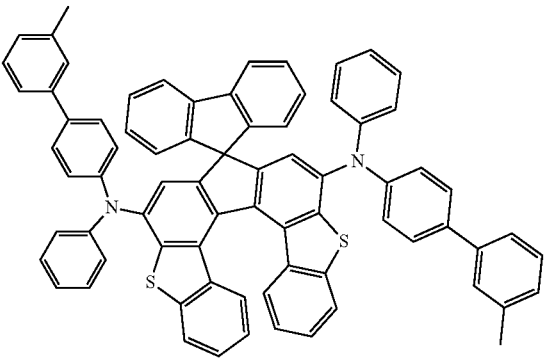
<Chemical Formula 119>
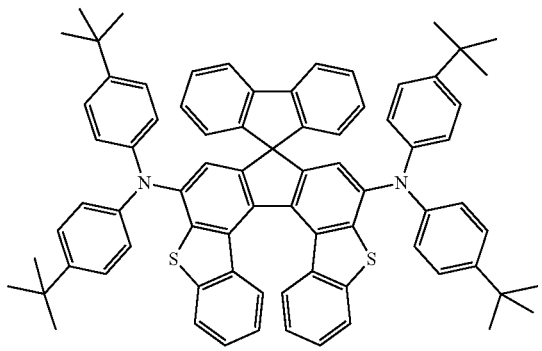
<Chemical Formula 120>
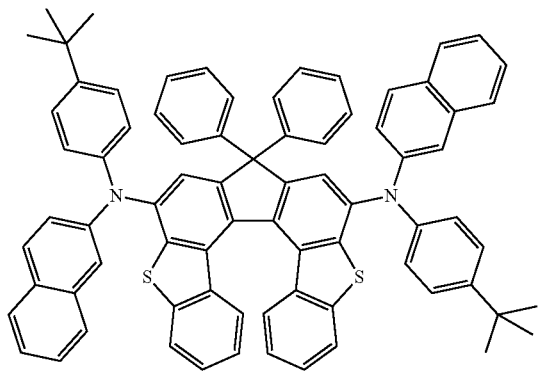
<Chemical Formula 121>
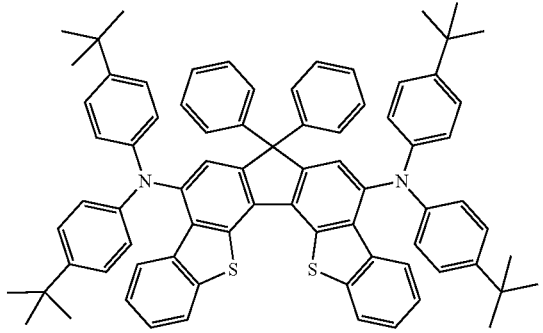

<Chemical Formula 122>
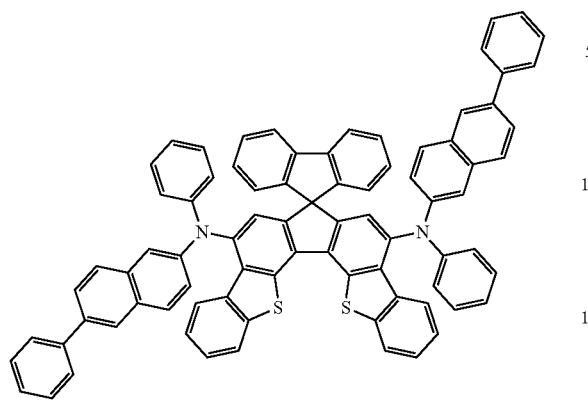
<Chemical Formula 123>
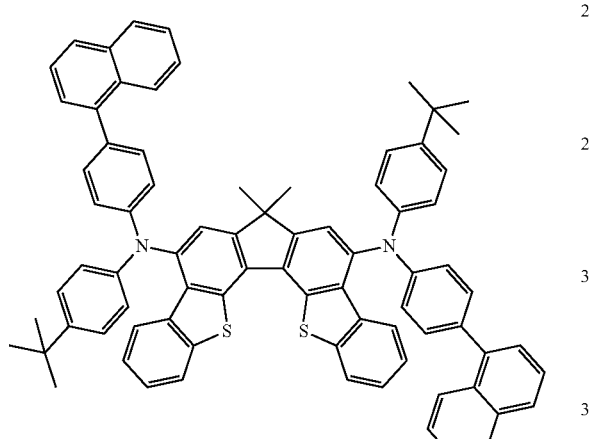
<Chemical Formula 124>
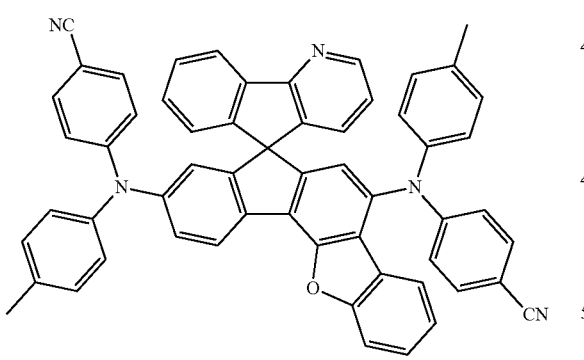
<Chemical Formula 125>
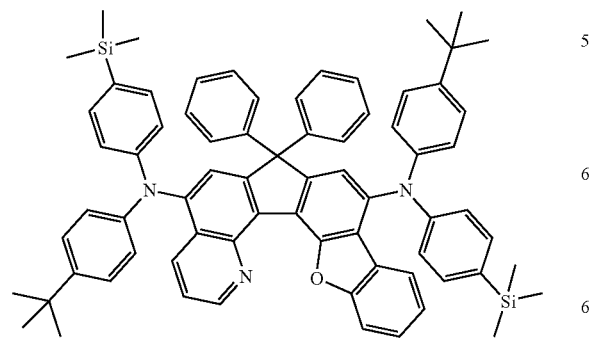
<Chemical Formula 126>
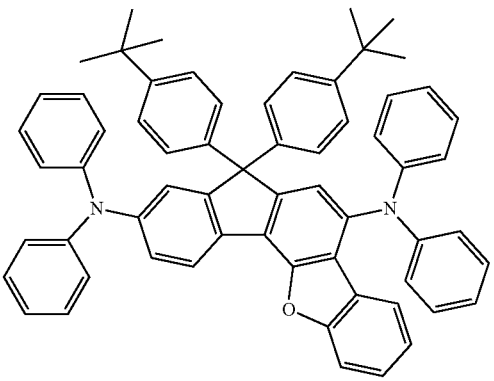
<Chemical Formu;a 127>
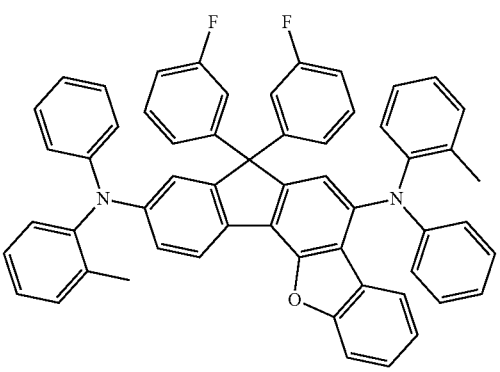
<Chemical Formula 128>
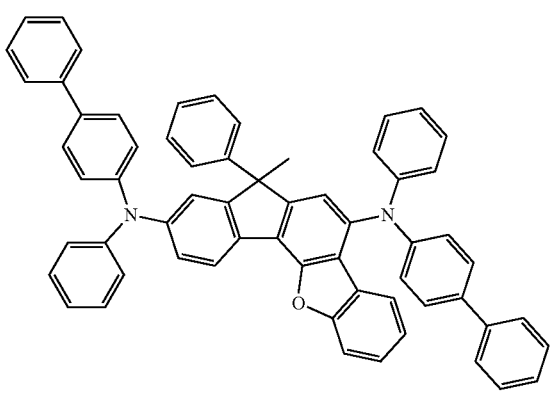
<Chemical Formula 129>
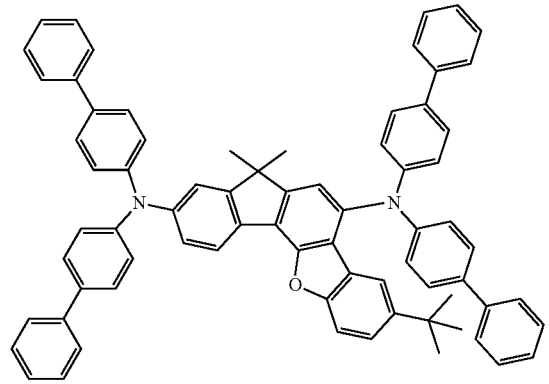

<Chemical Formula 130>
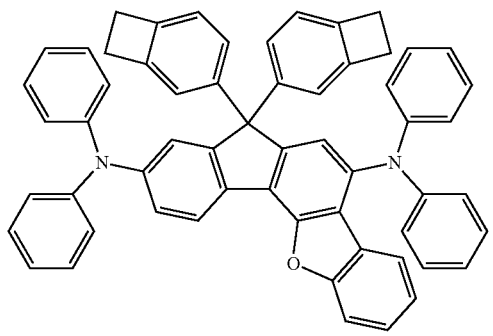
<Chemical Formula 131>
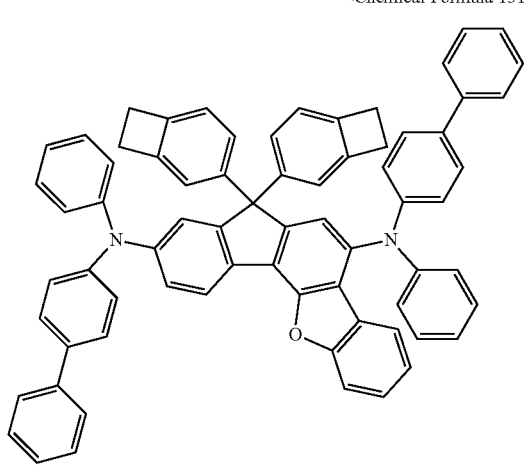
<Chemical Formula 132>
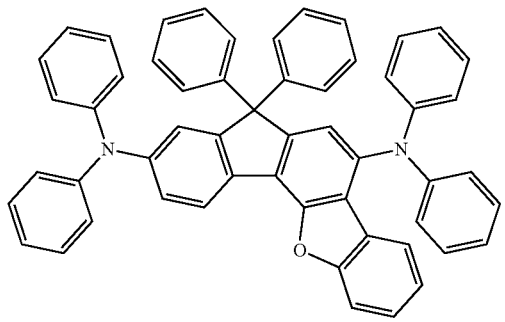
<Chemical Formula 133>
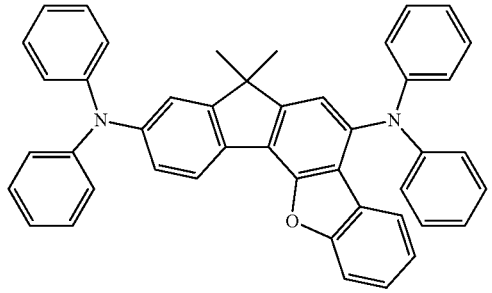
<Chemical Formula 134>
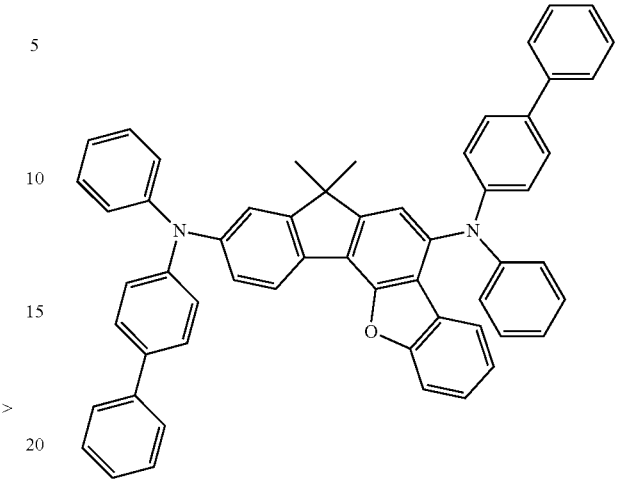
<Chemical Formula 135>
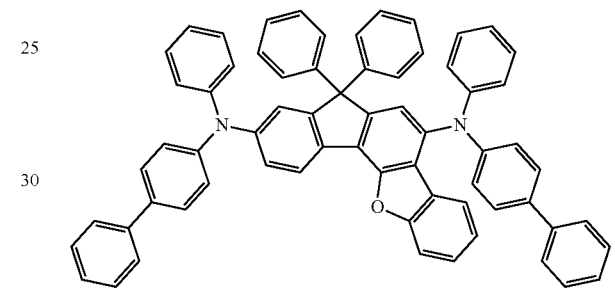
<Chemical Formula 136>
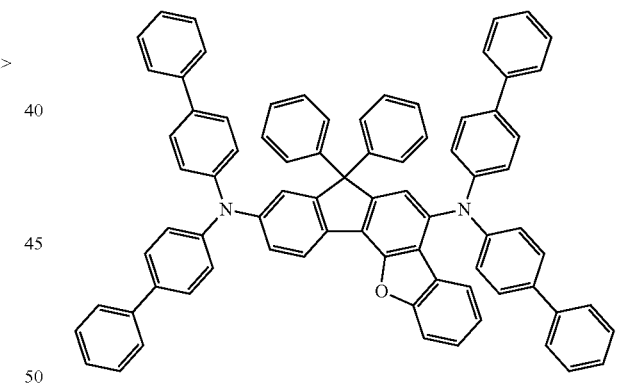
<Chemical Formula 137>
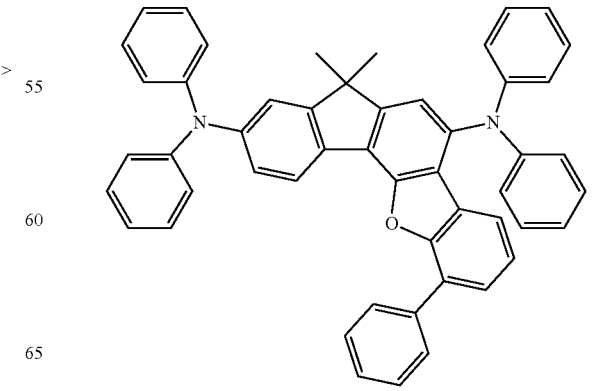

<Chemical Formula 138>
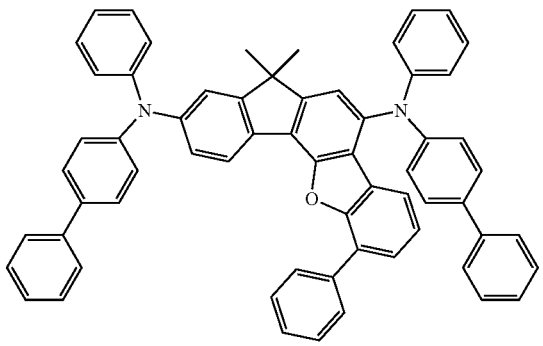
<Chemical Formula 139>
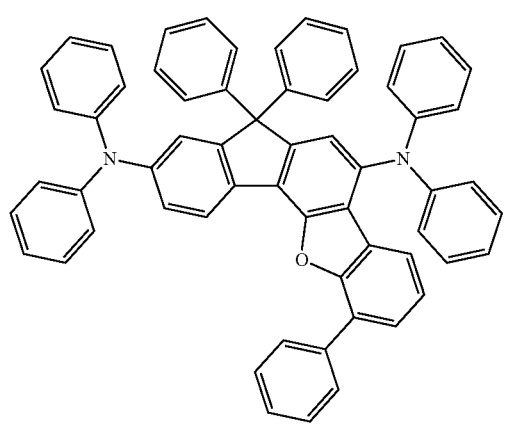
<Chemical Formula 140>
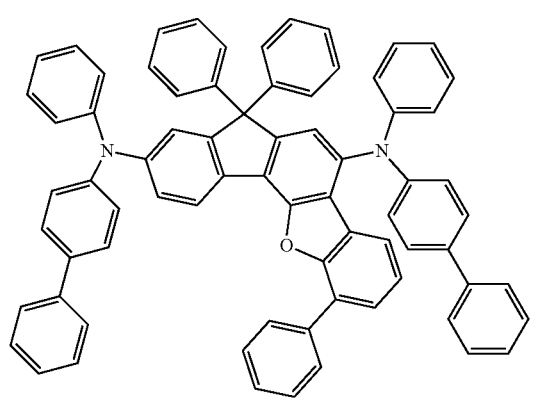
<Chemical Formula 141>
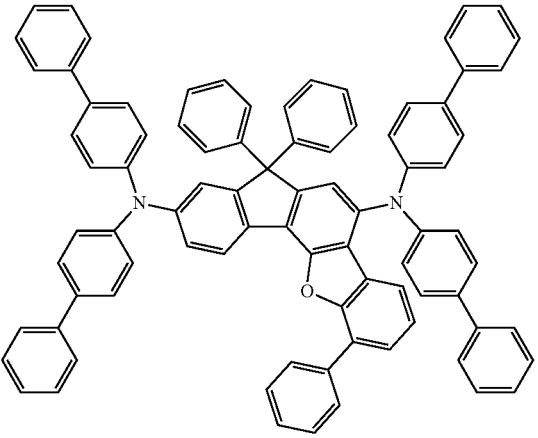
<Chemical Formula 142>
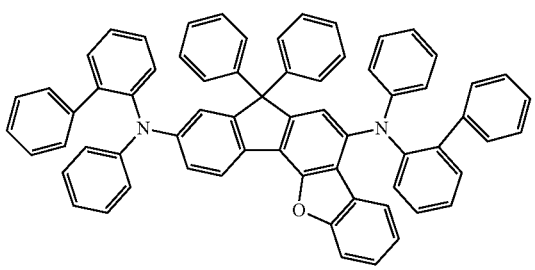
<Chemical Formula 143>
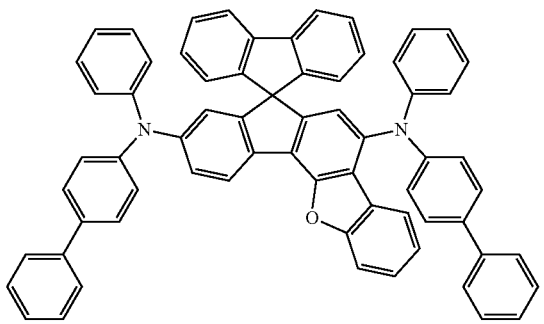
<Chemical Formula 144>
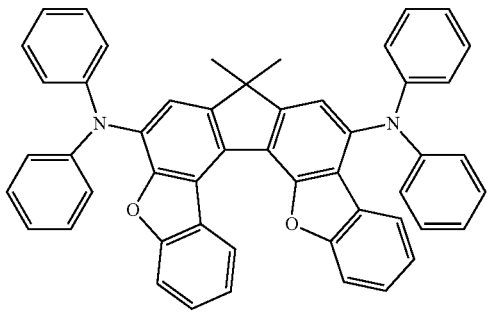
Moreover, one or two of $A_1$, $A_2$, E, and F in Chemical Formulas A and B may be independently a substituted or unsubstituted heteroaromatic ring of 2 to 40 carbon atoms. In a particular embodiment, one of A₁, A₂, E, and F in Chemical Formulas A and B may be a substituted or unsubstituted heteroaromatic ring of 2 to 40 carbon atoms.

Meanwhile, the amine compound represented by Chemical Formula A or B may be used in either the hole injecting layer or the hole transport layer only or both of the hole injecting layer or the hole transport layer.

When the amine compound represented by Chemical Formula A or B is used in only either of the hole injecting layer and the hole transport layer, the other layer in which the amine compound is not used may employ a typically available compound.

When the amine compound represented by Chemical Formula A or B is used in the hole transport layer only, an electron donating molecule having a low ionization potential is used as a material in a hole transport layer. Predominantly, diamine, triamine or tetraamine derivatives having a triphenylamine skeleton are employed, as exemplified by N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

On the other hand, when the amine compound represented by Chemical Formula A or B is used in only a hole injecting layer (HIL), which is provided beneath the hole transport layer, no particular limitations are imposed on the hole injecting layer material, as long as it is one that is typically used in the art. Examples include CuPc (copperphthalocyanine), and the starburst amines TCTA (4,4',4"-tri(N-carbazolyl)triphenyl-amine), and m-MTDATA (4,4',4"-tris-(3-methylphenylphenyl amino)triphenylamine).

In addition, the light-emitting layer in the organic light-emitting diode according to the present invention may comprise a host and a dopant.

In this regard, the dopant may include at least one of the amine compound represented by the following Chemical Formula D1 or D2. Furthermore, various well-known dopant materials may be used in combination in the organic light-emitting diode.

[Chemical Formula D1]

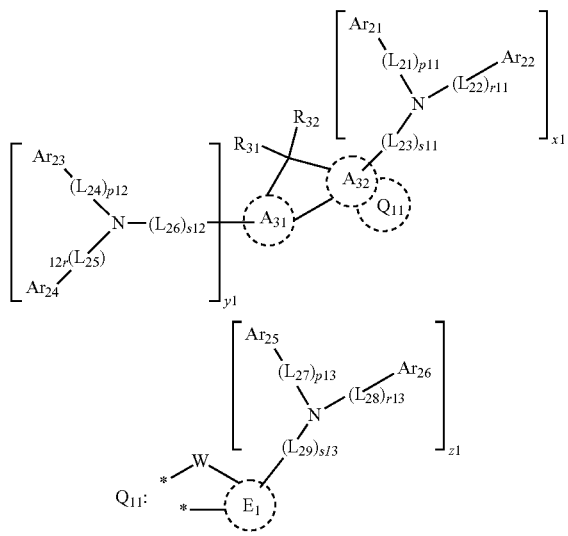

[Chemical Formula D2]

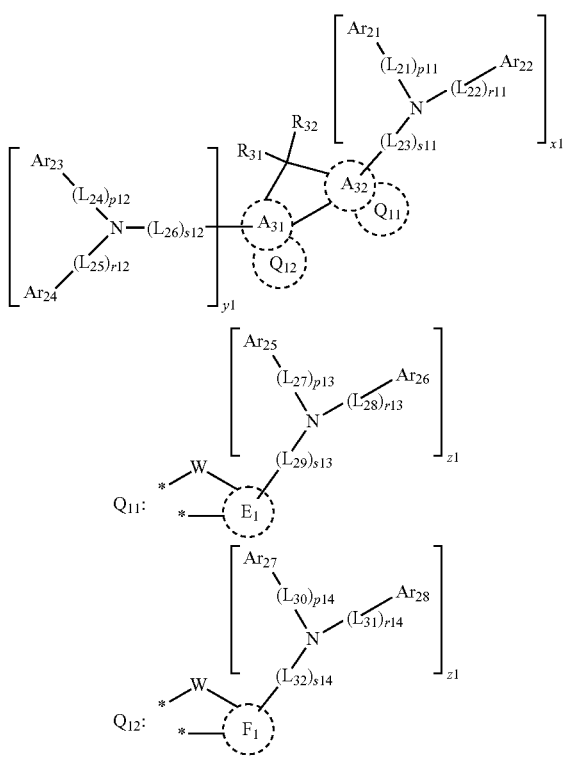

wherein,

A₃₁, A₃₂, E₁, and F₁, which may be the same or different, are each independently a substituted or unsubstituted aromatic hydrocarbon ring of 6 to 50 carbon atoms, or a substituted or unsubstituted heteroaromatic ring of 2 to 40 carbon atoms;

wherein two adjacent carbon atoms within the aromatic ring of A₃₁ and two adjacent carbon atoms within the aromatic ring of A₃₂ form a 5-membered ring with a carbon atom connected to both substituents R₃₁ and R₃₂, thus establishing a fused ring structure;

linkers L₂₁ to L₃₂, which may be the same or different, are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is selected from among N—R₃₃, CR₃₄R₃₅, SiR₃₆R₃₇, GeR₃₈R₃₉, O, S, and Se;

R₃₁ to R₃₉ and Ar₂₁ to Ar₂₈, which may be the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to 30 carbon atoms, a substituted or unsubstituted aryl germanium of 1 to 30 carbon atoms, a cyano, a nitro, and a halogen, wherein $R_{31}$ and $R_{32}$ may be connected to each other to form a mono- or polycyclic aliphatic or aromatic ring which may bear at least one heteroatom selected from among N, O, P, Si, S, Ge, Se, and Te as a ring member;

p11 to p14, r11 to r14, and s11 to s14 are each independently an integer of 1 to 3, under which when any of them is 2 or greater, the corresponding linkers $L_{21}$ to $L_{32}$ may be the same or different, x1 is an integer of 1 or 2, and y1 and z1, which may be the same or different, are each independently an integer of 0 to 3, a connection may be made between $Ar_{21}$ and $Ar_{22}$, between $Ar_{23}$ and $Ar_{24}$, between $Ar_{25}$ and $Ar_{26}$, and between $Ar_{27}$ and $Ar_{28}$ to form respective rings;

two adjacent carbon atoms within the $A_{32}$ ring in Chemical Formula D1 are linked to respective * of structure formula $Q_{11}$ to form a fused ring, and two adjacent carbon atoms within the $A_{31}$ ring in Chemical Formula D2 are linked to respective * of structure formula $Q_{12}$ to form a fused ring and two adjacent carbon atoms within the $A_{32}$ ring in Chemical Formula D2 are linked to respective * of structure formula $Q_{11}$ to form a fused ring.

According to an embodiment of the present disclosure, $A_{31}$, $A_{32}$, $E_1$, and $F_1$ in the compounds represented by Chemical Formula D1 and Chemical Formula D2, which may be the same or different, may each be independently a substituted or unsubstituted aromatic hydrocarbon ring of 6 to 50 carbon atoms.

When $A_{31}$, $A_{32}$, $E_1$, and $F_1$ in [Chemical Formula D1] or [Chemical Formula D2] each correspond to a substituted or unsubstituted aromatic hydrocarbon ring of 6 to 50 carbon atoms as mentioned above, the substituted or unsubstituted aromatic hydrocarbon rings of 6 to 50 carbon atoms may be the same or different and are each independently one selected from among [Structural Formula 10] to [Structural Formula 21]:

[Structural Formula 10]

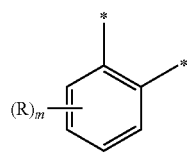

[Structural Formula 11]

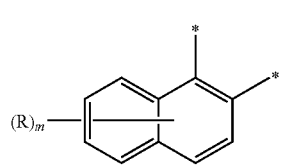

[Structural Formula 12]

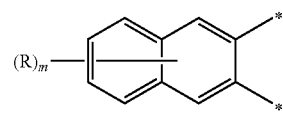

[Structural Formula 13]

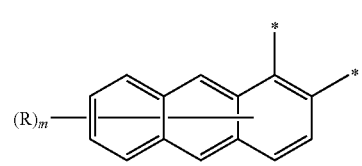

[Structural Formula 14]

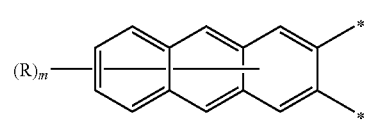

[Structural Formula 15]

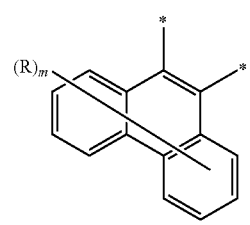

[Structural Formula 16]

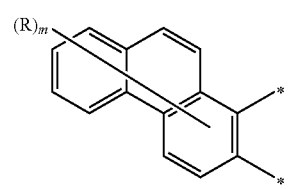

[Structural Formula 17]

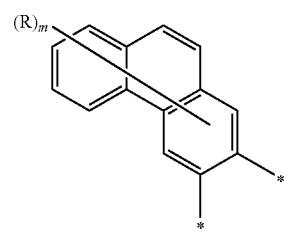

[Structural Formula 18]

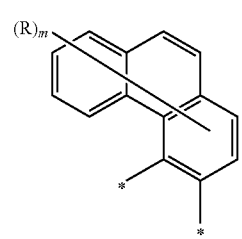

[Structural Formula 19]

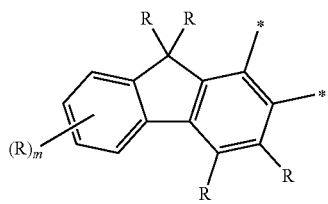

[Structural Formula 20]

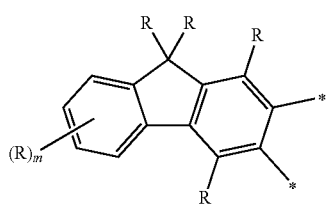

[Structural Formula 21]

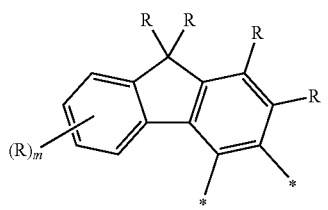

wherein,

"-*" denotes a bonding site participating in forming a 5-membered ring bearing the carbon atom connected to both substituents $R_{31}$ and $R_{32}$ as a ring member or in forming a 5-membered ring bearing W of structural formula $Q_{11}$ or $Q_{12}$ as a ring member;

when the aromatic hydrocarbon ring corresponds to the $A_{31}$ ring or the $A_{32}$ ring and is connected to structure formula $Q_{11}$ or $Q_{12}$, two adjacent carbon atoms within the ring are linked to * of structural formula $Q_{11}$ or $Q_{12}$ to form a fused ring;

R is as defined for $R_{31}$ and $R_{32}$ above; and m is an integer of 1 to 8 wherein when m is 2 or greater or when R exists as multiple radicals, the resulting R's may be the same or different.

In an embodiment according to the present disclosure, the linkers $L_{21}$ to $L_{32}$ in Chemical Formulas D1 and D2 may be the same or different and may each be independently a single bond or any one selected from the following [Structural Chemical 22] to [Structural Chemical 30], wherein p11 to p14, r11 to r14, and s11 to s14 may each be 1 or 2 and x1 may be 1:

[Structural Formula 22]

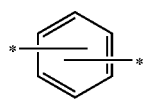

[Structural Formula 23]

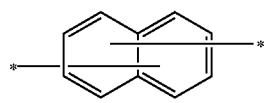

[Structural Formula 24]

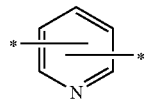

[Structural Formula 25]

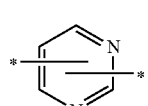

[Structural Formula 26]

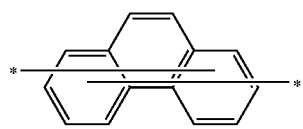

[Structural Formula 27]

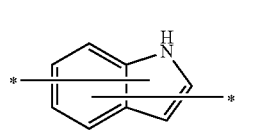

[Structural Formula 28]

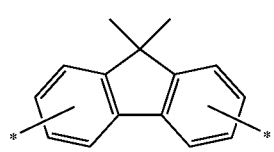

[Structural Formula 29]

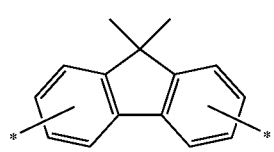

[Structural Formula 30]

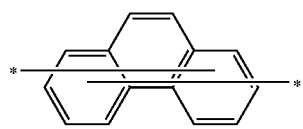

In the linkers, each of unsubstituted carbon atoms of the aromatic ring moiety may be bound with a hydrogen atom or a deuterium atom.

According to a more particular embodiment of the present disclosure, in Chemical Formulas D1 and D2, x and y may each be 1 and z may be 0 (zero).

The amine compound represented by Chemical Formula D1 or D2 may be any one selected from the following Compound 401 to Compound 639, but is not limited thereto:

<Compound 401>
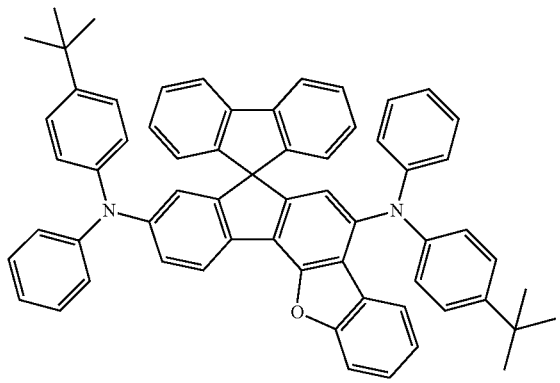
<Compound 402>
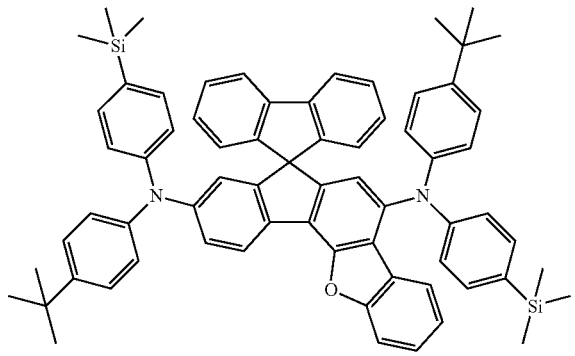
<Compound 403>
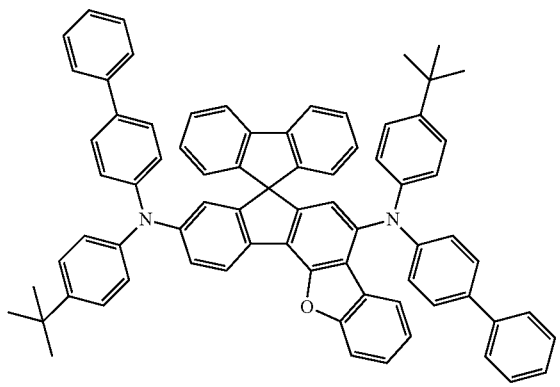
<Compound 404>
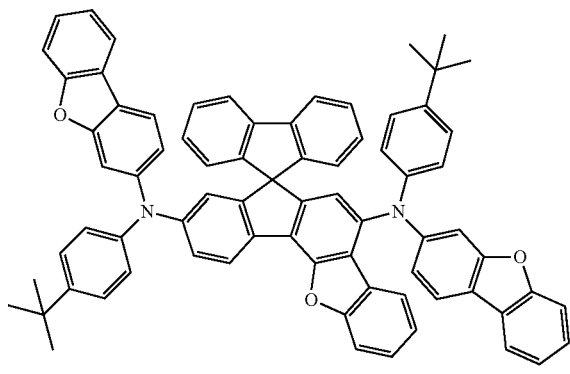
<Compound 405>
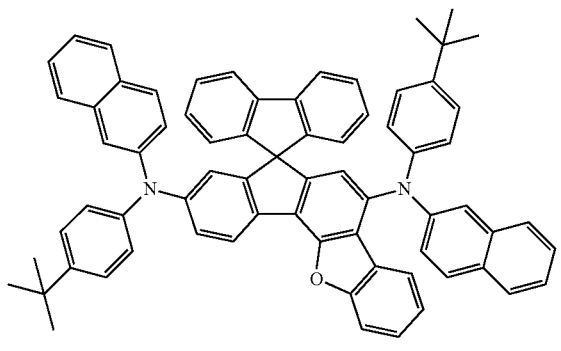
<Compound 406>
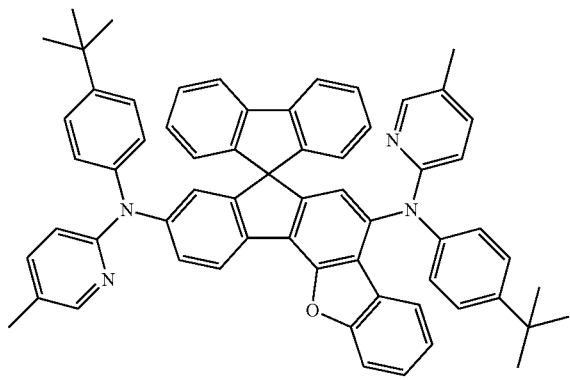
<Compound 407>
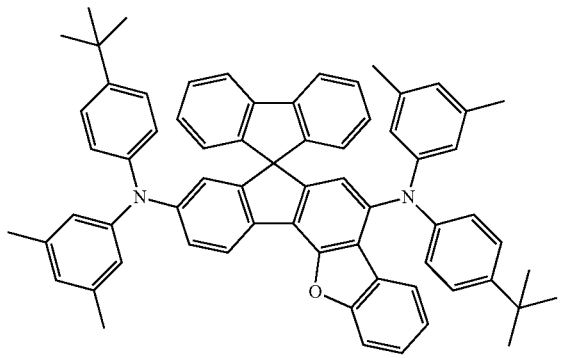
<Compound 408>
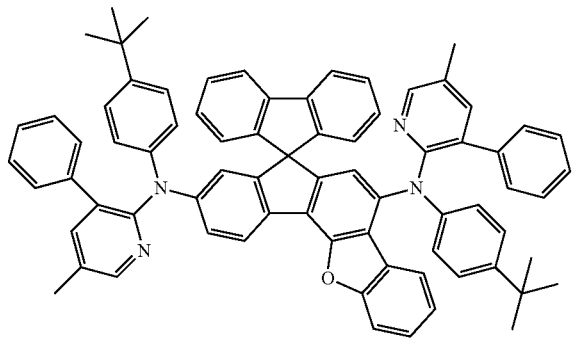

-continued
<Compound 409>
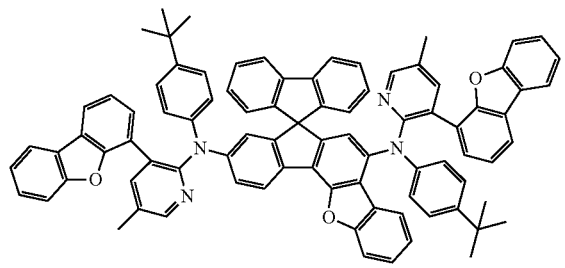
<Compound 410>
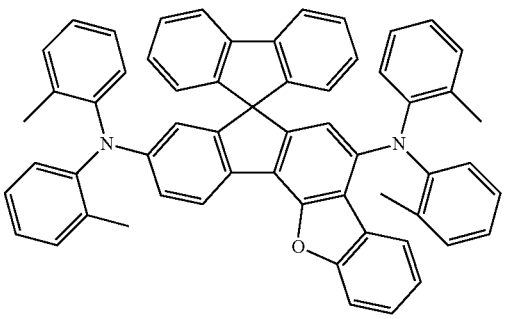
<Compound 411>
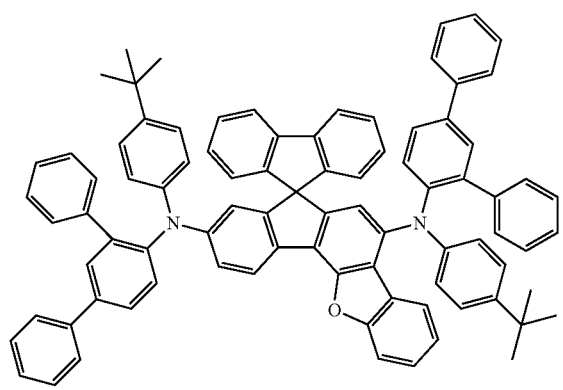
<Compound 412>
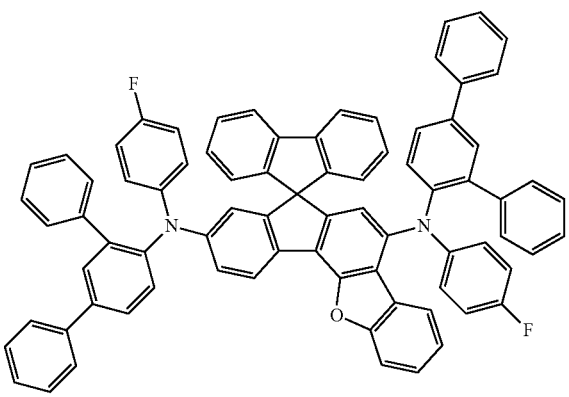
<Compound 413>
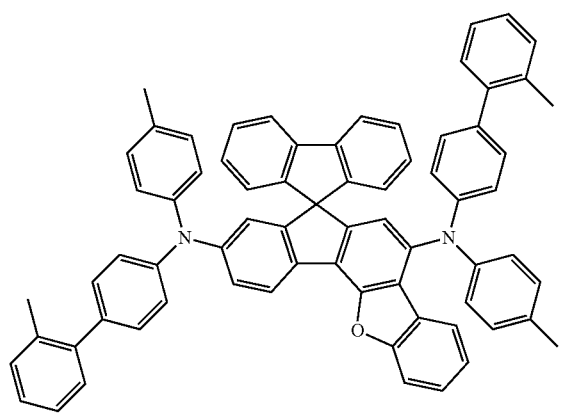
<Compound 414>
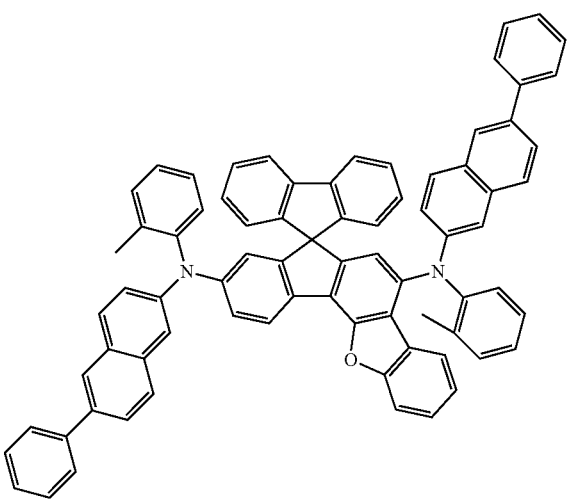

-continued
<Compound 415>
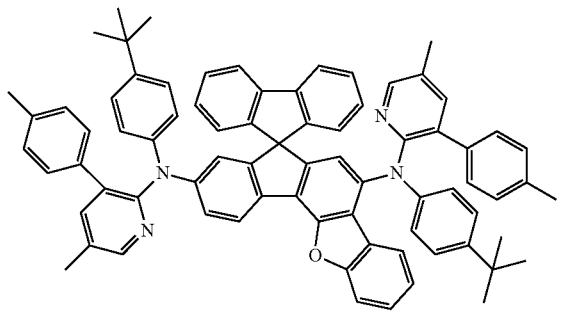
<Compound 416>
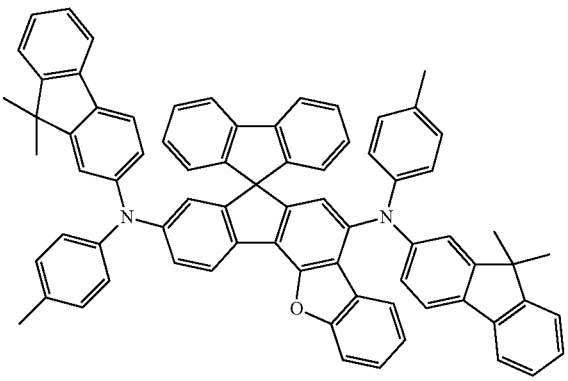
<Compound 417>
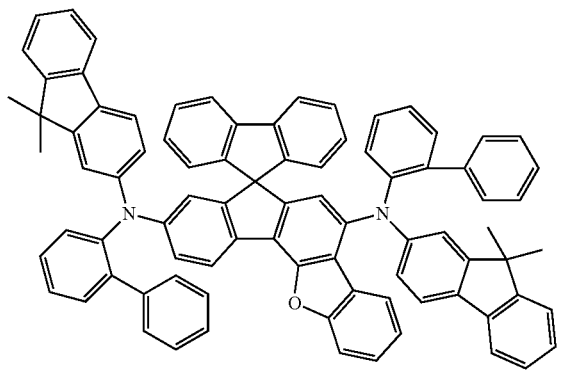
<Compound 418>
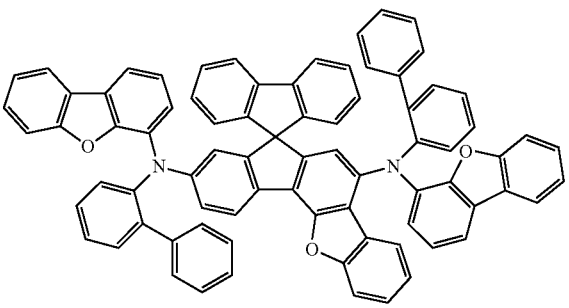
<Compound 419>
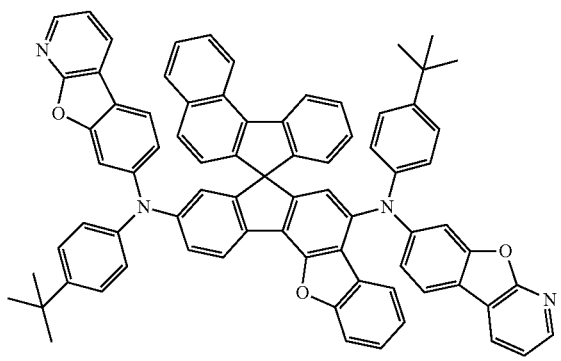
<Compound 420>
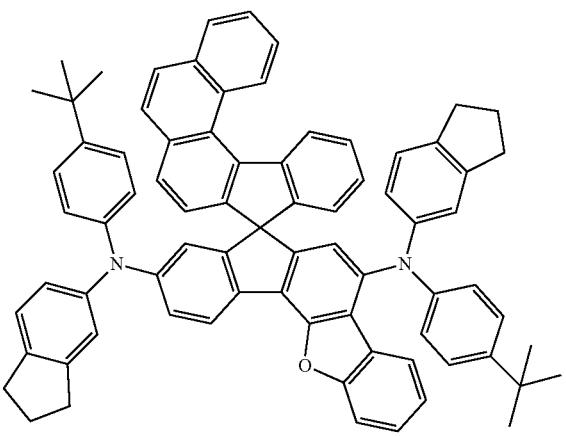
<Compound 421>
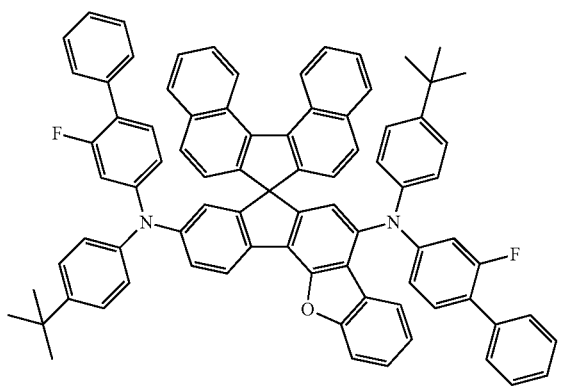
<Compound 422>
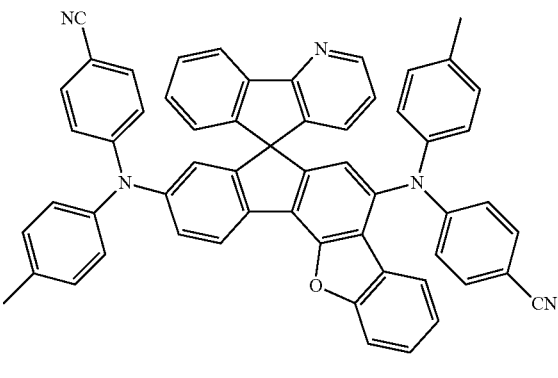

<Compound 423>
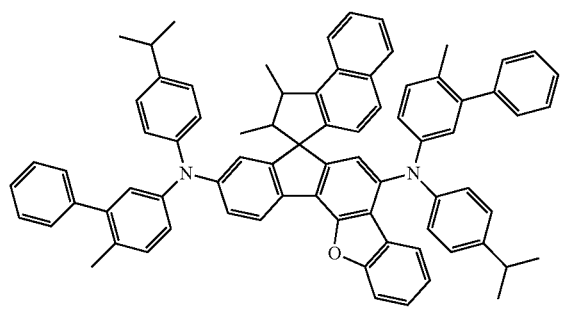
<Compound 424>
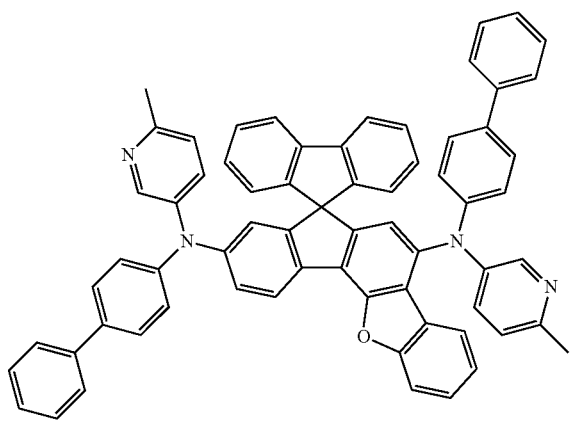
<Compound 425>
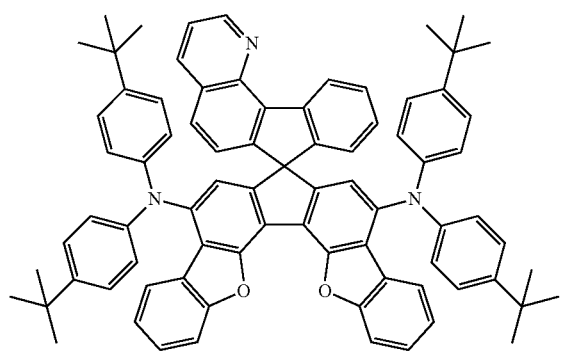
<Compound 426>
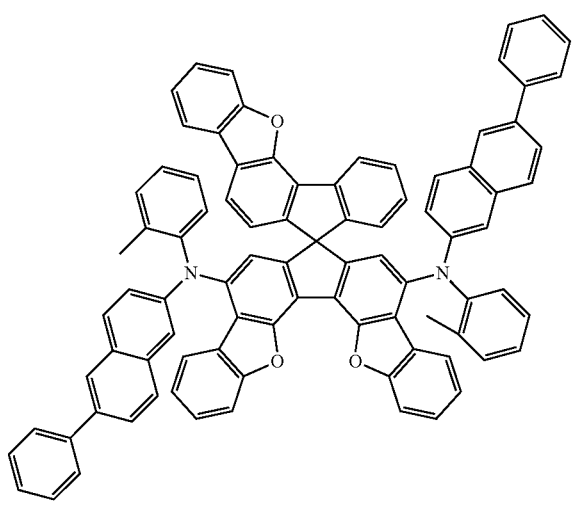
<Compound 427>
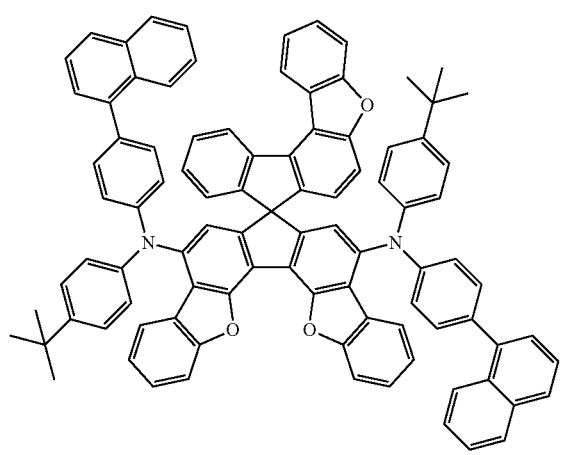
<Compound 428>
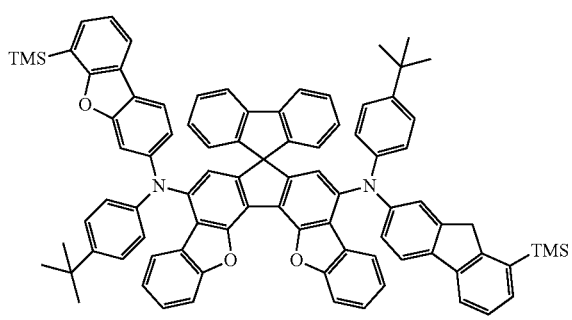

<Compound 429>
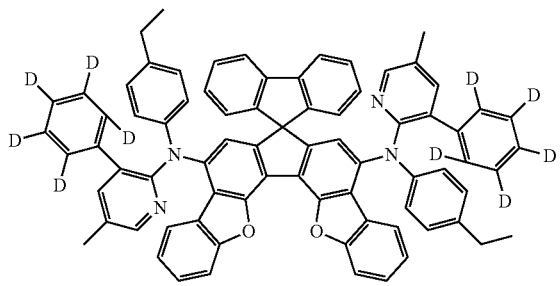
<Compound 430>
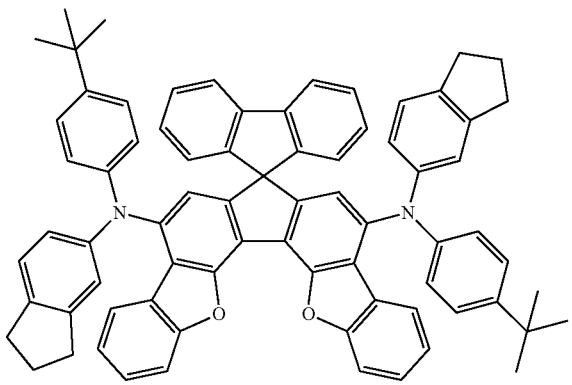
<Compound 431>
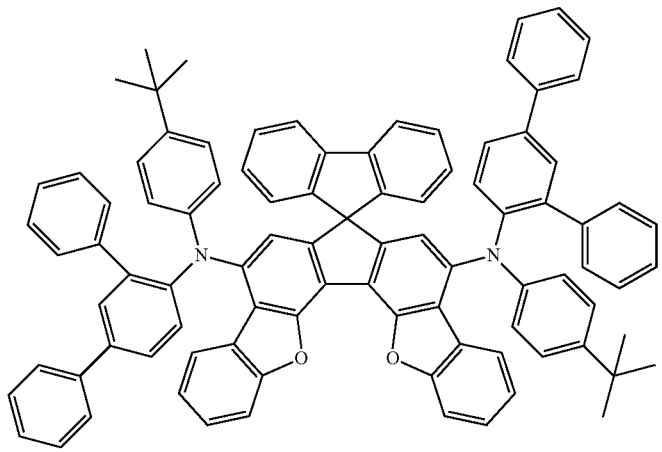
<Compound 432>
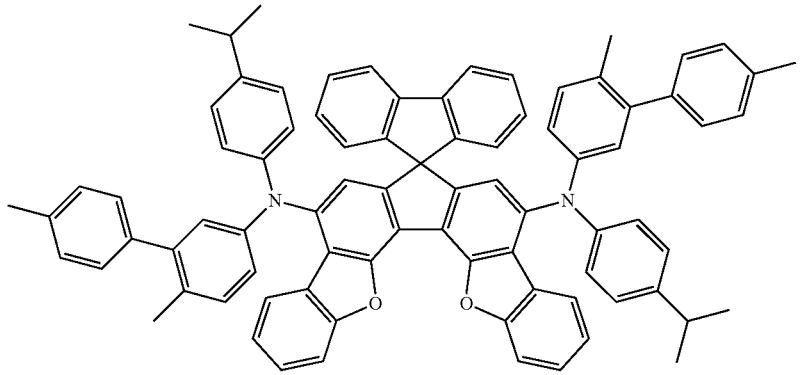
<Compound 433>
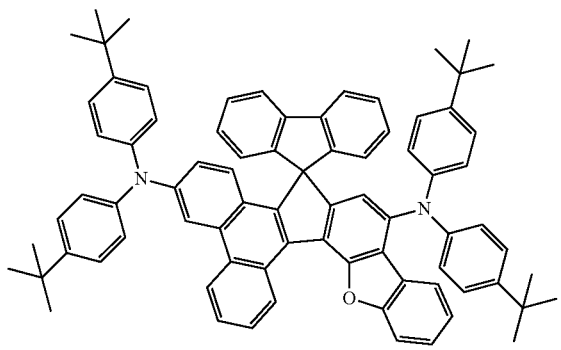
<Compound 434>
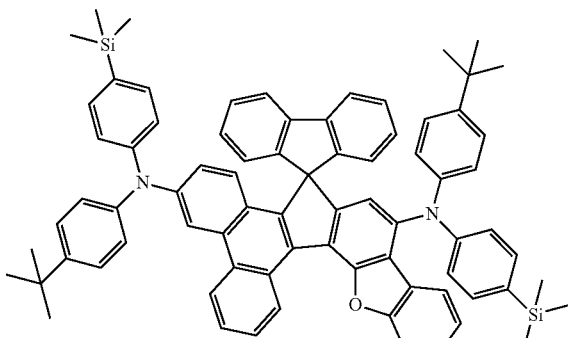

<Compound 435>
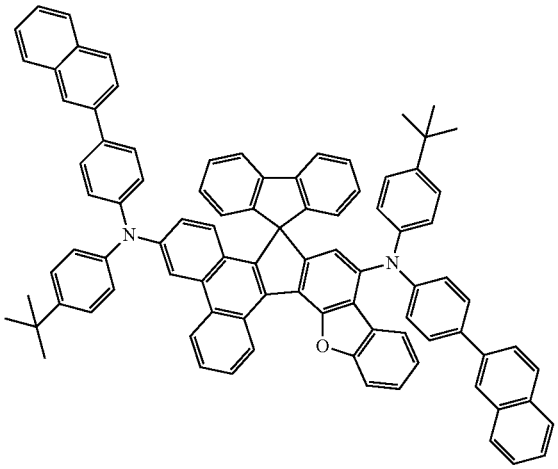
<Compound 436>
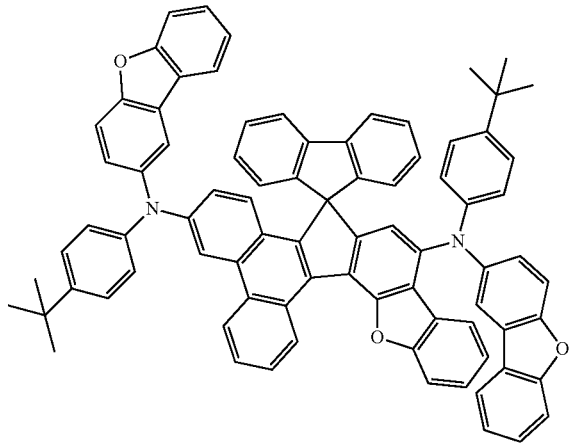
<Compound 437>
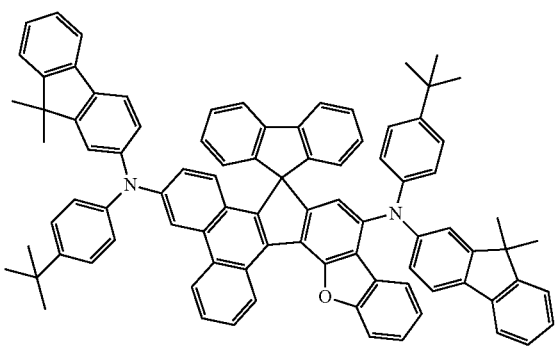
<Compound 438>
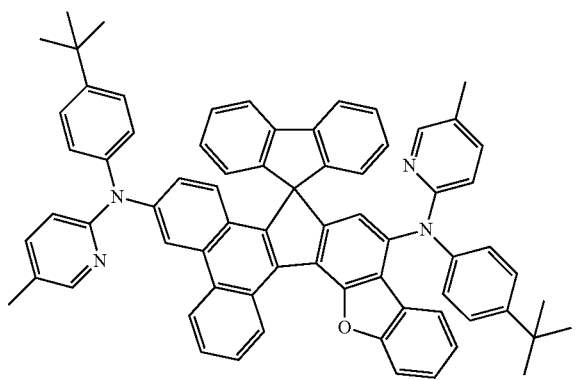
<Compound 439>
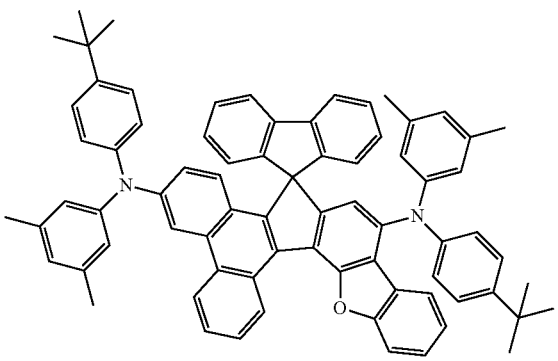
<Compound 440>
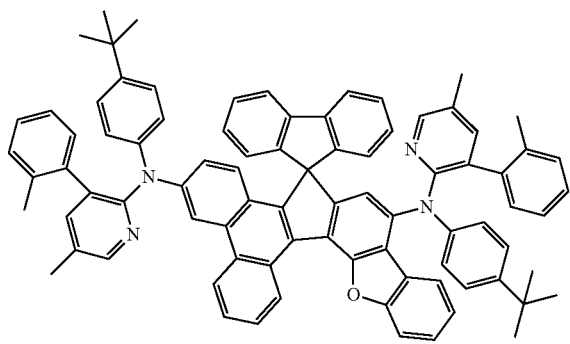
<Compound 441>
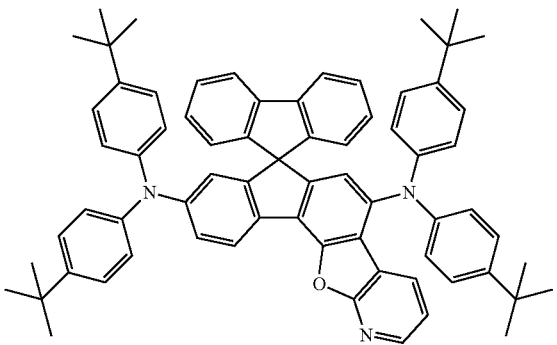
<Compound 442>
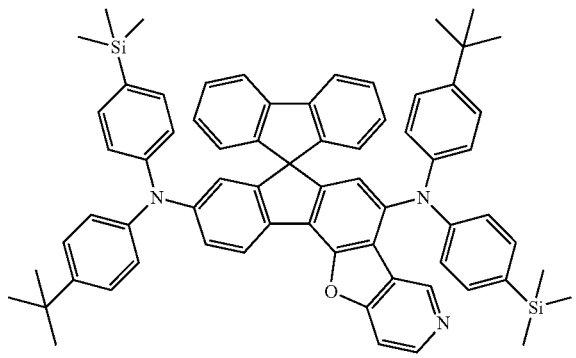

-continued
<Compound 443>
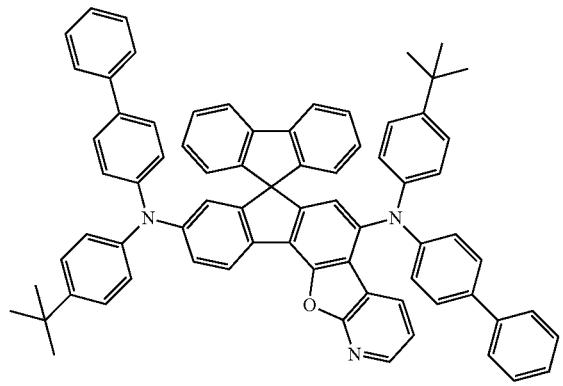
<Compound 444>
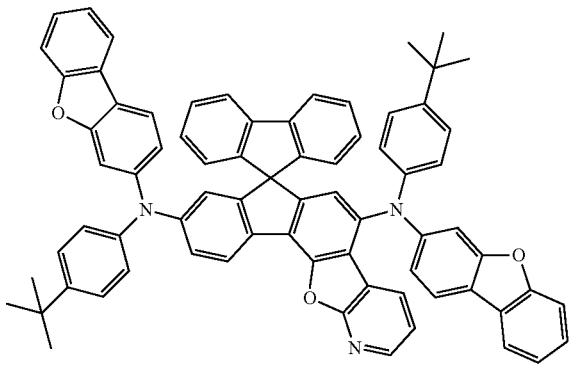
<Compound 445>
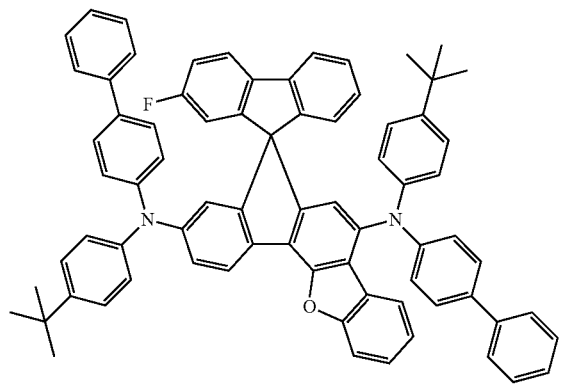
<Compound 446>
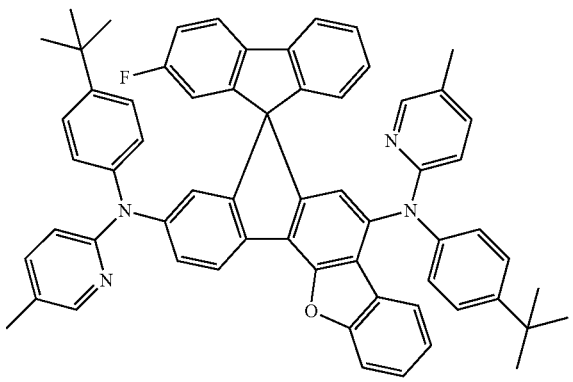
<Compound 447>
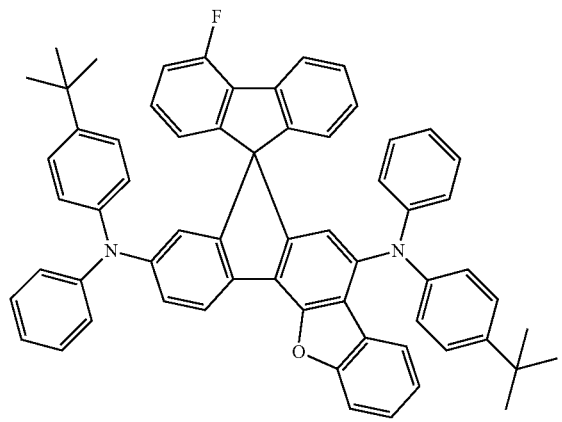
<Compound 448>
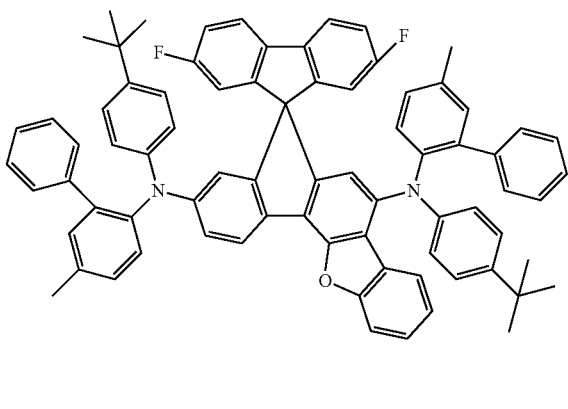
<Compound 449>
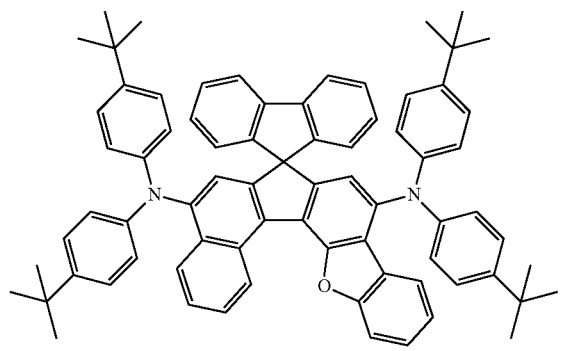
<Compound 450>
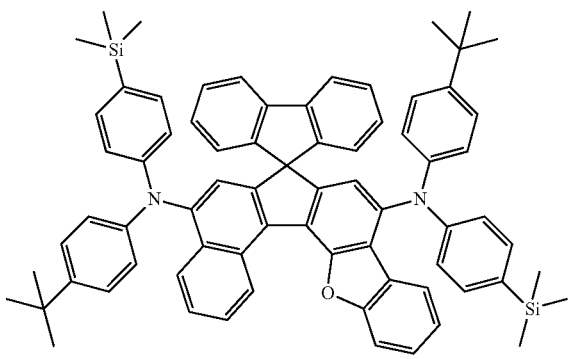

-continued
<Compound 451> <Compoound 452>
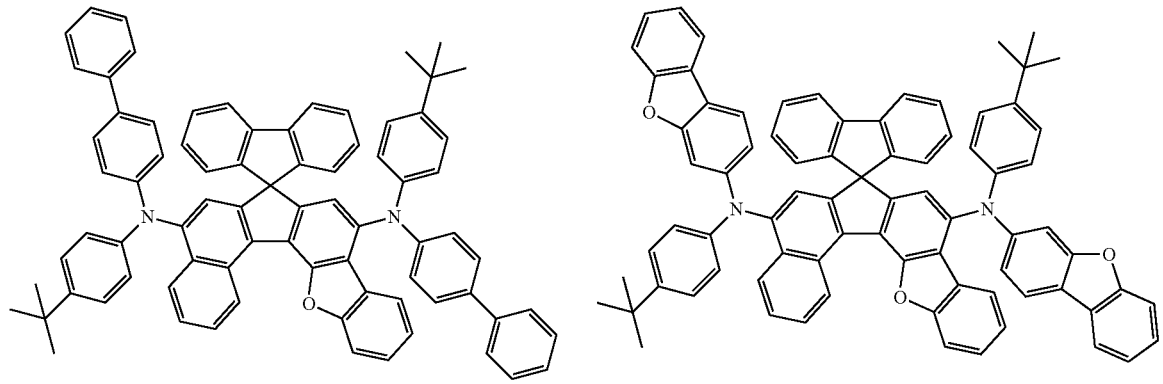
<Compound 453> <Compound 454>
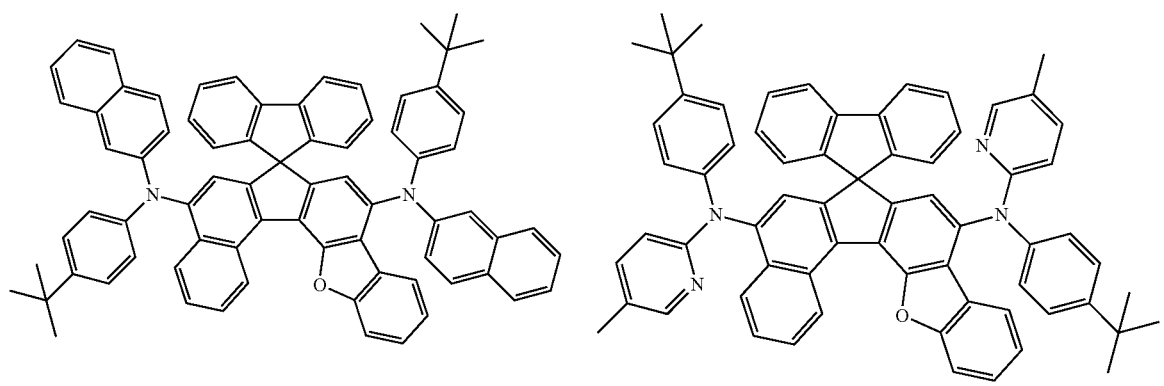
<Compound 455> <Compound 456>
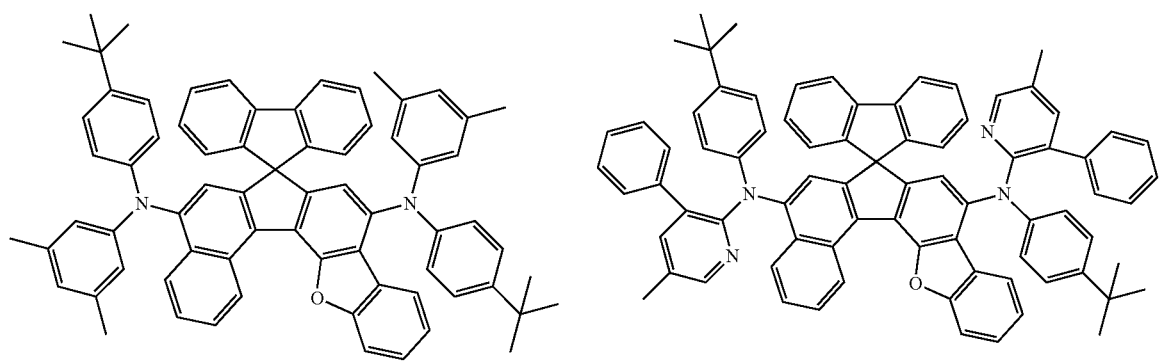
<Compound 457>
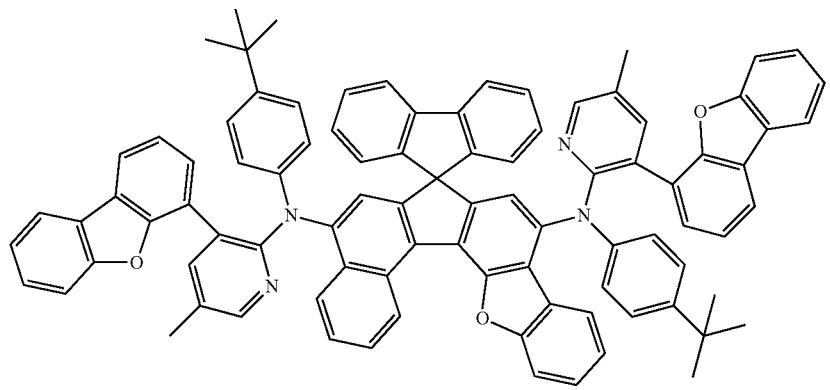

-continued
<Compound 458>
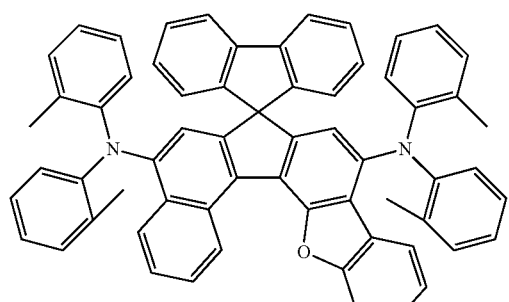
<Compound 459>
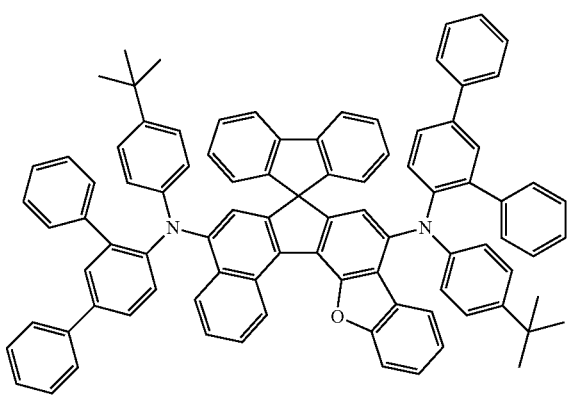
<Compound 460>
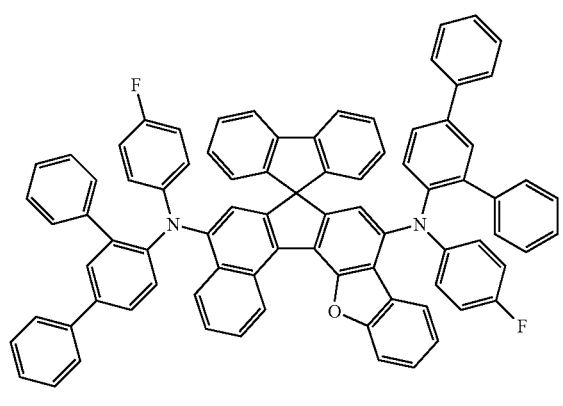
<Compound 461>
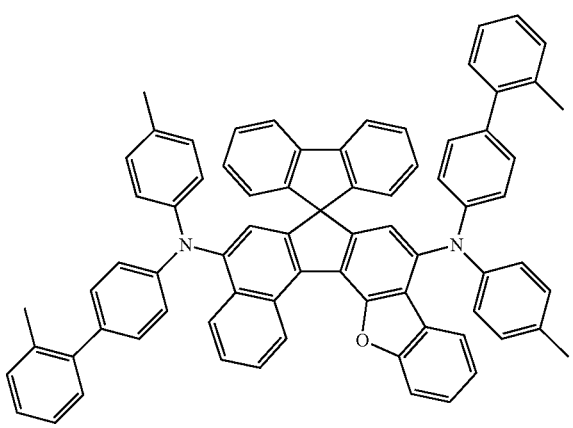
<Compound 462>
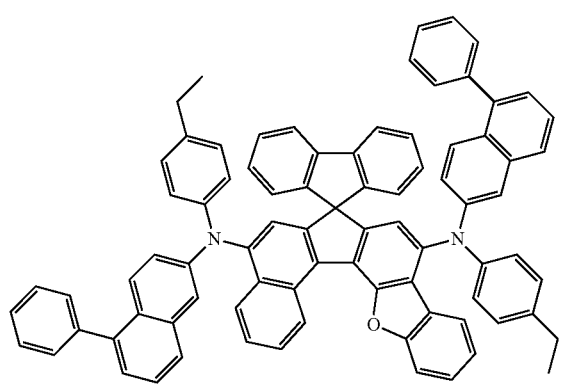
<Compound 463>
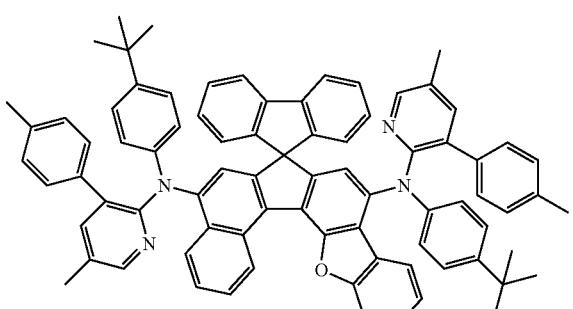

<Compound 464>
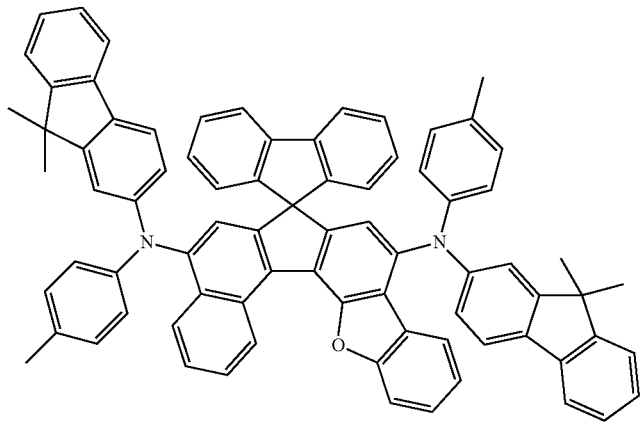
<Compound 465>
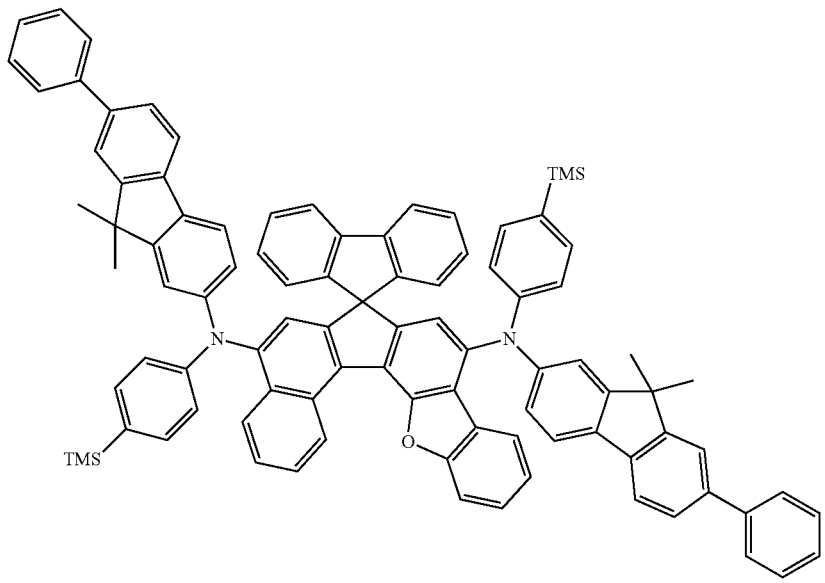
<Compound 466>
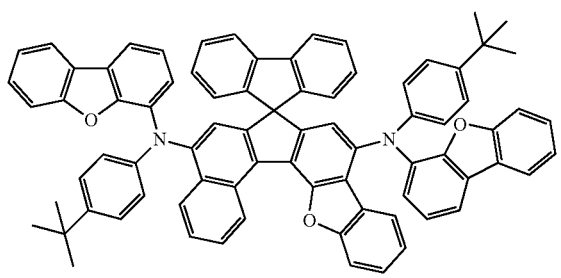
<Compound 467>
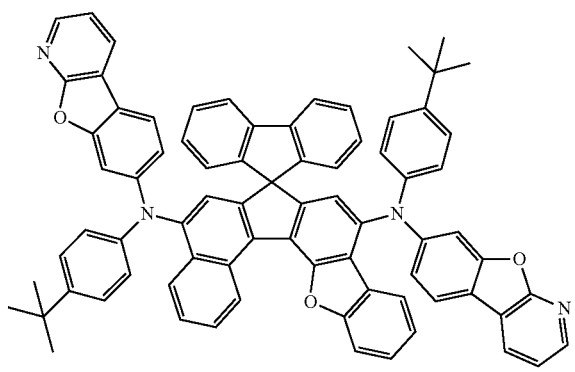

-continued
<Compound 468>
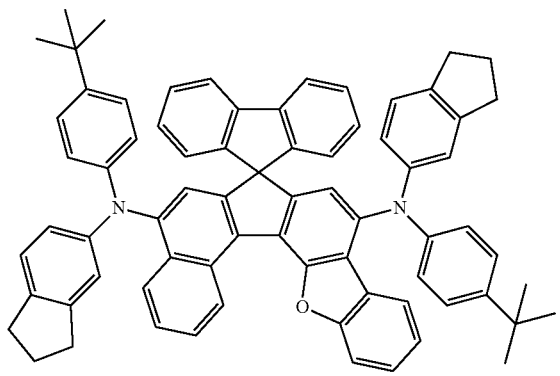
<Compound 469>
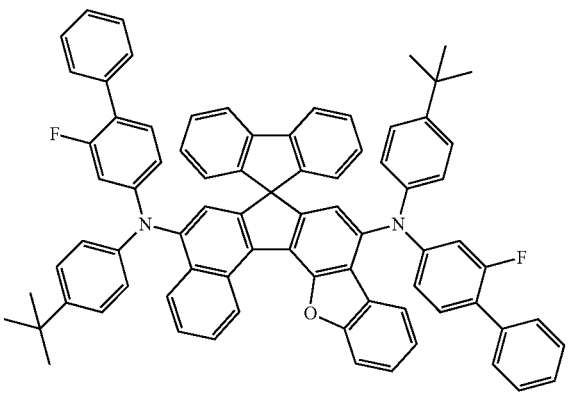
<Compound 470>
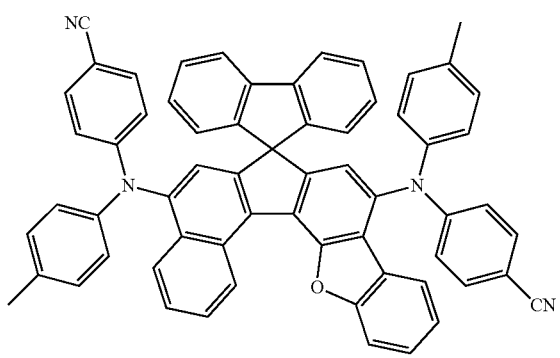
<Compound 471>
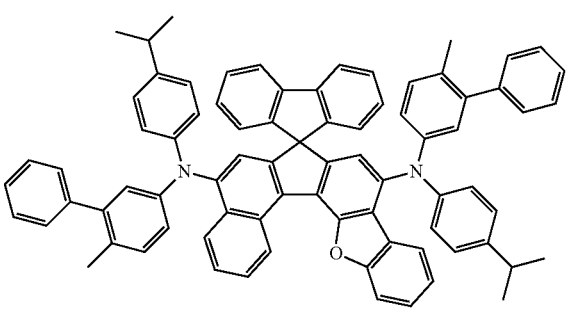
<Compound 472>
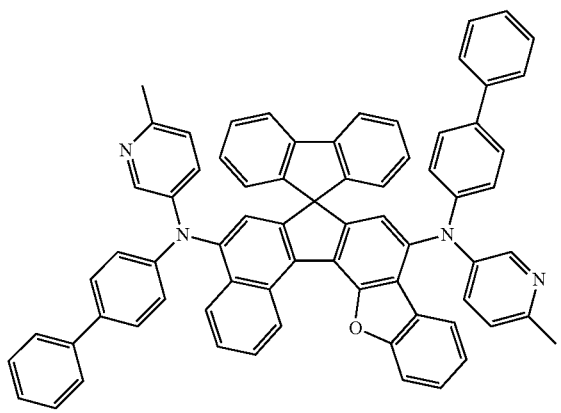
<Compound 473>
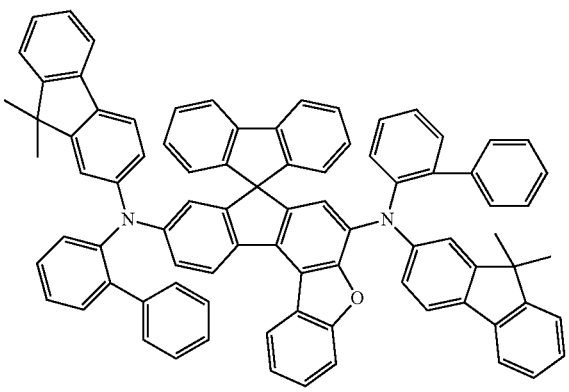
<Compound 474>
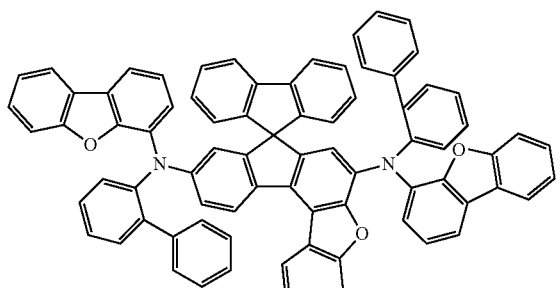
<Compound 475>
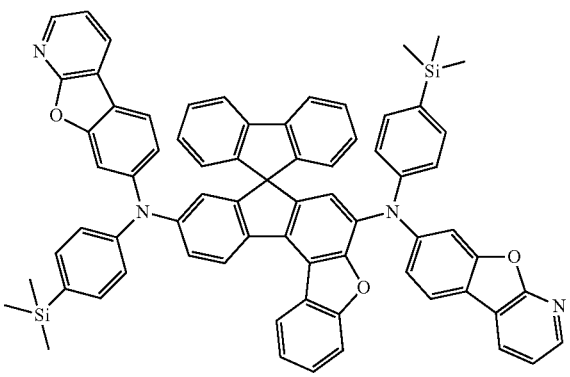

-continued
<Compound 476>
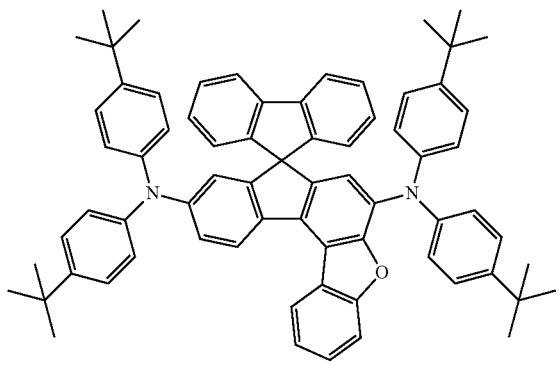
<Compound 477>
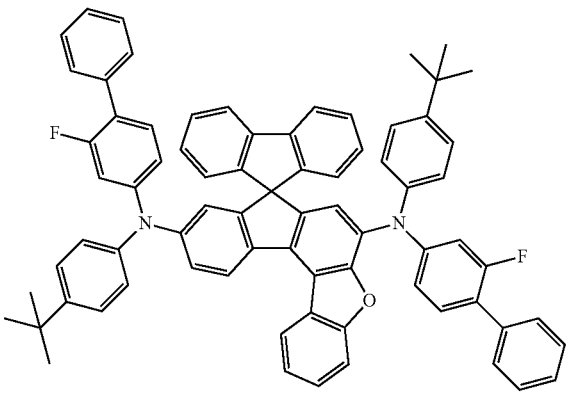
<Compound 478>
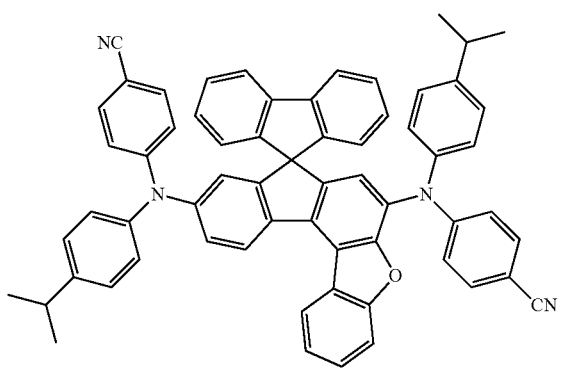
<Compound 479>
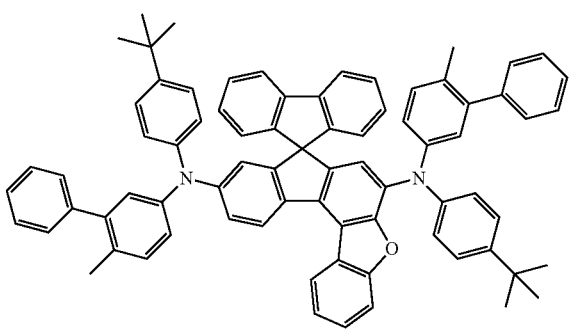
<Compound 480>
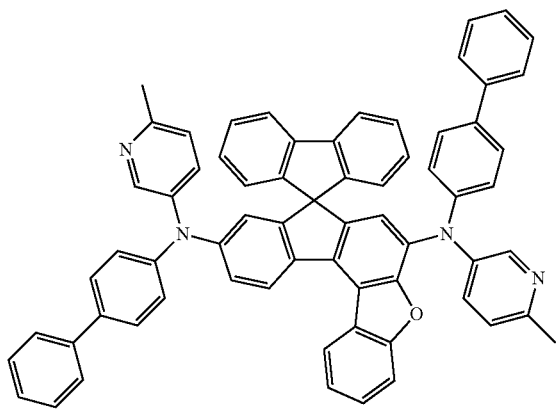
<Compound 481>
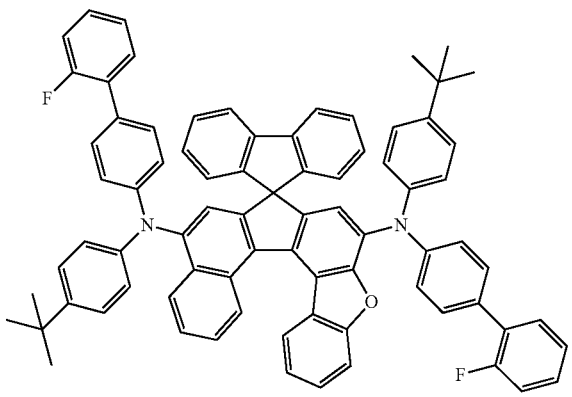
<Compound 482>
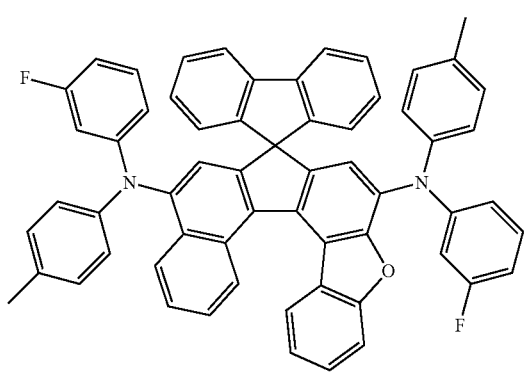
<Compound 483>
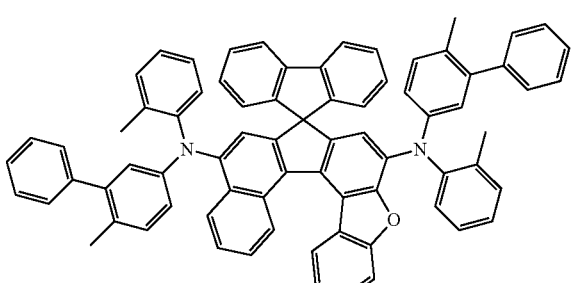

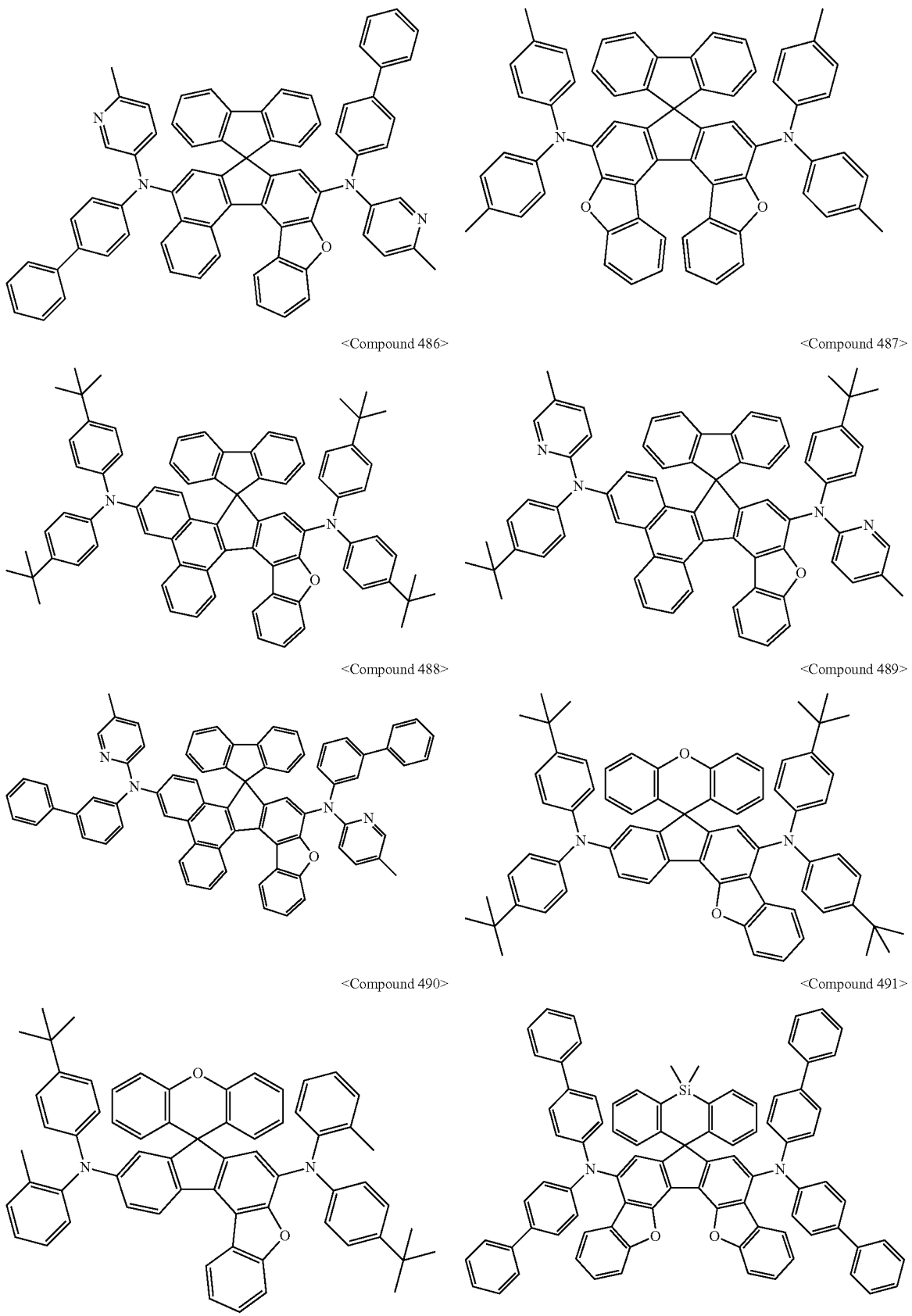

-continued
<Compound 492>
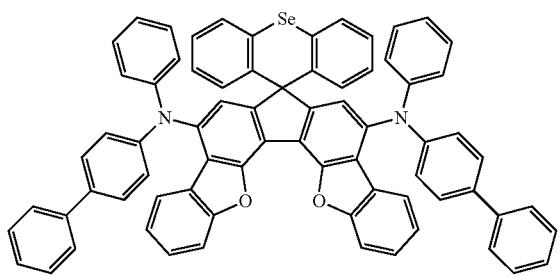
<Compound 493>
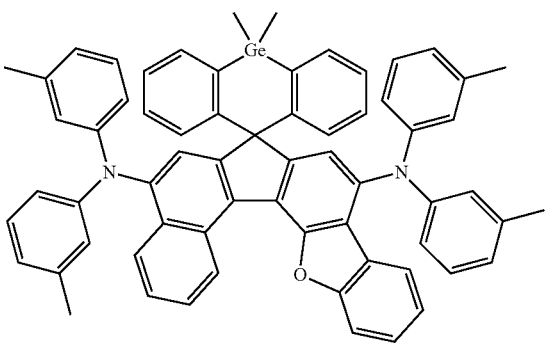
<Compound 494>
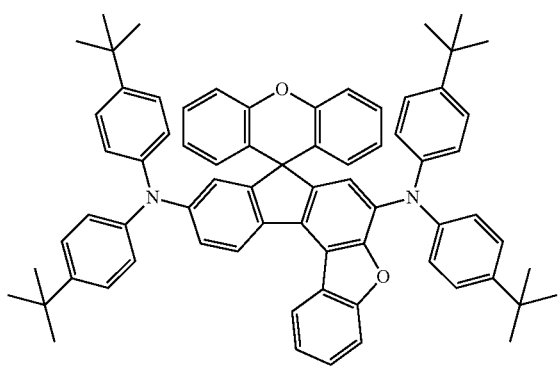
<Compound 495>
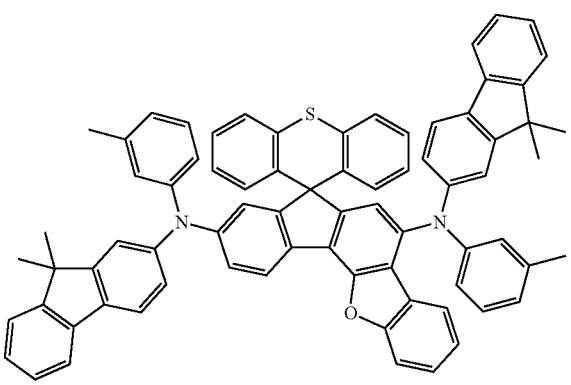
<Compound 496>
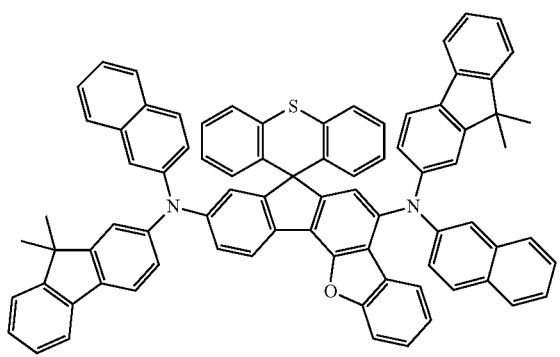
<Compound 497>
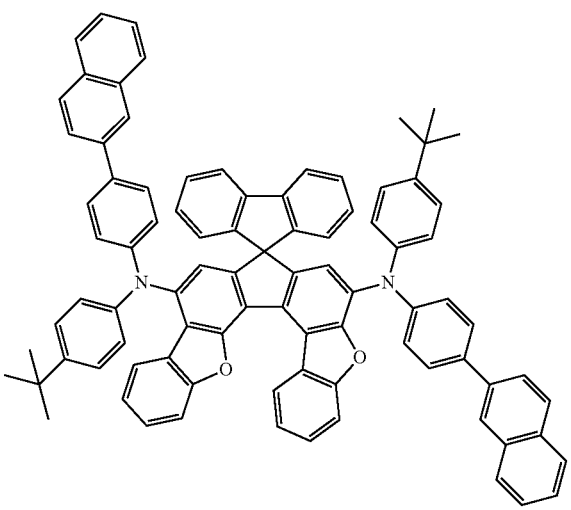

-continued
<Compound 498>
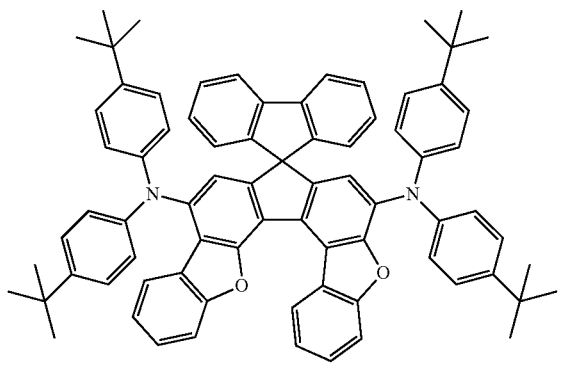
<Compound 499>
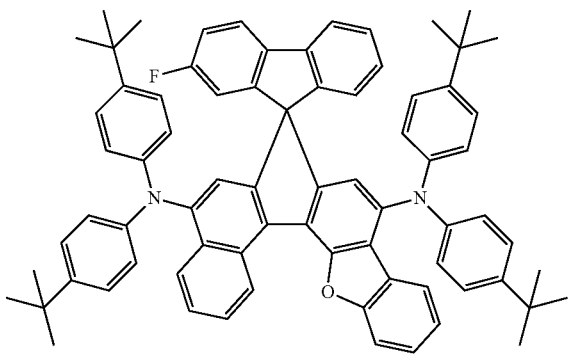
<Compound 500>
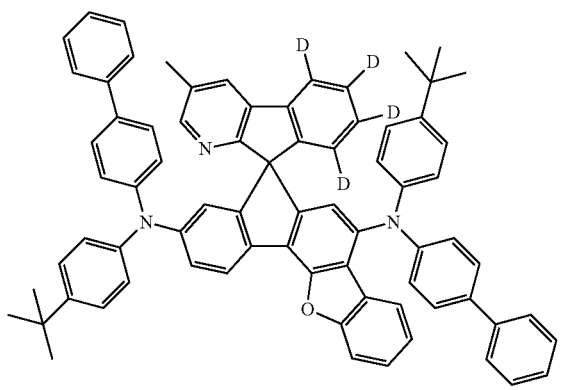
<Compound 501>
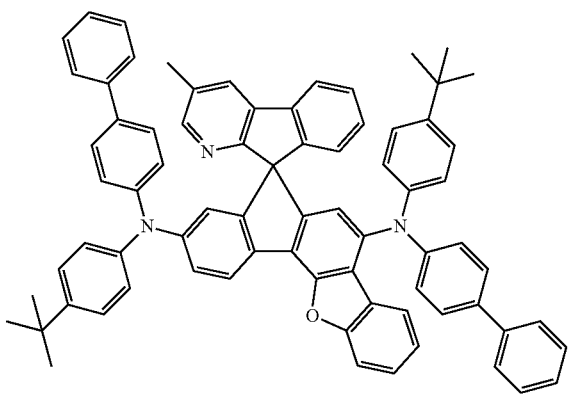
<Compound 502>
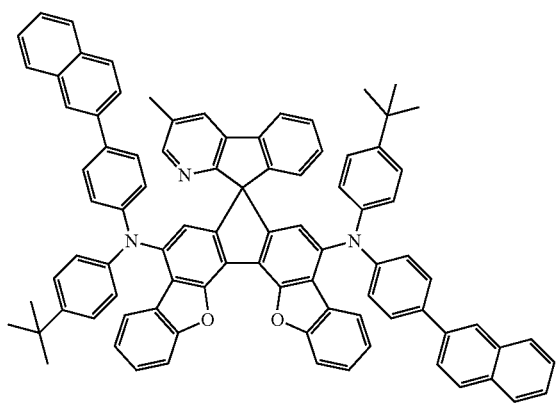
<Compound 503>
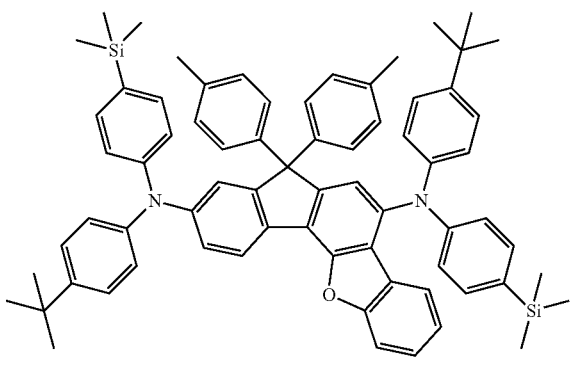
<Compound 504>
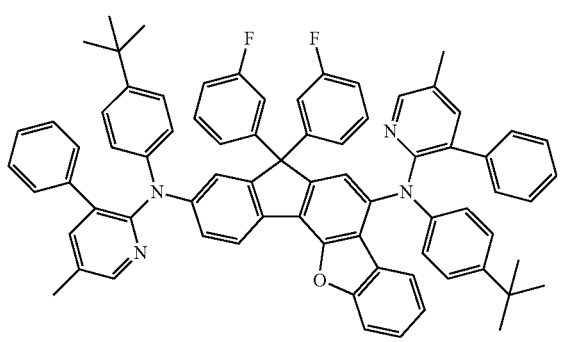
<Compound 505>
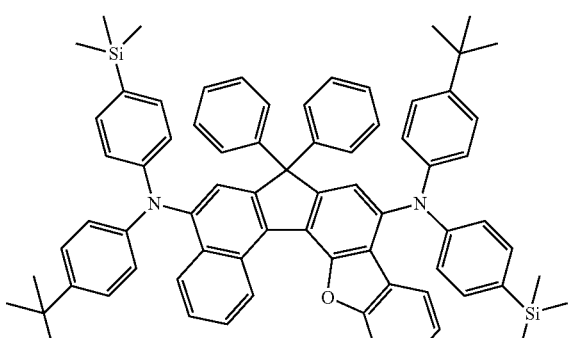

-continued
<Compound 506>
<Compound 507>
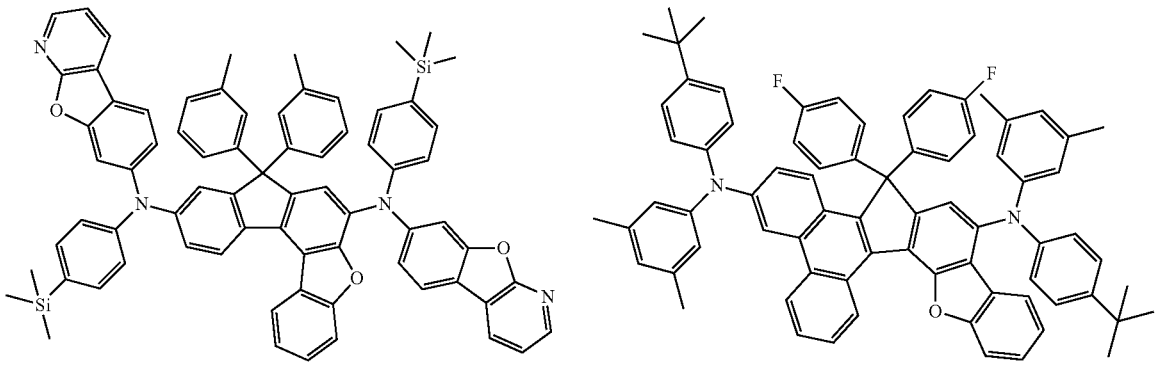
<Compound 508>
<Compound 509>
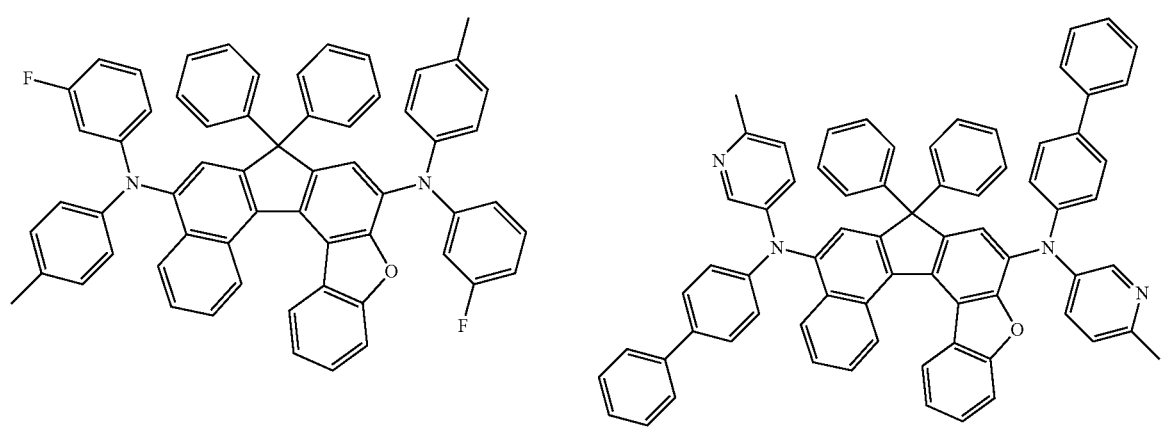
<Compound 510>
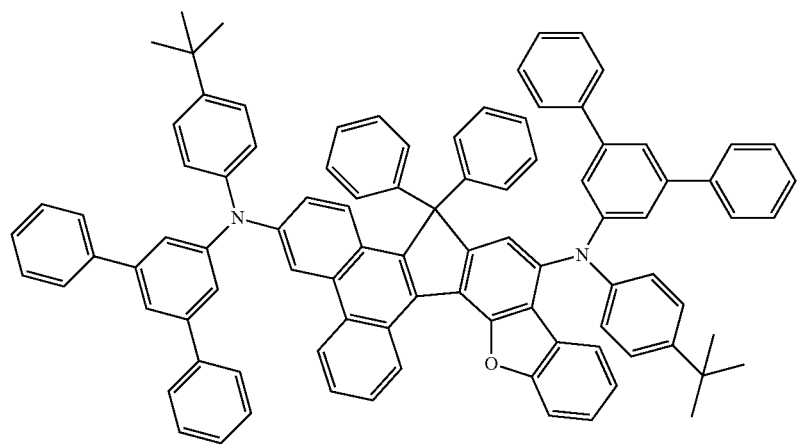

-continued
<Compound 511>
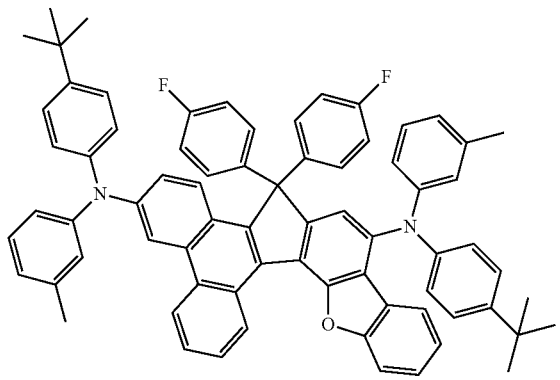
<Compound 512>
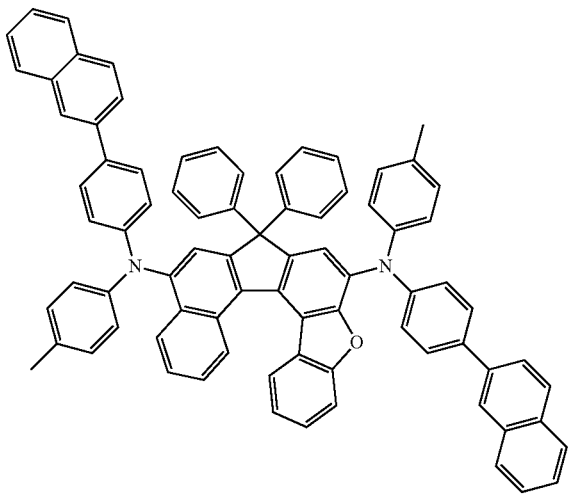
<Compound 513>
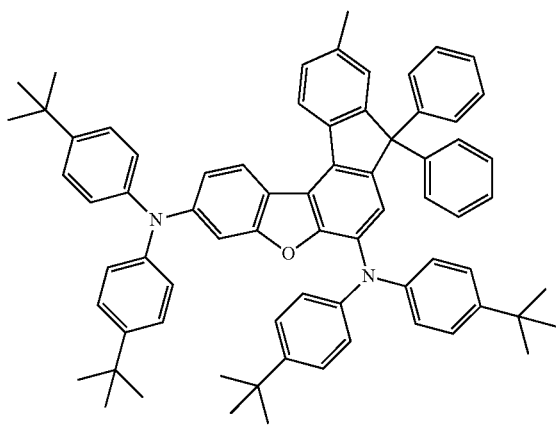
<Compound 514>
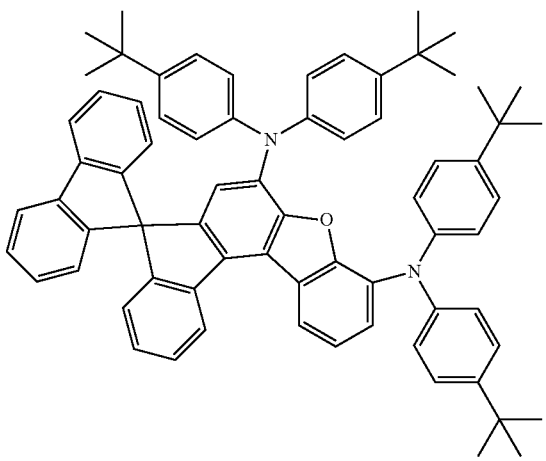
<Compound 515>
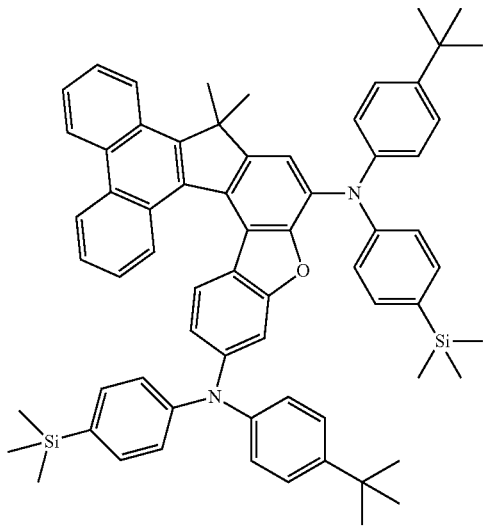
<Compound 516>
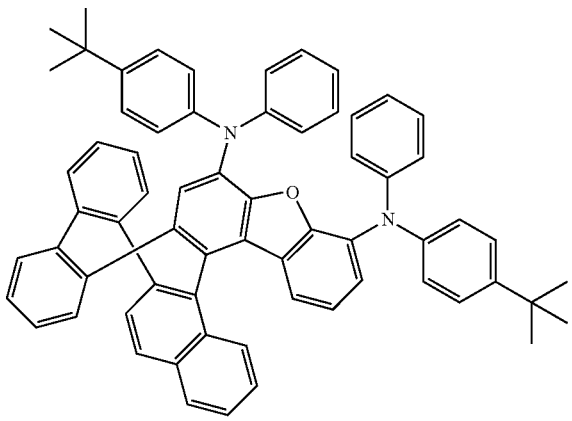

<Compound 517>
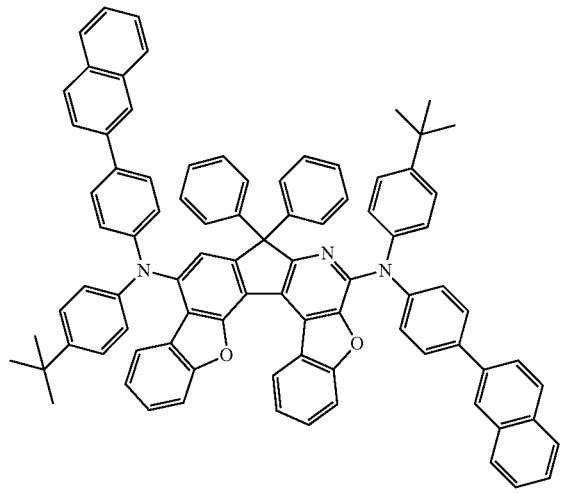
<Compound 518>
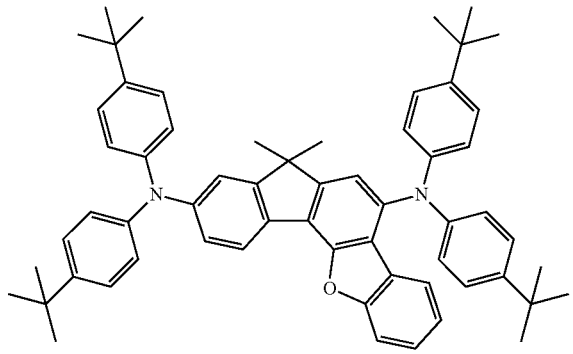
<Compound 519>
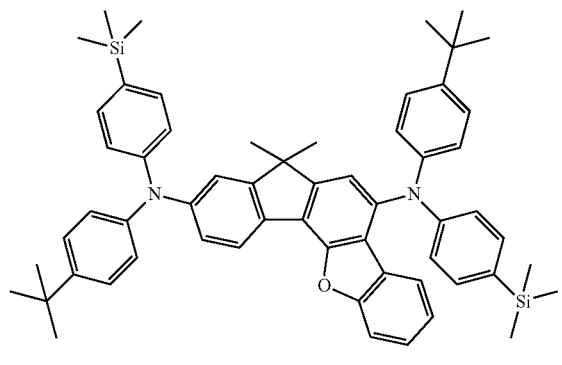
<Compound 520>
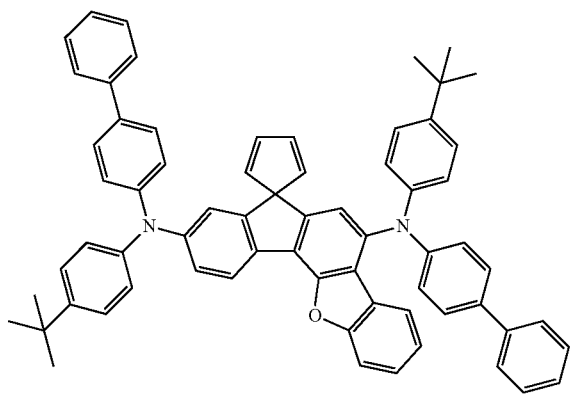
<Compound 521>
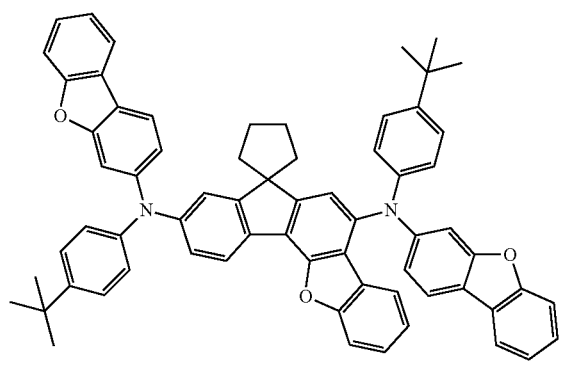
<Compound 522>
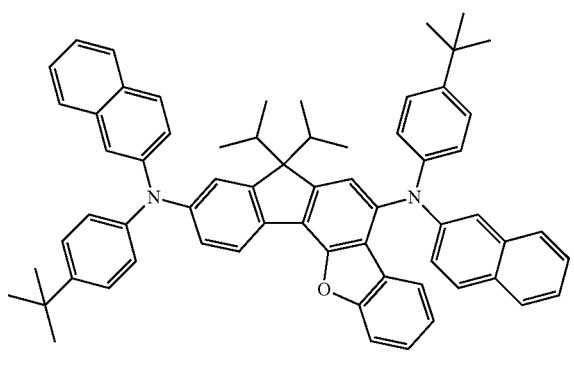

-continued
<Compound 523>
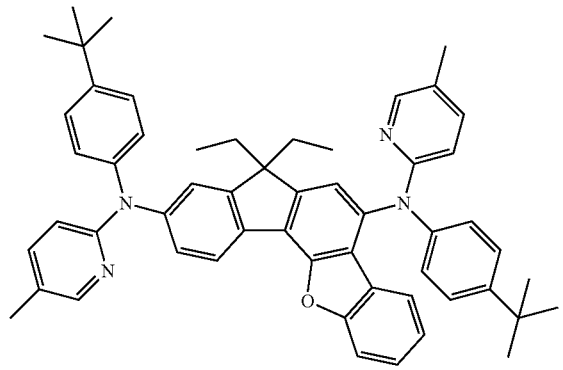
<Compound 524>
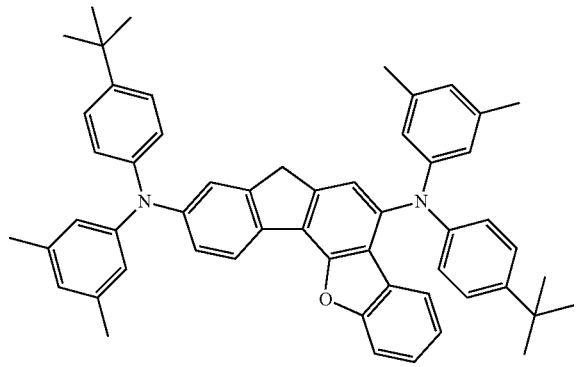
<Compound 525>
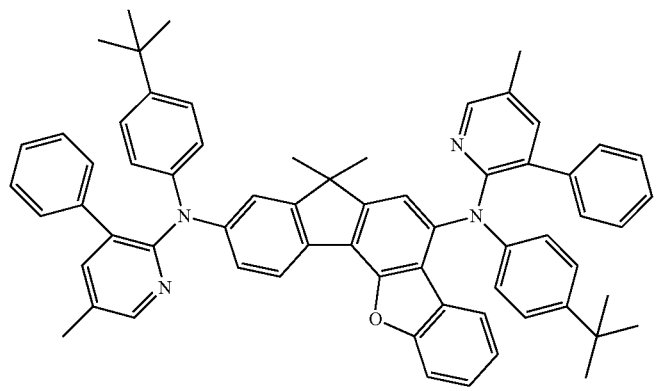
<Compound 526>
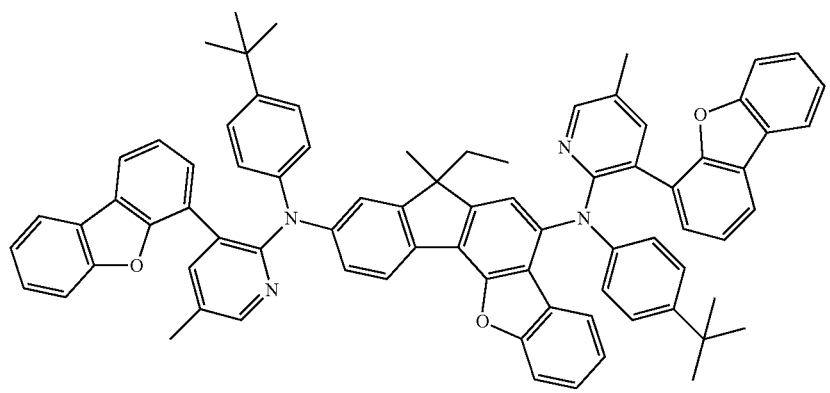
<Compound 527>
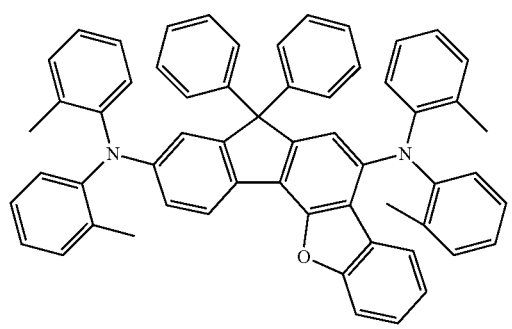
<Compound 528>
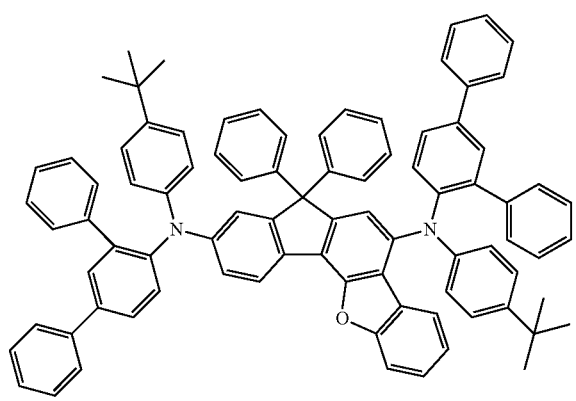

-continued
<Compound 529>
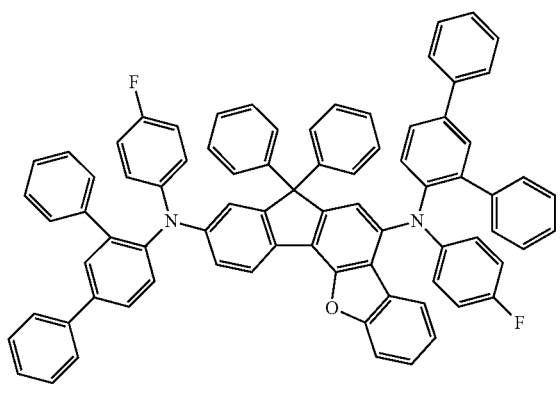
<Compound 530>
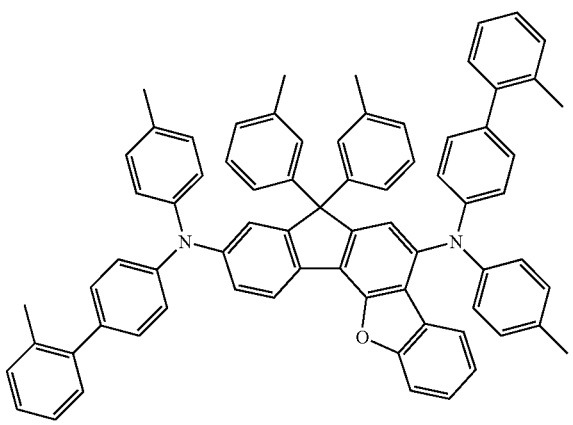
<Compound 531>
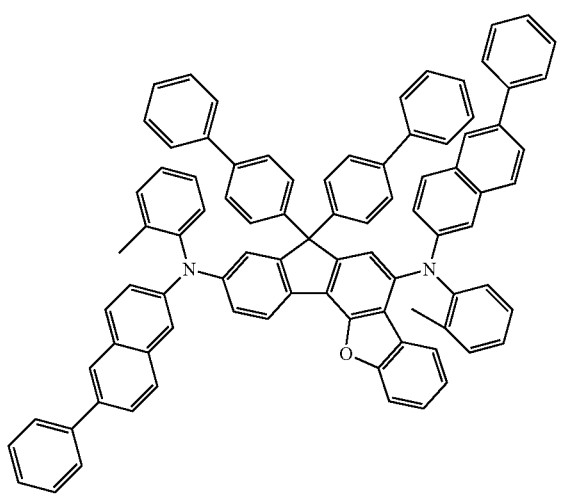
<Compound 532>
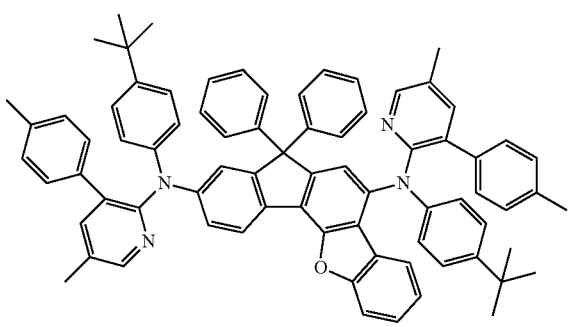
<Compound 533>
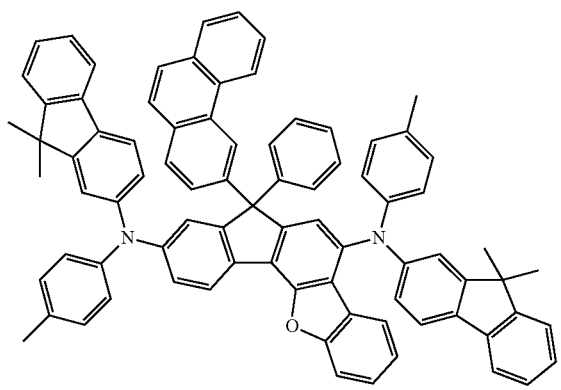
<Compound 534>
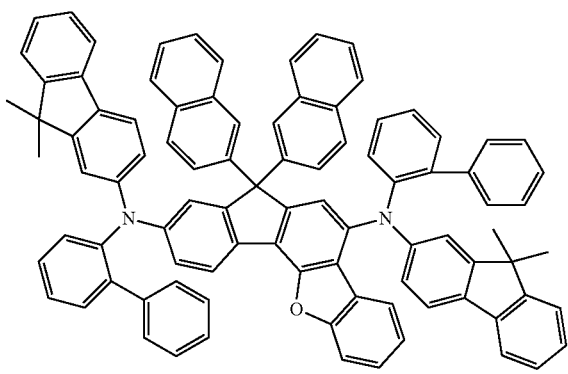

-continued
<Compound 535>
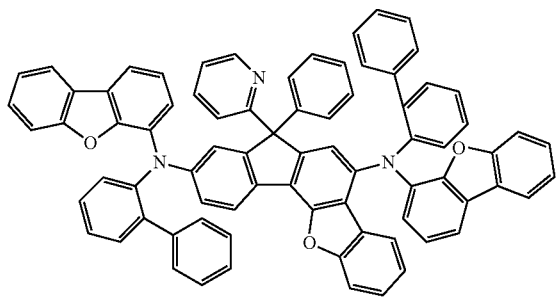
<Compound 536>
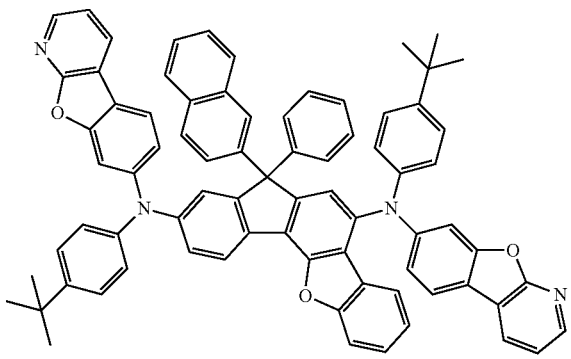
<Compound 537>
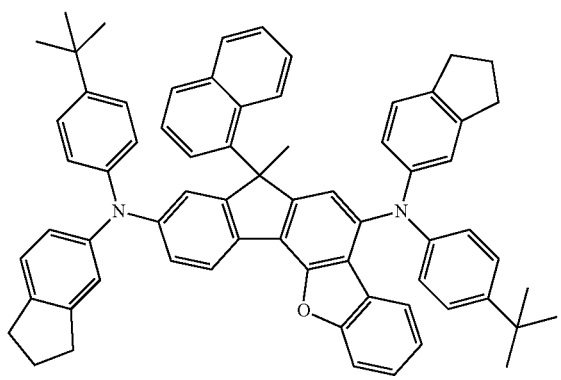
<Compound 538>
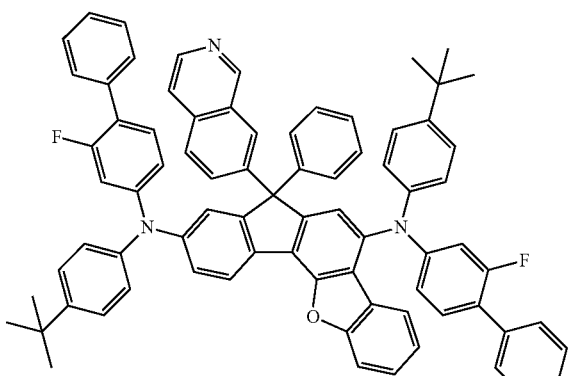
<Compound 539>
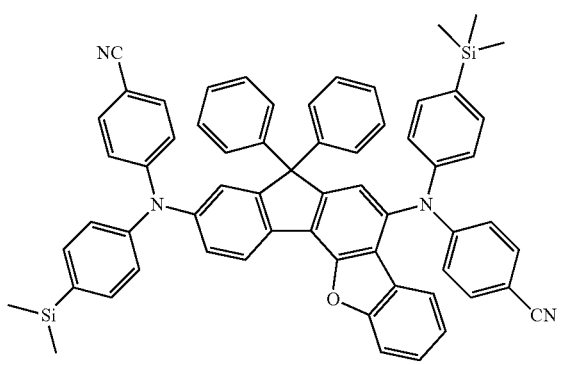
<Compound 540>
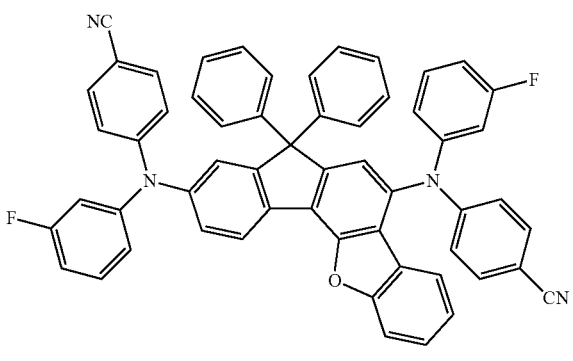
<Compound 541>
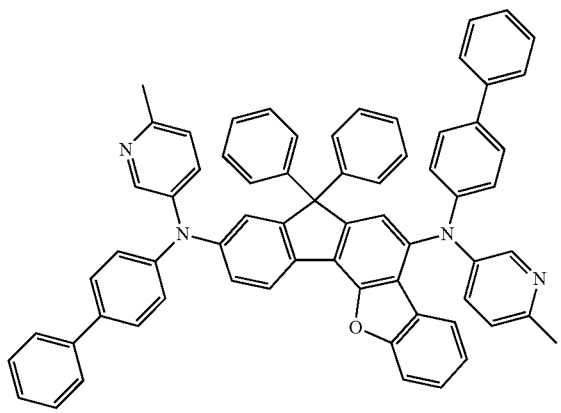
<Compound 542>
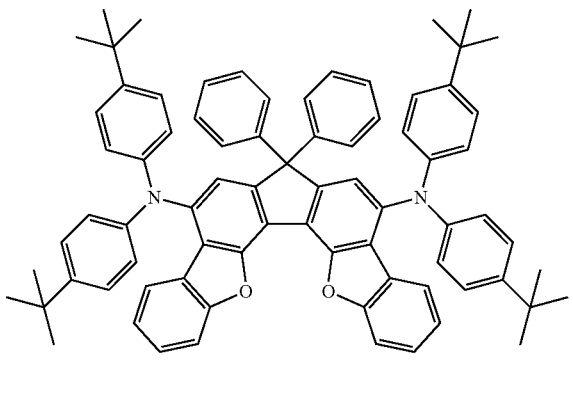

-continued
<Compound 543>
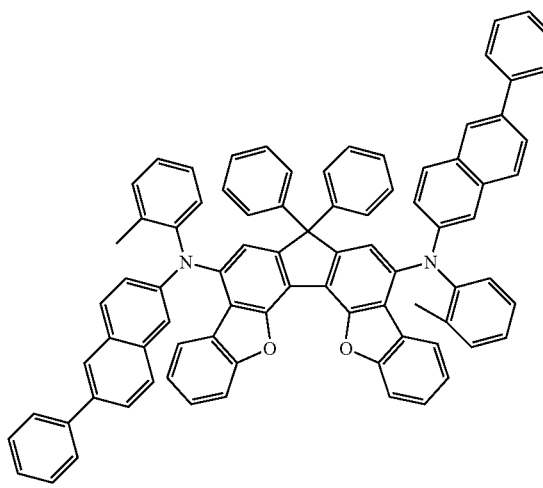
<Compound 544>
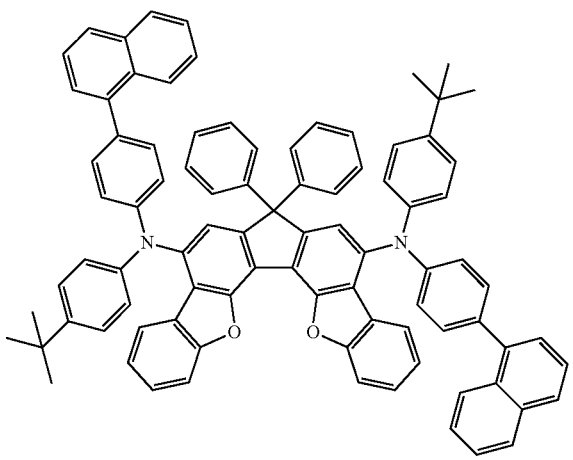
<Compound 545>
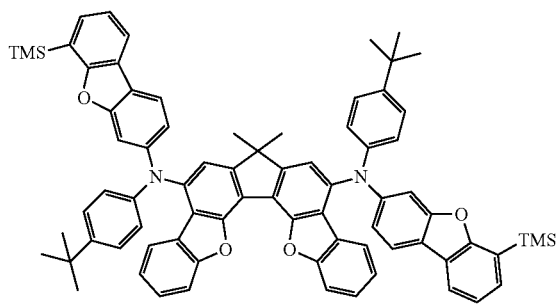
<Compound 546>
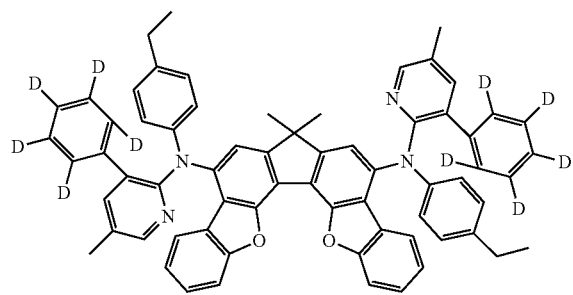
<Compound 547>
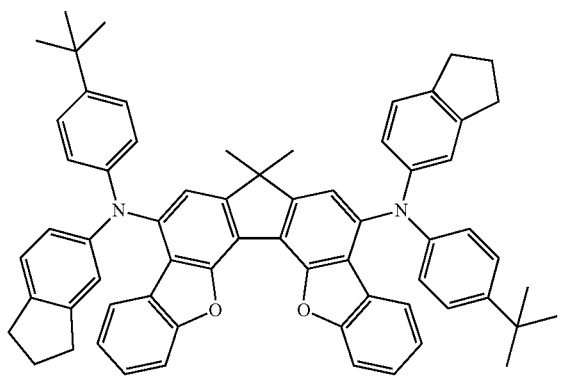
<Compound 548>
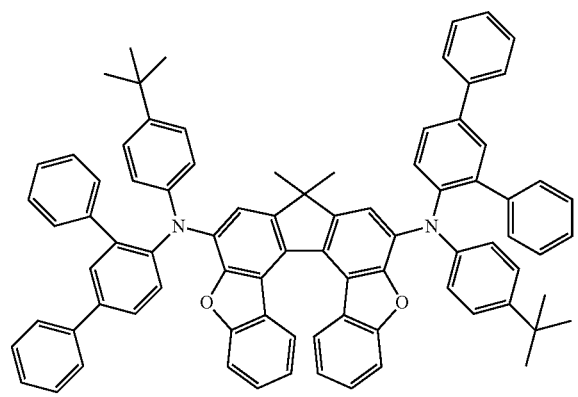
<Compound 549>
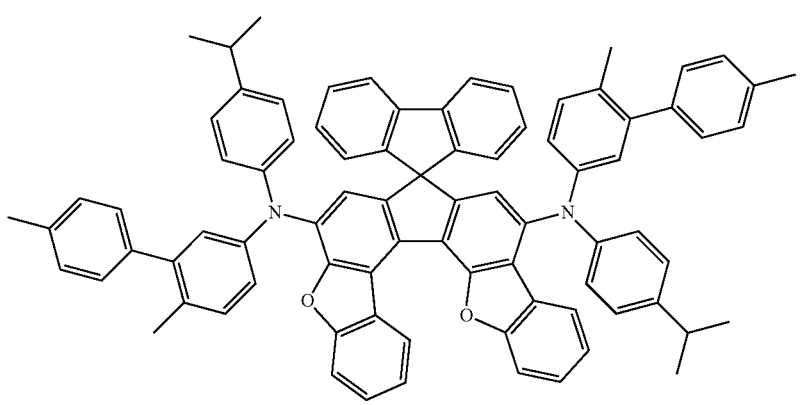

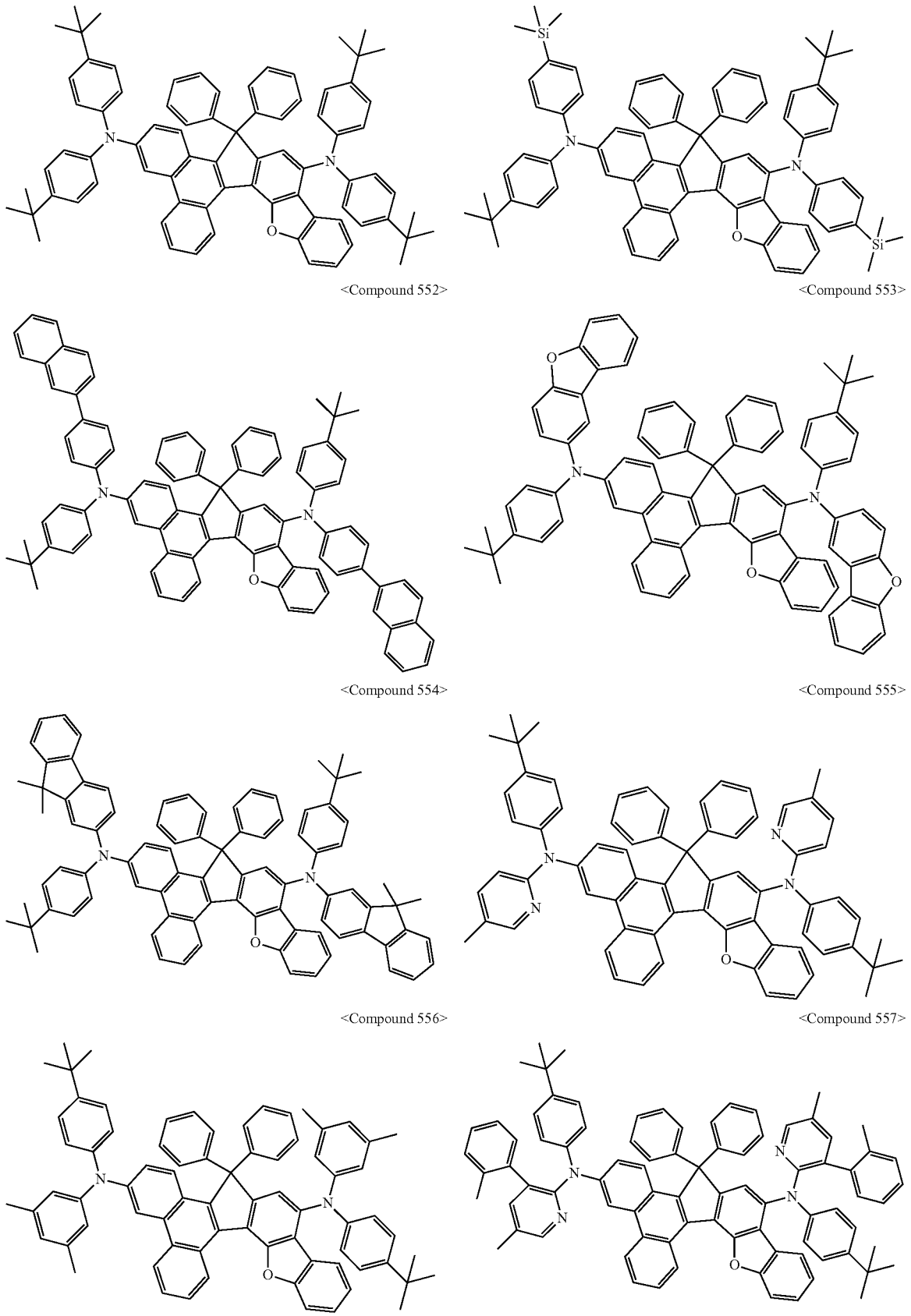

-continued
<Compound 558>
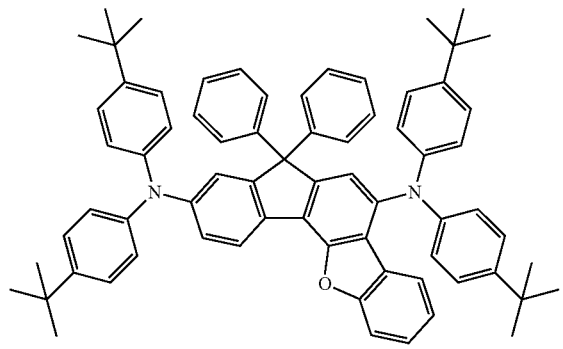
<Compound 559>
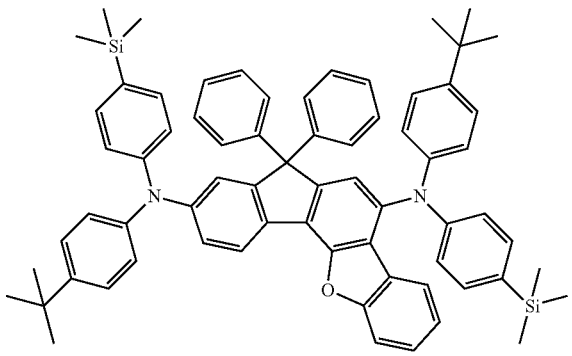
<Compound 560>
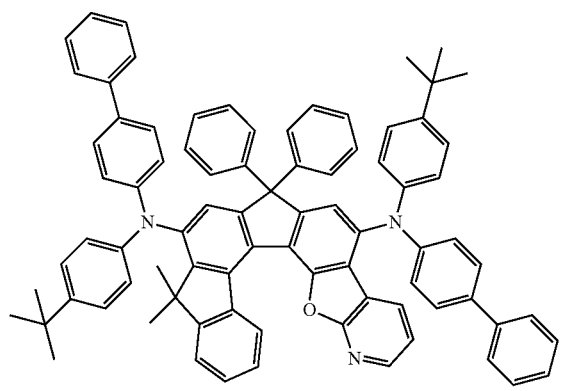
<Compound 561>
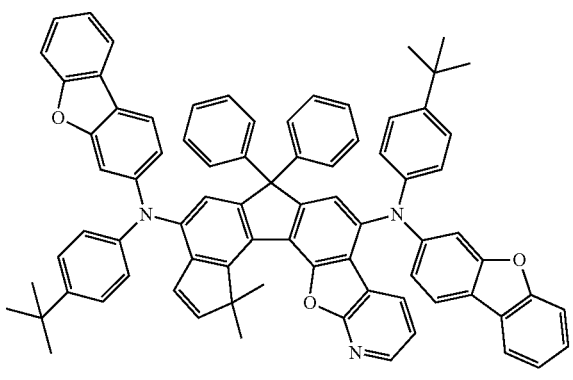
<Compound 562>
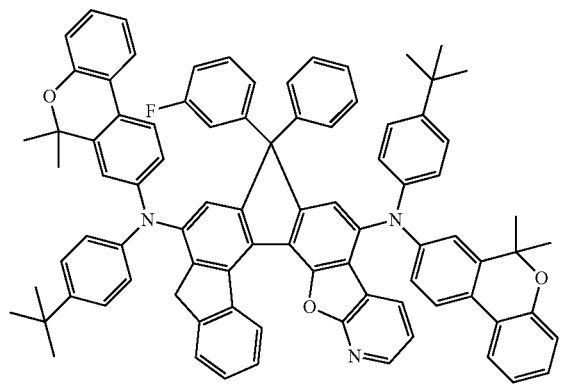
<Compound 563>
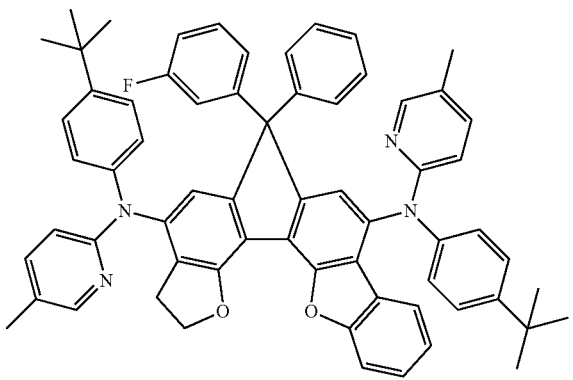
<Compound 564>
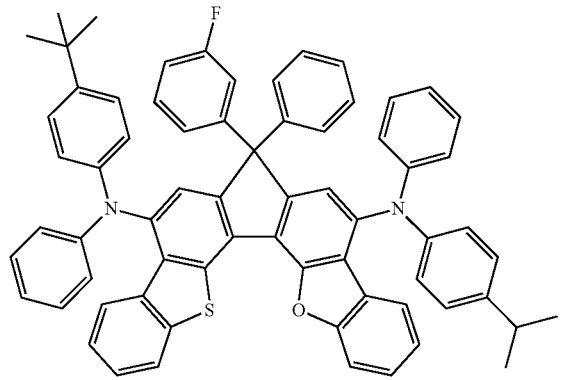
<Compound 565>
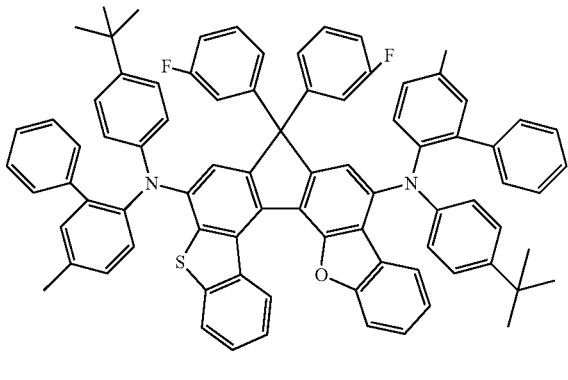

-continued
<Compound 566>
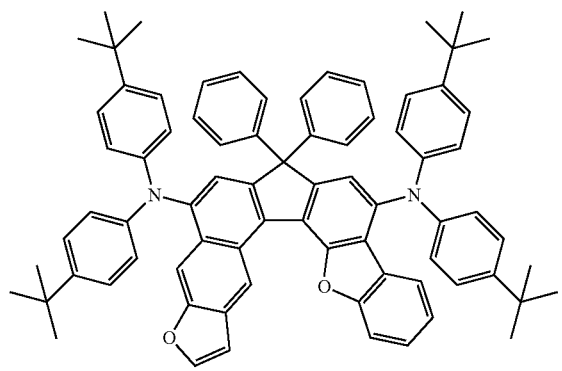
<Compound 567>
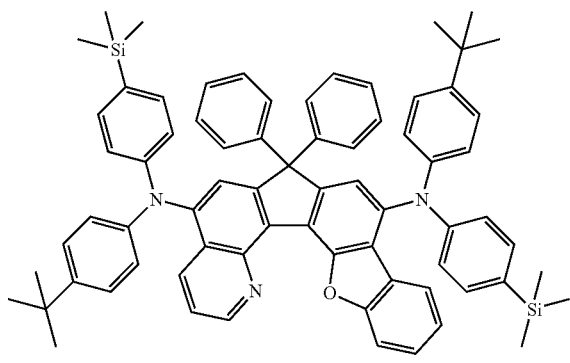
<Compound 568>
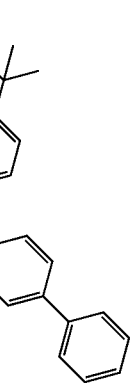
<Compound 569>
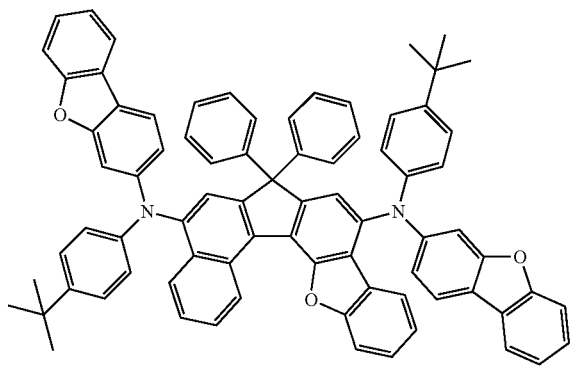
<Compound 570>
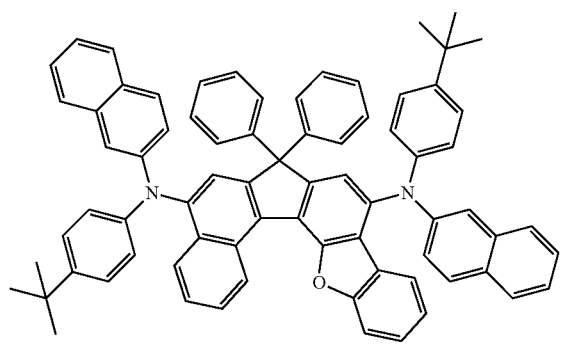
<Compound 571>
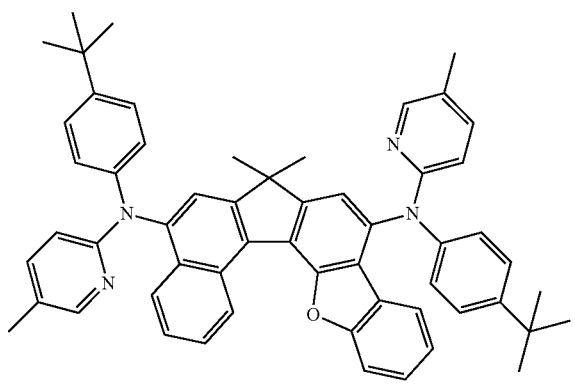
<Compound 572>
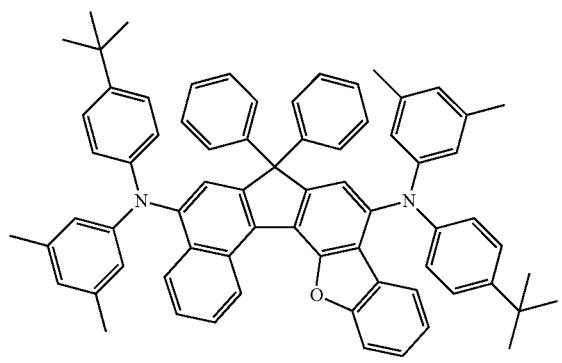
<Compound 573>
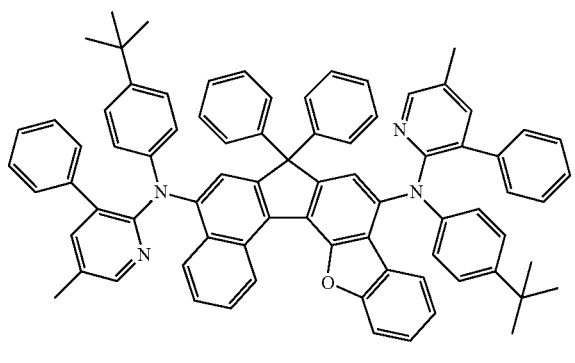

-continued
<Compound 574>
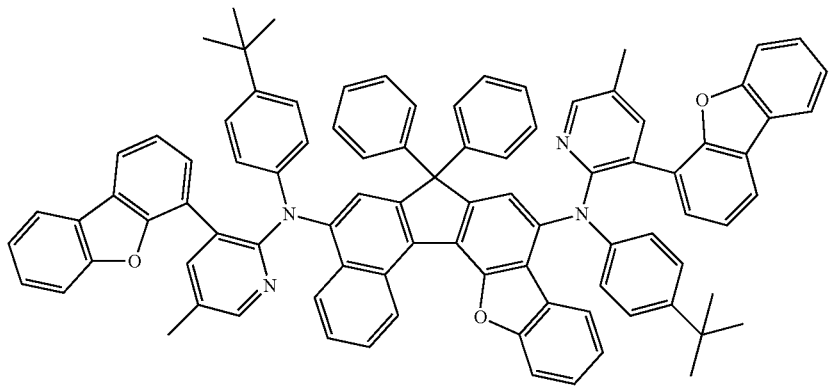
<Compound 575>
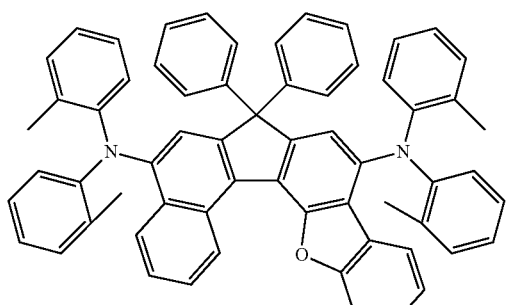
<Compound 576>
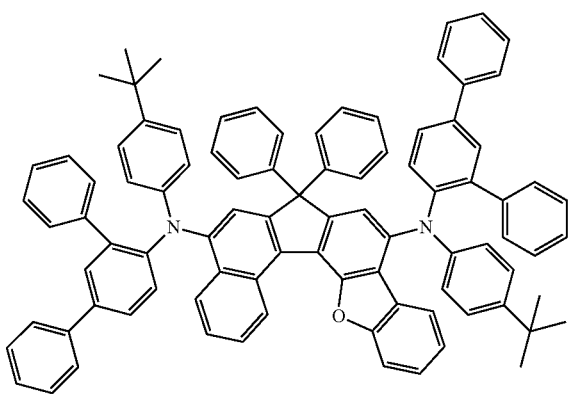
<Compound 577>
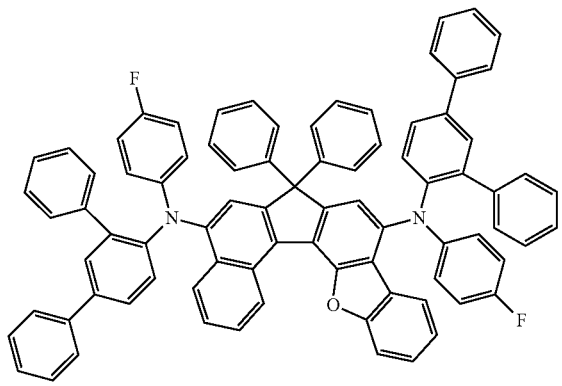
<Compound 578>
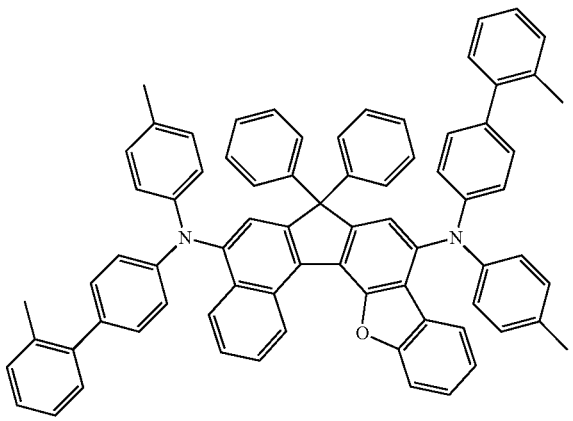
<Compound 579>
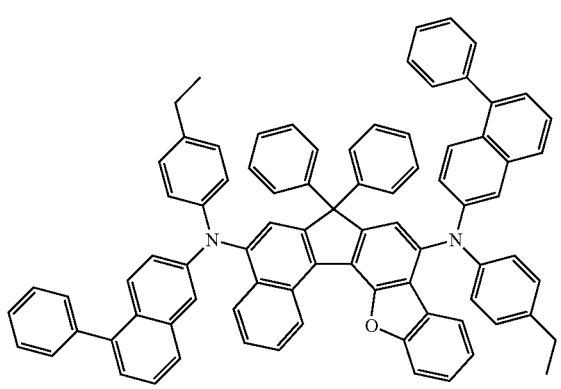
<Compound 580>
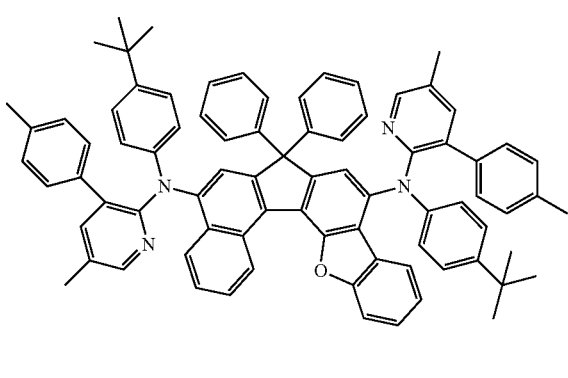

<Compound 581>
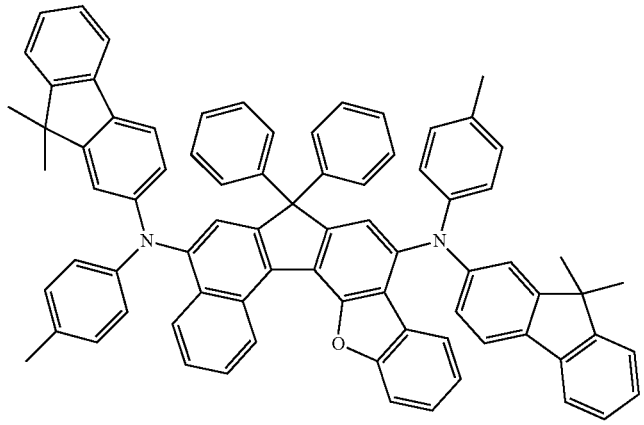
<Compound 582>
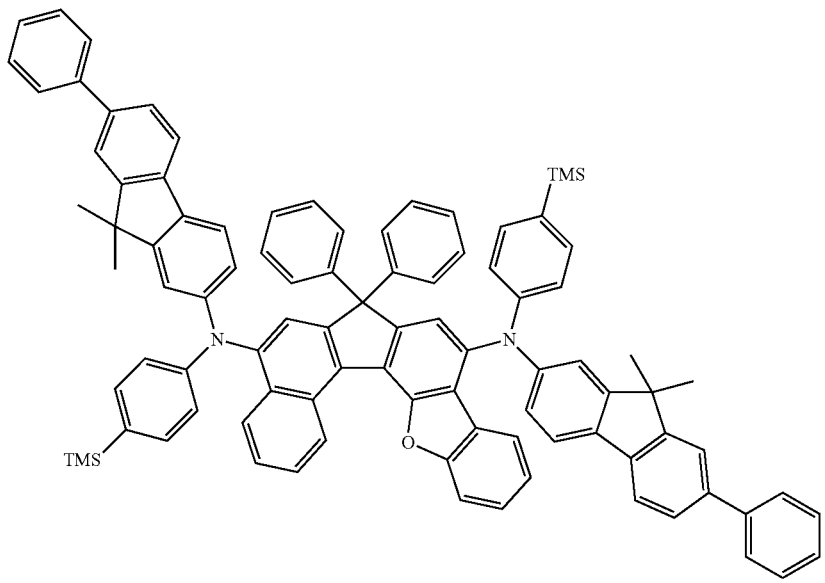
<Compound 583>
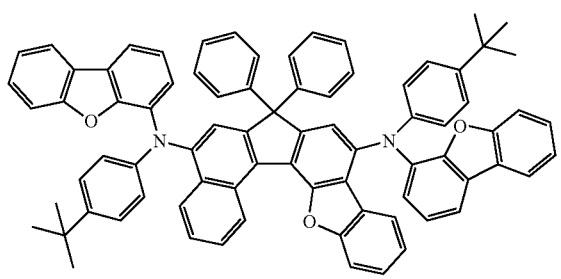
<Compound 584>
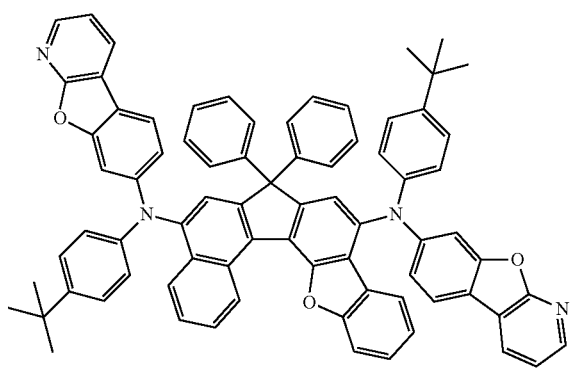

-continued
<Compound 585>
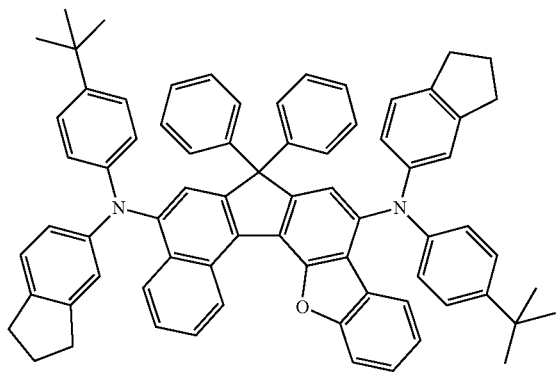
<Compound 586>
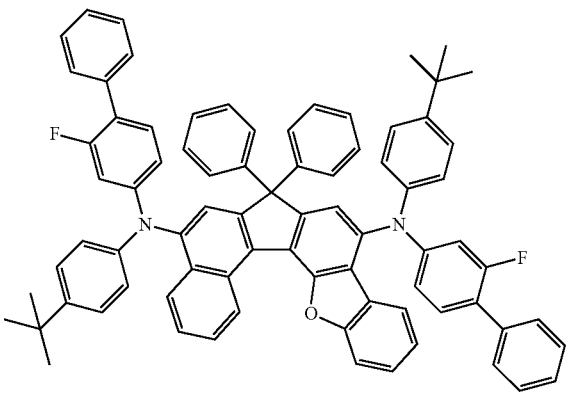
<Compound 587>
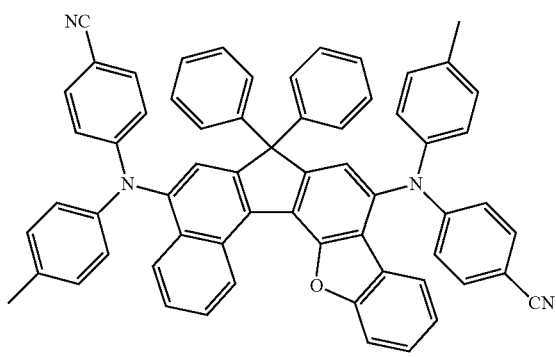
<Compound 588>
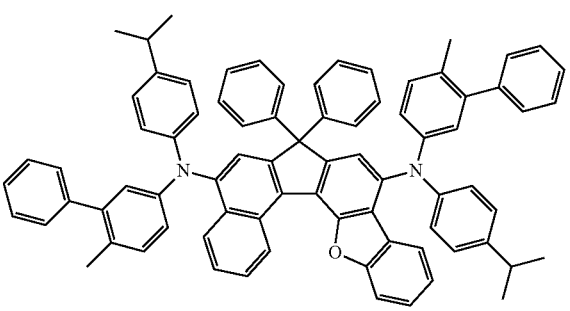
<Compound 589>
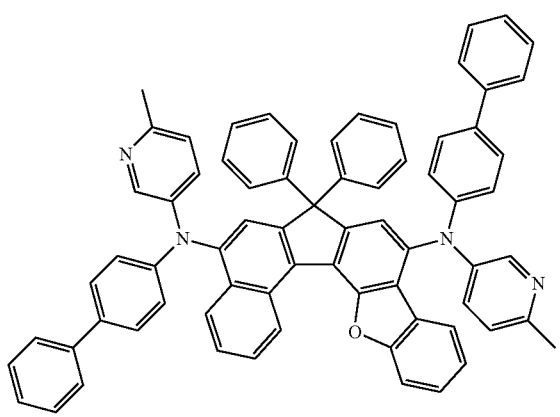
<Compound 590>
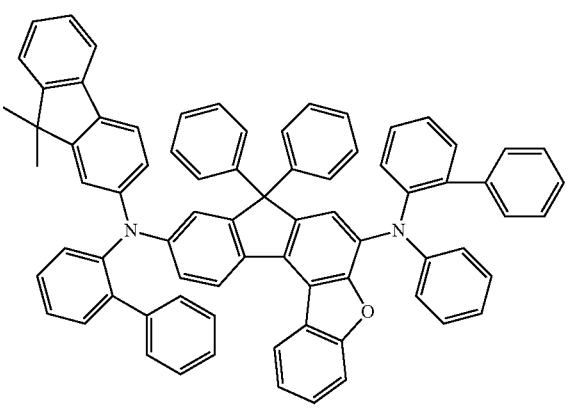

-continued
<Compound 591>
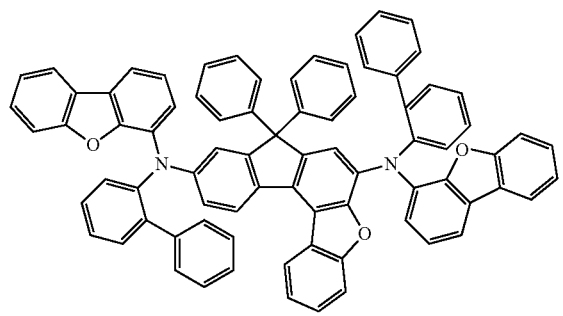
<Compound 592>
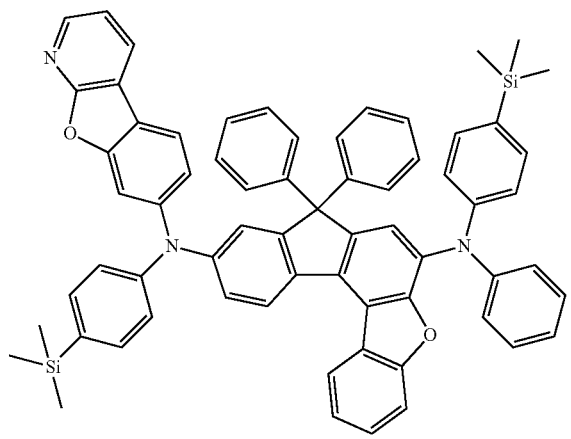
<Compound 593>
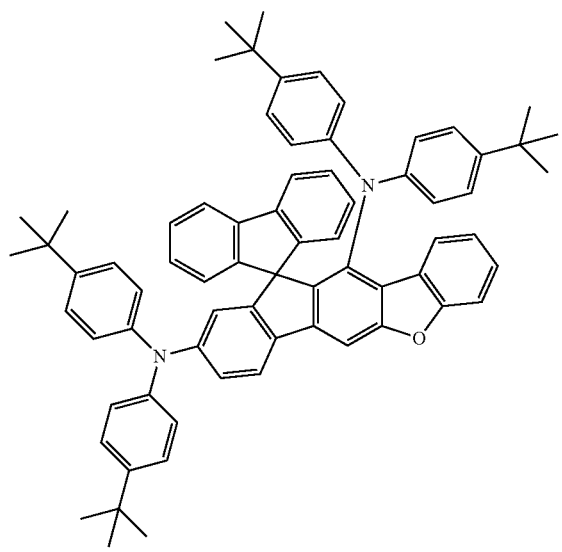
<Compound 594>
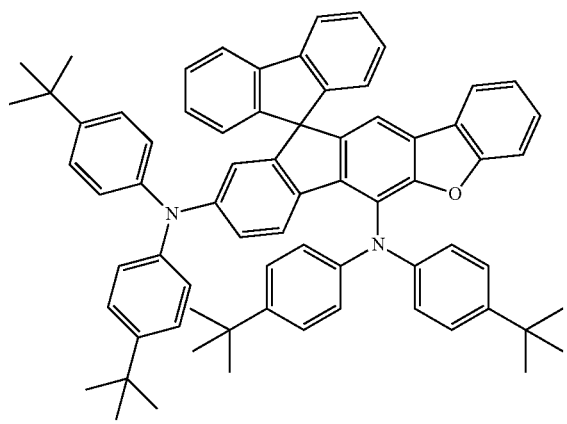
<Compound 595>
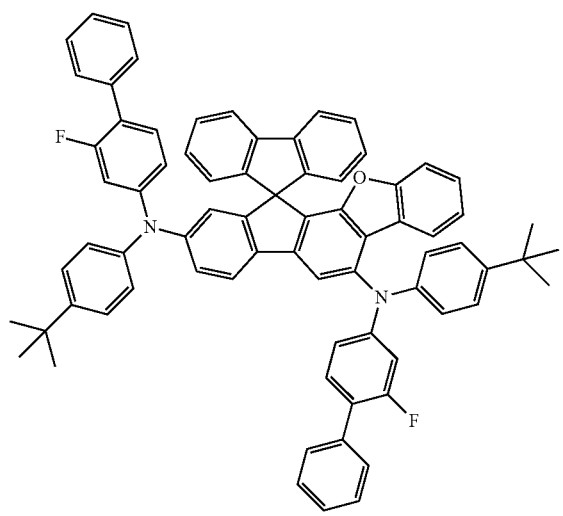
<Compound 596>
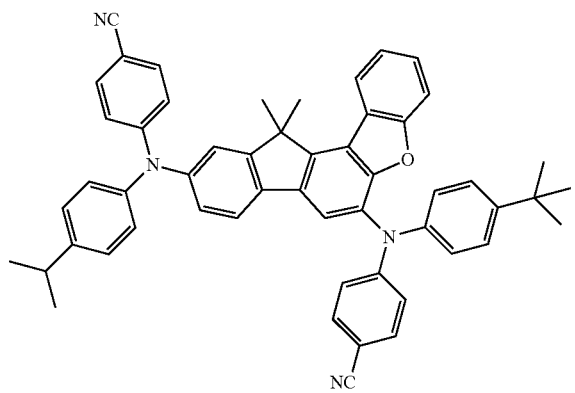

<Compound 597>
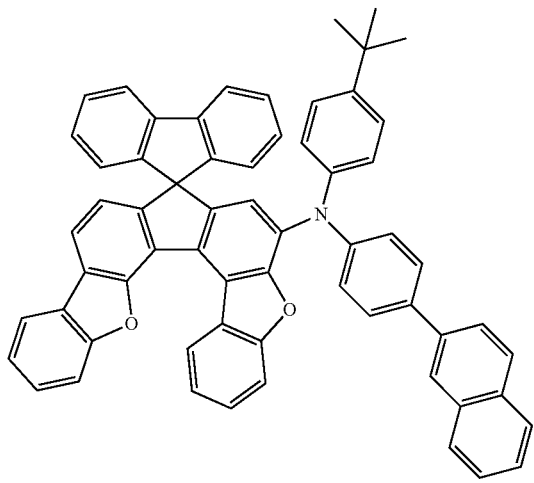
<Compound 598>
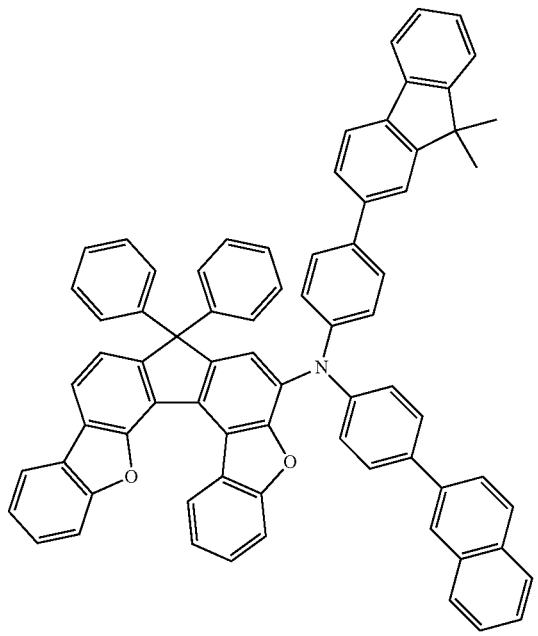
<Compound 599>
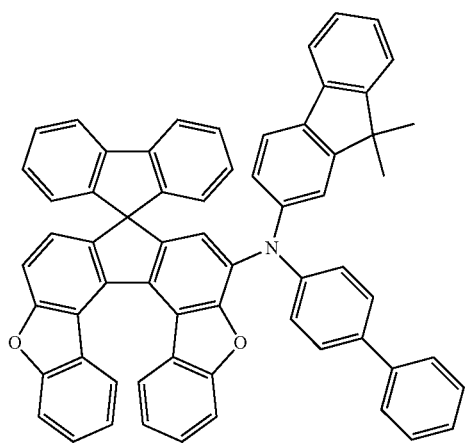
<Compound 600>
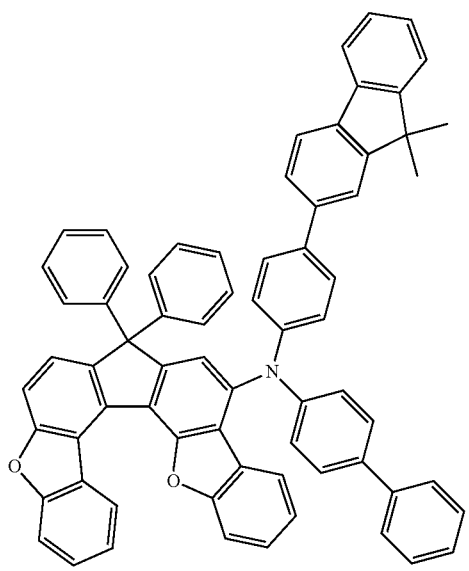

<Compound 601>
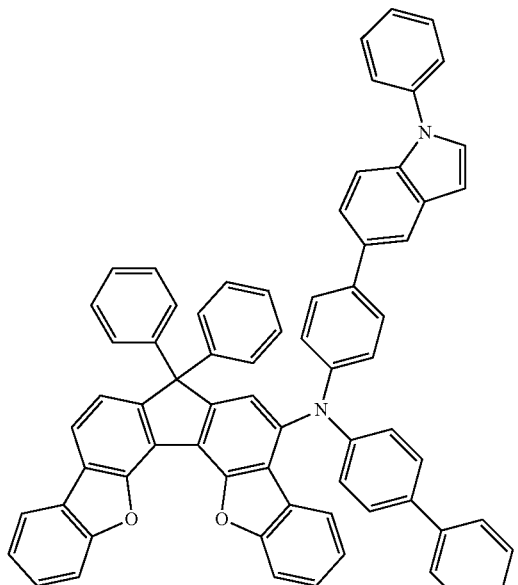
<Compound 602>
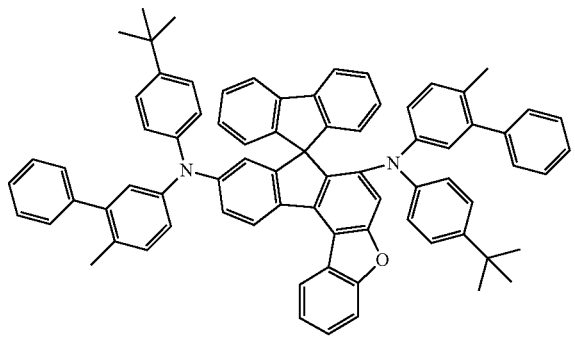
<Compound 603>
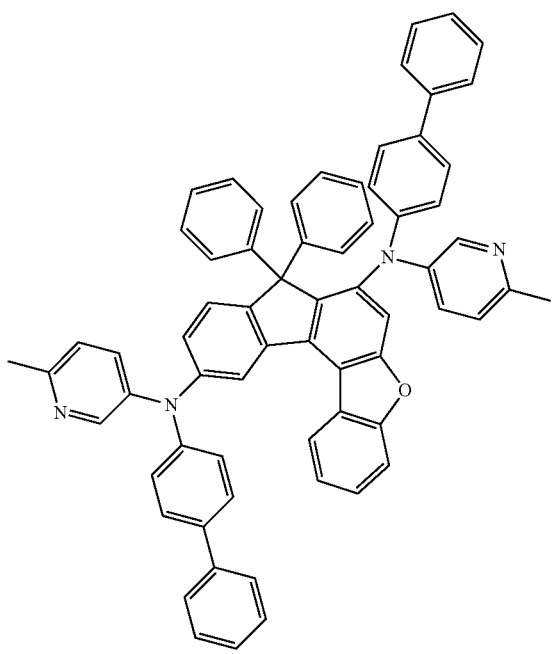
<Compound 604>
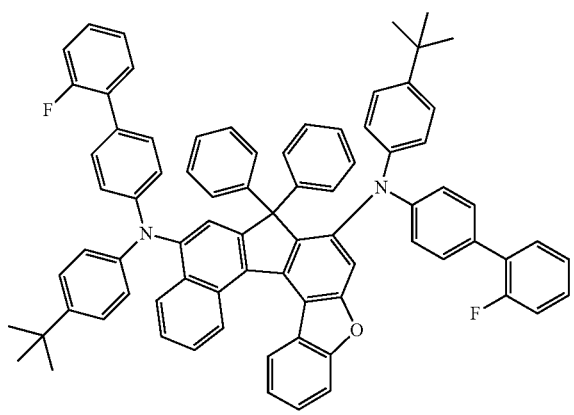
<Compound 605>
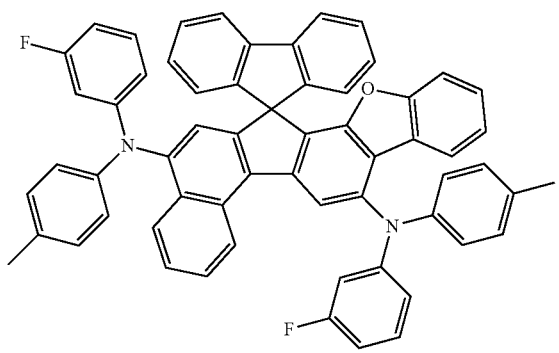
<Compound 606>
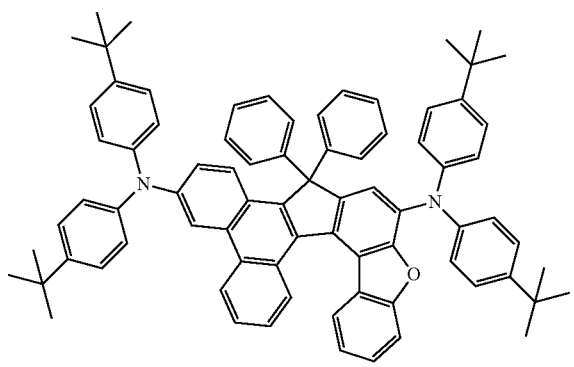

<Compound 607>
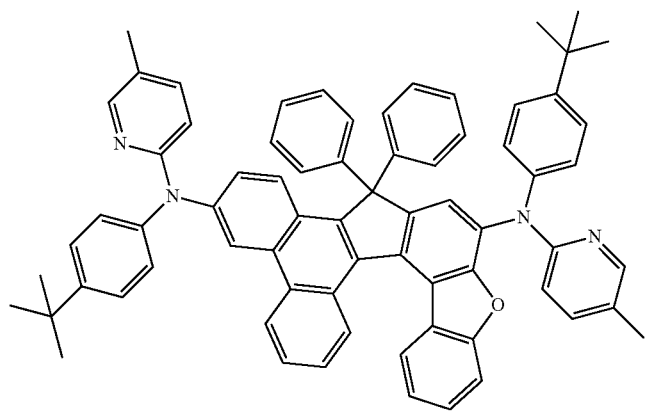
<Compound 608>
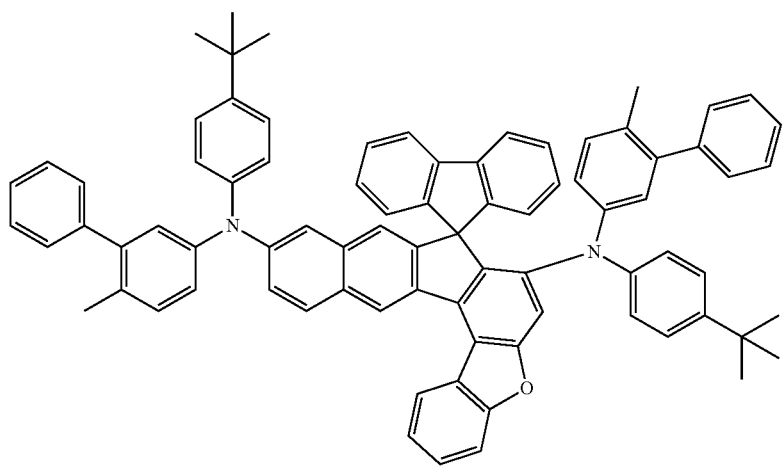
<Compound 609>
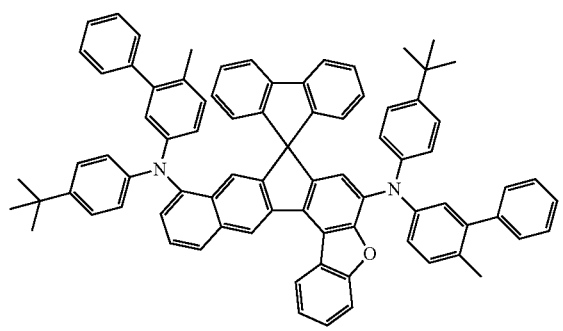
<Compound 610>
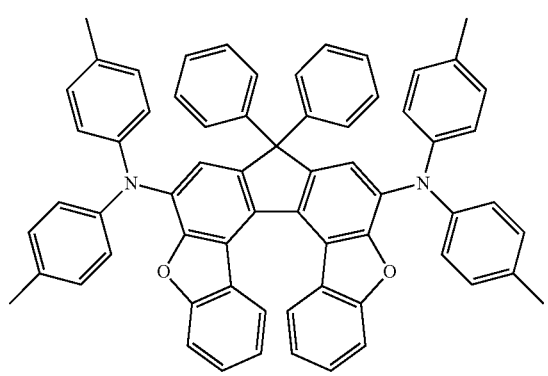

<Compound 611>
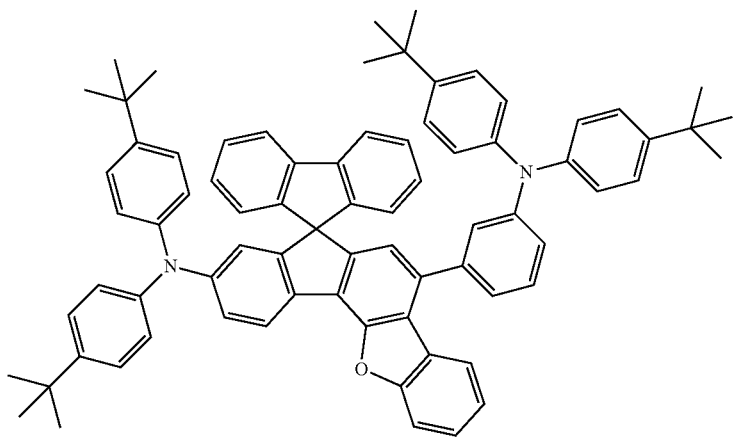
<Compound 612>
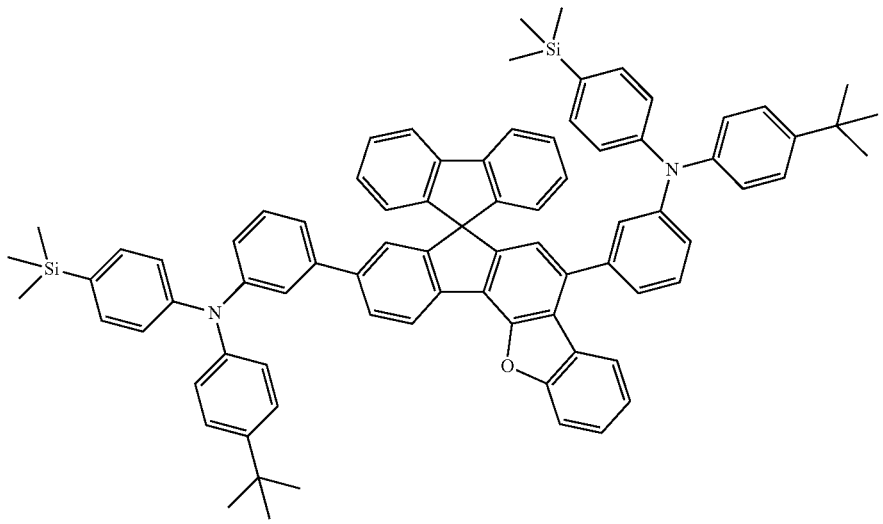
<Compound 613>
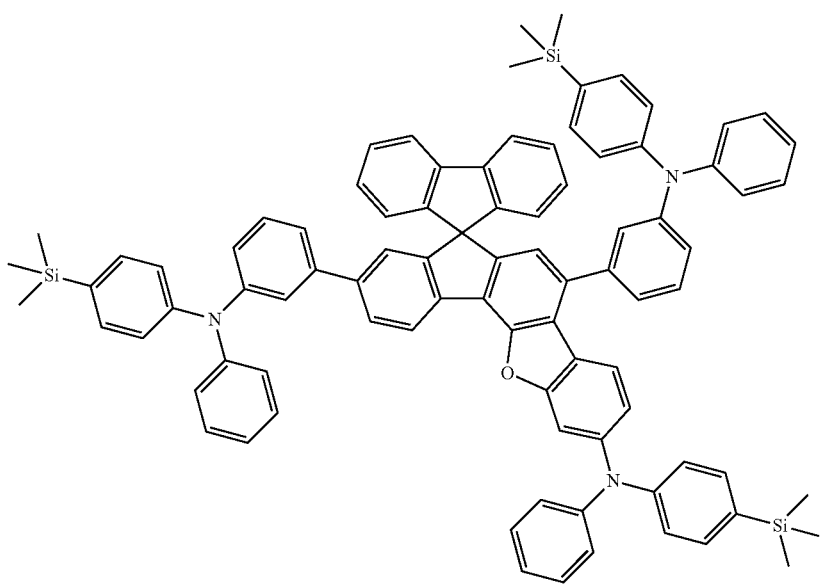

-continued
<Compound 614>
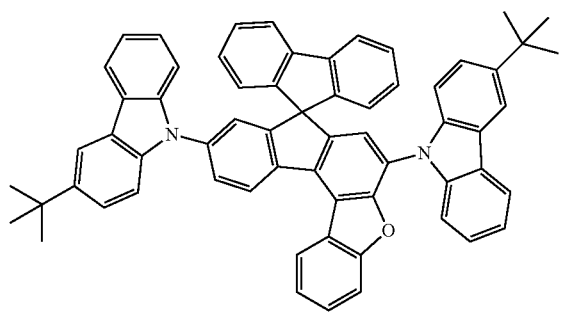
<Compound 615>
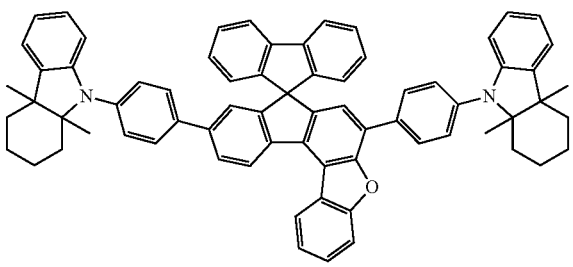
<Compound 616>
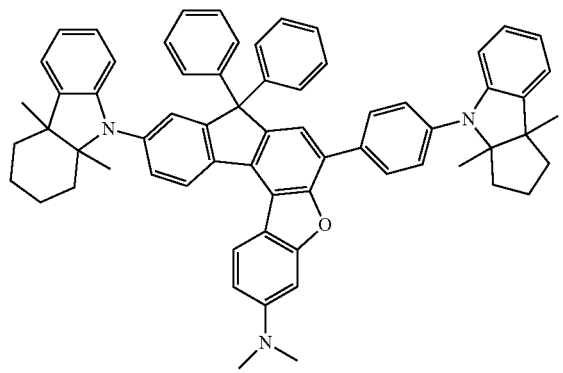
<Compound 617>
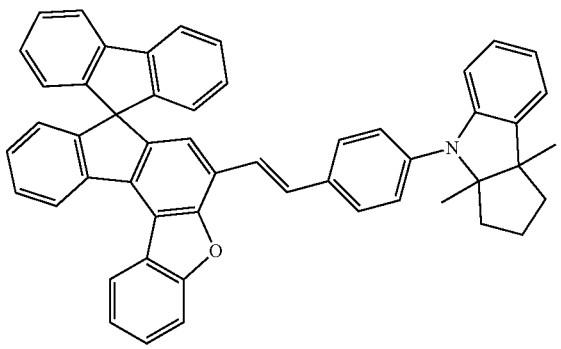
<Compound 618>
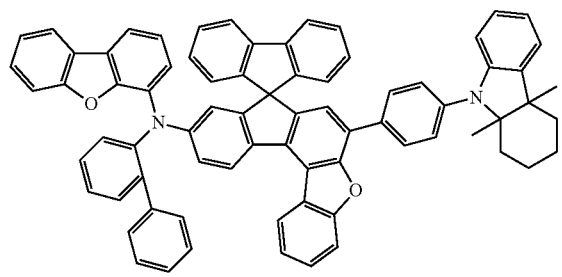
<Compound 619>
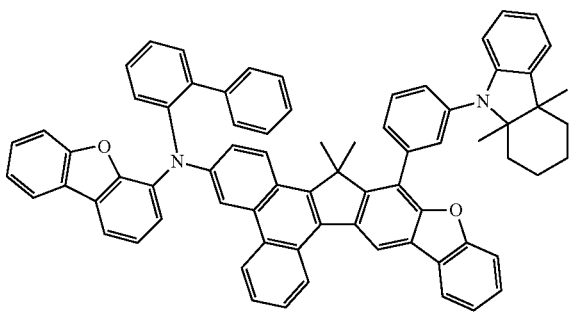
<Compound 620>
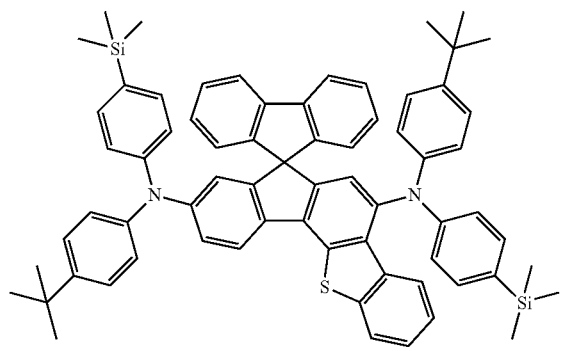
<Compound 621>
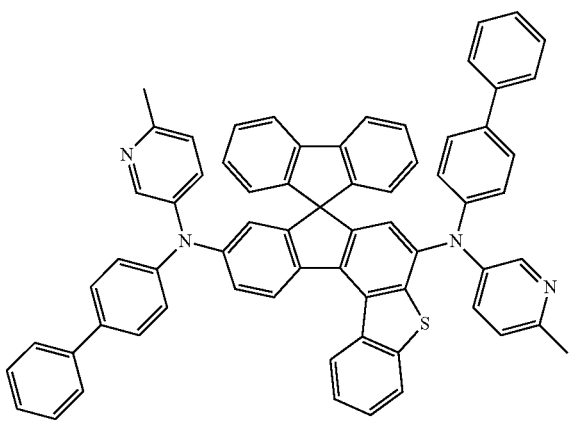

-continued
<Compound 622>
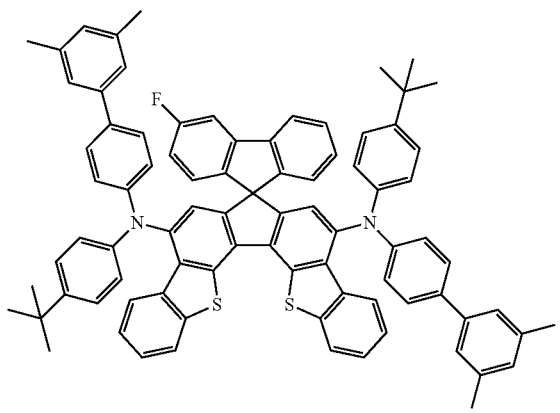
<Compound 623>
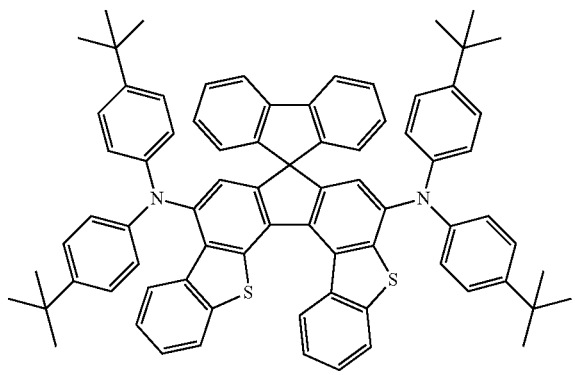
<Compound 624>
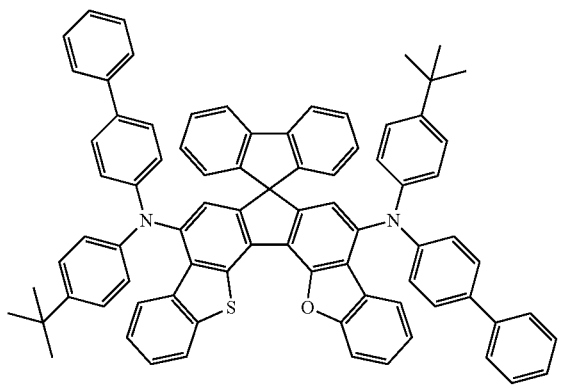
<Compound 625>
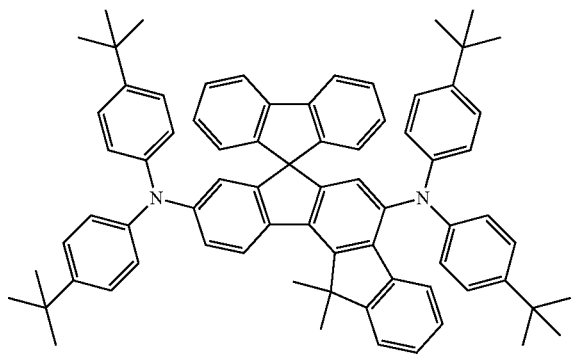
<Compound 626>
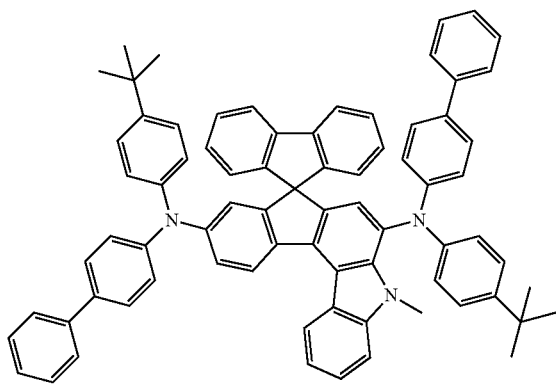
<Compound 627>
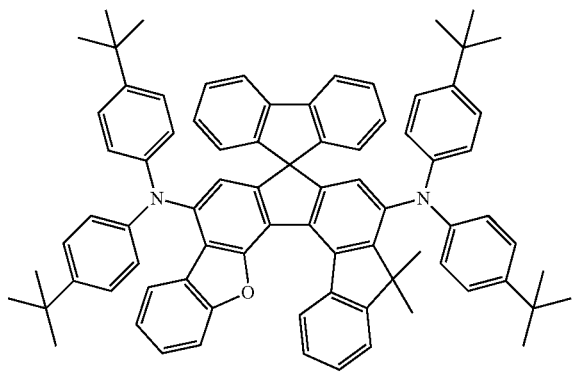

<Compound 628>
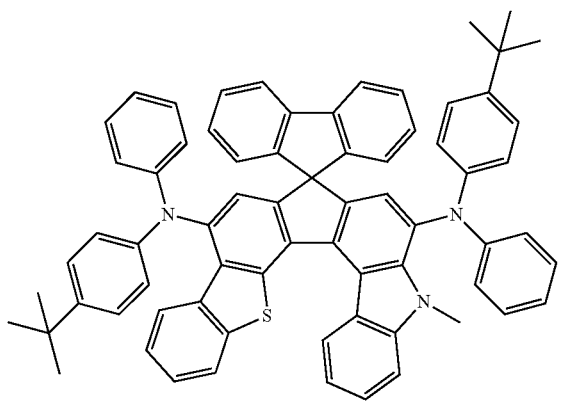
<Compound 629>
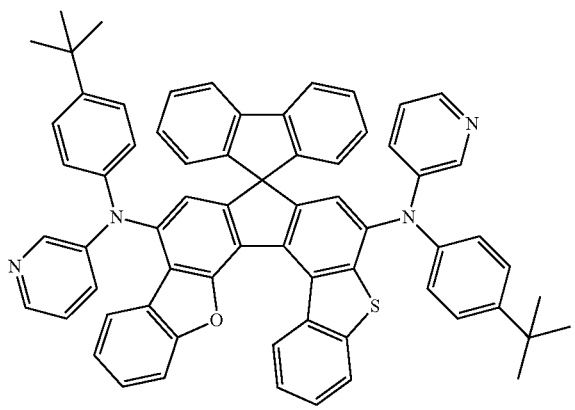
<Compound 630>
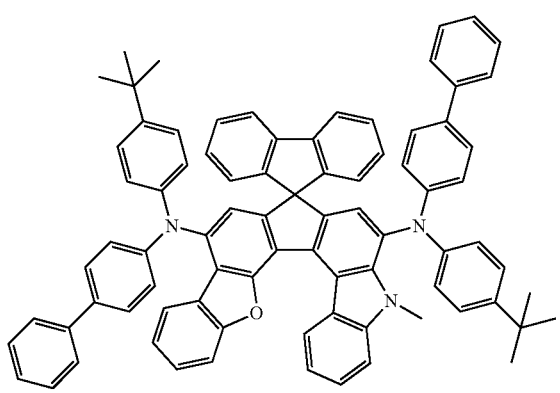
<Compound 631>
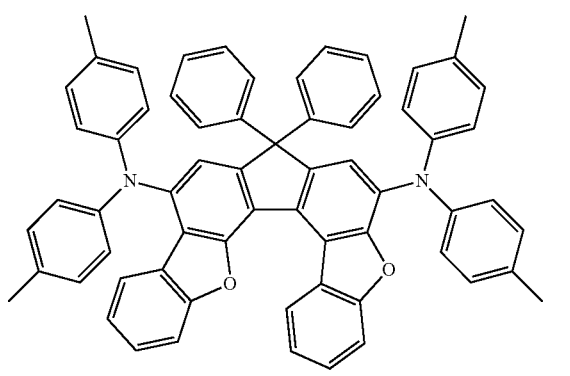
<Compound 632>
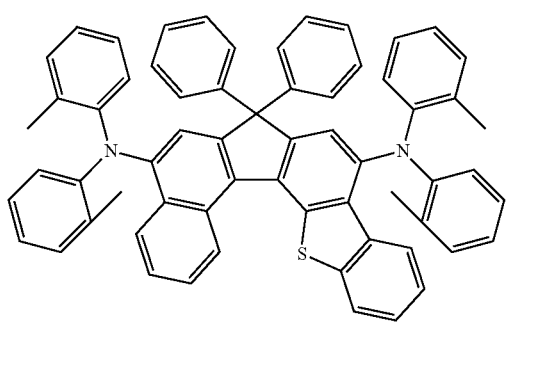
<Compound 633>
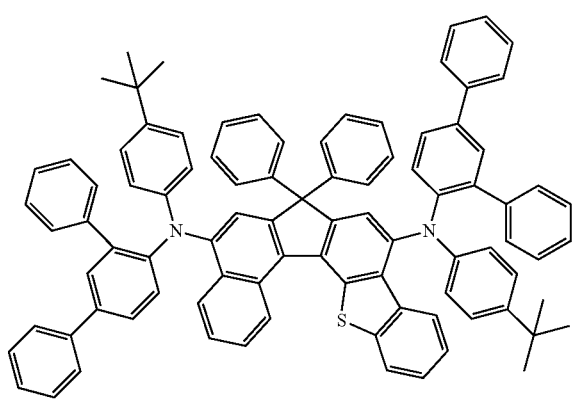
<Compound 634>
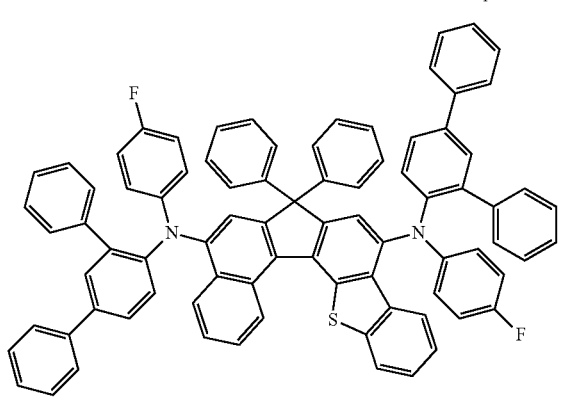
<Compound 635>
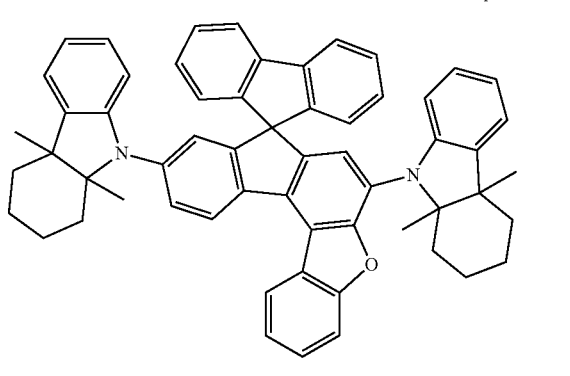

-continued

<Compound 636>

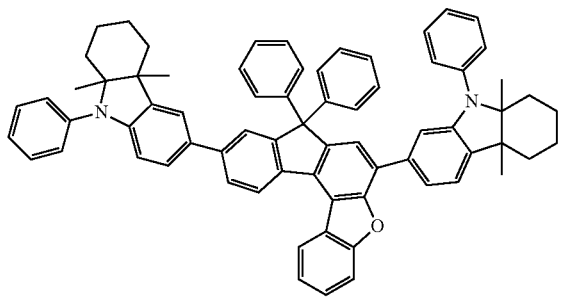

<Compound 637>

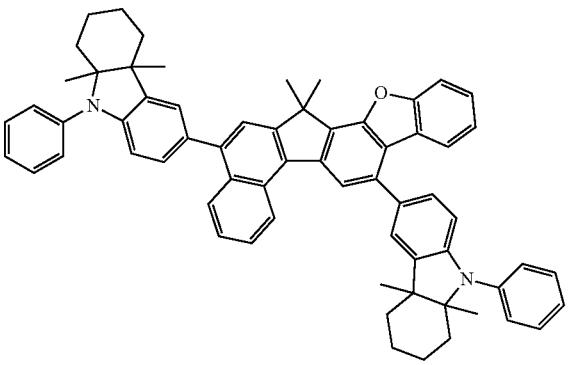

<Compound 638>

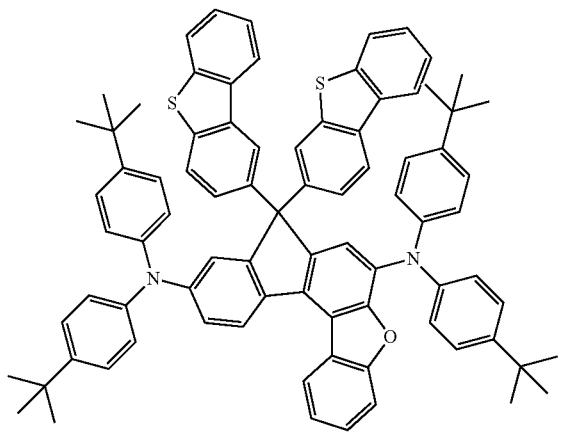

<Compound 639>

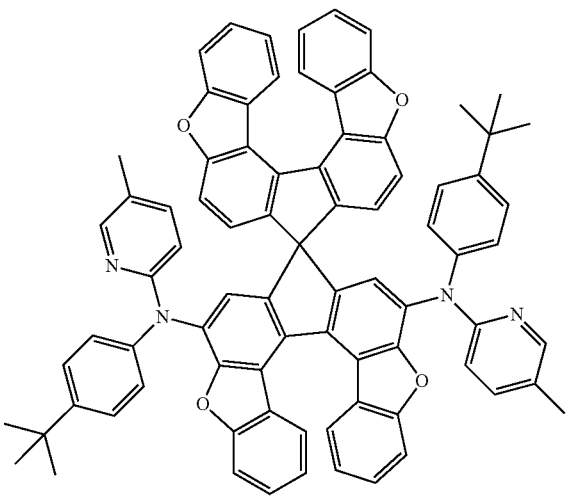

Moreover, the host used in the light-emitting layer may include at least one compound represented by the following [Chemical Formula H] and may further various well-known host materials:

[Chemical Formula H]

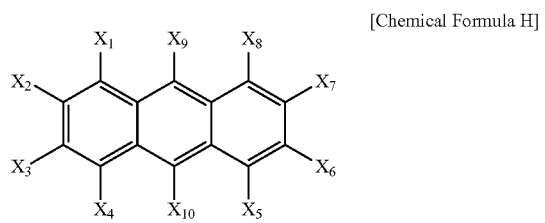

wherein, $X_1$ to $X_{10}$, which may be the same or different, are each independently selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 5 to 50 carbon atoms, a substituted or unsubstituted heteroaryl of 3 to 50 carbon atoms bearing O, N, or S as a heteroatom, a substituted or unsubstituted silicone, a substituted or unsubstituted boron, a substituted or unsubstituted silane, a carbonyl, a phosphoryl, an amino, a nitrile, a hydroxy, a nitro, a halogen, an amide, and an ester, wherein adjacent radicals may form an aliphatic, an aromatic, an aliphatic hetero, or an aromatic hetero fused ring.

More particularly, the host may be represented by any one selected from [Compound 701] to [Compound 896], but is not limited thereto:

[Compound 701]
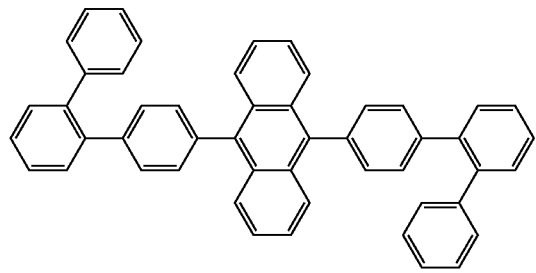
[Compound 702]
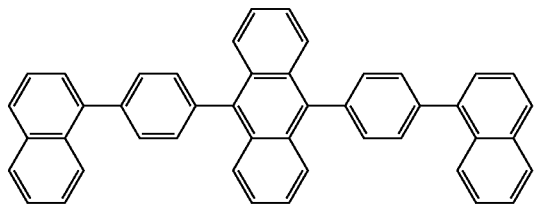
[Compound 703]
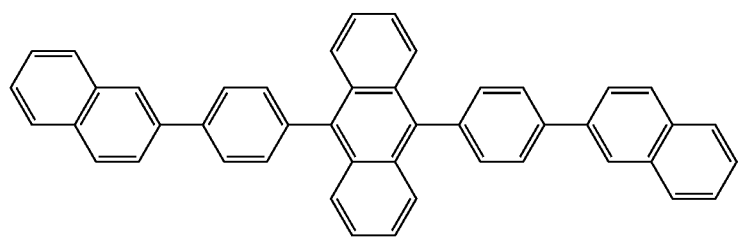
[Compound 704]
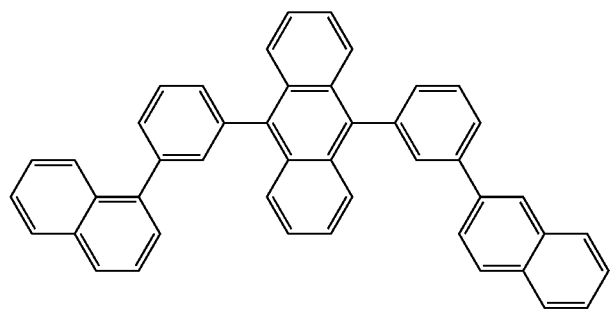
[Compound 705]
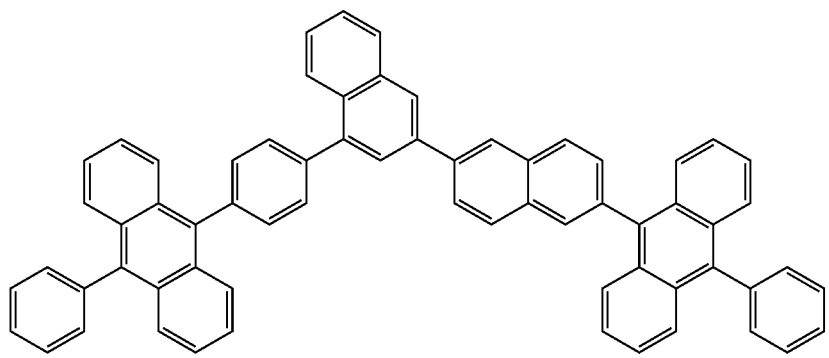
[Compound 706]
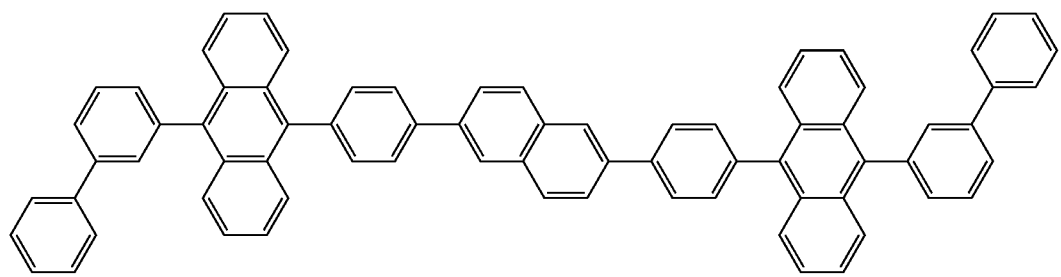

[Compound 707]
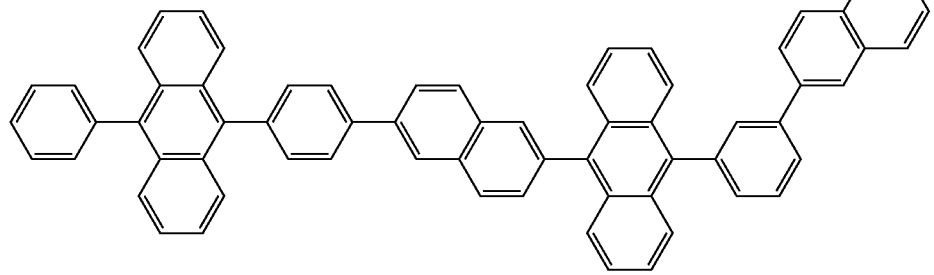
[Compound 708]
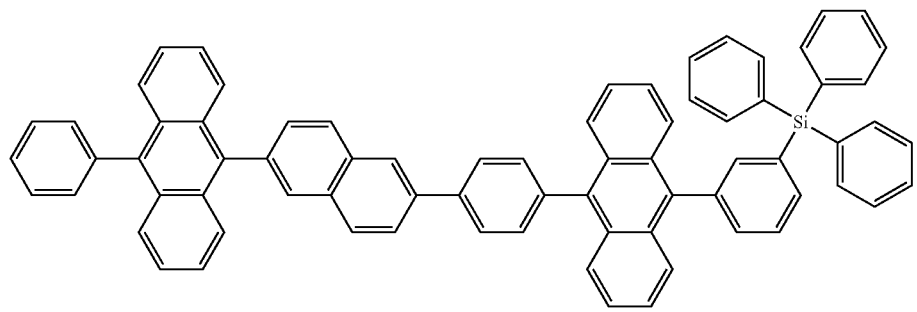
[Compound 709]
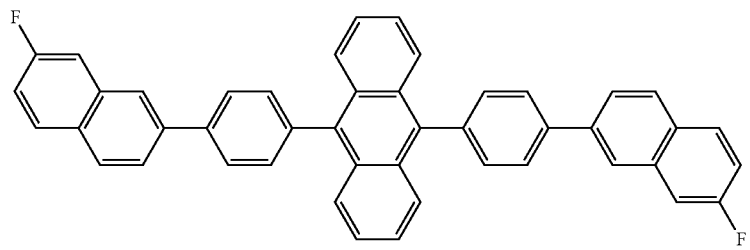
[Compound 710]
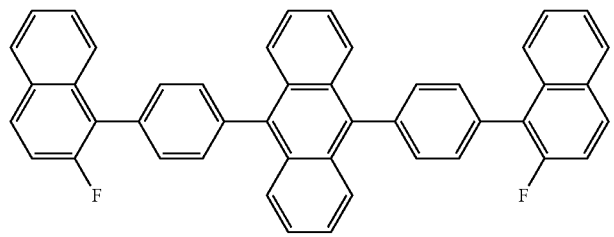
[Compound 711]
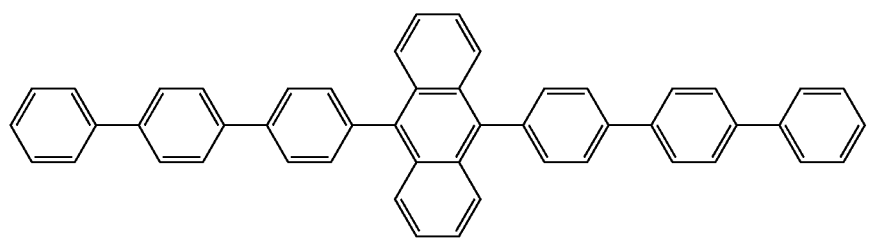
[Compound 712]
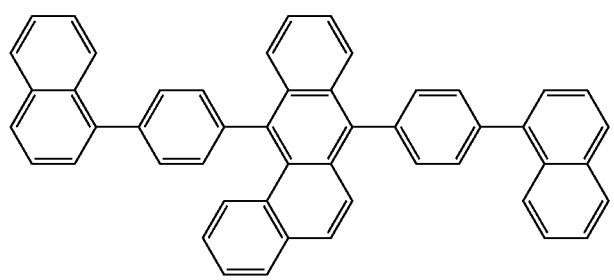

[Compound 713]
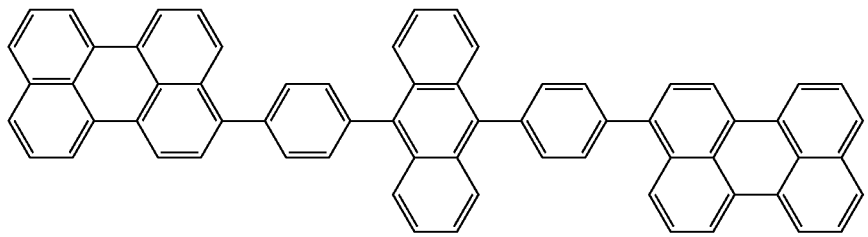
[Compound 714]
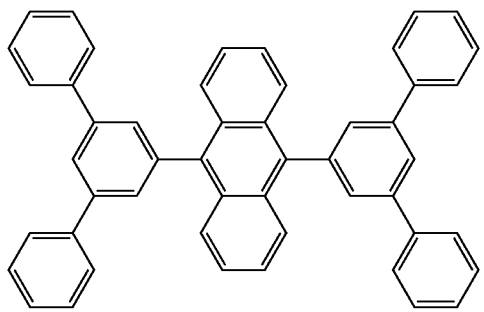
[Compound 715]
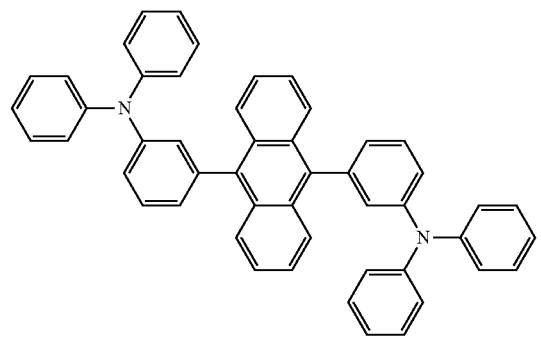
[Compound 716]
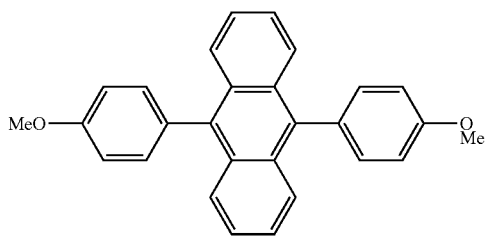
[Compound 717]
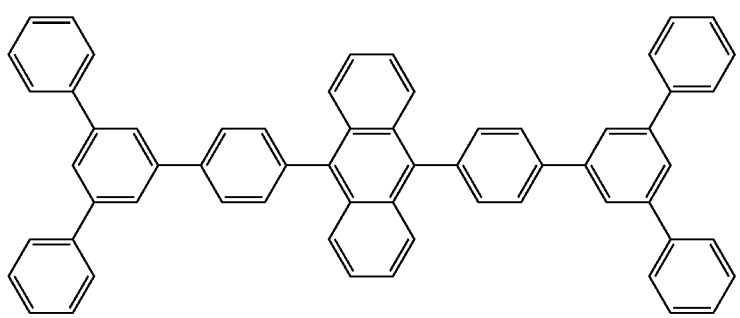
[Compound 718]
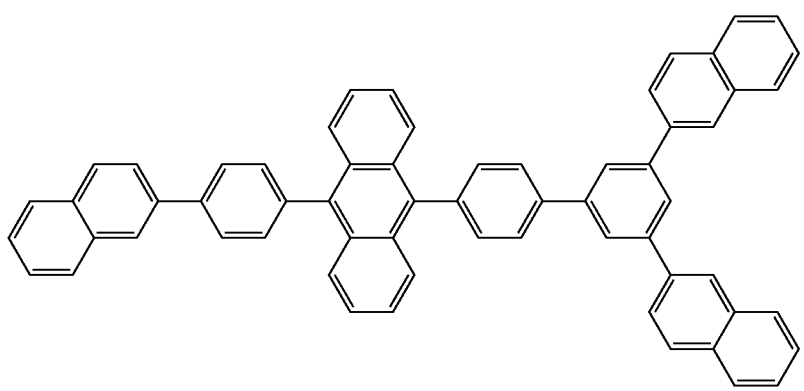

[Compound 719]
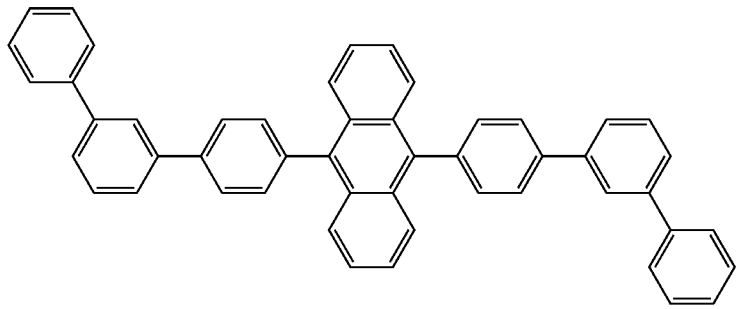
[Compound 720]
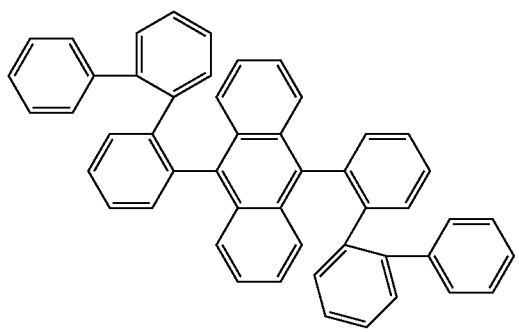
[Compound 721]
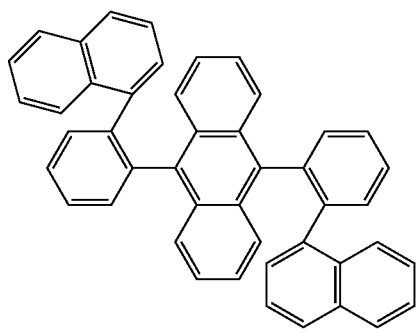
[Compound 722]
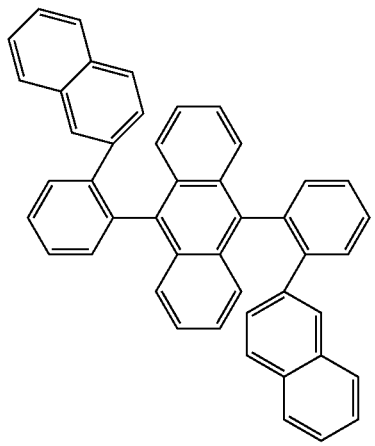
[Compound 723]
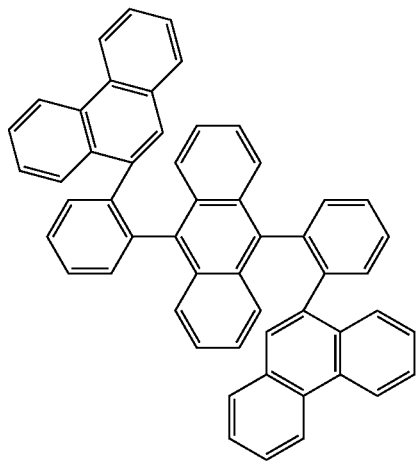
[Compound 724]
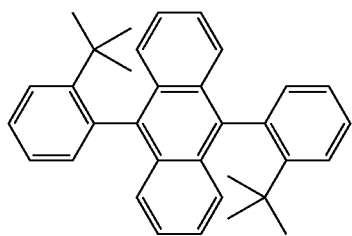
[Compound 725]
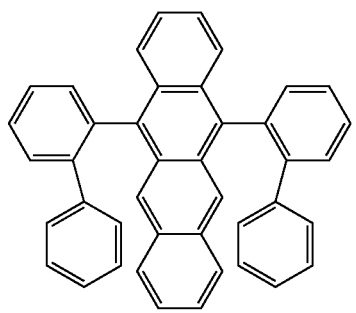

-continued
[Compound 726]
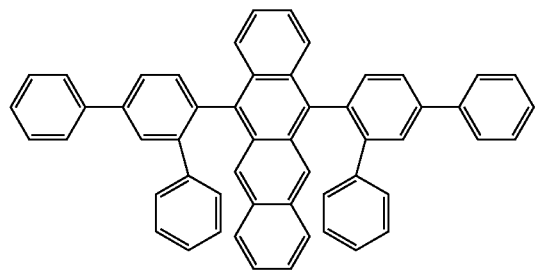
[Compound 727]
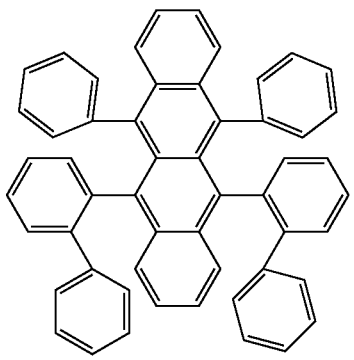
[Compound 728]
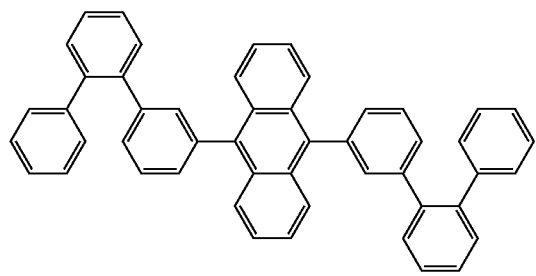
[Compound 729]
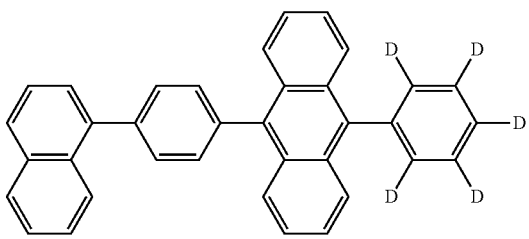
[Compound 730]
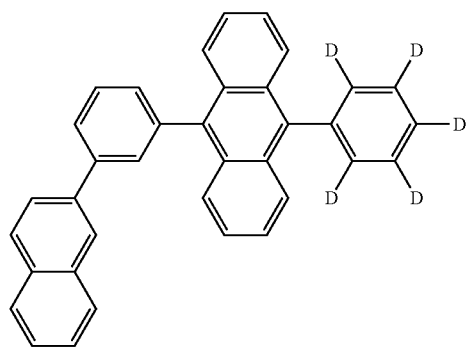
[Compound 731]
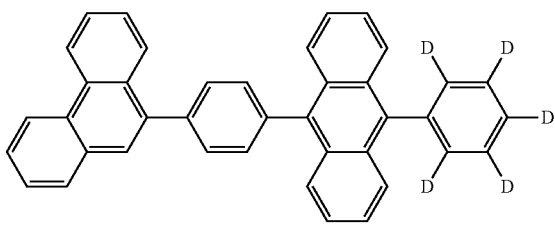
[Compound 732]
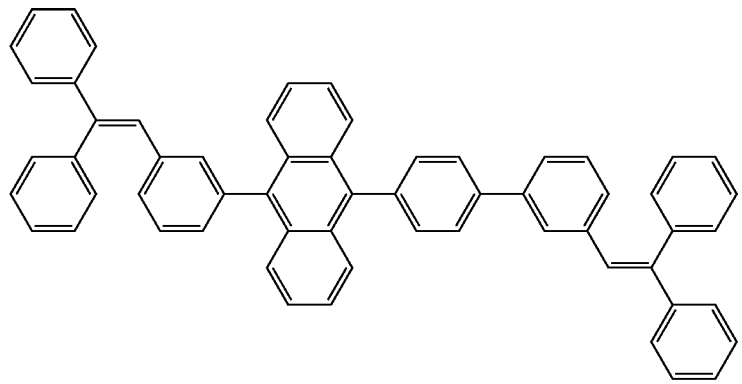

-continued
[Compound 733]
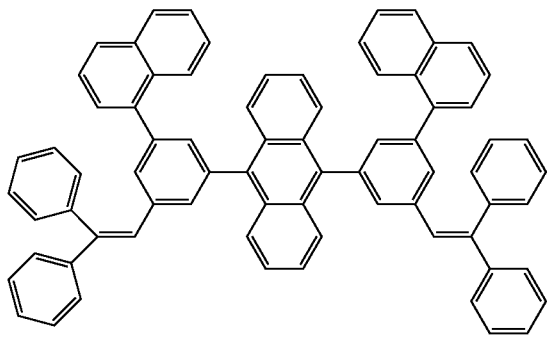
[Compound 734]
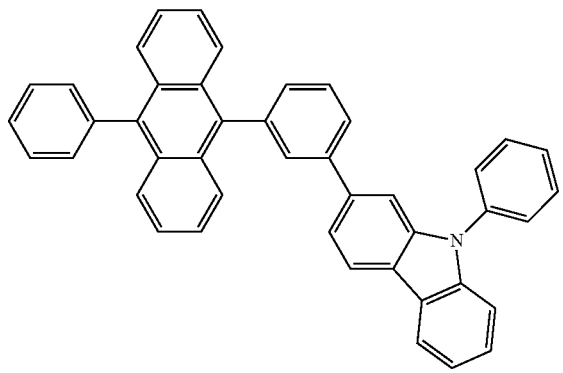
[Compound 735]
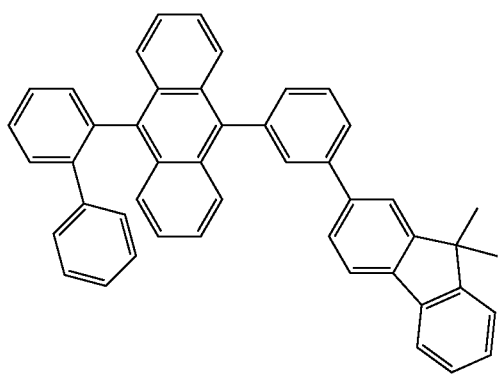
[Compound 736]
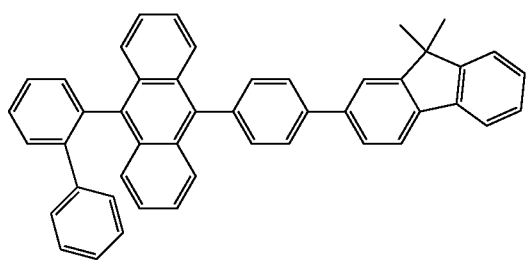
[Compound 737]
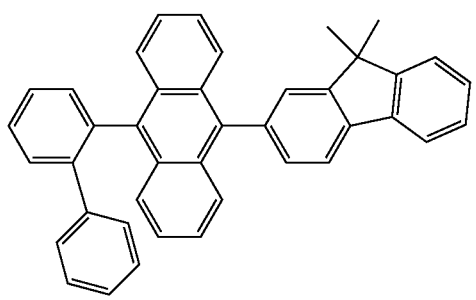
[Compound 738]
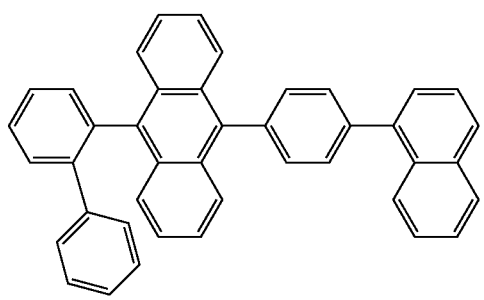
[Compound 739]
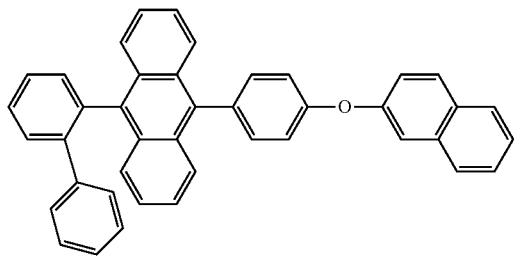
[Compound 740]
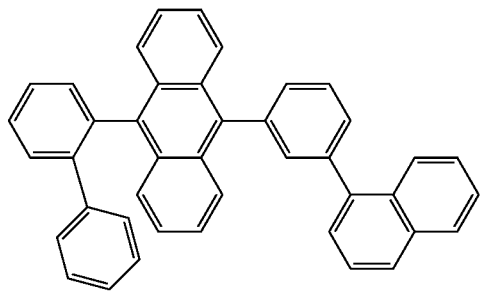

-continued
[Compound 741]
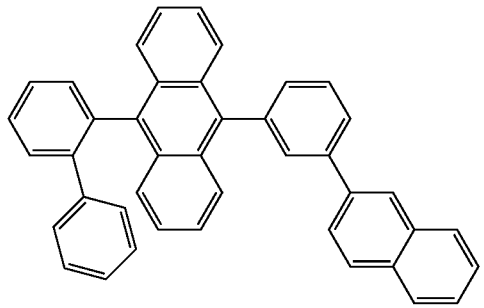
[Compound 742]
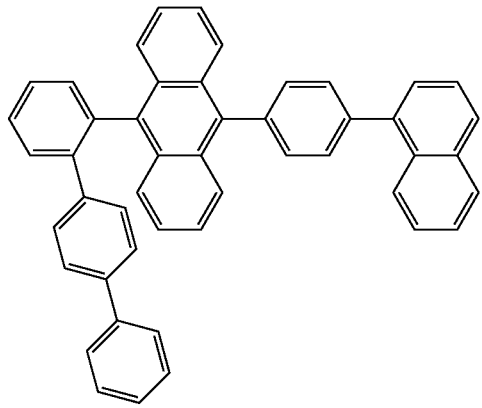
[Compound 743]
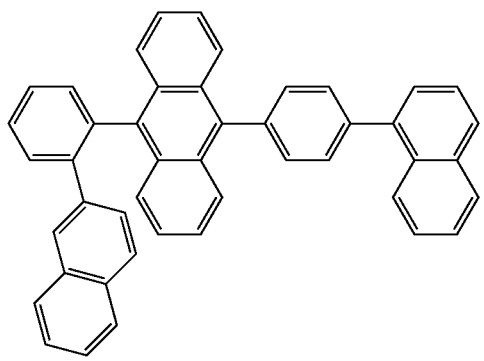
[Compound 744]
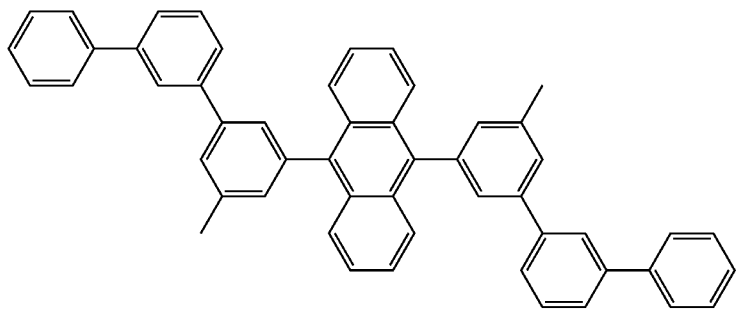
[Compound 745]
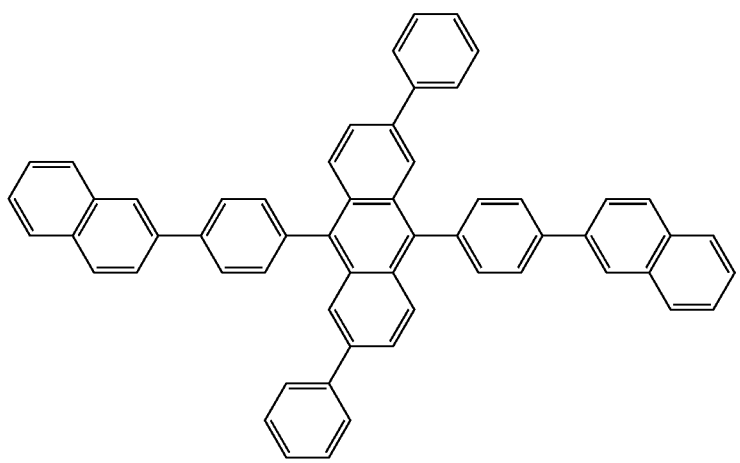

[Compound 746]
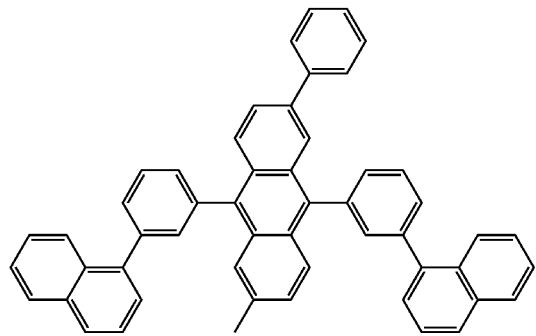
[Compound 747]
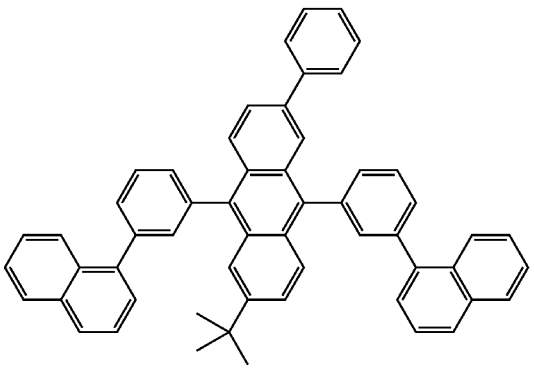
[Compound 748]
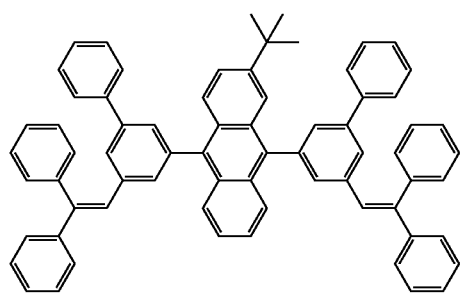
[Compound 749]
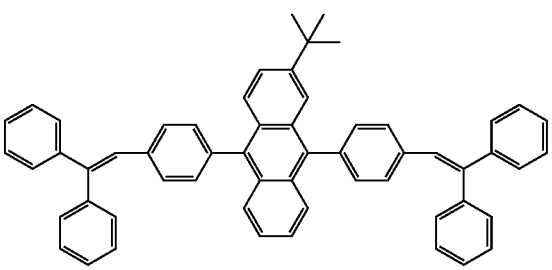
[Compound 750]
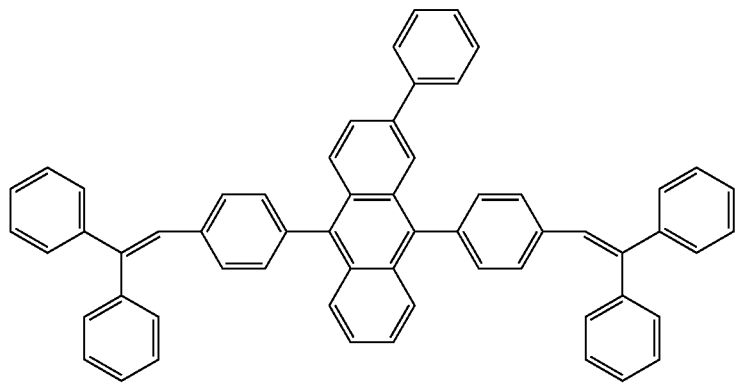
[Compound 751]
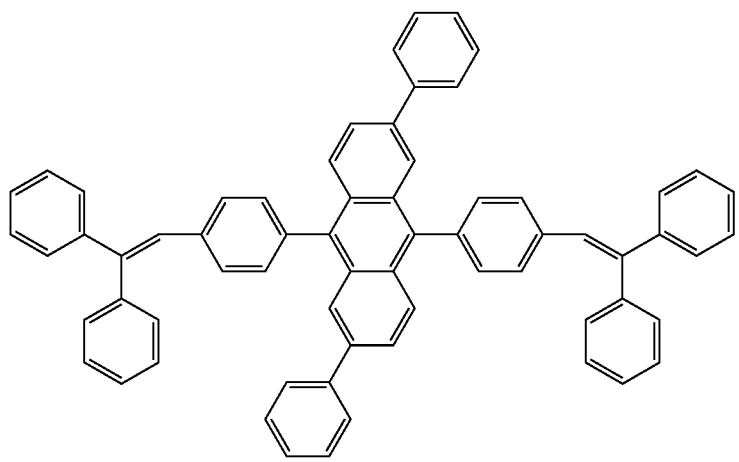

[Compound 752]
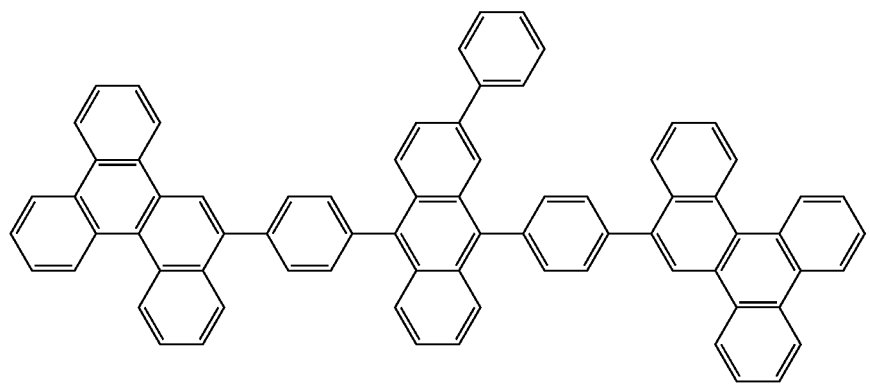
[Compound 753]
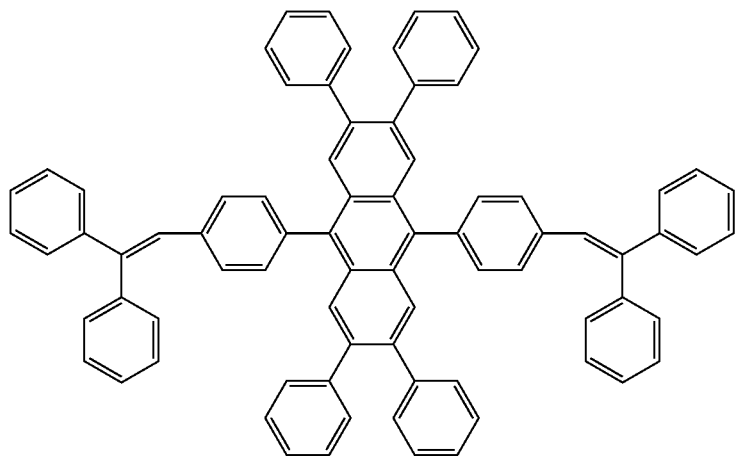
[Compound 754]
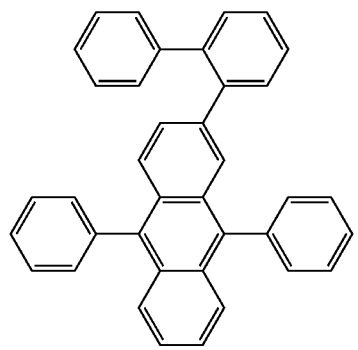
[Compound 755]
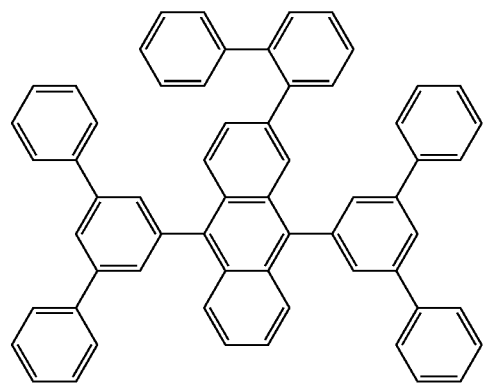
[Compound 756]
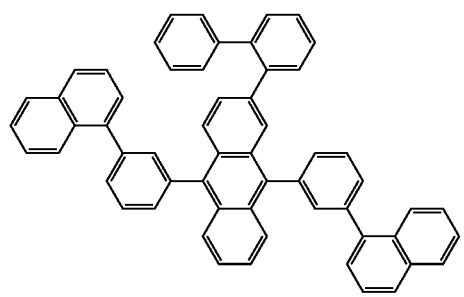
[Compound 757]
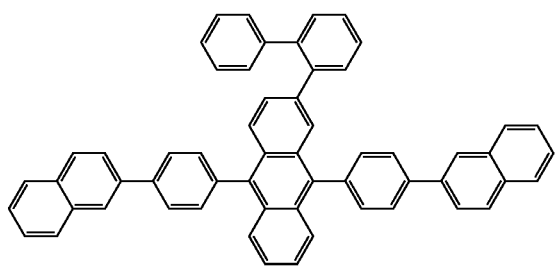

[Compound 758]
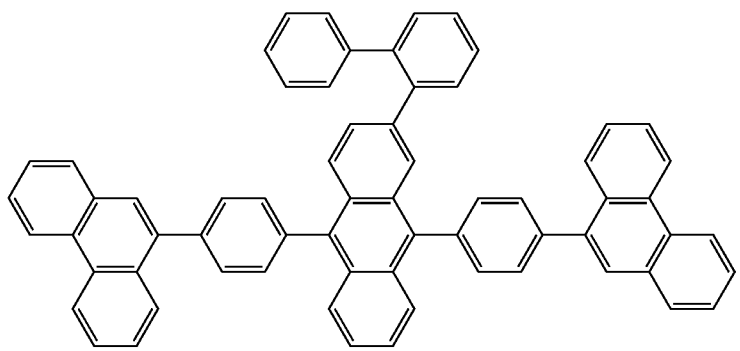
[Compound 759]
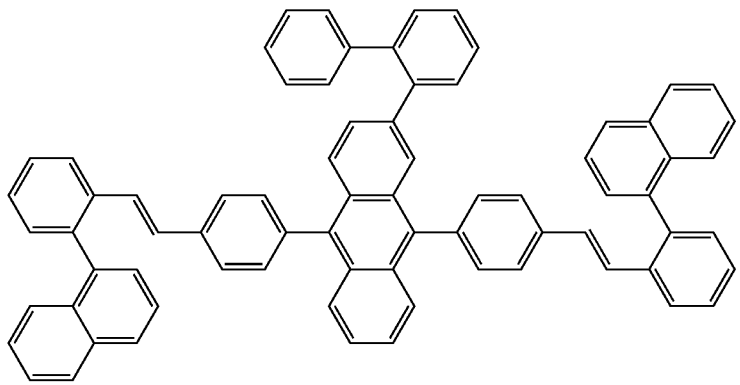
[Compound 760]
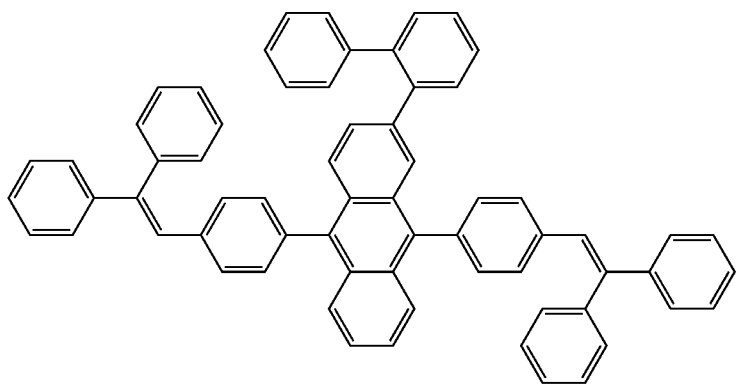
[Compound 761]
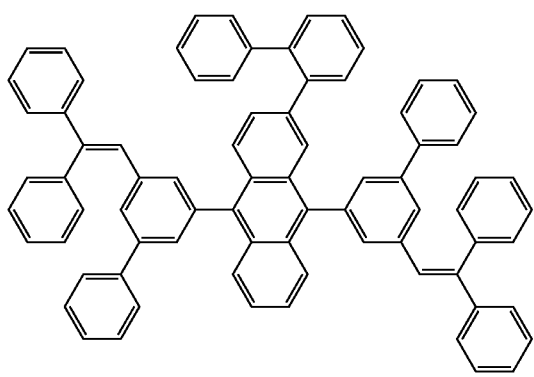
[Compound 762]
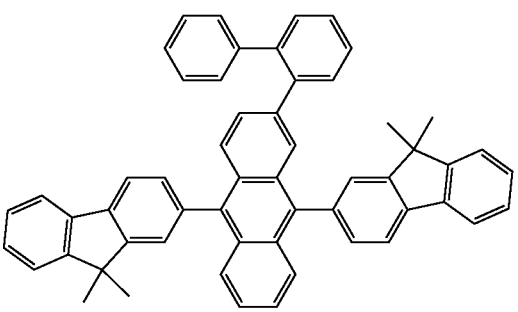

[Compound 763]
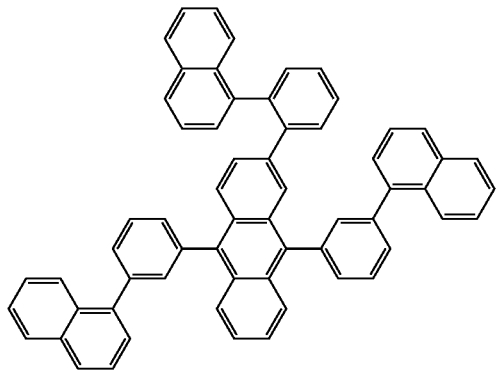
[Compound 764]
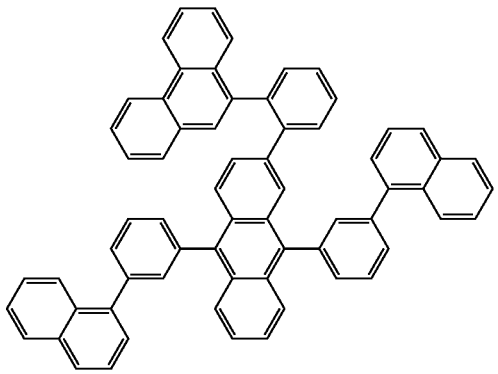
[Compound 765]
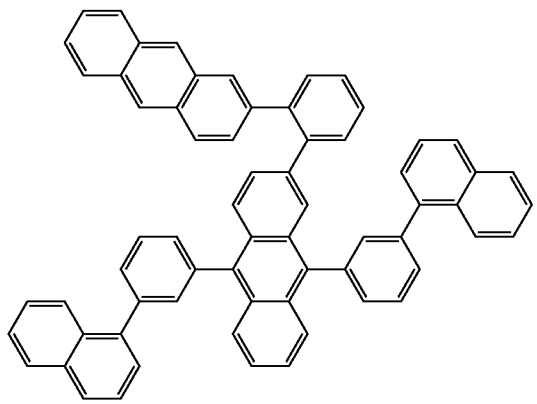
[Compound 766]
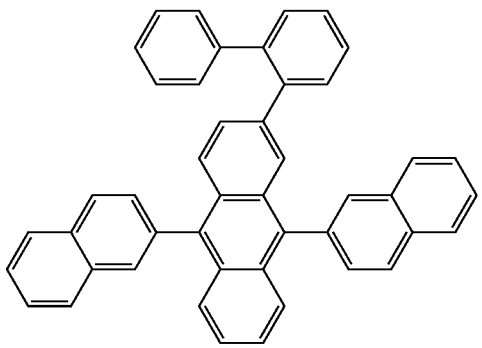
[Compound 767]
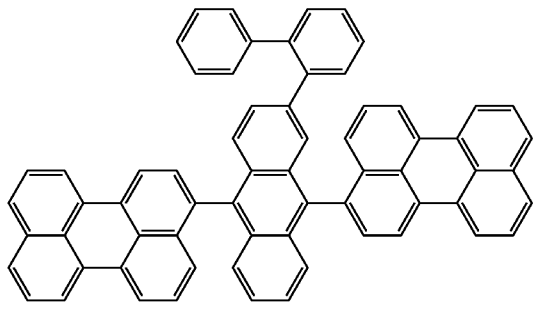
[Compound 768]
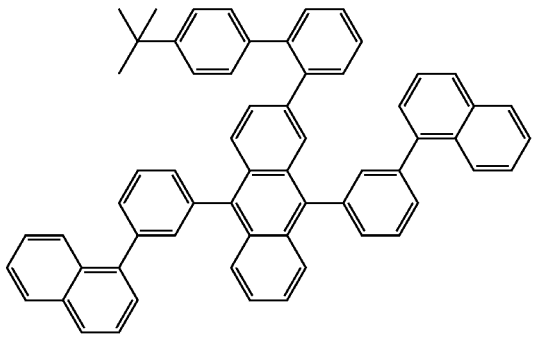
[Compound 769]
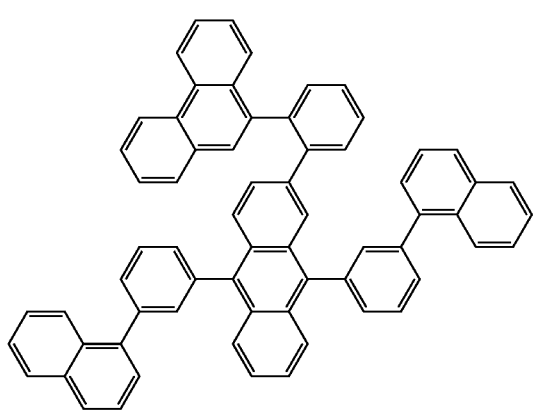
[Compound 770]
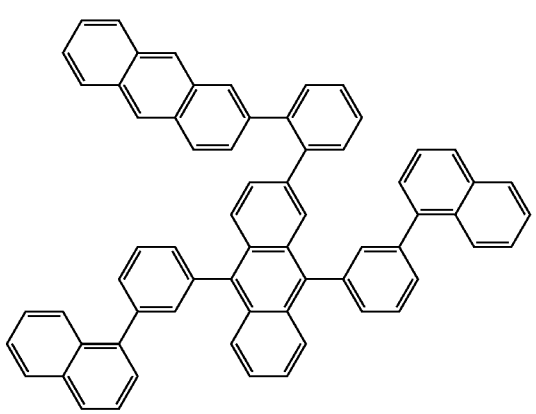

[Compound 771]
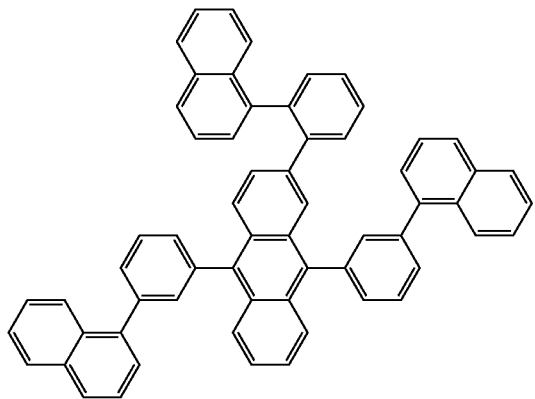
[Compound 772]
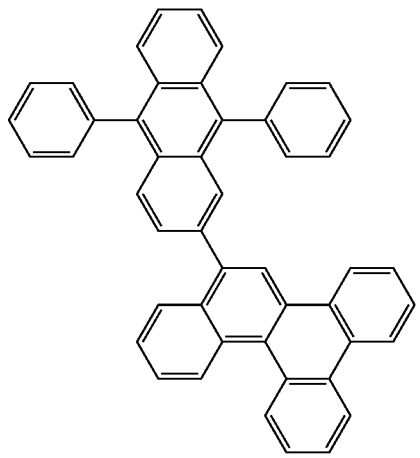
[Compound 773]
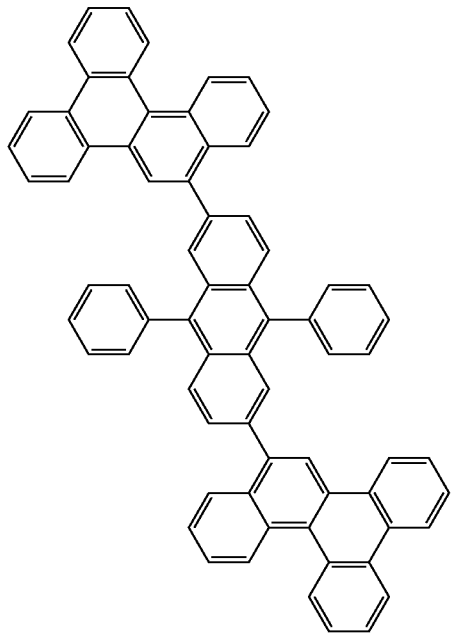
[Compound 774]
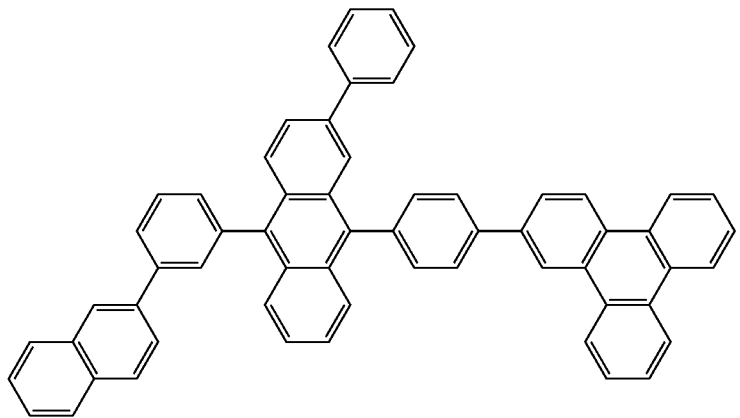

[Compound 775]
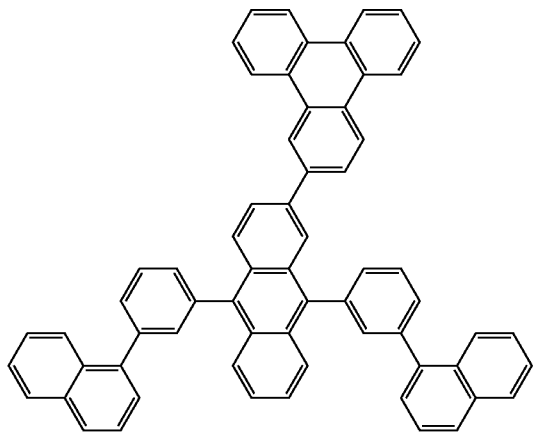
[Compound 776]
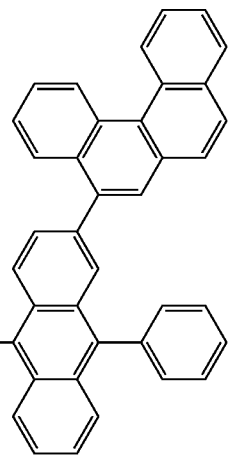
[Compound 777]
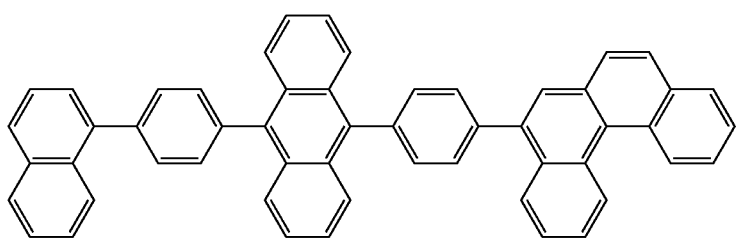
[Compound 778]
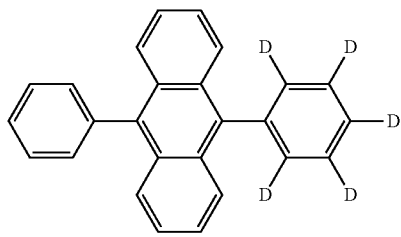
[Compound 779]
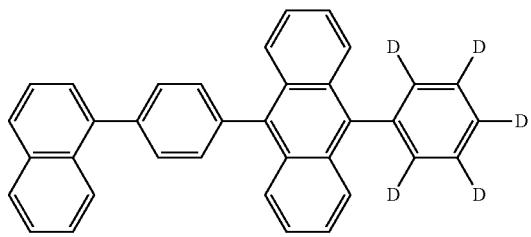
[Compound 780]
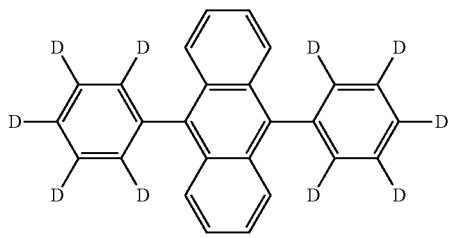
[Compound 781]
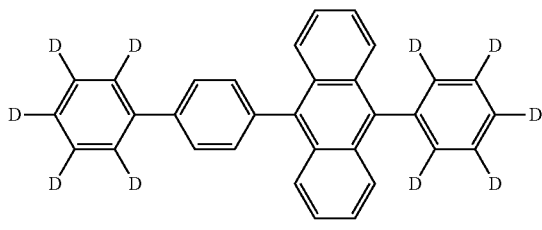
[Compound 782]
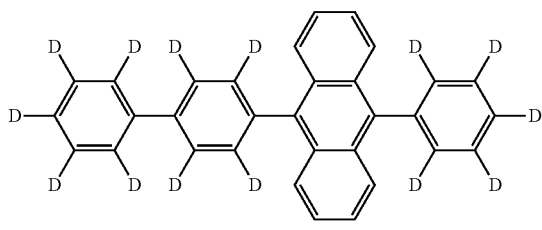
[Compound 783]
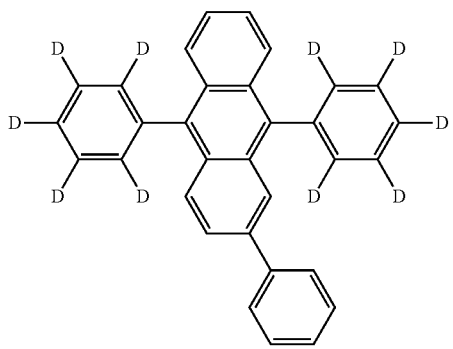

[Compound 784]
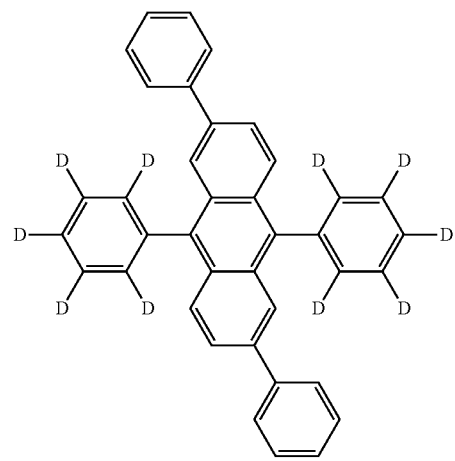
[Compound 785]
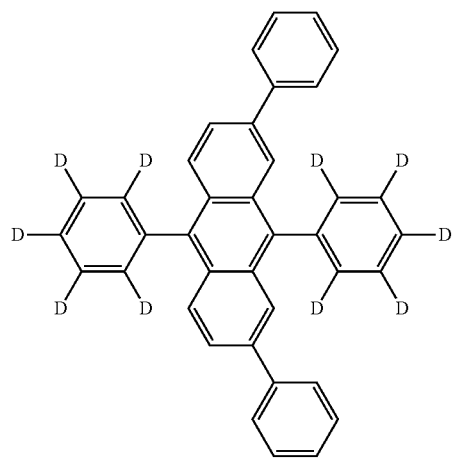
[Compound 786]
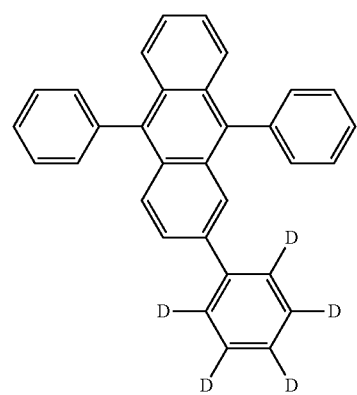
[Compound 787]
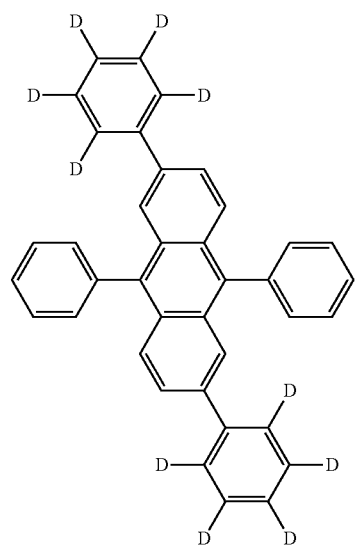
[Compound 788]
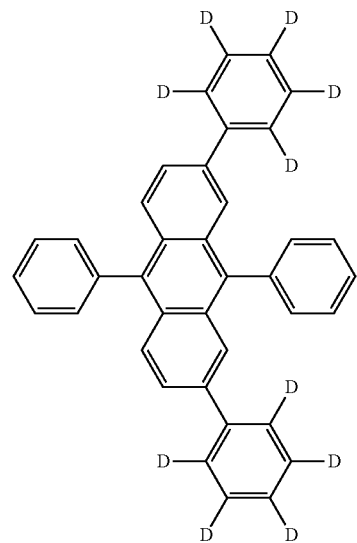
[Compound 789]
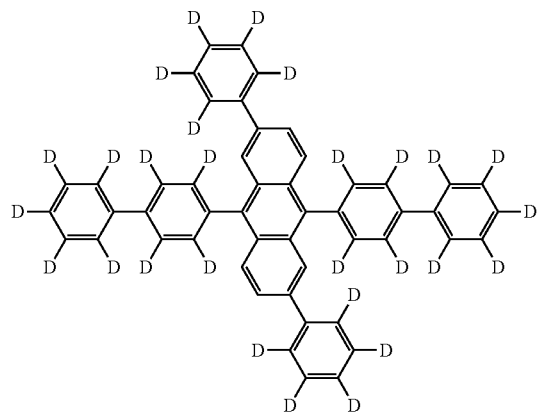

[Compound 790]
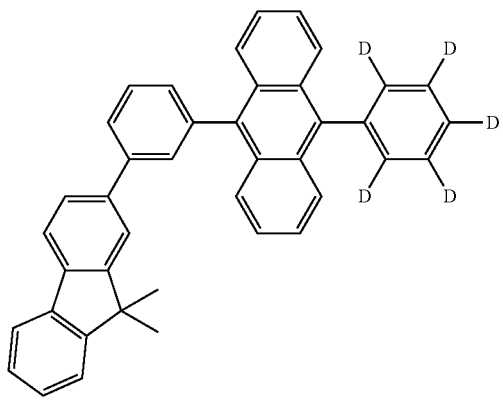
[Compound 791]
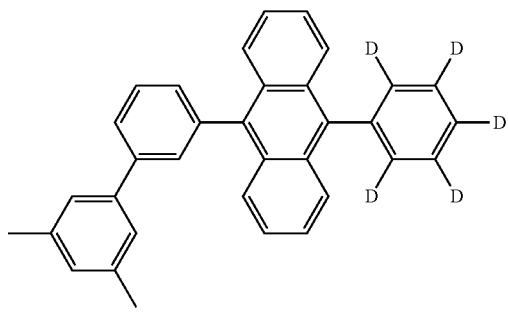
[Compound 792]
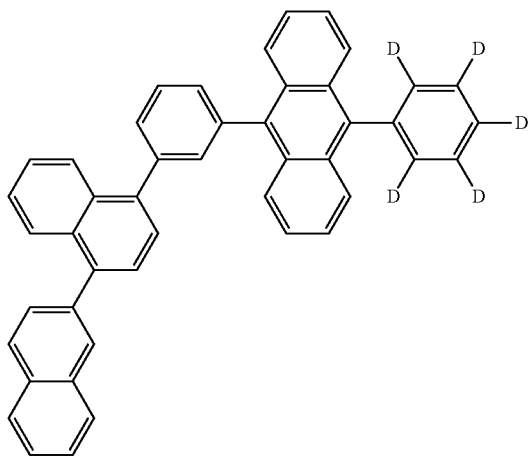
[Compound 793]
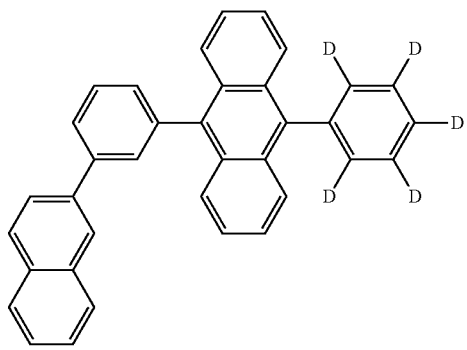
[Compound 794]
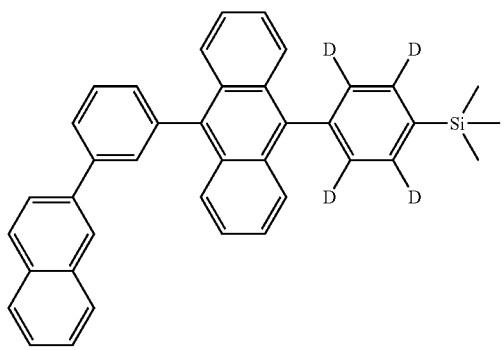
[Compound 795]
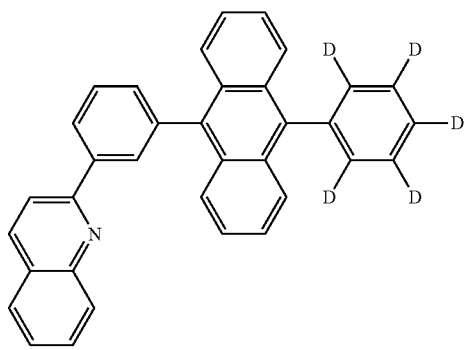
[Compound 796]
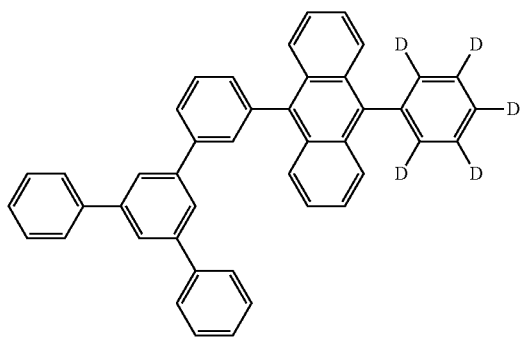
[Compound 797]
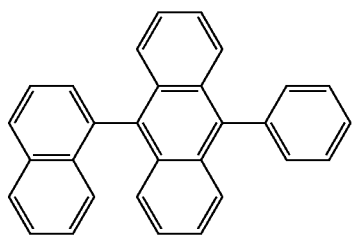

[Compound 798]
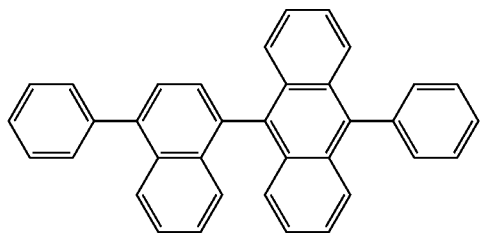
[Compound 799]
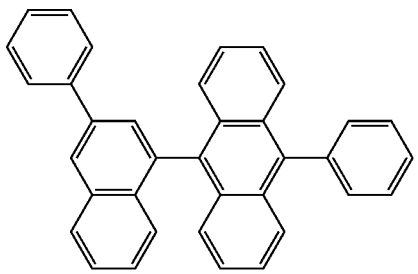
[Compound 800]
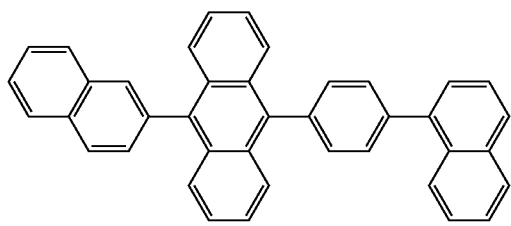
[Compound 801]
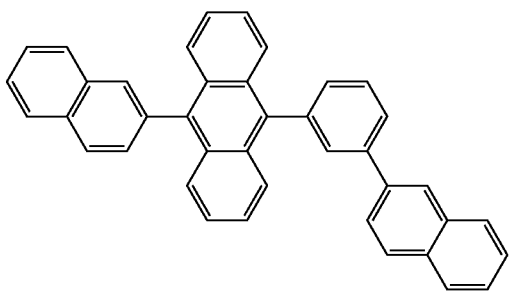
[Compound 802]
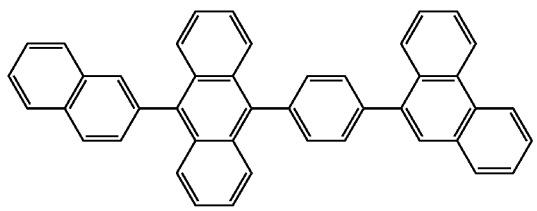
[Compound 803]
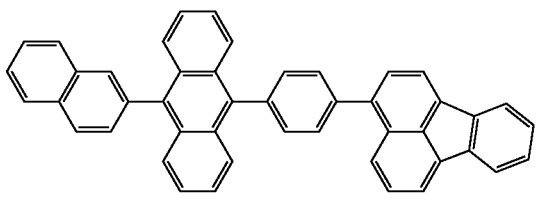
[Compound 804]
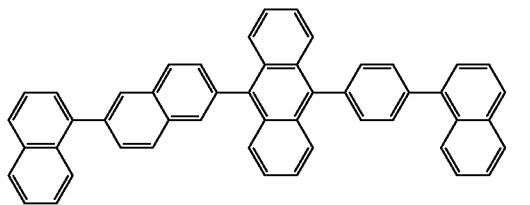
[Compound 805]
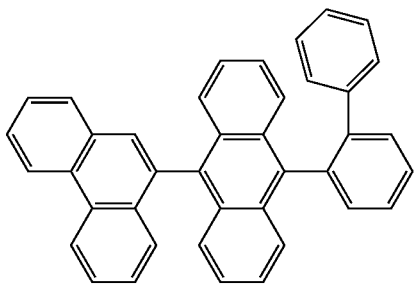
[Compound 806]
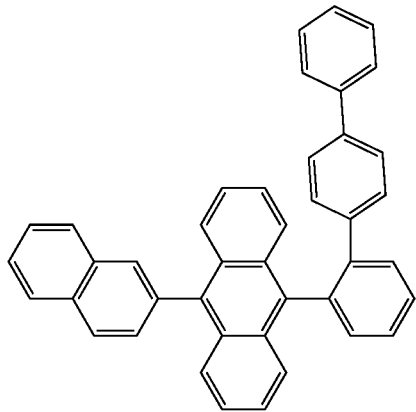
[Compound 807]
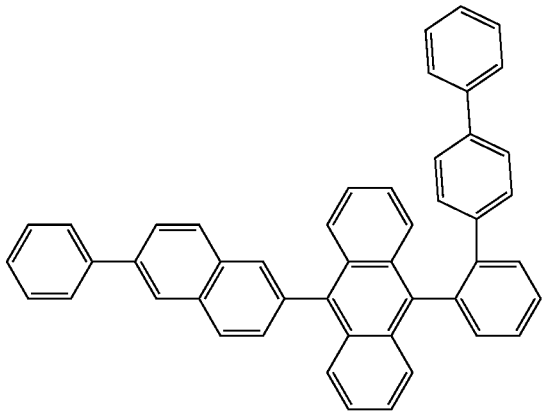

-continued
[Compound 808]
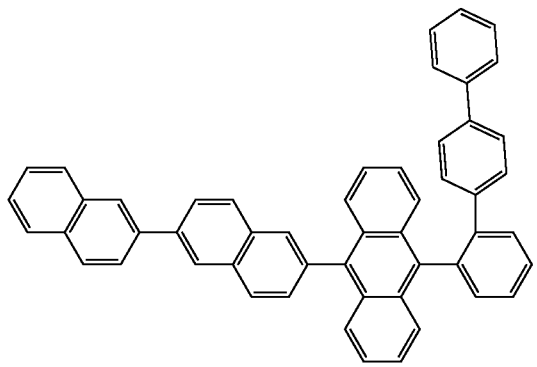
[Compound 809]
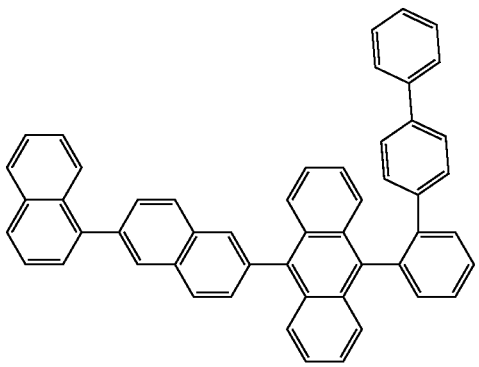
[Compound 810]
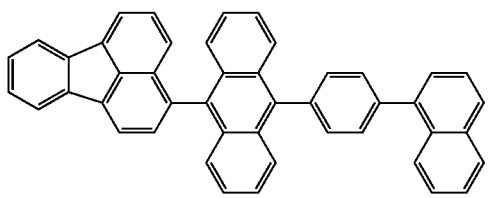
[Compound 811]
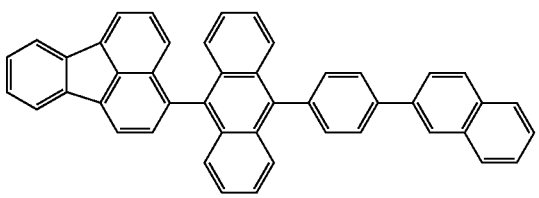
[Compound 812]
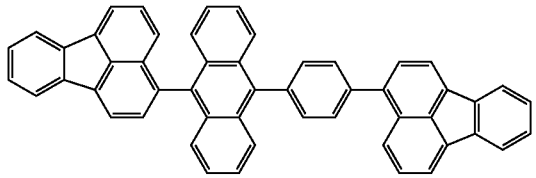
[Compound 813]
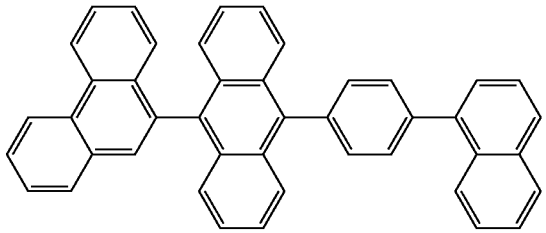
[Compound 814]
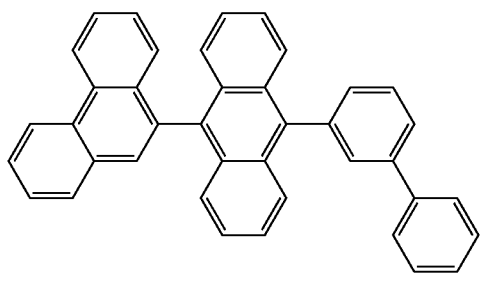
[Compound 815]
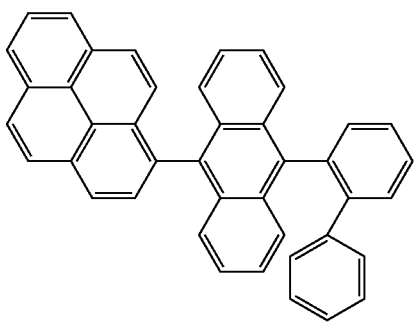
[Compound 816]
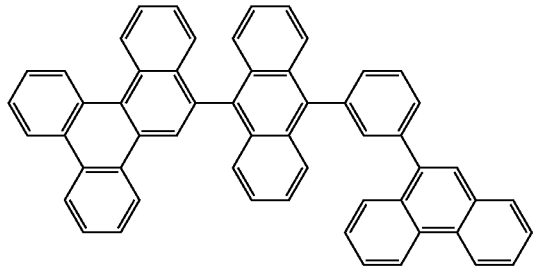
[Compound 817]
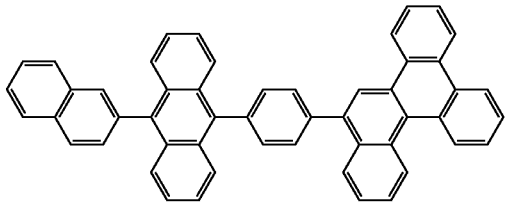

-continued
[Compound 818]
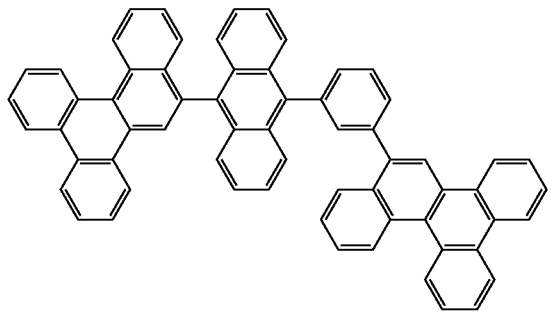
[Compound 819]
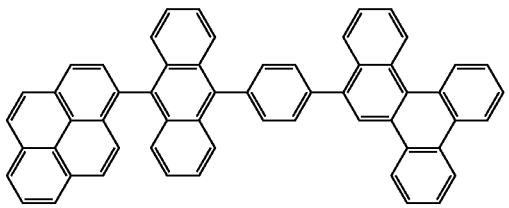
[Compound 820]
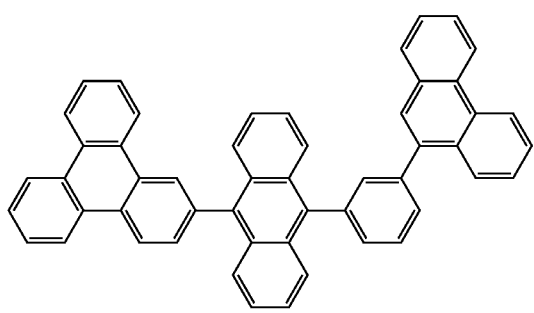
[Compound 821]
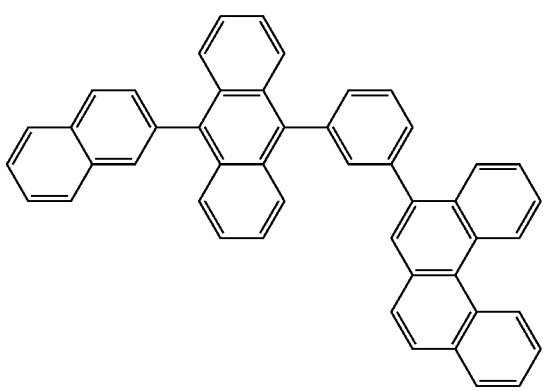
[Compound 822]
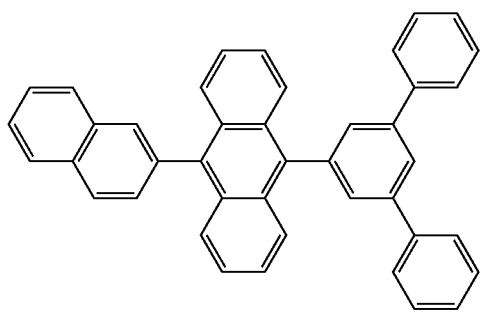
[Compound 823]
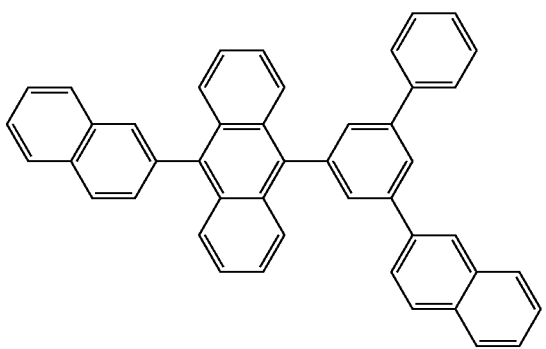
[Compound 824]
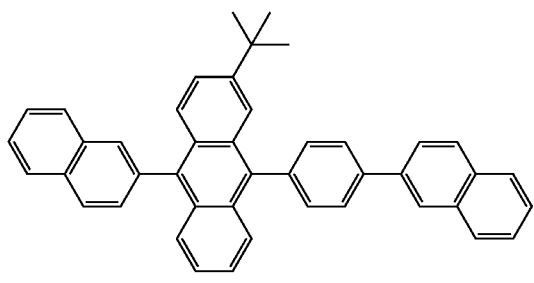
[Compound 825]
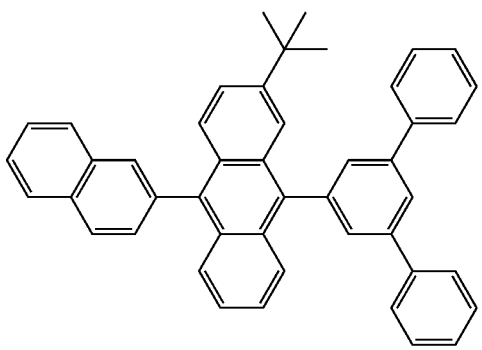

-continued
[Compound 826]
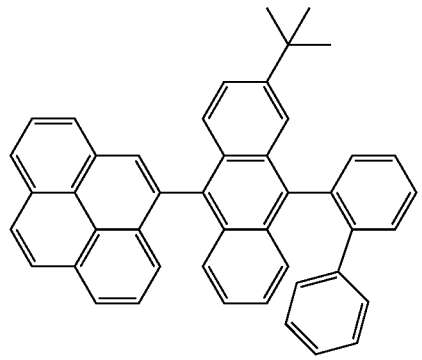
[Compound 827]
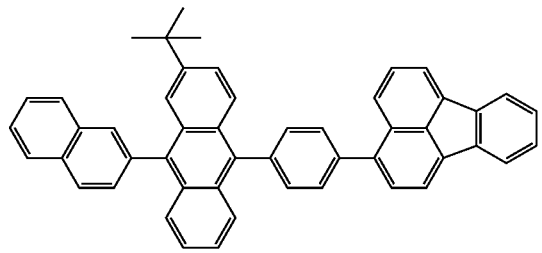
[Compound 828]
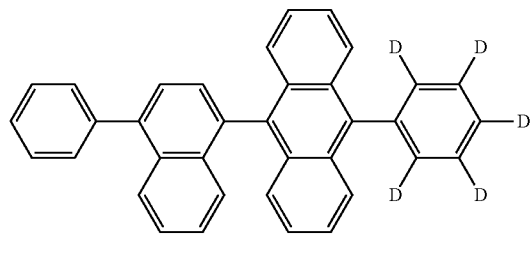
[Compound 829]
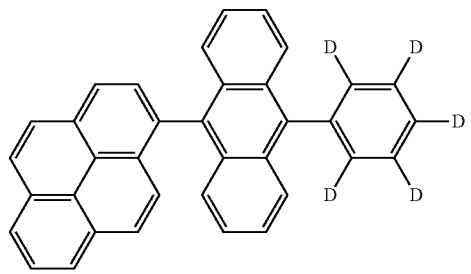
[Compound 830]
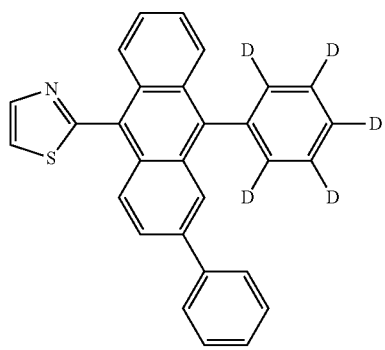
[Compound 831]
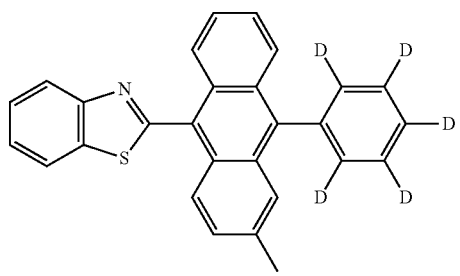
[Compound 832]
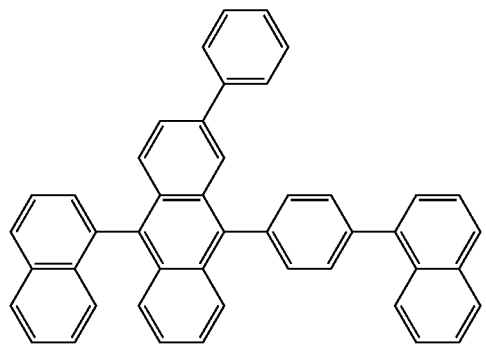
[Compound 833]
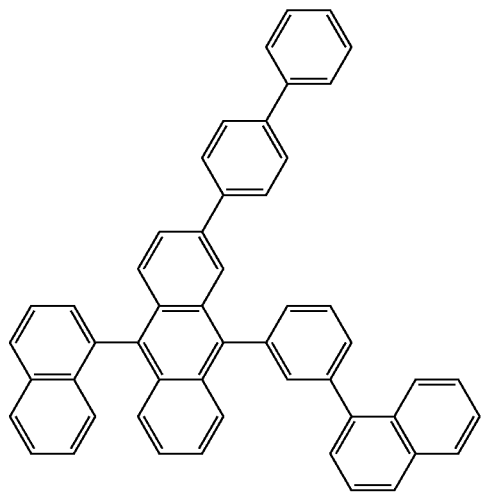

-continued
[Compound 834]
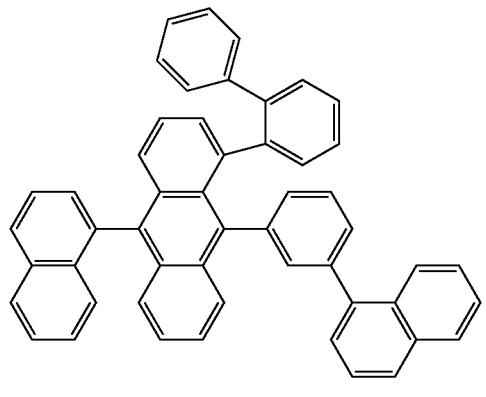
[Compound 835]
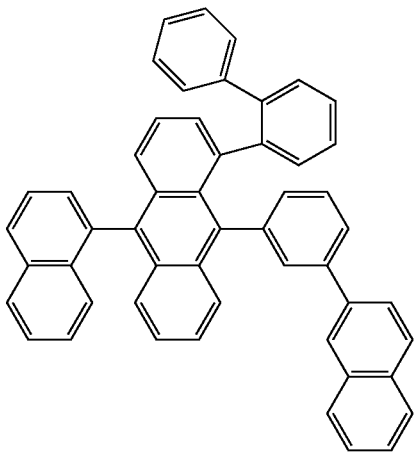
[Compound 836]
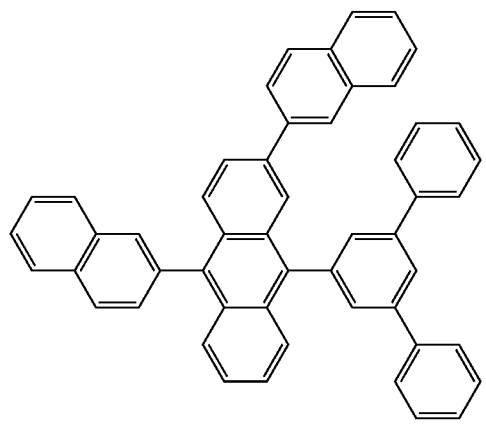
[Compound 837]
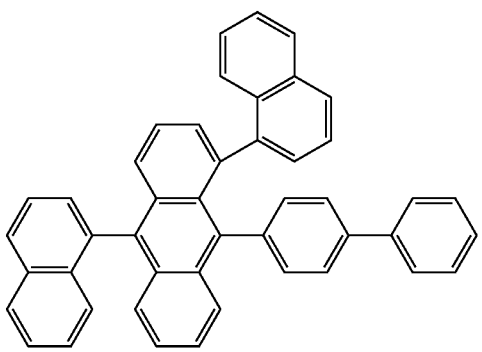
[Compound 838]
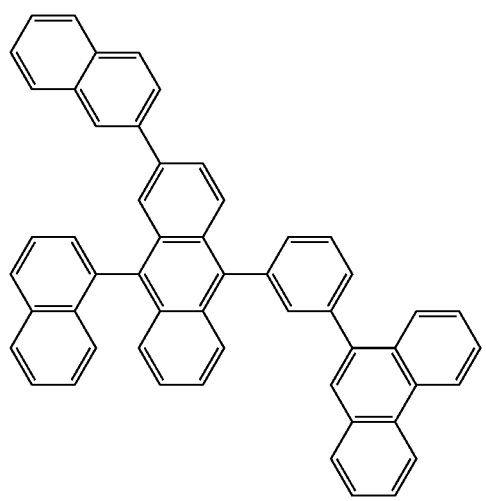
[Compound 839]
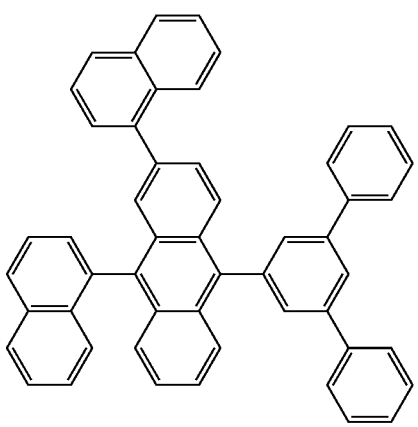

[Compound 840]
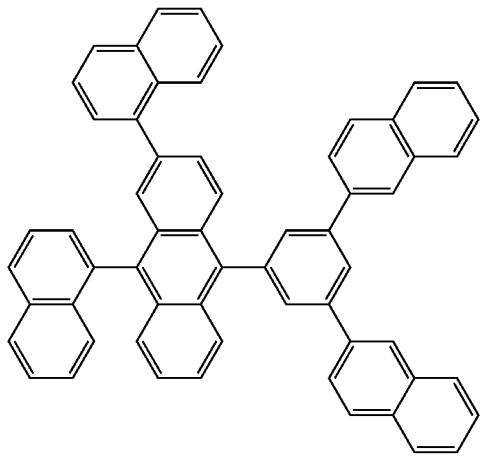
[Compound 841]
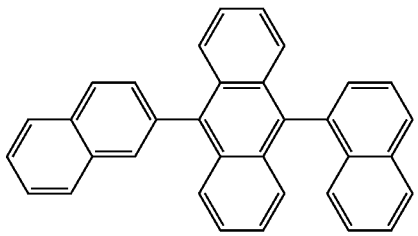
[Compound 842]
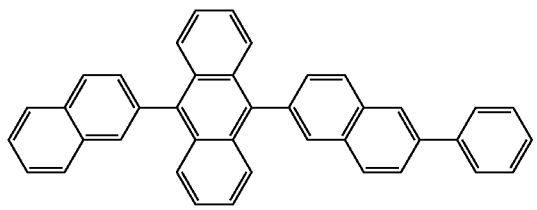
[Compound 843]
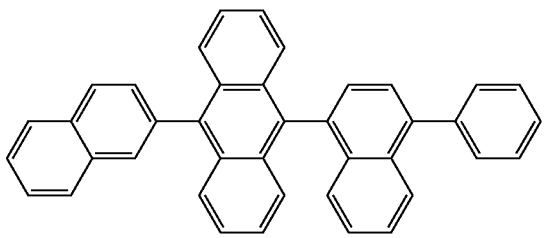
[Compound 844]
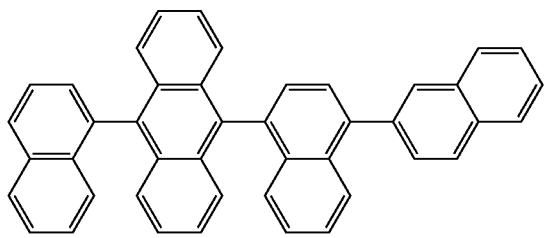
[Compound 845]
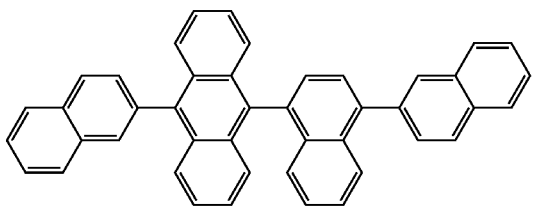
[Compound 846]
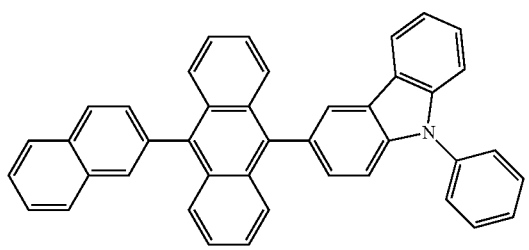
[Compound 847]
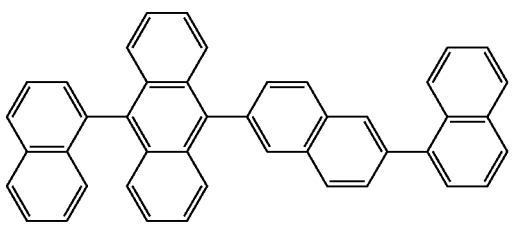
[Compound 848]
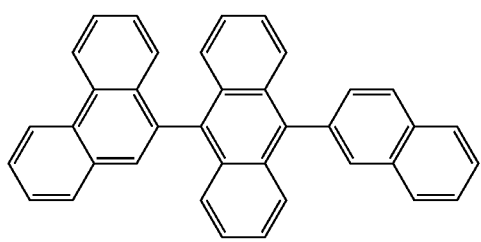
[Compound 849]
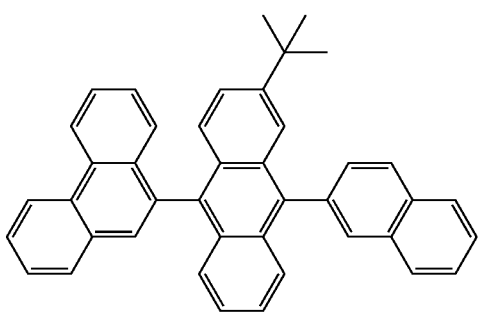

-continued
[Compound 850]
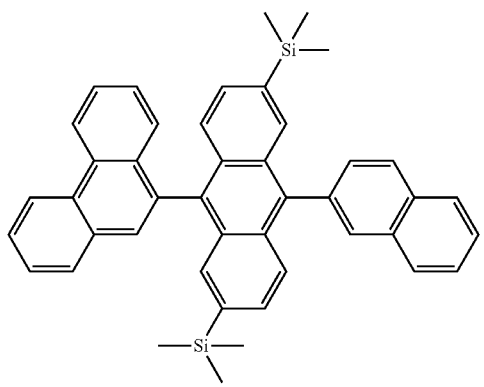
[Compound 851]
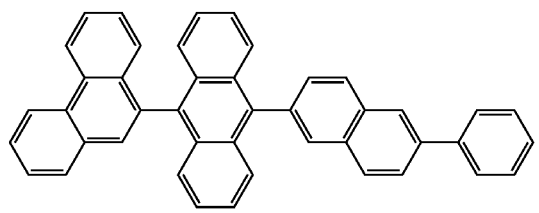
[Compound 852]
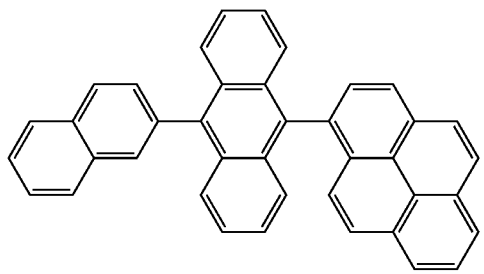
[Compound 853]
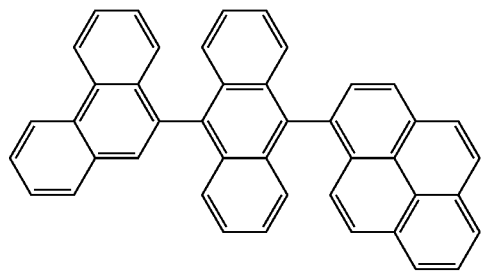
[Compound 854]
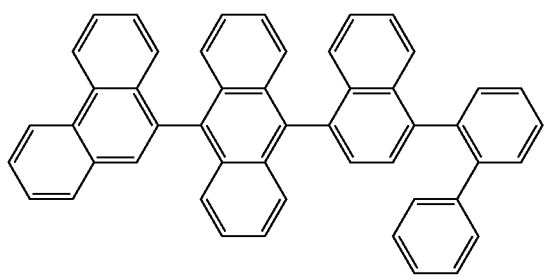
[Compound 855]
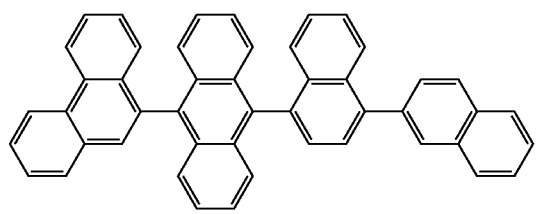
[Compound 856]
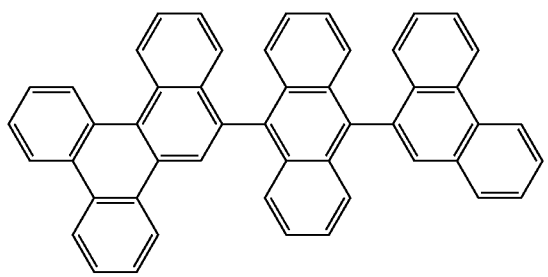
[Compound 857]
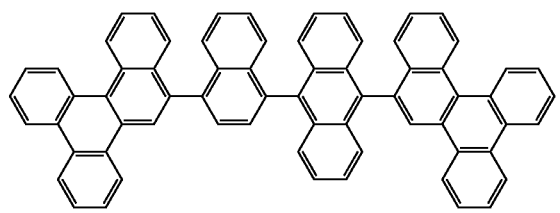

[Compound 858]
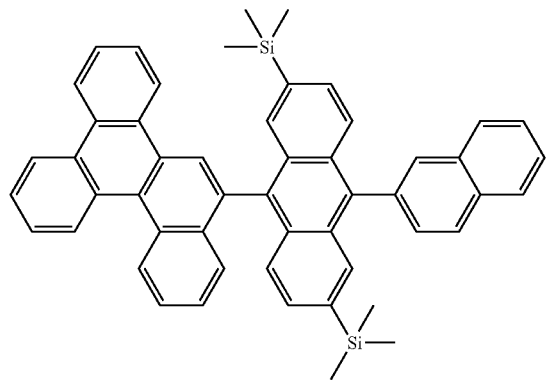
[Compound 859]
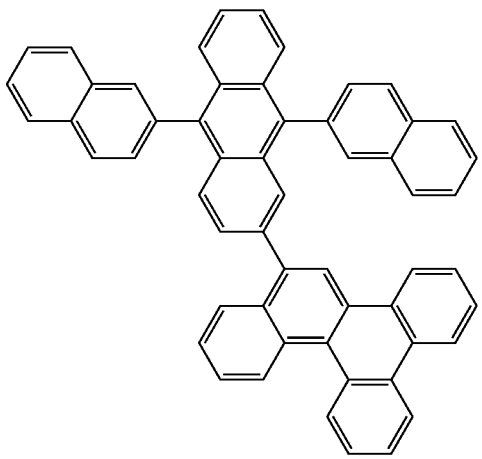
[Compound 860]
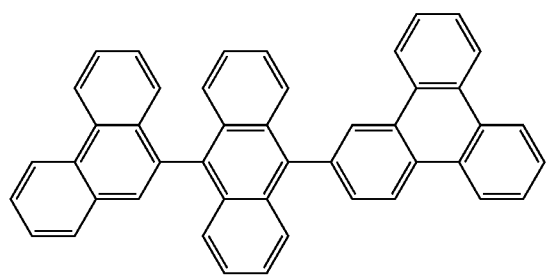
[Compound 861]
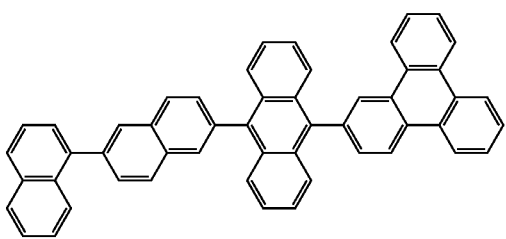
[Compound 862]
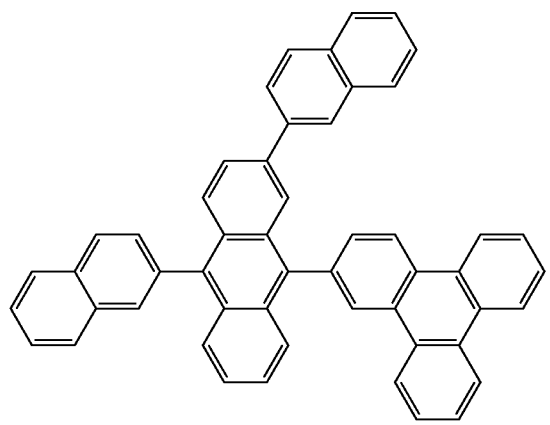
[Compound 863]
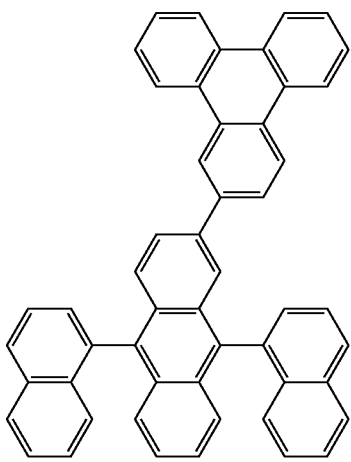
[Compound 864]
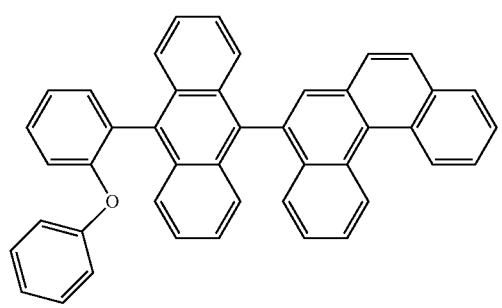

-continued
[Compound 865]
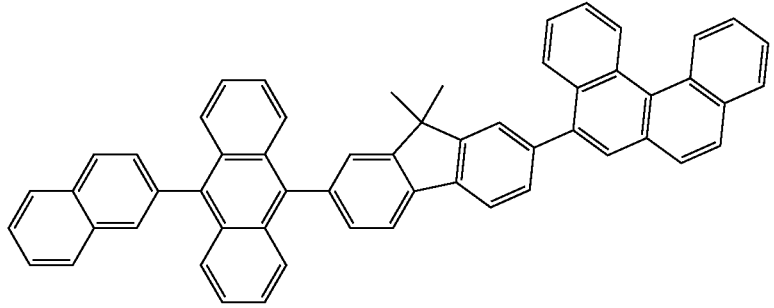
[Compound 866]
[Compound 867]
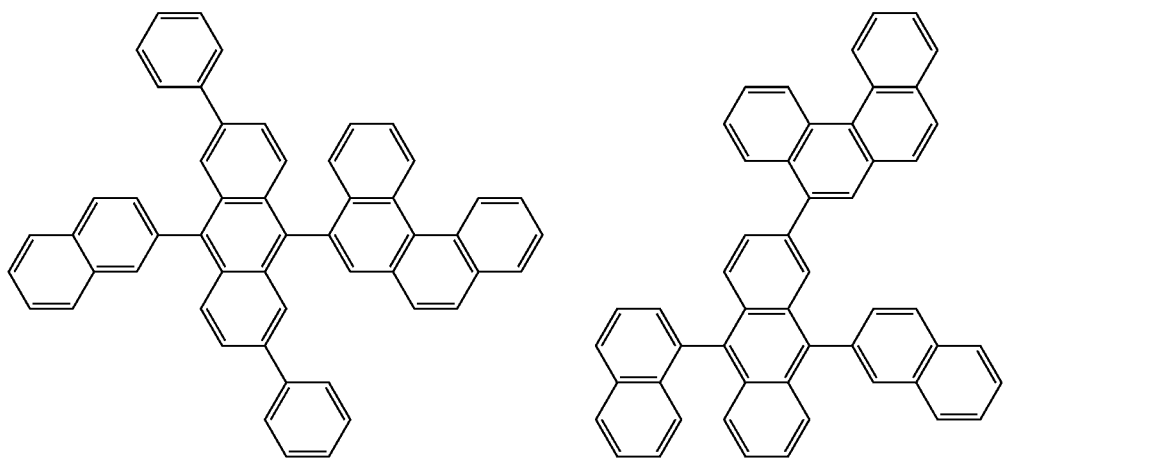
[Compound 868]
[Compound 869]
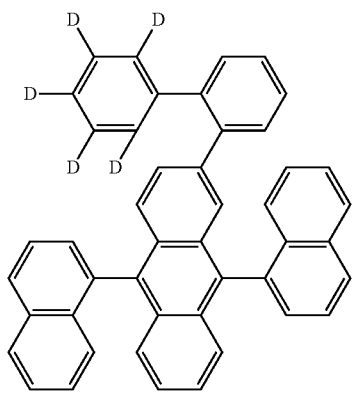
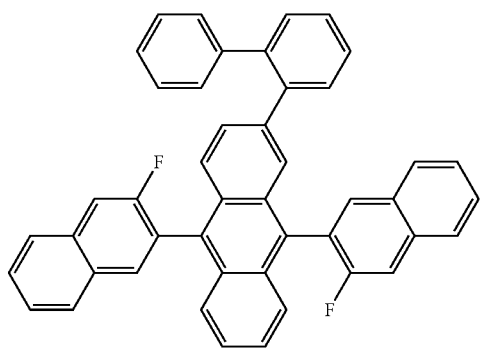
[Compound 870]
[Compound 871]
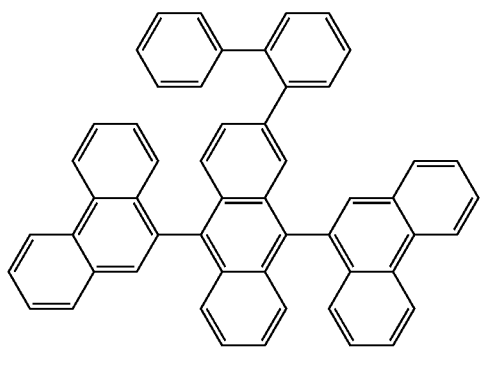
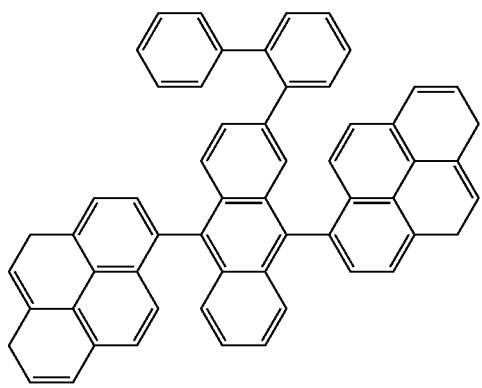

-continued
[Compound 872]
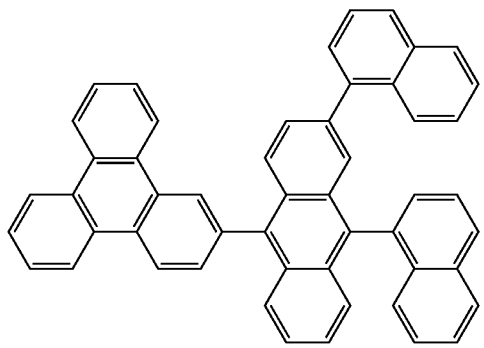
[Compound 873]
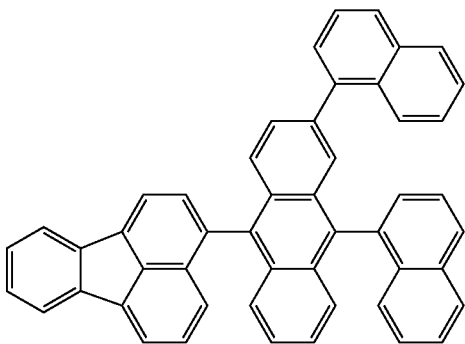
[Compound 874]
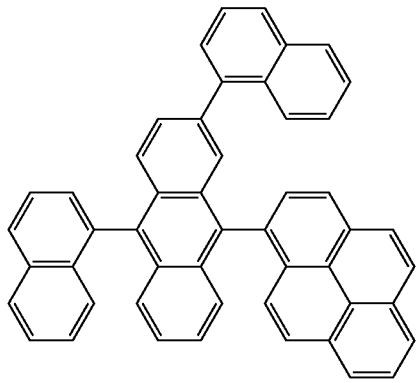
[Compound 875]
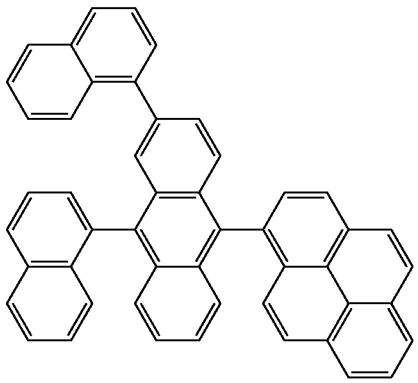
[Compound 876]
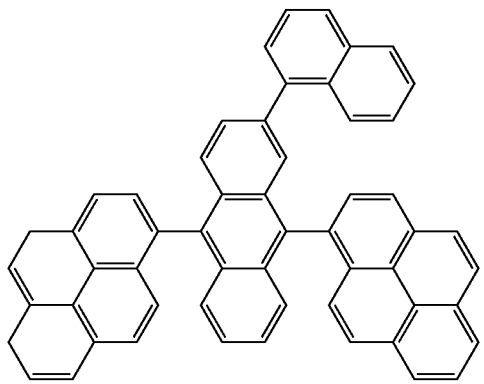
[Compound 877]
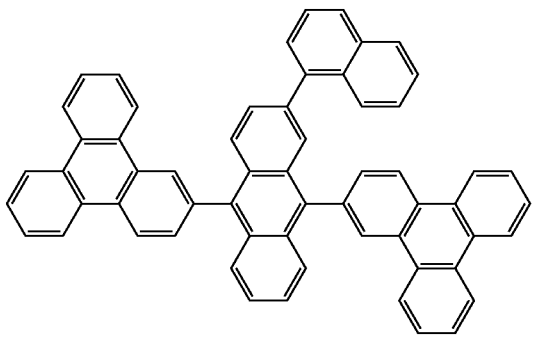
[Compound 878]
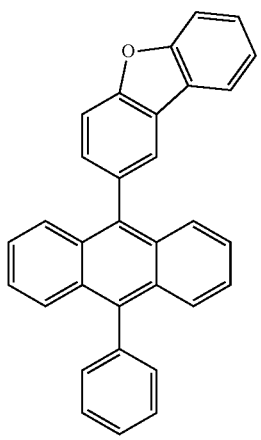
[Compound 879]
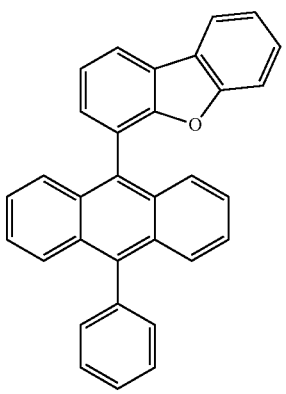

-continued
[Compound 880]
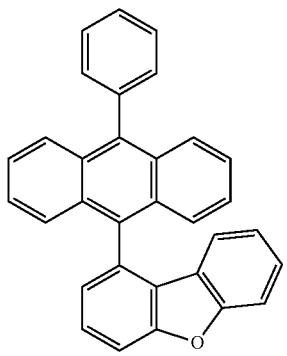
[Compound 881]
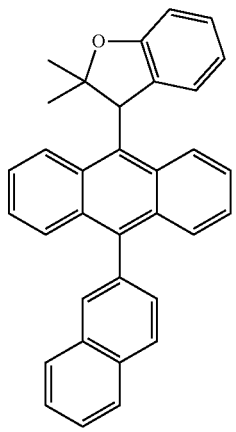
[Compound 882]
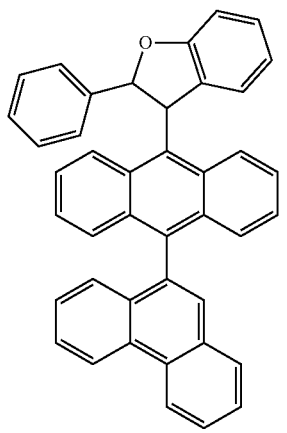
[Compound 883]
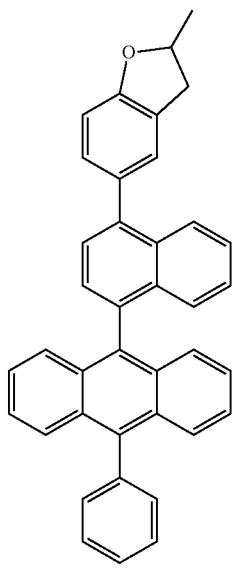
[Compound 884]
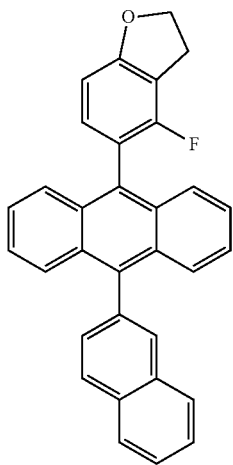
[Compound 885]
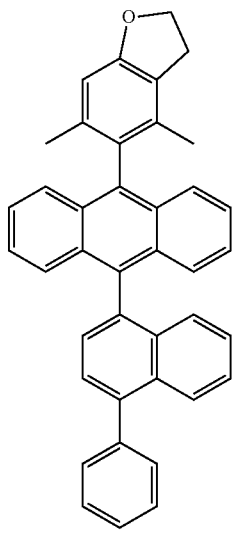

[Compound 886]
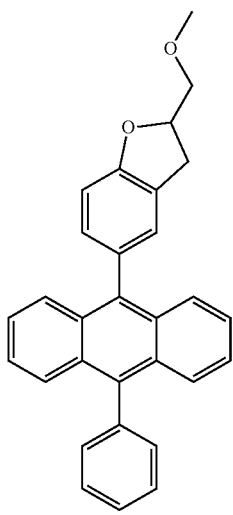
[Compound 887]
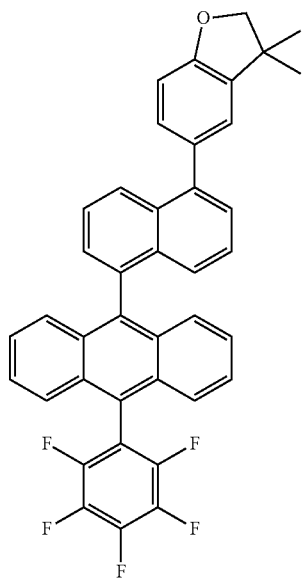
[Compound 888]
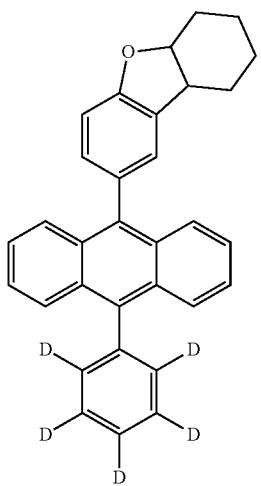
[Compound 889]
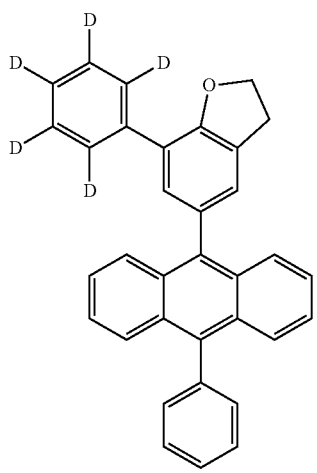
[Compound 890]
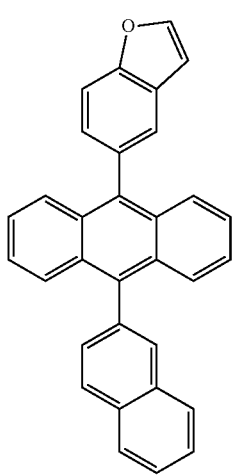
[Compound 891]
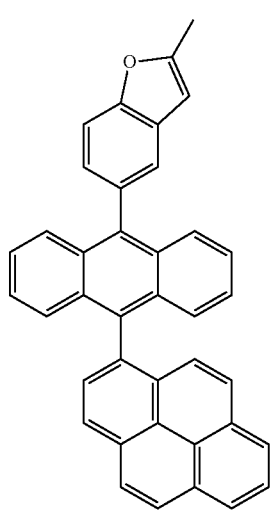

[Compound 892]
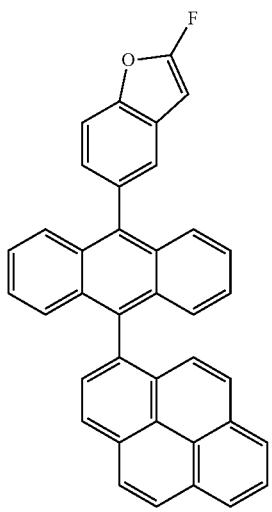
[Compound 893]
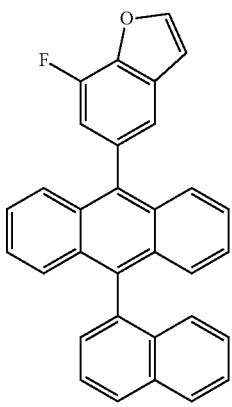
[Compound 894]
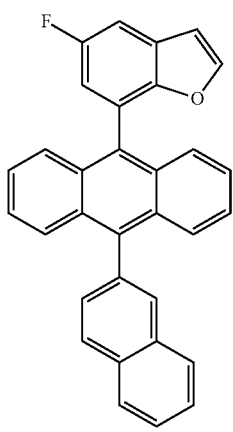
[Compound 895]
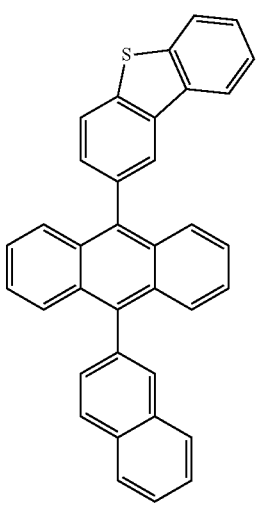
[Compound 896]
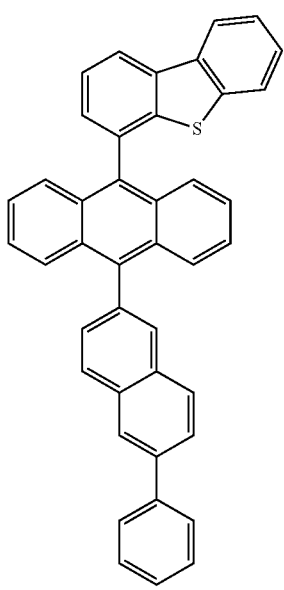
In the case where the light-emitting layer contains a host and a dopant, the content of the dopant may range from about 0.01 to 20 parts by weight, based on 100 parts by weight of the host, but is not limited thereto.

A material for use in the electron transport layer of the present disclosure functions to stably carry the electrons injected from the electron injection electrode (cathode), and may be an electron transport material known in the art. Examples of the electron transport material known in the art include quinoline derivatives, particularly, tris(8-quinolinorate)aluminium (Alq3), Liq, TAZ, BAlq, beryllium bis(benzoquinolin-10-olate) (Bebq$_2$), compound 201, compound 202, BCP, and oxadiazole derivatives such as PBD, BMD, and BND, but are not limited thereto:

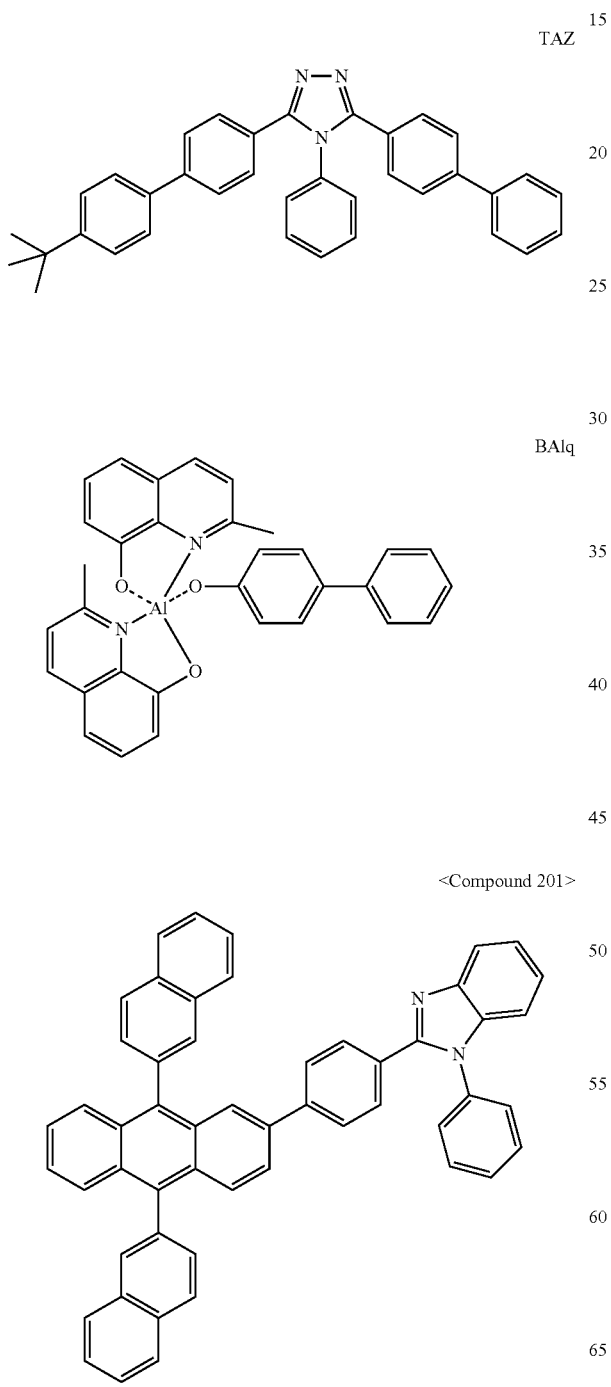

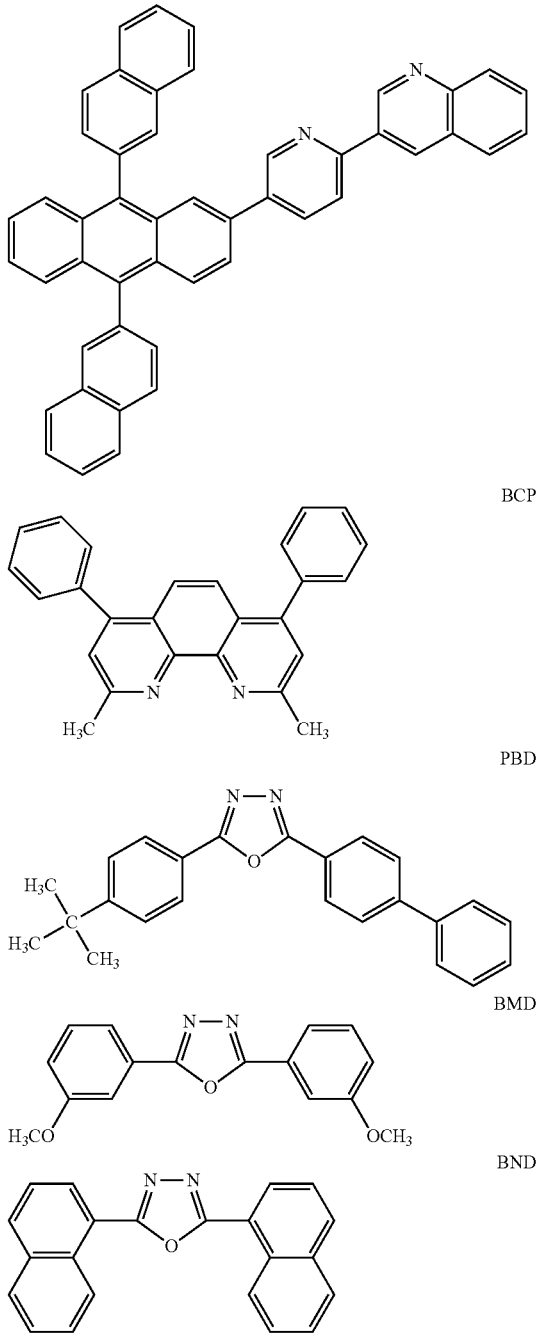

In addition, the organic metal compound represented by Chemical Formula F may be used, either alone or in combination with the aforementioned electron transport layer material in the present disclosure:

$$Y_m\text{-M-}(OA)_n \qquad \text{[Chemical Formula F]}$$

wherein,

Y is a ligand that contains two moieties respectively responsible for forming a single bond through a direct bond to M and for forming a coordinate bond with M, each moiety being selected from among C, N, O and S, and which is chelated by the single bond and the coordinate bond;

M is an alkali metal, an alkaline earth metal, an aluminum (Al) atom, or a boron (B) atom
wherein
when M is an alkali metal, m=1 and n=0;
when M is an alkaline earth metal, m=1 and n=1, or m=2 and n=0; or
when M is aluminum or a boron, m is an integer of 1 to 3 and n is an integer of 0 to 2, satisfying the relationship m+n=3; and
OA is a monodentate ligand capable of forming a single bond or a coordinate bond with M,
wherein
O is oxygen, and
A is selected from among a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing at least one of O, N, and S as a heteroatom, In the present disclosure, Y's, which may be the same or different, are each one selected from among, but not limited to, the following [Structural Formula C1] to [Structural Formula C39]:

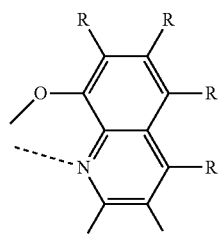

[Structural Formula C1]

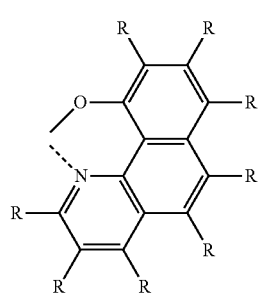

[Structural Formula C2]

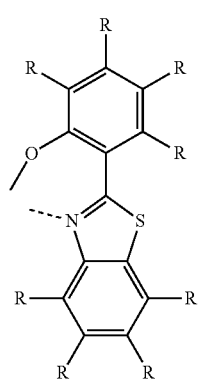

[Structural Formula C3]

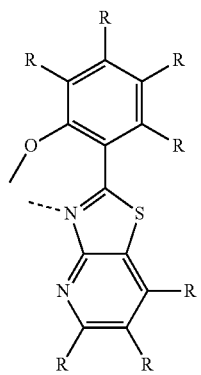

[Structural Formula C4]

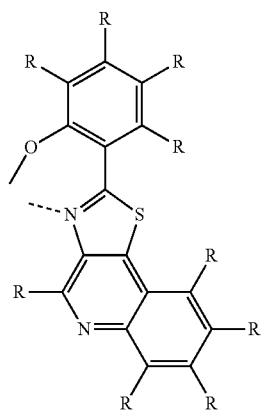

[Structural Formula C5]

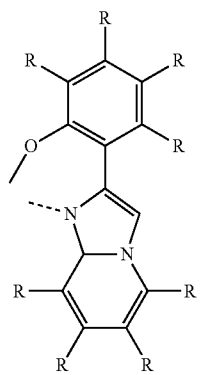

[Structural Formula C6]

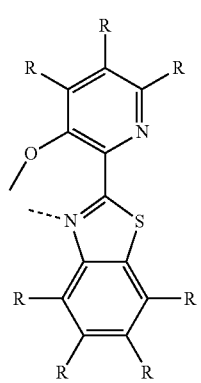

[Structural Formula C7]

[Structural Formula C8]
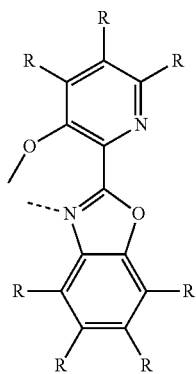
[Structural Formula C9]
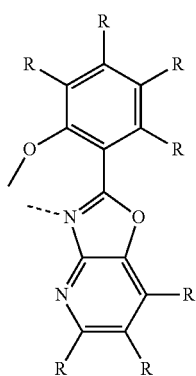
[Structural Formula C10]
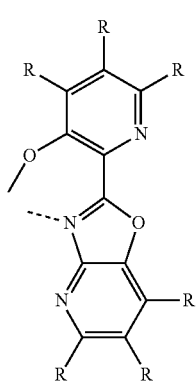
[Structural Formula C11]
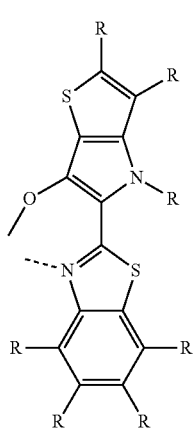
[Structural Formula C12]
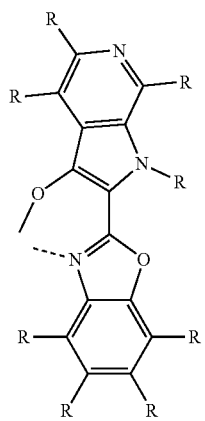
[Structural Formula C13]
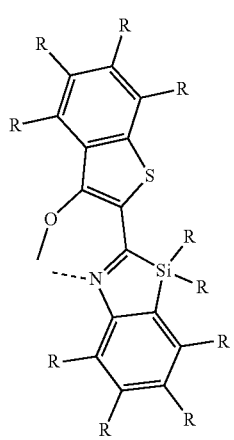
[Structural Formula C14]
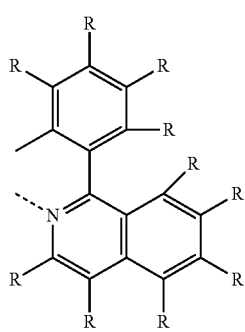
[Structural Formula C15]
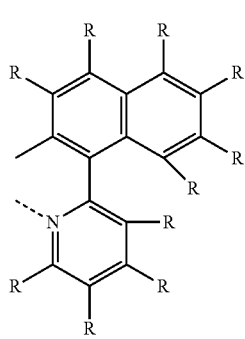

[Structural Formula C16]
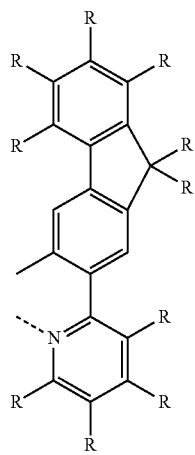
[Structural Formula C17]
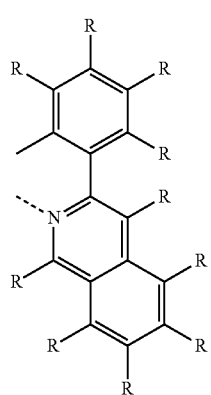
[Structural Formula C18]
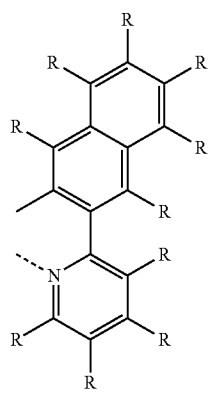
[Structural Formula C19]
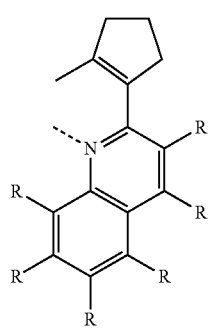
[Structural Formula C20]
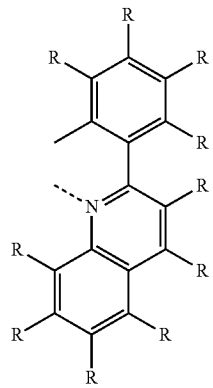
[Structural Formula C21]
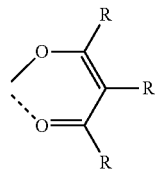
[Structural Formula C22]
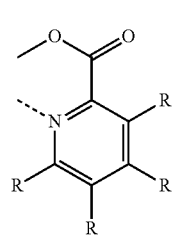
[Structural Formula C23]
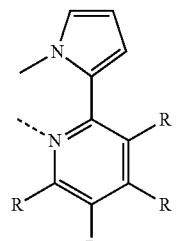
[Structural Formula C24]
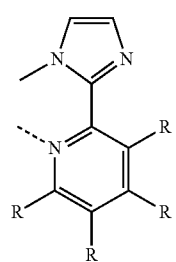
[Structural Formula C25]
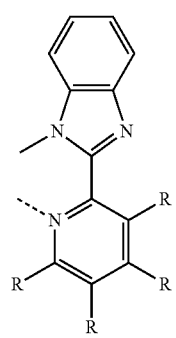

[Structural Formula C26]
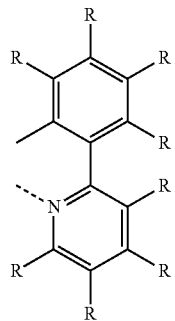
[Structural Formula C27]
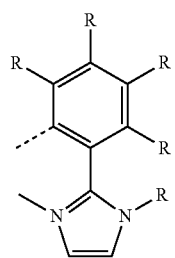
[Structural Formula C28]
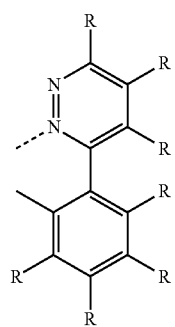
[Structural Formula C29]
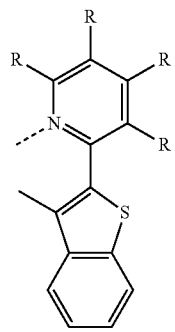
[Structural Formula C30]
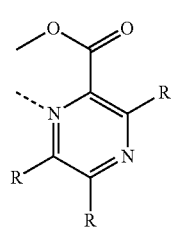
[Structural Formula C31]
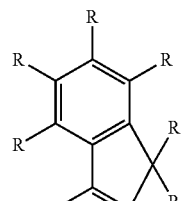
[Structural Formula C32]
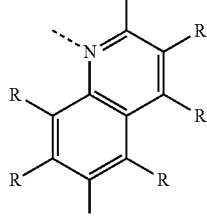
[Structural Formula C33]
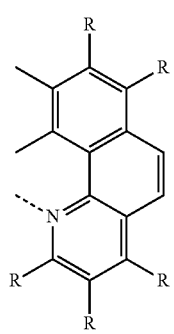
[Structural Formula C34]
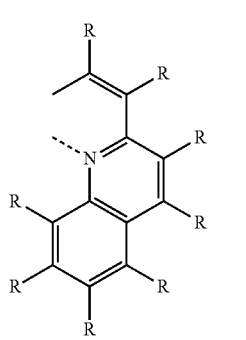

-continued

[Structural Formula C35]
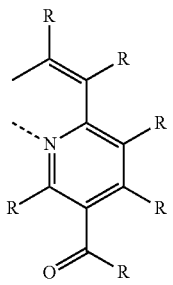

[Structural Formula C36]
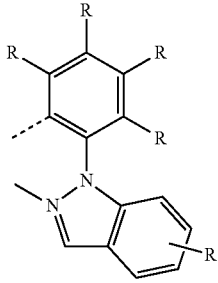

[Structural Formula C37]
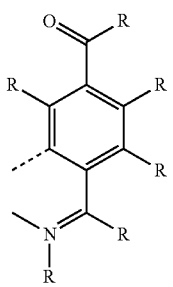

[Structural Formula C38]
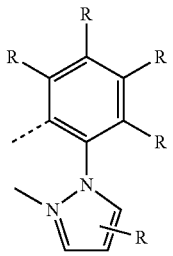

[Structural Formula C39]
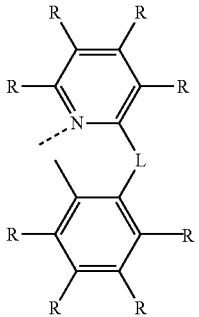

wherein,
R's, which may be the same or different, are each independently selected from among a hydrogen atom, a deuterium atom, a halogen, a cyano, a substituted or unsubstituted alkyl of 1 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may form a spiro or fused ring with an adjacent substituent via an alkylene or alkenylene linker, wherein the term 'substituted' in the expression "a substituted or unsubstituted" means having at least one substituent selected from the group consisting of a deuterium atom, a cyano, a halogen, a hydroxy, a nitro, an alkyl, an alkoxy, an alkylamino, an arylamino, a heteroarylamino, an alkylsilyl, an arylsilyl, an aryloxy, an aryl, a heteroaryl, a germanium, a phosphorus, and a boron.

An electron injecting layer (EIL) that functions to facilitate electron injection from the cathode, thus improving the power efficiency of the diode, may be further deposited on the electron transport layer. So long as it is conventionally used in the art, any material can be available for the electron injecting layer without particular limitations. Examples include LiF, NaCl, CsF, $Li_2O$, and BaO. A deposition condition of the EIL may be almost the same as that for the hole injection layer.

The electron injecting layer may range in thickness from about 1 Å to about 100 Å and particularly from about 3 Å to about 90 Å. Given the thickness range for the electron injecting layer, the diode can exhibit satisfactory electron injection properties without actually elevating a driving voltage.

In the organic light-emitting diode according to a particular embodiment of the present disclosure, the first electrode is an anode and the second electrode is a cathode. In this regard, the organic light-emitting diode may further comprise at least one of a functional layer capable of both hole injection and hole transport, an electron transport layer, and an electron injecting layer, wherein the electron transport layer and the electron injecting layer may be sequentially disposed between between the light-emitting layer and the cathode.

In the organic light-emitting diode of the present disclosure, more particularly, a hole injecting layer, a hole transport layer, and a light-emitting layer are sequentially deposited between the first electrode and the second electrode, wherein the hole injecting layer or the hole transport layer comprises at least one of the amine compounds represented by Chemical Formula A or B; and the light-emitting layer comprises at least one of the amine compounds represented by Chemical Formula D1 and D2.

As used herein, the expression "(an organic layer) comprises at least one organic compound" is construed to mean that the organic layer may comprise one organic compound falling within the scope of the present disclosure or two or more different compounds falling within the scope of the present disclosure.

Furthermore, at least one selected from among the hole injecting layer, the hole transport layer, the electron blocking layer, the light-emitting layer, the electron transport layer, and the electron injecting layer may be deposited using a deposition process or a solution process. Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

Below, the organic light-emitting diode of the present disclosure is explained with reference to FIG. 1.

FIG. 1 is a schematic cross-sectional view of the structure of an organic light-emitting diode according to some embodiments of the present disclosure. The organic light-emitting diode includes an anode 20, a hole transport layer 40, an organic light-emitting layer 50, an electron transport layer 60, and a cathode 80, and optionally a hole injecting layer 30 or an electron injecting layer 70. In addition, one or two intermediate layers may be further formed in the organic light-emitting diode.

Reference is made to FIG. 1 with regard to the fabrication of the organic light-emitting diode of the present disclosure.

First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode electrode 20 by thermal deposition in a vacuum or by spin coating to form a hole injection layer 30. Subsequently, using thermal deposition in a vacuum or spin coating, a hole transport layer material is applied to the hole injection layer 30 to form a hole transport layer 40.

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitation. Representative among hole barrier materials are BAlq, BCP, and TPBI.

Given the material represented by Chemical Formula A or B in the electron transport layer thereof, the organic light-emitting diode according to the present disclosure can be advantageously improved in efficiency. Moreover, the use of the material represented by Chemical Formula D1 or D2 in the light-emitting layer guarantee more improved efficiency to the organic light-emitting diode.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

A better understanding of the present disclosure may be obtained through the following examples which are set forth to illustrate, but are not to be construed as limiting the present disclosure.

Synthesis of Compounds for Hole Transport Layer and Hole Injection Layer

Synthesis Example 1: Synthesis of Compound of Chemical Formula 2

Synthesis Example 1-(1): Synthesis of [Intermediate 1-a]

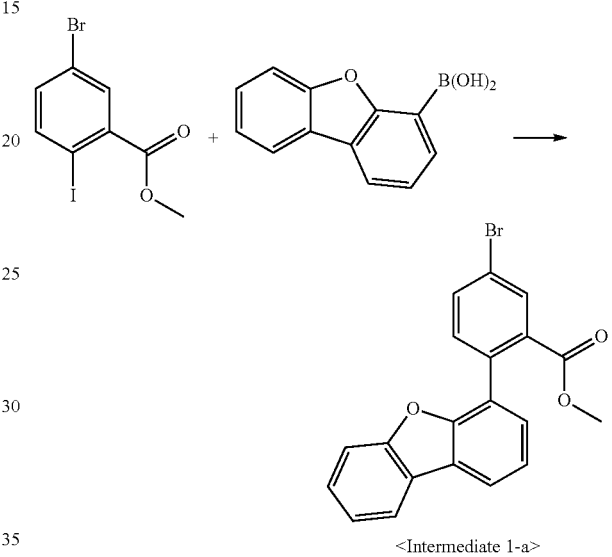

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (75.0 g, 60.1%).

Synthesis Example 1-(2): Synthesis of [Intermediate 1-b]

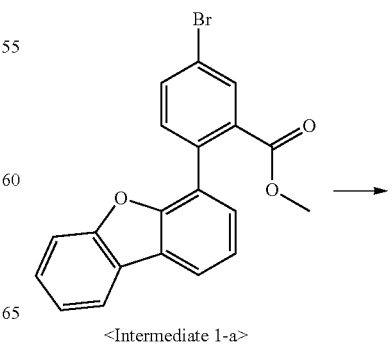

<Intermediate 1-a>

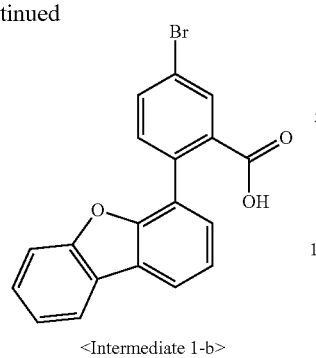

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 1-b>. (14.5 g, 88.6%)

Synthesis Example 1-(3): Synthesis of [Intermediate 1-c]

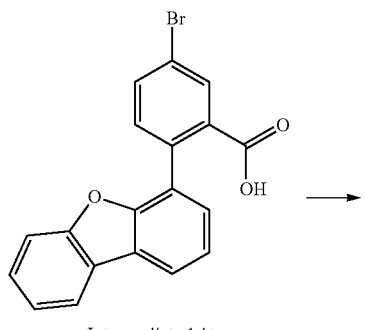

<Intermediate 1-b>

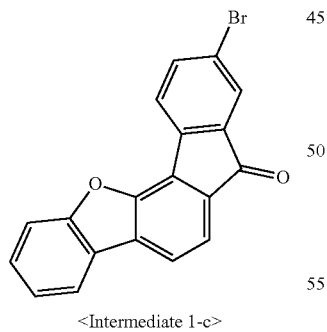

<Intermediate 1-c>

In a 250-mL round-bottom flask reactor, <Intermediate 1-b> (14.5 g, 39 mmol) and methanesulfonic acid (145 ml) were stirred together for 3 hrs at 80° C.

After the completion of the reaction was confirmed using thin-layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4): Synthesis of [Intermediate 1-d]

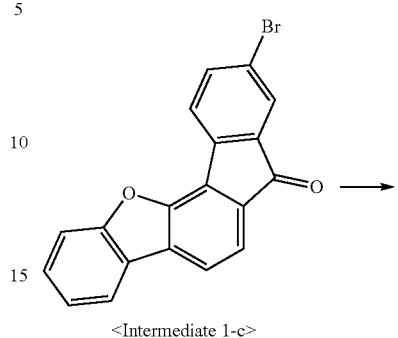

<Intermediate 1-c>

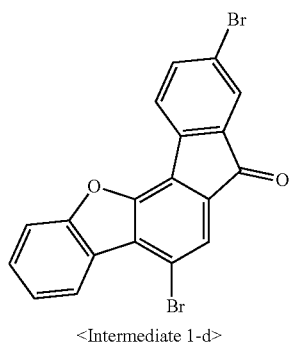

<Intermediate 1-d>

In a 1-L round-bottom flask reactor, <Intermediate 1-c> (11.5 g, 33 mmol) and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 1-d>. (11.0 g, 78%)

Synthesis Example 1-(5): Synthesis of [Intermediate 1-e]

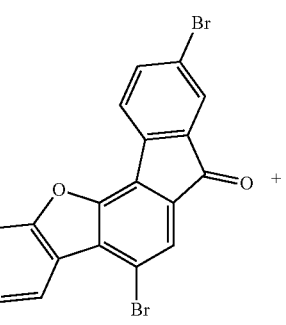

<Intermediate 1-d>

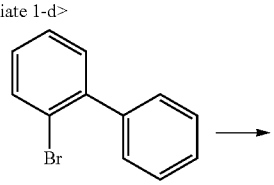

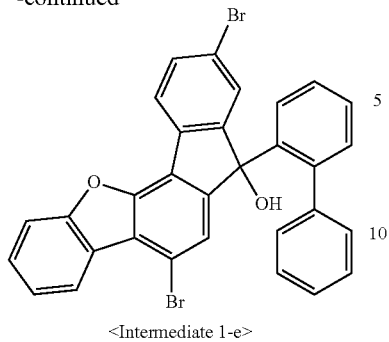

<Intermediate 1-e>

In a 250-ml round-bottom flask reactor, 2-bromobiphenyl (8.4 g, 0.036 mol) and tetrahydrofuran (110 ml) were frozen at −78° C. in a nitrogen atmosphere. At the same temperature, n-butyl lithium (19.3 ml, 0.031 mol) was dropwise added to the reaction solution, which was then stirred for 2 hrs. Thereafter, <Intermediate 1-d> (11.0 g, 0.026 mol) was added little by little to the reaction solution and stirred at room temperature. When the reaction mixture started to change color, the reaction was monitored via TLC. After the reaction was stopped with H$_2$O (50 ml), extraction was conducted with ethyl acetate and water. The organic layer was separated, concentrated in a vacuum, and recrystallized in acetonirile to afford <Intermediate 1-e> as a solid. (12.2 g, 81.5%)

Synthesis Example 1-(6): Synthesis of [Intermediate 1-f]

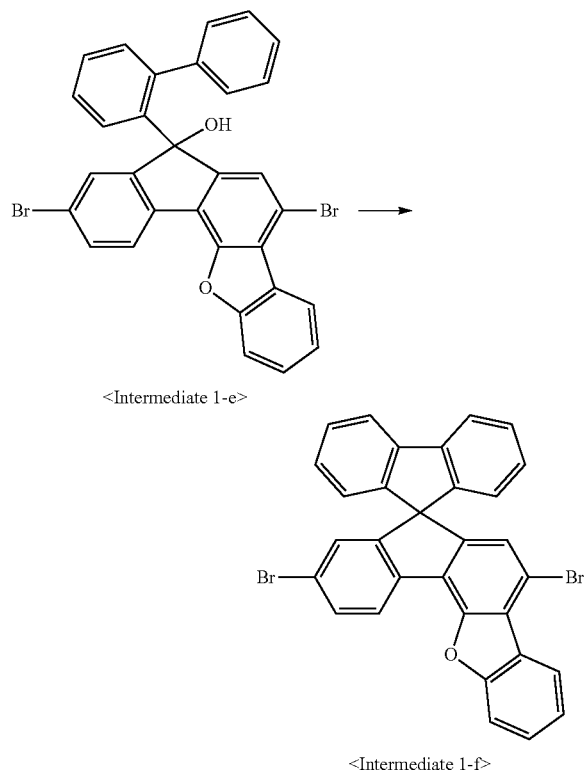

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin-layer chromatography. The reaction mixture was then cooled to room temperature and filtered. The filtrate was washed with H$_2$O and methanol and dissolved in monochlorobenzene. Following silica gel chromatography, the fraction was concentrated and cooled to room temperature to give <Intermediate 1-f>. (10.7 g, 90%)

Synthesis Example 1-(7): Synthesis of [Chemical Formula 2]

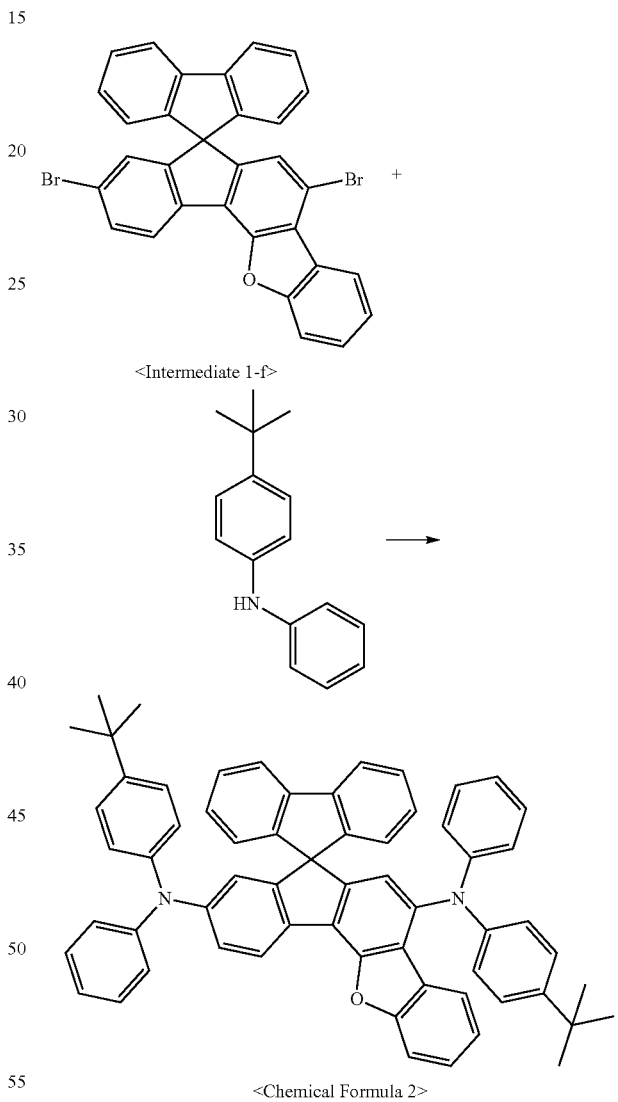

In a 250-ml round-bottom flask reactor, a mixture of <Intermediate 1-f> (5.0 g, 0.009 mol), (4-tert-butylphenyl) amine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 2 as a solid (2.9 g, 38%).

MS (MALDI-TOF): m/z 852.41 [M+]

Synthesis Example 2: Synthesis of Compound of Chemical Formula 19

Synthesis Example 2-(1): Synthesis of [Intermediate 2-a]

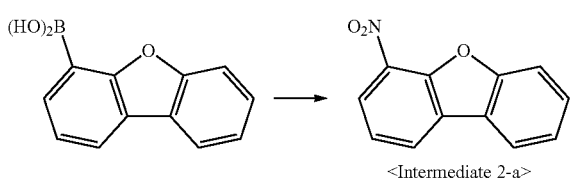 [SMILES: OB(O)c1cccc2c1oc1ccccc12 ; O=[N+]([O-])c1cccc2c1oc1ccccc12]

<Intermediate 2-a>

In a 2-L round-bottom flask reactor, 4-dibenzoboronic acid (85.0 g, 0.401 mol), bismuth (III) nitrate pentahydrate (99.2 g, 0.200 mol), and toluene (400 ml) were stirred together at 70° C. for 3 hrs under a nitrogen atmosphere. After completion of the reaction, the reaction mixture was cooled to room temperature, and the precipitates thus formed were filtered and washed with toluene to afford <Intermediate 2-a> (61.5 g, 72%).

Synthesis Example 2-(2): Synthesis of [Intermediate 2-b]

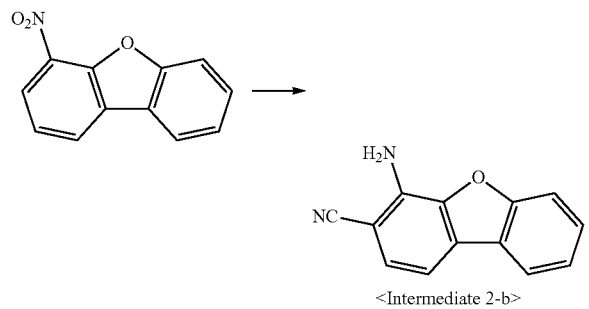

<Intermediate 2-b>

In a 2-L round-bottom flask reactor, ethylcyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. <Intermediate 2-a> (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded <Intermediate 2-b> (20.0 g, 16%).

Synthesis Example 2-(3): Synthesis of [Intermediate 2-c]

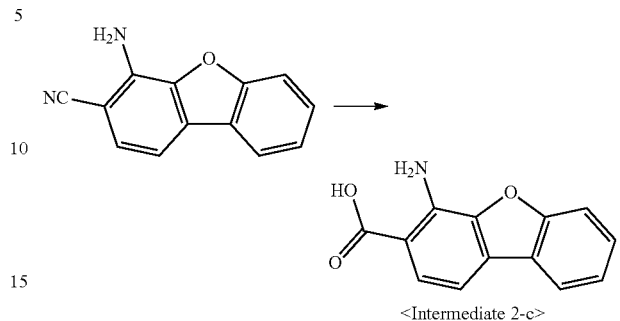

<Intermediate 2-c>

In a 2-L round-bottom flask reactor, <Intermediate 2-b> (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford <Intermediate 2-c> (17.0 g, 88.5%).

Synthesis Example 2-(4): Synthesis of [Intermediate 2-d]

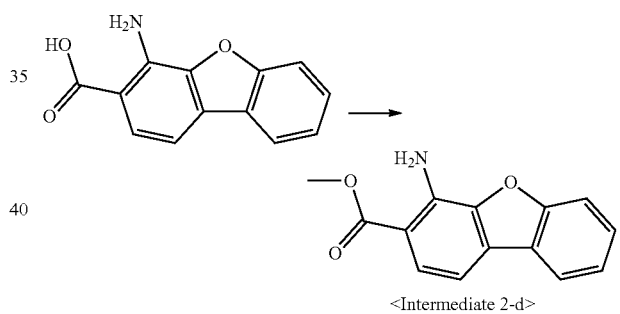

<Intermediate 2-d>

In a 2-L round-bottom flask reactor, <Intermediate 2-c> (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford <Intermediate 2-d> (14.0 77.6%).

Synthesis Example 2-(5): Synthesis of [Intermediate 2-e]

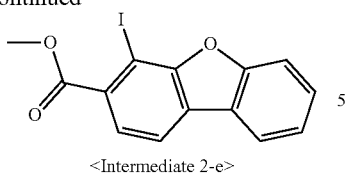

<Intermediate 2-e>

In a 1-L round-bottom flask reactor, a mixture of <Intermediate 2-d> (32.6 g, 0.135 mol), HCl (30 ml), and water (150 ml) was cooled to 0° C. and stirred for 1 hr. At the same temperature, an aqueous solution (75 ml) of sodium nitrite (11.2 g, 0.162 mol) was added and then stirred for 1 hr. An aqueous solution (75 ml) of potassium iodide (44.8 g, 0.270 mol) was dropwise added, taking care not to increase the temperature of the reaction solution above 5° C. Stirring was continued for 5 hrs at room temperature, and after completion of the reaction, the reaction mixture was washed with an aqueous sodium thiosulfate solution and extracted with ethyl acetate and water. The organic layer was separated and concentrated in a vacuum. Purification through column chromatography gave <Intermediate 2-e> (22.8 g, 48%).

Synthesis Example 2-(6): Synthesis of [Intermediate 2-f]

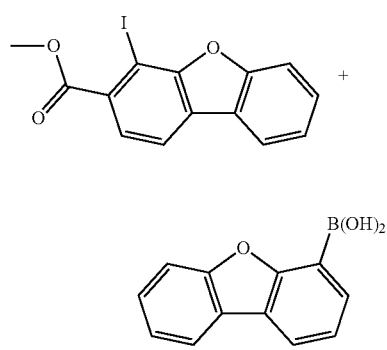

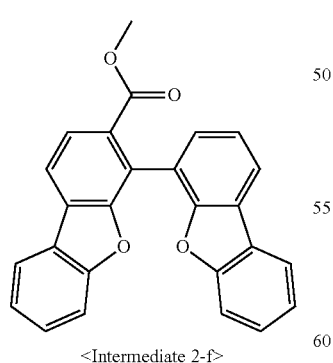

<Intermediate 2-f>

The same procedure as in Synthesis Example 1-(1), with the exception of using <Intermediate 2-e> instead of methyl 5-bromo-2-iodobenzoate, was conducted to synthesize <Intermediate 2-f> (yield 84%).

Synthesis Example 2-(7): Synthesis of [Intermediate 2-g]

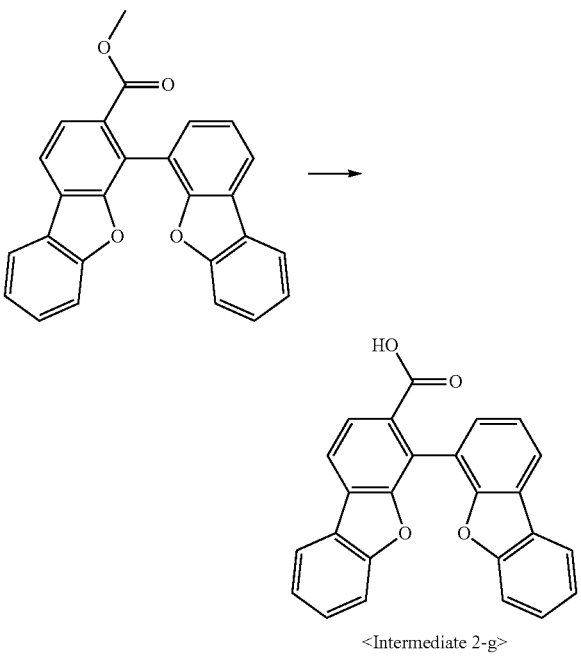

<Intermediate 2-g>

The same procedure as in Synthesis Example 1-(2), with the exception of using <Intermediate 2-f> instead of <Intermediate 1-a>, was conducted to synthesize <Intermediate 2-g> (yield 85%).

Synthesis Example 2-(8): Synthesis of [Intermediate 2-h]

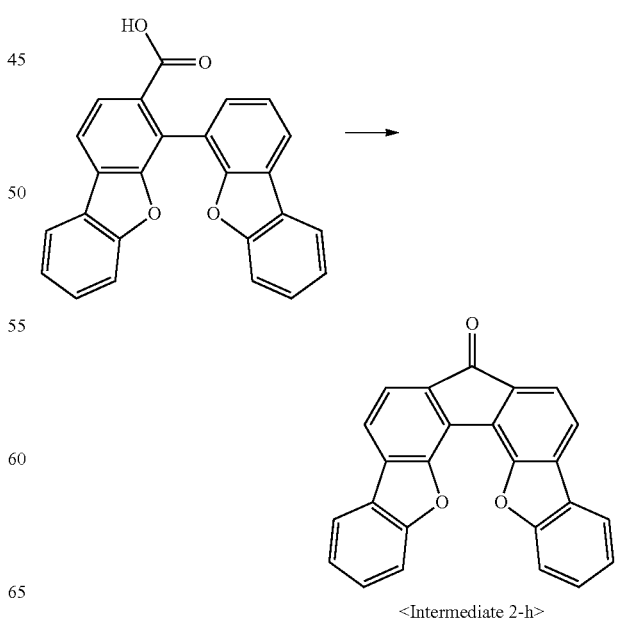

<Intermediate 2-h>

The same procedure as in Synthesis Example 1-(3), with the exception of using <Intermediate 2-g> instead of <Intermediate 1-b>, was conducted to synthesize <Intermediate 2-h> (yield 78%).

Synthesis Example 2-(9): Synthesis of [Intermediate 2-i]

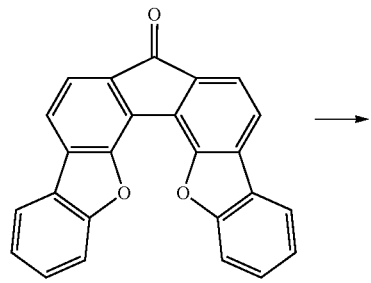

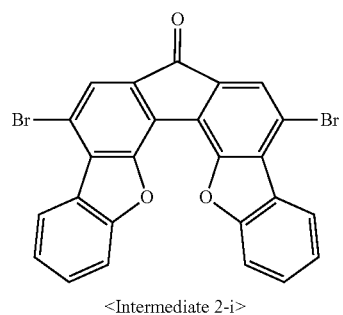

<Intermediate 2-i>

The same procedure as in Synthesis Example 1-(4), with the exception of using <Intermediate 2-h> instead of <Intermediate 1-c>, was conducted to synthesize <Intermediate 2-i> (yield 62%).

Synthesis Example 2-(10): Synthesis of [Intermediate 2-j]

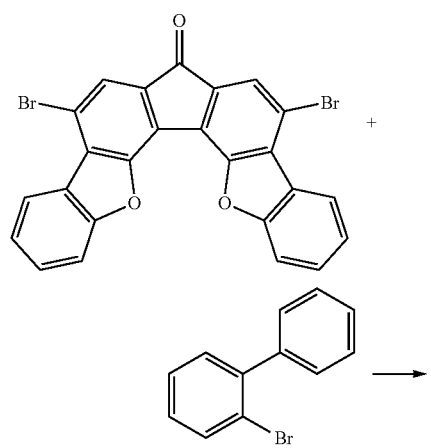

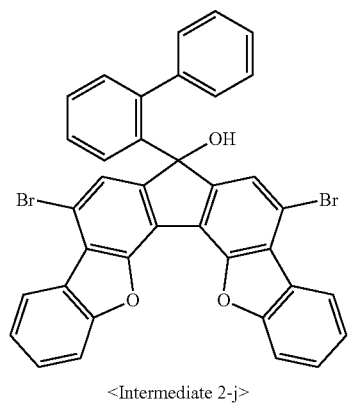

<Intermediate 2-j>

The same procedure as in Synthesis Example 1-(5), with the exception of using <Intermediate 2-i> instead of <Intermediate 1-d>, was conducted to synthesize <Intermediate 2-j> (yield 72%).

Synthesis Example 2-(11): Synthesis of [Intermediate 2-k]

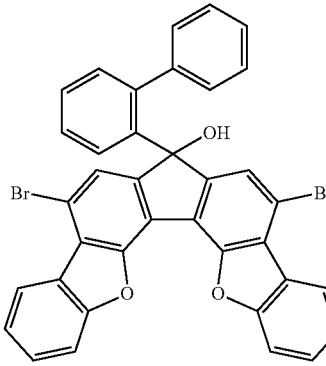

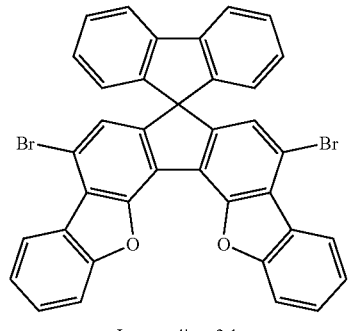

<Intermediate 2-k>

The same procedure as in Synthesis Example 1-(6), with the exception of using <Intermediate 2-j> instead of <Intermediate 1-e>, was conducted to synthesize <Intermediate 2-k> (yield 86%).

Synthesis Example 2-(12): Synthesis of [Chemical Formula 19]

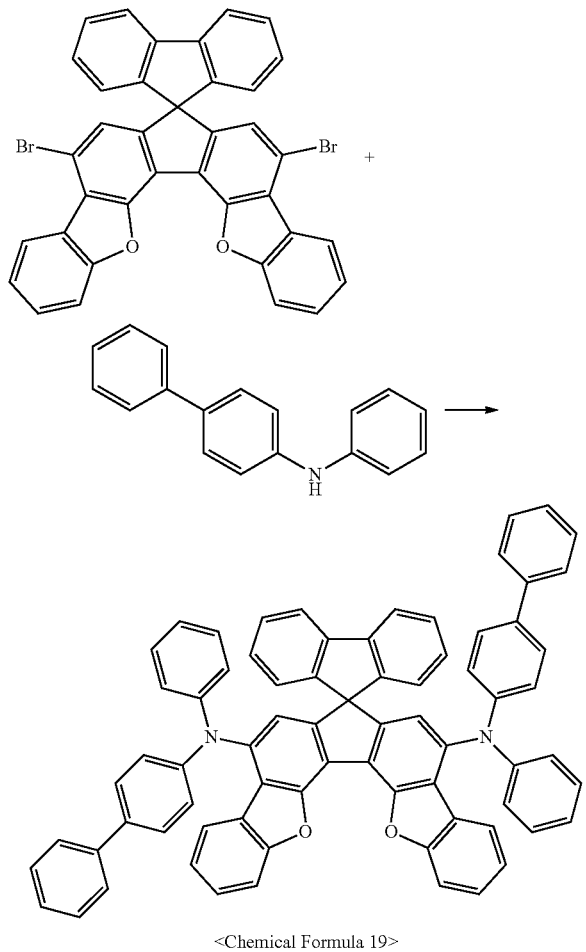

<Chemical Formula 19>

The same procedure as in Synthesis Example 1-(7), with the exception of using <Intermediate 2-k> and N-phenyl-4-biphenylamine instead of <Intermediate 1-f> and (4-tert-butylphenyl)-phenylamine, respectively, was conducted to synthesize <Chemical Formula 19> (yield 35%).

MS (MALDI-TOF): m/z 982.36 [M$^+$]

Synthesis Example 3: Synthesis of Compound of Chemical Formula 32

Synthesis Example 3-(1): Synthesis of [Intermediate 3-a]

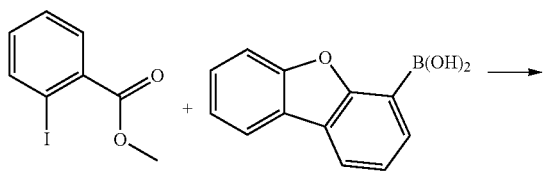

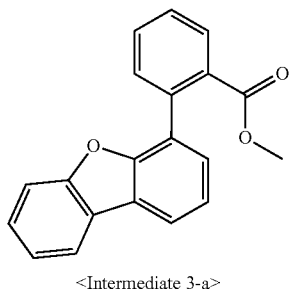

<Intermediate 3-a>

In a 500-mL round-bottom flask reactor, methyl 2-iodobenzoate (19.1 g, 73 mmol), 4-dibenzofuran boronic acid (18.7 g, 88 mmol), tetrakis(triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 3-a>. (9.5 g, 43%)

Synthesis Example 3-(2): Synthesis of [Intermediate 3-b]

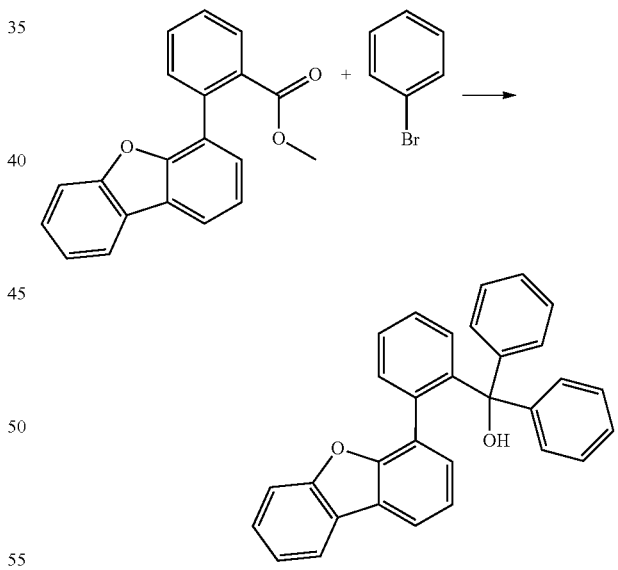

<Intermediate 3-b>

In a 2-L round-bottom flask reactor, bromobenzene (13.2 g, 83.97 mmol) and tetrahydrofuran (250 ml) were stirred together at a low temperature in a nitrogen atmosphere. At −78° C., n-butyl lithium (ca. 58 ml) was dropwise added over 2 hrs, followed by <Intermediate 3-a> (9.4 g 31.1 mmol). After completion of the reaction, the reaction mixture was stirred, together with water (100 ml), for 30 min, and extraction gave <Intermediate 3-b>. (3.2 g, 24%)

Synthesis Example 3-(3): Synthesis of [Intermediate 3-c]

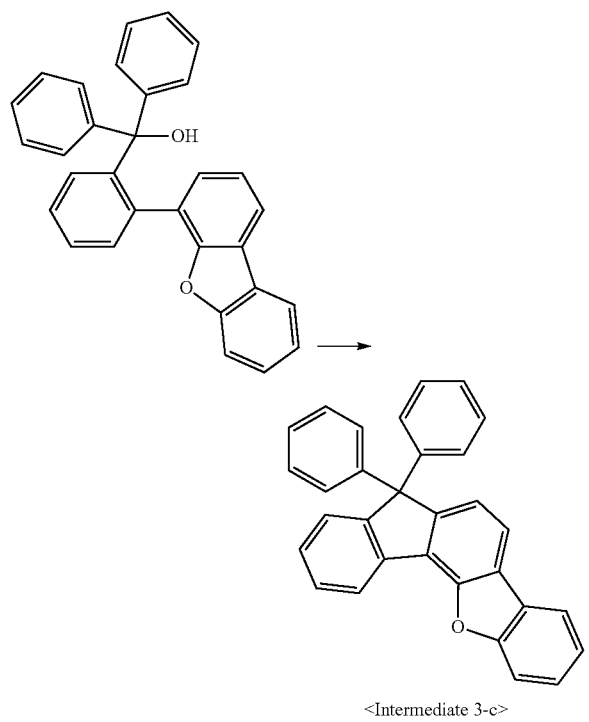

<Intermediate 3-c>

In a 2-L round-bottom flask reactor, <Intermediate 3-b> (55.0 g, 129 mmol), acetic acid (500 ml), and sulfuric acid (10 ml) were stirred together for 5 hrs under reflux. After completion of the reaction, the reaction mixture was cooled to room temperature, and the precipitates thus produced were filtered and washed with methanol to afford <Intermediate 3-c>. (50 g, 95%)

Synthesis Example 3-(4): Synthesis of [Intermediate 3-d]

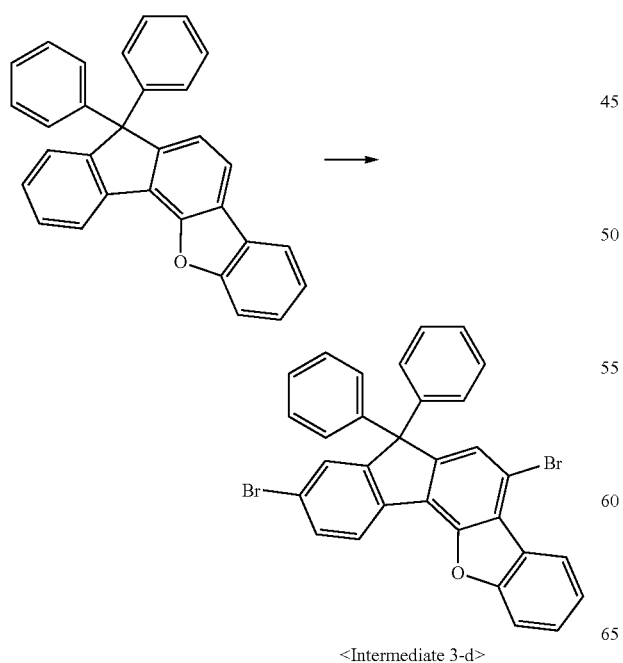

<Intermediate 3-d>

In a 2-L round bottom flask reactor, <Intermediate 3-c> (50 g, 122 mmol) and 600 ml of dichloromethane were stirred together at room temperature. A dilution of bromine (13.7 ml, 85 mmol) in 50 ml of dichloromethane was dropwise added, followed stirring for about 3 hrs. Recrystallization in methanol afforded <Intermediate 3-d>. (45.6 g, yield 66%)

Synthesis Example 3-(5): Synthesis of [Intermediate 3-e]

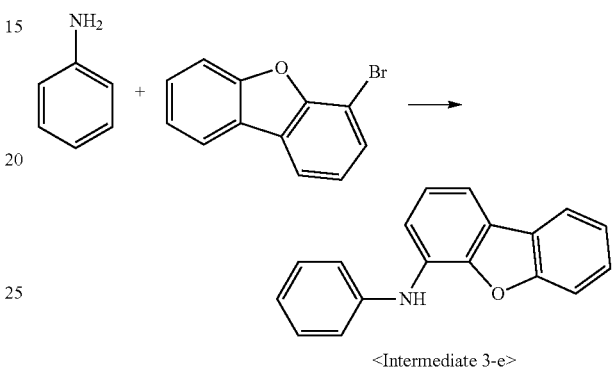

<Intermediate 3-e>

In a 500-ml round-bottom flask reactor, aniline (20 g, 215 mmol), 4-bromodibenzofuran (53.1 g, 215 mmol), bis-dibenzylidene acetone dipalladium (3.9 g, 4 mmol), 2,2'-bis (diphenylphosphine)-1,1'-binaphthyl (1.2 g, 4 mmol), sodium tert-butoxide (41.3 g, 43 mmol), and toluene (200 ml) were stirred together under reflux. The reaction mixture was cooled to room temperature and washed with methanol. Recrystallization in dichloromethane and methane gave [Intermediate 3-e]. (37.9 g, 68%)

Synthesis Example 3-(6): Synthesis of [Chemical Formula 32]

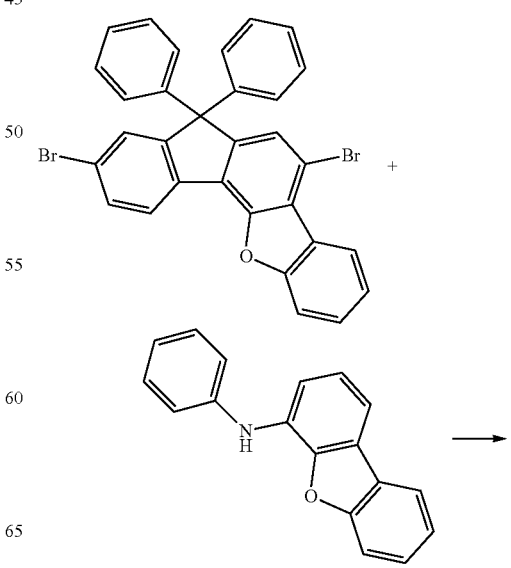

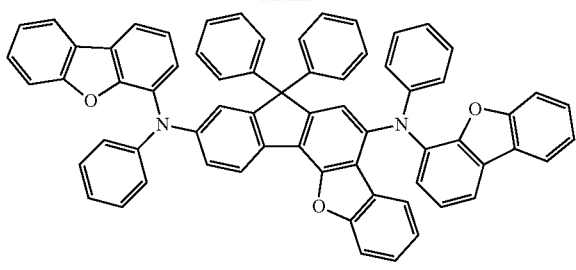

<Chemical Formula 32>

The same procedure as in Synthesis Example 1-(7), with the exception of using <Intermediate 3-d> and <Intermediate 3-e> instead of <Intermediate 1-f> and (4-tert-butylphenyl)-phenylamine, respectively, was conducted to synthesize <Chemical Formula 32> (yield 37%).

MS (MALDI-TOF): m/z 922.32 [M$^+$]

Synthesis Example 4: Synthesis of Compound of Chemical Formula 34

Synthesis Example 4-(1): Synthesis of [Chemical Formula 34]

The same procedures as in Synthesis Examples 1-(1) to 1-(7), with the exception of using dibenzofuran-1-boronic acid and bis(4-tert-butylphenyl)amine instead of dibenzofuran-4-boronic acid in Synthesis Example 1-(1) and (4-tert-butylphenyl)-phenylamine in Synthesis Example 1-(7), respectively, was conducted to synthesize <Chemical Formula 34>. (yield 35%)

MS (MALDI-TOF): m/z 964.53 [M$^+$]

Synthesis Example 5: Synthesis of Compound of Chemical Formula 43

Synthesis Example 5-(1): Synthesis of [Intermediate 5-a]

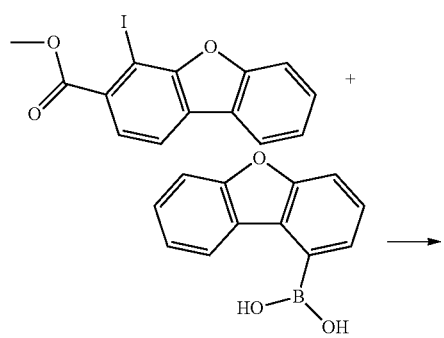

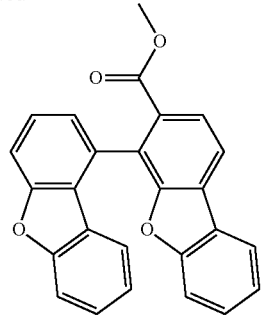

<Intermediate 5-a>

In a 250-mL round-bottom flask reactor, <Intermediate 2-e> (9.3 g, 25 mmol), 1-dibenzofuran boronic acid (8.3 g, 28 mmol), tetrakis(triphenylphosphine)palladium (0.6 g, 0.05 mmol), and potassium carbonate (6.7 g, 50 mmol) were stirred together with toluene (50 mL), tetrahydrofuran (50 mL), and water (20 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 5-a> (5.3 g, 52.3%).

Synthesis Example 5-(2): Synthesis of [Intermediate 5-b]

<Intermediate 5-b>

In a 100-mL round-bottom flask reactor, <Intermediate 5-a> (5.3 g, 15 mmol), sodium hydroxide (0.7 g, 17 mmol) and ethanol (50 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 2-g>. (4.5 g, 88.0%)

Synthesis Example 5-(3): Synthesis of
[Intermediate 5-c]

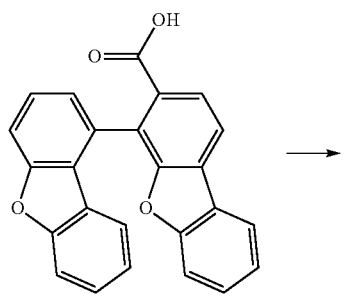

<Intermediate 5-c>

In a 100-mL round-bottom flask reactor, <Intermediate 5-b> (4.5 g, 12 mmol) and methanesulfonic acid (30 ml) were stirred together for 3 hrs at 80° C. After the completion of the reaction was confirmed using thin-layer chromatography, the reaction mixture was cooled to room temperature and dropwise added to ice water (50 ml). After stirring for 30 min, the solid thus formed was filtered and washed with water and methanol to afford <Intermediate 5-c> (3.8 g, 88.8%).

Synthesis Example 5-(4): Synthesis of
[Intermediate 5-d]

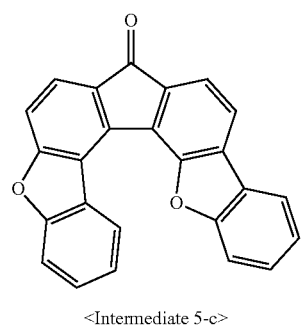

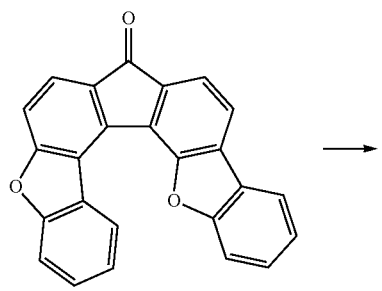

<Intermediate 5-d>

In a 100-mL round-bottom flask reactor, <Intermediate 5-c> (3.8 g, 11 mmol) and dichloromethane (40 ml) were stirred together at room temperature. A dilution of bromine (1.1 ml, 22 mmol) in dichloromethane (10 ml) was dropwise added, followed by stirring at room temperature for 8 hrs. After completion of the reaction, the reaction mixture was stirred together with acetone (20 ml). The solid thus formed was filtered and washed with acetone. Recrystallization in monochlorobenzene afforded <Intermediate 5-d> (3.0 g, 55%).

Synthesis Example 5-(5): Synthesis of
[Intermediate 5-e]

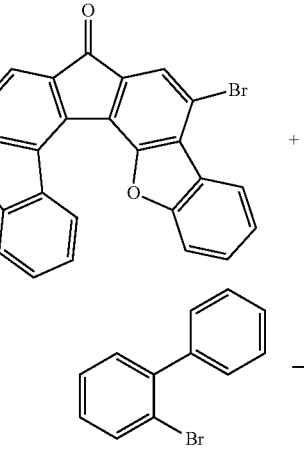

+

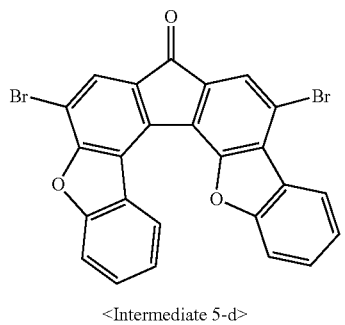

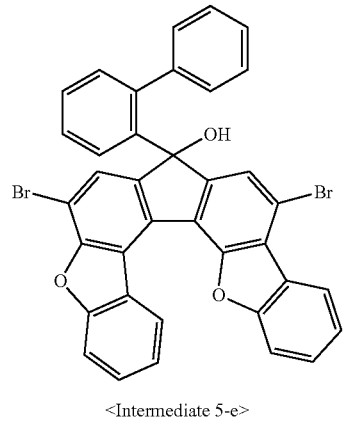

<Intermediate 5-e>

In a 100-ml round-bottom flask reactor, 2-bromobiphenyl (2.1 g, 0.009 mol) and tetrahydrofuran (30 ml) were chilled at −78° C. in a nitrogen atmosphere. At the same temperature, n-butyl lithium (4.8 ml, 0.008 mol) was dropwise added to the reaction solution, which was then stirred for 2 hrs. Thereafter, <Intermediate 5-d> (3.0 g, 0.006 mol) was added little by little to the reaction solution and stirred at room temperature. After the reaction was stopped with H$_2$O (10 ml), extraction was conducted with ethyl acetate and water. The organic layer was separated, concentrated in a vacuum, and recrystallized in acetonitrile to afford <Intermediate 5-e> as a solid (2.5 g, 64%).

Synthesis Example 5-(6): Synthesis of [Intermediate 5-f]

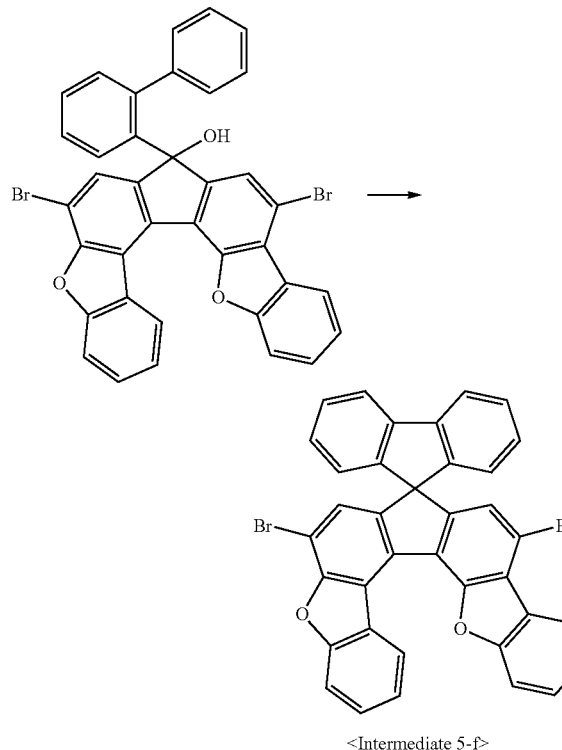

<Intermediate 5-f>

In a 100-ml round-bottom flask reactor, a mixture of <Intermediate 5-e> (2.5 g, 0.04 mol), acetic acid (25 ml), and sulfuric acid (0.5 ml) was stirred for 5 hrs under reflux. When a precipitate was formed, the completion of the reaction was monitored using thin-layer chromatography. The reaction mixture was then cooled to room temperature and filtered. The filtrate was washed with $H_2O$ and methanol and dissolved in monochlorobenzene. Following silica gel chromatography, the fraction was concentrated and cooled to room temperature to give <Intermediate 5-f> (2.2 g, 90%).

Synthesis Example 5-(7): Synthesis of [Intermediate 5-g]

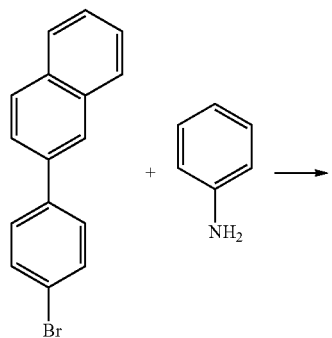

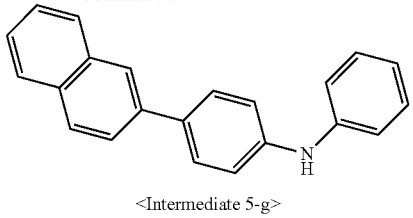

<Intermediate 5-g>

In a 250-ml round-bottom flask reactor, 1-bromo-4-(2-naphthyl)benzene (9.9 g, 0.035 mol), aniline (3.6 g, 0.039 mol), tris(dibenzylideneacetone)dipalladium(0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together under reflux for 3 hours. After completion of the reaction, the reaction solution was cooled to room temperature and extracted with ethyl acetate and water. The organic layer thus formed was treated with magnesium sulfate and concentrated in a vacuum. Column chromatographic isolation afforded <Intermediate 5-g> (8.3 g, 80%).

Synthesis Example 5-(8): Synthesis of [Chemical Formula 43]

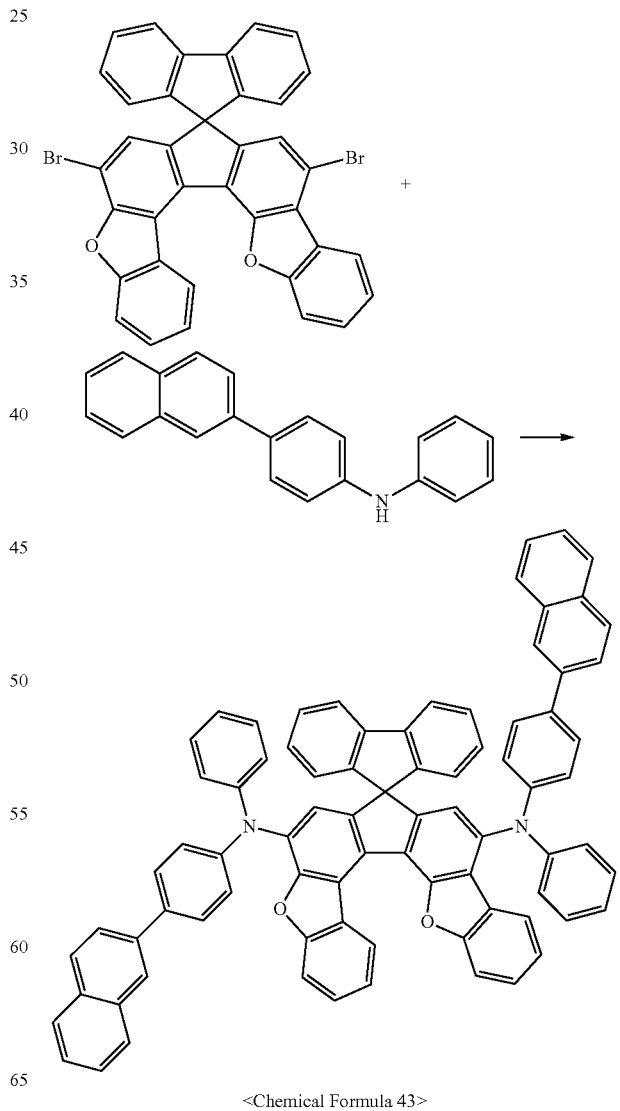

<Chemical Formula 43>

The same procedure as in Synthesis Example 1-(7), with the exception of using <Intermediate 5-f> and <Intermediate 5-g> instead of <Intermediate 1-f> and (4-tert-butylphenyl)phenylamine, respectively, was conducted to synthesize <Chemical Formula 43> (yield 38%).

MS (MALDI-TOF): m/z 1082.39 [M$^+$]

Synthesis Example 6: Synthesis of Compound of Chemical Formula 45

Synthesis Example 6-(1): Synthesis of [Intermediate 6-a]

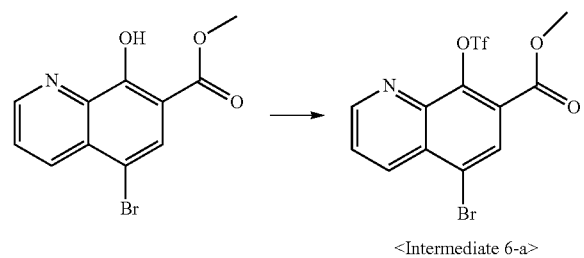 [SMILES: COC(=O)c1cc(Br)c2cccnc2c1O ; COC(=O)c1cc(Br)c2cccnc2c1OS(=O)(=O)C(F)(F)F]
<Intermediate 6-a>

In a 2-L round-bottom flask reactor, methyl-4-bromo-1-hydroxy-2-naphthoate (50 g, 178 mmol) and dichloromethane were stirred together. In a nitrogen atmosphere, pyridine (28.1 g, 356 mmol) was added to the reaction solution and stirred for 20 min at room temperature. After being cooled to 0° C., the reaction solution was added with drops of trifluoromethanesulfonic anhydride (65.24 g, 231 mmol) in a nitrogen atmosphere. When the reaction was completed as monitored by TLC after three hours of stirring, water (20 ml) was added, followed by stirring for 10 min. The reaction solution was concentrated in a vacuum. Column chromatographic isolation afforded <Intermediate 6-a> (45 g, 61%).

Synthesis Example 6-(2): Synthesis of [Intermediate 6-b]

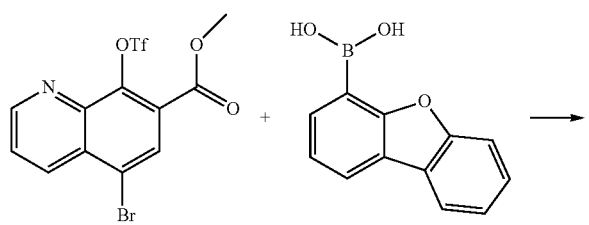

<Intermediate 6-b>

To a 1-L round-bottom flask reactor were added <Intermediate 6-a> (45.0 g, 0.109 mol), 4-dibenzofuran boronic acid (25.4 g, 0.120 mol), tetrakis(triphenylphosphine)palladium (2.5 g, 0.22 mmol), and potassium carbonate (30.1 g, 0.218 mol), followed by toluene (300 mL), ethanol (130 mL), and water (90 mL). The temperature of the reactor was elevated to 80° C. at which stirring was conducted for 5 hours. When the reaction was completed, the temperature of the reactor was lowered to room temperature at which extraction with ethyl acetate was performed to isolate an organic layer. The organic layer was concentrated in a vacuum and isolated by column chromatography to afford <Intermediate 6-b> (22.0 g, 46.1%).

Synthesis Example 6-(3): Synthesis of [Intermediate 6-c]

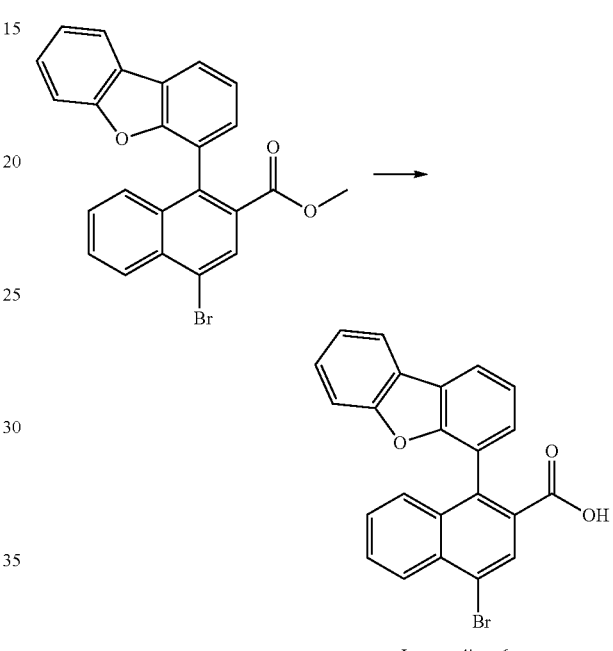

<Intermediate 6-c>

In a 1-L round-bottom flask reactor, <Intermediate 6-b> (22.0 g, 0.051 mol) was stirred together with sodium hydroxide (2.65 g, 0.066 mol) for 48 hrs under reflux. After completion of the reaction, the reaction mixture was cooled to room temperature. The chilled solution was acidified with drops of 2-N HCl, followed by stirring for 30 min. The solid thus formed was filtered and recrystallized in dichloromethane and n-hexane to afford <Intermediate 6-c> (17.6 g, 83%).

Synthesis Example 6-(4): Synthesis of [Intermediate 6-d]

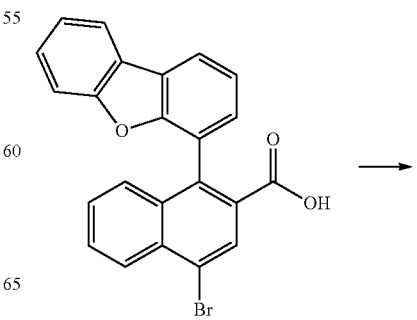

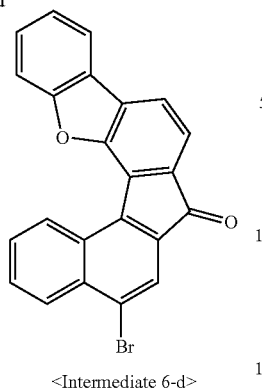

<Intermediate 6-d>

In a 500-mL round-bottom flask reactor, <Intermediate 6-c> (17.6 g, 0.042 mol) and methanesulfonic acid (170 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the precipitates thus formed were filtered and washed with water and methanol. They were dissolved in monochlorobenzene and filtered through a silica gel pad. The filtrate was concentrated by heating and recrystallized in acetone to afford <Intermediate 6-d> (12 g, 71%).

Synthesis Example 6-(5): Synthesis of [Intermediate 6-e]

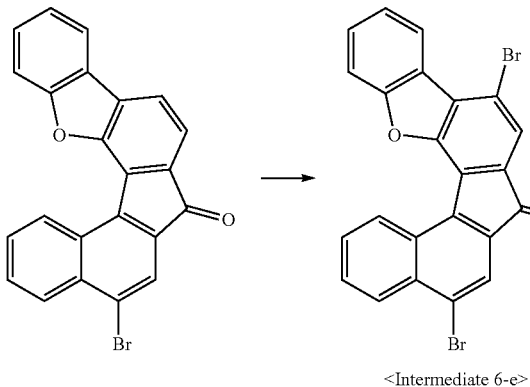

<Intermediate 6-e>

In a 1-L round-bottom flask reactor, <Intermediate 6-d> (12.0 g, 0.030 mol) and dichloromethane (360 ml) were stirred together at room temperature. A dilution of bromine (3.1 ml, 0.06 mol) in dichloromethane (40 ml) was dropwise added, followed by stirring at room temperature for 12 hrs. After completion of the reaction, methanol (100 ml) was added to induce the formation of precipitates. They were then filtered and washed with methanol. Recrystallization in 1,2-dichlorobenzene and acetone afforded <Intermediate 6-e> (10.3 g, 72%).

Synthesis Example 6-(6): Synthesis of [Intermediate 6-f]

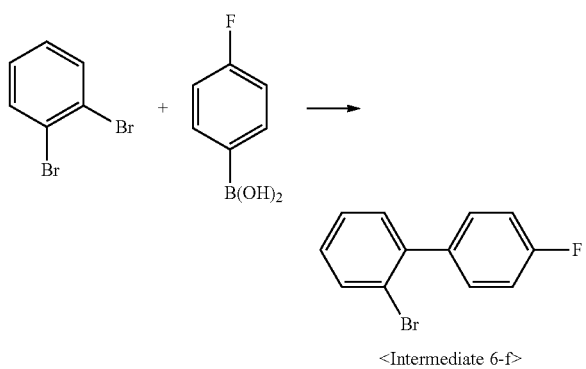

<Intermediate 6-f>

In a 500-mL round-bottom flask reactor, 1,2-dibromobenzene (20.0 g, 0.085 mol), 4-fluorobenzoboronic acid (14.2 g, 0.102 mol), tetrakis(triphenylphosphine)palladium (2.9 g, 0.0025 mmol), and potassium carbonate (23.4 g, 0.169 mol) were placed, followed by toluene (100 mL), tetrahydrofuran (100 mL) and water (40 mL). The reaction mixture was heated to 80° C. and stirred for 10 hrs. After completion of the reaction, the reaction mixture was cooled to room temperature and extracted with ethyl acetate. The organic layer was isolated and concentrated in a vacuum. Purification through column chromatography afforded <Intermediate 6-f> (14.1 g, 66.2%)

Synthesis Example 6-(7): Synthesis of [Intermediate 6-g]

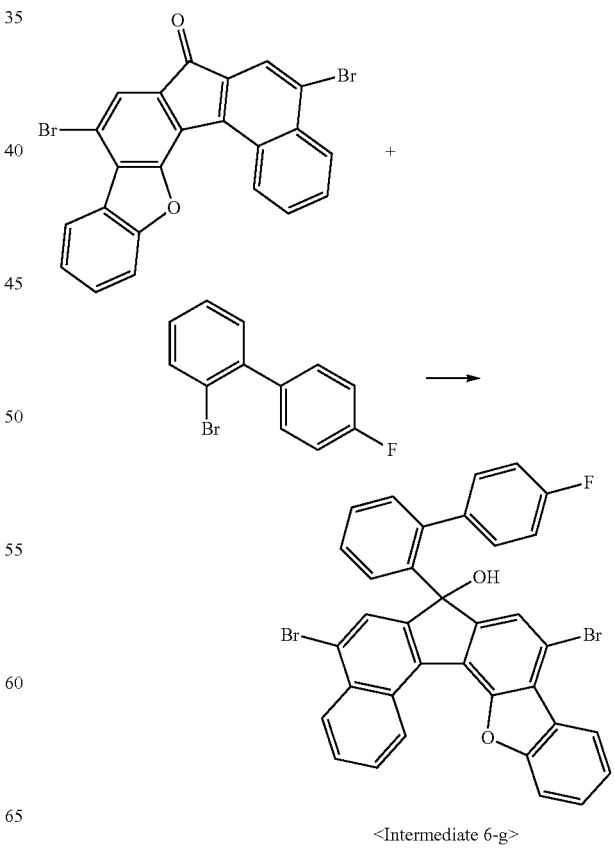

<Intermediate 6-g>

The same procedure as in Synthesis Example 1-(5), with the exception that <Intermediate 6-f> was used instead of <Intermediate 1-d>, was conducted to synthesize <Intermediate 6-g> (yield 78%).

Synthesis Example 6-(8): Synthesis of [Intermediate 6-h]

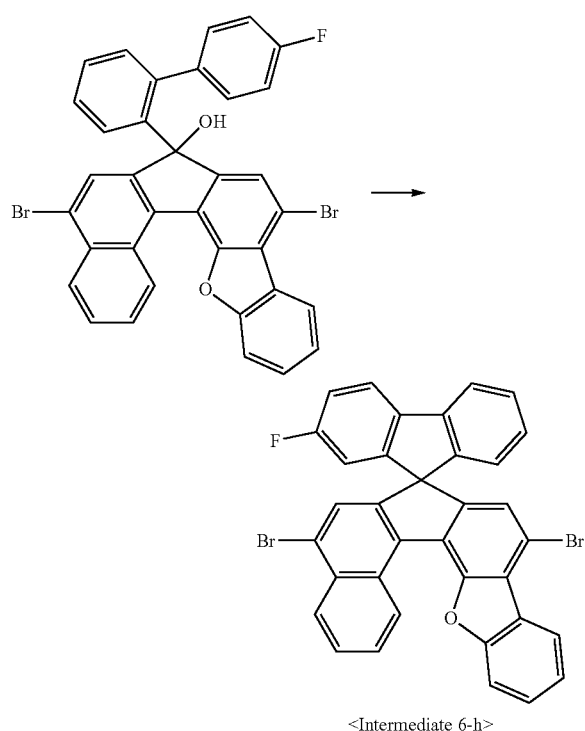

<Intermediate 6-h>

The same procedure as in Synthesis Example 1-(6), with the exception of using <Intermediate 6-g> instead of <Intermediate 1-e>, was conducted to synthesize <Intermediate 6-h> (yield 69%).

Synthesis Example 6-(9): Synthesis of [Chemical Formula 45]

The same procedure as in Synthesis Example 1-(7), with the exception of using <Intermediate 6-h> instead of <Intermediate 1-f>, was conducted to synthesize <Chemical Formula 45> (yield 35%).
MS (MALDI-TOF): m/z 920.41 [M+]

Synthesis Example 7: Synthesis of Compound of Chemical Formula 50

Synthesis Example 7-(1): Synthesis of [Chemical Formula 50]

The same procedure as in Synthesis Example 1-(7), with the exception of using <Intermediate 3-d> and N-(4-tert-butylphenyl)-2-naphthylamine instead of <Intermediate 1-f> and (4-tert-butylphenyl)phenylamine, respectively, was conducted to synthesize <Chemical Formula 50> (yield 36%).
MS (MALDI-TOF): m/z 954.45 [M+]

Synthesis Example 8: Synthesis of Compound of Chemical Formula 57

Synthesis Example 8-(1): Synthesis of [Intermediate 8-a]

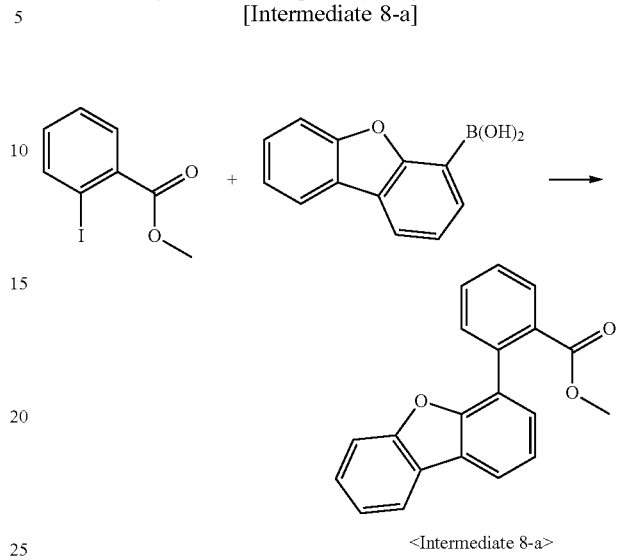

<Intermediate 8-a>

In a 500-mL round-bottom flask reactor, methyl 2-iodobenzoate (19.1 g, 73 mmol), 4-dibenzofuran boronic acid (18.7 g, 88 mmol), tetrakis(triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 8-a>. (9.5 g, 43%)

Synthesis Example 8-(2): Synthesis of [Intermediate 8-b]

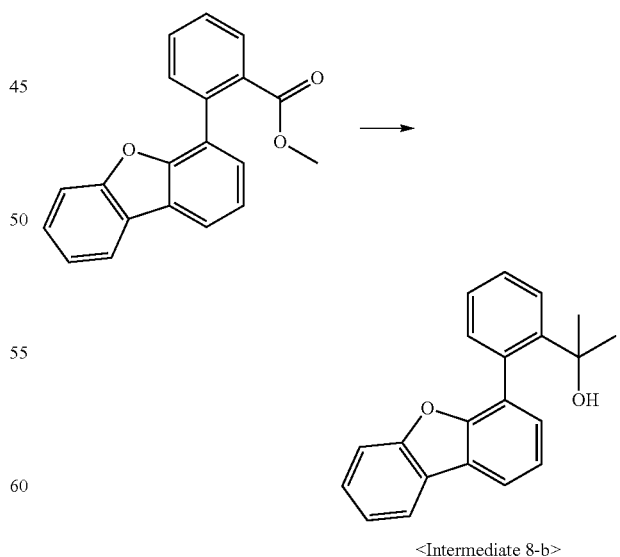

<Intermediate 8-b>

In a round-bottom flask, tetrahydrofuran (250 ml) was mixed with <Intermediate 8-a> (25 g, 80 mmol) and the mixture was cooled to −78° C. under a nitrogen atmosphere. After 30 min, drops of 1.0 M methyl magnesium bromide (210 ml, 240 mmol) were slowly added over 1 hour, followed by elevation to room temperature. At room temperature, stirring for 2 hours was conducted before dropwise addition of an aqueous ammonium chloride solution. Extraction, vacuum distillation, and recrystallization in hexane in sequence afforded <Intermediate 8-b> (19.4 g, yield 80%).

Synthesis Example 8-(3): Synthesis of [Intermediate 8-c]

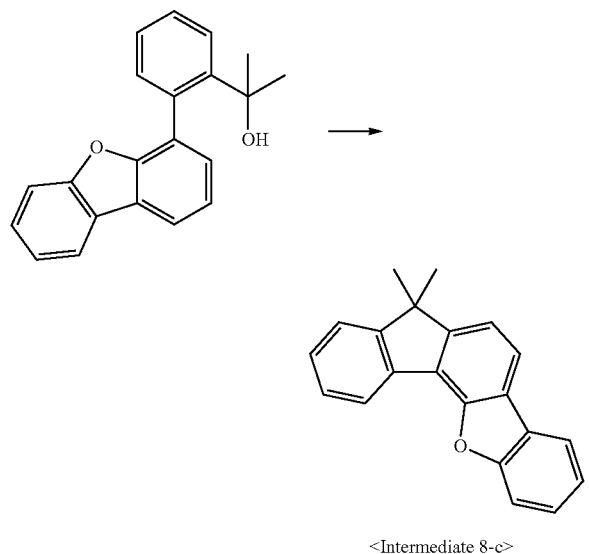

<Intermediate 8-c>

In a round-bottom flask reactor, acetic acid (300 ml) was stirred, together with <Intermediate 5-b> (20 g, 66 mmol), at 0° C. for 10 min and then together with phosphoric acid (350 mL) at room temperature for about 1 hr. Following neutralization with an aqueous sodium hydroxide solution, extraction and vacuum concentration were conducted sequentially. Purification via column chromatography afforded <Intermediate 8-c> (13.7 g, 73%).

Synthesis Example 8-(4): Synthesis of [Intermediate 8-d]

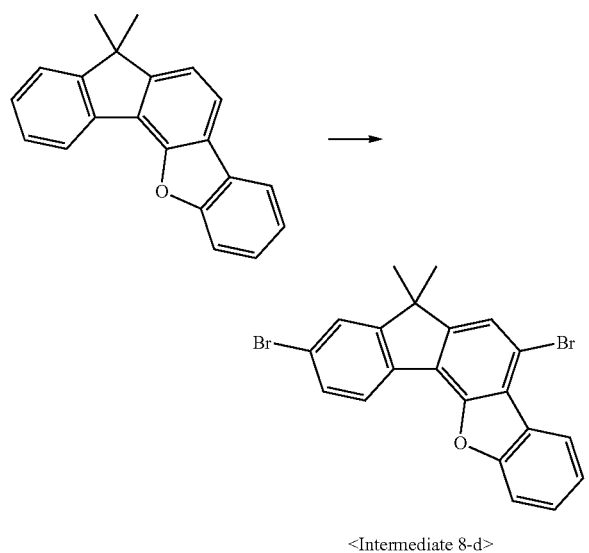

<Intermediate 8-d>

The same procedure as in Synthesis Example 1-(4), with the exception of using <Intermediate 8-c> instead of <Intermediate 1-c>, was carried out to afford <Intermediate 8-d> (yield 65%).

Synthesis Example 8-(5): Synthesis of [Intermediate 8-e]

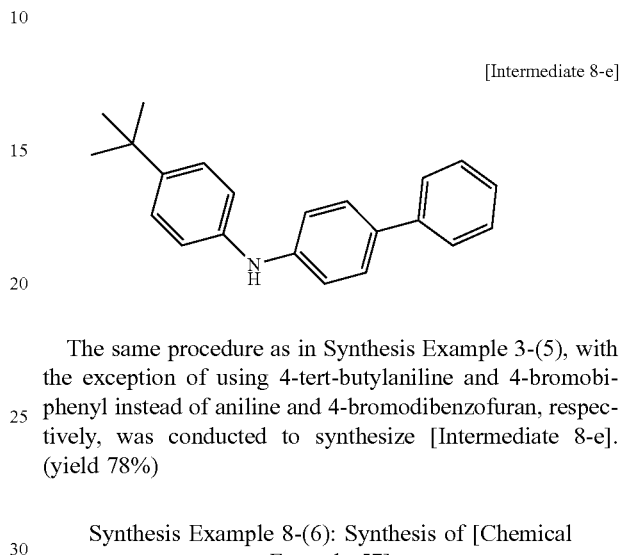

[Intermediate 8-e]

The same procedure as in Synthesis Example 3-(5), with the exception of using 4-tert-butylaniline and 4-bromobiphenyl instead of aniline and 4-bromodibenzofuran, respectively, was conducted to synthesize [Intermediate 8-e]. (yield 78%)

Synthesis Example 8-(6): Synthesis of [Chemical Formula 57]

The same procedure as in Synthesis Example 1-(7), with the exception of using <Intermediate 8-d> and <Intermediate 8-e> instead of <Intermediate 1-f> and (4-tert-butylphenyl)phenylamine, respectively, was conducted to synthesize <Chemical Formula 57> (yield 37%)

MS (MALDI-TOF): m/z 882.45 [M$^+$]

Synthesis Example 9: Synthesis of Compound of Chemical Formula 58

Synthesis Example 9-(1): Synthesis of [Chemical Formula 58]

The same procedure as in Synthesis Example 1-(7), with the exception of using <Intermediate 8-d> and bis(4-biphenylyl)amine instead of <Intermediate 1-f> and (4-tert-butylphenyl)phenylamine, respectively, was conducted to synthesize <Chemical Formula 58> (yield 37%).

MS (MALDI-TOF): m/z 922.39 [M$^+$]

Synthesis Example 10: Synthesis of Compound of Chemical Formula 63

Synthesis Example 10-(1): Synthesis of [Chemical Formula 63] The same procedure as in Synthesis Examples 8-(1) to 8-(6), with the exception of using (6-phenyldibenzo[b,d]furan-4-yl)boronic acid instead of dibenzofuran-4-boronic acid, was conducted to synthesize <Chemical Formula 63>. (yield 39%)

MS (MALDI-TOF): m/z 958.49 [M$^+$]

Synthesis Example 11: Synthesis of Compound of Chemical Formula 73

Synthesis Example 11-(1): Synthesis of [Intermediate 11-a]

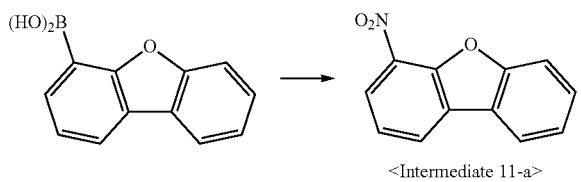 [SMILES: OB(O)c1cccc2c1oc1ccccc12 ; O=[N+]([O-])c1cccc2c1oc1ccccc12]

<Intermediate 11-a>

In a 1-L round-bottom flask reactor, 4-dibenzofuran boronic acid (85.0 g, 0.401 mol), bismuth (III) nitrate pentahydrate (99.2 g, 0.200 mol), and toluene (400 ml) were stirred together at 70° C. for 3 hrs in a nitrogen atmosphere. After completion of the reaction, the reaction mixture was cooled to room temperature and the solid thus formed was filtered and washed with toluene to afford <Intermediate 11-a>. (61.5 g, 72%)

Synthesis Example 11-(2): Synthesis of [Intermediate 11-b]

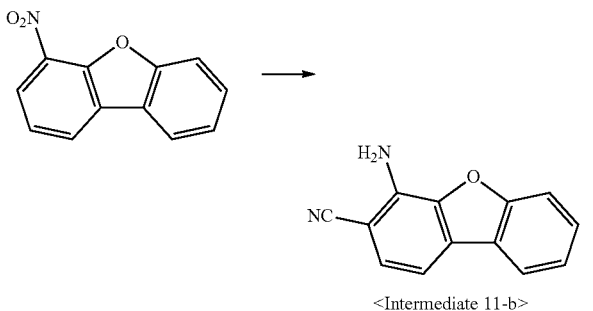

<Intermediate 11-b>

In a 2-L round-bottom flask reactor, ethyl cyanoacetate (202.9 g, 1.794 mol) and dimethyl formamide (500 ml) were placed. Potassium hydroxide (67.1 g, 1.196 mol) and potassium cyanide (38.95 g, 0.598 mol) were added, followed by dimethyl formamide (200 ml). The resulting mixture was stirred at room temperature, added with <Intermediate 11-a> (127.5 g, 0.737 mol) little by little, and then stirred at 50° C. for 72 hrs. After completion of the reaction, an aqueous sodium hydroxide solution (25%, 200 ml) was added and stirred for 3 hrs under reflux. After cooling to room temperature, extraction with ethyl acetate and water was conducted. The organic layer thus formed was separated, and concentrated in a vacuum. Purification by column chromatography afforded <Intermediate 11-b> (20.0 g, 16%).

Synthesis Example 11-(3): Synthesis of [Intermediate 11-c]

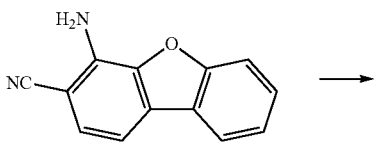

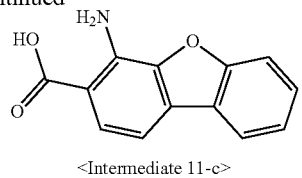

<Intermediate 11-c>

In a 2-L round-bottom flask reactor, a mixture of <Intermediate 11-b> (20.0 g, 0.096 mol), ethanol (600 ml), and an aqueous potassium hydroxide solution (170 ml, 142.26 g, 2.53 mol) was stirred for 12 hrs under reflux. After completion of the reaction mixture was cooled to room temperature, and then acidified with 6 N HCl (400 ml). Stirring for 20 min was followed by filtration. The solid thus obtained was washed with ethanol to afford <Intermediate 11-c> (17.0 g, 88.5%).

Synthesis Example 11-(4): Synthesis of [Intermediate 11-d]

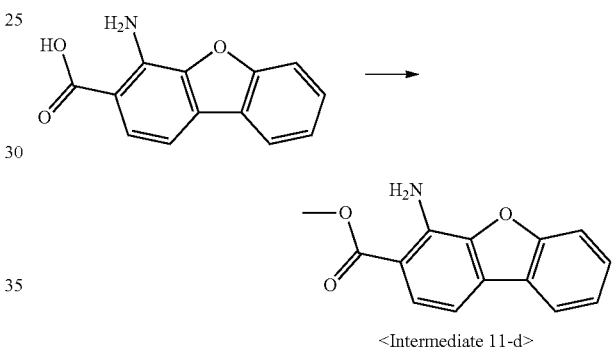

<Intermediate 11-d>

In a 2-L round-bottom flask reactor, a mixture of <Intermediate 11-c> (17.0 g, 0.075 mol) and sulfuric acid (15 ml) was stirred for 72 hrs under reflux. After completion of the reaction, the reaction mixture was extracted with ethyl acetate and water. The organic layer was separated and washed with an aqueous sodium hydrogen carbonate solution. An excess of methanol was added during the vacuum concentration of the organic layer, followed by filtration to afford <Intermediate 11-d> (14.0 g, 77.6%).

Synthesis Example 11-(5): Synthesis of [Intermediate 11-e]

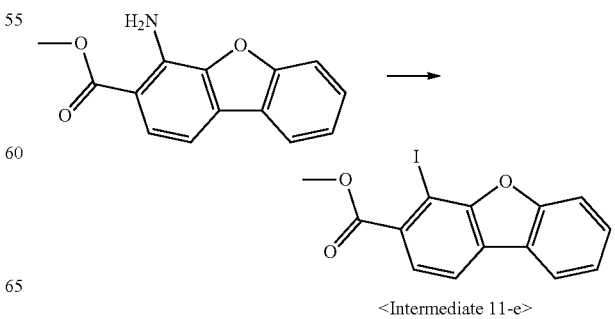

<Intermediate 11-e>

In a 500-mL round-bottom flask reactor, a mixture of <Intermediate 11-d> (14.0 g, 0.058 mol), HCl (20 ml), and water (100 ml) was cooled to 0° C. and stirred for 1 hr. At the same temperature, an aqueous solution (50 ml) of sodium nitrite (7.4 g, 0.116 mol) was added and then stirred for 1 hr. An aqueous solution (100 ml) of potassium iodide (30.0 g, 0.180 mol) was dropwise added, taking care not to increase the temperature of the reaction solution above 5° C. Stirring was continued for 5 hrs at room temperature, and after completion of the reaction, the reaction mixture was washed with an aqueous sodium thiosulfate solution and extracted with ethyl acetate and water. The organic layer was separated and concentrated in a vacuum. Purification through column chromatography gave <Intermediate 11-e> (9.1 g, 48%).

Synthesis Example 11-(6): Synthesis of [Intermediate 11-f]

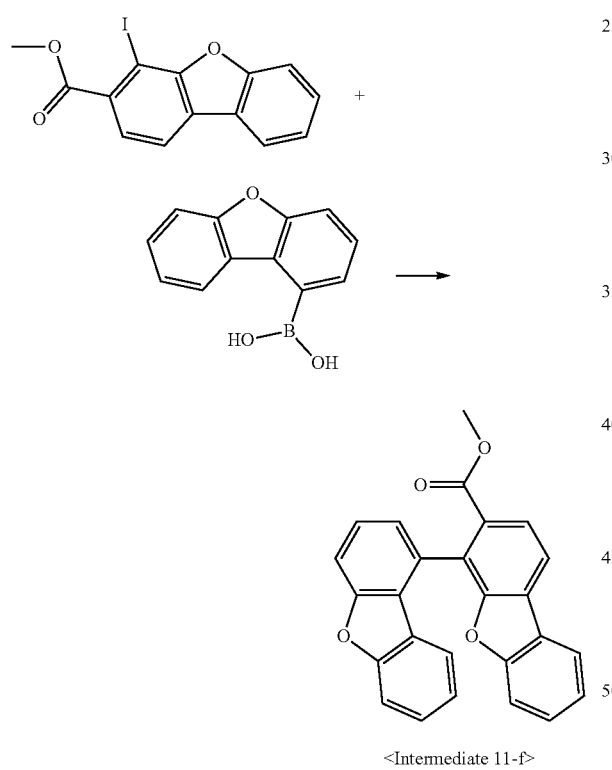

<Intermediate 11-f>

In a 250-mL round-bottom flask reactor, <Intermediate 11-e> (9.3 g, 25 mmol), 1-dibenzofuran boronic acid (8.3 g, 28 mmol), tetrakis(triphenylphosphine)palladium (0.6 g, 0.05 mmol), and potassium carbonate (6.7 g, 50 mmol) were stirred together with toluene (50 mL), tetrahydrofuran (50 mL), and water (20 mL) for 10 hours at 80° C. After completion of the reaction, the reaction mixture was cooled to room temperature and extracted with ethyl acetate. The organic layer thus formed was separated, concentrated in a vacuum, and purified by column chromatography to afford <Intermediate 11-f> (5.3 g, 52.3%).

Synthesis Example 11-(7): Synthesis of [Intermediate 11-g]

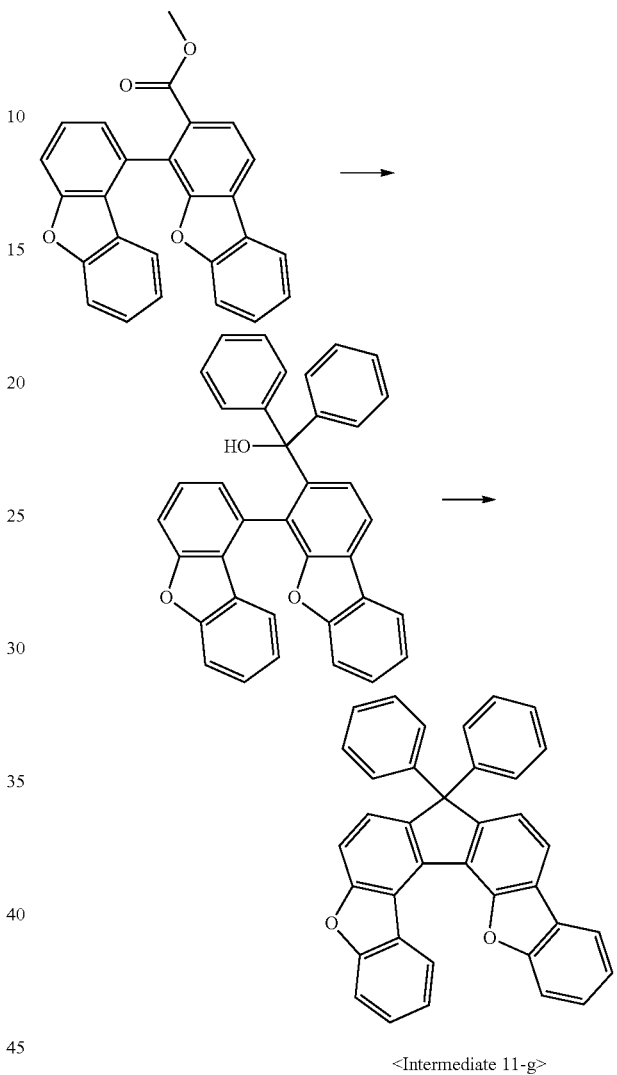

<Intermediate 11-g>

In a 500-ml round-bottom flask reactor, a mixture of bromobenzene (25.5 g, 0.163 mol) and tetrahydrofuran (170 ml) was cooled to −78° C. under a nitrogen atmosphere. n-Butyl lithium (1.6 M, 95.6 ml, 0.153 mol) was dropwise added to the cold mixture, after which stirring was conducted at the same temperature for one hour. <Intermediate 11-f> (20.0 g, 0.051 mol) was added to the mixture and then stirred at room temperature for 3 hours. After completion of the reaction, the reaction mixture was added with water (50 ml) and stirred for 30 min. Extraction with ethyl acetate and water gave an organic layer which was then isolated and concentrated in a vacuum. The concentrate was mixed with acetic acid (200 ml) and HCl (1 ml) and stirred at 80° C. After the reaction was completed, the reaction mixture was cooled to room temperature and the precipitate thus formed was filtered and washed with methanol to afford <Intermediate 11-g> (20.0 g, 78%).

Synthesis Example 11-(8): Synthesis of [Intermediate 11-h]

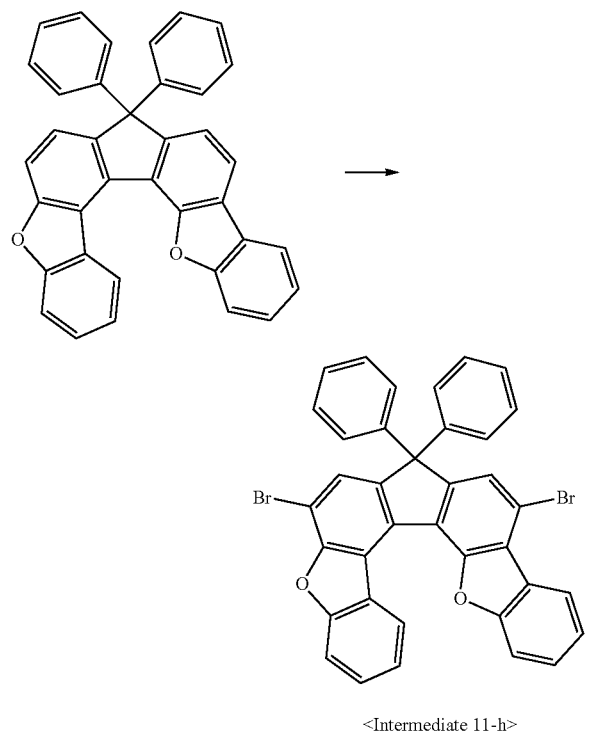

<Intermediate 11-h>

In a 100-mL round-bottom flask reactor, a mixture of <Intermediate 11-g> (20 g, 58 mmol) and dichloromethane (40 ml) was stirred at room temperature. A dilution of bromine (5.8 ml, 116 mmol) in dichloromethane (10 ml) was dropwise added to the reactor and stirred for 8 hours at room temperature. After completion of the reaction, acetone (20 ml) was added to the reactor and stirred. The solid thus formed was filtered and washed with acetone. Recrystallization in monochlorobenzene afforded <Intermediate 11-h> as a solid (15.8 g, 55%).

Synthesis Example 11-(9): Synthesis of [Chemical Formula 73]

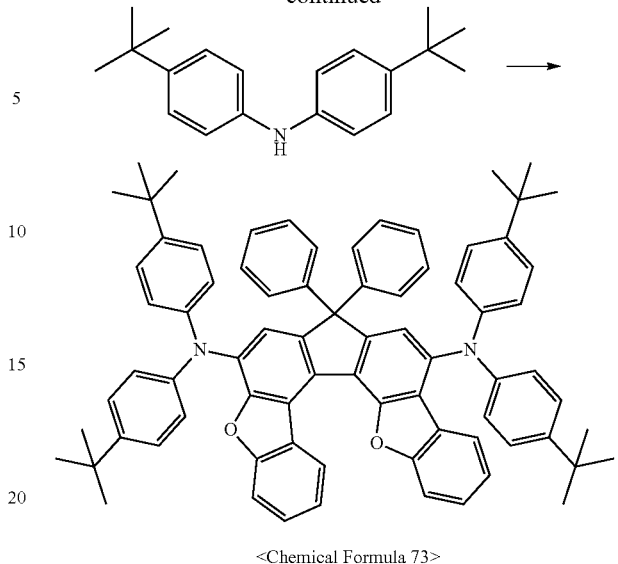

<Chemical Formula 73>

In a 100-ml round-bottom flask reactor, a mixture of <Intermediate 11-h> (4.0 g, 0.006 mol), bis(4-tert-butylphenyl)amine (4.5 g, 0.016 mol), palladium(II) acetate (0.08 g, 0.4 mmol), sodium tert-butoxide (3.2 g, 0.032 mol), tri-tert-butyl phosphine (0.08 g, 0.4 mmol), and toluene (50 ml) was stirred for 2 hours under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to afford the compound of <Chemical Formula 73> (2.7 g, 42%).

MS (MALDI-TOF): m/z 1056.56 [M$^+$]

Synthesis Example 12: Synthesis of Compound of Chemical Formula 86

Synthesis Example 12-(1): Synthesis of [Intermediate 12-a]

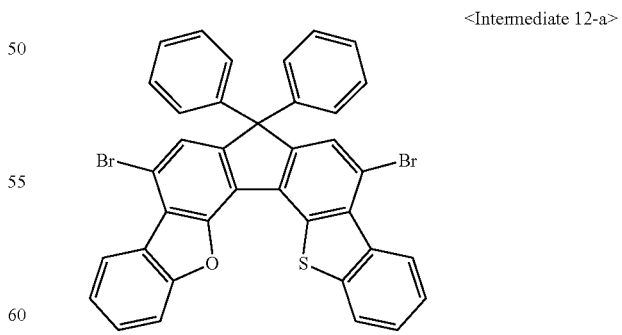

<Intermediate 12-a>

The same procedure as in Synthesis Examples 11-(6) to 11-(8), with the exception of using 4-dibenzothiophene boronic acid instead of dibenzofuran-1-boronic acid in Synthesis Example 11-(6), was conducted to synthesize <Intermediate 12-a>. (yield 52%)

Synthesis Example 12-(2): Synthesis of [Chemical Formula 86]

The same procedure as in Synthesis Example 1-(7), with the exception of using <Intermediate 12-a> instead of <Intermediate 1-f>, was conducted to synthesize <Chemical Formula 86> (yield 35%).

MS (MALDI-TOF): m/z 960.41 [M$^+$]

Synthesis Example 13: Synthesis of Compound of Chemical Formula 95

Synthesis Example 13-(1): Synthesis of [Intermediate 13-a]

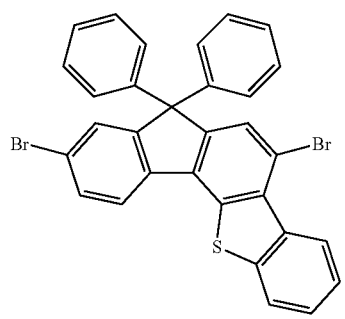

<Intermediate 13-a>

The same procedure as in Synthesis Example 3-(1), with the exception of using 4-dibenzothiophene boronic acid instead of dibenzofuran-4-boronic acid, was conducted to synthesize <Intermediate 13-a>. (yield 68%)

Synthesis Example 13-(2): Synthesis of [Intermediate 13-b]

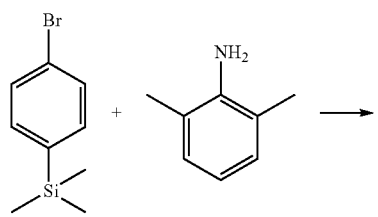

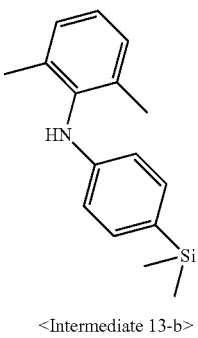

<Intermediate 13-b>

In a 250-ml round bottom flask, a mixture of 1-bromo-4-(trimethylsilyl)benzene (11.4 g, 0.050 mol), 2,6-dimethylaniline (6.2 g, 0.050 mol), palladium acetate (0.22 g, 1 mmol), 2,2'-bis(diphenylphosphino)-1-1'-binaphthyl (1.3 g, 2 mmol), sodium tert-butoxide (12.2 g, 0.120 mol), and toluene (100 mL) was fluxed for 12 hrs. After being cooled to room temperature, the reaction mixture was extracted with ethyl acetate. Column chromatography separated <Intermediate 13-b> (10.5 g, 78%).

Synthesis Example 13-(3): Synthesis of [Chemical Formula 95]

The same procedure as in Synthesis Example 1-(7), with the exception of using <Intermediate 13-a> and <Intermediate 13-b> instead of <Intermediate 1-f> and (4-tert-butylphenyl)phenylamine, respectively, was conducted to synthesize <Chemical Formula 95> (yield 37%).

MS (MALDI-TOF): m/z 958.42 [M$^+$]

Synthesis of Dopant

Synthesis Example 14: Synthesis of Compound of Chemical Formula 403

Synthesis Example 14-(1): Synthesis of [Chemical Formula 403]

The same procedure as in Synthesis Example 1-(7), with the exception of using <Intermediate 8-e> instead of (4-tert-butylphenyl)phenylamine, was conducted to synthesize <Chemical Formula 403> (yield 38%).

MS (MALDI-TOF): m/z 1004.47 [M$^+$]

Synthesis Example 15: Synthesis of Compound of Chemical Formula 631

Synthesis Example 15-(1): Synthesis of [Chemical Formula 631]

The same procedure as in Synthesis Example 1-(7), with the exception of using <Intermediate 11-h> and di-p-tolylamine instead of <Intermediate 1-f> and (4-tert-butylphenyl)-phenylamine, was conducted to synthesize <Chemical Formula 631> (yield 41%).

MS (MALDI-TOF): m/z 888.37 [M$^+$]

Additional Synthesis of Compounds for Hole Transport Layer or Hole Injecting Layer

Synthesis Example 16: Synthesis of Compound of Chemical Formula 124

Synthesis Example 16-(1): Synthesis of [Intermediate 16-a]

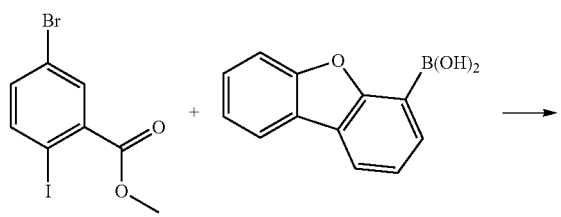

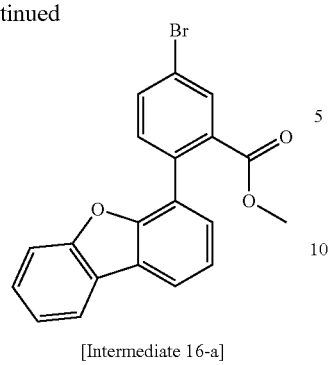

[Intermediate 16-a]

In a 500-mL round-bottom flask reactor, methyl 5-bromo-2-iodobenzoate (25.0 g. mmol), 4-dibenzofuran boronic acid (18.7 g, 88 mmol), tetrakis(triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 16-a> (75.0 g, 60.1%).

Synthesis Example 16-(2): Synthesis of [Intermediate 16-b]

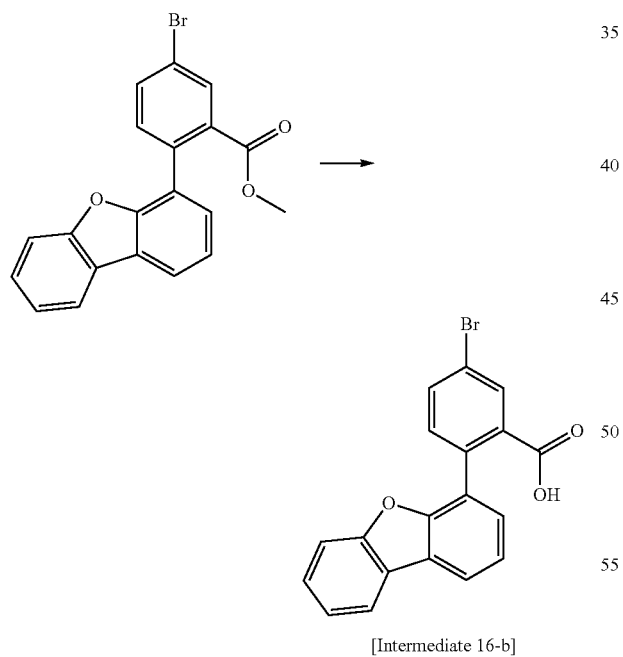

[Intermediate 16-b]

In a 500-mL round-bottom flask reactor, <Intermediate 16-a> (17.0 g, 45 mmol), sodium hydroxide (2.14 g, 54 mmol) and ethanol (170 ml) were stirred together for 48 hrs under reflux. After the completion of the reaction was confirmed by thin layer chromatography, the reaction mixture was cooled to room temperature. The chilled solution was acidified with drops of 2-N HCl, followed by stirring for 30 min. The solid thus formed was filtered, and recrystallized in dichloromethane and n-hexane to afford <Intermediate 16-b> (14.5 g, 88.6%).

Synthesis Example 16-(3): Synthesis of [Intermediate 16-c]

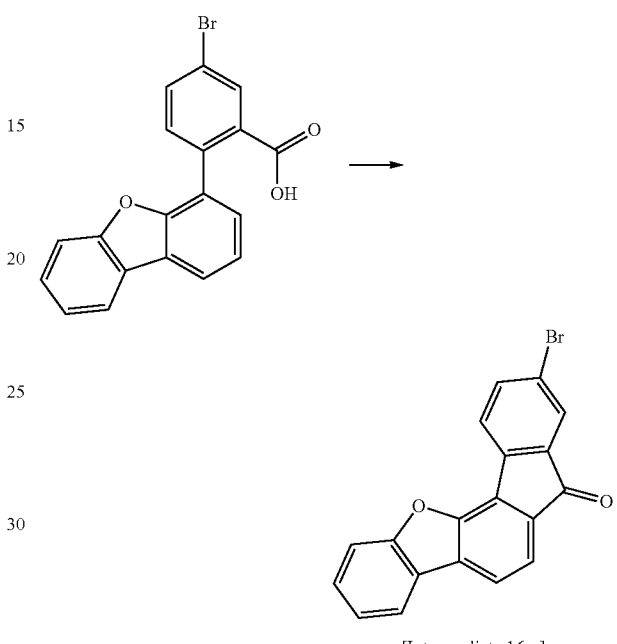

[Intermediate 16-c]

In a 250-mL round-bottom flask reactor, [Intermediate 16-b] (14.5 g, 39 mmol) and methanesulfonic acid (145 ml) were stirred together for 3 hrs at 80° C. After the completion of the reaction was confirmed by thin layer chromatography, the reaction mixture was cooled to room temperature and dropwise added to ice water (150 ml). After stirring for 30 min, the solid thus formed was filtered and washed with water and methanol to afford [Intermediate 16-c] (11.50 g, 83.4%).

Synthesis Example 16-(4): Synthesis of [Intermediate 16-d]

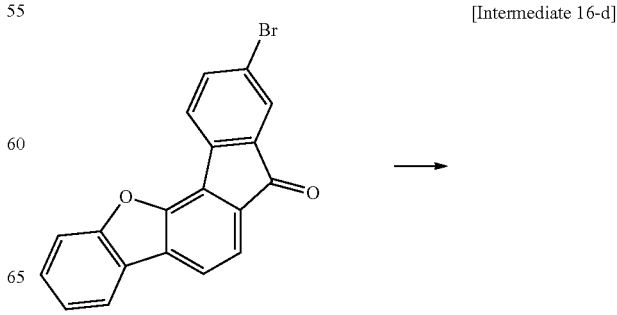

[Intermediate 16-d]

-continued

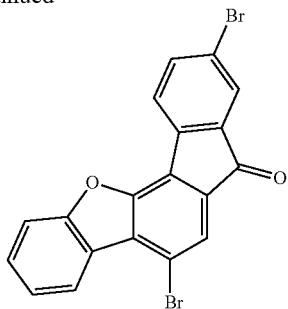

In a 1-L round-bottom flask reactor, [Intermediate 16-c] (11.5 g, 33 mmol) and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered, and washed with acetone. Recrystallization in monochlorobenzene afforded [Intermediate 16-d] (11.0 g, 78%).

Synthesis Example 16-(5): Synthesis of [Intermediate 16-e]

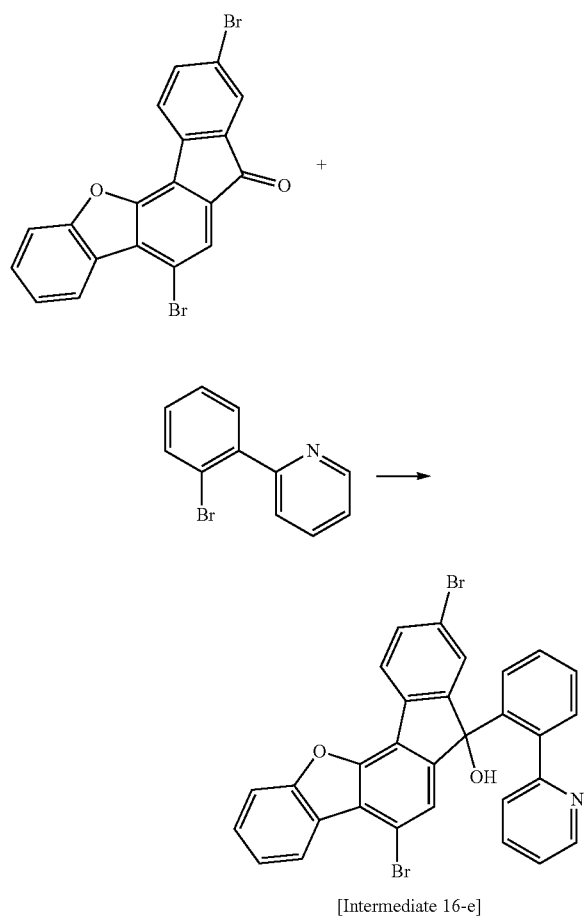

[Intermediate 16-e]

In a 250-ml round-bottom flask reactor, 2-(2-bromophenyl)pyridine (8.4 g, 0.036 mol) and tetrahydrofuran (110 ml) were chilled at −78° C. under a nitrogen atmosphere. At the same temperature, n-butyl lithium (19.3 ml, 0.031 mol) was dropwise added to the chilled reaction solution which was then stirred for 2 hrs. Thereafter, [Intermediate 16-d] (11.0 g, 0.026 mol) was added little by little to the reaction solution, and stirred at room temperature. When the reaction mixture started to change color, the reaction was monitored via thin layer chromatography. After the reaction was stopped with water (50 ml), extraction was conducted with ethyl acetate and water. The organic layer was separated, concentrated in a vacuum, and recrystallized in acetonitrile to afford [Intermediate 16-e] (11.4 g, 75%).

Synthesis Example 16-(6): Synthesis of [Intermediate 16-f]

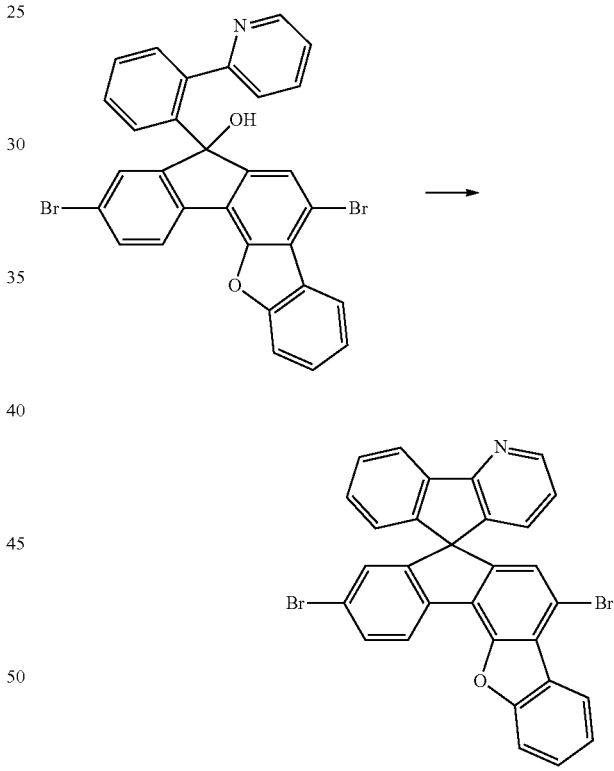

[Intermediate 16-f]

In a 250-ml round-bottom flask reactor, a mixture of [Intermediate 16-e] (12.2 g, 0.021 mol), acetic acid (120 ml), and sulfuric acid (2 ml) was stirred for 5 hrs under reflux. When a precipitate was formed, the completion of the reaction was monitored using thin layer chromatography. The reaction mixture was then cooled to room temperature and filtered. The filtrate was washed with H₂O and methanol and dissolved in monochlorobenzene. Following silica gel chromatography, the fraction was concentrated and cooled to room temperature to give [Intermediate 16-f] (10.3 g, 87%).

Synthesis Example 16-(7): Synthesis of [Chemical Formula 124]

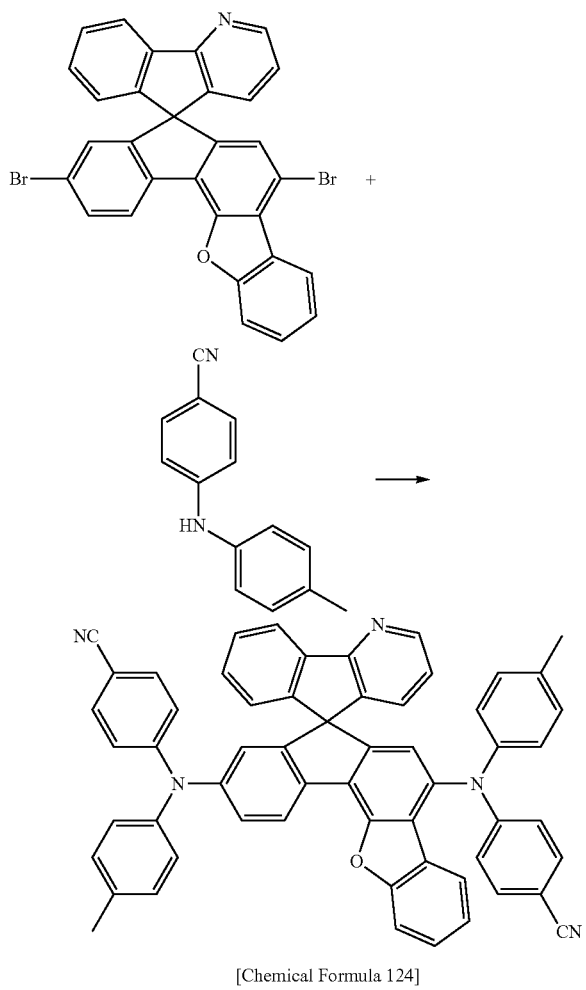

[Chemical Formula 124]

The same procedure as in Synthesis Example 1-(7) was carried out, with the exception of using [Intermediate 16-f] and 4-[(4-methylphenyl)aminobenzonitrile instead of [Intermediate 1-f] and (4-tert-butylphenyl)phenylamine, respectively, to afford [Chemical Formula 124] (yield 35%).
MS (MALDI-TOF): m/z 819.30 [M+]

Synthesis Example 17: Synthesis of Compound of Chemical Formula 125

Synthesis Example 17-(1): Synthesis of [Intermediate 17-a]

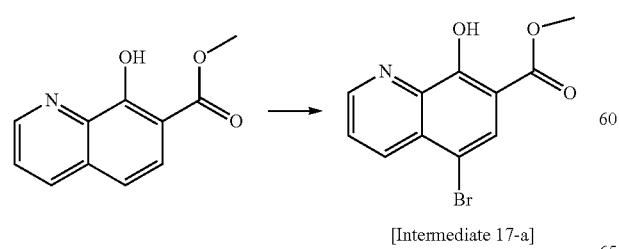

[Intermediate 17-a]

In a 1-L round-bottom flask reactor, methyl 8-hydroxyquinoline-7-carboxylate (39.2 g, 193 mmol) and acetic acid (390 ml) were stirred together at room temperature. A dilution of bromine (11.8 ml, 231 mmol) in acetic acid (80 ml) was dropwise added to the reaction solution which was then stirred for 5 hours at room temperature. After completion of the reaction, the solid thus formed was filtered and slurried in heptane to afford [Intermediate 17-a] (49 g, 90%).

Synthesis Example 17-(2): Synthesis of [Intermediate 17-b]

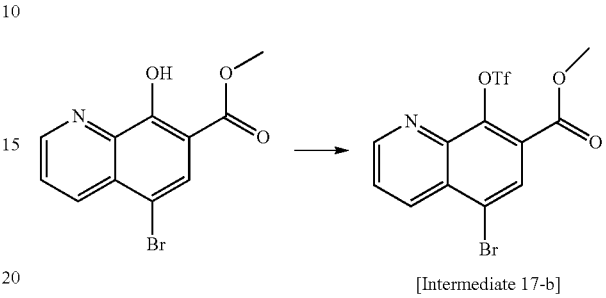

[Intermediate 17-b]

In a 2-L round-bottom flask reactor, [Intermediate 17-a] (49 g, 173 mmol) and dichloromethane were stirred together. In a nitrogen atmosphere, pyridine (27.4 g, 346 mmol) was added to the reaction solution and stirred for 20 min at room temperature. After being cooled to 0° C., the reaction solution was added with drops of trifluoromethanesulfonic anhydride (65.24 g, 231 mmol) in a nitrogen atmosphere. When the reaction was completed as monitored by TLC after three hours of stirring, water (20 ml) was added, followed by stirring for 10 min. The reaction solution was concentrated in a vacuum. Column chromatographic isolation afforded [Intermediate 17-b] (40.8 g, 57%).

Synthesis Example 17-(3): Synthesis of [Intermediate 17-c]

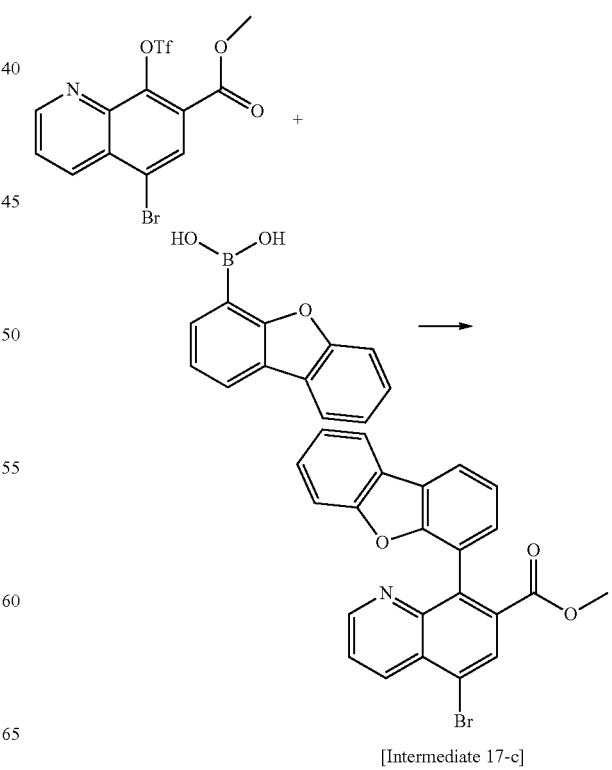

[Intermediate 17-c]

To a 1-L round-bottom flask reactor were added [Intermediate 17-b] (45.1 g, 0.109 mol), 4-dibenzofuran boronic acid (25.4 g, 0.120 mol), tetrakis(triphenylphosphine)palladium (2.5 g, 0.22 mmol), and potassium carbonate (30.1 g, 0.218 mol), followed by toluene (300 mL), ethanol (130 mL), and water (90 mL). The temperature of the reactor was elevated to 80° C. at which stirring was conducted for 5 hours. When the reaction was completed, the temperature of the reactor was lowered to room temperature at which extraction with ethyl acetate was performed to isolate an organic layer. The organic layer was concentrated in a vacuum and isolated by column chromatography to afford [Intermediate 17-c] (21.7 g, 46%).

Synthesis Example 17-(4): Synthesis of [Intermediate 17-d]

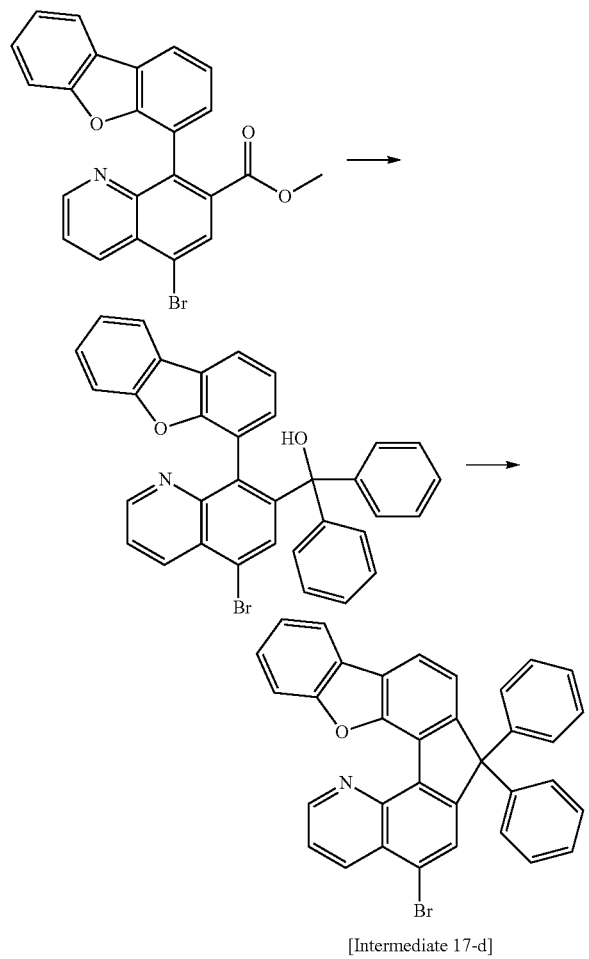

[Intermediate 17-d]

In a 500-ml round-bottom flask reactor, bromobenzene (25.46 g, 0.163 mol) and tetrahydrofuran (170 ml) were chilled to −78° C. in a nitrogen atmosphere. Normal butyl lithium (1.6 moles) (95.6 ml, 0.153 mol) was dropwise added to the chilled reaction solution. At the same temperature, stirring was conducted before adding [Intermediate 1-c] (22.0 g, 0.051 mol). Then, the solution was stirred for 3 hours at room temperature. After completion of the reaction, water (50 ml) was added before stirring for 30 min. Extraction with ethyl acetate and water formed an organic layer which was then isolated and concentrated in a vacuum. The concentrate was added with acetic acid (200 ml) and hydrochloric acid (1 ml), heated to 80° C., and stirred. After completion of the reaction, the reaction solution was cooled to room temperature and the solid thus formed was filtered and washed with methanol to afford [Intermediate 17-d] (16.5 g, 60%).

Synthesis Example 17-(5): Synthesis of [Intermediate 17-e]

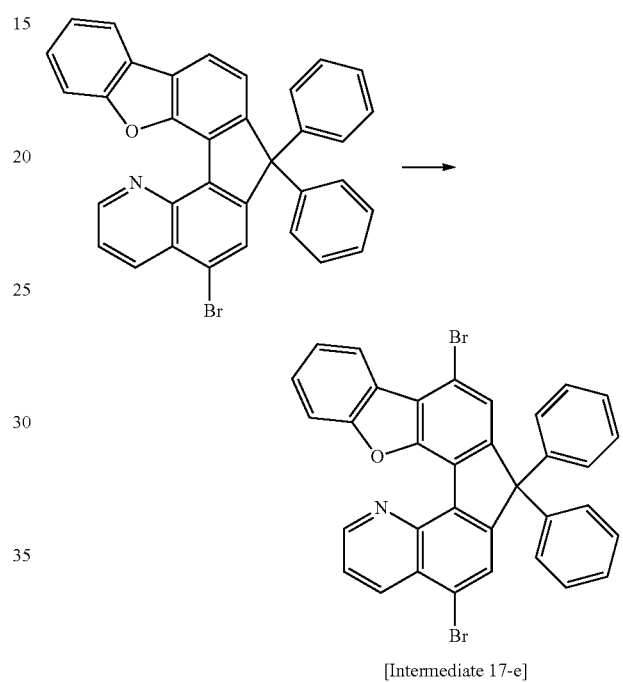

[Intermediate 17-e]

In a 1-L round-bottom flask reactor, [Intermediate 17-d] (19.9 g, 0.037 mol) and chloroform (600 ml) were added with drops of a dilution of bromine (5.7 ml, 0.112 mol) in chloroform (40 ml) while stirring at room temperature. Stirring was continued for 12 hours at room temperature. After completion of the reaction, methanol (100 ml) was added and the solid thus formed was filtered and washed with methanol. Recrystallization in 1,2-dichlorobenzene and acetone afforded [Intermediate 17-e] (15.3 g, 67%).

Synthesis Example 17-(6): Synthesis of [Intermediate 17-f]

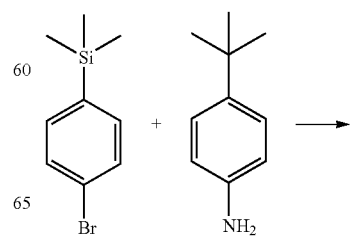

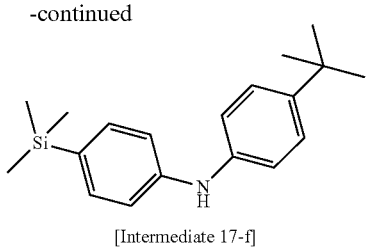

[Intermediate 17-f]

In a 250-ml round-bottom flask reactor, 1-bromo-4-(trimethylsilyl)benzene (8.0 g, 0.035 mol), 4-tert-butylaniline (5.8 g, 0.039 mol), tris(dibenzylideneacetone)dipalladium (0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together under reflux for 3 hours. After completion of the reaction, the reaction solution was cooled to room temperature and extracted with ethyl acetate and water. The organic layer thus formed was treated with magnesium sulfate and concentrated in a vacuum. Column chromatographic isolation afforded [Intermediate 17-f] (7.5 g, 72%).

Synthesis Example 17-(7): Synthesis of [Chemical Formula 125]

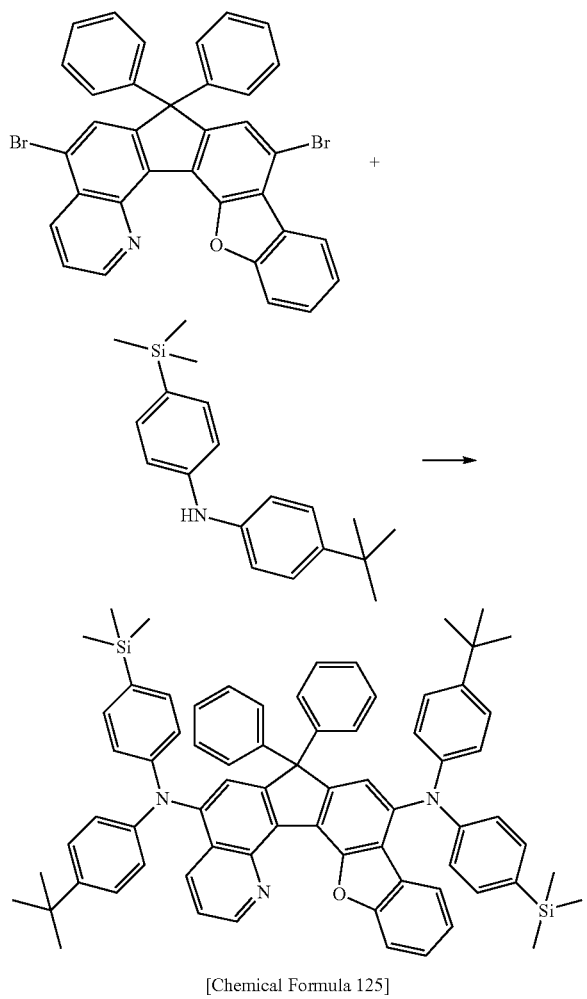

[Chemical Formula 125]

In a 250-ml round-bottom flask reactor, [Intermediate 17-e] (5.5 g, 0.009 mol), [Intermediate 17-f] (6.2 g, 0.021 mol), palladium(II) acetate (0.08 g, 0.4 mmol), sodium tert-butoxide (3.4 g, 0.035 mol), tri-tert-butylphosphine (0.07 g, 0.4 mmol), and toluene (60 ml) were stirred together under reflux for 2 hours. After completion of the reaction, the reaction solution was cooled to room temperature and extracted with dichloromethane and water. The organic layer thus formed was isolated, dried over magnesium sulfate, and concentrated in a vacuum. Recrystallization in dichloromethane and acetone subsequent to column chromatographic isolation afforded the compound of [Chemical Formula 125] (2.5 g, 27%).

MS (MALDI-TOF): m/z 1049.51 [M$^+$]

Synthesis Example 18: Synthesis of Compound of Chemical Formula 126

Synthesis Example 18-(1): Synthesis of [Intermediate 18-a]

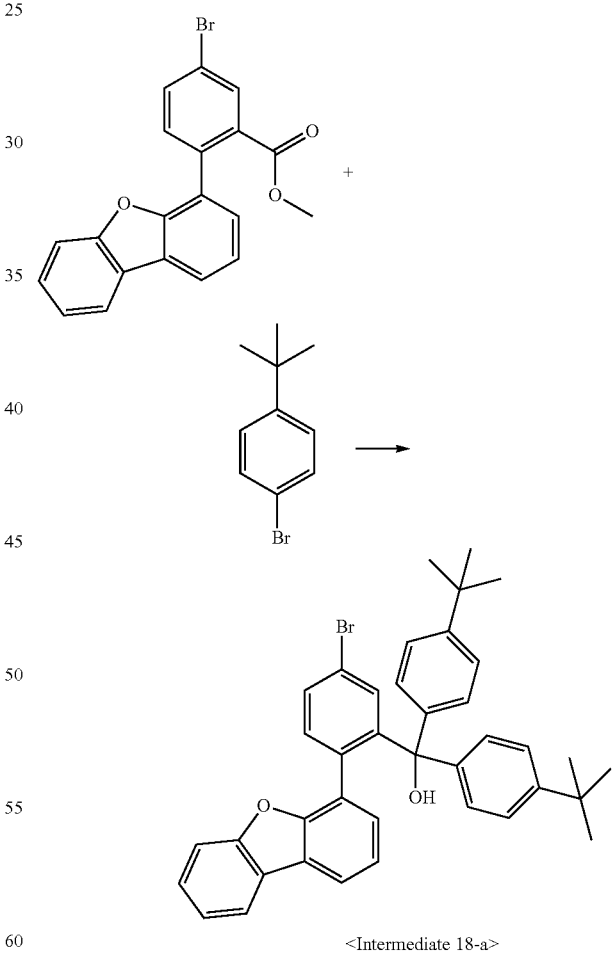

<Intermediate 18-a>

The same procedure as in Synthesis Example 3-(2), with the exception of using 1-bromo-4-tert-butylbenzene and <Intermediate 1-a> instead of bromobenzene and <Intermediate 3-a>, was conducted to synthesize <Intermediate 18-a> (yield 71%).

Synthesis Example 18-(2): Synthesis of [Intermediate 18-b]

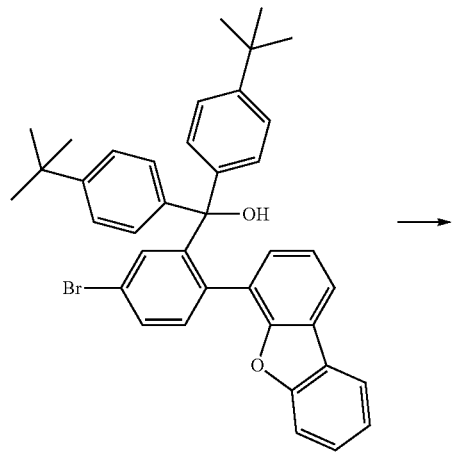

<Intermediate 18-b>

The same procedure as in Synthesis Example 3-(3), with the exception of using <Intermediate 18-a> instead of <Intermediate 3-b>, was conducted to synthesize <Intermediate 18-b> (yield 86%).

Synthesis Example 18-(3): Synthesis of [Intermediate 18-c]

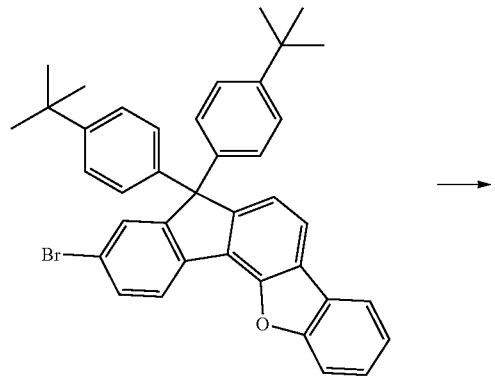

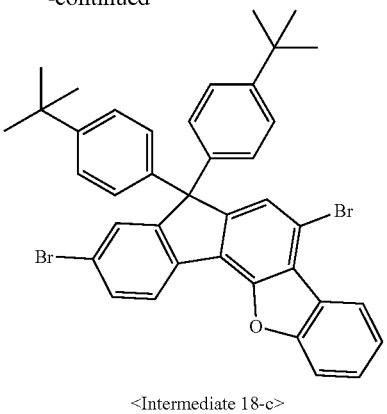

<Intermediate 18-c>

The same procedure as in Synthesis Example 3-(4), with the exception of using <Intermediate 18-b> instead of <Intermediate 3-c>, was conducted to synthesize <Intermediate 18-c> (yield 87%).

Synthesis Example 18-(4): Synthesis of [Chemical Formula 126]

The same procedure as in Synthesis Example 1-(7), with the exception of using [Intermediate 18-c] and diphenylamine instead of <Intermediate 1-f> and (4-tert-butylphenyl)-phenylamine, was conducted to synthesize [Chemical Formula 126] (yield 64%).
MS (MALDI-TOF): m/z 854.42 [M$^+$]

Synthesis Example 19: Synthesis of Compound of Chemical Formula 127

Synthesis Example 19-(1): Synthesis of [Intermediate 19-a]

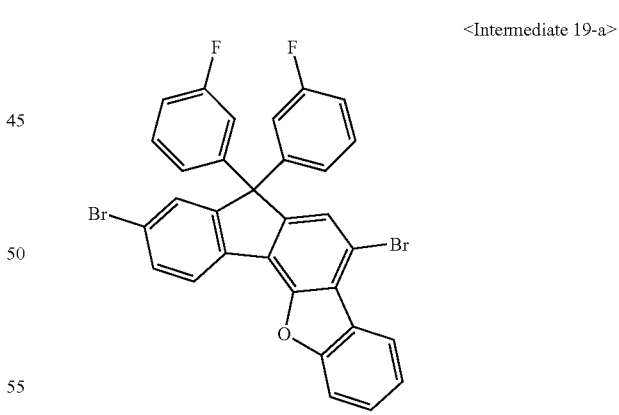

<Intermediate 19-a>

The same procedures as in Synthesis Examples 3-(1) to 3-(4), with the exception of using 3-bromofluorobenzene instead of bromobenzene, was conducted to synthesize <Intermediate 19-a>. (yield 57%)

Synthesis Example 19-(2): Synthesis of [Chemical Formula 127]

The same procedure as in Synthesis Example 1-(7), with the exception of using [Intermediate 19-a] and 2-methyl-N-

(2-methylphenyl)aniline instead of <Intermediate 1-f> and (4-tert-butylphenyl)-phenylamine, respectively, was conducted to synthesize [Chemical Formula 127] (yield 34%).

MS (MALDI-TOF): m/z 806.31 [M$^+$]

Synthesis Example 20: Synthesis of Compound of Chemical Formula 128

Synthesis Example 20-(1): Synthesis of [Intermediate 20-a]

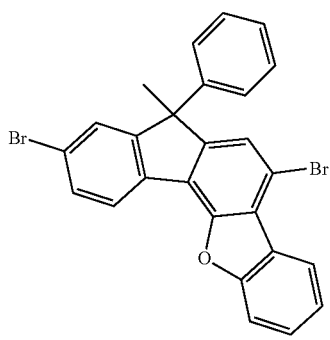

<Intermediate 20-a>

The same procedure as in Synthesis Examples 3-(1) to 3-(4), with the exception of using 1-bromo-2-iodobenzene and acetophenone instead of 2-iodobenzoate in Synthesis Example 3-(1) and <Intermediate 3-a> in Synthesis Example 3-(2), respectively, was conducted to synthesize <Intermediate 20-a>. (yield 65%)

Synthesis Example 20-(2): Synthesis of [Chemical Formula 128]

The same procedure as in Synthesis Example 1-(7), with the exception of using <Intermediate 20-a> and N-phenyl-4-biphenylamine instead of <Intermediate 1-f> and (4-tert-butylphenyl)phenylamine, was conducted to synthesize [Chemical Formula 128] (yield 44%).

MS (MALDI-TOF): m/z 832.35 [M$^+$]

Synthesis Example 21: Synthesis of Compound of Chemical Formula 129

Synthesis Example 21-(1): Synthesis of [Intermediate 21-a]

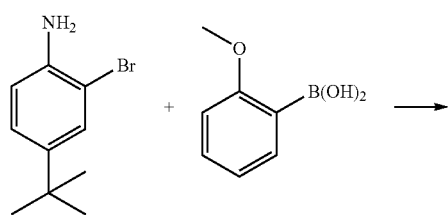

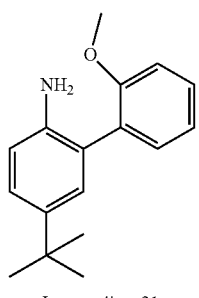

<Intermediate 21-a>

In a 500-mL round-bottom flask reactor, 2-bromo-4-tert-butylaniline (16.7 g. mmol), 2-methoxyphenyl boronic acid (13.4 g, 88 mmol), tetrakis(triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 21-a>. (12.1 g, 65%)

Synthesis Example 21-(2): Synthesis of [Intermediate 21-b]

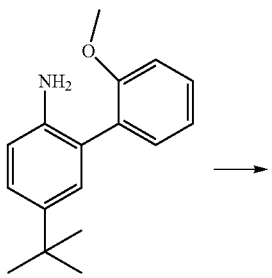

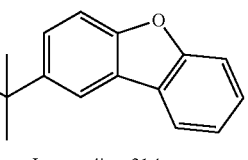

<Intermediate 21-b>

In a 1-L round-bottom flask reactor, a mixture of <Intermediate 21-a> (40.0 g, 157 mmol) and water (160 ml) was stirred. Drops of sulfuric acid (38 mL) were added little by little to the mixture which was then cooled to 0° C. An aqueous sodium nitrite solution (480 mL) was dropwise added and stirred for 3 hours before heating to room temperature. After completion of the reaction, water was evaporated to isolate the organic layer which was then purified by column chromatography to afford <Intermediate 21-b>. (29.9 g, 85%)

Synthesis Example 21-(3): Synthesis of [Intermediate 21-c]

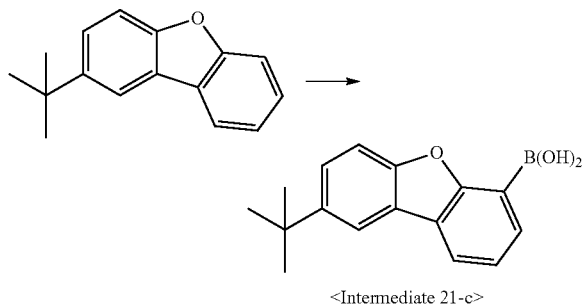

<Intermediate 21-c>

In a 1-L round-bottom flask, <Intermediate 21-b> (40.0 g, 178 mmol) was dissolved in tetrahydrofuran (240 ml) under a nitrogen atmosphere. The solution was added with drops of 1.6 M n-butyl lithium (144.5 mL, 232 mmol) while being stirred at −78° C. Thereafter, the solution was stirred for 12 hours at room temperature. Subsequently, drops of trimethyl borate (24.1 g, 232 mmol) were slowly added at −78° C. to the solution which was then stirred at room temperature for 1 hr. After completion of the reaction, drops of 2 N HCl (125 mL) was slowly added at room temperature while stirring for 30 min to acidify the solution to a pH of 2. Extraction was made with water and ethyl acetate, and the organic layer thus formed was isolated and concentrated in a vacuum, followed by recrystallization in heptane and toluene to afford <Intermediate 21-c>. (34.4 g, 72%)

Synthesis Example 21-(4): Synthesis of [Intermediate 21-d]

<Intermediate 21-d>

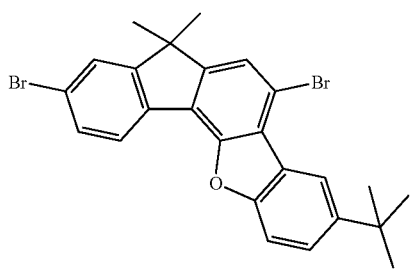

The same procedure as in Synthesis Examples 8-(1) and 8-(4), with the exception of using <Intermediate 21-c> instead of dibenzofuran-4-boronic acid in Synthesis Example 8-(1), was conducted to synthesize <Intermediate 21-d>. (yield 67%)

Synthesis Example 21-(5): Synthesis of [Chemical Formula 129]

The same procedure as in Synthesis Example 1-(7), with the exception of using <Intermediate 21-d> and bis(4-biphenylyl)amine instead of <Intermediate 1-f> and <Intermediate 21-d>, was conducted to synthesize [Chemical Formula 129] (yield 48%).
MS (MALDI-TOF): m/z 978.45 [M⁺]

Examples 1 to 13 and 16 to 21: Fabrication of Organic Light-Emitting Diodes

An ITO glass substrate was patterned to have a translucent area of 2 mm×2 mm and cleansed. The ITO glass was mounted in a vacuum chamber that was then set to have a base pressure of $1 \times 10^{-6}$ torr. On the ITO glass substrate, films were sequentially formed of DNTPD (400 Å) and each of the compounds (200 Å) listed in Table 1 below. A light-emitting layer (250 Å) was formed of [BH] as a host and 3 wt % of each of the compounds list in Table 1 as a dopant and covered with [HBL] (50 Å) to form a hole barrier layer. Then, [Chemical Formula E-1] was deposited to form an electron transport layer (200 Å), on which an electron injecting layer of [Chemical Formula E-2] (5 Å) was formed and then covered with an Al layer (1000 Å) to fabricate an organic light-emitting diode. The organic light-emitting diodes thus obtained were measured at 0.4 mA for luminescence properties:

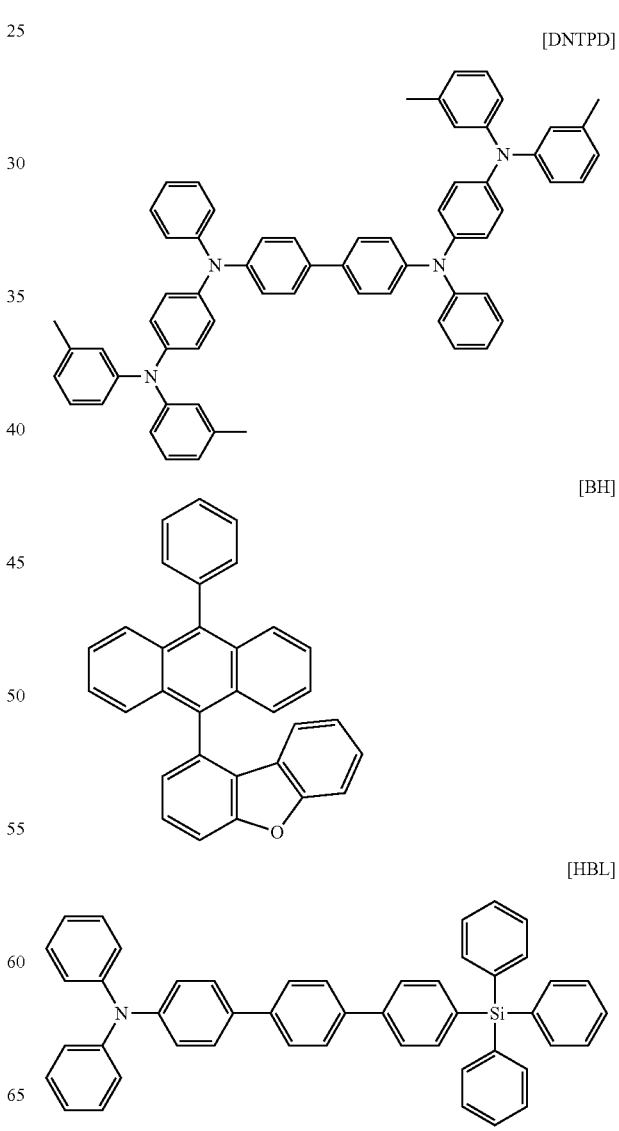

-continued

[Chemical Formula E-1]

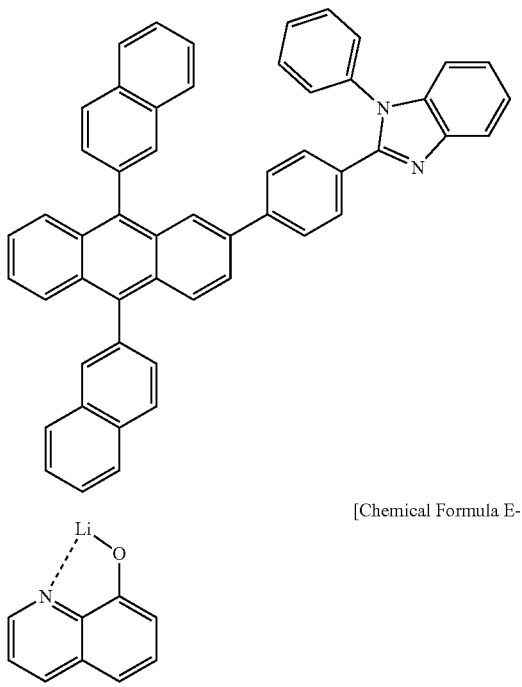

[Chemical Formula E-2]

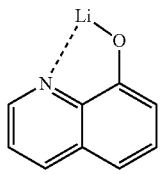

Comparative Examples 1 and 2

An organic light-emitting diode was fabricated in the same manner as in Example 1, with the exception that the conventional compound [HT] was used, instead of the compounds used for the hole transport layer in Examples 1 to 13. The luminescence of the organic light-emitting diodes thus obtained was measured at 0.4 mA and the measurements are summarized in Table 1. The structure of [HT] is as follows:

[HT]

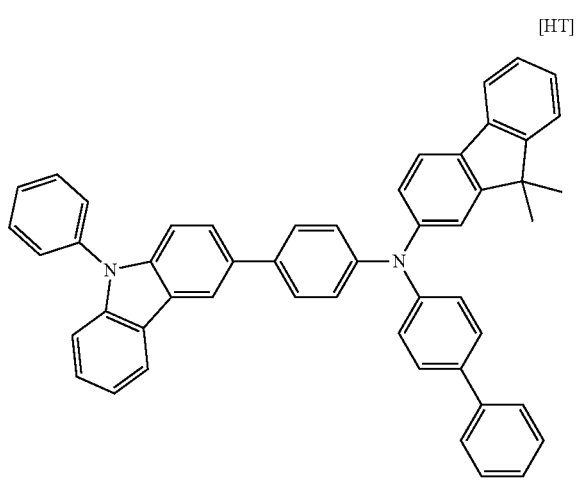 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

Examples 14 and 15

An organic light-emitting diode was fabricated in the same manner as in Examples 1 to 13, with the exception that [BD] was used, instead of the dopant compound used in Examples 1 to 13. The luminescence of the organic light-emitting diodes thus obtained was measured at 0.4 mA and the measurements are summarized in Table 1. The structure of [BD] is as follows:

[BD]

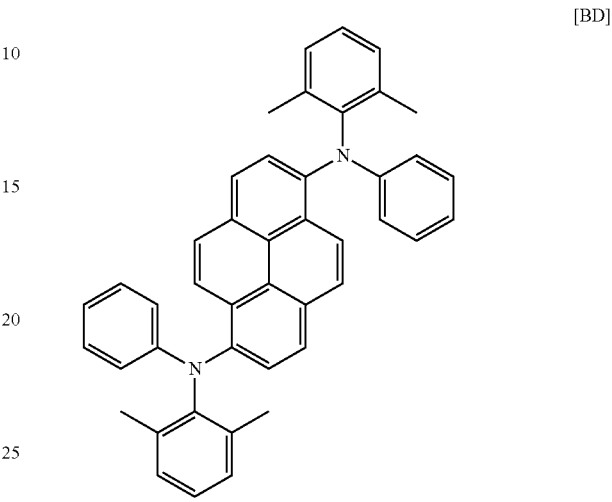

TABLE 1

| Ex. No. | Hole Transport Compound | Dopant | CIEx | CIEy | Cd/A |
|---|---|---|---|---|---|
| 1 | Chemical Formula 2 | Compound 631 | 0.136 | 0.112 | 10.17 |
| 2 | Chemical Formula 32 | | 0.136 | 0.112 | 10.59 |
| 3 | Chemical Formula 50 | | 0.137 | 0.112 | 10.23 |
| 4 | Chemical Formula 57 | | 0.137 | 0.113 | 10.24 |
| 5 | Chemical Formula 58 | | 0.136 | 0.113 | 10.98 |
| 6 | Chemical Formula 95 | | 0.137 | 0.112 | 10.52 |
| 7 | Chemical Formula 19 | Compound 403 | 0.136 | 0.112 | 10.48 |
| 8 | Chemical Formula 34 | | 0.136 | 0.111 | 10.37 |
| 9 | Chemical Formula 43 | | 0.137 | 0.112 | 10.18 |
| 10 | Chemical Formula 45 | | 0.136 | 0.112 | 10.32 |
| 11 | Chemical Formula 63 | | 0.136 | 0.112 | 10.26 |
| 12 | Chemical Formula 73 | | 0.137 | 0.113 | 10.18 |
| 13 | Chemical Formula 86 | | 0.136 | 0.112 | 10.76 |
| C. Ex. 1 | HT | Compound 631 | 0.136 | 0.113 | 9.75 |
| C. Ex. 2 | HT | Compound 403 | 0.136 | 0.114 | 9.46 |
| 14 | Chemical Formula 19 | BD | 0.135 | 0.118 | 9.89 |
| 15 | Chemical Formula 32 | | 0.136 | 0.119 | 9.82 |
| 16 | Chemical Formula 124 | Compound 631 | 0.137 | 0.112 | 10.19 |
| 17 | Chemical Formula 125 | | 0.136 | 0.113 | 10.46 |
| 18 | Chemical Formula 126 | | 0.136 | 0.112 | 10.51 |
| 19 | Chemical Formula 127 | | 0.136 | 0.112 | 10.82 |
| 20 | Chemical Formula 128 | | 0.137 | 0.112 | 10.36 |
| 21 | Chemical Formula 129 | | 0.137 | 0.113 | 10.24 |

As is understood from data of Table 1, the organic light-emitting diodes of Examples 1 to 21 have greater emission efficiencies compared to those of Comparative Examples 1 and 2. Particularly, the organic light-emitting diodes of Examples 1 to 13 and 16 to 21 exhibit very improved emission efficiencies and are thus highly industrially applicable.

INDUSTRIAL APPLICABILITY

Exhibiting high emission efficiency compared to conventional organic light-emitting diodes, the organic light-emitting diode of the present invention is expected to be highly industrially applicable.

The invention claimed is:

1. An organic light-emitting diode, comprising:
a first electrode; a second electrode facing the first electrode;
a hole injecting layer or a hole transport layer interposed between the first electrode and the second electrode; and
a light-emitting layer,
wherein the hole injecting layer or the hole transport layer comprises at least one of the amine compounds represented by the following Chemical Formula A or B:

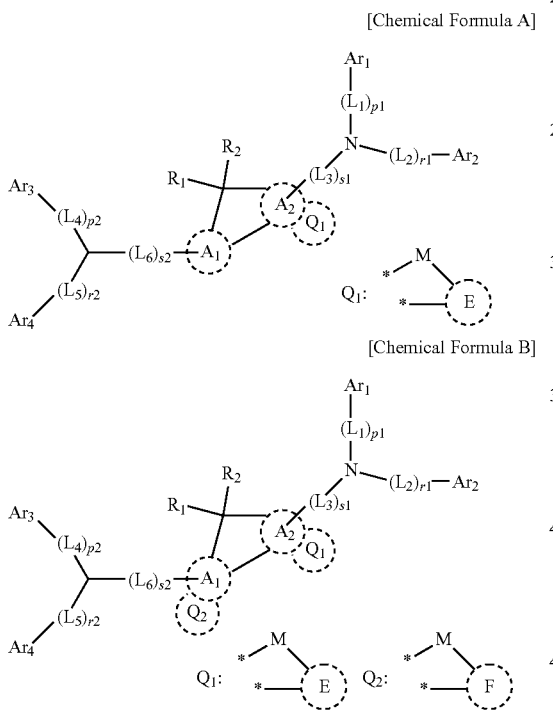

[Chemical Formula A]

[Chemical Formula B]

wherein,
$A_1$, $A_2$, E, and F, which may be the same or different, are each independently a substituted or unsubstituted aromatic hydrocarbon ring of 6 to 50 carbon atoms, or a substituted or unsubstituted heteroaromatic ring of 2 to 40 carbon atoms;
wherein two adjacent carbon atoms within the aromatic ring of $A_1$ and two adjacent carbon atoms within the aromatic ring of $A_2$ form a 5-membered ring with a carbon atom connected to both substituents $R_1$ and $R_2$, thus establishing a fused ring structure;
linkers $L_1$ to $L_6$, which may be the same or different, are each independently selected from among a single bond and a substituted or unsubstituted arylene of 6 to 60 carbon atoms;
M is selected from among N-$R_3$, C$R_4R_5$, Si$R_6R_7$, O, and S;
$R_1$ to $R_7$ and $Ar_1$ to $Ar_4$, which may be the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms, a cyano, a nitro, and a halogen,
wherein $R_1$ and $R_2$ may be connected to each other to form a five-membered ring, which may be part of a monocyclic or polycyclic aliphatic or aromatic ring system;
p1 and p2, r1 and r2, and s1 and s2 are each independently an integer of 1 to 3, under which when any of them is 2 or greater, the corresponding linkers $L_1$ to $L_6$ may be the same or different,
$Ar_1$ and $Ar_2$ may be connected to each other to form a ring and $Ar_3$ and $Ar_4$ may be connected to each other to form a ring;
two adjacent carbon atoms within the $A_2$ ring in Chemical Formula A are linked to respective * of structure formula $Q_1$ to form a fused ring, and
two adjacent carbon atoms within the $A_1$ ring in Chemical Formula B are linked to respective * of structure formula $Q_2$ to form a fused ring and two adjacent carbon atoms within the $A_2$ ring in Chemical Formula B are linked to respective * of structure formula $Q_1$ to form a fused ring,
wherein the term "substituted" in the expression "substituted or unsubstituted" used for [Chemical Formula A] and [Chemical Formula B] means having at least one substituent selected from the group consisting of a deuterium atom, a cyano, a halogen, a nitro, an alkyl of 1 to 24 carbon atoms, a halogenated alkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkylsilyl of 1 to 24 carbon atoms, and an arylsilyl of 6 to 24 carbon atoms.

2. The organic light-emitting diode of claim 1, wherein $A_1$, $A_2$, E, and F in [Chemical Formula A] or [Chemical Formula B], which may be the same or different, are independently respective substituted or unsubstituted aromatic hydrocarbon ring of 6 to 50 carbon atoms.

3. The organic light-emitting diode of claim 2, wherein the substituted or unsubstituted aromatic hydrocarbon rings of 6 to 50 carbon atoms are same or different and are each independently any one selected from [Structural Formula 10] to [Structural Formula 21]:

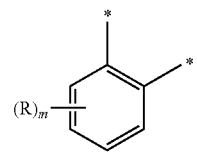

[Structural Formula 10]

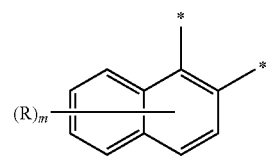

[Structural Formula 11]

[Structural Formula 12]
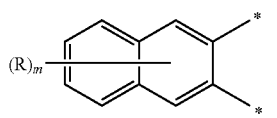

[Structural Formula 13]
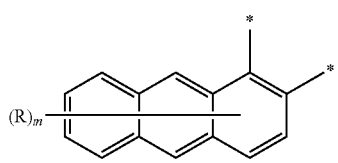

[Structural Formula 14]
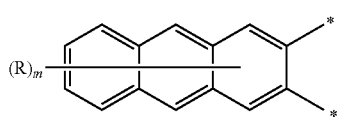

[Structural Formula 15]
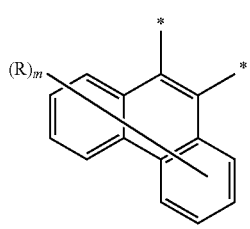

[Structural Formula 16]
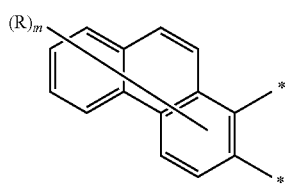

[Structural Formula 17]
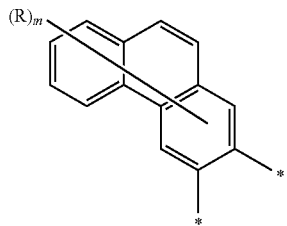

[Structural Formula 18]
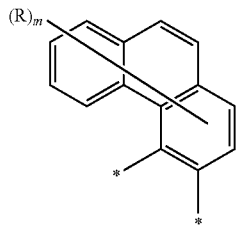

[Structural Formula 19]
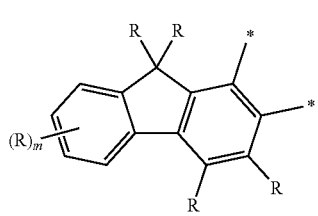

[Structural Formula 20]
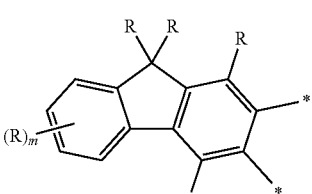

[Structural Formula 21]
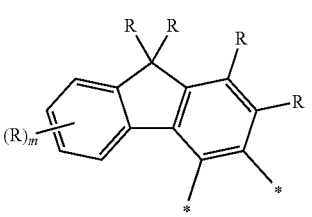

wherein

"-*" denotes a bonding site for forming a 5-membered ring bearing the carbon atom connected to the substituents $R_1$ and $R_2$ or a bonding site for forming a 5-membered ring bearing M of Structural Formula $Q_1$ and $Q_2$;

when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R is as defined for $R_1$ and $R_2$ above; and m is an integer of 1 to 8 wherein when m is 2 or greater or when R exists as multiple radicals, the resulting R's may be the same or different.

4. The organic light-emitting diode of claim 1, wherein the amine compound represented by Chemical Formula A or B is contained in the hole transport layer.

5. The organic light-emitting diode of claim 1, wherein the linkers $L_1$ to $L_6$ in Chemical Formulas A and B are same or different and are each independently a single bond or any one selected from among the following Structural Formulas 22, 23, 25, 27, 28, and 30, and p1 and p2, r1 and r2, and s1 and s2 are each 1 or 2:

[Structural Formula 22]
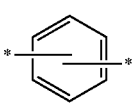

[Structural Formula 23]
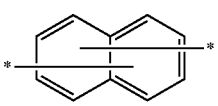

[Structural Formula 25]
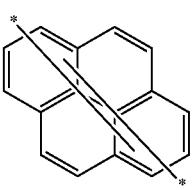

[Structural Formula 27]
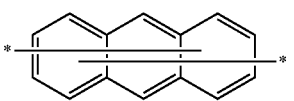

-continued

[Structural Formula 28]

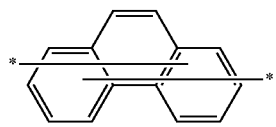

[Structural Formula 30]

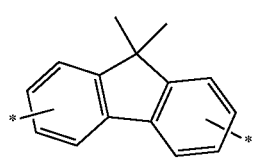

wherein, each of the unsubstituted carbon atoms of the aromatic ring moiety is bound with a hydrogen atom or a deuterium atom.

6. The organic light-emitting diode of claim 1, wherein $R_1$ and $R_2$ are same or different and are connected to each other to form a ring or are each a substituted or unsubstituted aryl of 6 to 50 carbon atoms which remains unconnected.

7. The organic light-emitting diode of claim 1, wherein the amine compound represented by Chemical Formula A or B is any one of the compounds represented by the following Chemical Formulas 1 to 144:

<Chemical Formula 1>

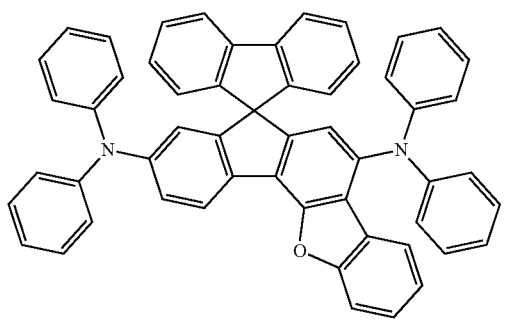

<Chemical Formula 2>

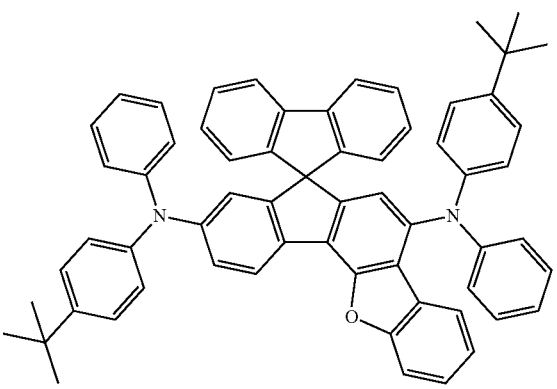

<Chemical Formula 3>

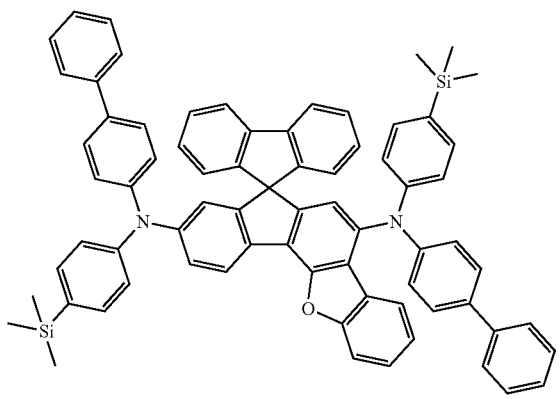

<Chemical Formula 4>

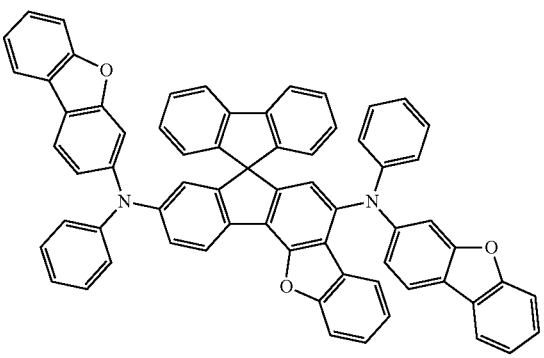

<Chemical Formula 5>

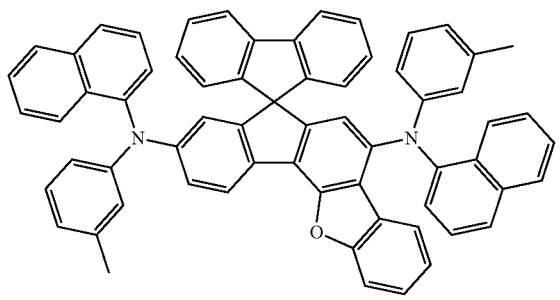

<Chemical Formula 6>

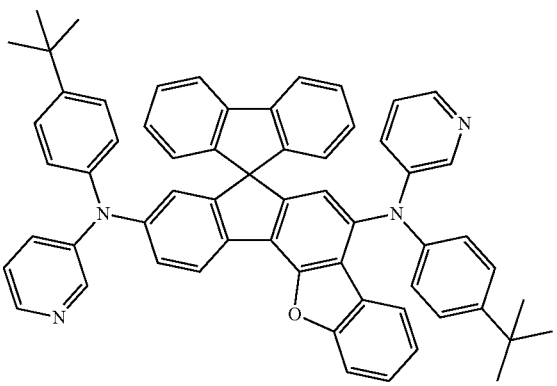

-continued
<Chemical Formula 7>
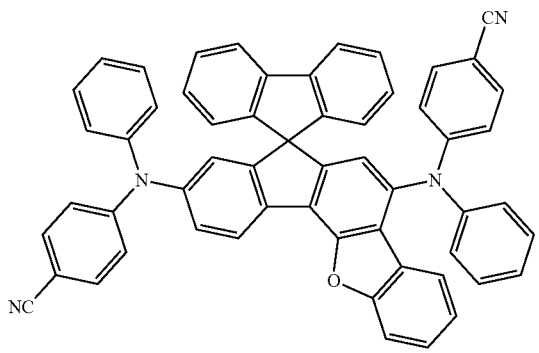
<Chemical Formula 8>
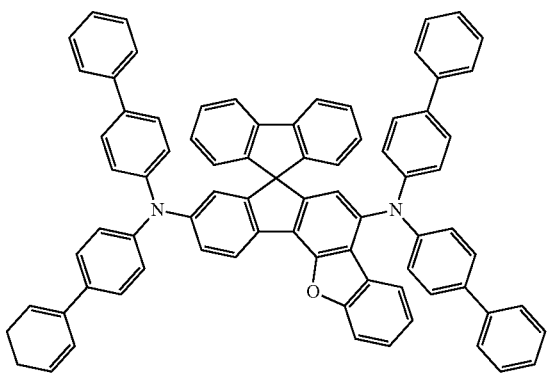
<Chemical Formula 9>
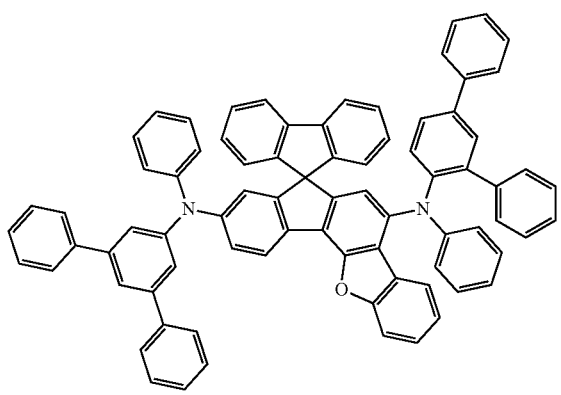
<Chemical Formula 10>
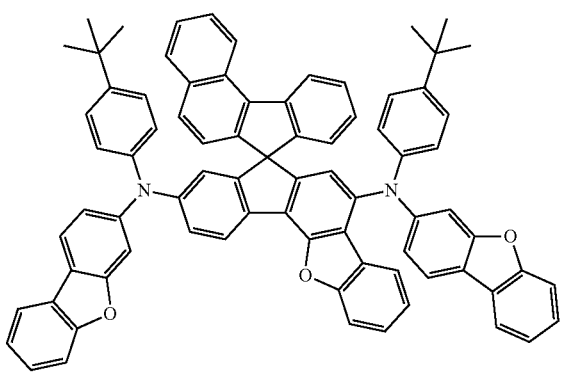
<Chemical Formula 11>
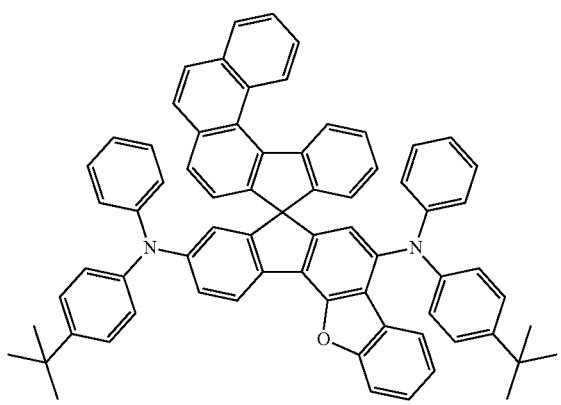
<Chemical Formula 12>
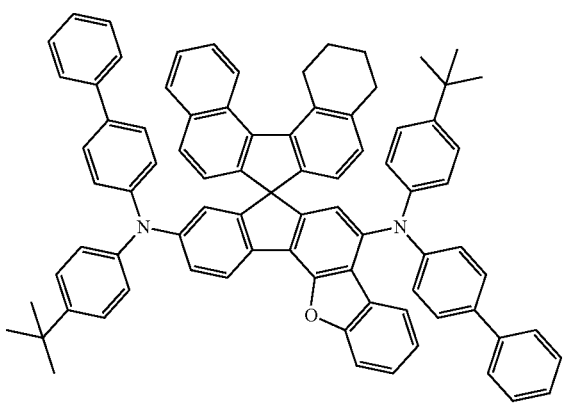

-continued
<Chemical Formula 13>
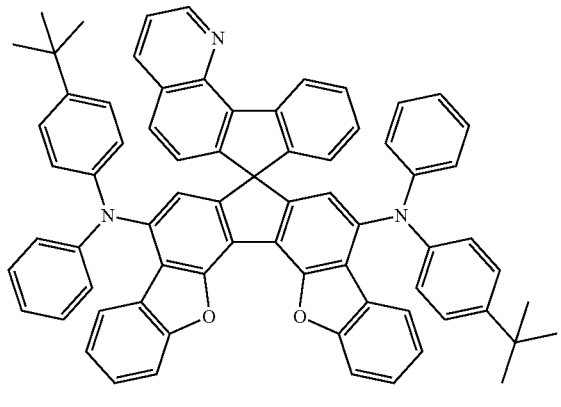
<Chemical Formula 14>
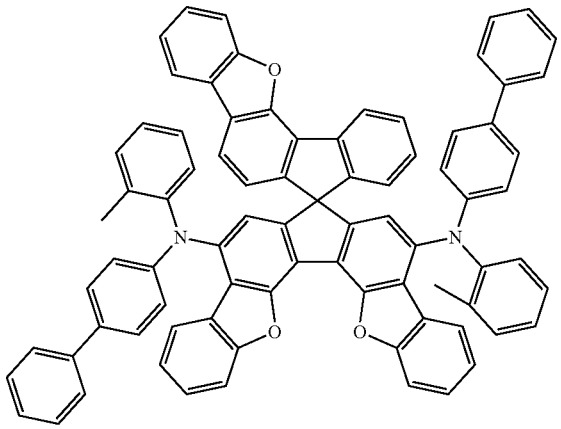
<Chemical Formula 15>
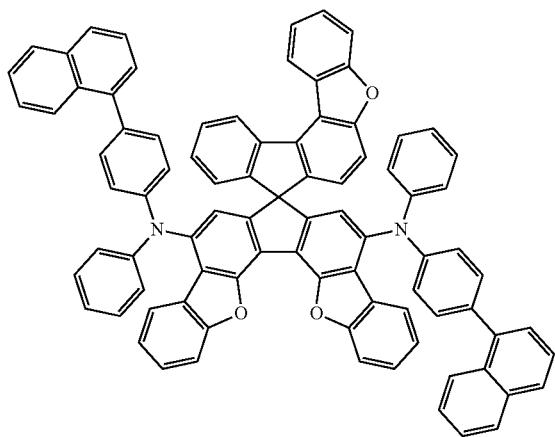
<Chemical Formula 16>
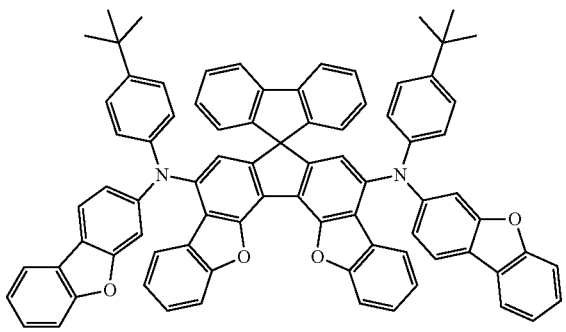
<Chemical Formula 17>
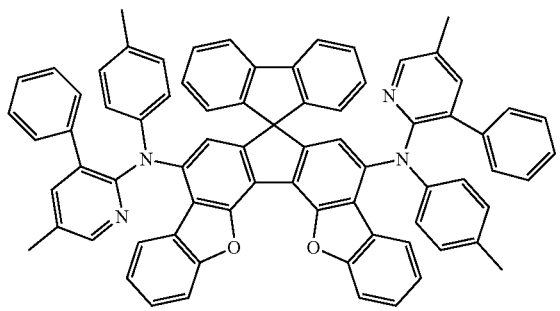
<Chemical Formula 18>
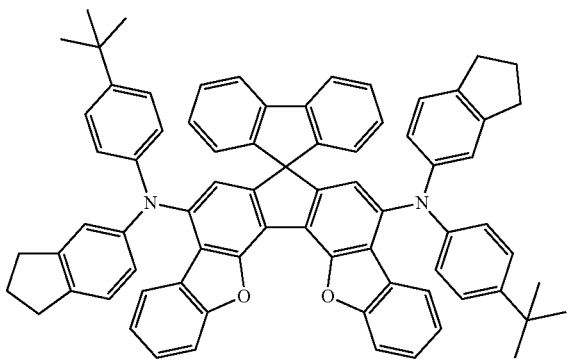

<Chemical Formula 19>
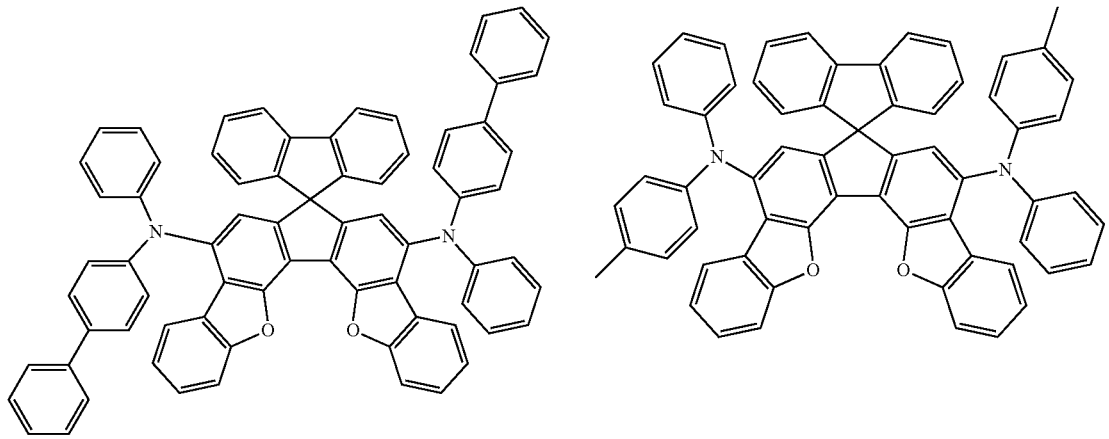
<Chemical Formula 20>
<Chemical Formula 21>
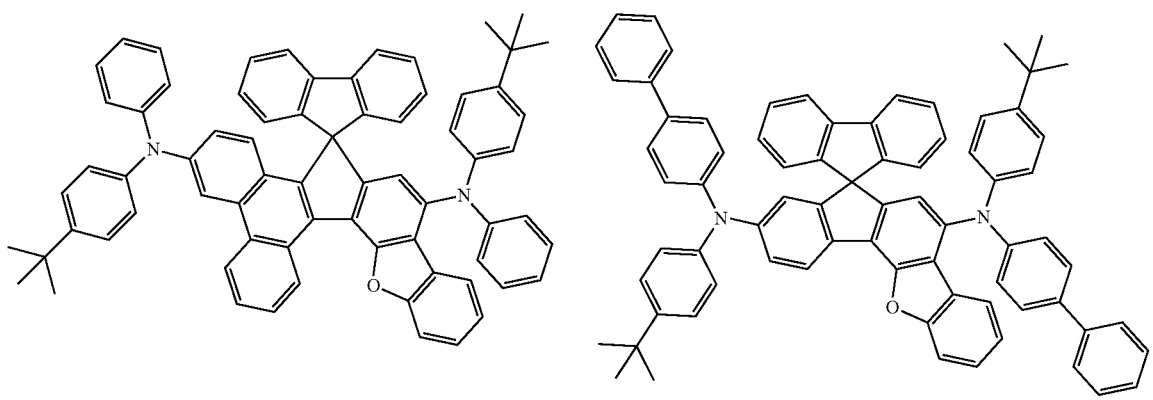
<Chemical Formula 22>
<Chemical Formula 23>
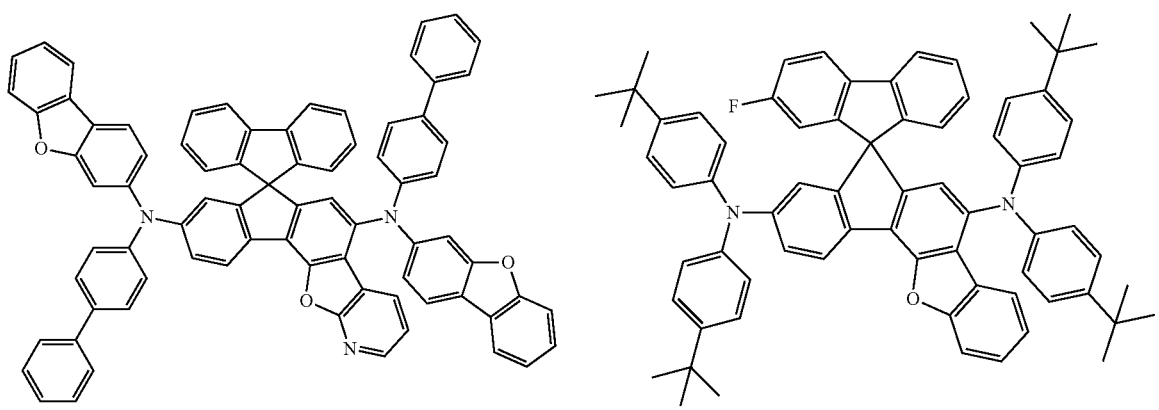
<Chemical Formula 24>

-continued
<Chemical Formula 25>
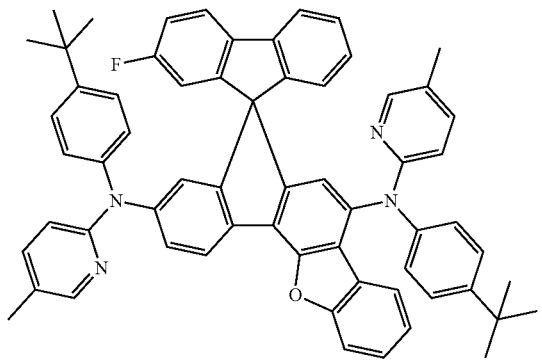
<Chemical Formula 26>
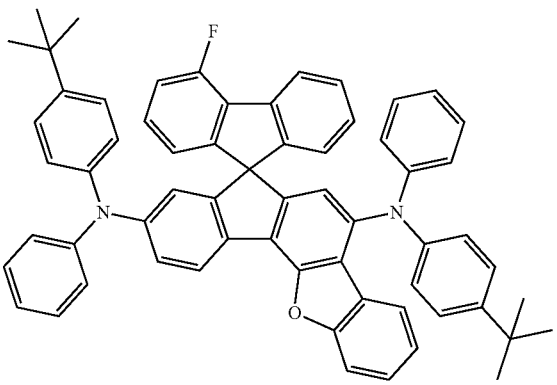
<Chemical Formula 27>
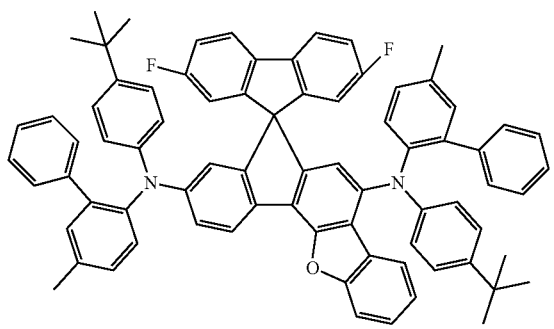
<Chemical Formula 28>
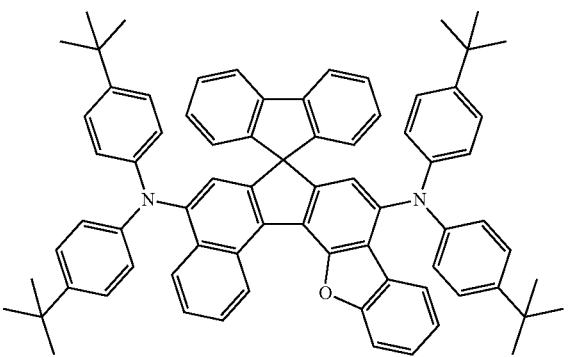
<Chemical Formula 29>
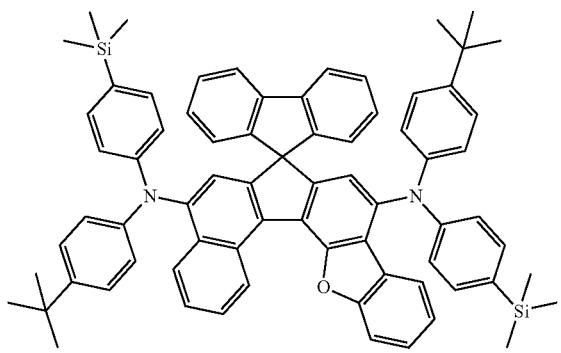
<Chemical Formula 30>
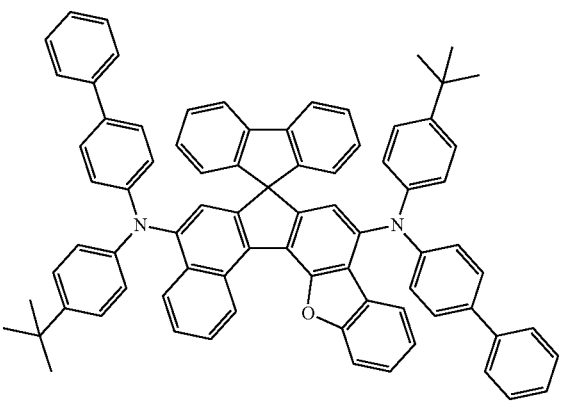
<Chemical Formula 31>
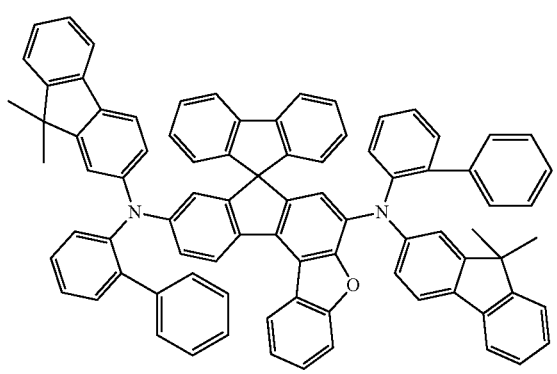
<Chemical Formula 32>
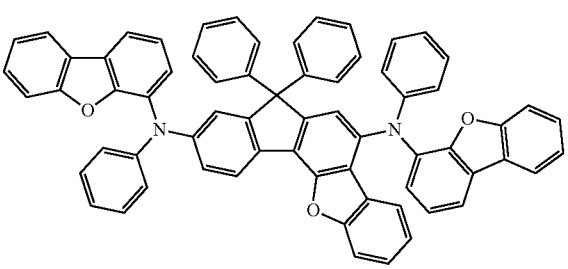

-continued
<Chemical Formula 33>
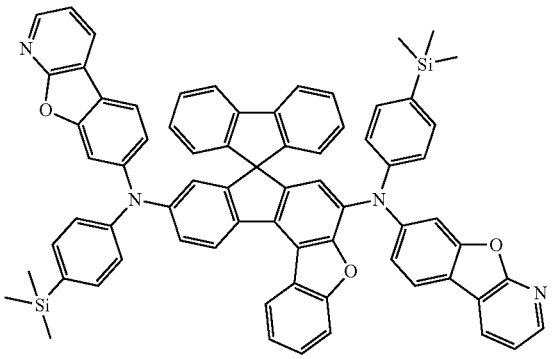
<Chemical Formula 34>
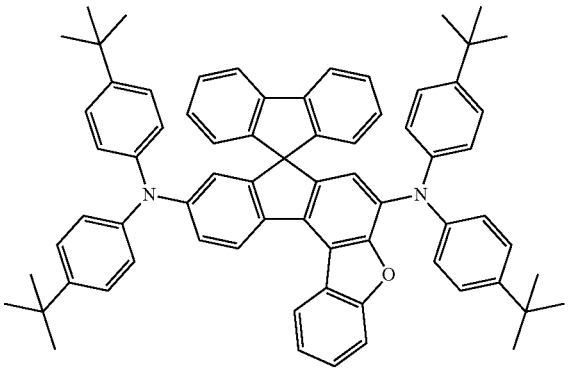
<Chemical Formula 35>
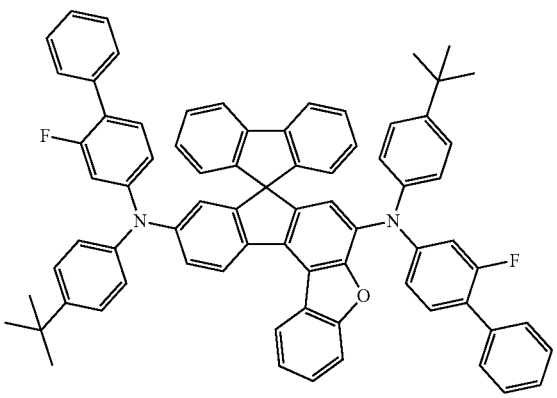
<Chemical Formula 36>
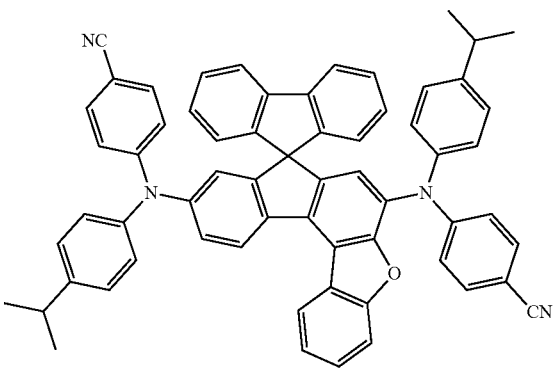
<Chemical Formula 37>
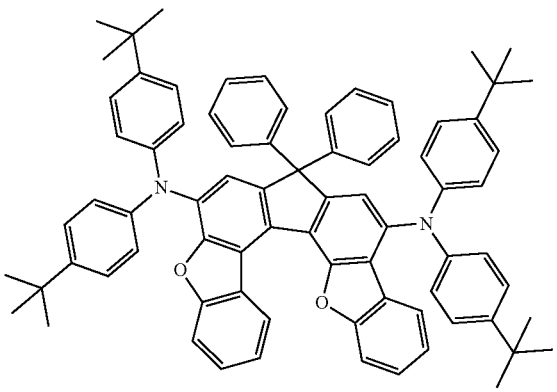
<Chemical Formula 38>
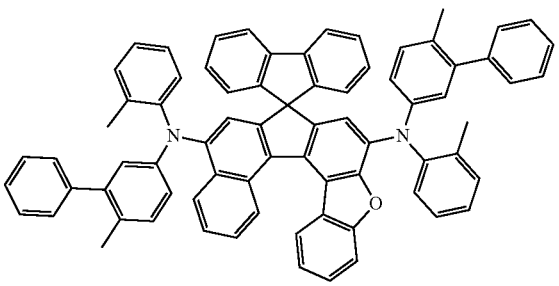
<Chemical Formula 39>
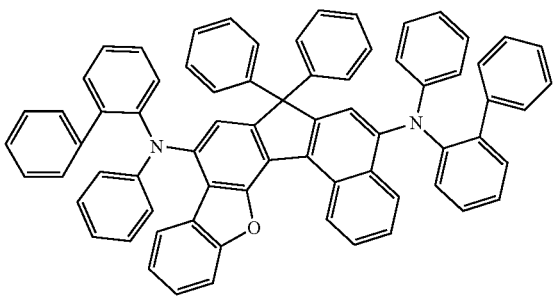
<Chemical Formula 40>
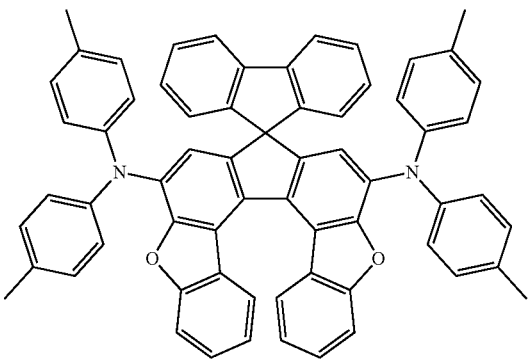

-continued
<Chemical Formula 41>
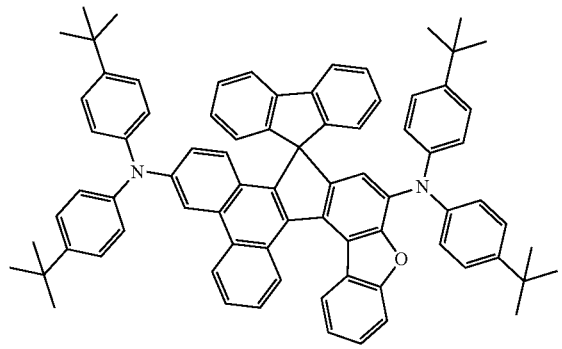
<Chemical Formula 42>
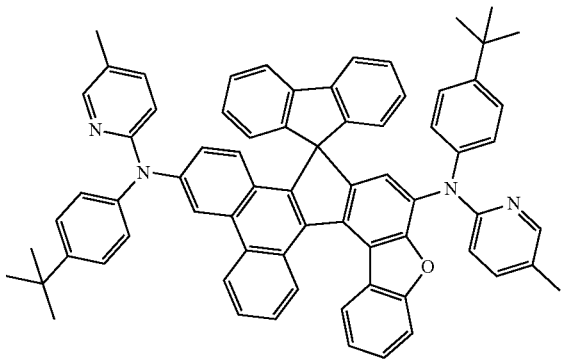
<Chemical Formula 43>
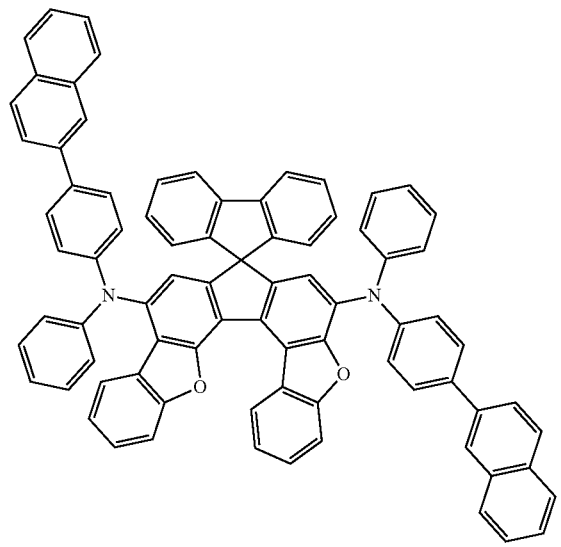
<Chemical Formula 44>
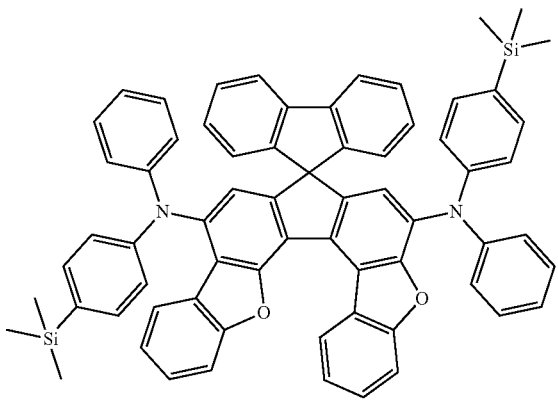
<Chemical Formula 45>
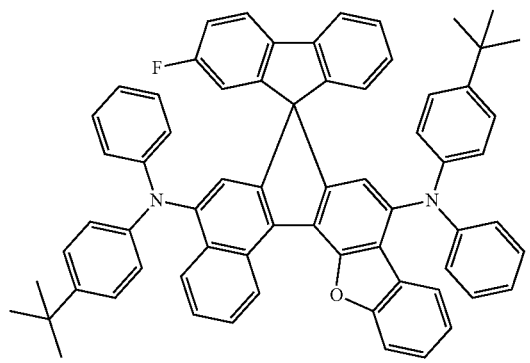
<Chemical Formula 46>
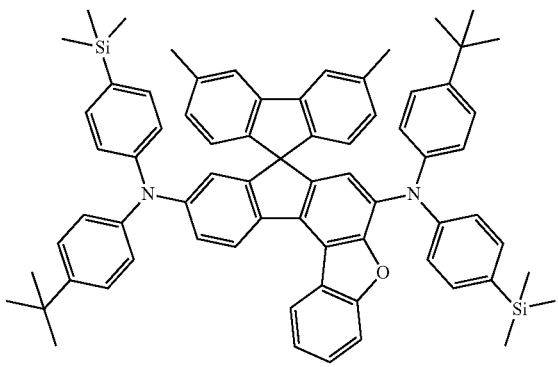

<Chemical Formula 47>
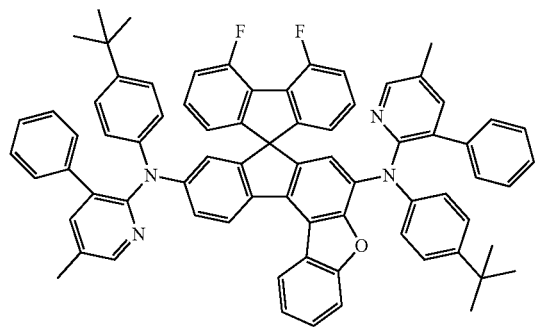
<Chemical Formula 48>
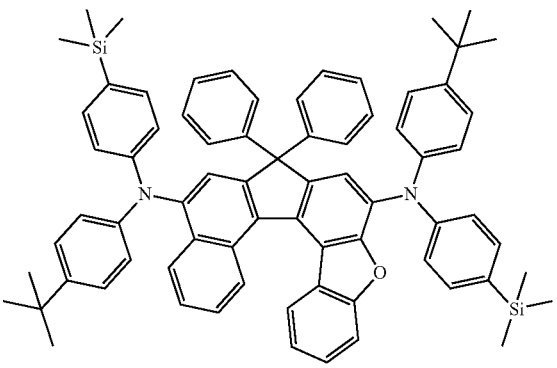
<Chemical Formula 49>
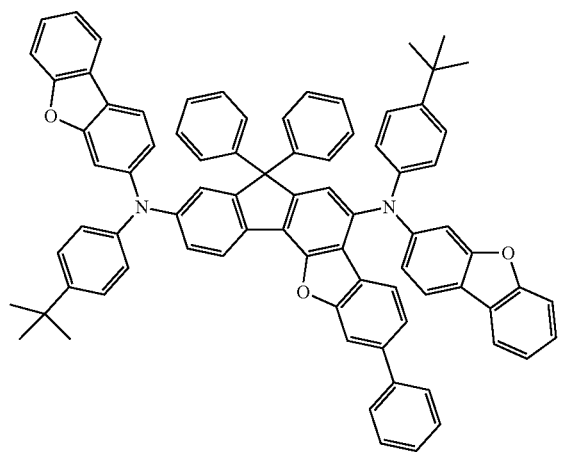
<Chemical Formula 50>
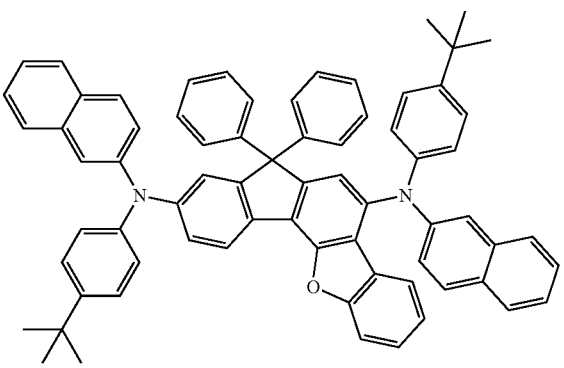
<Chemical Formula 51>
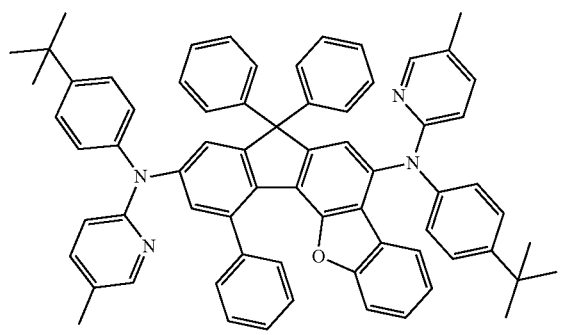
<Chemical Formula 52>
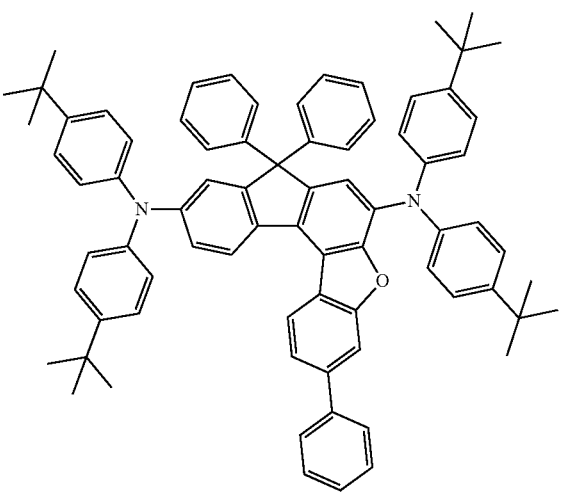

-continued
<Chemical Formula 53>
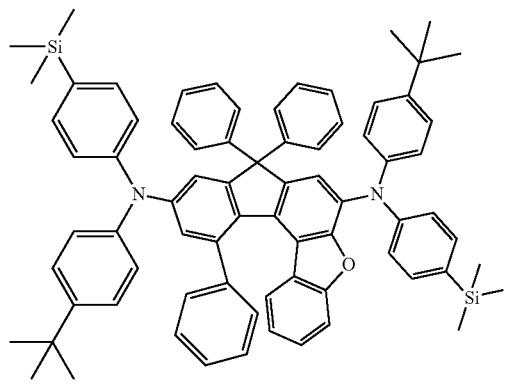
<Chemical Formula 54>
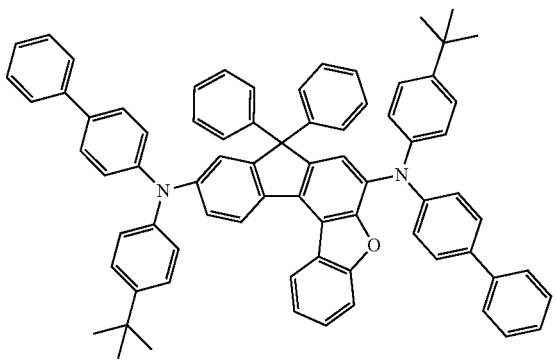
<Chemical Formula 55>
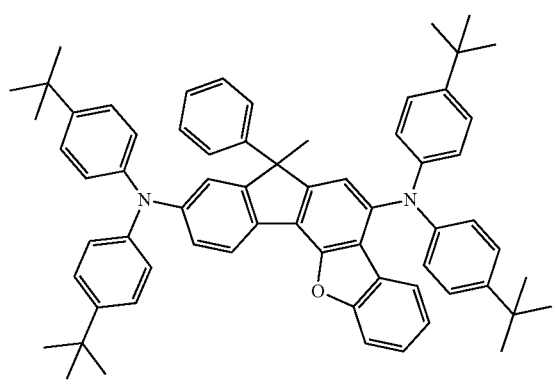
<Chemical Formula 56>
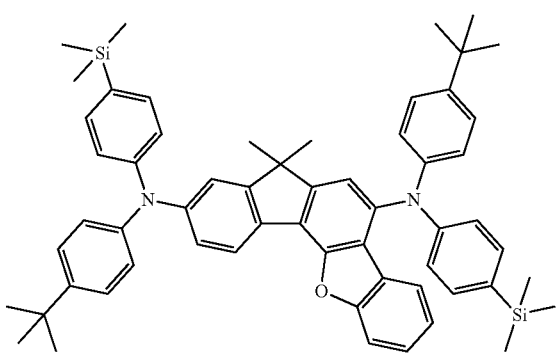
<Chemical Formula 57>
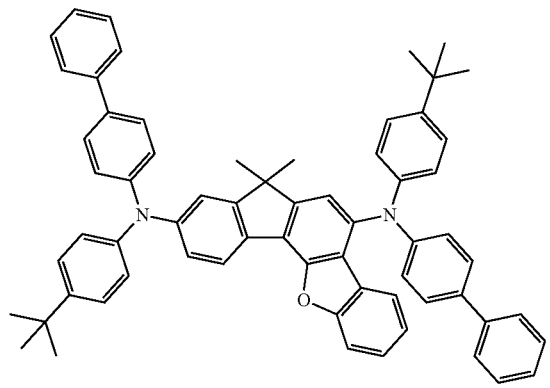
<Chemical Formula 58>
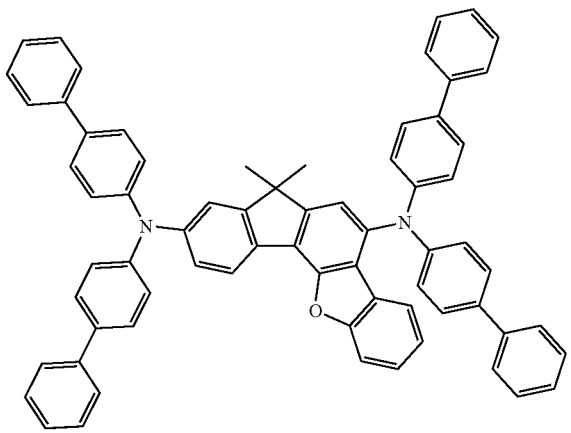
<Chemical Formula 59>
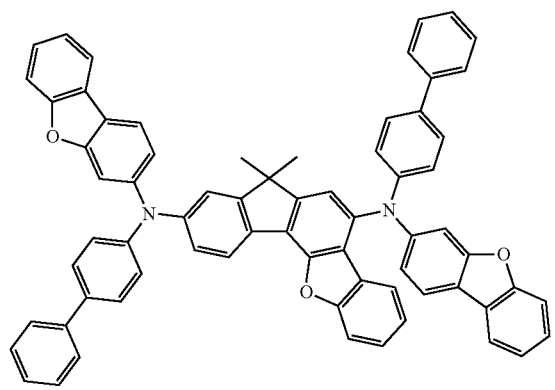
<Chemical Formula 60>
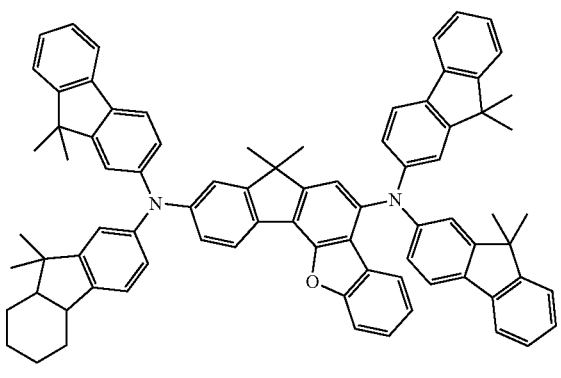

-continued
<Chemical Formula 61>
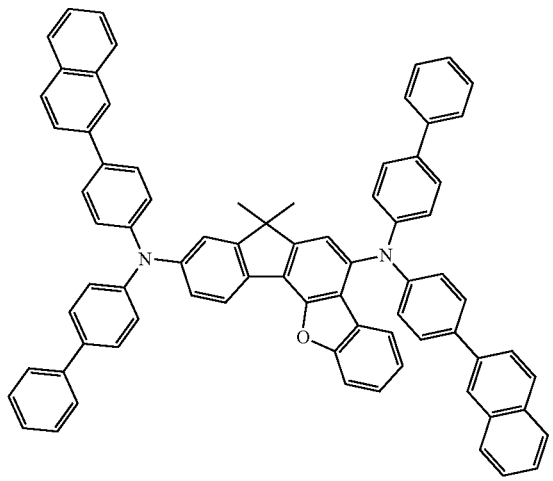
<Chemical Formula 62>
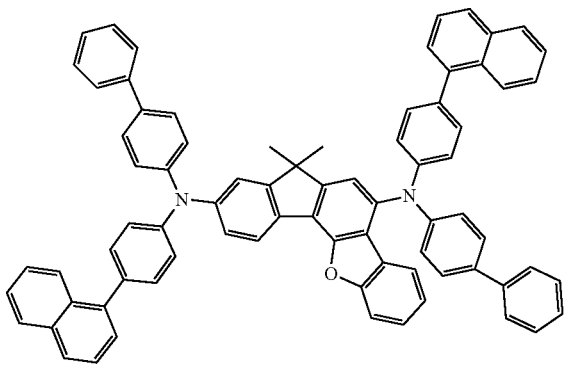
<Chemical Formula 63>
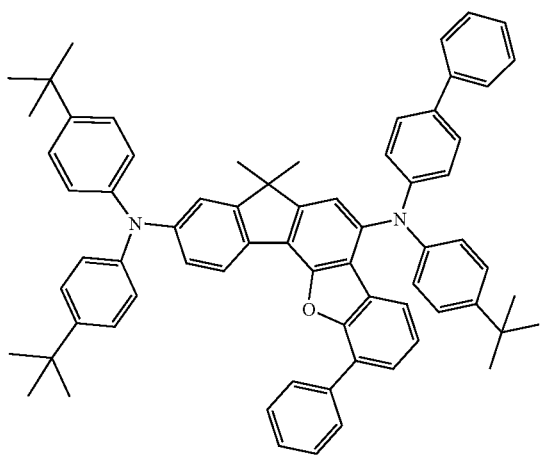
<Chemical Formula 64>
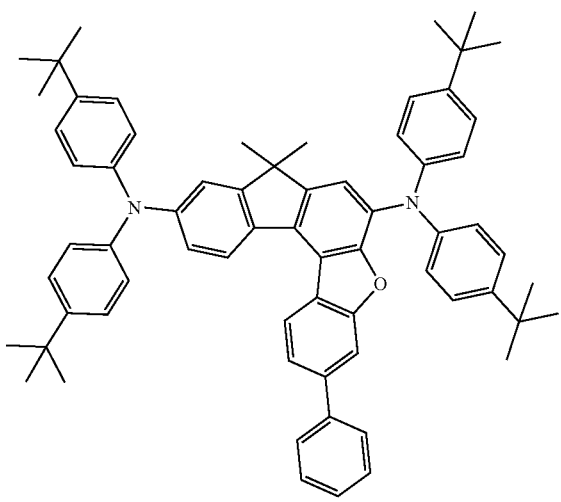
<Chemical Formula 65>
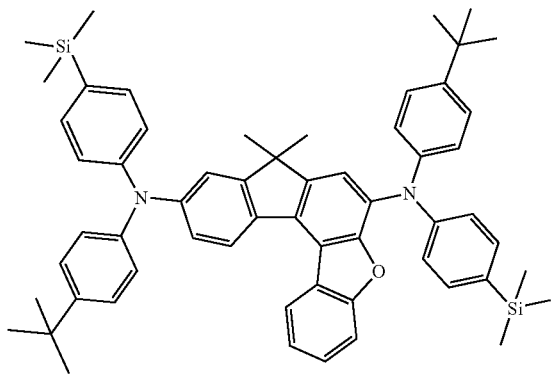
<Chemical Formula 66>
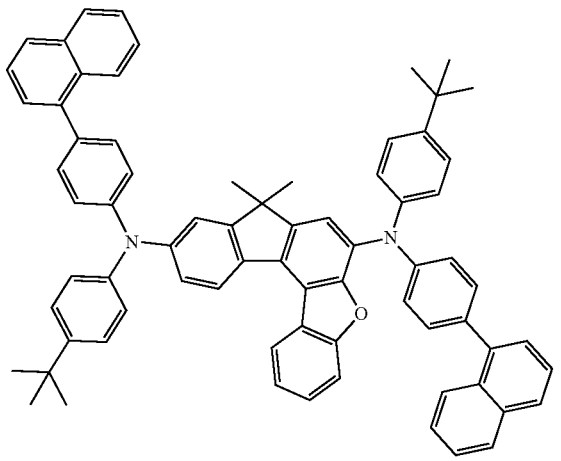

<Chemical Formula 67>
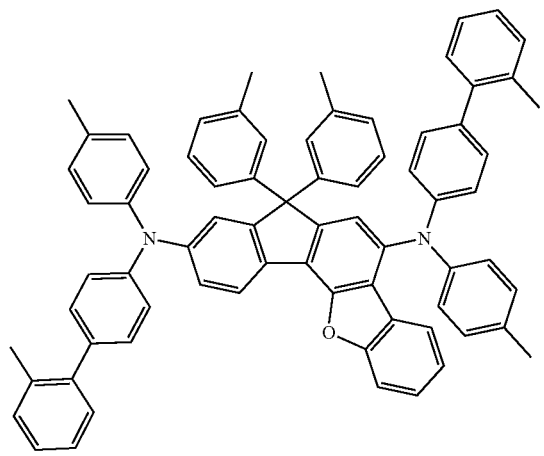
<Chemical Formula 68>
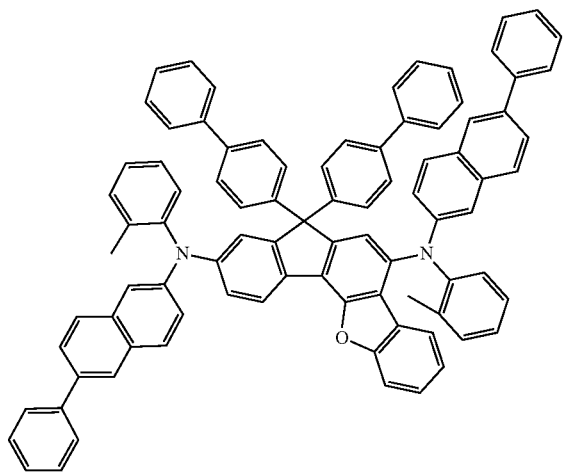
<Chemical Formula 69>
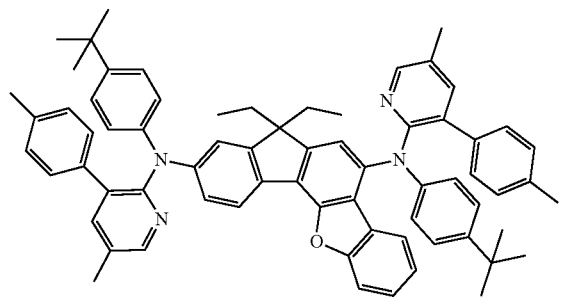
<Chemical Formula 70>
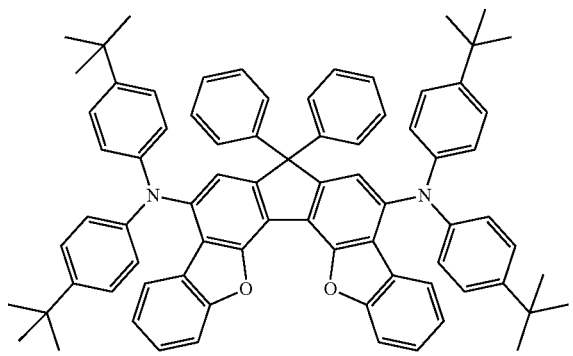
<Chemical Formula 71>
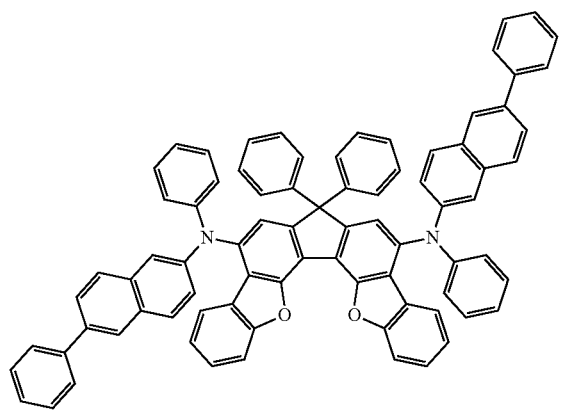
<Chemical Formula 72>
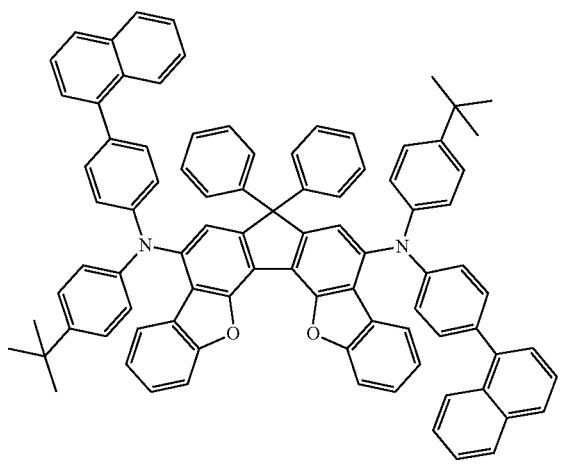

<Chemical Formula 73>
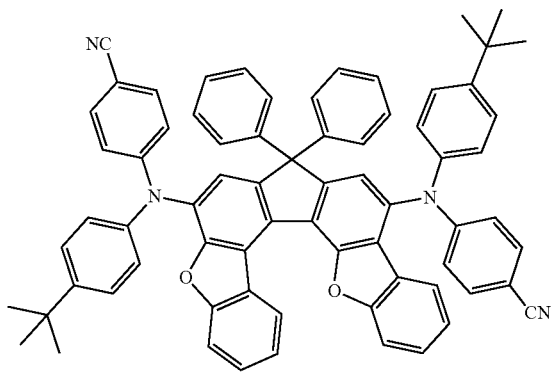
<Chemical Formula 74>
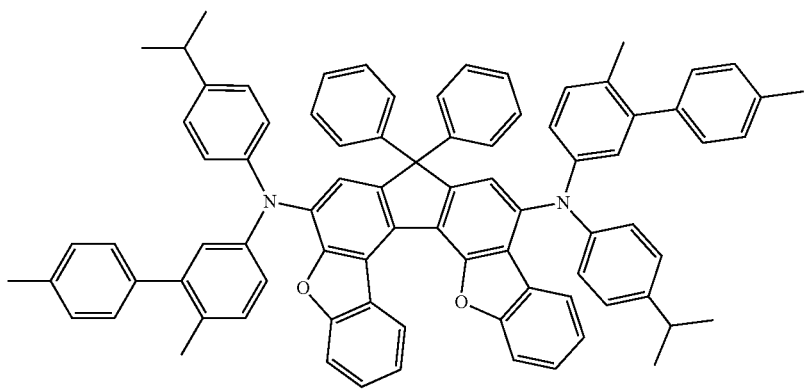
<Chemical Formula 75>
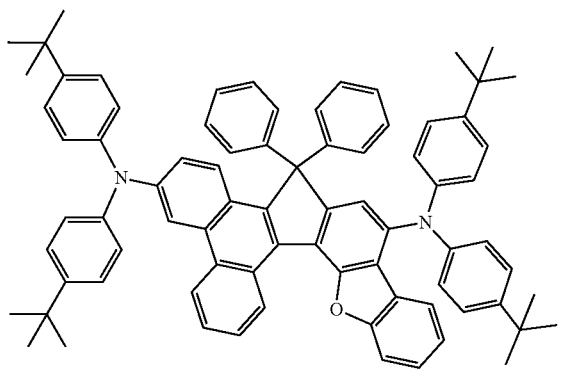
<Chemical Formula 76>
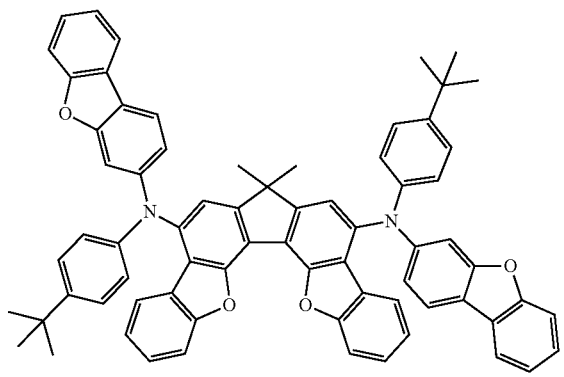
<Chemical Formula 77>
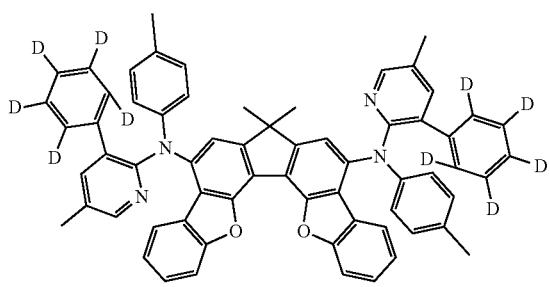
<Chemical Formula 78>
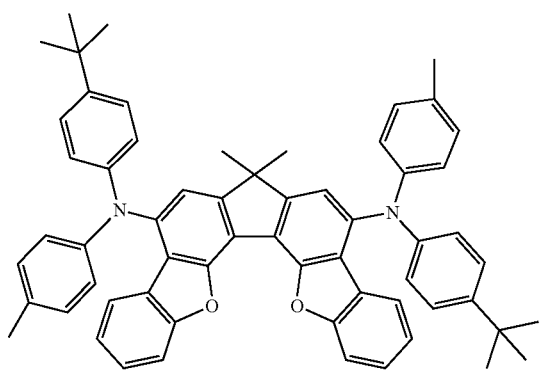

<Chemical Formula 79>
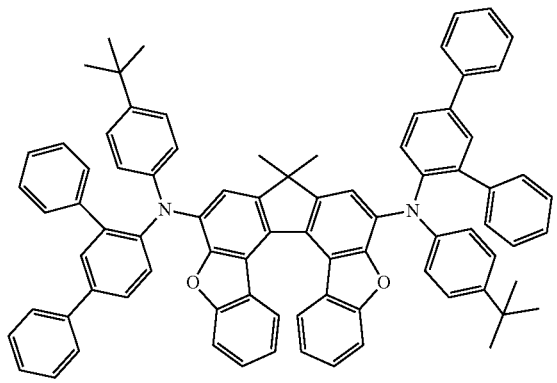
<Chemical Formula 80>
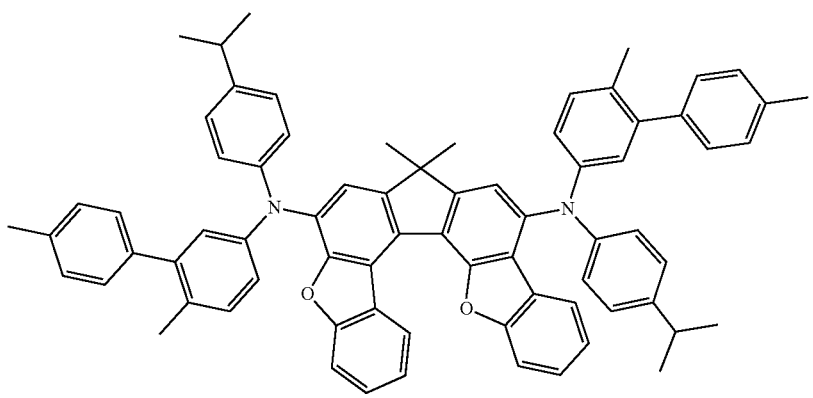
<Chemical Formula 81>
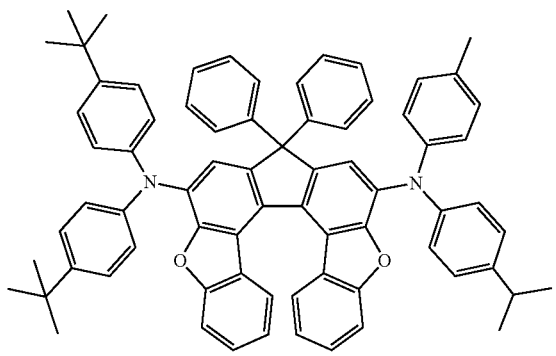
<Chemical Formula 82>
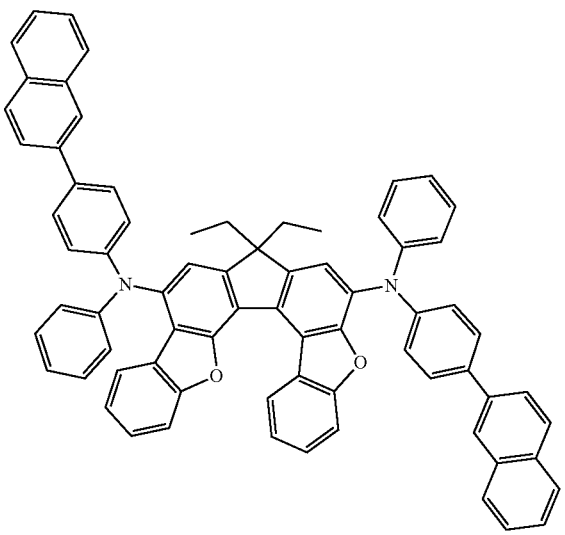

<Chemical Formula 83>
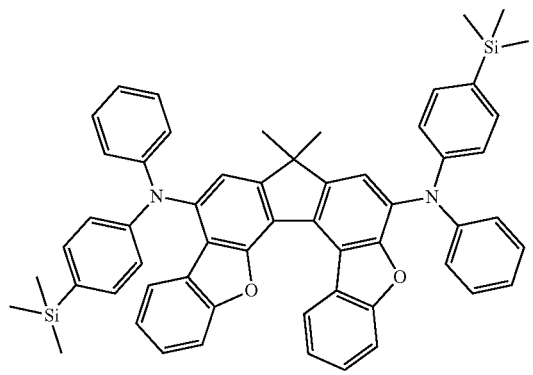
<Chemical Formula 84>
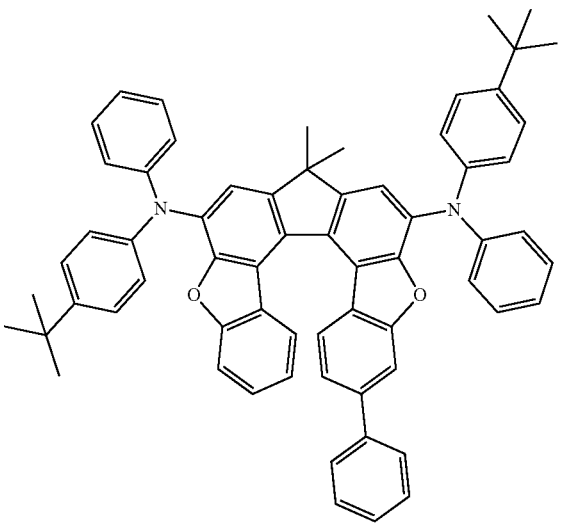
<Chemical Formula 85>
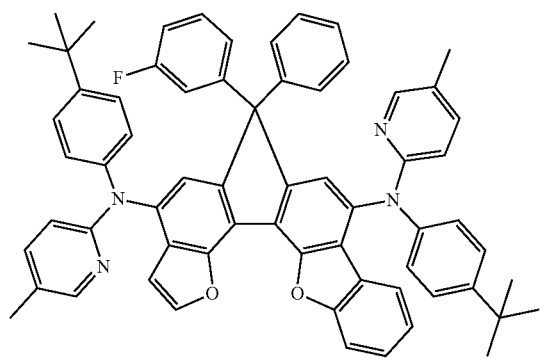
<Chemical Formula 86>
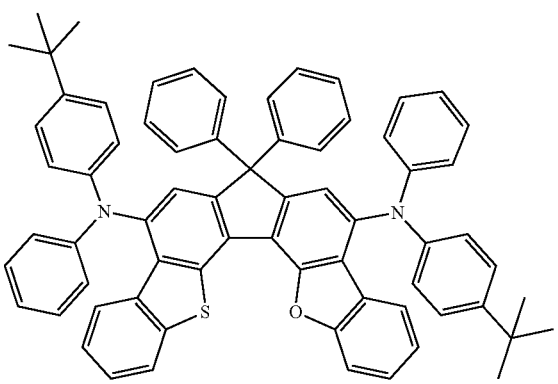
<Chemical Formula 87>
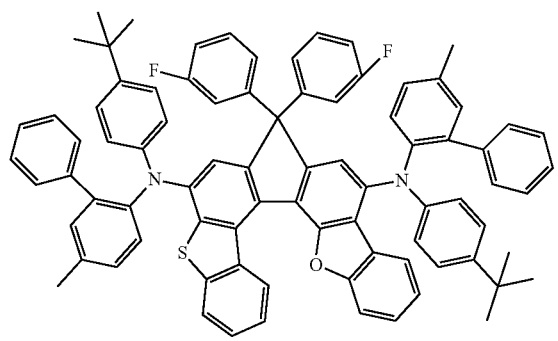
<Chemical Formula 88>
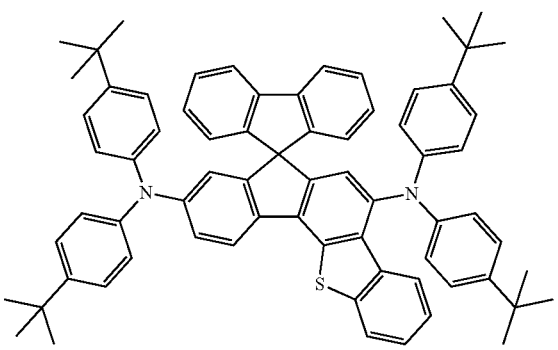

-continued
<Chemical Formula 89>
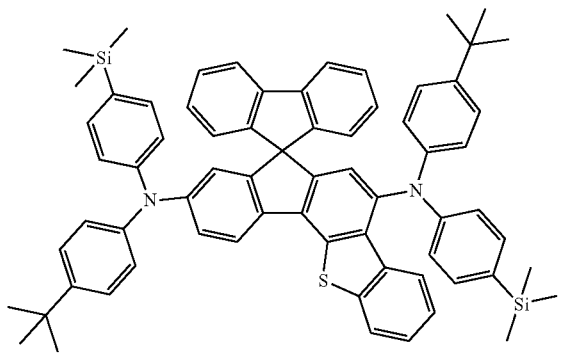
<Chemical Formula 90>
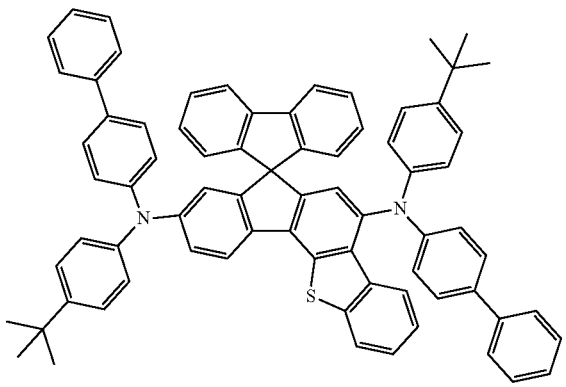
<Chemical Formula 91>
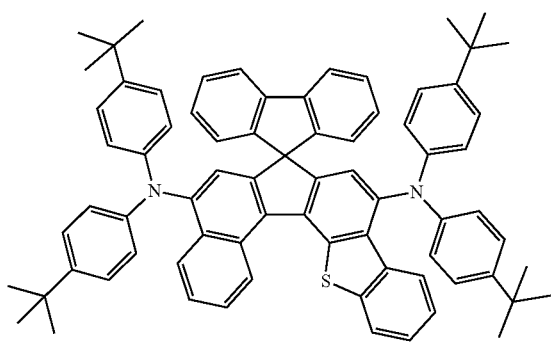
<Chemical Formula 92>
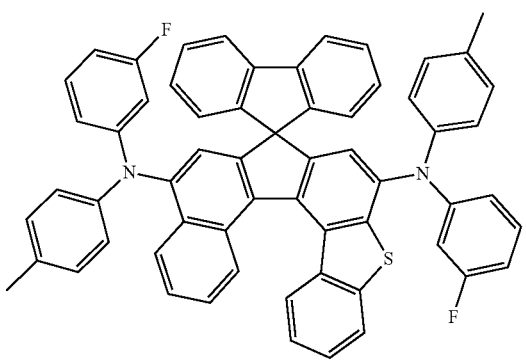
<Chemical Formula 93>
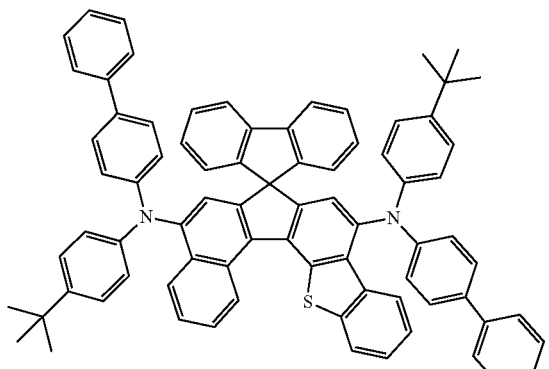
<Chemical Formula 94>
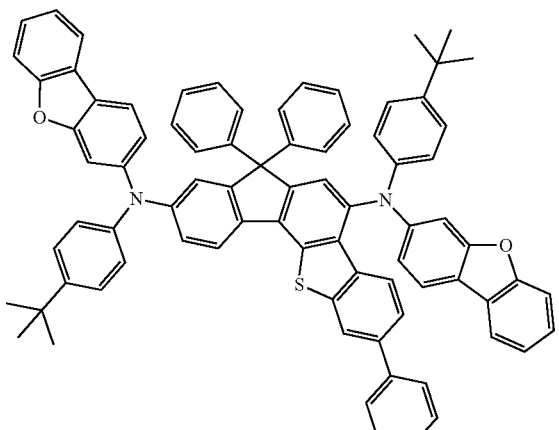
<Chemical Formula 95>
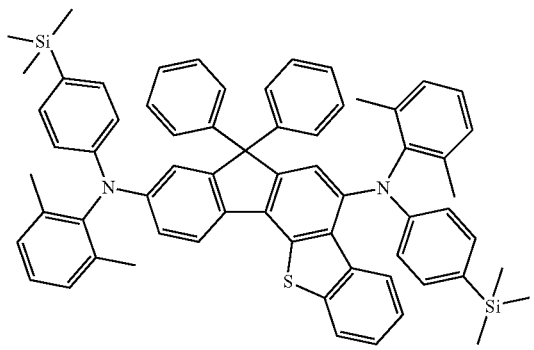
<Chemical Formula 96>
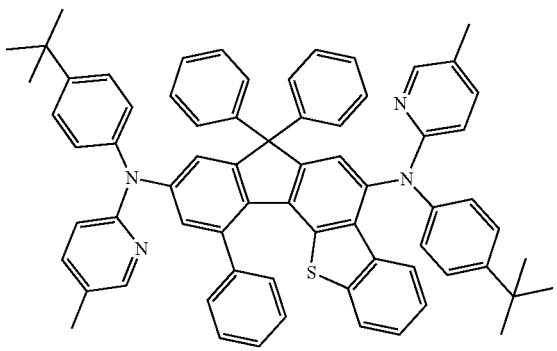

-continued
<Chemical Formula 97>
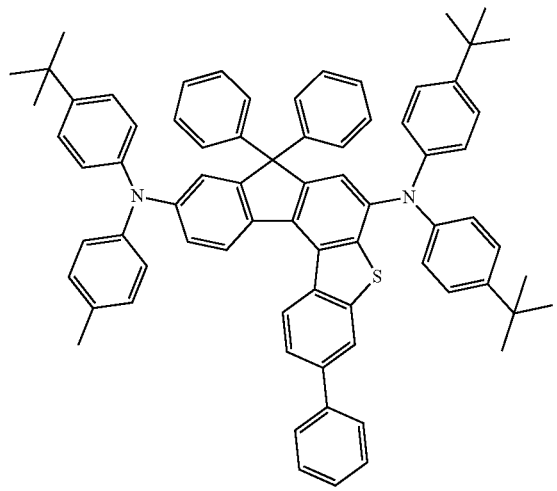
<Chemical Formula 98>
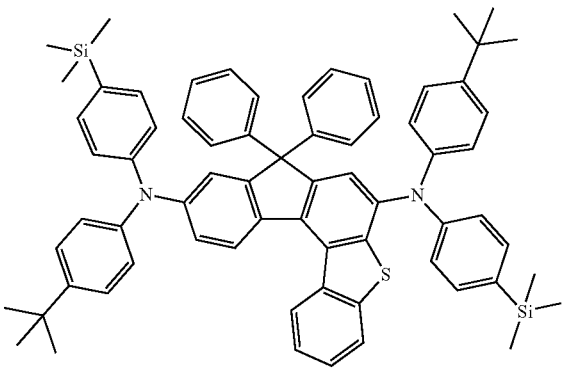
<Chemical Formula 99>
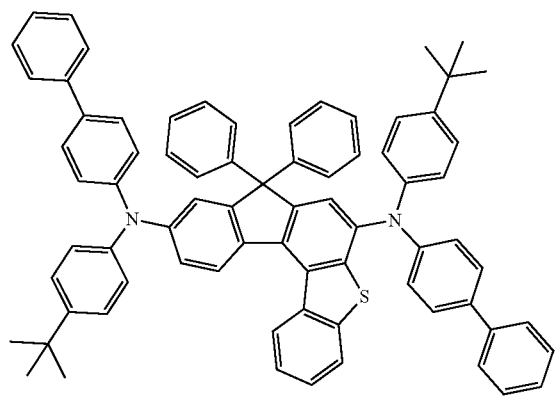
<Chemical Formula 100>
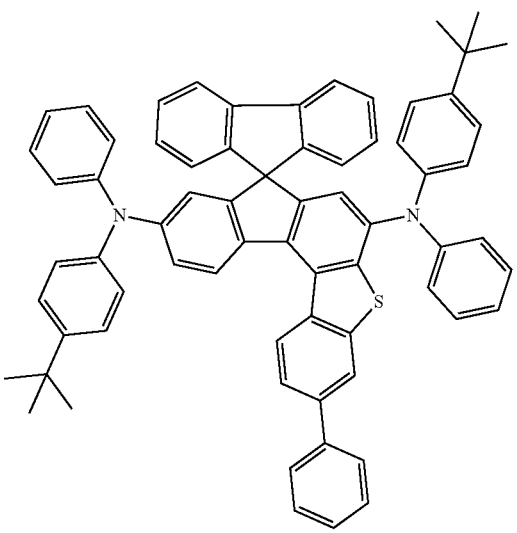
<Chemical Formula 101>
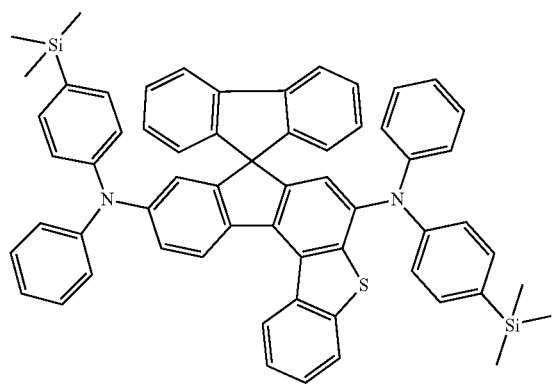
<Chemical Formula 102>
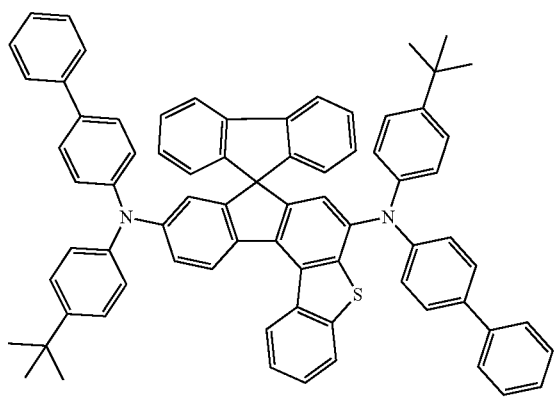

-continued
<Chemical Formula 103>
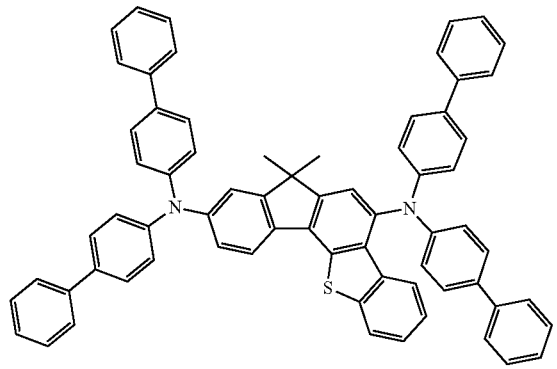
<Chemical Formula 104>
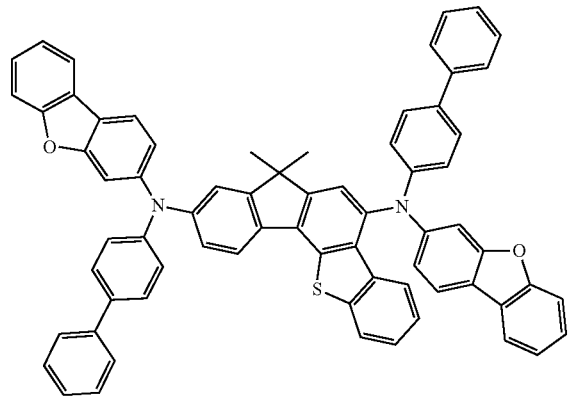
<Chemical Formula 105>
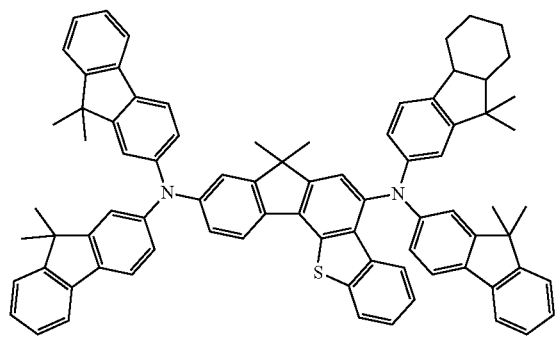
<Chemical Formula 106>
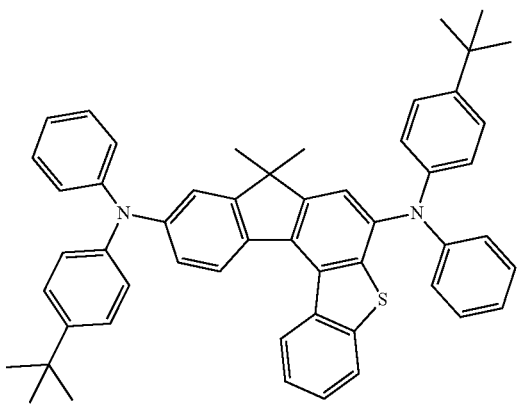
<Chemical Formula 107>
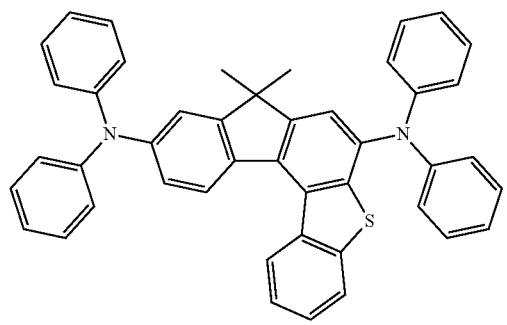
<Chemical Formula 108>
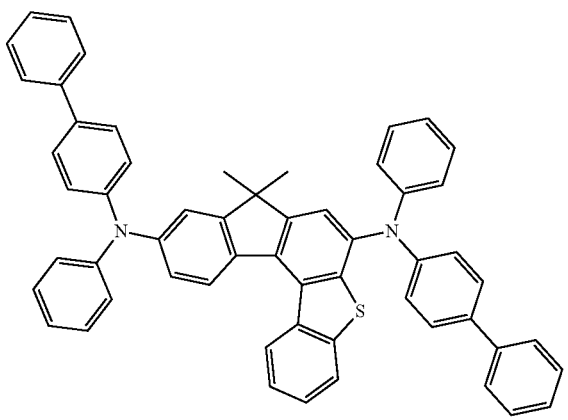

<Chemical Formula 109>
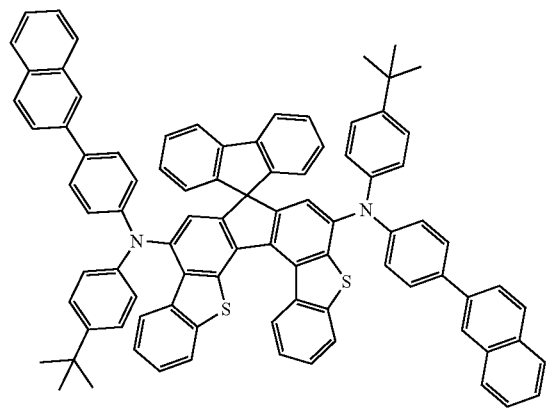
<Chemical Formula 110>
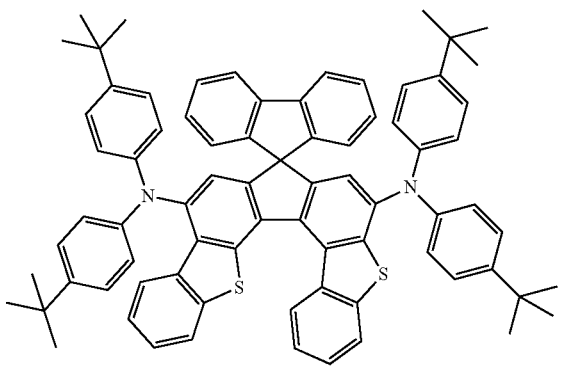
<Chemical Formula 111>
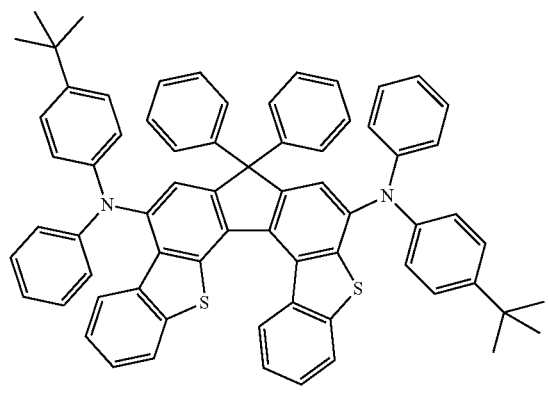
<Chemical Formula 112>
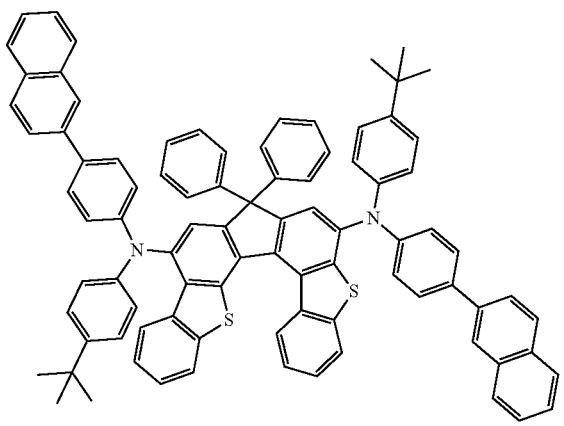
<Chemical Formula 113>
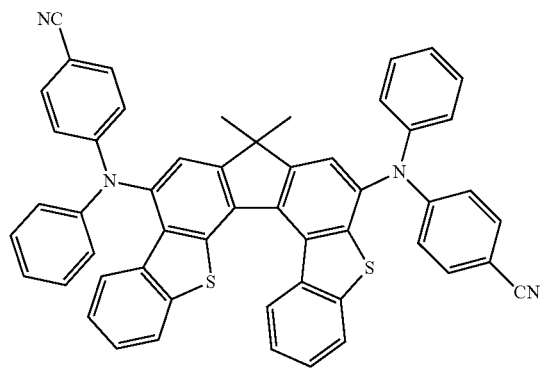
<Chemical Formula 114>
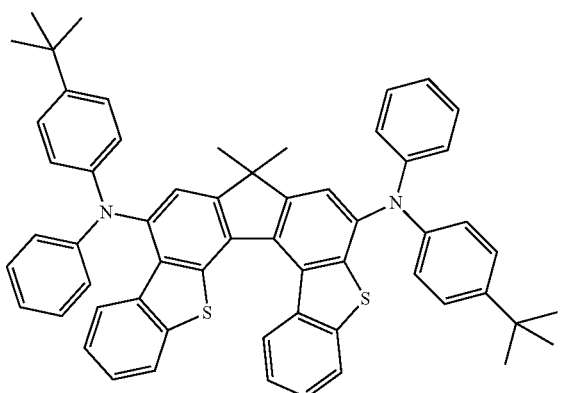

<Chemical Formula 115>
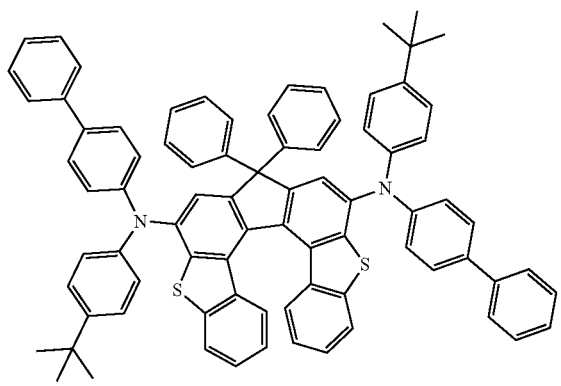
<Chemical Formula 116>
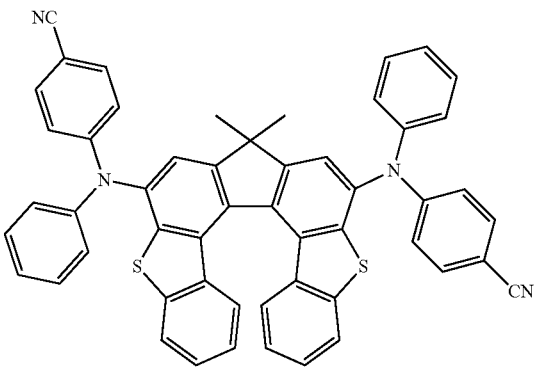
<Chemical Formula 117>
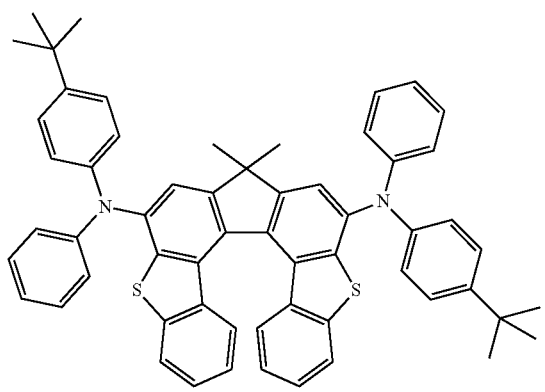
<Chemical Formula 118>
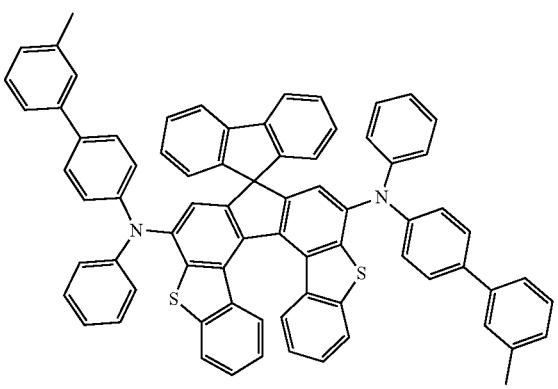
<Chemical Formula 119>
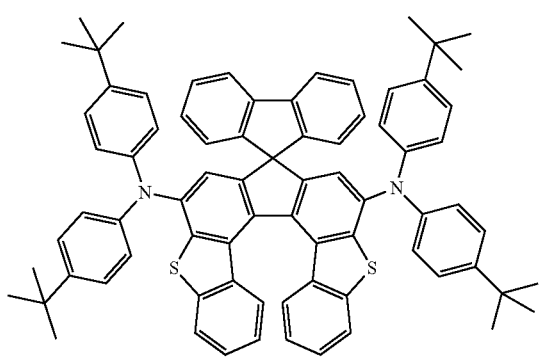
<Chemical Formula 120>
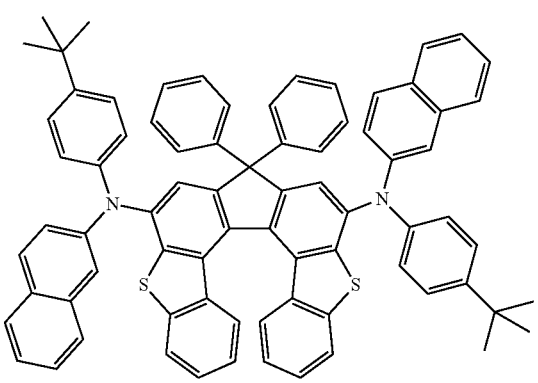
<Chemical Formula 121>
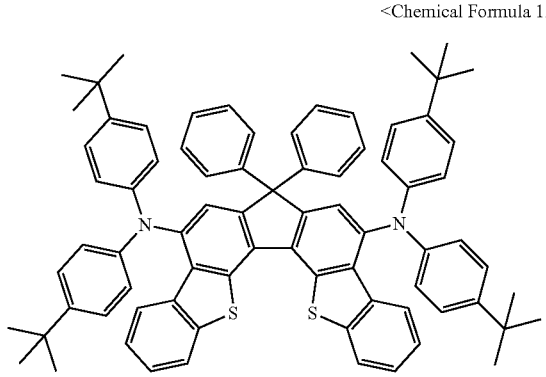
<Chemical Formula 122>
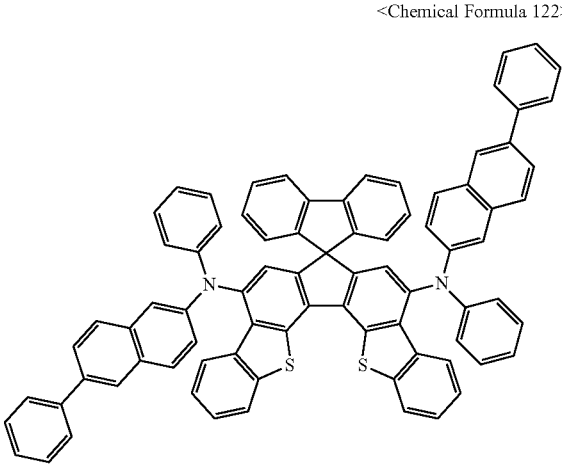

-continued
<Chemical Formula 123>
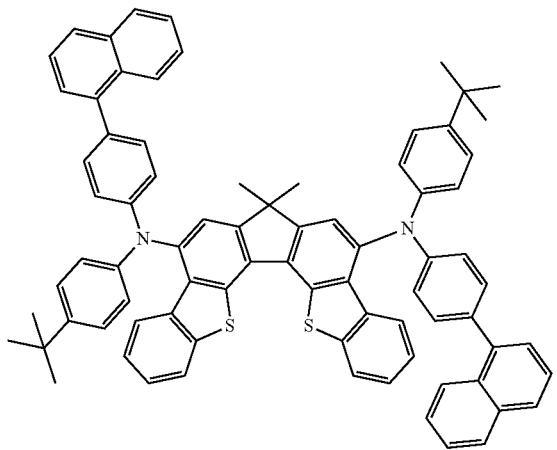
<Chemical Formula 124>
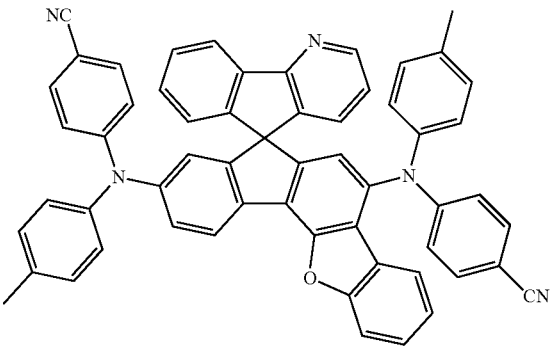
<Chemical Formula 125>
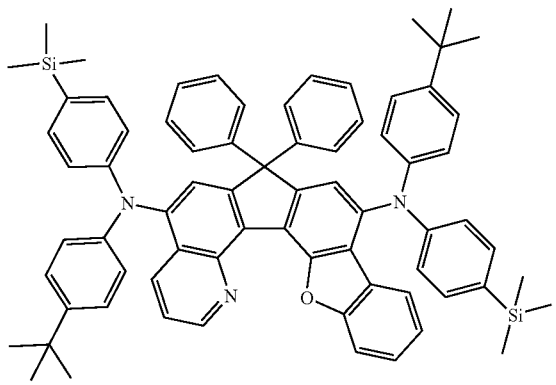
<Chemical Formula 126>
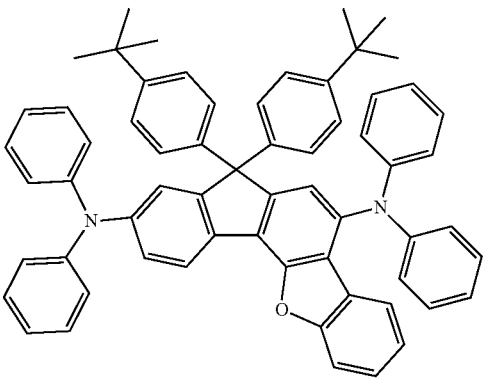
<Chemical Formula 127>
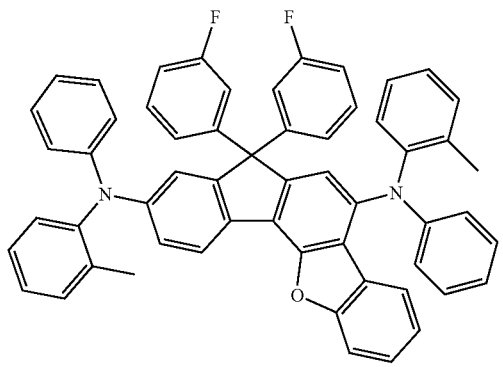
<Chemical Formula 128>
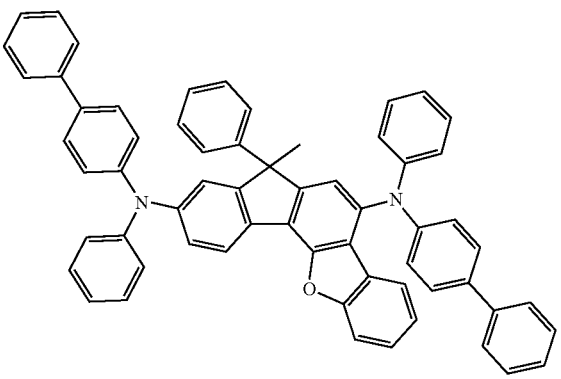

-continued
<Chemical Formula 129>
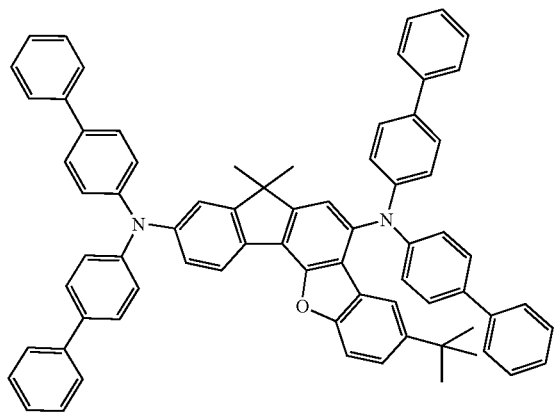
<Chemical Formula 130>
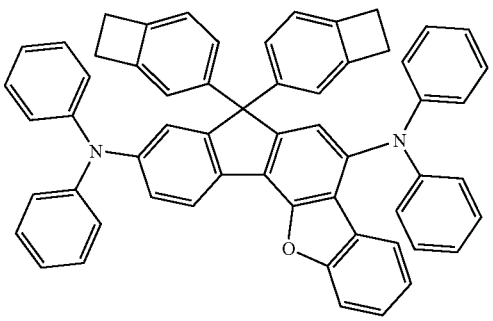
<Chemical Formula 131>
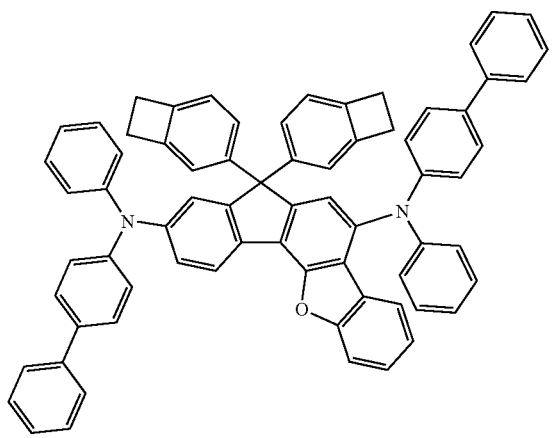
<Chemical Formula 132>
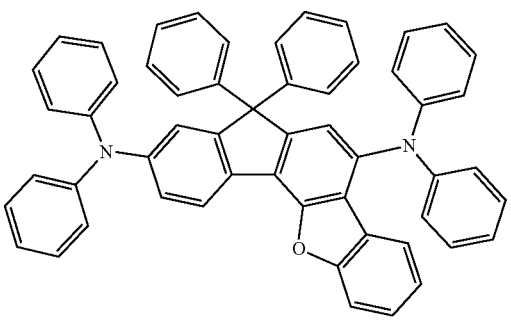
<Chemical Formula 133>
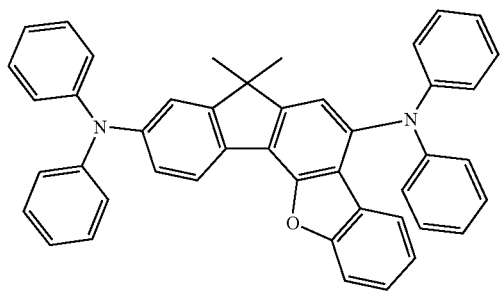
<Chemical Formula 134>
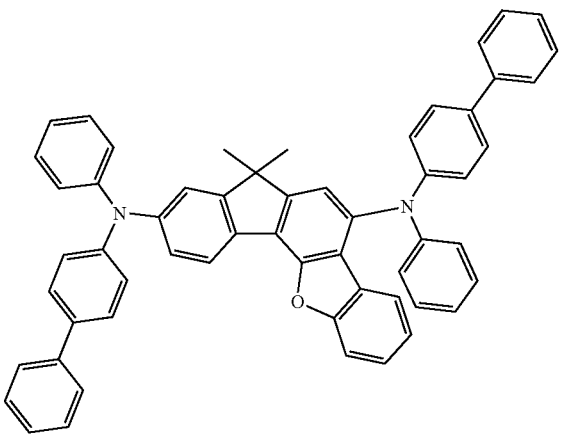

-continued
<Chemical Formula 135>
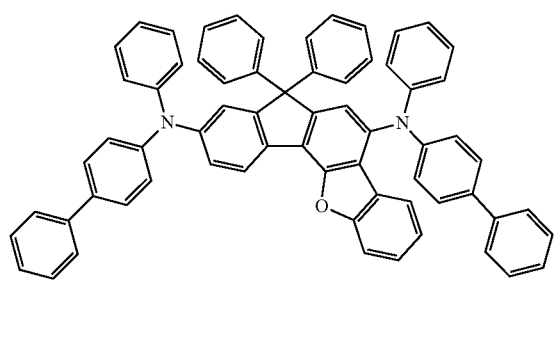
<Chemical Formula 136>
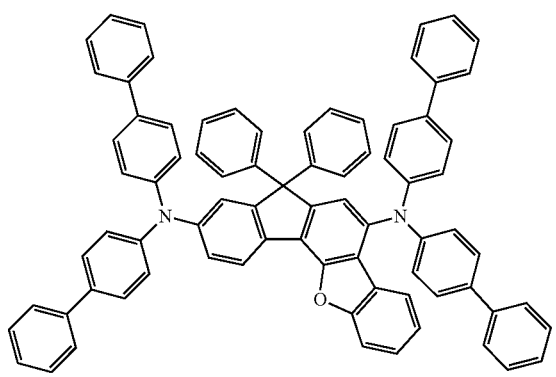
<Chemical Formula 137>
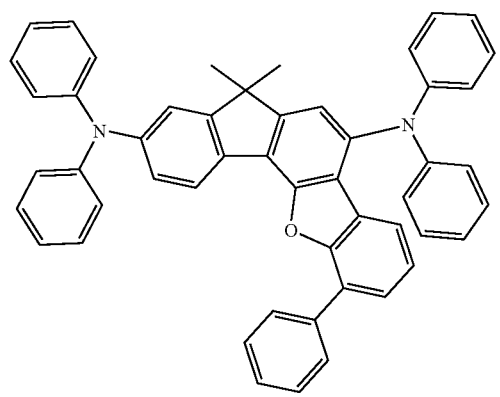
<Chemical Formula 138>
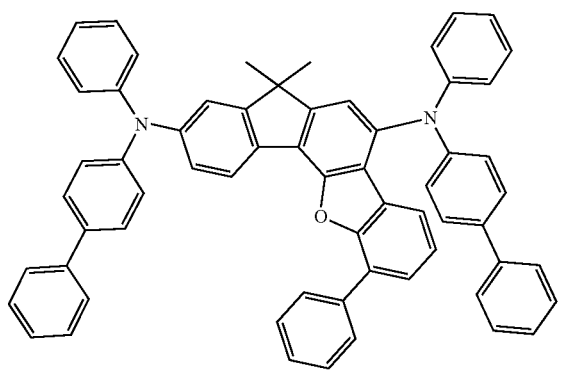
<Chemical Formula 139>
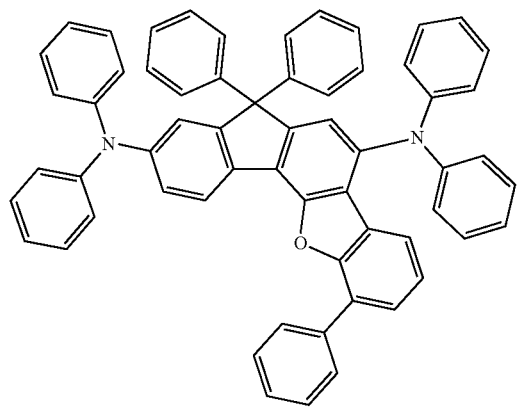
<Chemical Formula 140>
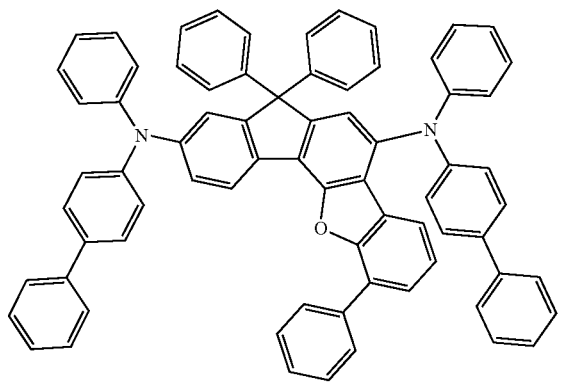

-continued

<Chemical Formula 141>

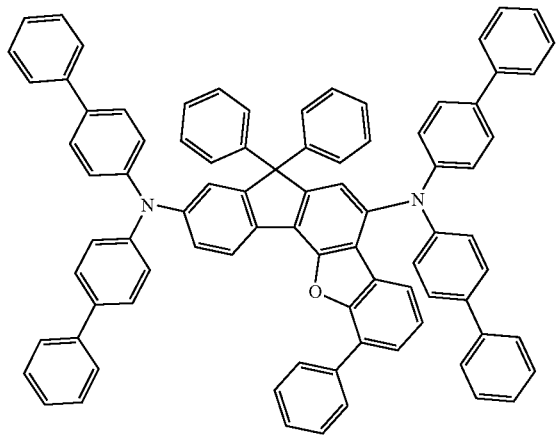

<Chemical Formula 142>

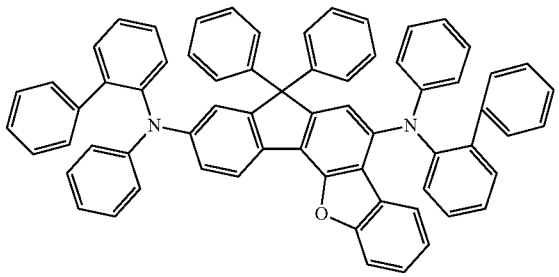

<Chemical Formula 143>

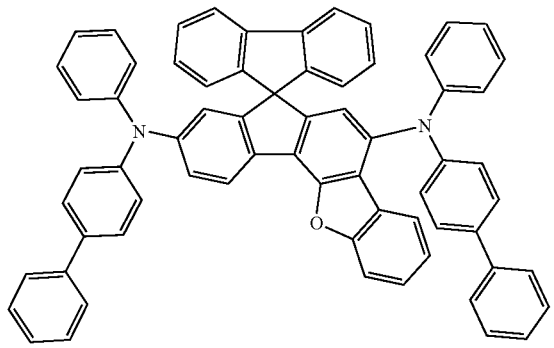

<Chemical Formula 144>

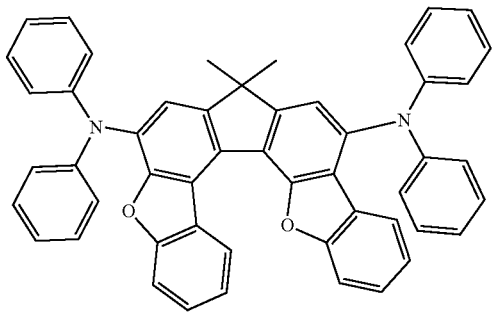

8. The organic light-emitting diode of claim 1, wherein one or two of $A_1$, $A_2$, E, and F in Chemical Formulas A and B are each independently a substituted or unsubstituted heteroaromatic ring of 2 to 40 carbon atoms.

9. The organic light-emitting diode of claim 8, wherein one of $A_1$, $A_2$, E, and F in Chemical Formulas A and B is a substituted or unsubstituted heteroaromatic ring of 2 to 40 carbon atoms.

10. The organic light-emitting diode of claim 1, wherein the light-emitting layer comprises at least one of the amine compounds represented by the following Chemical Formulas D1 and D2:

-continued

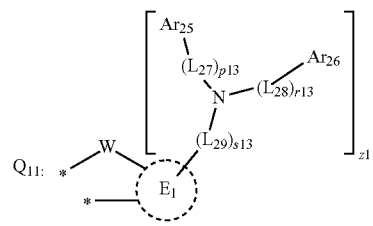

[Chemical Formula D1]

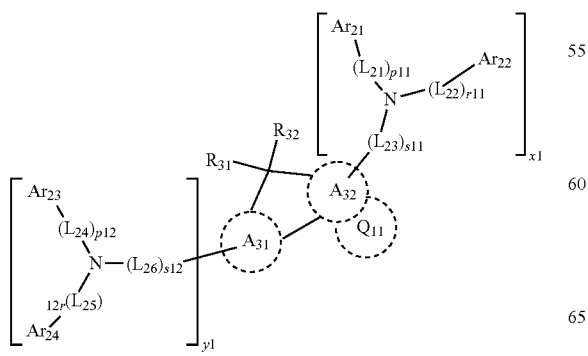

[Chemical Formula D2]

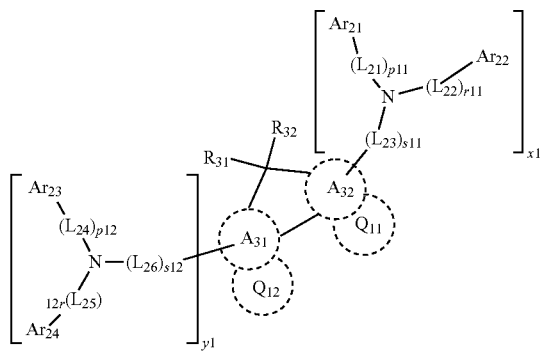

-continued

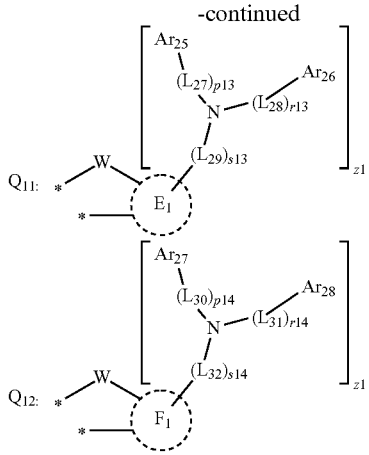

wherein, $A_{31}$, $A_{32}$, $E_1$, and $F_1$, which may be the same or different, are each independently a substituted or unsubstituted aromatic hydrocarbon ring of 6 to 50 carbon atoms, or a substituted or unsubstituted heteroaromatic ring of 2 to 40 carbon atoms;

wherein two adjacent carbon atoms within the aromatic ring of $A_{31}$ and two adjacent carbon atoms within the aromatic ring of $A_{32}$ form a 5-membered ring with a carbon atom connected to both substituents $R_{31}$ and $R_{32}$, thus establishing a fused ring structure;

linkers $L_{21}$ to $L_{32}$, which may be the same or different, are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is selected from among N-$R_{33}$, $CR_{34}R_{35}$, $SiR_{36}R_{37}$, $GeR_{38}R_{39}$, O, S, and Se;

$R_{31}$ to $R_{39}$ and $Ar_{21}$ to $Ar_{28}$, which may be the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to 30 carbon atoms, a substituted or unsubstituted aryl germanium of 1 to 30 carbon atoms, a cyano, a nitro, and a halogen, wherein $R_{31}$ and $R_{32}$ may be connected to each other to form a mono- or polycyclic aliphatic or aromatic ring which may bear at least one heteroatom selected from among N, O, P, Si, S, Ge, Se, and Te as a ring member;

p11 to p14, r11 to r14, and s11 to s14 are each independently an integer of 1 to 3, under which when any of them is 2 or greater, the corresponding linkers L21 to L32 may be the same or different, x1 is an integer of 1 or 2, and y1 and z1, which may be the same or different, are each independently an integer of 0 to 3, a connection may be made between $Ar_{21}$ and $Ar_{22}$, between $Ar_{23}$ and $Ar_{24}$, between $Ar_{25}$ and $Ar_{26}$, and between $Ar_{27}$ and $Ar_{28}$ to form respective rings;

two adjacent carbon atoms within the $A_{32}$ ring in Chemical Formula D1 are linked to respective * of structure formula $Q_{11}$ to form a fused ring, and two adjacent carbon atoms within the $A_{31}$ ring in Chemical Formula D2 are linked to respective * of structure formula $Q_{12}$ to form a fused ring and two adjacent carbon atoms within the $A_{32}$ ring in Chemical Formula D2 are linked to respective * of structure formula $Q_{11}$ to form a fused ring.

11. The organic light-emitting diode of claim 10, wherein $A_{31}$, $A_{32}$, $E_1$, and $F_1$ in the compounds represented by Chemical Formula D1 and Chemical Formula D2 are same or different and are each independently a substituted or unsubstituted aromatic hydrocarbon ring of 6 to 50 carbon atoms.

12. The organic light-emitting diode of claim 10, wherein the linkers $L_{21}$ to $L_{32}$ in Chemical Formulas D1 and D2 are same or different and are each independently a single bond or any one selected from the following [Structural Chemical 22] to [Structural Chemical 30], p11 to p14, r11 to r14, and s11 to s14 are each 1 or 2, and x1 is 1:

[Structural Formula 22]

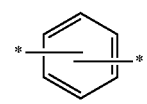

[Structural Formula 23]

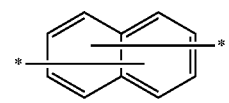

[Structural Formula 24]

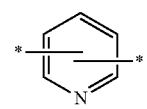

[Structural Formula 25]

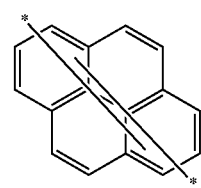

[Structural Formula 26]

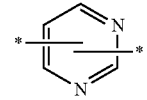

305
-continued

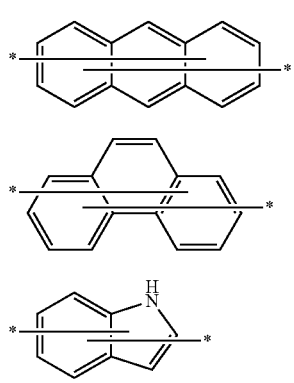

[Structural Formula 27]

[Structural Formula 28]

[Structural Formula 29]

306
-continued

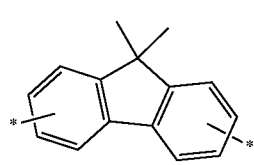

[Structural Formula30]

wherein each of unsubstituted carbon atoms of the aromatic ring moiety can be bound with a hydrogen atom or a deuterium atom.

13. The organic light-emitting diode of claim 12, wherein the amine compound represented by Chemical Formula D1 or D2 is any one selected from the following Compound 401 to Compound 639:

<Compound 401>

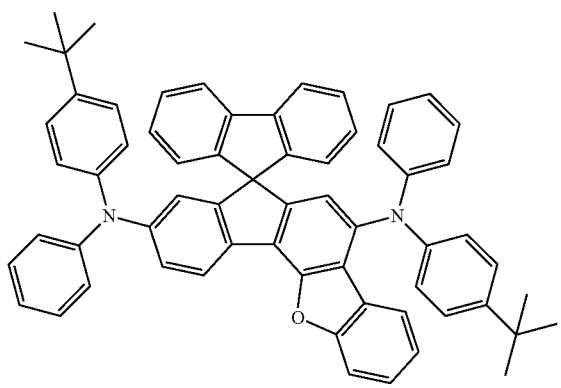

<Compound 402>

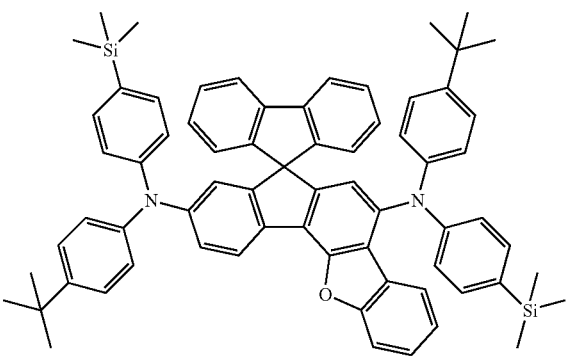

<Compound 403>

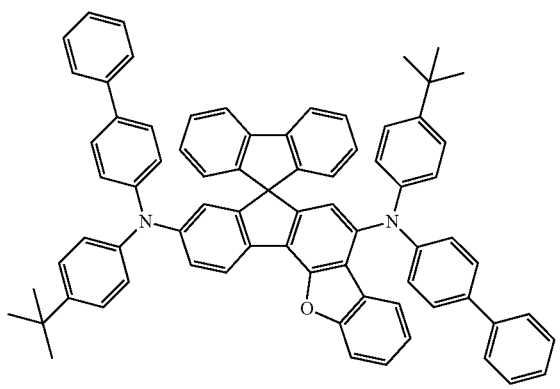

<Compound 404>

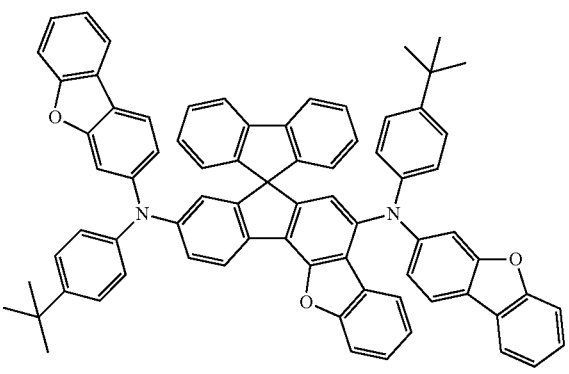

<Compound 405>

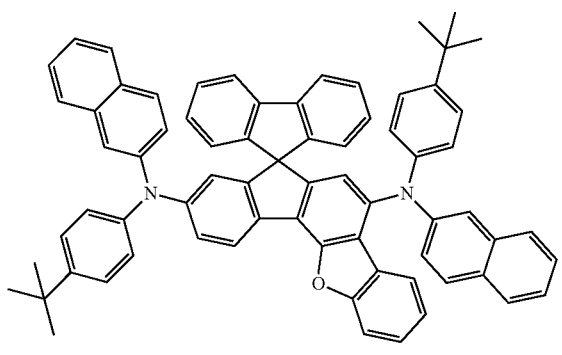

<Compound 406>

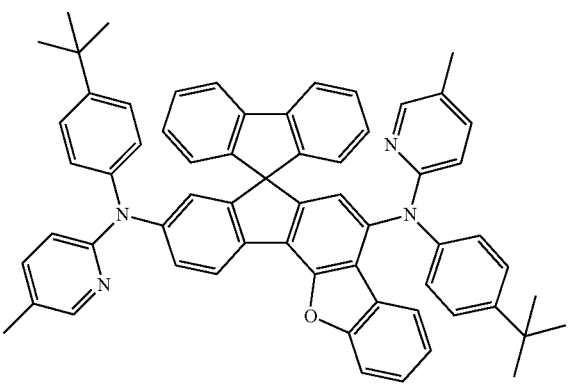

-continued
<Compound 407>
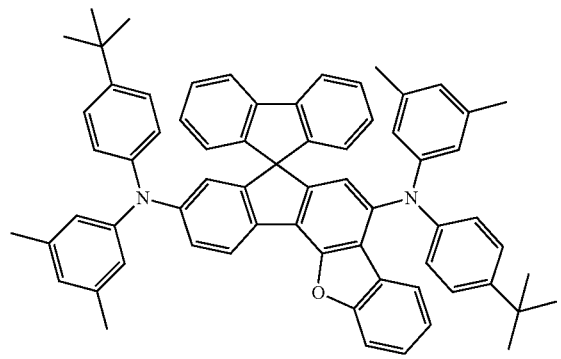
<Compound 408>
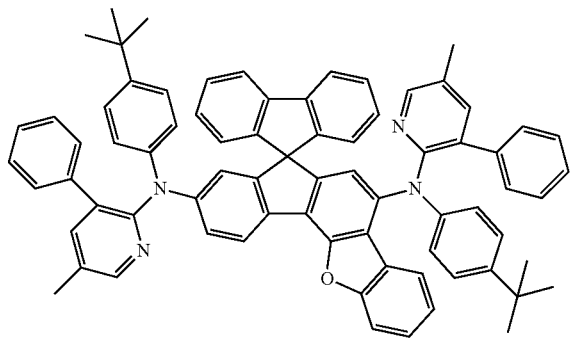
<Compound 409>
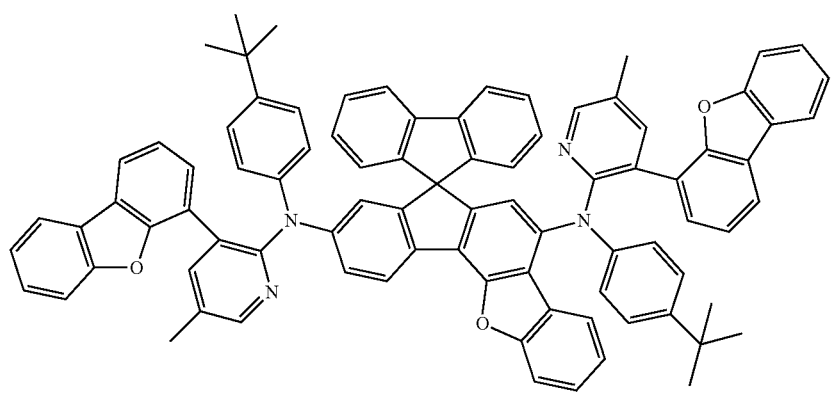
<Compound 410>
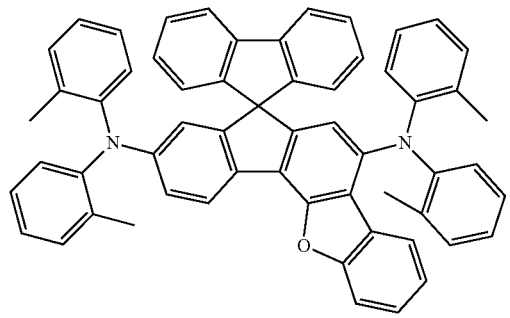
<Compound 411>
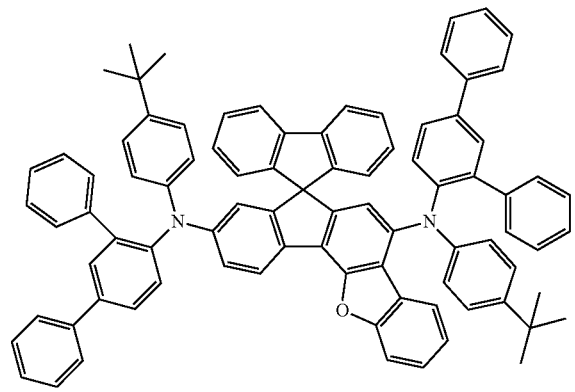
<Compound 412>
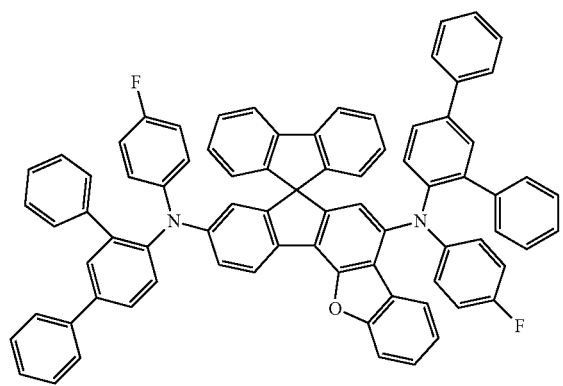
<Compound 413>
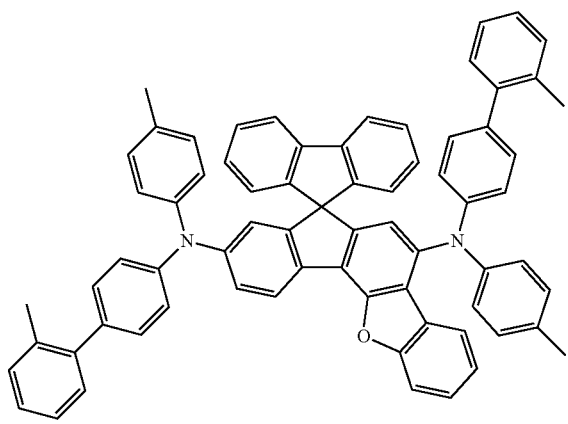

-continued
<Compound 414>
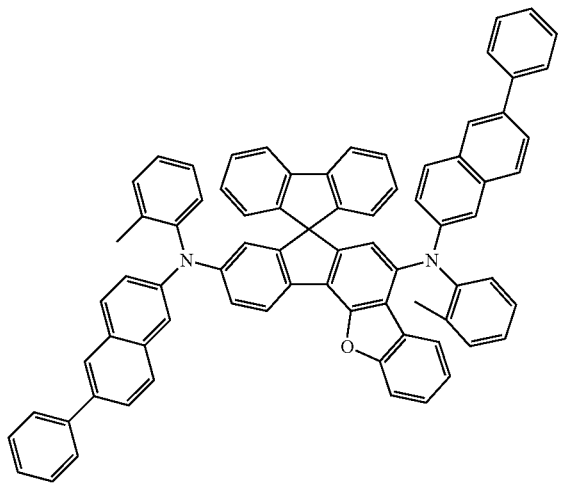
<Compound 415>
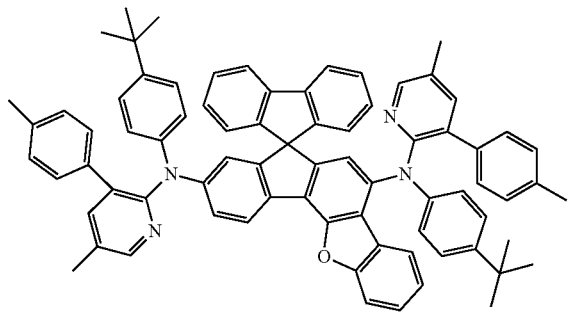
<Compound 416>
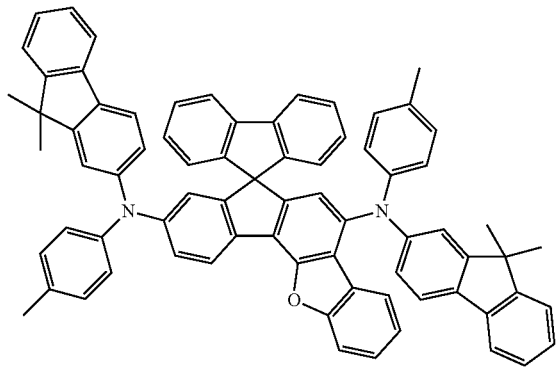
<Compound 417>
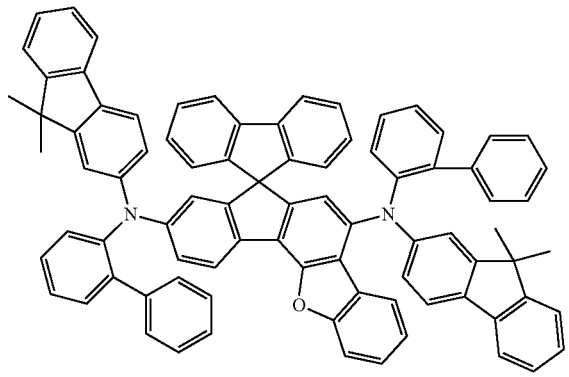
<Compound 418>
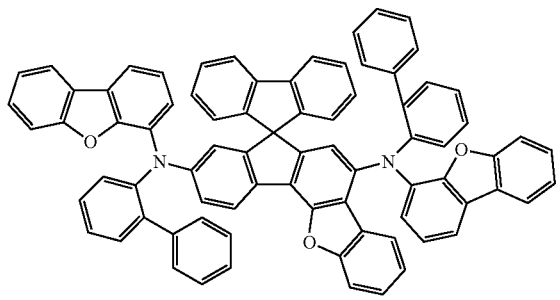
<Compound 419>
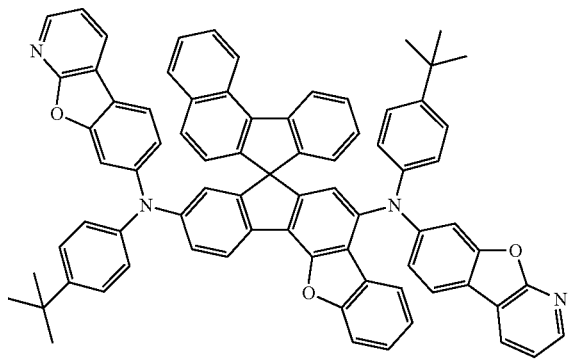

-continued
<Compound 420>
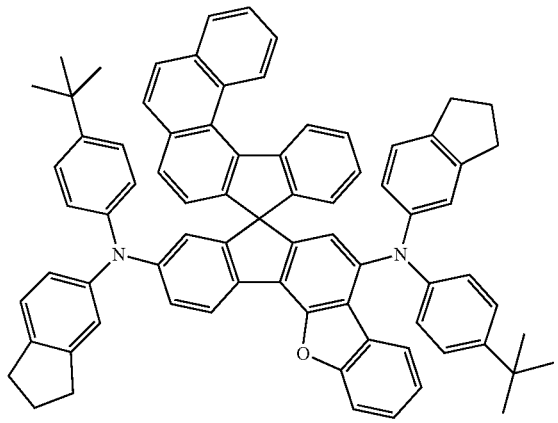
<Compound 421>
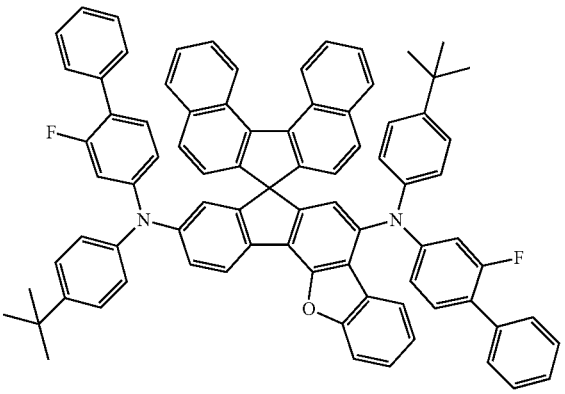
<Compound 422>
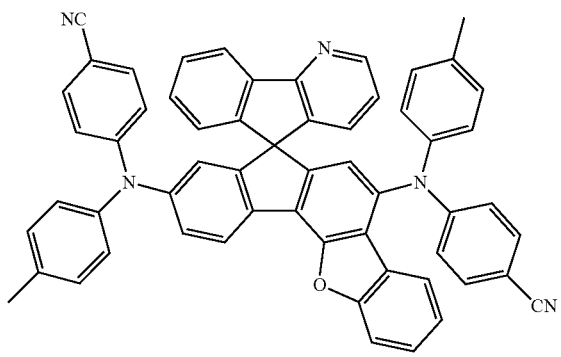
<Compound 423>
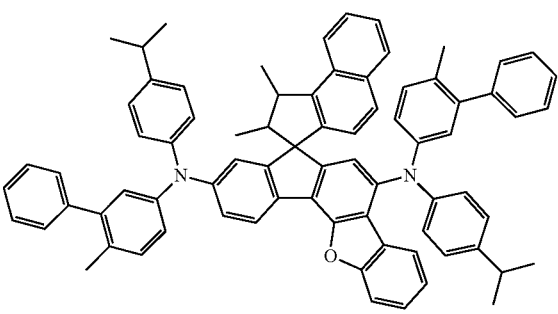
<Compound 424>
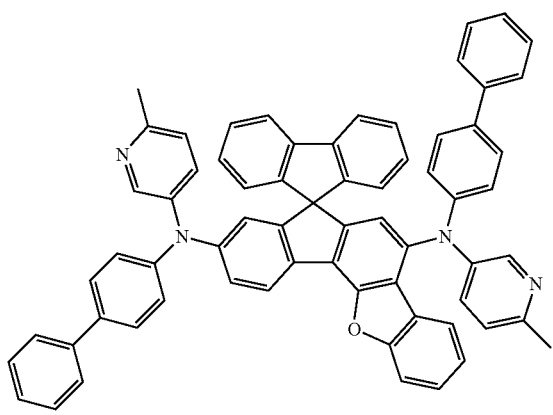
<Compound 425>
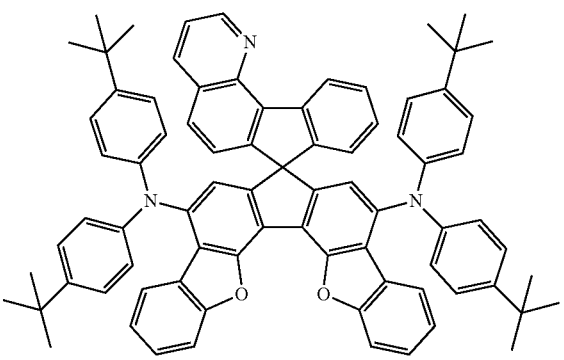

-continued
<Compound 426>
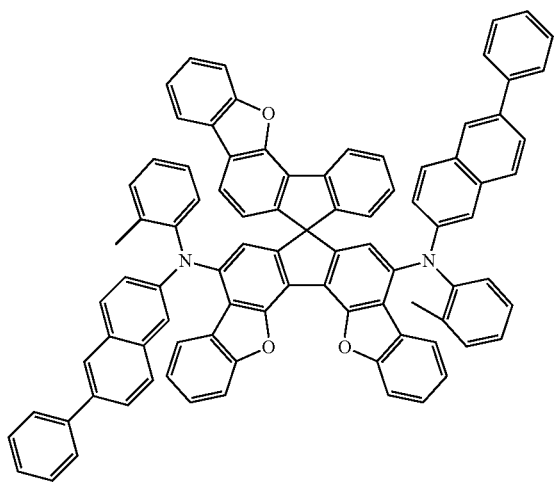
<Compound 427>
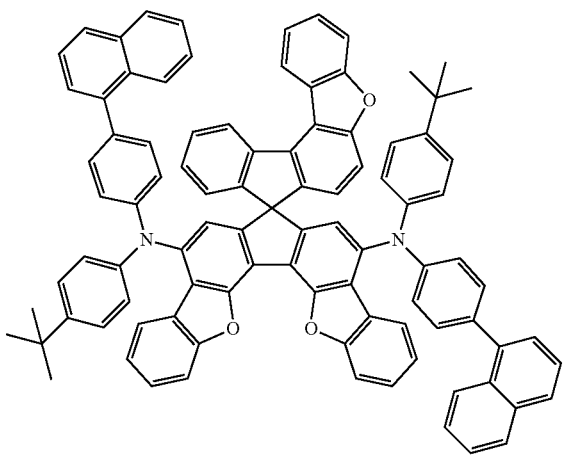
<Compound 428>
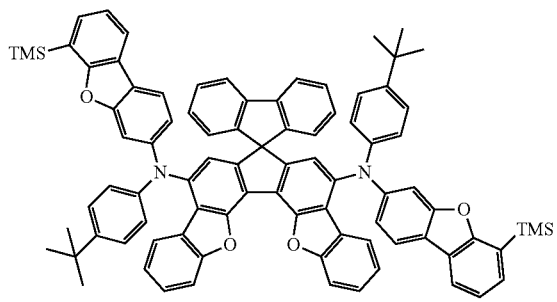
<Compound 429>
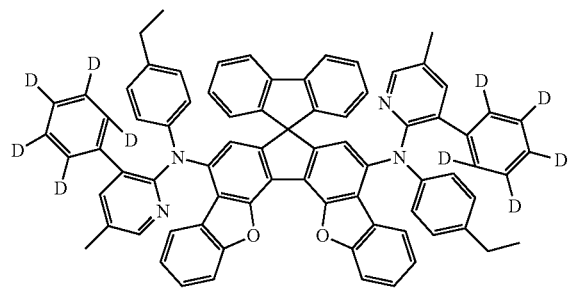
<Compound 430>
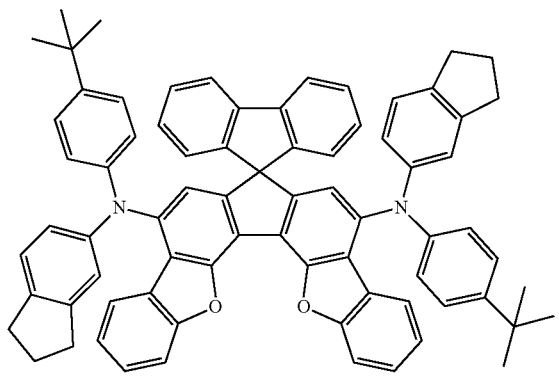
<Compound 431>
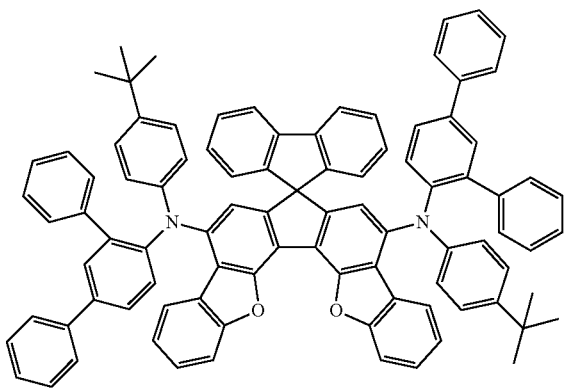
<Compound 432>
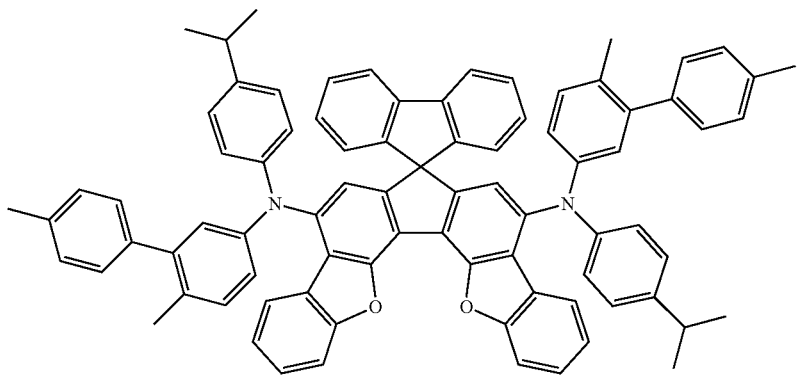

-continued
<Compound 433>
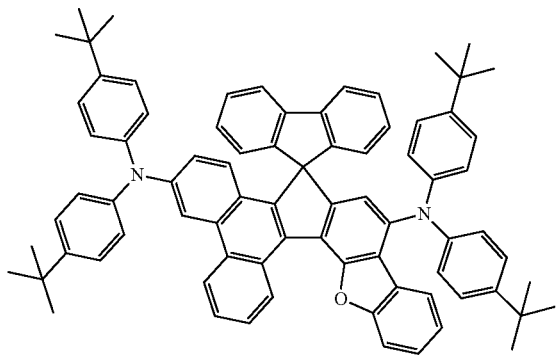
<Compound 434>
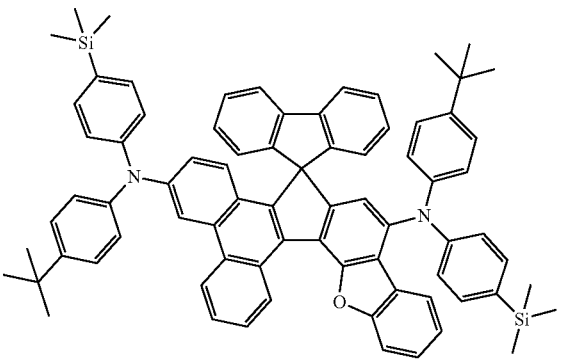
<Compound 435>
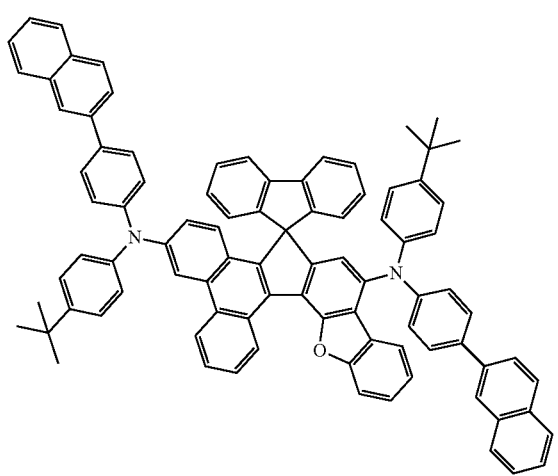
<Compound 436>
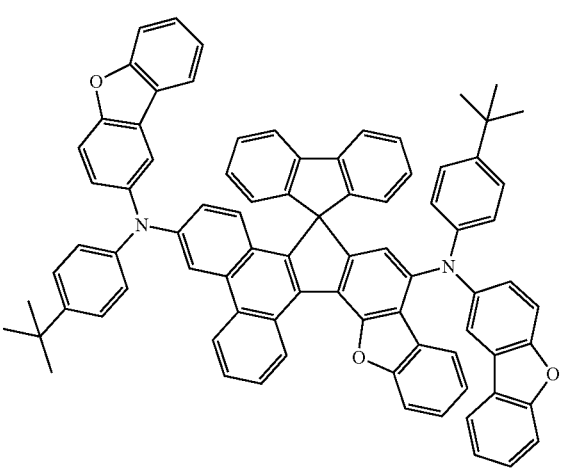
<Compound 437>
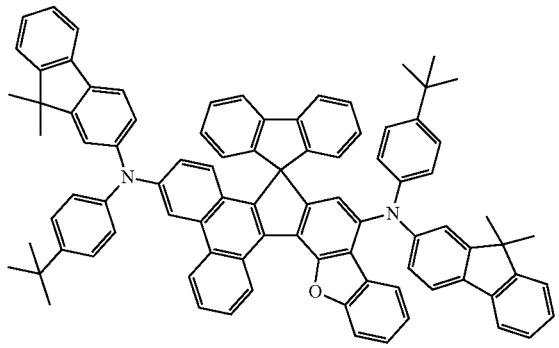
<Compound 438>
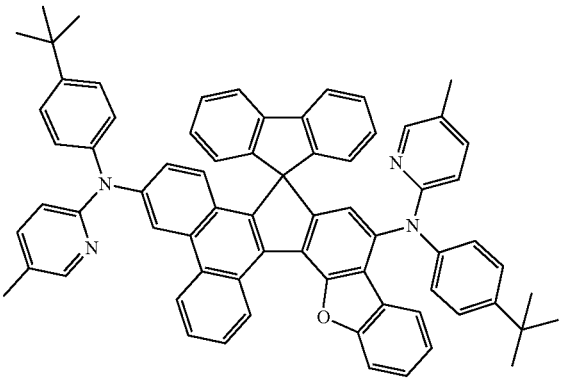
<Compound 439>
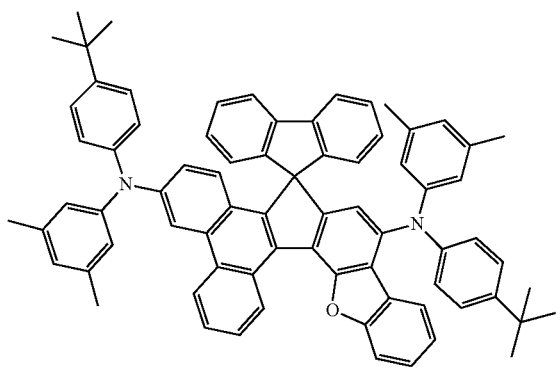
<Compound 440>
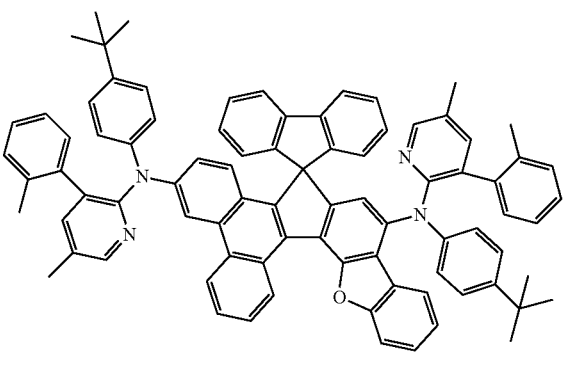

-continued
<Compound 441>
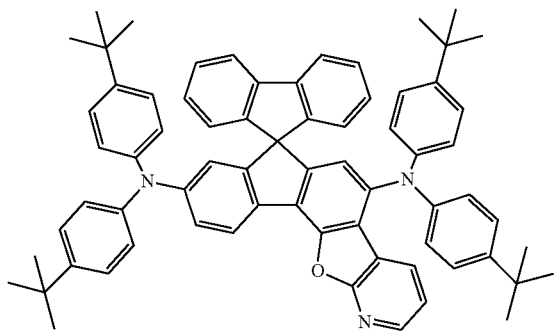
<Compound 442>
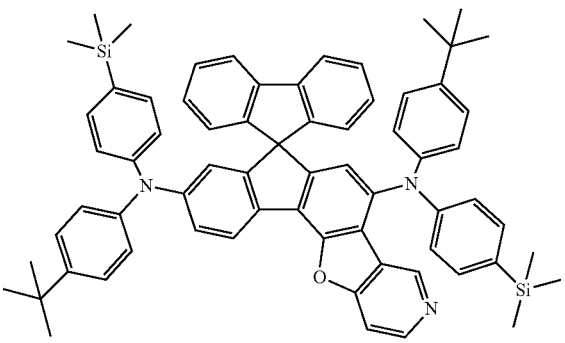
<Compound 443>
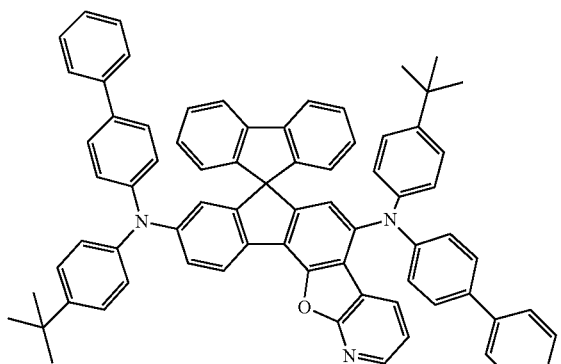
<Compound 444>
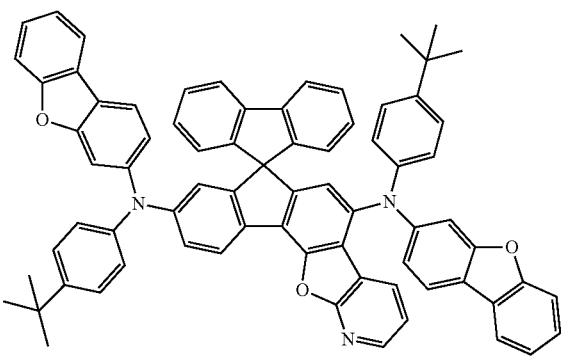
<Compound 445>
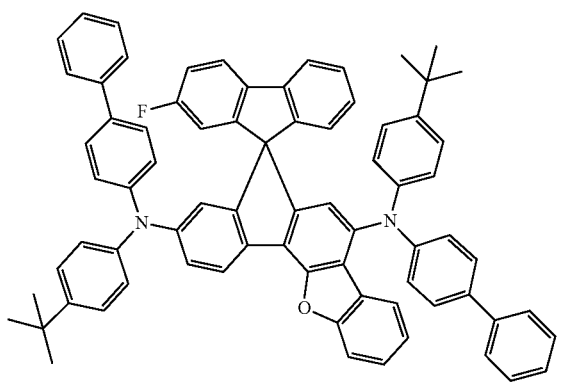
<Compound 446>
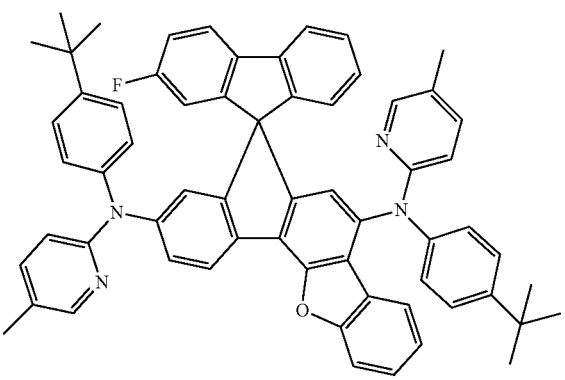
<Compound 447>
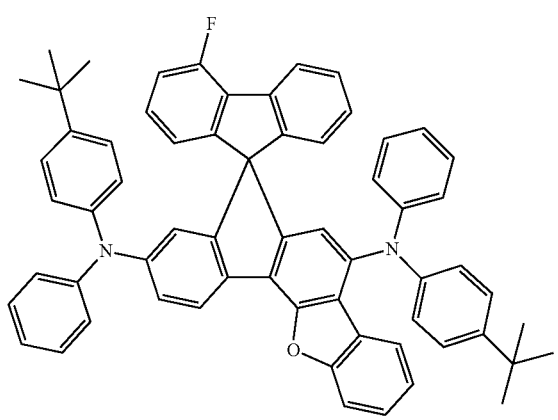
<Compound 448>
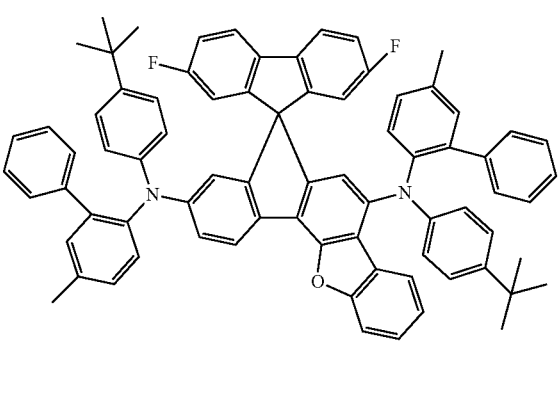

-continued
<Compound 449>
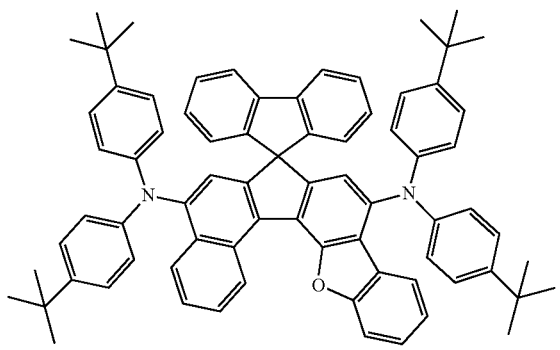
<Compound 450>
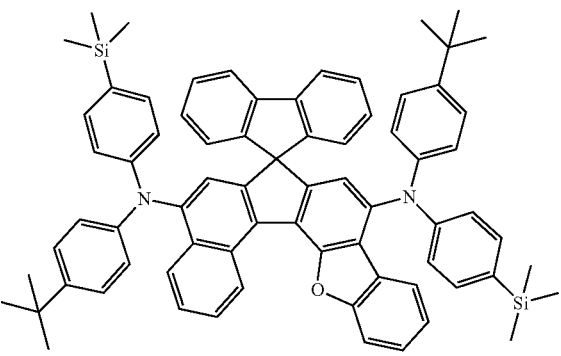
<Compound 451>
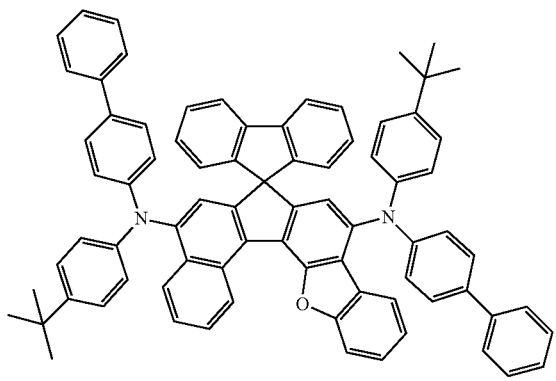
<Compound 452>
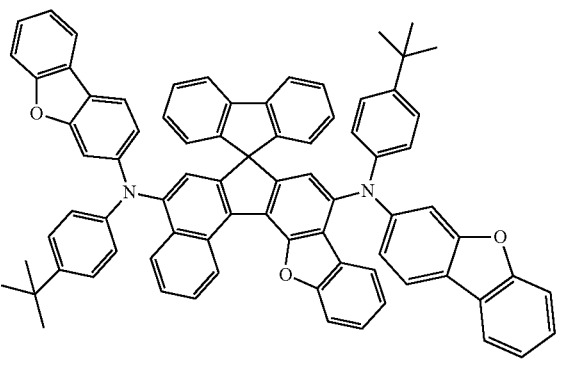
<Compound 453>
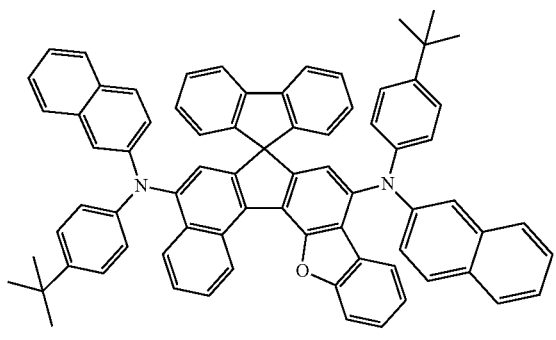
<Compound 454>
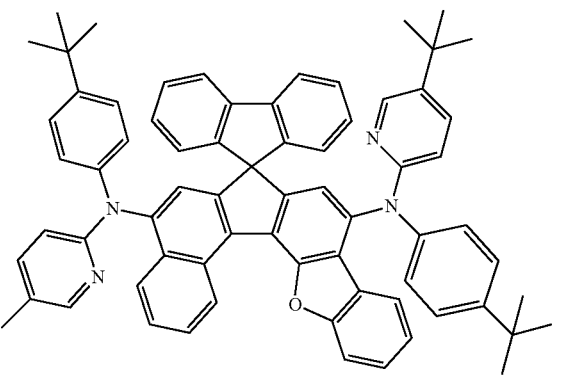
<Compound 455>
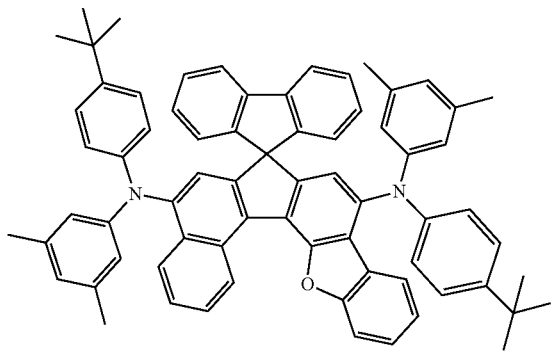
<Compound 456>
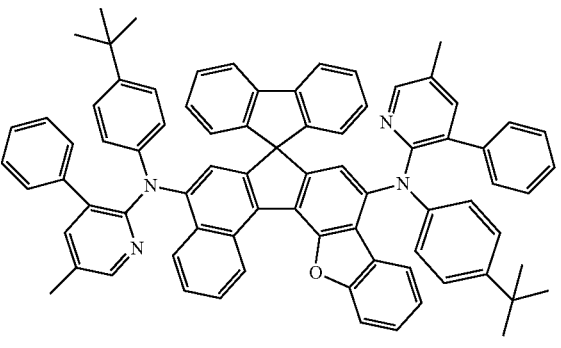

<Compound 457>
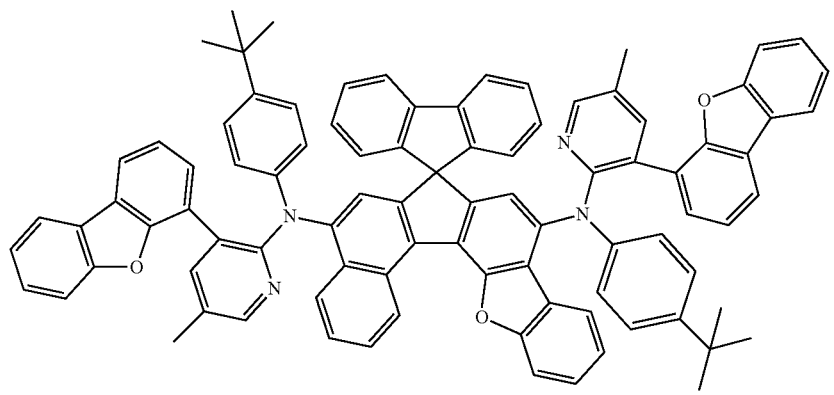
<Compound 458>
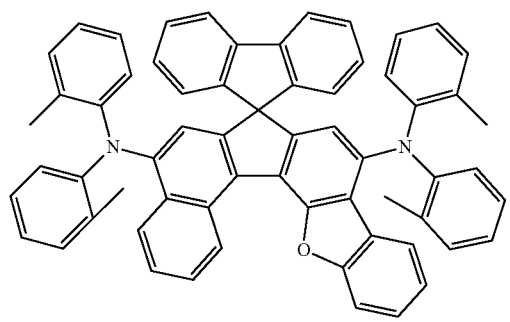
<Compound 459>
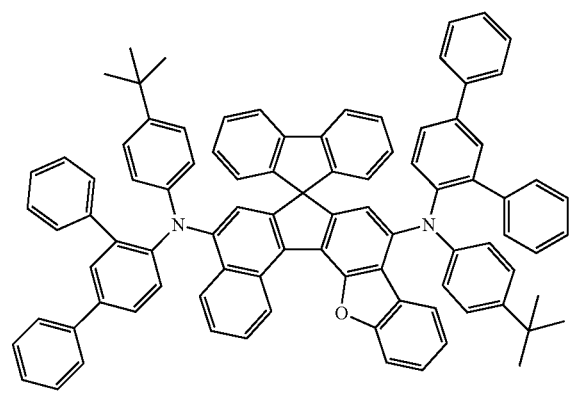
<Compound 460>
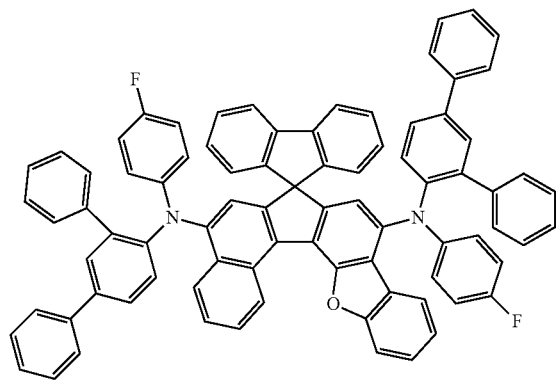
<Compound 461>
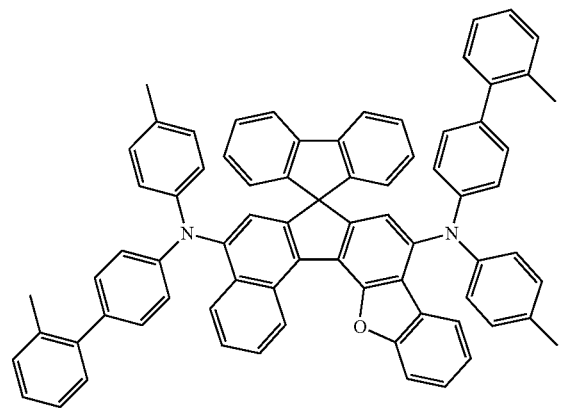

<Compound 462>
<Compound 463>
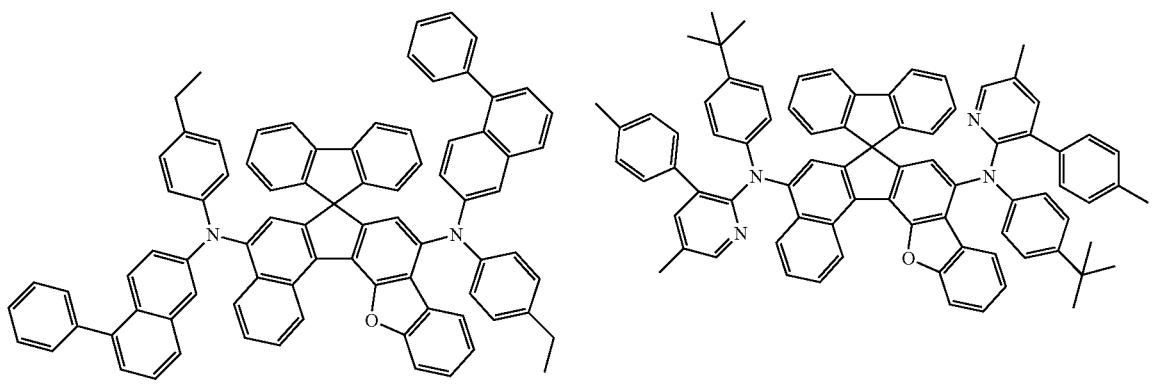
<Compound 464>
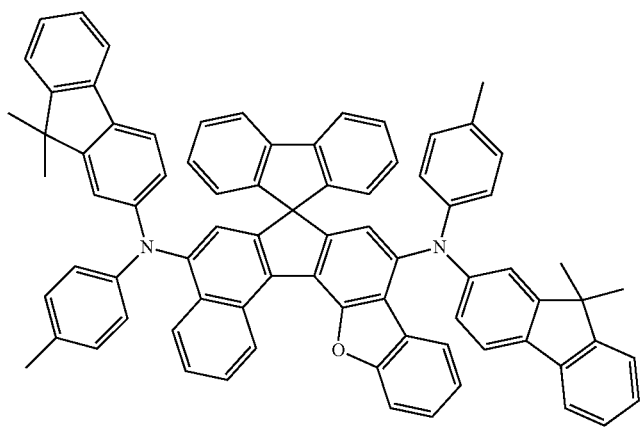
<Compound 465>
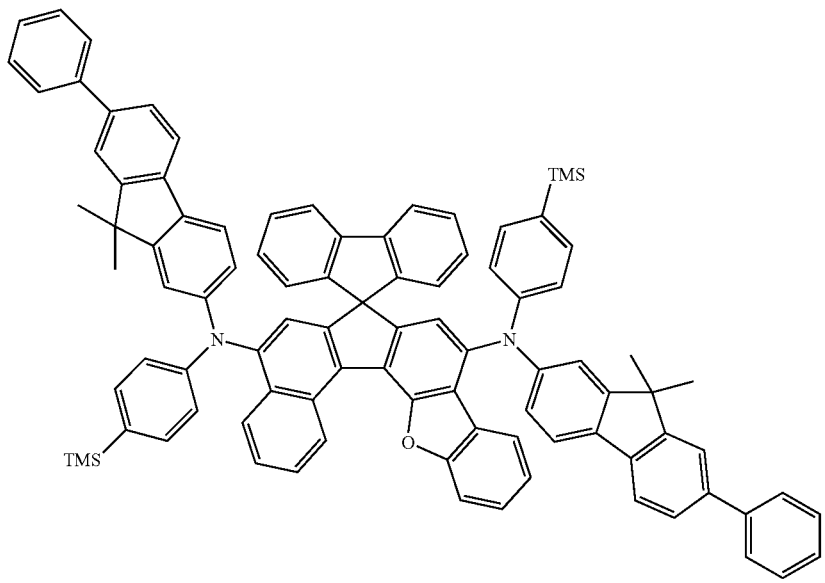

-continued
<Compound 466>
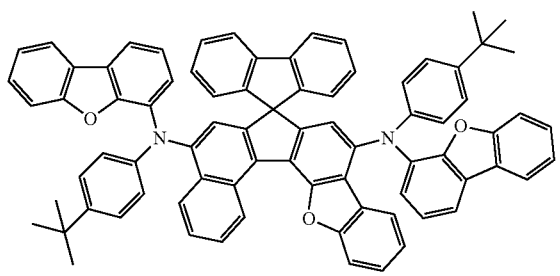
<Compound 467>
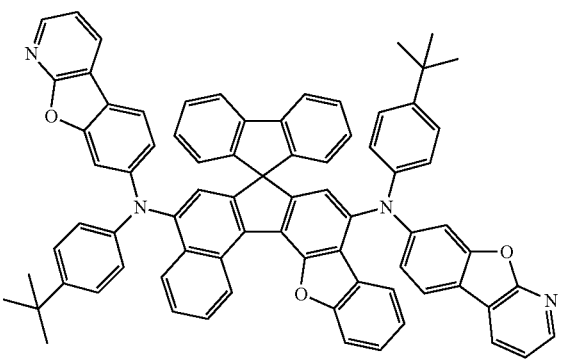
<Compound 468>
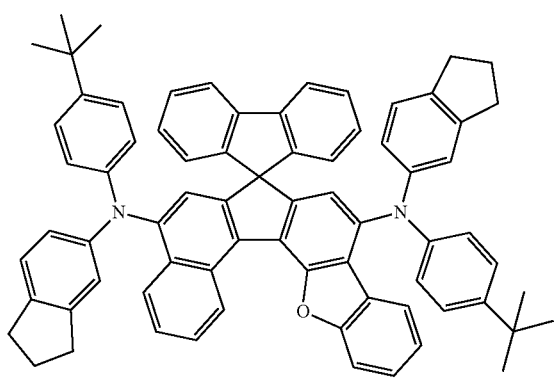
<Compound 469>
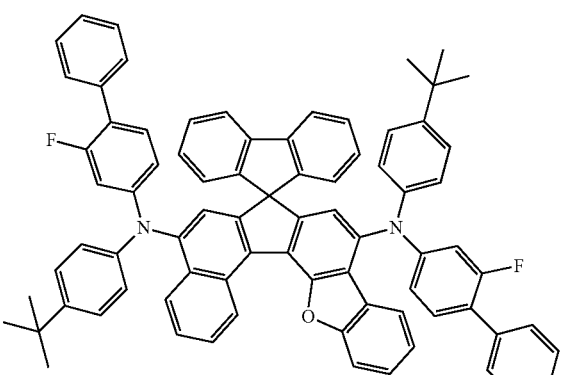
<Compound 470>
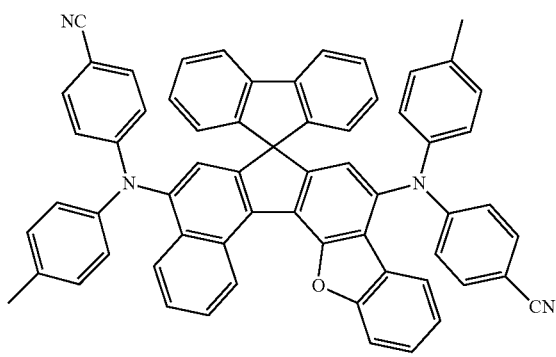
<Compound 471>
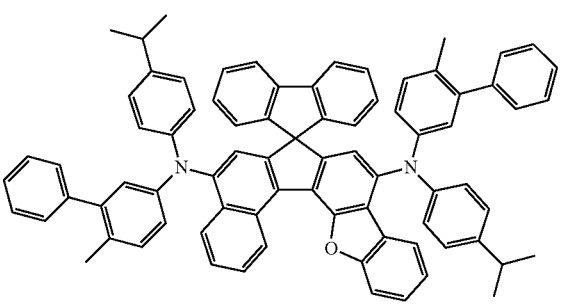
<Compound 472>
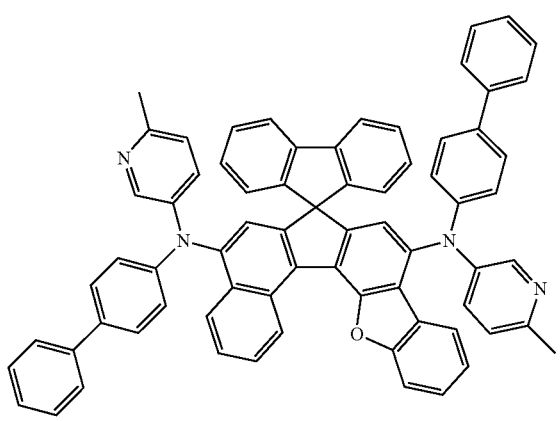
<Compound 473>
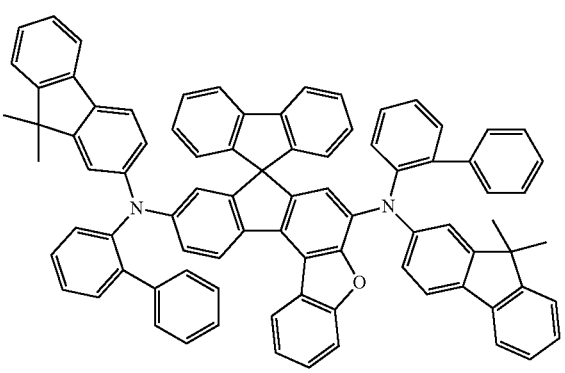

-continued
<Compound 474>
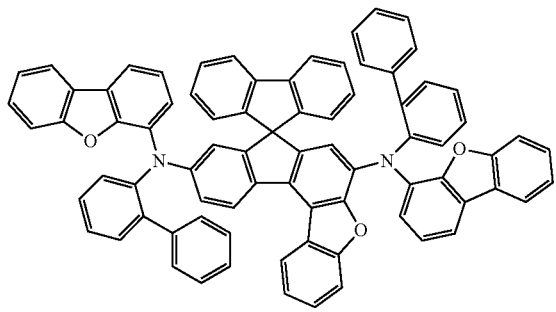
<Compound 475>
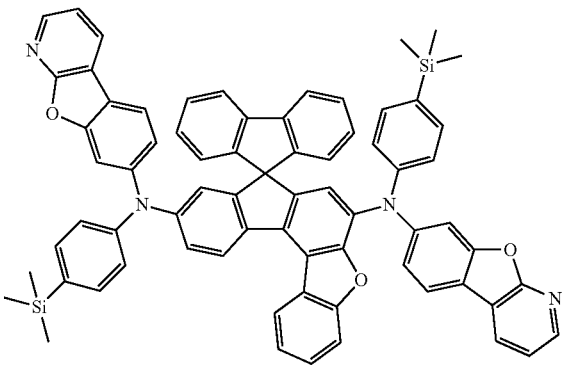
<Compound 476>
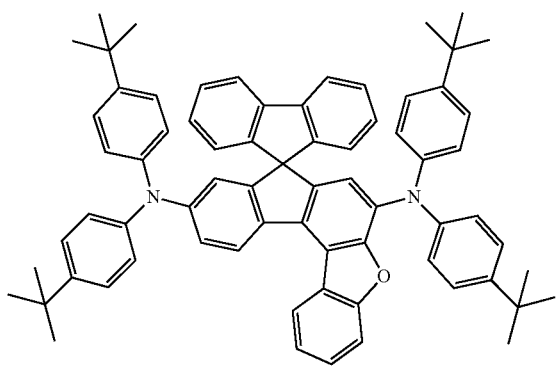
<Compound 477>
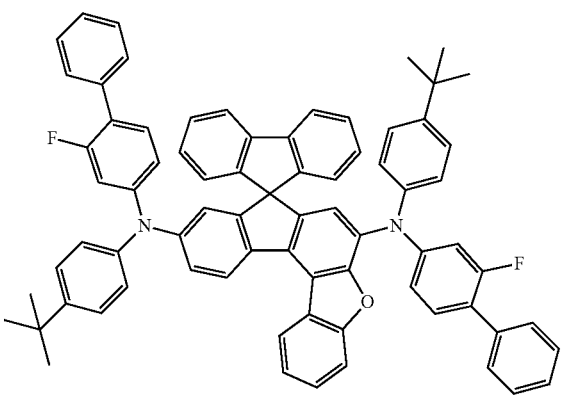
<Compound 478>
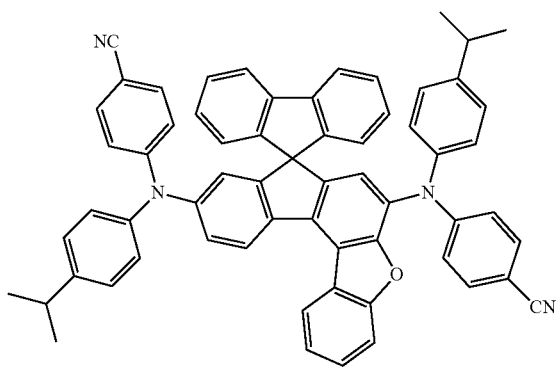
<Compound 479>
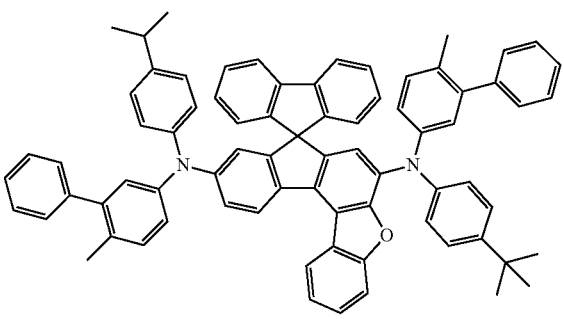
<Compound 480>
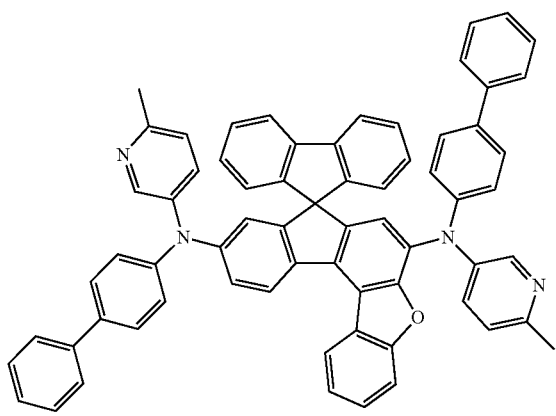
<Compound 481>
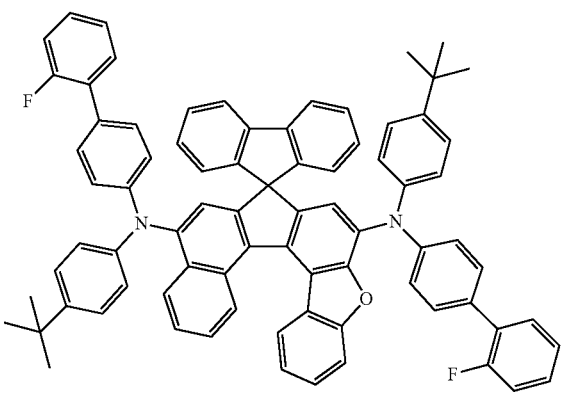

-continued
<Compound 482>
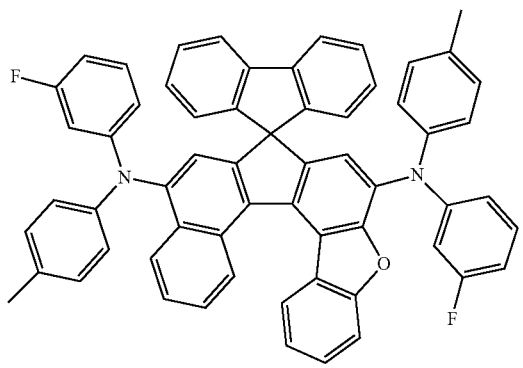
<Compound 483>
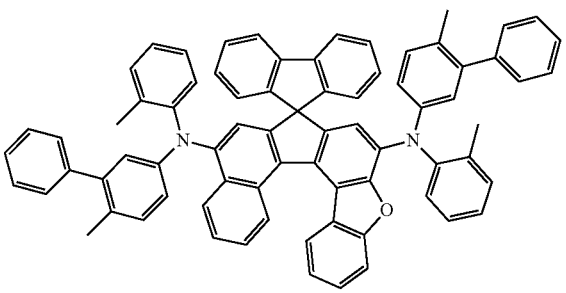
<Compound 484>
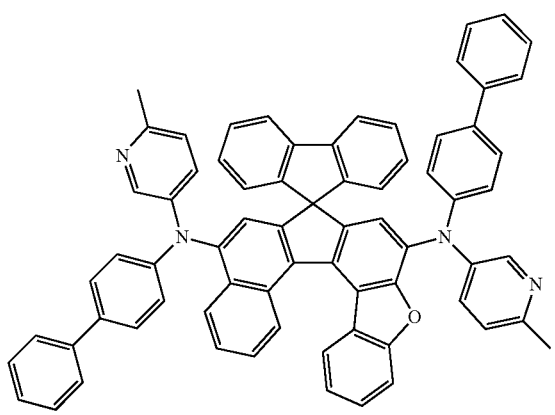
<Compound 485>
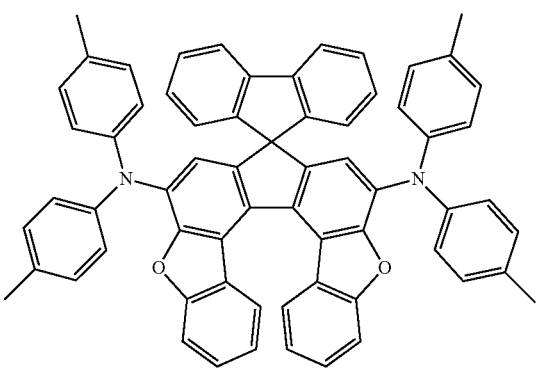
<Compound 486>
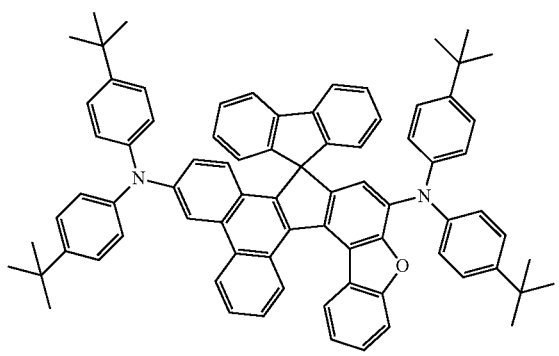
<Compound 487>
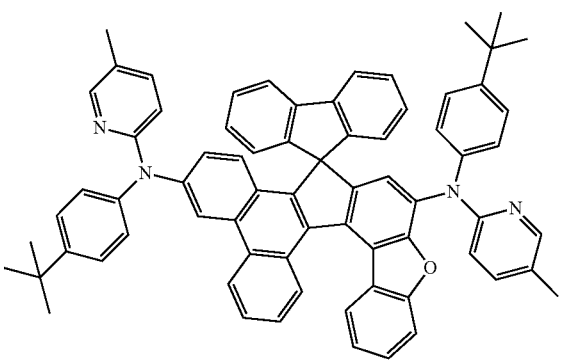
<Compound 488>
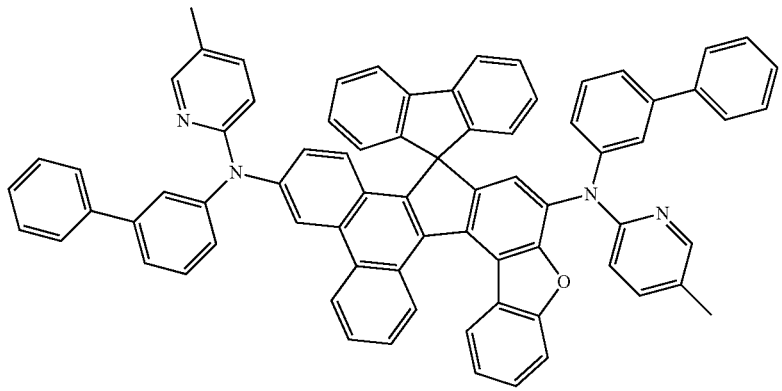

-continued
<Compound 489>
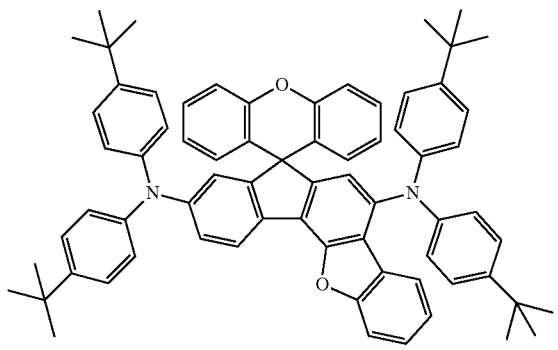
<Compound 490>
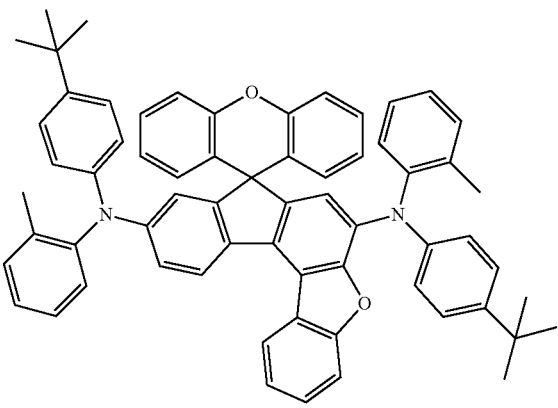
<Compound 491>
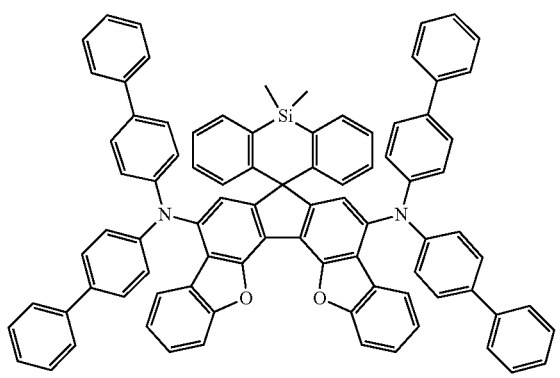
<Compound 492>
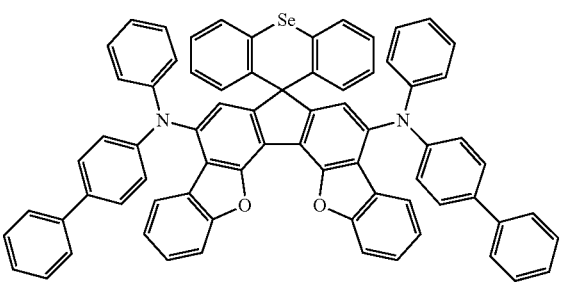
<Compound 493>
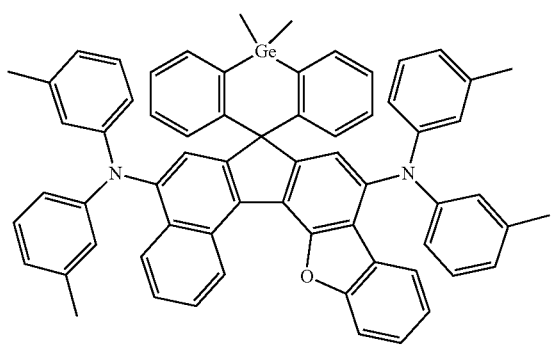
<Compound 494>
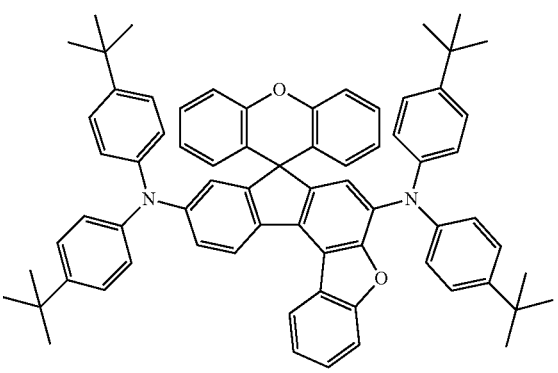
<Compound 495>
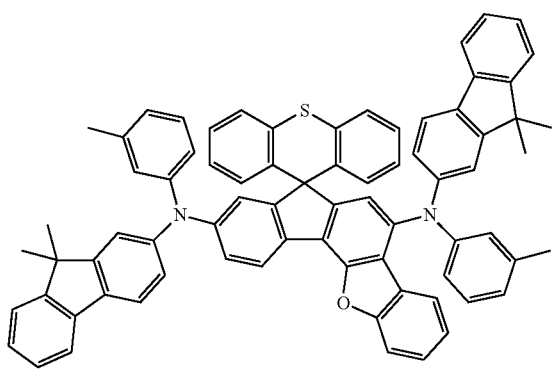
<Compound 496>
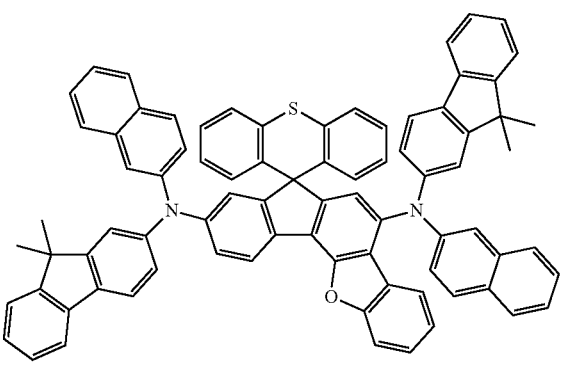

-continued
<Compound 497>
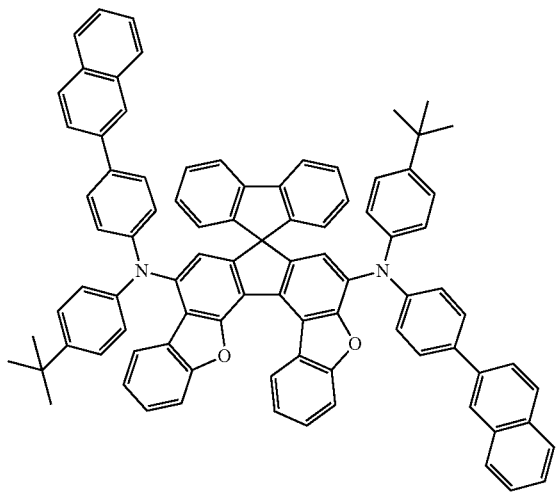
<Compound 498>
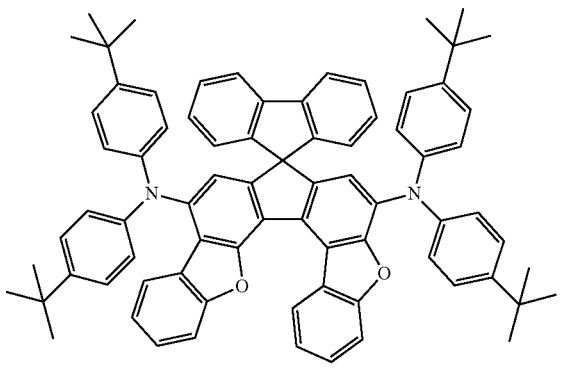
<Compound 499>
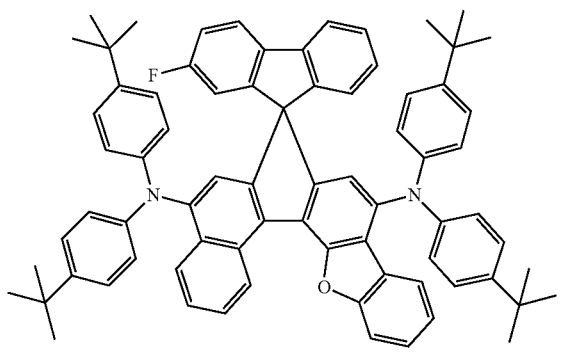
<Compound 500>
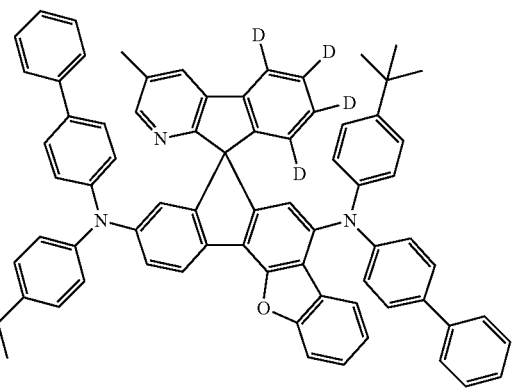
<Compound 501>
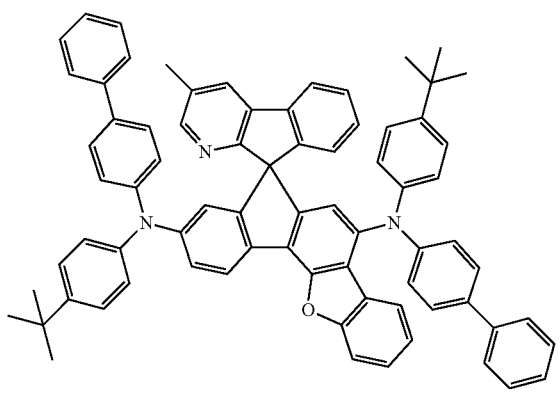
<Compound 502>
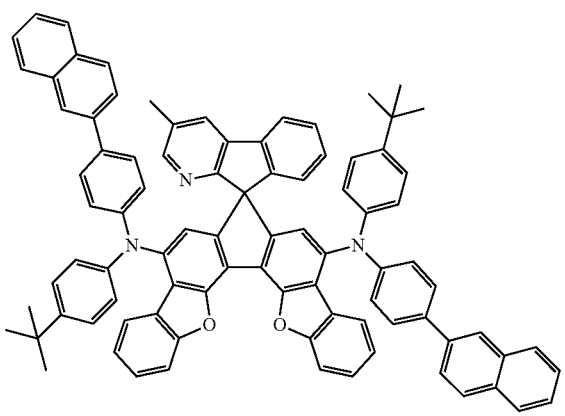

-continued
<Compound 503>
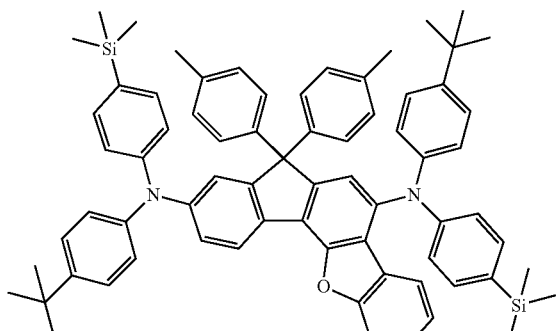
<Compound 504>
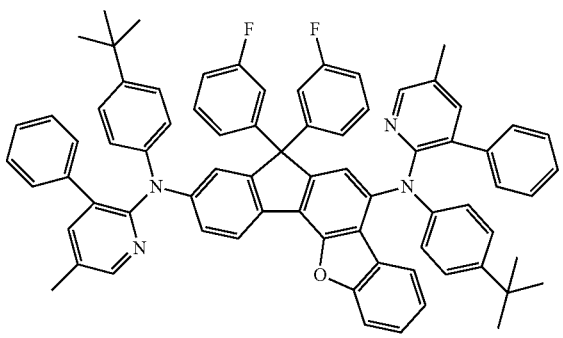
<Compound 505>
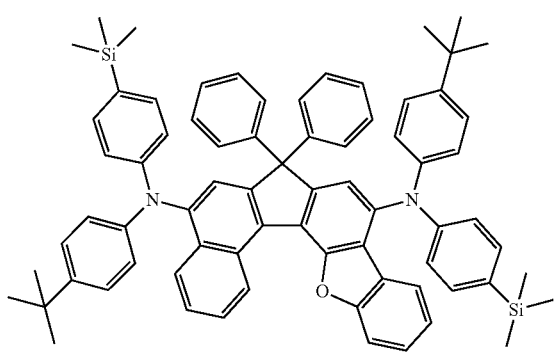
<Compound 506>
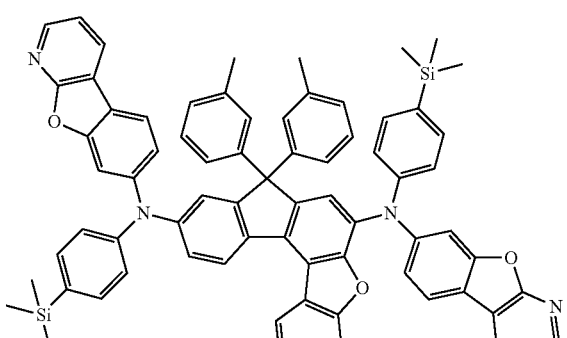
<Compound 507>
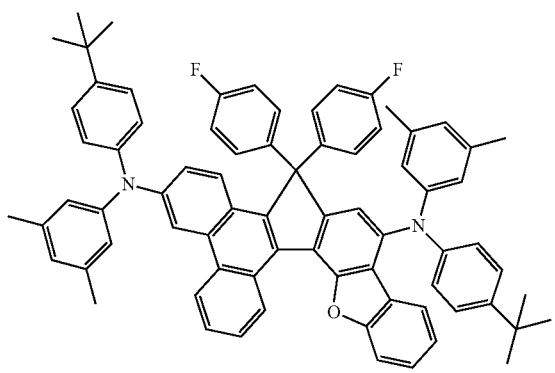
<Compound 508>
<Compound 509>
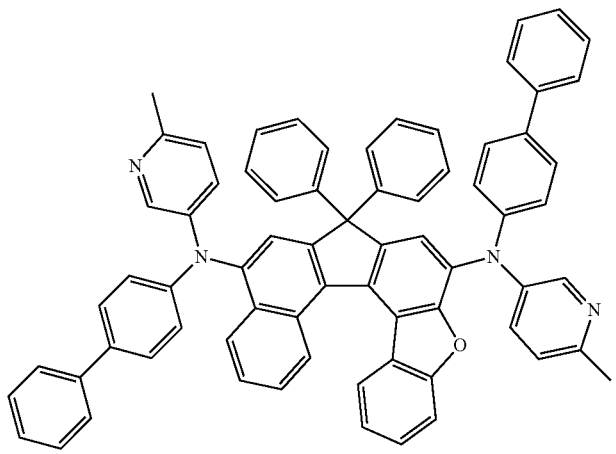

-continued
<Compound 510>
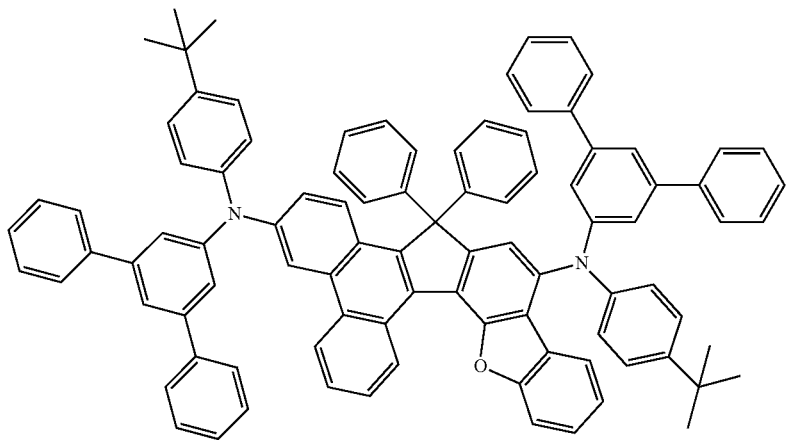
<Compound 511>
<Compound 512>
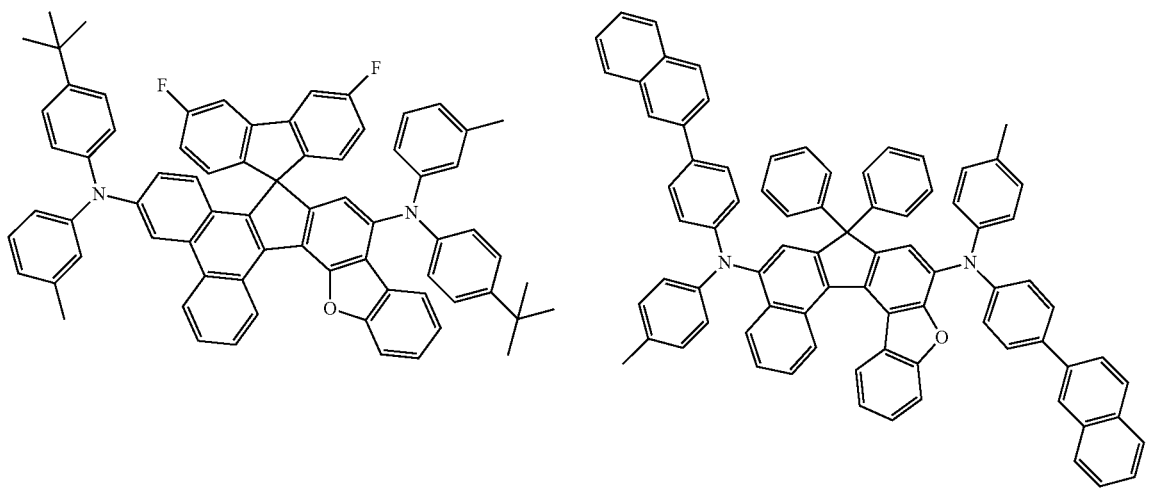
<Compound 513>
<Compound 514>
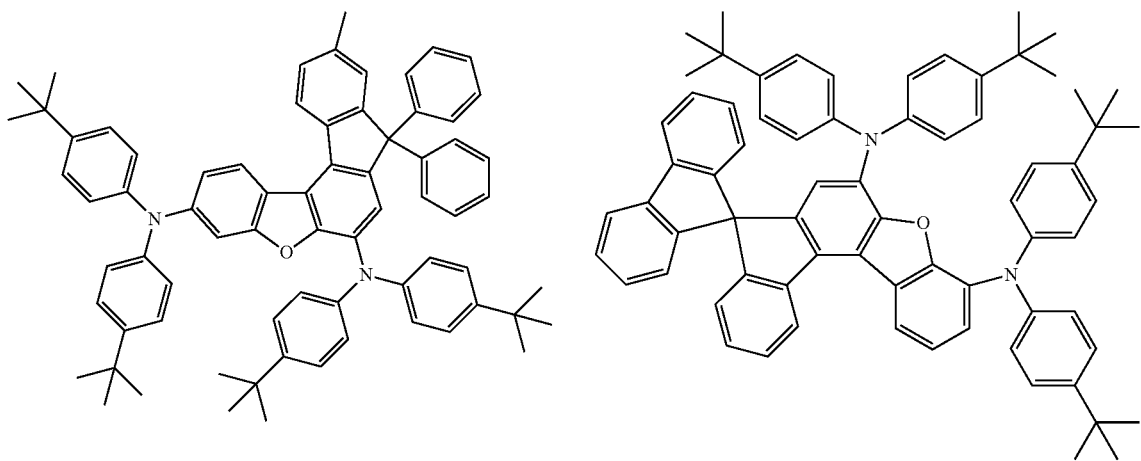

-continued
<Compound 515>
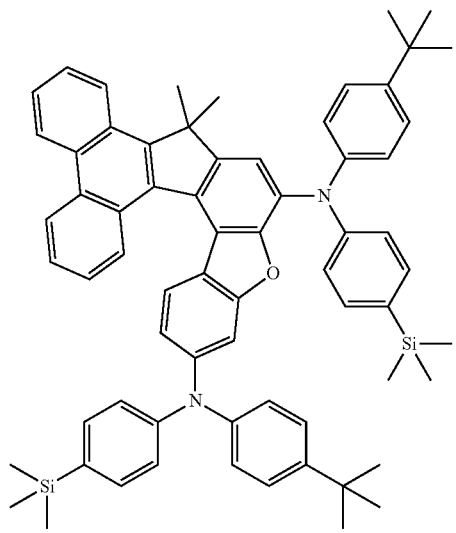
<Compound 516>
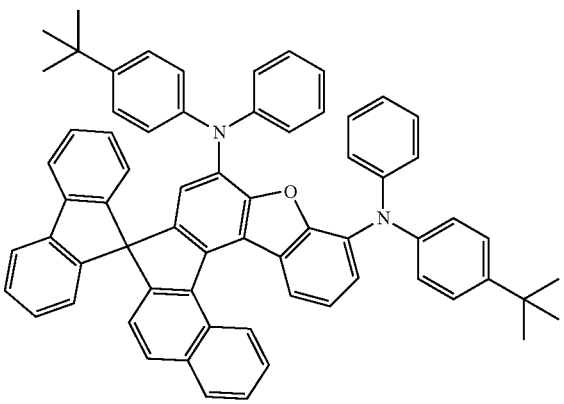
<Compound 517>
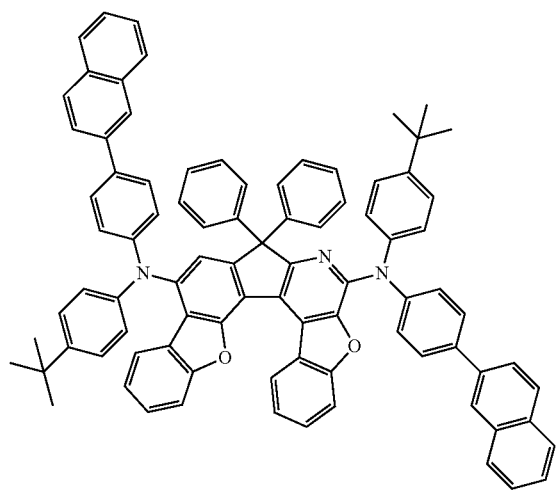
<Compound 518>
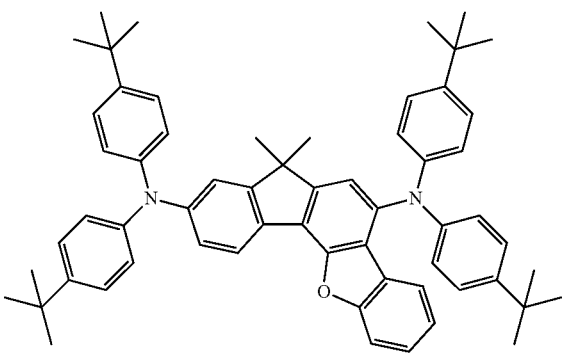
<Compound 519>
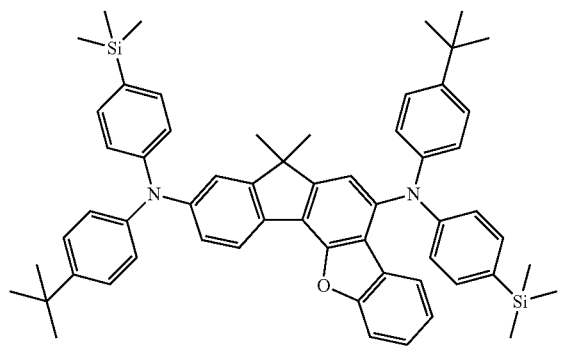
<Compound 520>
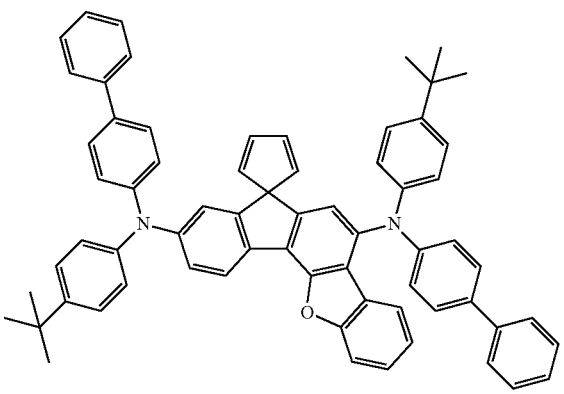

-continued
<Compound 521>
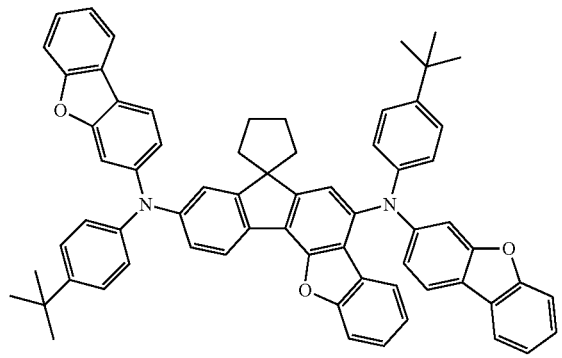
<Compound 522>
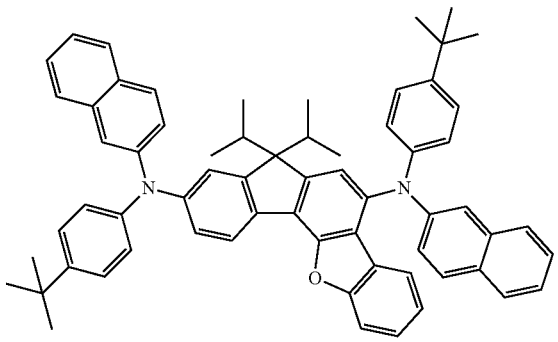
<Compound 523>
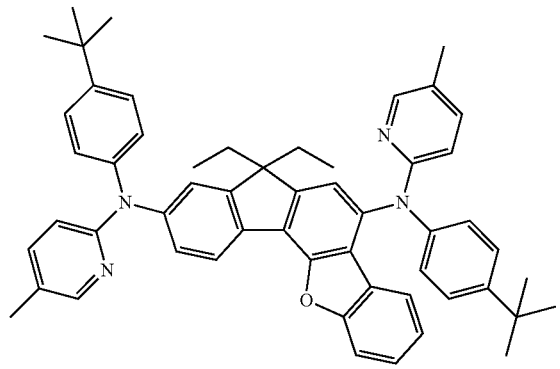
<Compound 524>
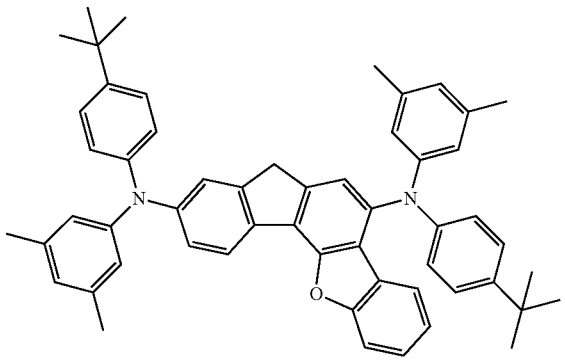
<Compound 525>
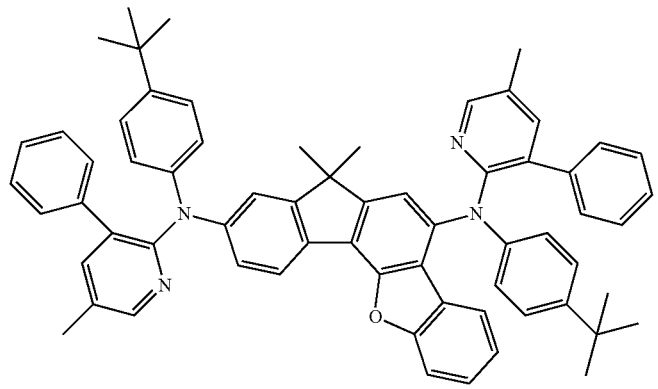
<Compound 526>
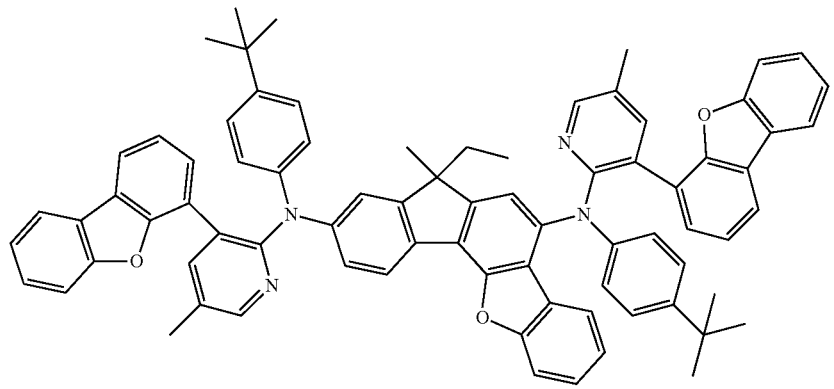

-continued
<Compound 527>
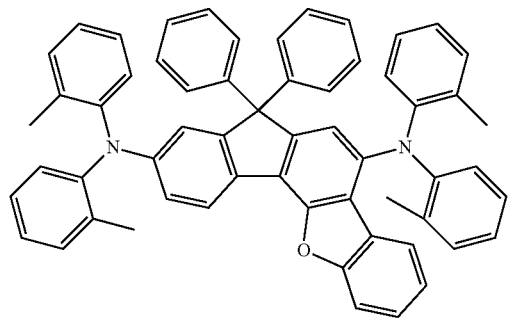
<Compound 528>
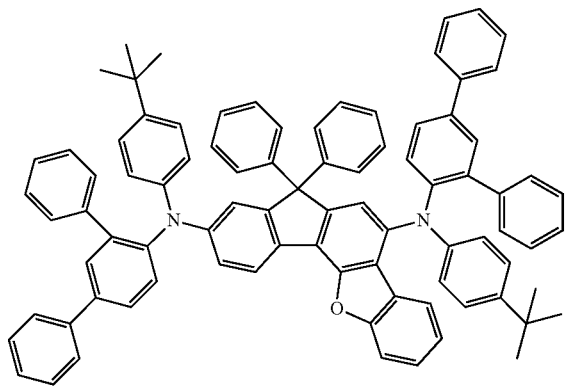
<Compound 529>
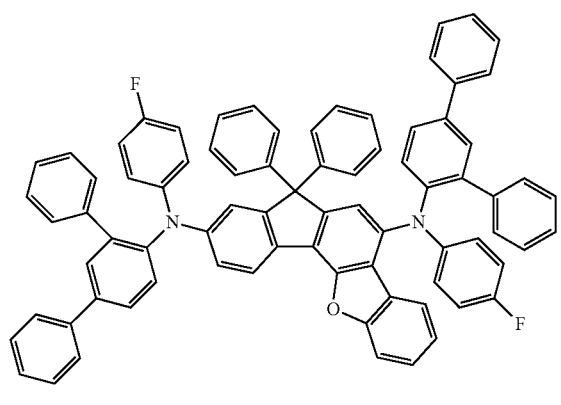
<Compound 530>
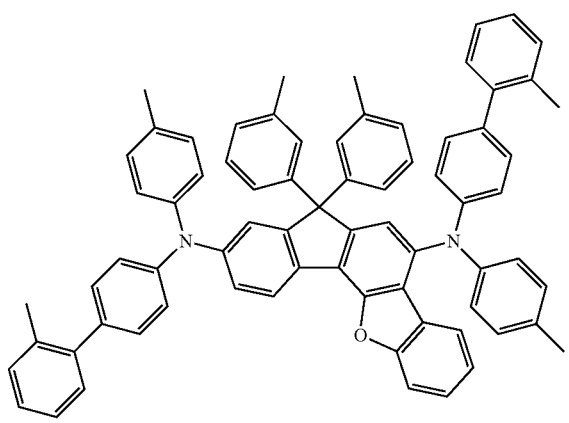
<Compound 531>
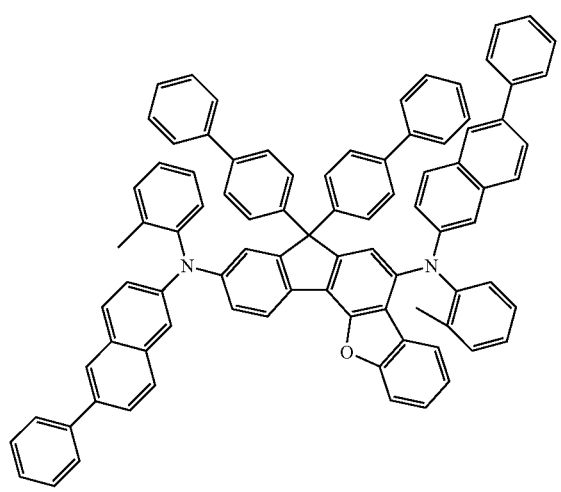
<Compound 532>
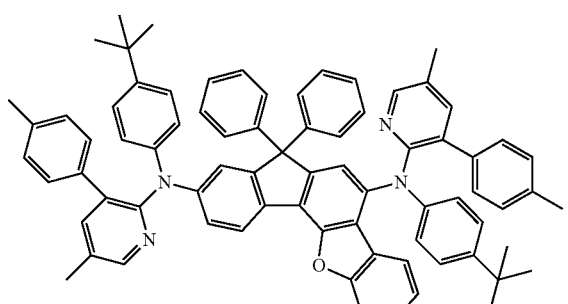

-continued
<Compound 533>
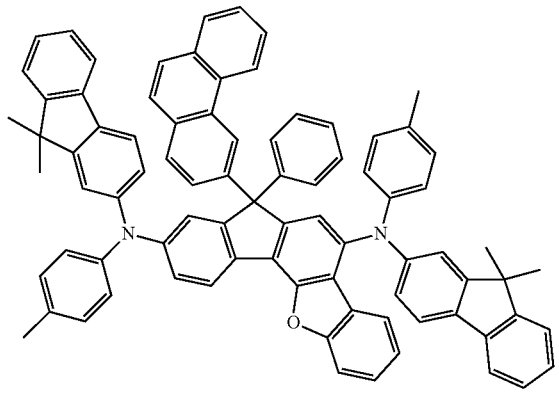
<Compound 534>
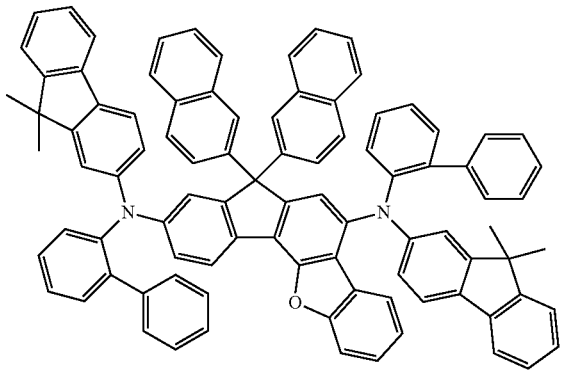
<Compound 535>
<Compound 536>
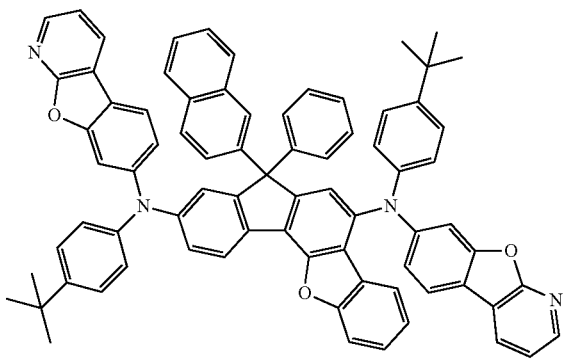
<Compound 537>
<Compound 538>
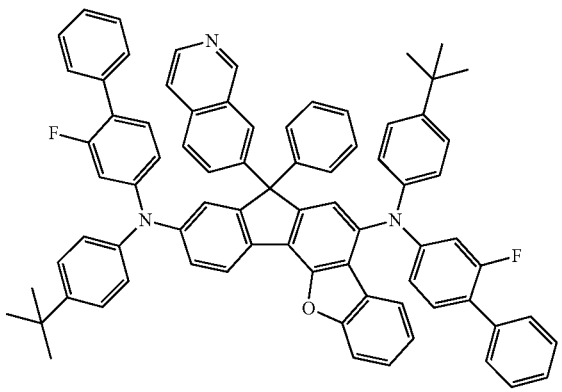
<Compound 539>
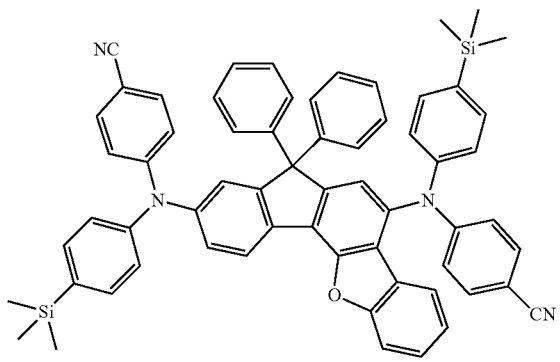
<Compound 540>
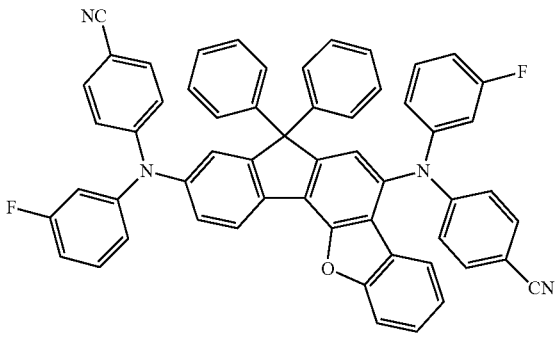

-continued
<Compound 541>
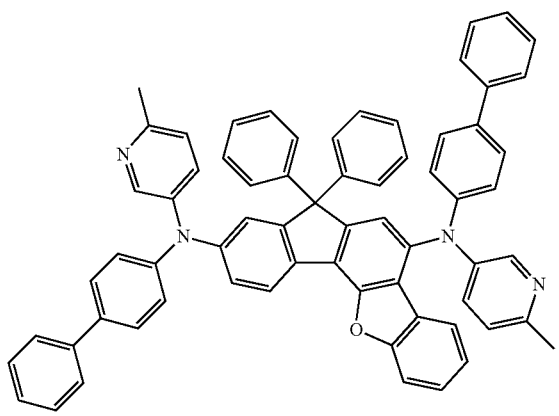
<Compound 542>
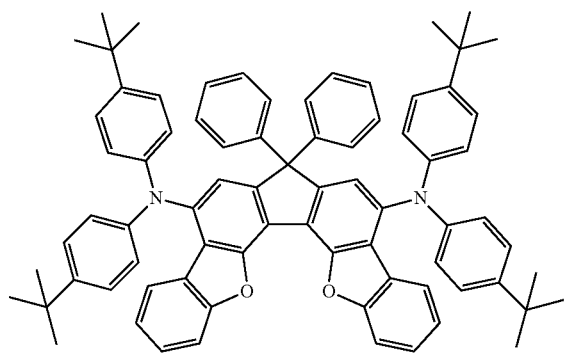
<Compound 543>
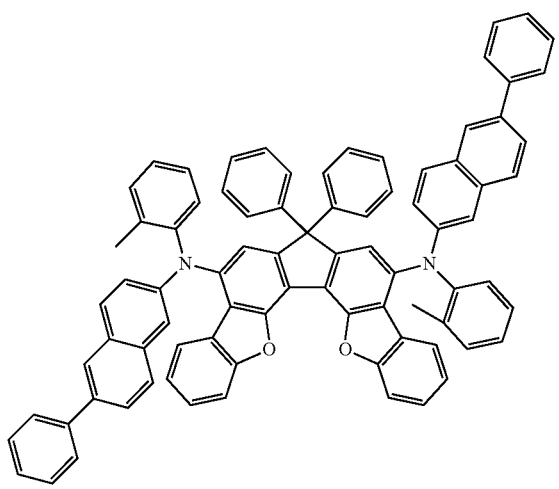
<Compound 544>
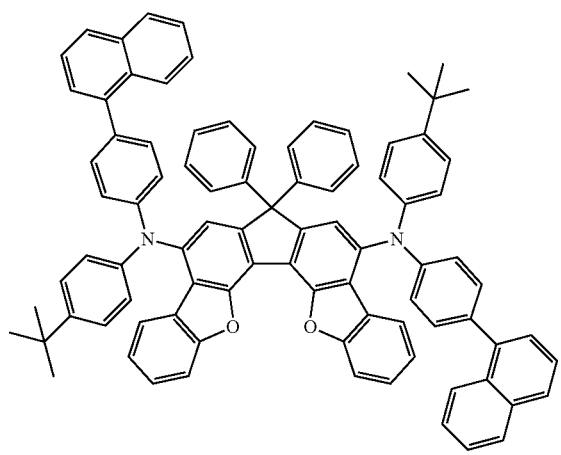
<Compound 545>
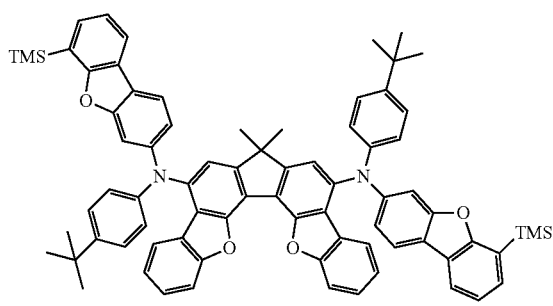
<Compound 546>
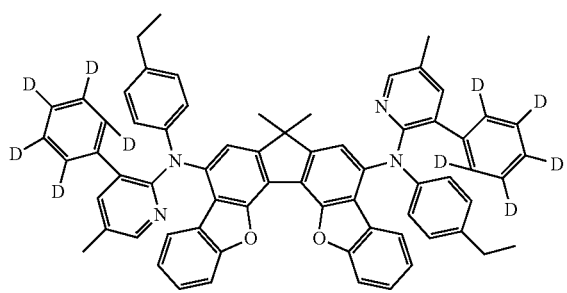
<Compound 547>
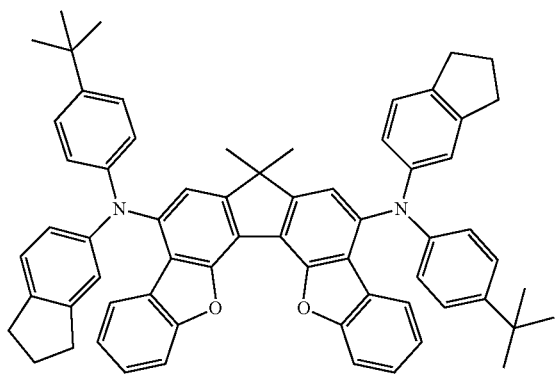
<Compound 548>
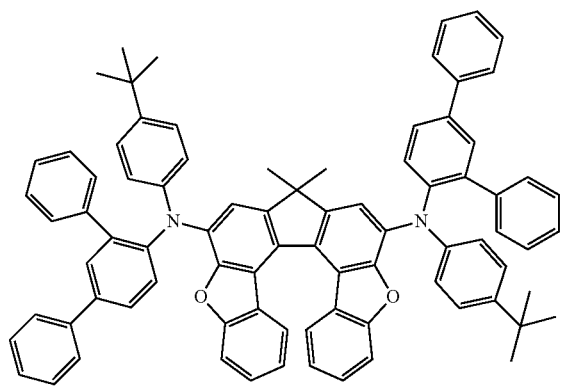

<Compound 549>
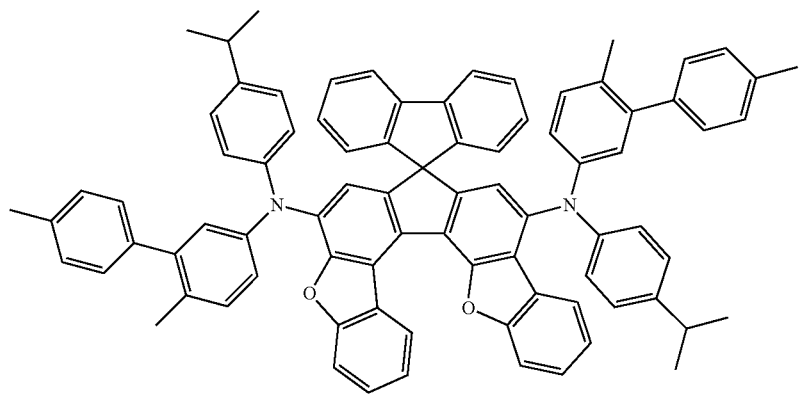
<Compound 550>
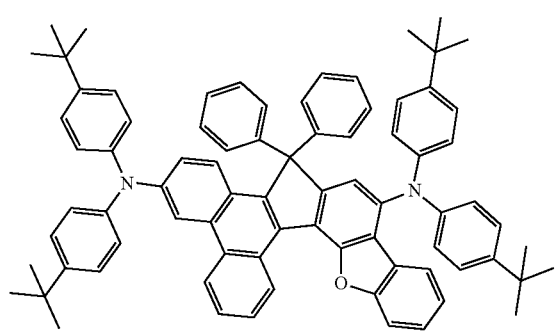
<Compound 551>
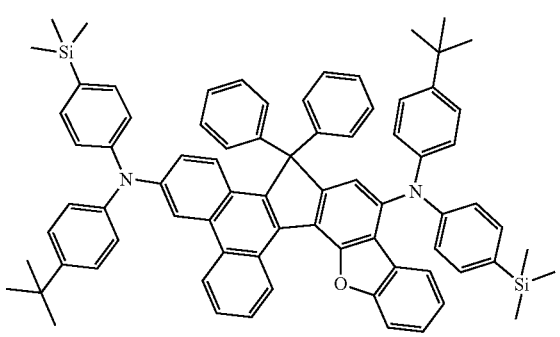
<Compound 552>
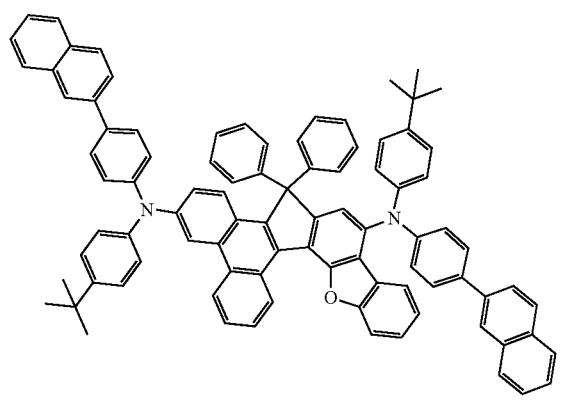
<Compound 553>
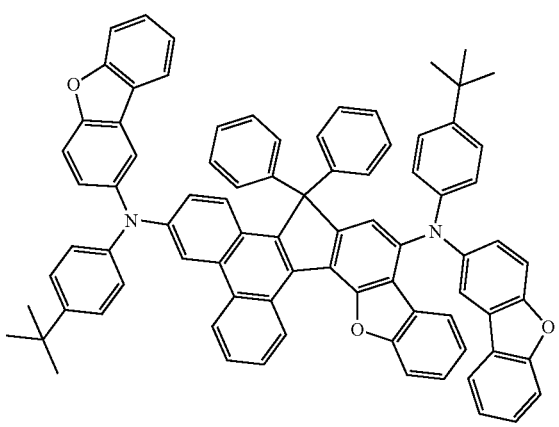
<Compound 554>
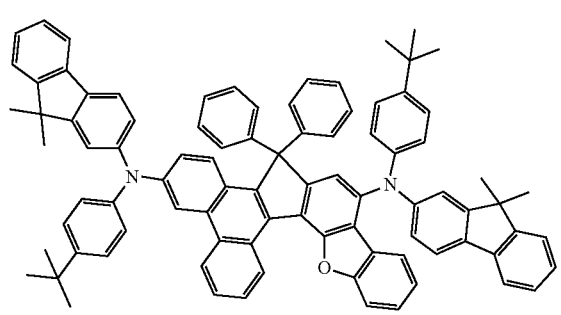
<Compound 555>
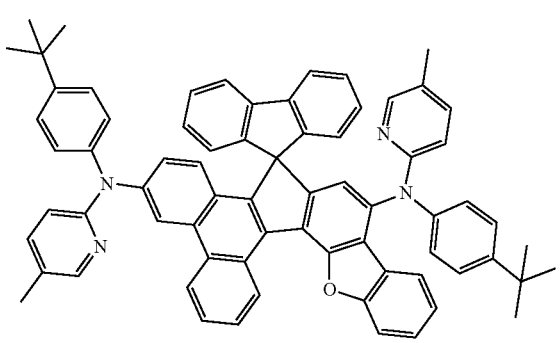

-continued
<Compound 556>
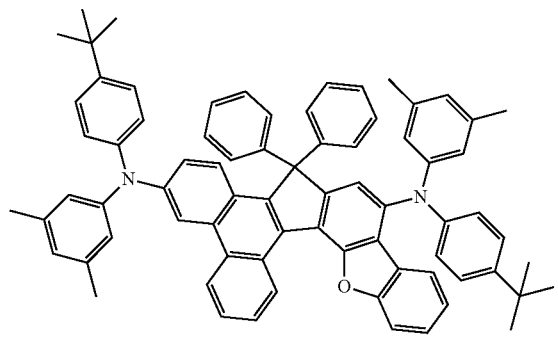
<Compound 557>
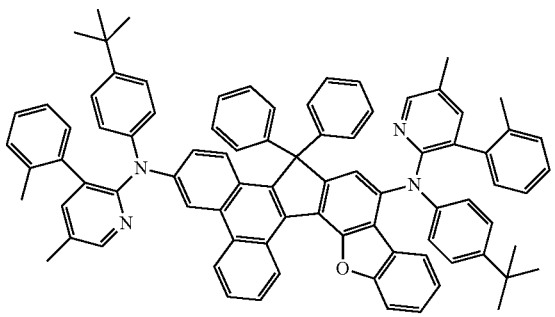
<Compound 558>
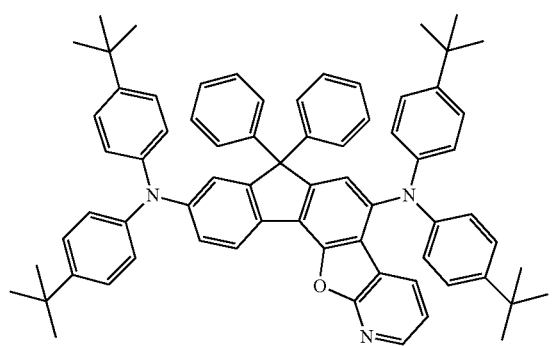
<Compound 559>
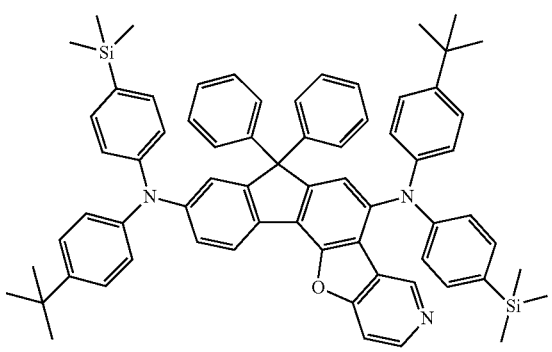
<Compound 560>
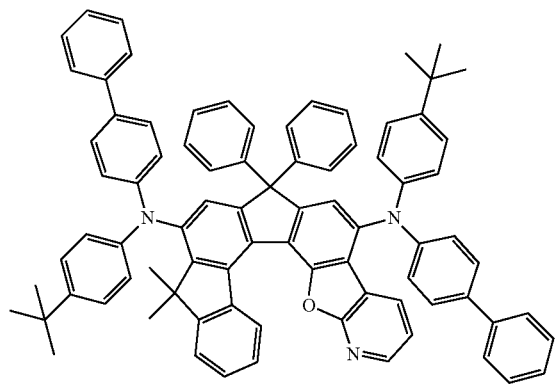
<Compound 561>
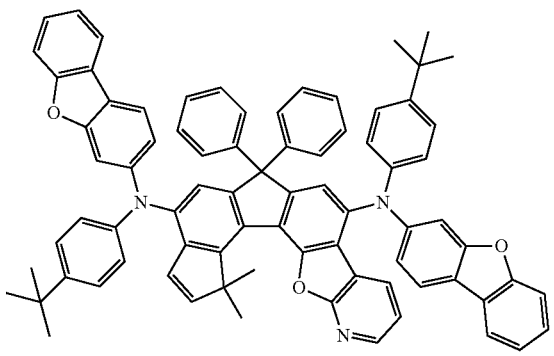
<Compound 562>
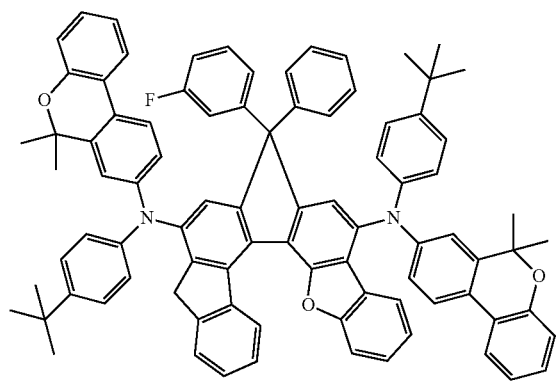
<Compound 563>
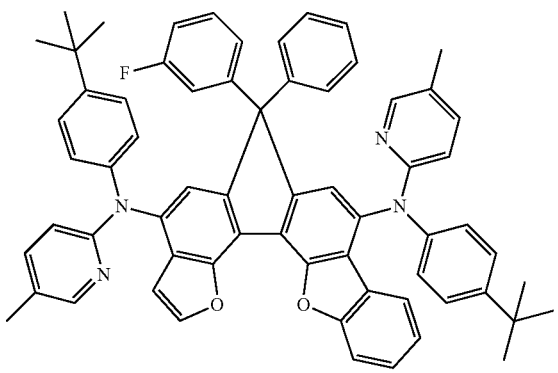

-continued
<Compound 564>
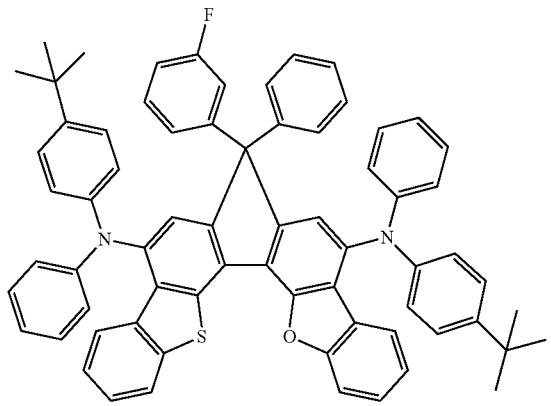
<Compound 565>
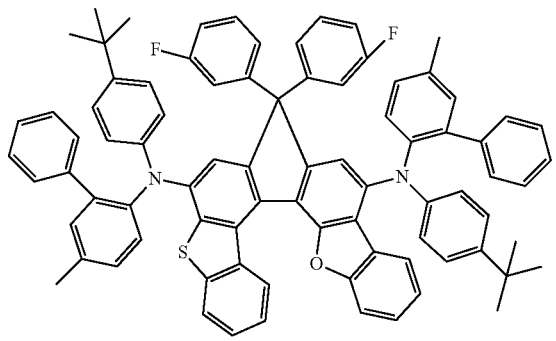
<Compound 566>
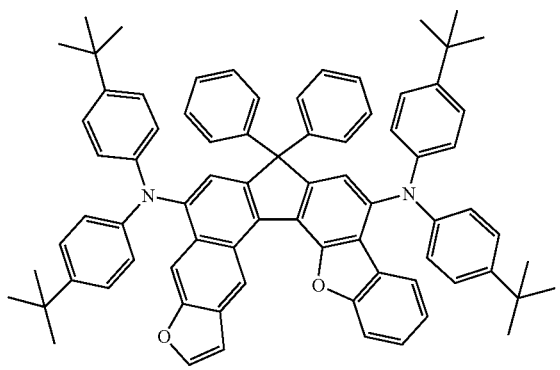
<Compound 567>
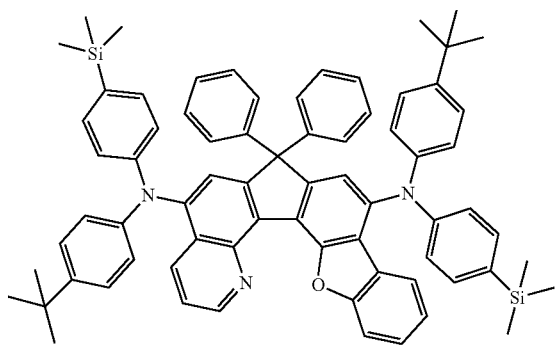
<Compound 568>
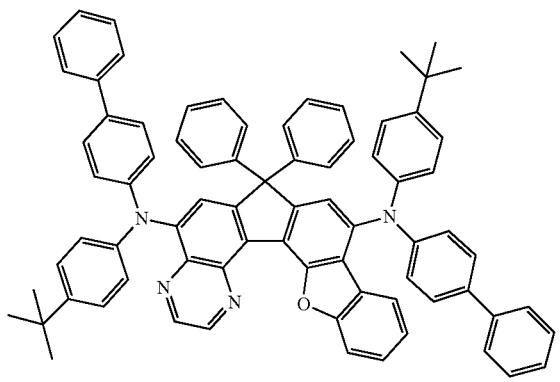
<Compound 569>
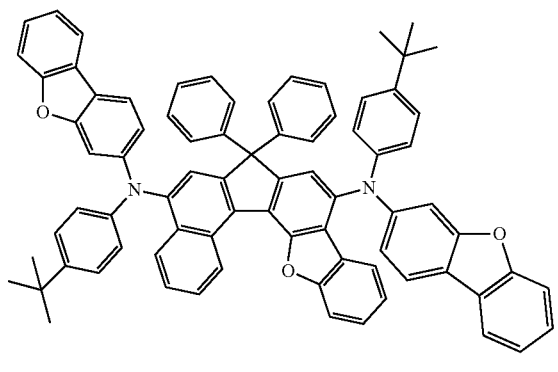
<Compound 570>
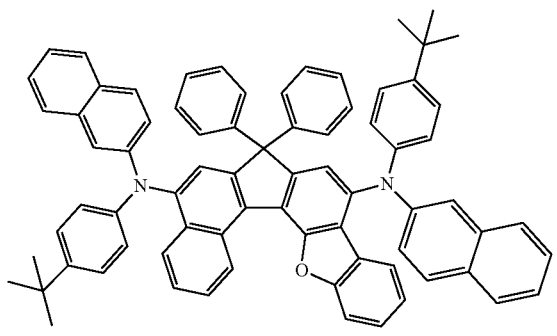
<Compound 571>
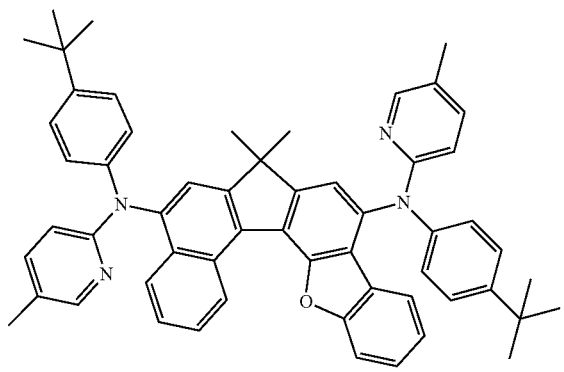

<Compound 572>
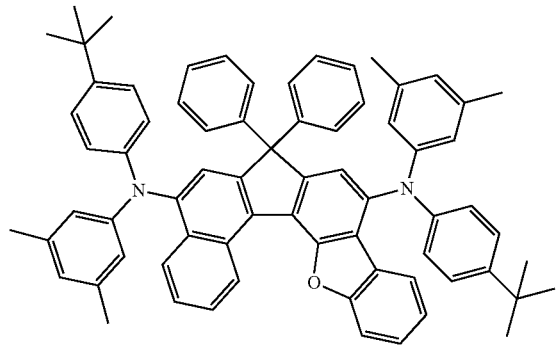
<Compound 573>
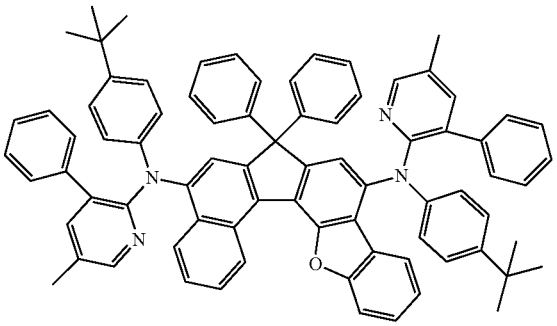
<Compound 574>
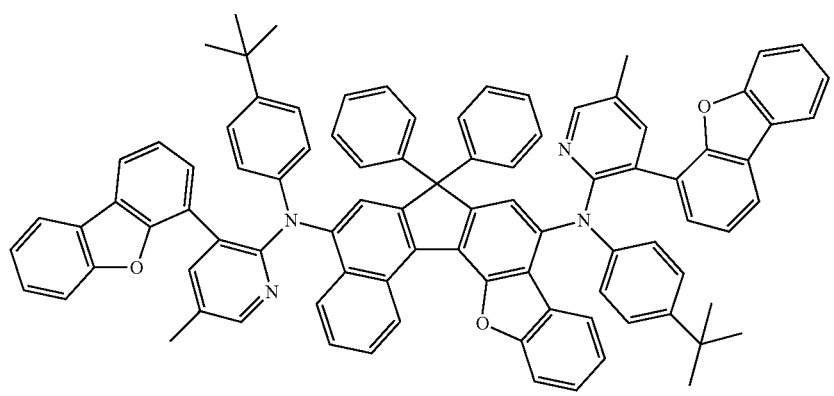
<Compound 575>
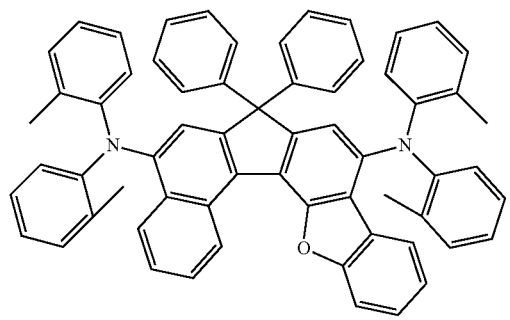
<Compound 576>
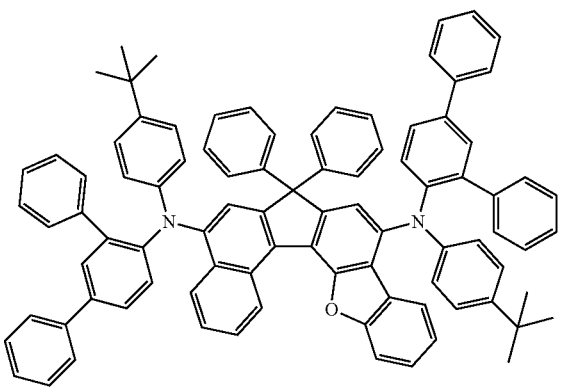
<Compound 577>
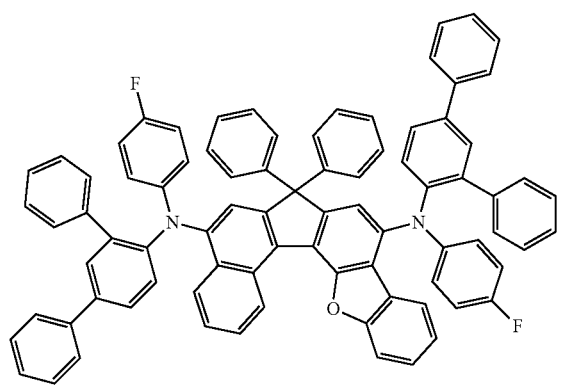
<Compound 578>
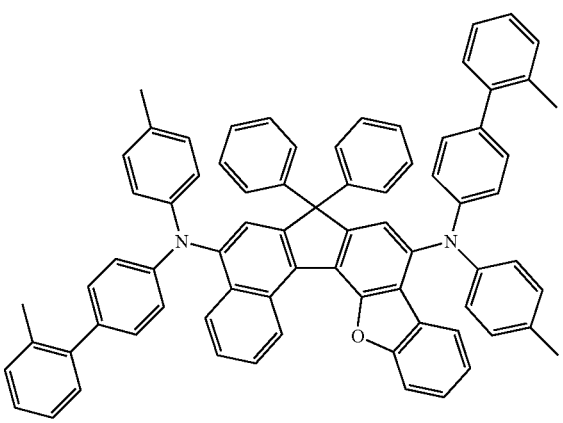

<Compound 579>
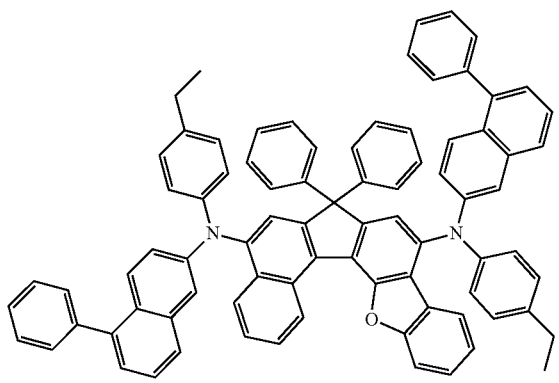
<Compound 580>
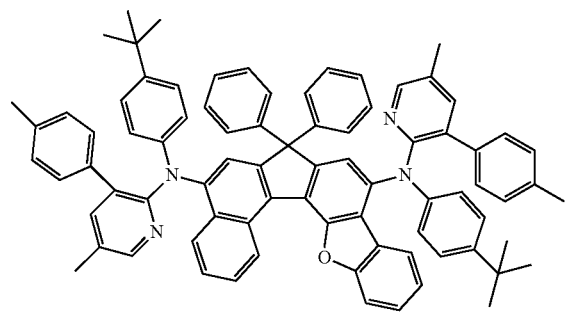
<Compound 581>
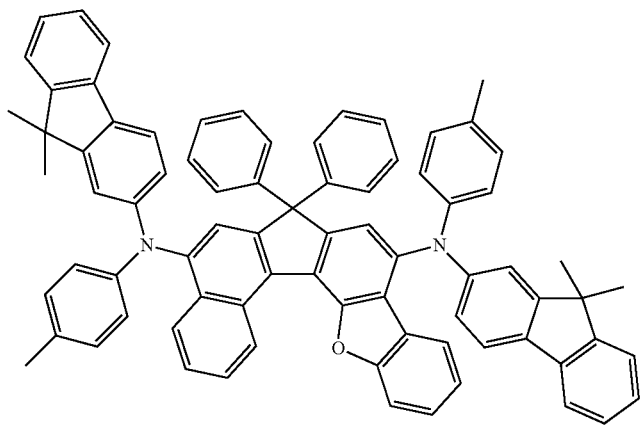
<Compound 582>
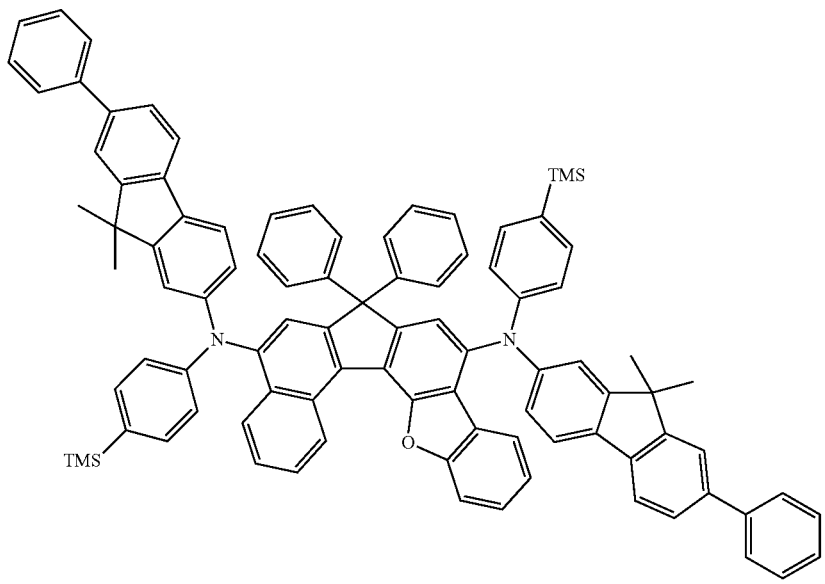

-continued
<Compound 583>
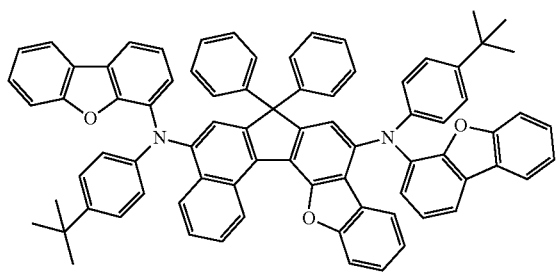
<Compound 584>
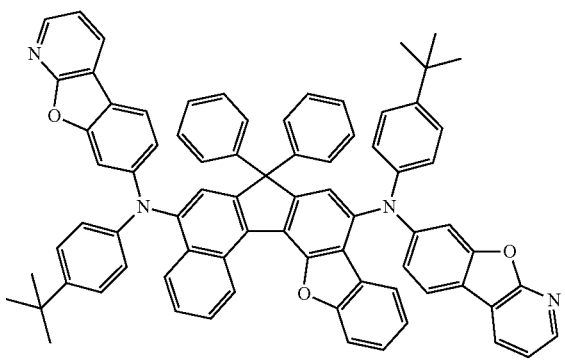
<Compound 585>
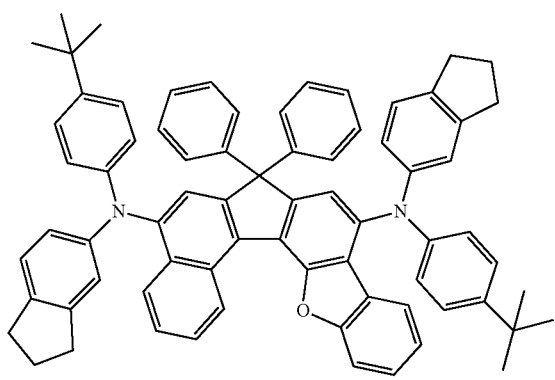
<Compound 586>
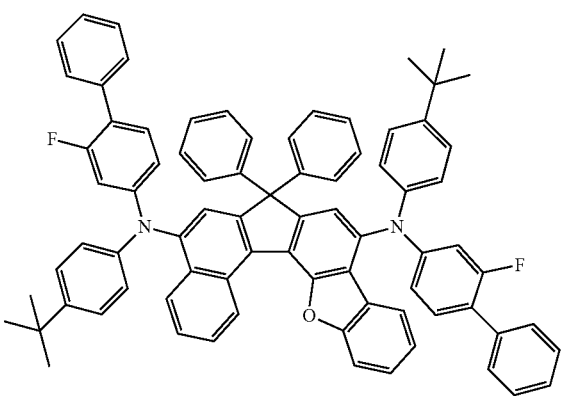
<Compound 587>
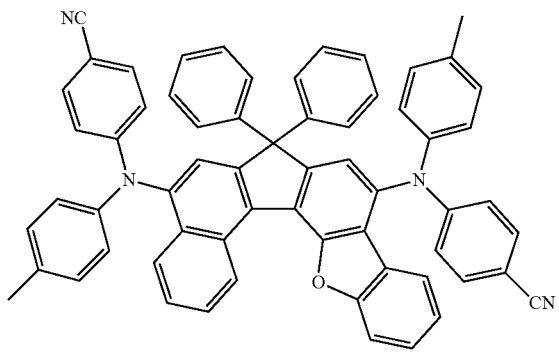
<Compound 588>
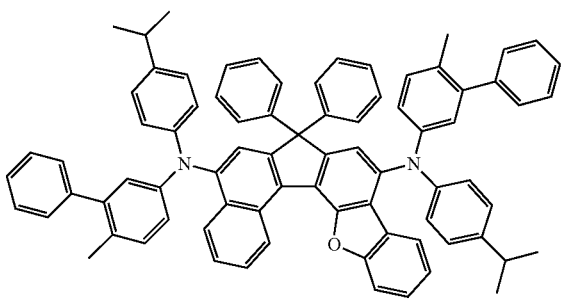
<Compound 589>
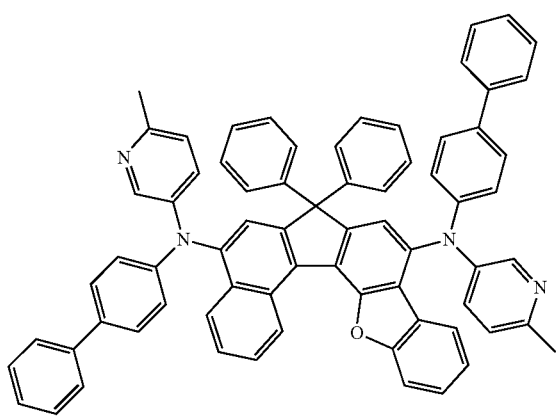
<Compound 590>
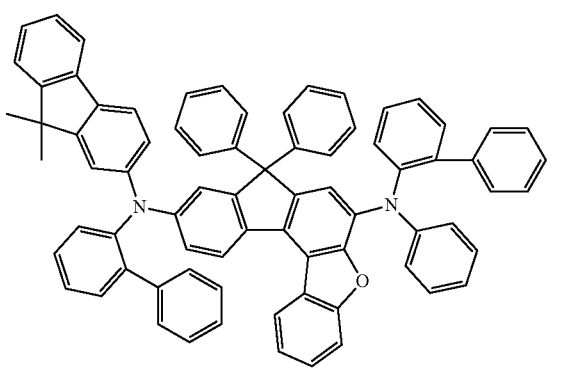

-continued
<Compound 591>
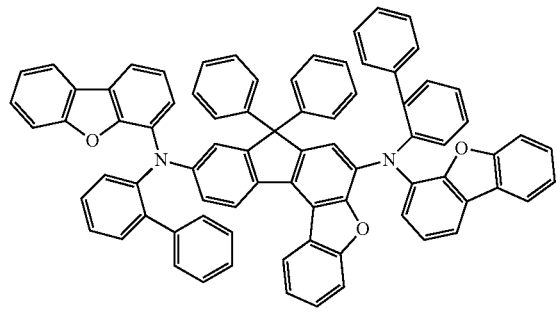
<Compound 592>
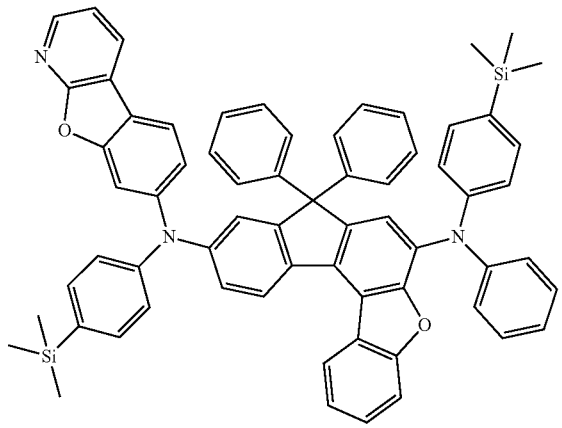
<Compound 593>
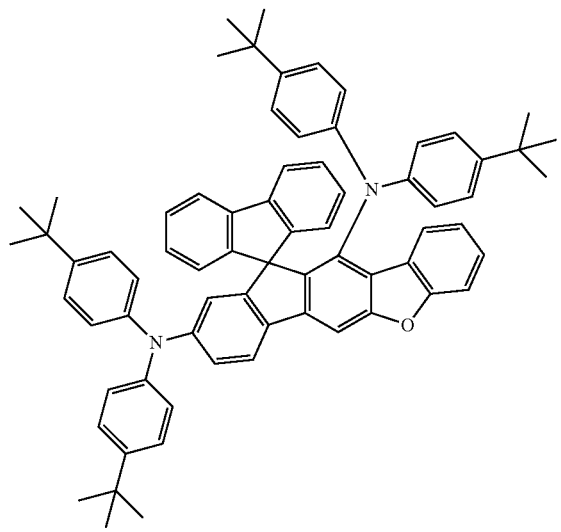
<Compound 594>
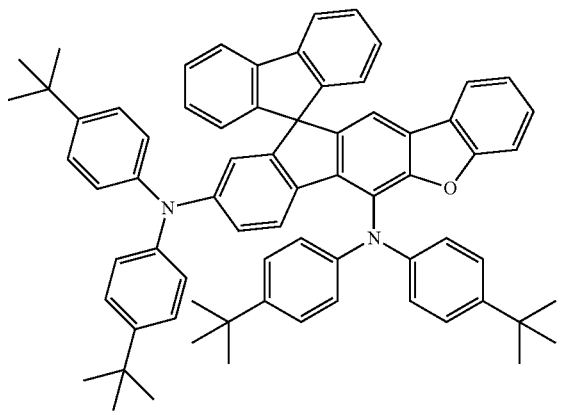
<Compound 595>
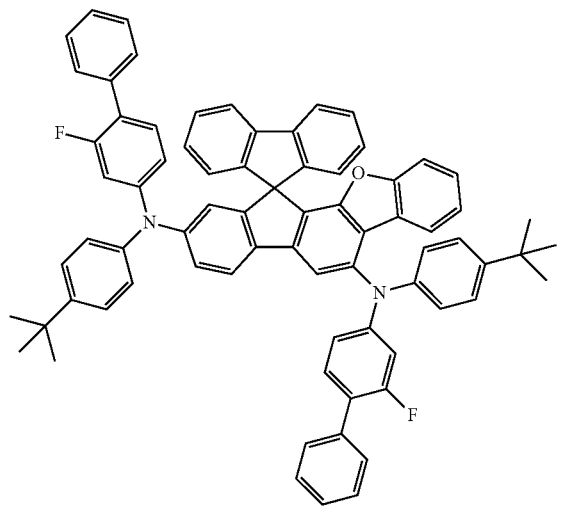
<Compound 596>
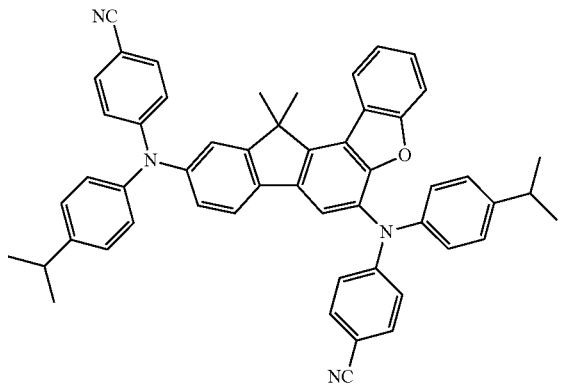

-continued
<Compound 597>
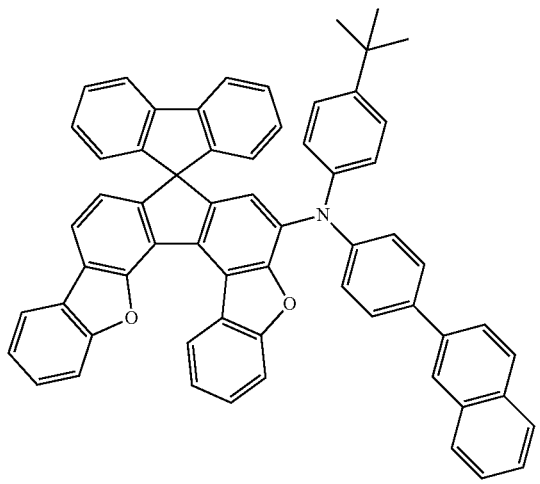
<Compound 598>
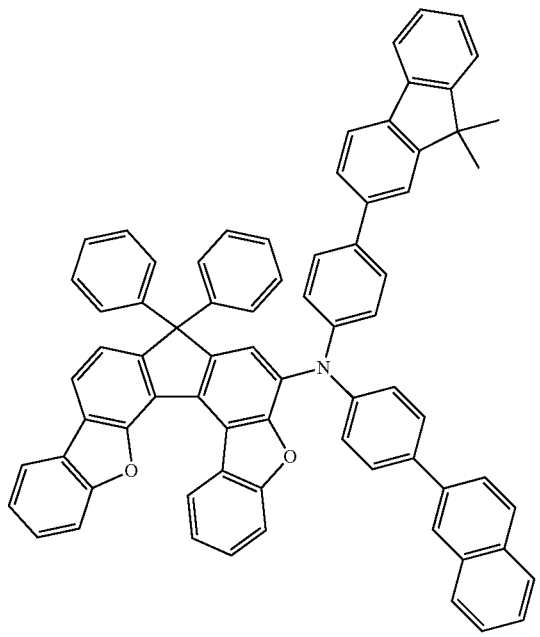
<Compound 599>
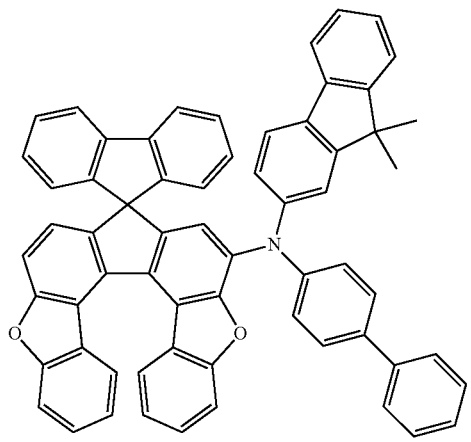
<Compound 600>
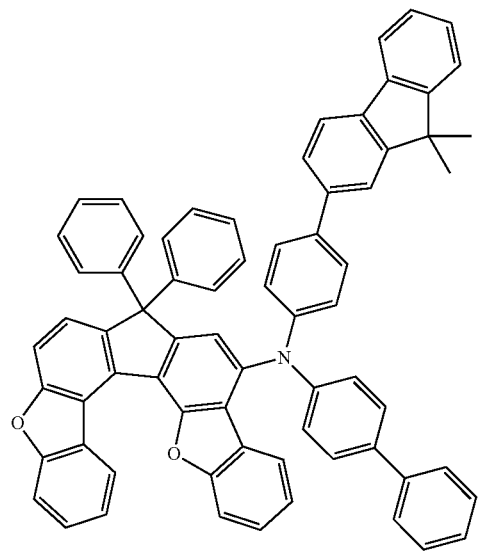

-continued
<Compound 601>
<Compound 602>
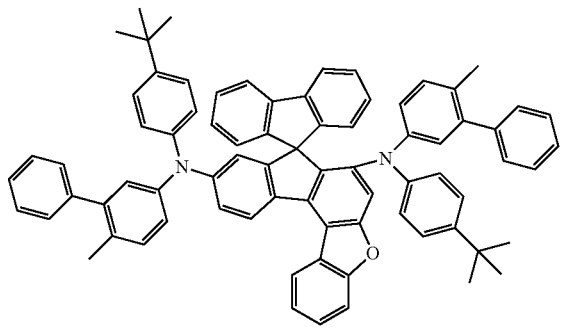
<Compound 603>
<Compound 604>
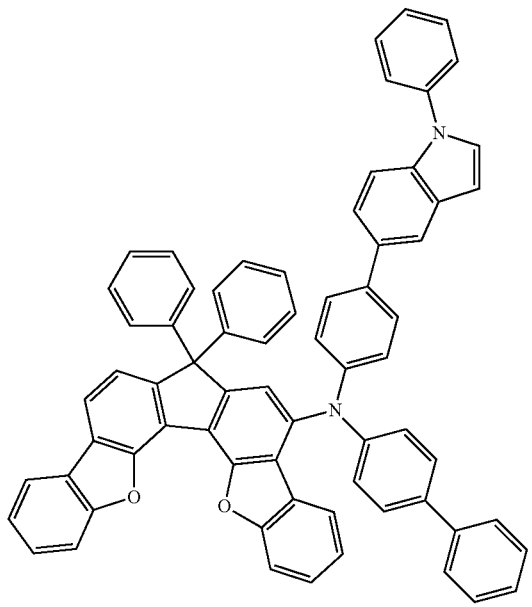
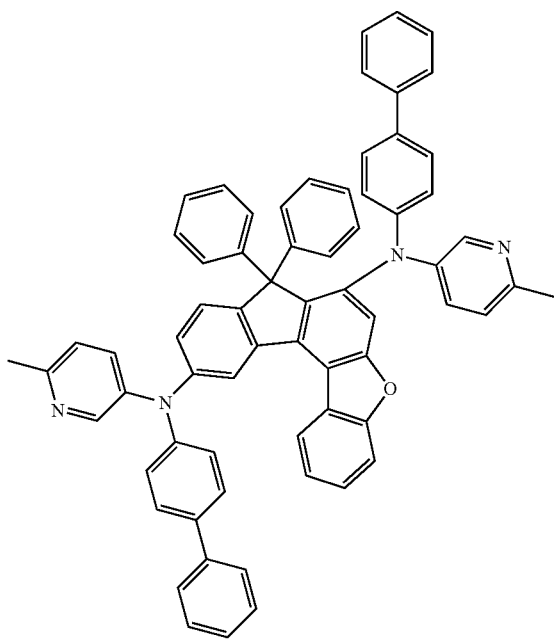
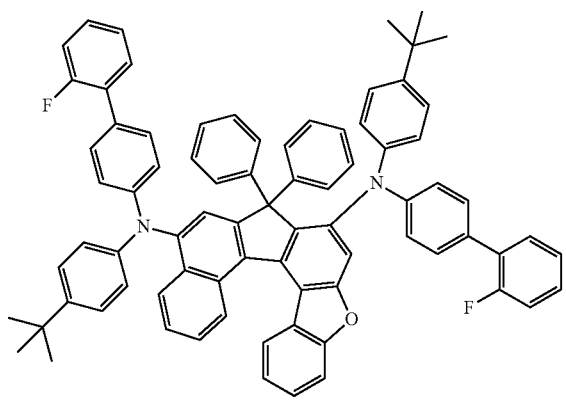
<Compound 605>
<Compound 606>
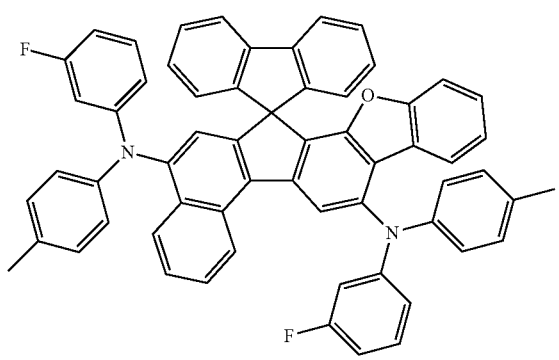
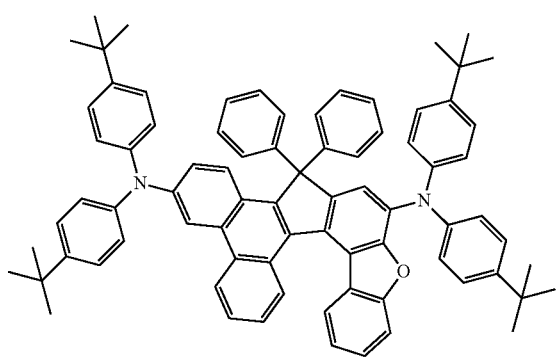

<Compound 607>
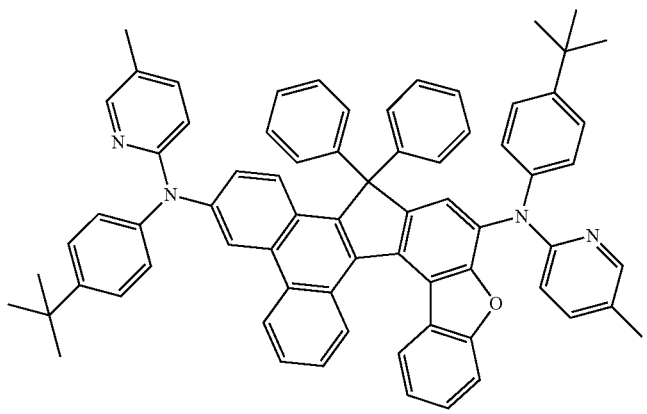
<Compound 608>
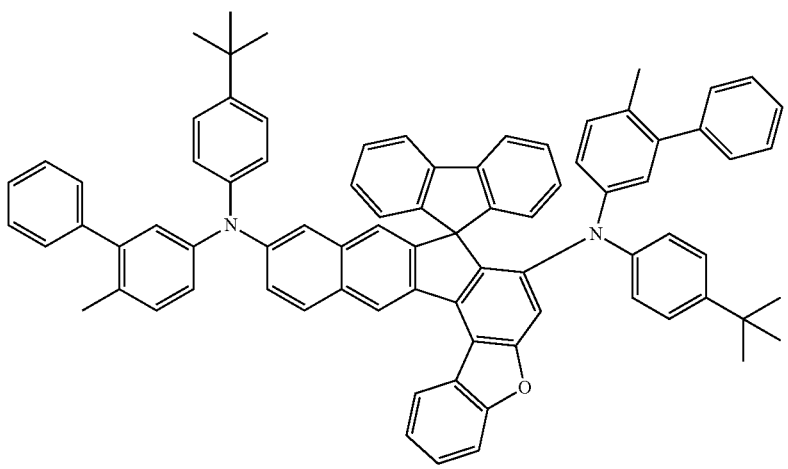
<Compound 609>
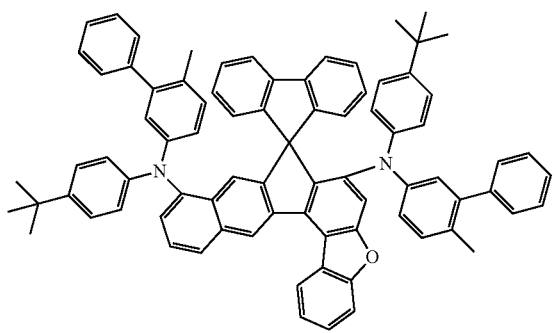
<Compound 610>
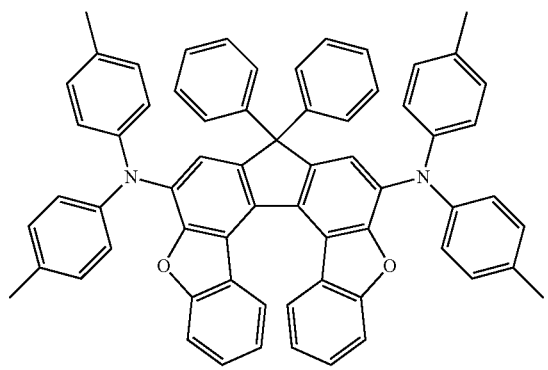

<Compound 611>
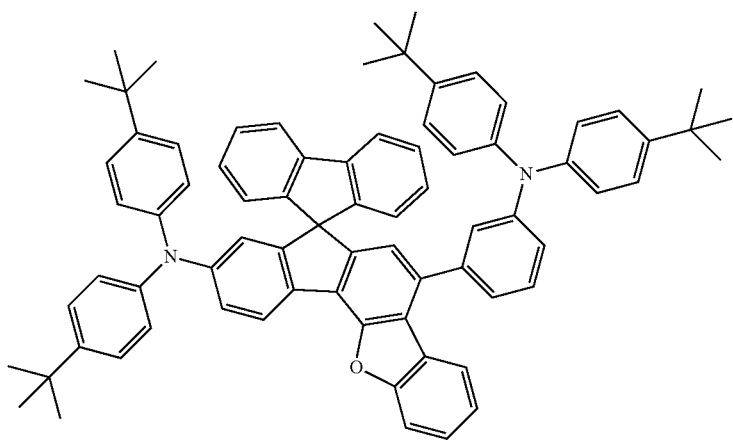
<Compound 612>
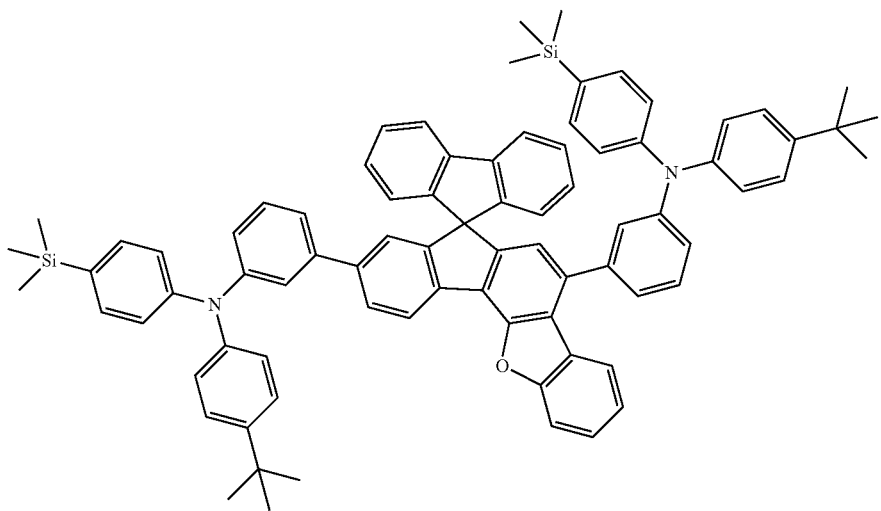
<Compound 613>
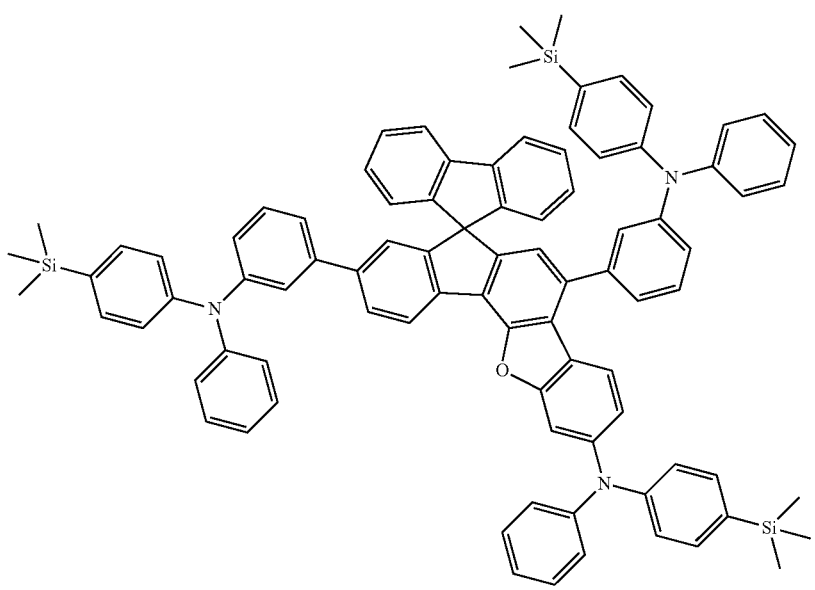

-continued
<Compound 614>
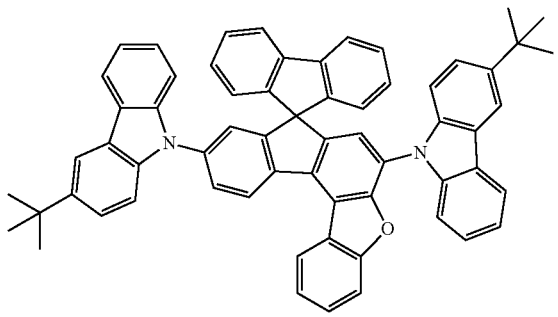
<Compound 615>
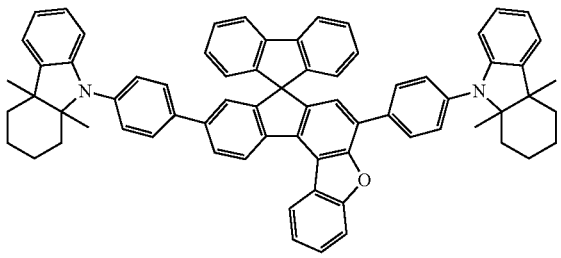
<Compound 616>
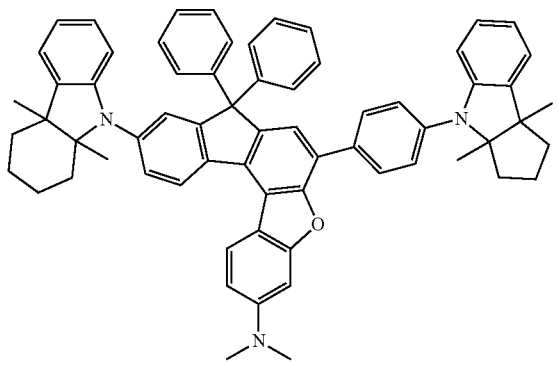
<Compound 617>
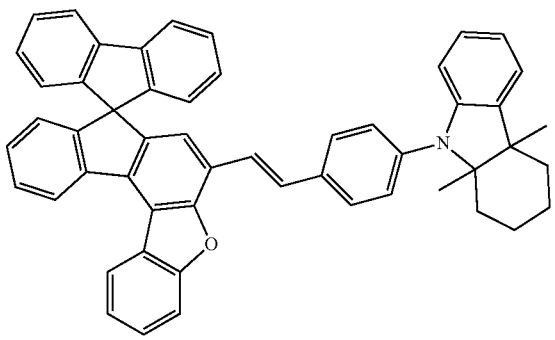
<Compound 618>
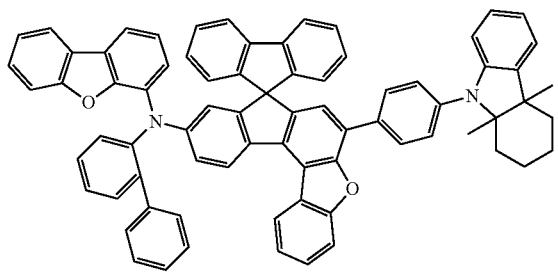
<Compound 619>
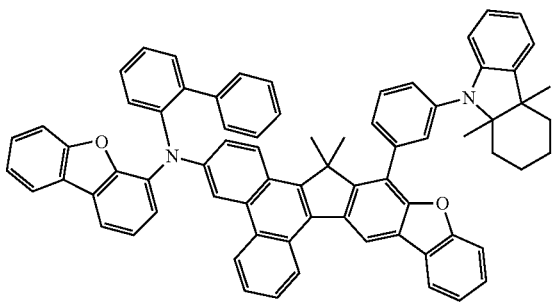
<Compound 620>
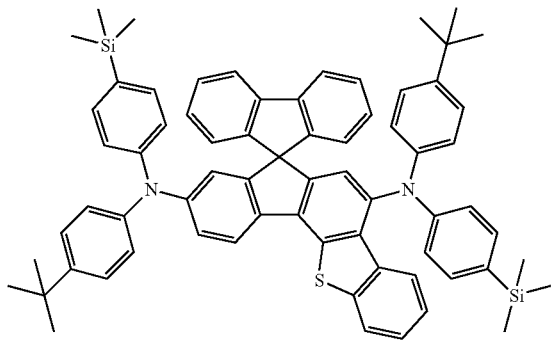
<Compound 621>
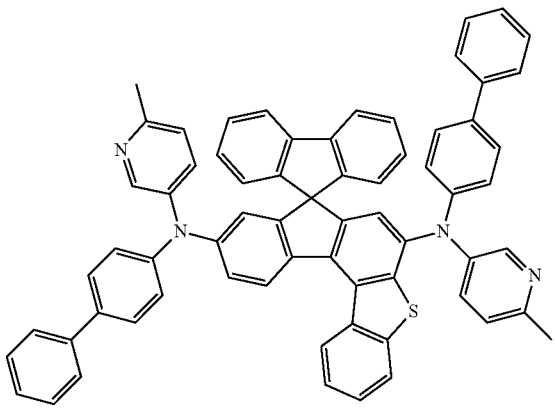

-continued
<Compound 622>
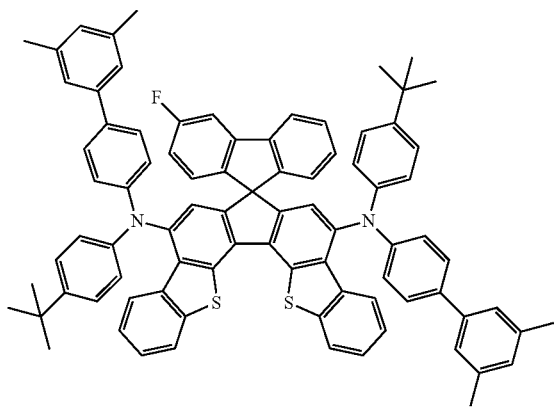
<Compound 623>
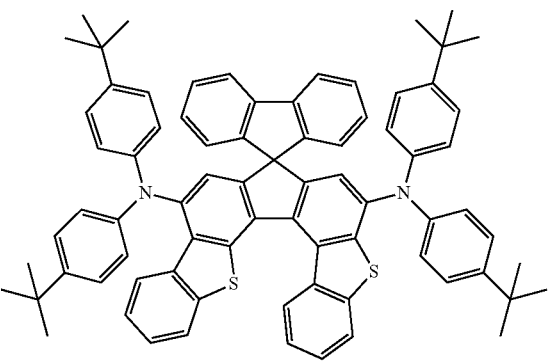
<Compound 624>
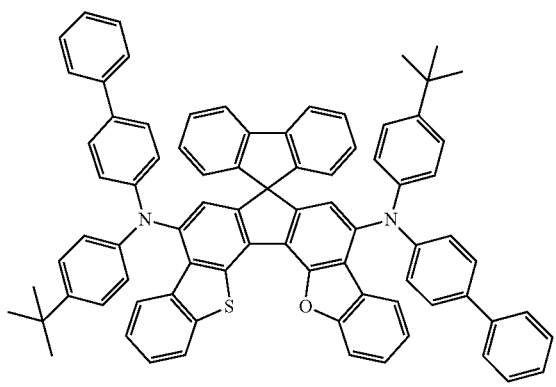
<Compound 625>
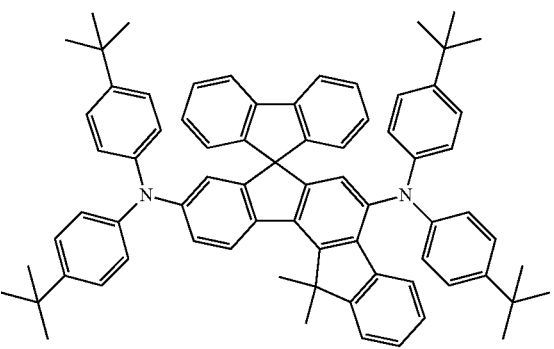
<Compound 626>
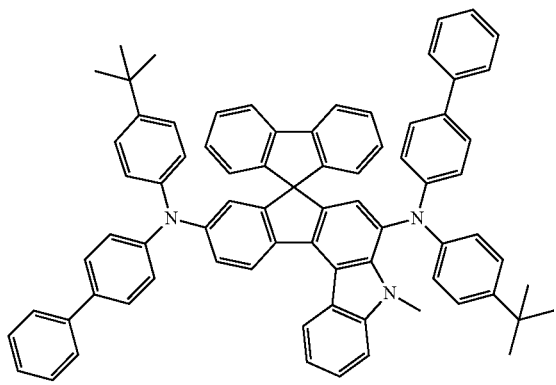
<Compound 627>
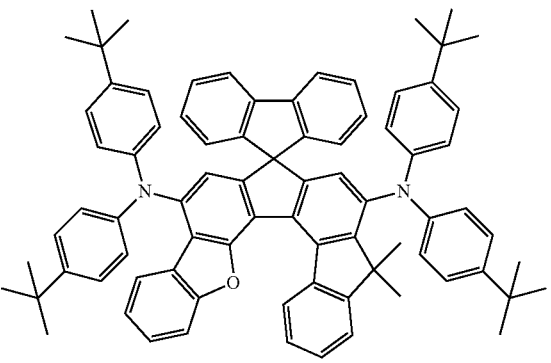
<Compound 628>
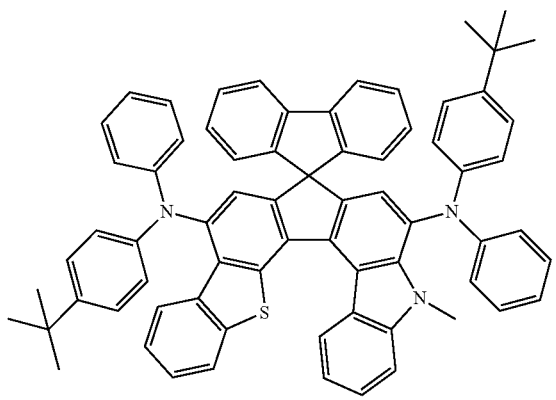
<Compound 629>
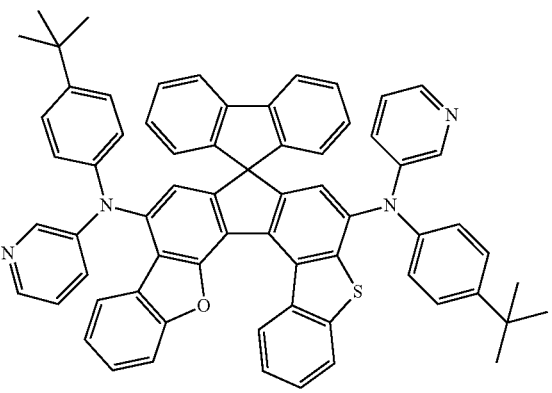

-continued
<Compound 630>
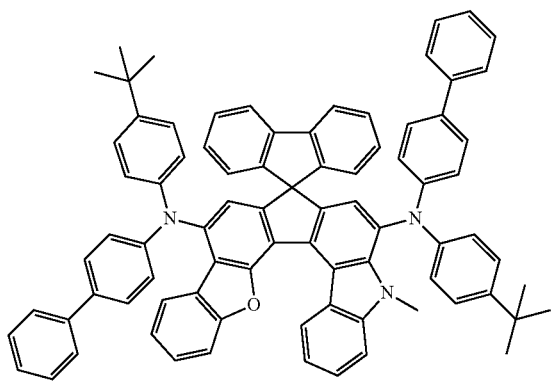
<Compound 631>
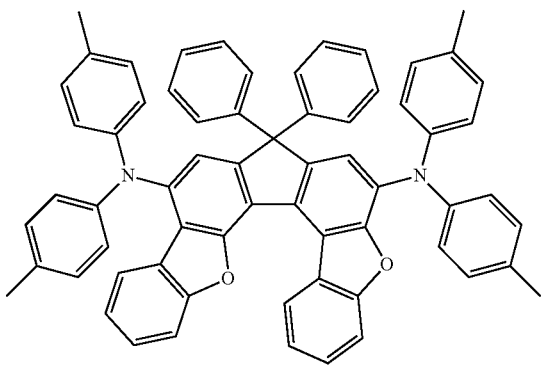
<Compound 632>
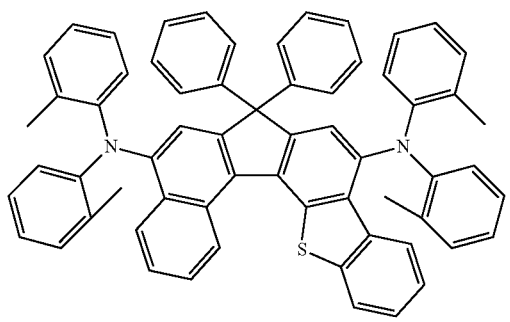
<Compound 633>
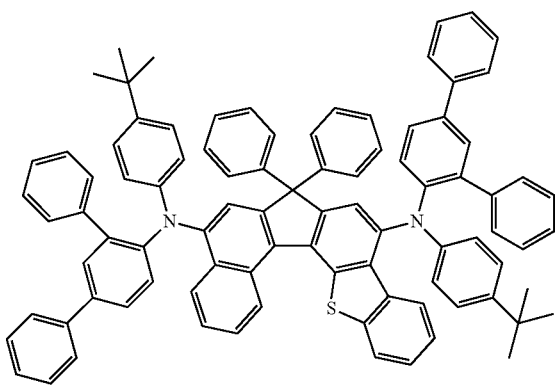
<Compound 634>
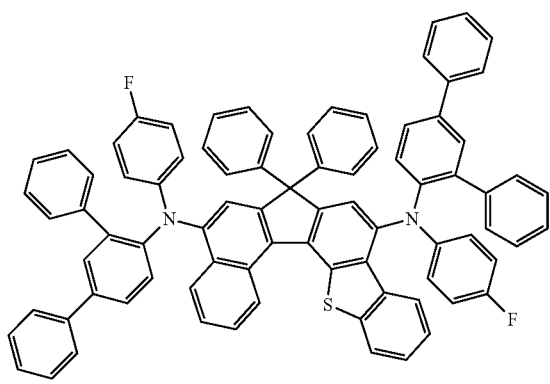
<Compound 635>
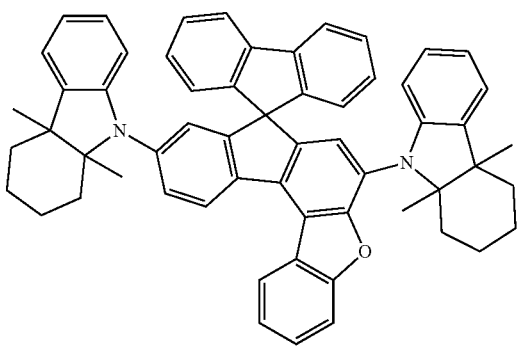
<Compound 636>
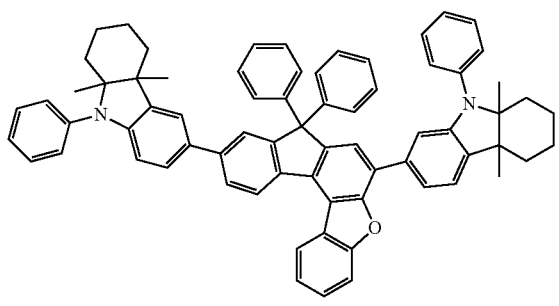
<Compound 637>
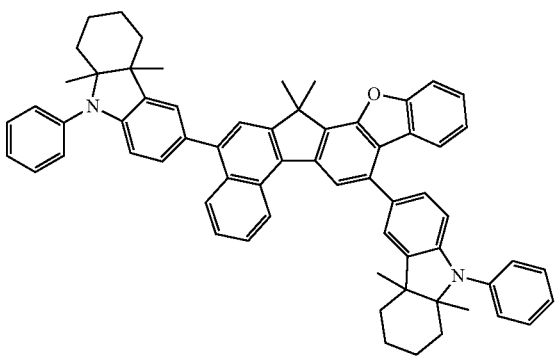

<Compound 638>

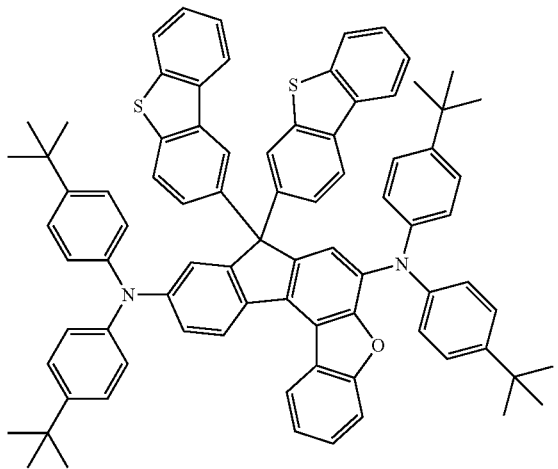

<Compound 639>

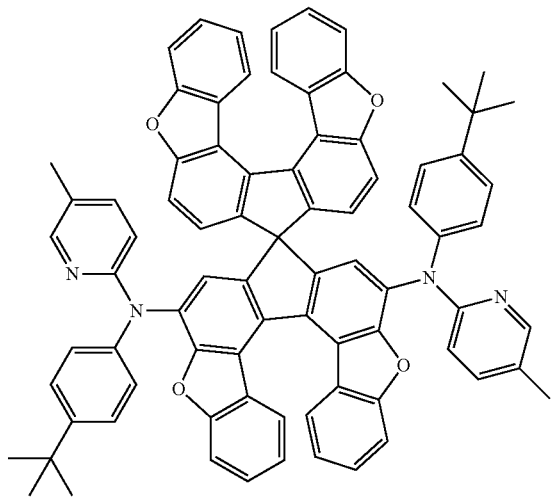

14. The organic light-emitting diode of claim 1, further comprising at least one of a hole injection layer, a hole transport layer, a functional layer capable of both hole injection and hole transport, an electron transport layer, and an electron injecting layer in addition to the light-emitting layer.

15. The organic light-emitting diode of claim 14, wherein the at least one selected from among the layers is formed using a deposition process or a solution process.

16. The organic light-emitting diode of claim 1, wherein the organic light-emitting diode is used for a device selected from among a flat display device, a flexible display device, a monochrome or grayscale flat illumination device, and a monochrome or grayscale flexible illumination device.

* * * * *